United States Patent
Brucklacher-Waldert et al.

(10) Patent No.: US 12,077,595 B2
(45) Date of Patent: *Sep. 3, 2024

(54) SINGLE DOMAIN ANTIBODIES THAT BIND TO CD137

(71) Applicant: CRESCENDO BIOLOGICS LIMITED, Cambridge (GB)

(72) Inventors: Verena Brucklacher-Waldert, Cambridge (GB); Carolyn Edwards, Cambridge (GB); James Legg, Cambridge (GB); Jayesh Majithiya, Cambridge (GB); Brian McGuinness, Cambridge (GB); Christine Rossant, Cambridge (GB); Yumin Teng, Cambridge (GB)

(73) Assignee: Crescendo Biologics Limited, Cambridge (GB)

(*) Notice: Subject to any disclaimer, the term of this patent is extended or adjusted under 35 U.S.C. 154(b) by 813 days.

This patent is subject to a terminal disclaimer.

(21) Appl. No.: 16/763,059

(22) PCT Filed: Nov. 13, 2018

(86) PCT No.: PCT/GB2018/053279
§ 371 (c)(1),
(2) Date: May 11, 2020

(87) PCT Pub. No.: WO2019/092451
PCT Pub. Date: May 16, 2019

(65) Prior Publication Data
US 2020/0362047 A1    Nov. 19, 2020

(30) Foreign Application Priority Data

Nov. 13, 2017  (GB) .................................... 1718734
Nov. 13, 2017  (GB) .................................... 1718735
May 24, 2018   (GB) .................................... 1808589

(51) Int. Cl.
*C07K 16/28*   (2006.01)
*C07K 16/30*   (2006.01)
*A61K 39/00*   (2006.01)

(52) U.S. Cl.
CPC ...... *C07K 16/2878* (2013.01); *C07K 16/2896* (2013.01); *C07K 16/30* (2013.01); *A61K 2039/505* (2013.01); *C07K 2317/24* (2013.01); *C07K 2317/31* (2013.01); *C07K 2317/565* (2013.01); *C07K 2317/569* (2013.01); *C07K 2317/75* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,728,114 B2 * | 6/2010 | Mach | A61P 1/04 530/388.22 |
| 7,851,598 B2 | 12/2010 | Davis | |
| 9,872,852 B2 | 1/2018 | Chupak et al. | |
| 10,202,458 B2 | 2/2019 | Goetsch et al. | |
| 10,323,090 B2 | 6/2019 | Bowman et al. | |
| 10,975,161 B2 | 4/2021 | Balloi et al. | |
| 11,117,964 B2 | 9/2021 | Hsu et al. | |
| 11,236,174 B2 | 2/2022 | McGuinness et al. | |
| 11,312,771 B2 | 4/2022 | Edwards et al. | |
| 11,591,398 B2 | 2/2023 | Hayes et al. | |
| 11,814,429 B2 | 11/2023 | Edwards et al. | |
| 2010/0122358 A1 | 5/2010 | Bruggemann et al. | |
| 2013/0202623 A1 | 8/2013 | Chomont et al. | |
| 2014/0356908 A1 | 12/2014 | Grosveld et al. | |
| 2015/0210769 A1 | 7/2015 | Freeman et al. | |
| 2015/0210796 A1 | 7/2015 | Kim et al. | |
| 2017/0240644 A1 | 8/2017 | Zhou et al. | |
| 2018/0362666 A1 | 12/2018 | Teng et al. | |
| 2019/0023807 A1 | 1/2019 | Balloi et al. | |
| 2019/0144561 A1 | 5/2019 | McGuinness et al. | |
| 2019/0322749 A1 | 10/2019 | Edwards et al. | |
| 2020/0131274 A1 | 4/2020 | Royle et al. | |
| 2020/0216540 A1 | 7/2020 | Geuijen et al. | |
| 2020/0227870 A1 | 7/2020 | Lollo et al. | |
| 2020/0239570 A1 | 7/2020 | Edwards et al. | |
| 2020/0239573 A1 | 7/2020 | Hayes et al. | |
| 2020/0362051 A1 | 11/2020 | Brucklacher-Waldert et al. | |
| 2020/0392244 A1 | 12/2020 | Balloi et al. | |
| 2021/0015937 A1 | 1/2021 | Edwards et al. | |
| 2021/0340233 A1 | 11/2021 | Edwards et al. | |
| 2022/0112305 A1 | 4/2022 | McGuinness et al. | |

(Continued)

FOREIGN PATENT DOCUMENTS

| | | |
|---|---|---|
| CN | 103087171 A | 5/2013 |
| CN | 105384825 A | 3/2016 |

(Continued)

OTHER PUBLICATIONS

Harlow et al. (Antibodies, A Laboratory Manual, Cold Spring Harbor laboratory, 1988, pp. 37-47). (Year: 1988).*
Saerens et al. (J Mol Biol. Sep. 23, 2005;352(3):597-607). (Year: 2005).*
Muyldermans et al., Reviews in Molecular Biotechnology 74 (2001), 277-302. (Year: 2001).*
Zabetakis et al. (PLoS One 8(10): e77678, 2013). (Year: 2013).*
Edwards et al. (J. Mol. Biol. (2003) 334, 103-118). (Year: 2003).*
Lloyd et al. (Protein Engineering, Design & Selection vol. 22 no. 3 pp. 159-168, 2009). (Year: 2009).*
Vajdos et al. (J Mol Biol. Jul. 5, 2002;320(2):415-28). (Year: 2002).*

(Continued)

*Primary Examiner* — Zachary S Skelding
(74) *Attorney, Agent, or Firm* — Sterne, Kessler, Goldstein & Fox P.L.L.C.

(57) ABSTRACT

The disclosure relates to CD137 binding agents and the use of such binding agents in the treatment, prevention and detection of disease.

15 Claims, 8 Drawing Sheets

Figure 1:
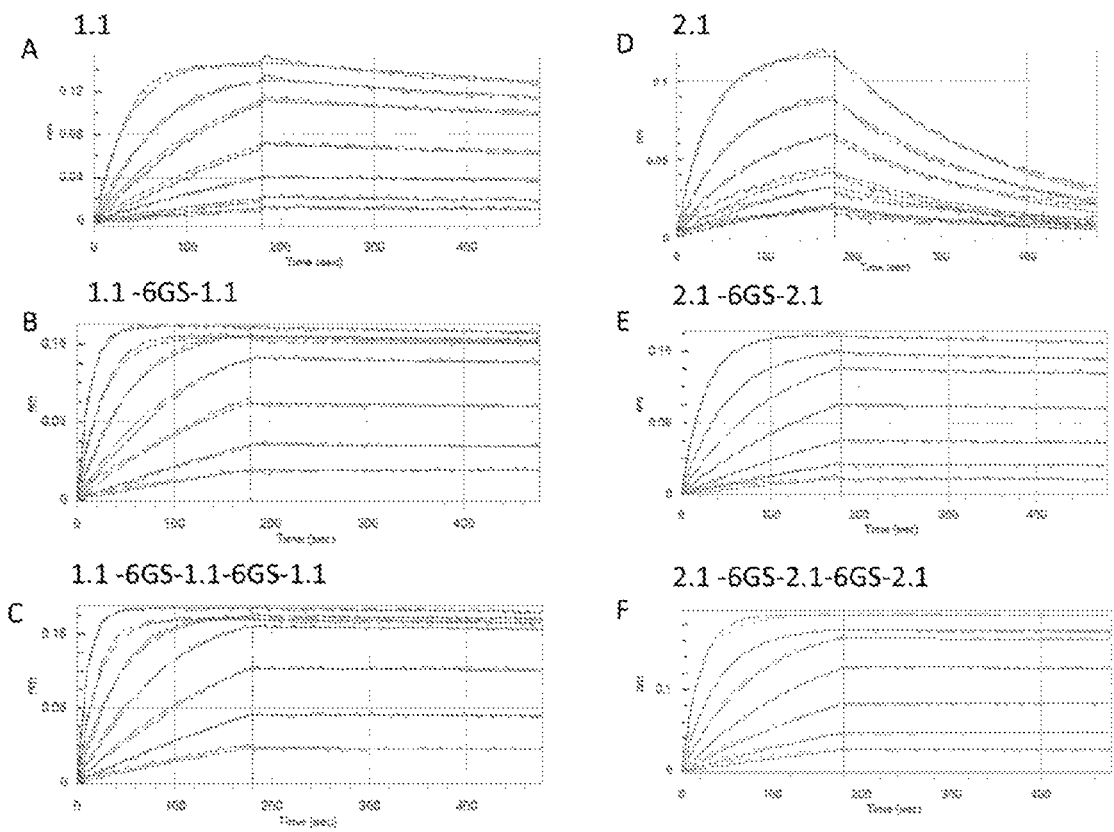

Specification includes a Sequence Listing.

(56) References Cited

U.S. PATENT DOCUMENTS

| | | |
|---|---|---|
| 2022/0220215 A1 | 7/2022 | Enever et al. |
| 2022/0227850 A1 | 7/2022 | Dunlevy et al. |
| 2022/0306744 A1 | 9/2022 | Edwards |
| 2023/0357405 A1 | 11/2023 | Hayes et al. |

FOREIGN PATENT DOCUMENTS

| | | | |
|---|---|---|---|
| CN | 105968203 A | 9/2016 | |
| CN | 105968204 A | 9/2016 | |
| CN | 105968205 A | 9/2016 | |
| EP | 2363404 A2 | 9/2011 | |
| EP | 2363404 B1 | 9/2016 | |
| EP | 3470426 A1 | 4/2019 | |
| JP | 2021502104 A | 1/2021 | |
| WO | WO-2003000737 A2 | 1/2003 | |
| WO | WO-2004076618 A2 | 9/2004 | |
| WO | WO-2006089230 A2 | 8/2006 | |
| WO | WO-2007117264 A2 | 10/2007 | |
| WO | WO-2009114335 A2 | 9/2009 | |
| WO | WO-2009117335 A2 | 9/2009 | |
| WO | WO-2010036959 A2 | 4/2010 | |
| WO | WO-2011110621 A1 | 9/2011 | |
| WO | WO-2012072731 A2 | 6/2012 | |
| WO | WO-2013045916 A1 | 4/2013 | |
| WO | WO-2013126712 A1 | 8/2013 | |
| WO | WO-2013167883 A1 | 11/2013 | |
| WO | WO-2014141192 A1 | 9/2014 | |
| WO | WO-2014198223 A1 | 12/2014 | |
| WO | WO-2015034820 A1 | 3/2015 | |
| WO | WO-2015112900 A1 | 7/2015 | |
| WO | WO-2015116539 A1 | 8/2015 | |
| WO | WO-2015142675 A2 | 9/2015 | |
| WO | WO-2015143079 A1 | 9/2015 | |
| WO | WO-2015156268 A1 | 10/2015 | |
| WO | WO-2015200119 A1 | 12/2015 | |
| WO | WO-2016020856 A2 | 2/2016 | |
| WO | WO-2016025880 A1 | 2/2016 | |
| WO | WO-2016062990 A1 | 4/2016 | |
| WO | WO-2016073760 A1 | 5/2016 | |
| WO | WO-2016106159 A1 | 6/2016 | |
| WO | WO-2016184882 A1 | 11/2016 | |
| WO | WO-2016197497 A1 | 12/2016 | |
| WO | WO-2017019846 A1 | 2/2017 | |
| WO | WO-2017020801 A1 | 2/2017 | |
| WO | WO-2017060144 A1 | 4/2017 | |
| WO | WO-2017087589 A2 | 5/2017 | |
| WO | WO-2017122017 A1 | 7/2017 | |
| WO | WO-2017122018 A1 | 7/2017 | |
| WO | WO-2017122019 A1 | 7/2017 | |
| WO | WO-2017123650 A2 | 7/2017 | |
| WO | WO-2017182672 A1 | 10/2017 | |
| WO | WO-2017191476 A1 | 11/2017 | |
| WO | WO-2017201488 A1 | 11/2017 | |
| WO | WO-2017205738 A1 | 11/2017 | |
| WO | WO-2018104444 A1 | 6/2018 | |
| WO | WO-2018121473 A1 | 7/2018 | |
| WO | WO-2018127709 A1 | 7/2018 | |
| WO | WO-2018127710 A1 | 7/2018 | |
| WO | WO-2018127711 A1 | 7/2018 | |
| WO | WO-2018224439 A1 | 12/2018 | |
| WO | WO-2019012260 A1 | 1/2019 | |
| WO | WO-2019072868 A1 * | 4/2019 | ............. A61P 35/00 |
| WO | WO-2019092451 A1 | 5/2019 | |
| WO | WO-2019092452 A1 | 5/2019 | |
| WO | WO-2019158942 A1 | 8/2019 | |
| WO | WO-2020099871 A1 | 5/2020 | |
| WO | WO-2020229842 A1 | 11/2020 | |
| WO | WO-2020229844 A1 | 11/2020 | |

OTHER PUBLICATIONS

Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Muyldermans et al., Annu. Rev. Biochem. 2013. 82:775-97, (2013). (Year: 2013).*
Agata, Y., et al., "Expression of the PD-1 Antigen on the Surface of Stimulated Mouse T and B lymphocytes," International Immunology 8(5):765-772, Oxford University Press, United Kingdom (May 1996).
An, Z., ed., "Section 3.4.3—Glycan Profiles of Recombinant IgG Produced in Rodent Cell Lines," in *Therapeutic Monoclonal Antibodies: From Bench to Clinic*, pp. 73-76, John Wiley & Sons, United States (2009).
Bennett, F., et al., "Program Death-1 Engagement Upon TCR Activation has Distinct Effects on Costimulation and Cytokine-driven Proliferation: Attenuation of ICOS, IL-4, and IL-21, but not CD28, IL-7, and IL-15 responses," The Journal of Immunology 170(2):711-718, The American Association of Immunologists, United States (Jan. 2003).
Berglund, L., et al., "The Epitope Space of the Human Proteome," Protein Science 17(4):606-613, Cold Spring Harbor Laboratory Press, United States (Apr. 2008).
Caldas, C., et al., "Humanization of the Anti-CD18 Antibody 6.7: An Unexpected Effect of a Framework Residue in Binding to Antigen," Molecular Immunology 39(15):941-952, Pergamon Press, United Kingdom (May 2003).
Callahan, M.K and Wolchok, J.D., "At the Bedside: CTLA-4- and PD-1-Blocking Antibodies In Cancer Immunotherapy," Journal of Leukocyte Biology 94(1):41-53, Wiley on behalf of the Society for Leukocyte Biology, United States (May 2013).
Castelli, C., et al., "Lymphocyte Activation Gene-3 (LAG-3, CD223) in Plasmacytoid Dendritic Cells (pDCs): a Molecular Target for the Restoration of Active Antitumor Immunity," Oncoimmunology 3(11):e967146, 4 pages, Taylor & Francis, United States (Nov. 2014).
Chen, L., et al. "Epitope-directed antibody selection by site-specific photocrosslinking," Science Advances 6(14): eaaz7825, 9 pages, American Association for the Advancement of Science, United States (Apr. 2020).
ClinicalTrials.gov, "Safety Study of Anti-LAG-3 in CLL, HL and NHL," Identifier NCT02061761, accessed at https://clinicaltrials.gov/archive/NCT02061761/2014_08_28, last accessed on Jan. 13, 2015, 4 pages.
Colman, P. M., "Effects of Amino Acid Sequence Changes on Antibody-Antigen Interactions," Research in Immunology 145(1):33-36, Elsevier, France (Jan. 1994).
Communication from the Examining Division for EP Application No. EP 19 707 094.9, European Patent Office, Munich, Germany, dated Nov. 22, 2021, 4 pages.
Dietz, L.J., et al., "Volumetric Capillary Cytometry: A New Method for Absolute Cell Enumeration," Cytometry 23(3):177-186, John Wiley & Sons, United States (1996).
Drabek, D., et al., "Expression Cloning and Production of Human Heavy-Chain-Only Antibodies from Murine Transgenic Plasma Cells," Frontiers in Immunology 7: 619, pp. 1-10, Frontiers Media SA, United States (Dec. 2016).
Du, J., et al., "Molecular Basis of Recognition of Human Osteopontin by 23C3, a Potential Therapeutic Antibody for Treatment of Rheumatoid Arthritis," Journal of Molecular Biology 382(4):835-842, Elsevier, United Kingdom (Oct. 2008).
Edwards, B.M., et al., "The Remarkable Flexibility of the Human Antibody Repertoire; Isolation of Over One Thousand Different Antibodies to a Single Protein, BLyS," Journal of Molecular Biology 334(1):103-118, Elsevier, United Kingdom (Nov. 2003).
Fan, G., et al., "Bispecific Antibodies and their Applications," Journal of Hematology & Oncology 8, Article No. 130, 14 pages, BioMed Central: Part of Springer Nature, United Kingdom (Dec. 2015).
Francisco, L.M., et al., "The PD-1 Pathway in Tolerance and Autoimmunity," Immunological Reviews 236:219-242, Blackwell, United Kingdom (Jul. 2010).

(56) References Cited

OTHER PUBLICATIONS

GenBank, "Alpha-synuclein," Accession No. P37840.1, accessed at https://www.ncbi.nlm.nih.gov/protein/P37840, accessed on Sep. 24, 2020, 13 pages.

GenBank, "C-type lectin domain family 4 member G isoform 1 [Homo sapiens]," Accession No. NP_940894.1, accessed at https://www.ncbi.nlm.nih.gov/protein!NP_940894, accessed on Sep. 24, 2020, 3 pages.

GenBank, "galectin-3 [Homo sapiens]," Accession No. BAA22164.1, accessed at https://www.ncbi.nlm.nih.gov/protein/BAA22164, accessed on Sep. 24, 2020, 2 pages.

GenBank, "Macaca fascicularis chromosome 11, Macaca fascicularis_5.0, whole genome shotgun sequence," Accession No. NC_022282.1, accessed at https://www.ncbi.nlm.nih.gov/nuccore/NC_022282, accessed on Sep. 24, 2020, 2 pages.

GenBank, "E3 ubiquitin-protein ligase CBL-B isoform b [Homo sapiens]," Accession No. NP_001308717.1, accessed at https://www.ncbi.nlm.nih.gov/protein/NP_001308717, accessed on Sep. 24, 2020, 4 pages.

GenBank, "*Homo sapiens* lymphocyte activating 3 (LAG3), mRNA," Accession No. NM_002286.6, accessed at https://www.ncbi.nlm.nih.gov/nuccore/NM_002286, accessed on Sep. 24, 2020, 5 pages.

GenBank, "Human hPD-1 (hPD-1) mRNA, complete cds," Accession No. U64863.1, accessed at https://www.ncbi.nlm.nih.gov/nuccore/U64863 on May 11, 2022, 3 pages.

GenBank, "Macaca mulatta lymphocyte activating 3 (LAG3), mRNA," Accession No. XM_001108923.4, accessed at https://www.ncbi.nlm.nih.gov/nuccore/XM_001108923, accessed on May 11, 2022, 2 pages.

Geng, Y., et al., "Single domain antibodies against immune checkpoint targets PD-1 and PD-L1," Immunome Res 12:2(Suppl), 2nd International Conference on Antibodies and Therapeutics, Jul. 11-12, 2016, Philadelphia, United States, 1 page (Jul. 2016).

Goel, M., et al., "Plasticity Within the Antigen-combining Site May Manifest as Molecular Mimicry in the Humoral Immune Response," Journal of Immunology 173(12):7358-7367, American Association of Immunologists, United States (Dec. 2004).

Gordon, S. R., et al., "PD-1 expression by tumor-associated macrophages inhibits phagocytosis and tumor immunity," with methods and extended data, Nature 545(7655): 495-499 (13 pages total), Nature Publishing Group, United Kingdom (May 2017).

Grosso, J.F., et al., "LAG-3 Regulates CD8$^+$ T Cell Accumulation and Effector Function in Murine Self- and Tumor-tolerance Systems," The Journal of Clinical Investigation 117(11):3383-3392, American Society for Clinical Investigation, United States (Nov. 2007).

He, J., et al., "Development of PD-1/PD-L1 Pathway in Tumor Immune Microenvironment and Treatment for Non-Small Cell Lung Cancer," Nature Scientific Reports 5, Article No. 13110, 9 pages, Springer Nature (Aug. 2015).

Homayouni, V., et al., "Preparation and characterization of novel nanobody against T-cell immunoglobulin and mucin-3 (TIM-3)," Iranian Journal of Basic Medical Sciences 19(11):1201-1208, Mashhad University of Medical Sciences, Iran (Nov. 2016).

Huang, C,T., et al., "Role of LAG-3 in Regulatory T Cells," Immunity 21(4):503-513, Cell Press, United States (Oct. 2004).

Huang, R.Y., et al., "Compensatory Upregulation of PD-1, LAG-3, and CTLA-4 Limits the Efficacy of Single-Agent Checkpoint Blockade In Metastatic Ovarian Cancer," Oncoimmunology 6(1):e1249561, 13 pages, Taylor & Francis, United States (Oct. 2016).

Huard, B., et al., "Characterization of the Major Histocompatibility Complex Class II Binding Site on LAG-3 Protein," Proc Natl Acad Sci USA 94(11):5744-5749, National Academy of Sciences, United States (May 1997).

Huard, B., et al., "Lymphocyte-activation Gene 3/major Histocompatibility Complex Class II Interaction Modulates the Antigenic Response of CD4$^+$ T Lymphocytes," European Journal of Immunology 24(12):3216-3221, Wiley-VCH, Germany (Dec. 1994).

Huard, B., et al., "T Cell Major Histocompatibility Complex Class II Molecules Down-regulate CD4$^+$ T Cell Clone Responses Following LAG-3 Binding," European Journal of Immunology 26(5):1180-1186, Wiley-VCH, Germany (May 1996).

International Preliminary Report on Patentability for International Application No. PCT/GB2019/053220, The International Bureau of WIPO, Switzerland, dated May 18, 2021, 11 pages.

International Preliminary Report on Patentability for International Application No. PCT/GB2020/051199, The International Bureau of WIPO, Switzerland, dated Nov. 16, 2021, 8 pages.

International Preliminary Report on Patentability for International Application No. PCT/GB2020/051201, The International Bureau of WIPO, Switzerland, dated Nov. 16, 2021, 17 pages.

International Preliminary Report on Patentability for International Application No. PCT/GB2018/050035, The International Bureau of WIPO, Switzerland, dated Jul. 9, 2019, 11 pages.

International Preliminary Report on Patentability for International Application No. PCT/GB2018/050036, The International Bureau of WIPO, Switzerland, dated Jul. 9, 2019, 11 pages.

International Preliminary Report on Patentability for International Application No. PCT/GB2018/050037, The International Bureau of WIPO, Switzerland, dated Jul. 9, 2019, 12 pages.

International Preliminary Report on Patentability for International Application No. PCT/GB2018/053279, The International Bureau of WIPO, Switzerland, dated May 19, 2020, 11 pages.

International Preliminary Report on Patentability for International Application No. PCT/GB2018/053280, The International Bureau of WIPO, Switzerland, dated May 19, 2020, 12 pages.

International Preliminary Report on Patentability for International Application No. PCT/GB2019/050425, The International Bureau of WIPO, Switzerland, dated Aug. 18, 2020, 7 pages.

International Search Report and Written Opinion for International Application No. PCT/GB2018/050035, European Patent Office, Netherlands, dated Apr. 25, 2018, 16 pages.

International Search Report and Written Opinion for International Application No. PCT/GB2018/050036, European Patent Office, Netherlands, dated May 3, 2018, 16 pages.

International Search Report and Written Opinion for International Application No. PCT/GB2018/050037, European Patent Office, Netherlands, dated Apr. 25, 2018, 18 pages.

International Search Report and Written Opinion for International Application No. PCT/GB2019/050425, European Patent Office, Netherlands, dated Apr. 17, 2019, 10 pages.

International Search Report and Written Opinion for International Application No. PCT/GB2020/051201, European Patent Office, Netherlands, dated Oct. 13, 2020, 23 pages.

Ishida, Y., et al., "Induced Expression of PD-1, a Novel Member of the Immunoglobulin Gene Superfamily, Upon Programmed Cell Death," The EMBO Journal 11(11):3887-3895, Oxford University Press, United Kingdom (Nov. 1992).

Japanese Office Action dated Dec. 13, 2021, in Japanese Patent Application No. 2019-536937, filed Jan. 18, 2018, 21 pages.

Japanese Office Action dated Dec. 6, 2021, in Japanese Patent Application No. 2019-536936, filed Jan. 8, 2018, 17 pages.

Kabat, E.A., et al., "Sequences of proteins of immunological interest," 5th Edition, NIH publication No. 91-3242, pp. 1-1137, U.S. Department of Public Health and Human Services, National Institutes of Health, United States (1991).

Karwacz, K., et al., "PD-L1 Co-Stimulation Contributes To Ligand-Induced T Cell Receptor Down-Modulation On CD8$^+$ T Cells," EMBO Molecular Medicine 3(10): 581-592, Wiley-Blackwell, United Kingdom (Oct. 2011).

Keir, M.E., et al., "Programmed Death-1 (PD-1):PD-Ligand 1 Interactions Inhibit TCR-Mediated Positive Selection of Thymocytes," J Immunol 175(11):7372-7379, American Association of Immunologists, United States (Dec. 2005).

Kisielow, M., et al., "Expression of lymphocyte activation gene 3 (LAG-3) on B cells is induced by T cells," Eur. J. Immunol., 35(7):2081-2088, Wiley-VCH Verlag, Germany (Jul. 2005).

Kouo, T., et al., "Galectin-3 Shapes Antitumor Immune Responses by Suppressing CD8$^+$ T Cells via LAG-3 and Inhibiting Expansion of Plasmacytoid Dendritic Cells," Cancer Immunology Research 3(4):412-423, American Association for Cancer Research, (Apr. 2015).

(56) References Cited

OTHER PUBLICATIONS

Kraman, M., et al., "A LAG-3/PD-L1 bispecific antibody inhibits tumor growth in two syngeneic colon carcinoma models," Presented at the 31st annual Society for Immunotherapy of Cancer, , XP855369256, Retrieved from the Internet: URL:http://www.f-star.com/media/73722/A-LAG-3-PD-L1-bispecific-antibody-inhibits-tumour-growth-in-two-syngeneic-colon-carcinoma-models.pdf, 1 page (Nov. 2016).
Kunik, V., et al., "The Indistinguishability of Epitopes From Protein Surface is Explained By the Distinct Binding Preferences of Each of the Six Antigen-Binding Loops," Protein Engineering, Design and Selection 26(10):599-609, Oxford University Press, United Kingdom (Oct. 2013).
Kunik, V., et al., "Structural Consensus among Antibodies Defines the Antigen Binding Site," PLoS Computational Biology 8(2):e1002388, 12 pages, Public Library of Science, United States (Feb. 2012).
Lloyd, C., et al., "Modelling the Human Immune Response: Performance of a $10^{11}$ Human Antibody Repertoire Against a Broad Panel of Therapeutically Relevant Antigens," Protein Engineering, Design and Selection, 22(3):159-168, Oxford University Press, United Kingdom (Mar. 2009).
Lowther, D.E., et al., "PD-1 Marks Dysfunctional Regulatory T Cells in Malignant Gliomas," JCI insight 1(5): e85935, 15 pages, American Society for Clinical Investigation, United states (Apr. 2016).
Main, S., et al., "A potent human anti-eotaxin1 antibody, CAT-213: isolation by phage display and in vitro and in vivo efficacy," J Pharmacol Exp Ther 319(3):1395-1404, American Society for Pharmacology and Experimental Therapeutics, United States (2006).
Marks, J.D., "Chapter 19: Antibody Affinity Maturation by Chain Shuffling" in Methods in Molecular Biology, Antibody Engineering: Methods and Protocols, vol. 248, pp. 327-343, Springer Nature, Switzerland (2004).
Matsuzaki, J., et al., "Tumor-infiltrating NY-ESO-1-specific $CD8^+$ T Cells Are Negatively Regulated by LAG-3 and PD-1 in Human Ovarian Cancer," Proc Natl Acad Sci USA 107(17):7875-7880, National Academy of Sciences, United States (Apr. 2010).
McGuinness, B., "Humabody fragments: Small and perfectly formed," Biopharmadealmakers, accessed at www.crescendobiologics.com, pp. B12-B13, 2 pages (2013).
Miraglia, S., et al., "Homogeneous Cell- And Bead-Based Assays For High Throughput Screening Using Fluorometric Microvolume Assay Technology," Journal of Biomolecular Screening 4(4):193-204, Sage Publications, United States (1999).
Muyldermans, S., "Single Domain Camel Antibodies: Current Status, " Reviews in Molecular Biotechnology 74(4):277-302, Elsevier Science Publishers, Netherlands (2001).
Muyldermans, S., et al., "Recognition of Antigens by Single-Domain Antibody Fragments: the Superfluous Luxury of Paired Domains," Trends in Biochemical Sciences 26(4):230-235, Elsevier Trends Journals, United Kingdom (Apr. 2001).
Muyldermans, S., et al., "Nanobodies: Natural Single-domain Antibodies," Annual Review of Biochemistry, 82:17.1-17.23, Annual Reviews, United States (2013).
NCT02061761, "Safety Study of Anti-LAG-3 in Relapsed or Refractory Hematologic Malignancies," ClinicalTrials.gov, posted Feb. 13, 2014, accessed at https://www.clinicaltrials.gov/ct2/show/NCT02061761 on Dec. 14, 2020, 4 pages.
NCT02460224, "Safety and Efficacy of LAG525 Single Agent and in Combination With PDR001 in Patients With Advanced Malignancies," ClinicalTrials.gov, posted Jun. 2, 2015, accessed at https://www.clinicAltriAls.gov/ct2/show/NCT02460224 on Dec. 14, 2020, 5 pages.
Nishimura, H., et al., "Autoimmune Dilated Cardiomyopathy in PD-1 Receptor-deficient Mice," Science 291(5502):319-322, American Association for the Advancement of Science, United States (Jan. 2001).
Nishimura, H., et al., "Development of Lupus-like Autoimmune Diseases by Disruption of the PD-1 Gene Encoding an ITIM Motif-carrying Immunoreceptor," Immunity 11(2):141-151, Cell Press, United States (Aug. 1999).

Office Action dated Jun. 30, 2021, in U.S. Appl. No. 16/475,597, Hayes, et al., 371(c) filed Jul. 2, 2019, 23 pages.
Office Action dated Apr. 22, 2022, in U.S. Appl. No. 16/475,597, Hayes, et al., 371(c) filed Jul. 2, 2019, 26 pages.
Office action dated Jun. 11, 2021, in U.S. Appl. No. 16/475,599, inventor Edwards; C., et al., int'l filing date Jan. 8, 2018, 10 pages.
Office Action dated Mar. 1, 2022, in U.S. Appl. No. 16/475,590, inventor Edwards; B., et al., int'l filing date Jan. 8, 2018, 17 pages.
Office Action dated Nov. 15, 2021, in U.S. Appl. No. 16/475,597, Hayes et al., 371(c) filed Jul. 2, 2019, 15 pages.
Office action dated Sep. 20, 2021, in U.S. Appl. No. 16/475,590, inventor Edwards; B., et al., int'l filing date Jan. 8, 2018, 15 pages.
Padlan, E.A, "X-Ray Crystallography of Antibodies," Advances in Protein Chemistry 49:57-133, Academic Press, United States (1996).
Patel, T. P., et al., "Different Culture Methods Lead to Differences in Glycosylation of a Murine IgG Monoclonal Antibody," Biochemical Journal 285(Pt 3):839-845, Portland Press on behalf of the Biochemical Society, United Kingdom (1992).
Paul, W.E., "Structure and Function of Immunoglobulins," in Fundamental Immunology, Third Edition: pp. 292-295, Raven Press, New York, United States (1993).
Perez-Ruiz, E., et al., "Anti-CD 137 and PD-1/PD-L1 Antibodies En Route toward Clinical Synergy," Clinical Cancer Research 23(18):5326-5328, American Cancer Research, United States (Aug. 2017).
Posthumus, W.P.A., et al., "Analysis And Simulation of a Neutralizing Epitope of Transmissible Gastroenteritis Virus," Journal of Virology 64(7):3304-3309, American Society for Microbiology (Jul. 1990).
Riley, J. L., "PD-1 Signaling In Primary T Cells," Immunol Rev 229(1):114-125, Blackwell, United Kingdom (May 2009).
Roe, M., "Superior Human Single Domain VH Antibody Fragments from a Transgenic Mouse," Biopharmadealmakers, accessed at www.crescendobiologics.com, p. B23, 1 page (2013).
Rudikoff, S., et al., "Single Amino Acid Substitution Altering Antigen-binding Specificity," Proc Natl Acad Sci USA 79(6):1979-1983, National Academy of Sciences, United States (Mar. 1982).
Saerens, D., et al. "Identification of a universal VHH framework to graft non-canonical antigen-binding loops of camel single-domain antibodies," Journal of Molecular Biology 352(3):597-607, Elsevier, Netherlands (2005).
Triebel, F., et al., "LAG-3, A Novel Lymphocyte Activation Gene Closely Related to CD4," The Journal of Experimental Medicine 171(5):1393-1405, Rockefeller University Press, United States (May 1990).
Trinklein, N., et al., "Abstract LB-090: Sequence-based discovery of fully human anti-CD3 and anti-PDL1 single domain antibodies using novel transgenic rats," Cancer Research 76(14):1-4, American Association of cancer Research, United States (Jul. 2016).
Tseng, S.Y., et al., "B7-DC, a New Dendritic Cell Molecule With Potent Costimulatory Properties For T Cells, " Journal of Experimental Medicine 193(7):839-846, Rockefeller University Press, United States (Apr. 2001).
Tzartos, S.J., et al., "Epitope Mapping by Antibody Competition. Methodology and Evaluation of the Validity of the Technique," from Methods in Molecular Biology 66:55-66, Humana Press, United States (1996).
UK Search Report issued in application No. GB1700207.2, dated Nov. 24, 2017, 4 pages.
UniParc, "UPI0000119BF0," accessed at https://www.uniprot.org/uniparc/UPI0000119BF0, accessed on May 16, 2022, 1 page (Mar. 2003).
UniProt, "Programmed cell death protein 1," Accession No. Q15116, accessed at https://www.uniprot.org/uniprot/Q15116, accessed on Sep. 24, 2020, 7 pages.
UniProt, "E3 ubiquitin-protein ligase CBL," Accession No. P22681, accessed at https://www.uniprot.org/uniprot/P22681, accessed on Sep. 24, 2020, 10 pages.
UniProt, "E3 ubiquitin-protein ligase CBL-B," Accession No. Q13191, accessed at https://www.uniprot.org/uniprot/Q13191, accessed on Sep. 24, 2020, 10 pages.
Wang, C., et al., "In Vitro Characterization of the Anti-PD-1 Antibody Nivolumab, BMS-936558, and in Vivo Toxicology in

(56) References Cited

OTHER PUBLICATIONS

Non-human Primates," Cancer Immunology Research 2(9):846-856, American Association for Cancer Research, United States (Sep. 2014).
Wang, W., et al., "PD1 Blockade Reverses The Suppression of Melanoma Antigen-Specific CTL by CD4+ CD25$^{Hi}$ Regulatory T Cells," International Immunology 21(9):1065-1077, Oxford University Press, United Kingdom (Sep. 2009).
Wesolowski, J., et al., "Single Domain Antibodies: Promising Experimental and Therapeutic Tools in Infection and Immunity," Medical Microbiology and Immunology, 198(3):157-174, Springer-Verlag, Germany (Aug. 2009).
Wong, Y., et al., "Structural Requirements for a Specificity Switch and for Maintenance of Affinity Using Mutational Analysis of a Phase-Displayed Anti-Arsonate Antibody of Fab Heavy Chain First Complementarily-Determining Region," Journal of Immunology, 160(12):5990-5997, American Association of immunologists, United States (Jun. 1998).
Workman, C.J., et al., "Cutting Edge: Molecular Analysis of the Negative Regulatory Function of Lymphocyte Activation Gene-3," Journal of Immunology 169(10):5392-5395, American Association of Immunologists, United States (Nov. 2002).
Xu, F., et al.," LSECtin Expressed on Melanoma Cells Promotes Tumor Progression by Inhibiting Antitumor T-cell Responses," Cancer Research 74(13):3418-3428, American Association for Cancer Research, United States (Jul. 2014).
Yokosuka, T., et al., "Programmed Cell Death 1 Forms Negative Costimulatory Microclusters that Directly Inhibit T Cell Receptor Signaling By Recruiting Phosphatase SHP2," Journal Of Experimental Medicine 209(6):1201-1217, Rockefeller University Press, United States (May 2012).
Zabetakis, et al., "Contributions of the complementarity determining regions to the thermal stability of a single-domain antibody," PLoS One 8(10): e77678, 7 pages, Public Library of Science, United States (Oct. 2013).
Zhang, X., et al., "Structural and Functional Analysis of the Costimulatory Receptor Programmed Death-1," Immunity 20(3):337-347, Cell Press, United States (Mar. 2004).
Zak, K.M., et al., "Structural basis for small molecule targeting of the programmed death ligand 1 (PD-L1)," Oncotarget 7:30323-30335, Impact Journals, United States (Apr. 2016).
Translation of Japanese Office Action dated Jul. 4, 2022, in Japanese Patent Application No. 2019-536936, filed Jan. 18, 2018, 5 pages.
Office action dated Sep. 23, 2022, in U.S. Appl. No. 16/475,590, inventor Edwards; B., et al., int'l filing date Jan. 8, 2018, 11 pages.
Co-pending U.S. Appl. No. 17/706,839, filed Mar. 29, 2022, inventor Edwards; C., et al., (Unpublished).
Barve, A., et al., "Prostate cancer relevant antigens and enzymes for targeted drug delivery," J Control Release 187:118-32, Elsevier, Netherlands (2014).
Bayachou, M., et al., "Catalytic Two-Electron Reductions of N$_2$O and N$_3^-$ by Myglobin in Surfactant Films," Inorg Chem 39:289-293, American Chemical Society, United States (2000).
Bruggemann, M., et al., "A repertoire of monoclonal antibodies with human heavy chains from transgenic mice," Proc Natl Acad Sci USA 86(17):6709-6713, National Academy of Science, United States (1989).
Bulliard, Y., et al., "OX40 engagement depletes intratumoral Tregs via activating Fc-gamma-Rs, leading to antitumor efficacy," Immunology and Cell Biology 92:475-480, Australian Society for Immunology Inc., Australia (2014).
Chalupny, N.J., et al., "T-cell activation molecule 4-1BB binds to extracellular matrix proteins," Proc Natl Acad Sci USA 89:10360-10364, National Academy of Science, United States (1992).
Chatalic, K.L.S., et al., "A Novel $^{111}$In-Labeled Anti-Prostate-Specific Membrane Antigen Nanobody for Targeted SPECT/CT Imaging of Prostate Cancer," The Journal of Nuclear Medicine 56(7):1094-1099, Society of Nuclear Medicine and Molecular Imaging, United States (2015).

Cizeau, J., et al., "Abstract 5770: Engineering and characterization of anti-PSMA humabody-deBouganin fusion proteins," Cancer Research 78(13_Suppl):5770, AACR Annual Meeting 2018 (Apr. 14-18, 2018), 2 pages, American Association for Cancer Research, United States (2018).
Chothia, C., and Lesk, A.M., "Canonical structures for the hypervariable regions of immunoglobulins," J Mol Biol 196:901-917, Academic Press Ltd., United States (1987).
Crescendo Biologics, "Humabody fragments: small and perfectly formed," CrescendoBiologics.com, accessed at https://www.crescendobiologics.com/wp-content/uploads/2016/03/20150309-Crescendo0315.pdf, accessed on Oct. 13, 2020, 2 pages.
D'Huyvetter, M., et al., "Radiolabeled nanobodies as theranostic tools in targeted radionuclide therapy of cancer," Expert Opinion on Drug Delivery 11(12):1939-1954, Taylor and Francis Ltd., United Kingdom (2014).
Dubrot, J., et al., "Treatment with anti-CD137 mAbs causes intense accumulations of liver T cells without selective antitumor immunotherapeutic effects in this organ," Cancer Immunol Immunother 59(8): 1223-1233, Springer-Verlag, Germany (2010).
Evazalipour, M., et al., "Camel heavy chain antibodies against prostate-specific membrane antigen," Hybridoma 31(6):424-429, Mary Ann Liebert Inc., United States (2012).
Evazalipour, M., et al., "Generation and characterization of nanobodies targeting PSMA for molecular imaging of prostate cancer," Contrast Media & Molecular Imaging 9(3):211-220, Hindawi Ltd., Egypt (2014).
Examination Report corresponding to European Application No. 17700734.1, dated Jul. 24, 2020, 10 pages.
Examination Report corresponding to European Application No. 17701006.3, dated Jun. 5, 2019, 6 pages.
Fan, X., et al., "Ultrasonic nanobubbles carrying anti-PSMA nanobody: construction and application in prostate cancer-targeted imaging," PLoS One 10(6):e0127419, 13 pages, Public Library of Science, United States (2015).
Fisher, T.S., et al., "Targeting of 4-1BB by monoclonal antibody PF-05082566 enhances T-cell function and promotes anti-tumor activity," Cancer Immunol Immunother 61(10):1721-1733, Springer-Verlag, Germany (2012).
Gauttier, V., et al., "Agonistic anti-CD137 antibody treatment leads to antitumor response in mice with liver cancer," International Journal of Cancer 135:2857-2867, Wiley-Liss Inc., United States (2014).
Genbank, "Homo sapiens TNF receptor superfamily member 9 (TNFRSF9), mRNA," NCBI Reference Sequence: NM_001561.6, https://www.ncbi.nlm.nih.gov/nuccore/NM_001561, last accessed on May 19, 2020, 5 pages.
Genbank, "Tumor necrosis factor receptor superfamily member 9 precursor [Homo sapiens]," NCBI Reference Sequence: NP_001552.2, https://www.ncbi.nlm.nih.gov/protein/NP_001552.2, last accessed on May 19, 2020, 4 pages.
Holliger, P., and Hudson, P.J., "Engineered antibody fragments and the rise of single domains," Nature Biotechnology 23(9):1126-1136, Nature Publishing Group, United Kingdom (2005).
Holt, L.J., et al., "Domain antibodies: proteins for therapy," Trends in Biotechnology 21(11):484-490, Elsevier Ltd., Netherlands (2003).
Holt, L.J., et al., "Anti-serum albumin domain antibodies for extending the half-lives of short lived drugs," Protein Engineering, Design & Selection 21(5):283-288, Oxford University Press, United Kingdom (2008).
Houot, R., et al., "Therapeutic effect of CD137 immunomodulation in lymphoma and its enhancement of Treg depletion," Blood 114(16):3431-3438, American Society of Hematology, United States (2009).
International Preliminary Report on Patentability for International Application No. PCT/GB2017/050074, The International Bureau of WIPO, Switzerland, dated Jul. 17, 2018, 11 pages.
International Preliminary Report on Patentability for International Application No. PCT/GB2017/050075, The International Bureau of WIPO, Switzerland, dated Jul. 17, 2018, 7 pages.
International Preliminary Report on Patentability for International Application No. PCT/GB2017/051272, The International Bureau of WIPO, Switzerland, dated Nov. 6, 2018, 7 pages.

(56) References Cited

OTHER PUBLICATIONS

International Preliminary Report on Patentability for International Application No. PCT/GB2018/051941, The International Bureau of WIPO, Switzerland, dated Jan. 14, 2020, 6 pages.
International Search Report and Written Opinion for International Application No. PCT/GB2017/050074, European Patent Office, Netherlands, dated May 30, 2017, 17 pages.
International Search Report and Written Opinion for International Application No. PCT/GB2017/050075, European Patent Office, Netherlands, dated Mar. 23, 2017, 12 pages.
International Search Report and Written Opinion for International Application No. PCT/GB2017/051272, European Patent Office, Netherlands, dated Sep. 11, 2017, 17 pages.
International Search Report and Written Opinion for International Application No. PCT/GB2018/051941, European Patent Office, Netherlands, dated Sep. 14, 2018, 11 pages.
International Search Report and Written Opinion for International Application No. PCT/GB2018/053279, European Patent Office, Netherlands, dated Feb. 1, 2019, 15 pages.
International Search Report and Written Opinion for International Application No. PCT/GB2018/053280, European Patent Office, Netherlands, dated Feb. 11, 2019, 17 pages.
Jamnani, F.R., et al., "T cells expressing VHH-directed oligoclonal chimeric HER2 antigen receptors: Towards tumor-directed oligoclonal T cell therapy," *Biochimica et Biophysica Acta* 1840(1):378-86, Elsevier, Netherlands (2014).
Kabat, E.A., and Wu, T.T., "Attempts to locate complementary-determining residues in the variable positions of light and heavy chains," *Annals of the New York Academy of Sciences* 190(1):382-393, The New York Academy of Sciences, United States (1971).
Kwon, B.S., and Weissman, S.M., "cDNA sequeneces of two inducible T-cell genes," *Proc Natl Acad Sci USA* 86:1963-1967, National Academy of Science, United States (1989).
Lefranc, M-P., et al., "IMGT unique numbering for immunoglobulin and T cell receptor constant domains and Ig superfamily C-like domains," *Developmental and Comparative Immunology* 29:185-203, Elsevier Ltd., Netherlands (2005).
Madireddi, S., et al., "Galectin-9 controls the therapeutic activity of 4-1BB-targeting antibodies," *The Journal of Experimental Medicine* 211(7):1433-1448, The Rockefeller University Press, United States (2014).
McGuinness, B., et al., "Abstract 5766: Multifunctional biologics for targeted T-cell therapy based on in vivo matured fully human VH domains," *Cancer Research* 78(13_Suppl):5766, AACR Annual Meeting 2018 (Apr. 14-18, 2018), 2 pages, American Association for Cancer Research, United States (2018).
Muyldermans, S., "Single domain camel antibodies: current status," *Reviews in Molecular Biotechnology* 74:277-302, Elsevier Science B.V., Netherlands (2001).
Ren, L., et al., "Silencing of the immunoglobulins heavy chain locus by removal of all eight constant-region genes in a 200-kb region," *Genomics* 84:686-695, Elsevier Inc., Netherlands (2004).
Roovers, R.C., et al., "A biparatopic anti-EGFR nanobody efficiently inhibits solid tumour growth," *International Journal of Cancer* 129:2013-2024, Wiley-Liss Inc., United States (2011).
Sanchez-Paulete, A.R., et al., "Deciphering CD137 (4-1BB) signaling in T-cell costimulation for translation into successful cancer immunotherapy," *European Journal of Immunology* 46:513-522, Wiley-VCH Verlag GmbH & Co. KGaA, Germany (2016).
Segal, N.H., et al., "Results from an integrated safety analysis of urelumab, an agonist anti-CD137 monoclonal antibody," *Clinical Cancer Research* 23(8):1929-1936, American Association for Cancer Research, United States (2016).
UniProtKB, "Glutamate carboxypeptidase 2," UniProtKB—Q04609 (FOLH1_Human), https://www.uniprot.org/uniprot/Q04609, last accessed on May 19, 2020, 24 pages.
UniProtKB, "Tumor necrosis factor receptor superfamily member 9," UniProtKB—Q07011 (TNR9_Human), https://www.uniprot.org/uniprot/Q07011, last accessed on May 19, 2020, 12 pages.

Vinay, D.S., and Kwon, B.S., "Immunotherapy of cancer with 4-1BB," *Molecular Cancer Therapeutics* 11(5):1062-1070, American Association for Cancer Research, United States (2012).
Vinay, D.S., and Kwon, B.S., "4-1BB (CD137), an inducible costimulatory receptor, as a specific target for cancer therapy," *BMB Reports* 47(3):122-129, The Korean Society for Biochemistry and Molecular Biology, South Korea (2014).
Vinay, D.S., and Kwon, B.S., "Therapeutic potential of anti-CD137 (4-1BB) monoclonal antibodies, " *Expert Opinion on Therapeutic Targets* 20(3):361-373, Taylor & Francis Group, United Kingdom (2015).
Viuff, D., et al., "Generation of a double transgenic humanized neonatal Fc receptor (FcRn)/albumin mouse to study the pharmokinetics of albumin-linked drugs," *Journal of Controlled Release* 223:22-30, Elsevier B.V., Netherlands (2016).
Ward, E.S., et al., "Binding activities of a repertoire of single immunoglobulin variable domains secreted from *Escherichia coli*," *Nature* 341:544-546, Nature Publishing Group, United Kingdom (1989).
Zare, H., et al., "Production of nanobodies against prostate-specific membrane antigen (PSMA) recognizing LnCaP cells," *Int J Biol Markers* 29(2):e169-79, 12 pages, Sage Publications, United States (2014).
Zou, X., et al., "Block in development at the pre-B-II to immature B cell stage in mice without Ig kappa and Ig lambda light chain," *The Journal of Immunology* 170:1354-1361, The American Association of Immunologists, Inc., United States (2003).
Co-pending Application, U.S. Appl. No. 16/763,063, inventors Brucklacher-Waldert, V., et al., Int'l Filing Date: Nov. 13, 2018 (unpublished).
Co-pending Application, U.S. Appl. No. 16/069,497, inventors Balloi, E., et al., filed Jul. 11, 2018 (unpublished).
Bahara, N. H. H., et al., "Construction of a Semisynthetic Human VH Single-Domain Antibody Library and Selection of Domain Antibodies against α-Crystalline of *Mycobacterium tuberculosis*," *Journal of Biomolecular Screening* 21(1):35-43, Sage Publications Inc., United States (Jan. 2016).
Bruschi, C. V., and Gjuracic, K., "Yeast Artificial Chromosomes" in the Encyclopedia of Life Sciences, pp. 1-6, Macmillan Publishers Ltd., United Kingdom (2002).
Chen, L., et al., "Epitope-directed antibody selection by site-specific photocrosslinking," *Science Advances* 6(14):eaaz7825, pp. 1-9, American Association for the Advancement of Science, United States (Apr. 2020).
Elsadek, B., and Kratz, F., "Impact of Albumin on Drug Delivery-New Applications on the Horizon," Journal of Controlled Release 157(1):4-28, Elsevier Science Publishers, Netherlands (published online Sep. 2011, published in print Jan. 2012).
International Search Report and Written Opinion for International Application No. PCT/GB2019/053220, dated Apr. 3, 2020, European Patent Office, Netherlands, 17 pages.
Marks, J. D., and Bradbury, A., "Chapter 8: Selection of Human Antibodies from Phage Display Libraries" in *Methods in Molecular Biology, Antibody Engineering: Methods and Protocols*, vol. 248, Lo, B., ed., pp. 161-176, Humana Press, United States (2004).
Strohl, W. R., "Fusion Proteins for Half-Life Extension of Biologics as a Strategy to Make Biobetters," *BioDrugs* 29(4):215-239, Springer, United States (Jul. 2015).
Vincke, C., et al., "Introduction to heavy chain antibodies and derived Nanobodies," in *Single Domain Antibodies, Methods in Molecular Biology* vol. 911, Saerens, D. and Muyldermans, S., eds., pp. 15-26, Humana Press, United States (Jul. 2012).
Bander, N.H., et al., "Targeted systemic therapy of prostate cancer with a monoclonal antibody to prostate-specific membrane antigen," *Seminars in Oncology* 30(5):667-677, W.B. Saunders Ltd., United Kingdom (2003).
Office Action dated Aug. 11, 2020, in U.S. Appl. No. 16/069,495, Balloi, E., et al., filed Jul. 11, 2018, 18 pages.
Vinay, D.S., and Kwon, B.S., "Role of 4-1BB in immune responses," *Seminars in Immunology* 10(6):481-489, Academic Press Inc., United States (1998).

(56) References Cited

OTHER PUBLICATIONS

Zapata, J.M., et al., "CD137 (4-1BB) Signalosome: Complexity Is a Matter of TRAFs," *Frontiers in Immunology* 9:2618, 12 pages, Frontiers Media S.A., Switzerland (Nov. 2018).
Communication under Rule 164(2)(a) EPC for European Application No. 17 724 869.7, dated Dec. 4, 2019, 6 pages.
Conrath, K. E., et al., "Camel single-domain antibodies as modular building units in bispecific and bivalent antibody constructs," *Journal of Biological Chemistry* 276(10):7346-7350, The American Society of Biochemistry and Molecular Biology, Inc., United States (2001).
Guo, Y., et al., "Chimeric Antigen Receptor-Modified T Cells for Solid Tumors: Challenges and Prospects," *Journal of Immunology Research* 2016:3850839, 11 pages, Hindawi Ltd., Egypt (2016).
Office Action for Japanese Patent Application No. 2018-537519, dated Feb. 5, 2021, Japan Patent Office, Japan, 9 pages.
Office Action for Japanese Patent Application No. 2018-537533, dated Feb. 16, 2021, Japan Patent Office, Japan, 6 pages.
Vincke, C., et al., "General strategy to humanize a camelid single-domain antibody and identification of a universal humanized nanobody scaffold," *Journal of Biological Chemistry* 284(5):3273-3284, The American Society of Biochemistry and Molecular Biology, Inc., United States (2009).
International Search Report and Written Opinion in International Application No. PCT/GB2020/051199, dated Aug. 20, 2020, European Patent Office, Netherlands, 13 pages.
Legg, J.W., et al., "CB307: A novel T-cell costimulatory Humabody® VH therapeutic for PSMA-positive tumors," presented at PEGS Boston, Apr. 2019, retrieved from: https://www.crescendobiologics.com/wp-content/uploads/2019/08/20190412-CB307-A-novel-T-cell-costimulatory-Humabody®-VH-therapeutic-for-PSMA-positive-tumors.pdf, 1 page.
Henry, K., et al., "Identification of cross-reactive single-domain antibodies against serum albumin using next-generation DNA sequencing," Protein Eng. Design Selection 28(10):379-383, Oxford Academic, England (2015).
Chen, C., et al., "Enhancement and destruction of antibody function by somatic mutation: unequal occurrence is controlled by V gene combinatorial associations," EMBO J 14(12):2784-2794, European Molecular Biology Organization Press, Germany (Jun. 1995).
Hawkey, N.M., et al., "Prostate-specific Membrane Antigen-targeted Theranostics: Past, Present, and Future Approaches," Clinical Advances in Hematology & Oncology 20(4):227-238, Millennium Medical Pub, United States (Apr. 2022).
Office Action dated Nov. 1, 2022, in Japanese Patent Application No. 2020-526175, filed Nov. 13, 2018, Japan Patent Office, Japan, 14 pages.
Office Action dated Nov. 1, 2022, in Japanese Patent Application No. 2020-526245, filed Jun. 29, 2018, Japan Patent Office, Japan, 12 pages.
Office Action dated Oct. 19, 2022, in U.S. Appl. No. 16/969,905, inventors Edwards, C., et al., 371(c) filed Aug. 13, 2020, 17 pages.
Reeck, G. R., et al., "'Homology' in Proteins and Nucleic Acids: A Terminology Muddle and a Way out of It," Cell 50:667, Cell Press, United States (Aug. 1987).
Steven, J., et al., "In Vitro Maturation of a Humanized Shark VNAR Domain to Improve Its Biophysical Properties to Facilitate Clinical Development," Front Immunol 8: Article 1361, pp. 1-15, Frontiers Media S.A., Switzerland (Oct. 2017).
Yan, J., et al., "Construction of a synthetic phage-displayed Nanobody library with CDR3 regions randomized by trinucleotide cassettes for diagnostic applications," J Transl Med 12:343, pp. 1-12, BioMed Central Ltd., United Kingdom (Dec. 2014).
Abdiche, Y.N., et al., "Assessing Kinetic and Epitopic Diversity Across Orthogonal Monoclonal Antibody Generation Platforms," mAbs, 8(2):264-277, Taylor & Francis Group, United States (Feb. 2016).
Boyd, S.D., et al., "Deep Sequencing and Human Antibody Repertoire Analysis," Current Opinion in Immunology 40:103-109, Elsevier, Netherlands (Apr. 2016).
Casset, F., et al., "A Peptide Mimetic of an Anti-CD4 Monoclonal Antibody By Rational Design," Biochemical and Biophysical Research Communications 307(1):198-205, Academic Press, United States (Jul. 2003).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, United Kingdom (Nov. 1999).
Conroy, P.J., et al., "Antibodies: From Novel Repertoires to Defining and Refining the Structure Of Biologically Important Targets," Methods 116:12-22, Elsevier, Netherlands (Jan. 2017).
Damschroder, M.M., et al., "Analysis of Human and Primate CD2 Molecules by Protein sequence and Epitope mapping with Anti-Human CD2 Antibodies," Molecular Immunology 41:985-1000, Elsevier, Netherlands (Jun. 2004).
De Pascalis, R., et al., "Grafting of 'Abbreviated' Complementarity-determining Regions Containing Specificity-determining Residues Essential for Ligand Contact to Engineer a Less Immunogenic Humanized Monoclonal Antibody," Journal of Immunology 169(6):3076-3084, The American Association of Immunologists, United States (Sep. 2002).
Ferrara, F., et al., "Recombinant Renewable Polyclonal Antibodies," mAbs 7(1):32-41, Taylor & Francis Group, United States (Dec. 2014).
Kanyavuz, A., et al., "Breaking the Law: Unconventional Strategies for Antibody Diversification," Nature Reviews: Immunology 19:355-368, Nature Reviews, United Kingdom (Jun. 2019).
Khan, L., et al., "Cross-neutralizing Anti-HIV-1 Human Single Chain Variable Fragments (scFvs) Against CD4 Binding Site and N332 Glycan Identified From a Recombinant Phage Library," Scientific Reports 7:45163, 12 pages, Nature Publishing Group, United Kingdom (Mar. 2017).
Konitzer, J.D., et al., "Generation of a Highly Diverse Panel of Antagonistic Chicken Monoclonal Antibodies Against the GIP Receptor," mAbs 9(3):536-549, Taylor & Francis Group, United States (Feb. 2017).
Lamminmäki, U. and Kankare, J.A., "Crystal Structure of a Recombinant Anti-estradiol Fab Fragment in Complex With 17beta-estradiol," The Journal of Biological Chemistry 276(39):36687-36694, Elsevier Inc., United States (Sep. 2001).
Lee, J., et al., "Molecular-level Analysis of the Serum Antibody Repertoire In Young Adults Before and After Seasonal Influenza Vaccination," Nature Medicine 22(12):1456-1464, with Supplemental Methods and Data, Nature Publishing Group, United Kingdom (Nov. 2016).
Maccallum, R. M., et al., "Antibody-antigen Interactions: Contact Analysis and Binding Site Topography," Journal of Molecular Biology 262(5):732-745, Academic Press, United Kingdom (Oct. 1996).
Office Action dated Apr. 10, 2023, in U.S. Appl. No. 16/099,099, inventors McGuinness, B., et al., 371(c) filed Nov. 5, 2018, 10 pages.
Office Action dated Apr. 25, 2023, in U.S. Appl. No. 16/763,063, inventors Brucklacher-Waldert, V., et al., 371(c) filed May 11, 2020, 11 pages.
Padlan, E. A., et al., "Structure of an Antibody-antigen Complex: Crystal Structure of the HyHEL-10 Fab-lysozyme Complex," Proceedings of the National Academy of Sciences of the United States of America 86(15):5938-5942, National Academy of Sciences, United States (Aug. 1989).
Parola, C., et al., "Integrating High-throughput Screening and Sequencing for Monoclonal Antibody Discovery and Engineering," Immunology 153:31-41, John Wiley & Sons Ltd., United States (Sep. 2017).
Sheehan, J., et al., "Phage and Yeast Display," Microbiology Spectrum 3(1):1-17, American Society for Microbiology Press, United States (Feb. 2015).
Van Regenmortel, M.H.V., "Development of a Preventive HIV Vaccine Requires Solving Inverse Problems Which Is Unattainable by Rational Vaccine Design," Hypothesis and Theory 8: Article 2009, 11 pages, Frontiers in Immunology, United Kingdom (Jan. 2018).

(56) References Cited

OTHER PUBLICATIONS

Wu, H., et al., "Humanization of a Murine Monoclonal Antibody by Simultaneous Optimization of Framework and CDR Residues," Journal of Molecular Biology 294(1):151-162, Elsevier, United Kingdom (Nov. 1999).

Zhou, T., et al., "Structural Repertoire of HIV-1-Neutralizing Antibodies Targeting the CD4 Supersite in 14 Donors," with Supplemental Information, Figures, Methods, and References, Cell 161:1280-1292, Elsevier, Netherlands (Jun. 2015).

Office action dated Feb. 23, 2023, in U.S. Appl. No. 16/475,590, inventors Edwards, B., et al., 371(c) filed Jul. 2, 2019, 9 pages.

Office action dated Apr. 11, 2023, in U.S. Appl. No. 16/969,905, inventors Edwards, C., et al., 371(c) filed Aug. 13, 2020, 9 pages.

Co-Pending U.S. Appl. No. 18/167,318, filed Feb. 10, 2023, inventor Hayes, P. et al. (Unpublished).

Office Action dated Jun. 9, 2023, for Japanese Patent Application No. 2020-526245, 6 pages.

Chinese Office Action dated May 27, 2023, in Chinese Patent Application No. 2019800881645, filed Nov. 13, 2019, 15 pages.

GenBank, "Immunoglobulin G heavy chain variable region, partial [*Homo sapiens*]," Accession No. AEX29928.1, accessed at https://www.ncbi.nlm.nih.gov/protein/AEX29928.1, accessed on Jan. 10, 2014, 2 pages.

GenBank, "Immunoglobulin heavy chain variable region, partial [*Homo sapiens*]," Accession No. ACS95976.1, accessed at https://www.ncbi.nlm.nih.gov/protein/ACS95976.1, accessed on Jul. 24, 2016, 2 pages.

Japanese Office Action dated May 26, 2023, in Japanese Patent Application No. 2021-211614, filed Dec. 24, 2021, 6 pages.

Co-Pending U.S. Appl. No. 18/343,126, filed Jun. 28, 2023, inventor McGuinness, et al. (Unpublished).

\* cited by examiner

F

G

SEQUENCE LISTING

```
<160> NUMBER OF SEQ ID NOS: 902

<210> SEQ ID NO 1
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO: 4

<400> SEQUENCE: 1

Ser His Trp Met Thr
1               5

<210> SEQ ID NO 2
<211> LENGTH: 17
<212> TYPE: PRT
<213> ORGANISM: Homo sapiens
<220> FEATURE:
```

```
<221> NAME/KEY: MISC_FEATURE
<222> LOCATION: (1)..(17)
<223> OTHER INFORMATION: CRD2 of SEQ ID NO: 4

<400> SEQUENCE: 2

His Ile Lys Glu Asp Gly Ser Glu Lys Tyr Tyr Glu Asp Ser Val Glu
1               5                   10                  15

Gly

<210> SEQ ID NO 3
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CRD3 of SEQ ID NO: 4

<400> SEQUENCE: 3

Gly Gly Asp Gly Tyr Ser Asp Ser His Phe Gly Val Asp Val
1               5                   10

<210> SEQ ID NO 4
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds CD137

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Glu Asp Ser Val
    50                  55                  60

Glu Gly Arg Phe Thr Val Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 5
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO: 8

<400> SEQUENCE: 5

Ser Tyr Trp Met Thr
1               5

<210> SEQ ID NO 6
```

```
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO: 8

<400> SEQUENCE: 6

His Ile Lys Glu Asp Gly Ser Glu Lys Tyr Tyr Val Asp Ser Val
1               5                   10                  15

Gly

<210> SEQ ID NO 7
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 of SEQ ID NO: 8

<400> SEQUENCE: 7

Gly Gly Asp Gly Tyr Ser Asp Ser His Tyr Gly Val Asp Val
1               5                   10

<210> SEQ ID NO 8
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds CD137

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Val Asp Ser Val
    50                  55                  60

Glu Gly Arg Phe Thr Ile Ser Arg Asp Asn Ala Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Tyr Gly Val Asp Val
            100                 105                 110

Trp Gly Gln Gly Thr Thr Val Thr Val Ser Ser
        115                 120

<210> SEQ ID NO 9
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR 1 of SEQ ID NO 12
```

<400> SEQUENCE: 9

Ser Tyr Trp Met Thr
1               5

<210> SEQ ID NO 10
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO: 12

<400> SEQUENCE: 10

Asn Ile Asn Gln Asp Gly Ser Glu Lys Tyr Tyr Val Asp Ser Val Glu
1               5                   10                  15

Gly

<210> SEQ ID NO 11
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR 3 of SEQ ID NO: 12

<400> SEQUENCE: 11

Gly Gly Leu Gly Tyr Gly Asp Ser His Tyr Gly Met Asp Val
1               5                   10

<210> SEQ ID NO 12
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Phe Arg Gln Ala Pro Gly Arg Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Gly Tyr Gly Asp Ser His Tyr Gly Met Asp Val
            100                 105                 110

Trp Gly Gln Gly Thr Thr Val Thr Val Ser Ser
        115                 120

<210> SEQ ID NO 13
<211> LENGTH: 5
<212> TYPE: PRT
<213> ORGANISM: Homo sapiens

```
<220> FEATURE:
<221> NAME/KEY: MISC_FEATURE
<222> LOCATION: (1)..(5)
<223> OTHER INFORMATION: CDR 1 of SEQ ID NO. 16

<400> SEQUENCE: 13

Asn Tyr Trp Met Thr
1               5

<210> SEQ ID NO 14
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CRD2 OF SEQ ID NO. 16

<400> SEQUENCE: 14

Asn Ile Asn Gln Asp Gly Ser Glu Lys Tyr Tyr Val Asp Ser Val Glu
1               5                   10                  15

Gly

<210> SEQ ID NO 15
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO.16

<400> SEQUENCE: 15

Gly Gly Leu Gly Tyr Gly Asp Ser His Tyr Gly Met Asp Val
1               5                   10

<210> SEQ ID NO 16
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Met Thr Trp Phe Arg Gln Ala Pro Gly Gly Gly Leu Glu Trp Val
            35                  40                  45

Ala Asn Ile Asn Gln Asp Gly Ser Glu Lys Tyr Tyr Val Asp Ser Val
        50                  55                  60

Glu Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Gly Tyr Gly Asp Ser His Tyr Gly Met Asp Val
            100                 105                 110

Trp Gly Gln Gly Thr Thr Val Thr Val Ser Ser
        115                 120
```

```
<210> SEQ ID NO 17
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 20

<400> SEQUENCE: 17

Asn Tyr Trp Met Ile
1               5

<210> SEQ ID NO 18
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO:20

<400> SEQUENCE: 18

Asn Ile Asn Gln Asp Gly Ser Glu Lys Tyr Tyr Val Asp Ser Val Glu
1               5                   10                  15

Gly

<210> SEQ ID NO 19
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CRD3 OF SEQ ID NO:20

<400> SEQUENCE: 19

Gly Gly Asp Gly Tyr Ser Gly Ser His His Gly Thr Asp Val
1               5                   10

<210> SEQ ID NO 20
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ile Trp Phe Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Gly Ser His His Gly Thr Asp Val
            100                 105                 110
```

```
Trp Gly Gln Gly Thr Thr Val Thr Val Ser Ser
        115                 120
```

<210> SEQ ID NO 21
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR 1 OF SEQ ID NO: 24

<400> SEQUENCE: 21

```
Ser Tyr Trp Met Ser
1               5
```

<210> SEQ ID NO 22
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO:24

<400> SEQUENCE: 22

```
Asn Ile Lys Gln Asp Gly Ser Glu Lys Tyr Tyr Val Asp Ser Val Lys
1               5                   10                  15

Gly
```

<210> SEQ ID NO 23
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO:24

<400> SEQUENCE: 23

```
Gly Gly Glu Gly Tyr Ser Thr Ser His Tyr Gly Met Asp Val
1               5                   10
```

<210> SEQ ID NO 24
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Gly Gly Glu Gly Tyr Ser Thr Ser His Tyr Gly Met Asp Val
            100                 105                 110

Trp Gly Gln Gly Thr Thr Val Thr Val Ser Ser
        115                 120

<210> SEQ ID NO 25
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR 1 of SEQ ID NO: 28

<400> SEQUENCE: 25

Ser Tyr Trp Met Leu
1               5

<210> SEQ ID NO 26
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 28

<400> SEQUENCE: 26

Asn Ile Asn Gln Asp Gly Ser Glu Lys Tyr Tyr Val Asp Ser Val Lys
1               5                   10                  15

Gly

<210> SEQ ID NO 27
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 28

<400> SEQUENCE: 27

Gly Gly Asp Gly Tyr Ser Asp Ser His Phe Gly Thr Asp Val
1               5                   10

<210> SEQ ID NO 28
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Ser Tyr
            20                  25                  30

Trp Met Leu Trp Phe Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Thr Leu Arg Ala Glu Asp Thr Ala Ile Tyr Tyr Cys
                 85                  90                  95

Ala Arg Gly Gly Asp Gly Tyr Ser Asp Ser His Phe Gly Thr Asp Val
            100                 105                 110

Trp Gly Gln Gly Thr Thr Val Thr Val Ser Ser
        115                 120

<210> SEQ ID NO 29
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 32

<400> SEQUENCE: 29

Ser Tyr Trp Met Phe
1               5

<210> SEQ ID NO 30
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO:32

<400> SEQUENCE: 30

Asn Ile Asn Gln Asp Gly Ser Glu Lys Tyr Tyr Val Asp Ser Val Glu
1               5                   10                  15

Gly

<210> SEQ ID NO 31
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO:32

<400> SEQUENCE: 31

Gly Gly Asp Gly Tyr Ser Asp Ser His Tyr Gly Thr Asp Val
1               5                   10

<210> SEQ ID NO 32
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds CD137

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Ser Tyr
            20                  25                  30
```

```
Trp Met Phe Trp Phe Arg Gln Ala Pro Gly Glu Gly Leu Glu Trp Val
            35                  40                  45

Ala Asn Ile Asn Gln Asp Gly Ser Glu Lys Tyr Tyr Val Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Ile Tyr Tyr Cys
                 85                  90                  95

Ala Arg Gly Gly Asp Gly Tyr Ser Asp Ser His Tyr Gly Thr Asp Val
                100                 105                 110

Trp Gly Gln Gly Thr Thr Val Thr Val Ser Ser
        115                 120
```

<210> SEQ ID NO 33
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 36

<400> SEQUENCE: 33

```
Asn Tyr Trp Met Thr
 1               5
```

<210> SEQ ID NO 34
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 36

<400> SEQUENCE: 34

```
Asn Ile Asn Gln Asp Gly Ser Glu Lys Tyr Tyr Val Asp Ser Val Glu
 1               5                  10                  15

Gly
```

<210> SEQ ID NO 35
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 36

<400> SEQUENCE: 35

```
Gly Gly Leu Gly Tyr Gly Asp Ser His Tyr Gly Met Asp Val
 1               5                  10
```

<210> SEQ ID NO 36
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Phe Arg Gln Ala Pro Gly Gly Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Val Ser Arg Asp Asn Ala Lys Asn Ser Leu Asp
65                  70                  75                  80

Leu Gln Met Asn Ser Leu Arg Ala Glu Asp Thr Ala Val Tyr Tyr Cys
                85                  90                  95

Ala Arg Gly Gly Leu Gly Tyr Gly Asp Ser His Tyr Gly Met Asp Val
            100                 105                 110

Trp Gly Gln Gly Thr Thr Val Thr Val Ser Ser
        115                 120

<210> SEQ ID NO 37
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 40

<400> SEQUENCE: 37

Asp Tyr Trp Met Asn
1               5

<210> SEQ ID NO 38
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 40

<400> SEQUENCE: 38

Asn Ile Lys Glu Asp Gly Ser Glu Lys Tyr Tyr Val Asp Ser Val Glu
1               5                   10                  15

Gly

<210> SEQ ID NO 39
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 40

<400> SEQUENCE: 39

Gly Gly Ala Gly Tyr Ser Met Ser His Tyr Gly Met Asp Val
1               5                   10

<210> SEQ ID NO 40
<211> LENGTH: 123
<212> TYPE: PRT
<213> ORGANISM: Homo sapiens

```
<220> FEATURE:
<221> NAME/KEY: MISC_FEATURE
<222> LOCATION: (1)..(123)
<223> OTHER INFORMATION: VH that binds CD137

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Ala Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Glu Gly Arg Phe Thr Ile Ser Arg Asp Asn Ala Lys Asn Ser Thr Tyr
65                  70                  75                  80

Leu Gln Met Asn Ser Leu Arg Val Glu Asp Thr Ala Val Tyr Tyr Cys
                85                  90                  95

Ala Arg Gly Gly Ala Gly Tyr Ser Met Ser His Tyr Gly Met Asp Val
            100                 105                 110

Trp Gly Gln Gly Thr Thr Val Thr Val Ser Ser
        115                 120

<210> SEQ ID NO 41
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 44

<400> SEQUENCE: 41

Asp Tyr Trp Met Asn
1               5

<210> SEQ ID NO 42
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 44

<400> SEQUENCE: 42

Asn Ile Lys Glu Asp Gly Ser Glu Lys Tyr Tyr Val Asp Ser Val Glu
1               5                   10                  15

Gly

<210> SEQ ID NO 43
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 44

<400> SEQUENCE: 43

Gly Gly Ala Gly Tyr Ser Met Ser His Tyr Gly Met Asp Val
1               5                   10
```

```
<210> SEQ ID NO 44
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Ser Asp Tyr
            20                  25                  30

Trp Met Asn Trp Ala Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Glu Gly Arg Phe Thr Ile Ser Arg Asp Asn Ala Lys Asn Ser Thr Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Tyr Ser Met Ser His Tyr Gly Met Asp Val
            100                 105                 110

Trp Gly Gln Gly Thr Thr Val Thr Val Ser Ser
        115                 120

<210> SEQ ID NO 45
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 48

<400> SEQUENCE: 45

Ser Tyr Trp Met Leu
1               5

<210> SEQ ID NO 46
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 48

<400> SEQUENCE: 46

Asn Ile Asn Gln Asp Gly Ser Glu Lys Tyr Tyr Val Asp Ser Val Lys
1               5                   10                  15

Gly

<210> SEQ ID NO 47
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 48
```

<400> SEQUENCE: 47

Gly Gly Asp Gly Tyr Ser Asn Ser His Phe Gly Thr Asp Val
1               5                   10

<210> SEQ ID NO 48
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Ser Tyr
            20                  25                  30

Trp Met Leu Trp Phe Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Thr Leu Arg Ala Glu Asp Thr Ala Ile Tyr Tyr Cys
                85                  90                  95

Ala Arg Gly Gly Asp Gly Tyr Ser Asn Ser His Phe Gly Thr Asp Val
            100                 105                 110

Trp Gly Gln Gly Thr Thr Val Thr Val Ser Ser
        115                 120

<210> SEQ ID NO 49
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 52

<400> SEQUENCE: 49

Ser Tyr Trp Met Phe
1               5

<210> SEQ ID NO 50
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 52

<400> SEQUENCE: 50

Asn Ile Asn Gln Asp Gly Ser Glu Lys Tyr Tyr Val Asp Ser Val Glu
1               5                   10                  15

Gly

<210> SEQ ID NO 51
<211> LENGTH: 14
<212> TYPE: PRT
<213> ORGANISM: Homo sapiens

```
<220> FEATURE:
<221> NAME/KEY: MISC_FEATURE
<222> LOCATION: (1)..(14)
<223> OTHER INFORMATION: CDR3 OF SEQ ID NO: 52

<400> SEQUENCE: 51

Gly Gly Asp Gly Tyr Ser Asp Ser His Tyr Gly Thr Asp Val
1               5                   10

<210> SEQ ID NO 52
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 52

Glu Val Gln Leu Val Glu Ser Gly Gly Gly Leu Val Lys Pro Gly Gly
1               5                   10                  15

Ser Leu Arg Leu Ser Cys Gly Ala Ser Gly Phe Thr Phe Ser Ser Tyr
            20                  25                  30

Trp Met Phe Trp Phe Arg Gln Ala Pro Gly Glu Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Asp Gly Tyr Ser Asp Ser His Tyr Gly Thr Asp Val
            100                 105                 110

Trp Gly Gln Gly Thr Thr Val Thr Val Ser Ser
        115                 120

<210> SEQ ID NO 53
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 56

<400> SEQUENCE: 53

Asn Tyr Trp Met Asn
1               5

<210> SEQ ID NO 54
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 56

<400> SEQUENCE: 54

Asn Ile Lys Glu Asp Gly Ser Glu Asn Tyr Tyr Val Asp Ser Val Lys
1               5                   10                  15

Gly
```

```
<210> SEQ ID NO 55
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 56

<400> SEQUENCE: 55

Gly Gly Glu Gly Tyr Ser Thr Ser His Tyr Gly Met Asp Val
 1               5                  10

<210> SEQ ID NO 56
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 56

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Ser Glu Asn Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Ser Thr Ser His Tyr Gly Met Asp Val
            100                 105                 110

Trp Gly Gln Gly Thr Thr Val Thr Val Ser Ser
        115                 120

<210> SEQ ID NO 57
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 60

<400> SEQUENCE: 57

Thr Tyr Trp Met Leu
 1               5

<210> SEQ ID NO 58
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 60
```

<400> SEQUENCE: 58

Asn Ile Asn Gln Asp Gly Ser Glu Lys Tyr Tyr Val Asp Ser Val Lys
1               5                   10                  15

Gly

<210> SEQ ID NO 59
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 60

<400> SEQUENCE: 59

Gly Gly Asp Gly Tyr Ser Asp Ser His Phe Gly Thr Asp Val
1               5                   10

<210> SEQ ID NO 60
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 60

Glu Val Gln Leu Val Glu Ser Gly Gly Leu Val Gln Pro Gly Gly
1               5                   10                  15

Ser Leu Arg Leu Ser Cys Gly Ala Ser Gly Phe Thr Phe Ser Thr Tyr
                20                  25                  30

Trp Met Leu Trp Phe Arg Gln Ala Pro Gly Lys Gly Leu Glu Trp Val
            35                  40                  45

Ala Asn Ile Asn Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Ser
65                  70                  75                  80

Leu Gln Met Asn Ser Leu Arg Ala Glu Asp Thr Ala Thr Tyr Tyr Cys
                85                  90                  95

Ala Arg Gly Gly Asp Gly Tyr Ser Asp Ser His Phe Gly Thr Asp Val
            100                 105                 110

Trp Gly Gln Gly Thr Thr Val Thr Val Ser Ser
        115                 120

<210> SEQ ID NO 61
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 64

<400> SEQUENCE: 61

Asn Tyr Trp Met Met
1               5

<210> SEQ ID NO 62
<211> LENGTH: 17
<212> TYPE: PRT
<213> ORGANISM: Homo sapiens

```
<220> FEATURE:
<221> NAME/KEY: MISC_FEATURE
<222> LOCATION: (1)..(17)
<223> OTHER INFORMATION: CDR2 OF SEQ ID NO: 64

<400> SEQUENCE: 62

Asn Ile Asn Gln Asp Gly Ser Glu Lys Tyr Phe Val Asp Ser Val Glu
1               5                   10                  15

Gly

<210> SEQ ID NO 63
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 64

<400> SEQUENCE: 63

Gly Gly Asp Gly Tyr Ser Ser Ser His Tyr Gly Thr Asp Val
1               5                   10

<210> SEQ ID NO 64
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
                20                  25                  30

Trp Met Met Trp Phe Arg Gln Ala Pro Gly Lys Gly Leu Glu Trp Val
            35                  40                  45

Ala Asn Ile Asn Gln Asp Gly Ser Glu Lys Tyr Phe Val Asp Ser Val
        50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Ser Ser His Tyr Gly Thr Asp Val
            100                 105                 110

Trp Gly Gln Gly Thr Thr Val Thr Val Ser Ser
        115                 120

<210> SEQ ID NO 65
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 68

<400> SEQUENCE: 65

Ser Tyr Trp Met Asn
1               5
```

```
<210> SEQ ID NO 66
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 68

<400> SEQUENCE: 66

Asn Ile Lys Glu Asp Gly Ser Glu Lys Tyr Tyr Val Asp Ser Val Lys
1               5                   10                  15
Gly

<210> SEQ ID NO 67
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 68

<400> SEQUENCE: 67

Gly Gly Asp Ser Tyr Gly Tyr Arg Asp Tyr Gly Met Asp Val
1               5                   10

<210> SEQ ID NO 68
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ser Tyr Gly Tyr Arg Asp Tyr Gly Met Asp Val
            100                 105                 110

Trp Gly Gln Gly Thr Thr Val Thr Val Ser Ser
        115                 120

<210> SEQ ID NO 69
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 72
```

```
<400> SEQUENCE: 69

Thr His Trp Met Asn
1               5

<210> SEQ ID NO 70
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR 2 OF SEQ ID NO: 72

<400> SEQUENCE: 70

Asn Ile Asn Gln Asp Gly Ser Glu Lys Tyr Tyr Val Asp Ser Val Glu
1               5                   10                  15

Gly

<210> SEQ ID NO 71
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 72

<400> SEQUENCE: 71

Gly Gly Val Gly Tyr Gly Asp Ser His Phe Gly Met Asp Val
1               5                   10

<210> SEQ ID NO 72
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr His
            20                  25                  30

Trp Met Asn Trp Ala Arg Gln Ala Pro Gly Lys Glu Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Asn Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Val Gly Tyr Gly Asp Ser His Phe Gly Met Asp Val
            100                 105                 110

Trp Gly Leu Gly Thr Thr Val Thr Val Ser Ser
        115                 120

<210> SEQ ID NO 73
<211> LENGTH: 5
<212> TYPE: PRT
<213> ORGANISM: Homo sapiens
```

-continued

```
<220> FEATURE:
<221> NAME/KEY: MISC_FEATURE
<222> LOCATION: (1)..(5)
<223> OTHER INFORMATION: CDR1 OF SEQ ID NO: 76

<400> SEQUENCE: 73

Ser Tyr Trp Met Ile
1               5

<210> SEQ ID NO 74
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 76

<400> SEQUENCE: 74

Asn Ile Asn Gln Asp Gly Ser Glu Lys Tyr Tyr Val Asp Ser Val Lys
1               5                   10                  15
Gly

<210> SEQ ID NO 75
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 76

<400> SEQUENCE: 75

Gly Gly Asp Asp Tyr Ser Asn Ser His Tyr Gly Met Asp Val
1               5                   10

<210> SEQ ID NO 76
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ile Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Asp Tyr Ser Asn Ser His Tyr Gly Met Asp Val
            100                 105                 110

Ser Gly Gln Gly Thr Thr Val Thr Val Ser Ser
        115                 120
```

-continued

```
<210> SEQ ID NO 77
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 80

<400> SEQUENCE: 77

Ser Tyr Trp Met Asn
1               5

<210> SEQ ID NO 78
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 80

<400> SEQUENCE: 78

Asn Ile Asn Gln Asp Gly Ser Glu Lys Tyr Tyr Val Asp Ser Val Gln
1               5                   10                  15

Gly

<210> SEQ ID NO 79
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 80

<400> SEQUENCE: 79

Gly Gly Phe Gly Tyr Gly Asp Ser His Tyr Gly Met Asp Val
1               5                   10

<210> SEQ ID NO 80
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds CD137

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Asn Trp Val Arg Gln Ala Pro Gly Lys Gly Leu Glu Trp Val
            35                  40                  45

Ala Asn Ile Asn Gln Asp Gly Ser Glu Lys Tyr Tyr Val Asp Ser Val
        50                  55                  60

Gln Gly Arg Phe Thr Ile Ser Arg Asp Asn Ala Asn Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Phe Gly Tyr Gly Asp Ser His Tyr Gly Met Asp Val
            100                 105                 110
```

```
Trp Gly Gln Gly Thr Thr Val Thr Val Ser Ser
            115                 120
```

<210> SEQ ID NO 81
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 84

<400> SEQUENCE: 81

```
Ser Tyr Trp Met Phe
1               5
```

<210> SEQ ID NO 82
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 84

<400> SEQUENCE: 82

```
Asn Val Asn Gln Asp Gly Ser Glu Lys Tyr Tyr Val Asp Ser Val Glu
1               5                   10                  15

Gly
```

<210> SEQ ID NO 83
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 84

<400> SEQUENCE: 83

```
Gly Gly Glu Gly Tyr Ser Asp Ser His Tyr Gly Thr Asp Val
1               5                   10
```

<210> SEQ ID NO 84
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds CD137

<400> SEQUENCE: 84

```
Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Ser Tyr
            20                  25                  30

Trp Met Phe Trp Phe Arg Gln Ala Pro Gly Lys Glu Leu Glu Trp Val
        35                  40                  45

Ala Asn Val Asn Gln Asp Gly Ser Glu Lys Tyr Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95
```

```
Ala Arg Gly Gly Glu Gly Tyr Ser Asp Ser His Tyr Gly Thr Asp Val
            100                 105                 110

Trp Gly Gln Gly Thr Thr Val Thr Val Ser Ser
        115                 120

<210> SEQ ID NO 85
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 88

<400> SEQUENCE: 85

Asn Tyr Trp Met Asn
1               5

<210> SEQ ID NO 86
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 88

<400> SEQUENCE: 86

Asn Ile Lys Glu Asp Gly Ser Glu Lys Tyr Tyr Val Asp Ser Val Glu
1               5                   10                  15

Gly

<210> SEQ ID NO 87
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 88

<400> SEQUENCE: 87

Gly Gly Glu Gly Tyr Gly Asp Ser His Tyr Gly Met Asp Val
1               5                   10

<210> SEQ ID NO 88
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 88

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60
```

```
Glu Gly Arg Phe Thr Ile Ser Arg Asp Asn Ala Arg Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Glu Gly Tyr Gly Asp Ser His Tyr Gly Met Asp Val
            100                 105                 110

Ser Gly Gln Gly Thr Thr Val Thr Val Ser Ser
        115                 120
```

<210> SEQ ID NO 89
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 92

<400> SEQUENCE: 89

```
Ser Tyr Trp Met Asn
1               5
```

<210> SEQ ID NO 90
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 92

<400> SEQUENCE: 90

```
Asn Ile Lys Gln Asp Gly Ser Glu Lys Tyr Tyr Val Asp Ser Val Lys
1               5                   10                  15

Gly
```

<210> SEQ ID NO 91
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 92

<400> SEQUENCE: 91

```
Gly Gly Glu Gly Tyr Gly Asp Asp His Tyr Gly Met Asp Val
1               5                   10
```

<210> SEQ ID NO 92
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 92

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Thr Ala Glu Asp Thr Ala Val Tyr Tyr Cys
                85                  90                  95

Ala Arg Gly Gly Glu Gly Tyr Gly Asp Asp His Tyr Gly Met Asp Val
                100                 105                 110

Trp Gly Gln Gly Thr Thr Val Thr Val Ser Ser
        115                 120
```

<210> SEQ ID NO 93
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 96

<400> SEQUENCE: 93

```
Ser Tyr Trp Met Ser
 1               5
```

<210> SEQ ID NO 94
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 96

<400> SEQUENCE: 94

```
Asn Ile Lys Gln Asp Gly Ser Glu Lys Tyr Tyr Val Asp Ser Val Lys
 1               5                  10                  15

Gly
```

<210> SEQ ID NO 95
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 96

<400> SEQUENCE: 95

```
Gly Gly Glu Gly Tyr Gly Asp Tyr His Tyr Gly Leu Asp Val
 1               5                  10
```

<210> SEQ ID NO 96
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 96

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Gly Asp Tyr His Tyr Gly Leu Asp Val
            100                 105                 110

Ser Gly Gln Gly Thr Thr Val Thr Val Ser Ser
        115                 120

<210> SEQ ID NO 97
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 100

<400> SEQUENCE: 97

Ser Tyr Trp Met Asn
1               5

<210> SEQ ID NO 98
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 100

<400> SEQUENCE: 98

Asn Ile Lys Gln Asp Gly Ser Glu Lys Tyr Tyr Val Asp Ser Val Lys
1               5                   10                  15

Gly

<210> SEQ ID NO 99
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 100

<400> SEQUENCE: 99

Gly Gly Asp Ser Tyr Gly Tyr Arg Asp Tyr Gly Met Asp Val
1               5                   10

<210> SEQ ID NO 100
<211> LENGTH: 123
<212> TYPE: PRT
<213> ORGANISM: Homo sapiens

```
<220> FEATURE:
<221> NAME/KEY: MISC_FEATURE
<222> LOCATION: (1)..(123)
<223> OTHER INFORMATION: VH that binds to CD137

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ser Tyr Gly Tyr Arg Asp Tyr Gly Met Asp Val
            100                 105                 110

Trp Gly Gln Gly Thr Thr Val Thr Val Ser Ser
        115                 120

<210> SEQ ID NO 101
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 104

<400> SEQUENCE: 101

Thr His Trp Met Asn
1               5

<210> SEQ ID NO 102
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 104

<400> SEQUENCE: 102

Asn Ile Asn Gln Asp Gly Ser Glu Lys Tyr Tyr Val Asp Ser Val Glu
1               5                   10                  15

Gly

<210> SEQ ID NO 103
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 104

<400> SEQUENCE: 103

Gly Gly Val Gly Tyr Gly Asp Ser His Phe Gly Met Asp Val
1               5                   10
```

-continued

<210> SEQ ID NO 104
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Thr His
            20                  25                  30

Trp Met Asn Trp Ala Arg Gln Ala Pro Gly Lys Glu Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Asn Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Val Gly Tyr Gly Asp Ser His Phe Gly Met Asp Val
            100                 105                 110

Trp Gly Leu Gly Thr Thr Val Thr Val Ser Ser
        115                 120

<210> SEQ ID NO 105
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 108

<400> SEQUENCE: 105

Ser Tyr Trp Met Leu
1               5

<210> SEQ ID NO 106
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 108

<400> SEQUENCE: 106

Asn Ile Asn Gln Asp Gly Ser Glu Lys Tyr Tyr Val Asp Ser Val Glu
1               5                   10                  15

Gly

<210> SEQ ID NO 107
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 108

<400> SEQUENCE: 107

Gly Gly Glu Gly Tyr Ser Asp Ser His His Gly Thr Asp Val
1               5                   10

<210> SEQ ID NO 108
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Ser Tyr
            20                  25                  30

Trp Met Leu Trp Phe Arg Gln Ala Pro Gly Glu Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Leu Thr Ile Ser Arg Asp Asn Ala Lys Asn Ala Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Glu Gly Tyr Ser Asp Ser His His Gly Thr Asp Val
            100                 105                 110

Trp Gly Gln Gly Thr Thr Val Thr Val Ser Ser
        115                 120

<210> SEQ ID NO 109
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 112

<400> SEQUENCE: 109

Asn Tyr Trp Met Asn
1               5

<210> SEQ ID NO 110
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 112

<400> SEQUENCE: 110

Asn Ile Lys Gln Asp Gly Ser Glu Lys Tyr Tyr Val Asp Ser Val Lys
1               5                   10                  15

Gly

<210> SEQ ID NO 111
<211> LENGTH: 14
<212> TYPE: PRT
<213> ORGANISM: Homo sapiens

```
<220> FEATURE:
<221> NAME/KEY: MISC_FEATURE
<222> LOCATION: (1)..(14)
<223> OTHER INFORMATION: CDR3 OF SEQ ID NO: 112

<400> SEQUENCE: 111

Gly Gly Asp Asn Tyr Ala Tyr Arg Asp Phe Gly Met Asp Val
1               5                   10

<210> SEQ ID NO 112
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Asn Tyr Ala Tyr Arg Asp Phe Gly Met Asp Val
            100                 105                 110

Trp Gly Gln Gly Thr Thr Val Thr Val Ser Ser
        115                 120

<210> SEQ ID NO 113
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 116

<400> SEQUENCE: 113

Asn Tyr Trp Met Phe
1               5

<210> SEQ ID NO 114
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 116

<400> SEQUENCE: 114

Asn Val Asn Gln Asp Gly Ser Glu Lys Tyr Tyr Val Asp Ser Val Glu
1               5                   10                  15

Gly
```

```
<210> SEQ ID NO 115
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 116

<400> SEQUENCE: 115

Gly Gly Glu Gly Tyr Ser Asp Ser His Tyr Gly Thr Asp Val
1               5                   10

<210> SEQ ID NO 116
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Asn Tyr
            20                  25                  30

Trp Met Phe Trp Phe Arg Gln Ala Pro Gly Lys Glu Leu Glu Trp Val
        35                  40                  45

Ala Asn Val Asn Gln Asp Gly Ser Glu Lys Tyr Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Glu Gly Tyr Ser Asp Ser His Tyr Gly Thr Asp Val
            100                 105                 110

Trp Gly Gln Gly Thr Thr Val Thr Val Ser Ser
        115                 120

<210> SEQ ID NO 117
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 120

<400> SEQUENCE: 117

Ser Tyr Trp Met Asn
1               5

<210> SEQ ID NO 118
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 120
```

<400> SEQUENCE: 118

Asn Ile Asn Gln Asp Gly Ser Glu Lys Tyr Tyr Val Asp Ser Val Lys
1               5                   10                  15

Gly

<210> SEQ ID NO 119
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 120

<400> SEQUENCE: 119

Gly Gly Glu Glu Tyr Gly Ser Ser His Tyr Gly Met Asp Val
1               5                   10

<210> SEQ ID NO 120
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 120

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Glu Tyr Gly Ser Ser His Tyr Gly Met Asp Val
            100                 105                 110

Trp Gly Leu Gly Thr Thr Val Thr Val Ser Ser
        115                 120

<210> SEQ ID NO 121
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 124

<400> SEQUENCE: 121

Ser Tyr Trp Met Asn
1               5

<210> SEQ ID NO 122
<211> LENGTH: 17
<212> TYPE: PRT
<213> ORGANISM: Homo sapiens

```
<220> FEATURE:
<221> NAME/KEY: MISC_FEATURE
<222> LOCATION: (1)..(17)
<223> OTHER INFORMATION: CDR2 OF SEQ ID NO: 124

<400> SEQUENCE: 122

Asn Ile Asn Gln Asp Gly Ser Glu Lys Tyr Tyr Val Asp Ser Val Lys
1               5                   10                  15

Gly

<210> SEQ ID NO 123
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 124

<400> SEQUENCE: 123

Gly Gly Asp Ser Tyr Gly Tyr Arg Asp Tyr Gly Met Asp Val
1               5                   10

<210> SEQ ID NO 124
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ser Tyr Gly Tyr Arg Asp Tyr Gly Met Asp Val
            100                 105                 110

Trp Gly Gln Gly Thr Thr Val Thr Val Ser Ser
        115                 120

<210> SEQ ID NO 125
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 128

<400> SEQUENCE: 125

Ser Tyr Trp Met Asn
1               5
```

```
<210> SEQ ID NO 126
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 128

<400> SEQUENCE: 126

Asn Ile Asn Gln Asn Gly Ser Glu Lys Tyr Tyr Val Asp Ser Val Glu
1               5                   10                  15
Gly

<210> SEQ ID NO 127
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 128

<400> SEQUENCE: 127

Gly Gly Phe Gly Tyr Gly Asp Ser His Tyr Gly Met Asp Val
1               5                   10

<210> SEQ ID NO 128
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Thr Pro Gly Lys Gly Leu Glu Trp Val
        35                  40                  45

Ala Asn Ile Asn Gln Asn Gly Ser Glu Lys Tyr Tyr Val Asp Ser Val
    50                  55                  60

Glu Gly Arg Phe Asn Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gly Gly Phe Gly Tyr Gly Asp Ser His Tyr Gly Met Asp Val
            100                 105                 110

Trp Gly Gln Gly Thr Thr Val Thr Val Ser Ser
        115                 120

<210> SEQ ID NO 129
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 132
```

```
<400> SEQUENCE: 129

Asn Tyr Trp Met Thr
1               5

<210> SEQ ID NO 130
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 132

<400> SEQUENCE: 130

Asn Ile Asn Gln Asp Glu Ser Glu Glu Tyr Tyr Val Asp Ser Val Lys
1               5                   10                  15

Gly

<210> SEQ ID NO 131
<211> LENGTH: 14
<212> TYPE: PRT
<213> ORGANISM: Homo sapiens
<220> FEATURE:
<221> NAME/KEY: MISC_FEATURE
<222> LOCATION: (1)..(131)
<223> OTHER INFORMATION: CDR3 OF SEQ ID NO: 132

<400> SEQUENCE: 131

Gly Gly Asp Gly Tyr Ser Asp Ser His Tyr Gly Thr Asp Val
1               5                   10

<210> SEQ ID NO 132
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 132

Glu Val Gln Leu Val Glu Ser Gly Gly Gly Leu Val Gln Ala Gly Gly
1               5                   10                  15

Ser Leu Arg Leu Ser Cys Val Ala Ser Gly Phe Thr Phe Ser Asn Tyr
                20                  25                  30

Trp Met Thr Trp Phe Arg Gln Ala Pro Gly Lys Gly Leu Glu Trp Val
            35                  40                  45

Ala Asn Ile Asn Gln Asp Glu Ser Glu Glu Tyr Tyr Val Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Ile Tyr Tyr Cys
                85                  90                  95

Ala Arg Gly Gly Asp Gly Tyr Ser Asp Ser His Tyr Gly Thr Asp Val
                100                 105                 110

Trp Gly Gln Gly Thr Thr Val Thr Val Ser Ser
            115                 120

<210> SEQ ID NO 133
<211> LENGTH: 5
<212> TYPE: PRT
<213> ORGANISM: Homo sapiens
```

```
<220> FEATURE:
<221> NAME/KEY: MISC_FEATURE
<222> LOCATION: (1)..(5)
<223> OTHER INFORMATION: CDR1 OF SEQ ID NO: 136

<400> SEQUENCE: 133

Asn Tyr Trp Met Asn
1               5

<210> SEQ ID NO 134
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 136

<400> SEQUENCE: 134

Asn Ile Lys Glu Asp Gly Ser Glu Asn Tyr Tyr Val Asp Ser Val Lys
1               5                   10                  15

Gly

<210> SEQ ID NO 135
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 136

<400> SEQUENCE: 135

Gly Gly Glu Gly Tyr Ser Thr Ser His Tyr Gly Met Asp Val
1               5                   10

<210> SEQ ID NO 136
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 136

Gln Val Gln Leu Gln Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Ser Glu Asn Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Ser Thr Ser His Tyr Gly Met Asp Val
            100                 105                 110

Trp Gly Gln Gly Thr Thr Val Thr Val Ser Ser
        115                 120
```

-continued

```
<210> SEQ ID NO 137
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 140

<400> SEQUENCE: 137

Asn Tyr Trp Met Asn
1               5

<210> SEQ ID NO 138
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 140

<400> SEQUENCE: 138

Asn Ile Lys Gln Asp Gly Ser Glu Lys Tyr Tyr Val Asp Ser Val Glu
1               5                   10                  15

Gly

<210> SEQ ID NO 139
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 140

<400> SEQUENCE: 139

Gly Gly Glu Gly Tyr Gly Glu Ser His Tyr Gly Met Asp Val
1               5                   10

<210> SEQ ID NO 140
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 140

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Gly Gly Glu Gly Tyr Gly Glu Ser His Tyr Gly Met Asp Val
            100                 105                 110
```

Ser Gly Gln Gly Thr Thr Val Thr Val Ser Ser
        115                 120

<210> SEQ ID NO 141
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 144

<400> SEQUENCE: 141

Thr Tyr Trp Met Asn
1               5

<210> SEQ ID NO 142
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 144

<400> SEQUENCE: 142

Asn Ile Lys Gln Asp Gly Ser Glu Lys Tyr Tyr Val Asp Ser Val Lys
1               5                   10                  15

Gly

<210> SEQ ID NO 143
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 144

<400> SEQUENCE: 143

Gly Gly Asp Ser Tyr Gly Tyr Arg Asp Tyr Gly Met Asp Val
1               5                   10

<210> SEQ ID NO 144
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH that binds to CD137

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ser Tyr Gly Tyr Arg Asp Tyr Gly Met Asp Val
            100                 105                 110

Trp Gly Gln Gly Thr Thr Val Thr Val Ser Ser
        115                 120

<210> SEQ ID NO 145
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 148

<400> SEQUENCE: 145

Tyr Tyr Trp Met Ile
1               5

<210> SEQ ID NO 146
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 148

<400> SEQUENCE: 146

Asn Ile Asn Gln Asp Gly Ser Glu Lys Tyr Tyr Val Asp Ser Val Lys
1               5                   10                  15

Gly

<210> SEQ ID NO 147
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 148

<400> SEQUENCE: 147

Gly Gly Asp Gly Tyr Ser Asn Ser His Phe Gly Met Asp Val
1               5                   10

<210> SEQ ID NO 148
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Trp Met Ile Trp Phe Arg Gln Ala Pro Gly Glu Glu Leu Glu Trp Val
        35                  40                  45

Ala Asn Ile Asn Gln Asp Gly Ser Glu Lys Tyr Tyr Val Asp Ser Val
    50                  55                  60

```
Lys Gly Arg Phe Ile Ile Ser Arg Asp Asn Ala Thr Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Gly Gly Asp Gly Tyr Ser Asn Ser His Phe Gly Met Asp Val
            100                 105                 110

Trp Gly Gln Gly Thr Thr Val Thr Val Ser Ser
        115                 120

<210> SEQ ID NO 149
<211> LENGTH: 5
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR1 OF SEQ ID NO: 152

<400> SEQUENCE: 149

Asn Tyr Trp Met Ile
1               5

<210> SEQ ID NO 150
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 152

<400> SEQUENCE: 150

Asn Ile Asn Gln Asp Gly Ser Glu Lys Tyr Tyr Val Asp Ser Val Lys
1               5                   10                  15

Gly

<210> SEQ ID NO 151
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 152

<400> SEQUENCE: 151

Gly Gly Glu Gly Tyr Ser Asp Ser His Tyr Gly Thr Asp Val
1               5                   10

<210> SEQ ID NO 152
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Trp Met Ile Trp Tyr Arg Gln Ala Pro Gly Glu Glu Leu Glu Trp Val
            35                  40                  45

Ala Asn Ile Asn Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Ile Tyr Tyr Cys
                 85                  90                  95

Ala Arg Gly Gly Glu Gly Tyr Ser Asp Ser His Tyr Gly Thr Asp Val
                100                 105                 110

Trp Gly Gln Gly Thr Thr Val Thr Val Ser Ser
            115                 120

<210> SEQ ID NO 153
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 156

<400> SEQUENCE: 153

Asn Tyr Trp Met Asn
 1               5

<210> SEQ ID NO 154
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 156

<400> SEQUENCE: 154

Asn Ile Asn Gln Asp Glu Ser Glu Lys Tyr Tyr Val Asp Ser Val Lys
 1               5                  10                  15

Gly

<210> SEQ ID NO 155
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 156

<400> SEQUENCE: 155

Gly Gly Phe Gly Tyr Gly Asp Ser His Phe Gly Met Asp Val
 1               5                  10

<210> SEQ ID NO 156
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137
```

<400> SEQUENCE: 156

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Glu Leu Glu Trp Val
        35                  40                  45

Ala Asn Ile Asn Gln Asp Glu Ser Glu Lys Tyr Tyr Val Asp Ser Val
    50                  55                  60

Lys Gly Arg Phe Thr Val Ser Arg Asp Asn Ala Lys Asn Ser Leu Phe
65                  70                  75                  80

Leu Gln Met Asn Ser Leu Arg Ala Asp Asp Thr Ala Val Tyr Tyr Cys
                85                  90                  95

Ala Arg Gly Gly Phe Gly Tyr Gly Asp Ser His Phe Gly Met Asp Val
            100                 105                 110

Trp Gly Gln Gly Thr Thr Val Thr Val Ser Ser
        115                 120

<210> SEQ ID NO 157
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 160

<400> SEQUENCE: 157

Asn Tyr Trp Met Phe
1               5

<210> SEQ ID NO 158
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 160

<400> SEQUENCE: 158

Asn Val Asn Gln Asp Gly Ser Glu Lys Tyr Tyr Val Asp Ser Val Glu
1               5                   10                  15

Gly

<210> SEQ ID NO 159
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 160

<400> SEQUENCE: 159

Gly Gly Glu Gly Tyr Ser Asp Ser His Tyr Gly Thr Asp Val
1               5                   10

<210> SEQ ID NO 160
<211> LENGTH: 123
<212> TYPE: PRT
<213> ORGANISM: Homo sapiens

```
<220> FEATURE:
<221> NAME/KEY: MISC_FEATURE
<222> LOCATION: (1)..(123)
<223> OTHER INFORMATION: VH binding to CD137

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Asn Tyr
            20                  25                  30

Trp Met Phe Trp Phe Arg Gln Ala Pro Gly Lys Glu Leu Glu Trp Val
        35                  40                  45

Ala Asn Val Asn Gln Asp Gly Ser Glu Lys Tyr Tyr Val Asp Ser Val
    50                  55                  60

Glu Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Glu Gly Tyr Ser Asp Ser His Tyr Gly Thr Asp Val
            100                 105                 110

Trp Gly Gln Gly Thr Thr Val Thr Val Ser Ser
        115                 120

<210> SEQ ID NO 161
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 164

<400> SEQUENCE: 161

Asn Tyr Trp Met Phe
1               5

<210> SEQ ID NO 162
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 164

<400> SEQUENCE: 162

Asn Val Asn Gln Asn Gly Ser Glu Lys Tyr Tyr Val Asp Ser Val Glu
1               5                   10                  15

Gly

<210> SEQ ID NO 163
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 164

<400> SEQUENCE: 163

Gly Gly Glu Gly Tyr Ser Asp Ser His Tyr Gly Thr Asp Val
1               5                   10
```

```
<210> SEQ ID NO 164
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Asn Tyr
            20                  25                  30

Trp Met Phe Trp Phe Arg Gln Ala Pro Gly Lys Glu Leu Glu Trp Val
        35                  40                  45

Ala Asn Val Asn Gln Asn Gly Ser Glu Lys Tyr Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Glu Gly Tyr Ser Asp Ser His Tyr Gly Thr Asp Val
            100                 105                 110

Trp Gly Gln Gly Thr Thr Val Thr Val Ser Ser
        115                 120

<210> SEQ ID NO 165
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 168

<400> SEQUENCE: 165

Asn Tyr Trp Met Asn
1               5

<210> SEQ ID NO 166
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 168

<400> SEQUENCE: 166

Asn Ile Lys Gln Asp Gly Ser Glu Lys Tyr Tyr Val Asp Ser Val Lys
1               5                   10                  15

Gly

<210> SEQ ID NO 167
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 168
```

<400> SEQUENCE: 167

Gly Gly Glu Gly Tyr Gly Asp Ser His Tyr Gly Met Asp Val
1               5                   10

<210> SEQ ID NO 168
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 168

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Glu Gly Tyr Gly Asp Ser His Tyr Gly Met Asp Val
            100                 105                 110

Ser Gly Gln Gly Thr Thr Val Thr Val Ser Ser
        115                 120

<210> SEQ ID NO 169
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 172

<400> SEQUENCE: 169

Asn Tyr Trp Met Ile
1               5

<210> SEQ ID NO 170
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 172

<400> SEQUENCE: 170

Asn Ile Asn Gln Asp Gly Ser Glu Lys Tyr Tyr Val Asp Ser Val Lys
1               5                   10                  15

Gly

<210> SEQ ID NO 171
<211> LENGTH: 14
<212> TYPE: PRT
<213> ORGANISM: Homo sapiens

```
<220> FEATURE:
<221> NAME/KEY: MISC_FEATURE
<222> LOCATION: (1)..(14)
<223> OTHER INFORMATION: CDR3 OF SEQ ID NO: 172

<400> SEQUENCE: 171

Gly Gly Asp Gly Tyr Ser Asn Ser His Tyr Gly Met Asp Val
1               5                   10

<210> SEQ ID NO 172
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 172

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ile Trp Tyr Arg Gln Ala Pro Gly Glu Glu Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Thr Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asn Ser His Tyr Gly Met Asp Val
            100                 105                 110

Trp Gly Gln Gly Thr Thr Val Thr Val Ser Ser
        115                 120

<210> SEQ ID NO 173
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 176

<400> SEQUENCE: 173

Asp Tyr Trp Met Ile
1               5

<210> SEQ ID NO 174
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 176

<400> SEQUENCE: 174

Asn Ile Asn Gln Asp Gly Ser Glu Lys Tyr Tyr Val Asp Ser Val Lys
1               5                   10                  15

Gly
```

```
<210> SEQ ID NO 175
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 176

<400> SEQUENCE: 175

Gly Gly Asp Gly Tyr Ser Asn Ser His Tyr Gly Met Asp Val
1               5                   10

<210> SEQ ID NO 176
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Ile Trp Tyr Arg Gln Ala Pro Gly Glu Glu Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Thr Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asn Ser His Tyr Gly Met Asp Val
            100                 105                 110

Trp Gly Gln Gly Thr Thr Val Thr Val Ser Ser
        115                 120

<210> SEQ ID NO 177
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 180

<400> SEQUENCE: 177

Lys Tyr Trp Met Ile
1               5

<210> SEQ ID NO 178
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 180
```

```
<400> SEQUENCE: 178

Asn Ile Asn Gln Asp Gly Ser Glu Lys Tyr Tyr Val Asp Ser Val Glu
1               5                   10                  15

Gly

<210> SEQ ID NO 179
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 180

<400> SEQUENCE: 179

Gly Gly Asp Asp Tyr Ser Asn Ser His Tyr Gly Met Asp Val
1               5                   10

<210> SEQ ID NO 180
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 180

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Lys Tyr
                20                  25                  30

Trp Met Ile Trp Val Arg Gln Ala Pro Glu Lys Gly Leu Glu Trp Val
            35                  40                  45

Ala Asn Ile Asn Gln Asp Gly Ser Glu Lys Tyr Tyr Val Asp Ser Val
        50                  55                  60

Glu Gly Arg Phe Thr Ile Ser Arg Asp Asn Val Asn Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Asp Tyr Ser Asn Ser His Tyr Gly Met Asp Val
            100                 105                 110

Ser Gly Gln Gly Thr Thr Val Thr Val Ser Ser
        115                 120

<210> SEQ ID NO 181
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 184

<400> SEQUENCE: 181

Asn Tyr Trp Met Ser
1               5

<210> SEQ ID NO 182
<211> LENGTH: 17
<212> TYPE: PRT
<213> ORGANISM: Homo sapiens
```

```
<220> FEATURE:
<221> NAME/KEY: MISC_FEATURE
<222> LOCATION: (1)..(17)
<223> OTHER INFORMATION: CDR2 OF SEQ ID NO: 184

<400> SEQUENCE: 182

Asn Ile Asn Gln Asp Gly Ser Glu Lys Tyr Tyr Val Asp Ser Val Lys
1               5                   10                  15
Gly

<210> SEQ ID NO 183
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 184

<400> SEQUENCE: 183

Gly Gly Glu Glu Tyr Ser Ser Ser His Tyr Gly Met Asp Val
1               5                   10

<210> SEQ ID NO 184
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ala Pro Gly Arg Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Glu Tyr Ser Ser Ser His Tyr Gly Met Asp Val
            100                 105                 110

Trp Gly Gln Gly Thr Thr Val Thr Val Ser Ser
        115                 120

<210> SEQ ID NO 185
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 188

<400> SEQUENCE: 185

Asn Tyr Trp Met Asn
1               5
```

```
<210> SEQ ID NO 186
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 188

<400> SEQUENCE: 186

Asn Ile Lys Gln Asp Gly Ser Glu Asn Tyr Tyr Val Asp Ser Val Lys
1               5                   10                  15
Gly

<210> SEQ ID NO 187
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 188

<400> SEQUENCE: 187

Gly Gly Glu Gly Tyr Ser Thr Ser His Tyr Gly Met Asp Val
1               5                   10

<210> SEQ ID NO 188
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ile Ala Ser Gly Phe Ser Phe Ser Asn Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Asn Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Ser Thr Ser His Tyr Gly Met Asp Val
            100                 105                 110

Trp Gly Gln Gly Thr Ala Val Thr Val Ser Ser
        115                 120

<210> SEQ ID NO 189
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 192
```

<400> SEQUENCE: 189

Ser Tyr Trp Met Ser
1               5

<210> SEQ ID NO 190
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 192

<400> SEQUENCE: 190

Asn Ile Lys Gln Asp Gly Ser Glu Lys Tyr Tyr Val Asp Ser Val Lys
1               5                   10                  15

Gly

<210> SEQ ID NO 191
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 192

<400> SEQUENCE: 191

Gly Gly Glu Gly Tyr Gly Val Asp His Tyr Gly Leu Asp Val
1               5                   10

<210> SEQ ID NO 192
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 192

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 193
<211> LENGTH: 5
<212> TYPE: PRT
<213> ORGANISM: Homo sapiens

```
<220> FEATURE:
<221> NAME/KEY: MISC_FEATURE
<222> LOCATION: (1)..(5)
<223> OTHER INFORMATION: CDR1 OF SEQ ID NO: 196

<400> SEQUENCE: 193

Ser Tyr Trp Met Leu
1               5

<210> SEQ ID NO 194
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 196

<400> SEQUENCE: 194

Asn Val Asn Gln Asp Gly Ser Glu Asn Tyr Tyr Val Asp Ser Val Glu
1               5                   10                  15

Gly

<210> SEQ ID NO 195
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 196

<400> SEQUENCE: 195

Gly Gly Glu Asp Tyr Gly Asn Ser His Phe Gly Met Asp Val
1               5                   10

<210> SEQ ID NO 196
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Ser Ser Tyr
                20                  25                  30

Trp Met Leu Trp Phe Arg Gln Ala Pro Gly Lys Glu Leu Glu Trp Val
            35                  40                  45

Ala Asn Val Asn Gln Asp Gly Ser Glu Asn Tyr Tyr Val Asp Ser Val
        50                  55                  60

Glu Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Val Tyr Tyr Cys
                85                  90                  95

Ala Arg Gly Gly Glu Asp Tyr Gly Asn Ser His Phe Gly Met Asp Val
            100                 105                 110

Trp Gly Gln Gly Thr Met Val Thr Val Ser Ser
        115                 120
```

```
<210> SEQ ID NO 197
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 200

<400> SEQUENCE: 197

Asn Tyr Trp Met Ile
1               5

<210> SEQ ID NO 198
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 200

<400> SEQUENCE: 198

Asn Ile Asn Gln Asp Gly Ser Glu Lys Tyr Tyr Val Asp Ser Val Lys
1               5                   10                  15

Gly

<210> SEQ ID NO 199
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 200

<400> SEQUENCE: 199

Gly Gly Asp Gly Tyr Ser Asn Ser His Tyr Gly Met Asp Val
1               5                   10

<210> SEQ ID NO 200
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 200

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Trp Met Ile Trp Tyr Arg Gln Ala Pro Gly Glu Glu Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Thr Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asn Ser His Tyr Gly Met Asp Val
            100                 105                 110
```

```
Trp Gly Gln Gly Thr Thr Val Thr Val Ser Ser
        115                 120

<210> SEQ ID NO 201
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 204

<400> SEQUENCE: 201

Asn Tyr Trp Met Ile
1               5

<210> SEQ ID NO 202
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 204

<400> SEQUENCE: 202

Asn Ile Asn Gln Asp Gly Ser Glu Lys Tyr Tyr Val Asp Ser Val Lys
1               5                   10                  15

Gly

<210> SEQ ID NO 203
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 204

<400> SEQUENCE: 203

Gly Gly Asp Gly Tyr Ser Asn Ser His Tyr Gly Met Asp Val
1               5                   10

<210> SEQ ID NO 204
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 204

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Ile Trp Tyr Arg Gln Ala Pro Gly Glu Glu Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Thr Asn Ser Leu Phe
65                  70                  75                  80

Leu Gln Met Asn Ser Leu Arg Ala Glu Asp Thr Ala Val Tyr Tyr Cys
                85                  90                  95
```

Ala Arg Gly Gly Asp Gly Tyr Ser Asn Ser His Tyr Gly Met Asp Val
            100                 105                 110

Trp Gly Gln Gly Thr Thr Val Thr Val Ser Ser
        115                 120

<210> SEQ ID NO 205
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 208

<400> SEQUENCE: 205

Lys Tyr Trp Met Ile
1               5

<210> SEQ ID NO 206
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 208

<400> SEQUENCE: 206

Asn Ile Asn Gln Asp Gly Ser Glu Lys Tyr Tyr Val Asp Ser Val Glu
1               5                   10                  15

Gly

<210> SEQ ID NO 207
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 208

<400> SEQUENCE: 207

Gly Gly Asp Asp Tyr Ser Ile Ser His Phe Gly Met Asp Val
1               5                   10

<210> SEQ ID NO 208
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 208

Glu Val Gln Leu Val Glu Ser Gly Gly Gly Leu Val Gln Ile Gly Gly
1               5                   10                  15

Ser Leu Arg Leu Ser Cys Ala Ala Ser Gly Phe Thr Phe Ser Lys Tyr
            20                  25                  30

Trp Met Ile Trp Val Arg Gln Ala Pro Glu Lys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Gly Asp Asp Tyr Ser Ile Ser His Phe Gly Met Asp Val
            100                 105                 110

Ser Gly Gln Gly Thr Arg Val Thr Val Ser Ser
            115                 120

<210> SEQ ID NO 209
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 212

<400> SEQUENCE: 209

Lys Tyr Trp Met Ile
1               5

<210> SEQ ID NO 210
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 212

<400> SEQUENCE: 210

Asn Ile Asn Gln Asp Gly Ser Glu Lys Tyr Tyr Val Asp Ser Val Glu
1               5                   10                  15

Gly

<210> SEQ ID NO 211
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 212

<400> SEQUENCE: 211

Gly Gly Asp Asp Tyr Ser His Ser His Tyr Gly Met Asp Val
1               5                   10

<210> SEQ ID NO 212
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 212

Glu Val Gln Leu Val Glu Ser Gly Gly Gly Leu Val Gln Ile Gly Gly
1               5                   10                  15

Ser Leu Arg Leu Ser Cys Val Ala Ser Gly Phe Thr Phe Ser Lys Tyr
            20                  25                  30

```
Trp Met Ile Trp Val Arg Gln Ala Pro Glu Lys Gly Leu Glu Trp Val
             35                  40                  45

Ala Asn Ile Asn Gln Asp Gly Ser Glu Lys Tyr Tyr Val Asp Ser Val
 50                  55                  60

Glu Gly Arg Phe Thr Ile Ser Arg Asp Asn Ala Asn Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Asp Tyr Ser His Ser His Tyr Gly Met Asp Val
                100                 105                 110

Ser Gly Gln Gly Thr Thr Val Thr Val Ser Ser
            115                 120

<210> SEQ ID NO 213
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 216

<400> SEQUENCE: 213

Asn Tyr Trp Met Asn
 1               5

<210> SEQ ID NO 214
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 216

<400> SEQUENCE: 214

Asn Ile Asn Gln Asp Gly Ser Glu Lys Tyr Tyr Val Asp Ser Val Lys
 1               5                  10                  15
Gly

<210> SEQ ID NO 215
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 216

<400> SEQUENCE: 215

Gly Gly Phe Gly Tyr Gly Asp Ser His Tyr Gly Met Asp Val
 1               5                  10

<210> SEQ ID NO 216
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137
```

<400> SEQUENCE: 216

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Asn Tyr
            20                  25                  30

Trp Met Asn Trp Val Arg Gln Ala Pro Gly Lys Glu Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Asp Asp Thr Ala Val Tyr Tyr Cys
                85                  90                  95

Ala Arg Gly Gly Phe Gly Tyr Gly Asp Ser His Tyr Gly Met Asp Val
            100                 105                 110

Trp Gly Gln Gly Thr Thr Val Thr Val Ser Ser
        115                 120

<210> SEQ ID NO 217
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 220

<400> SEQUENCE: 217

Ser Tyr Trp Leu Asn
1               5

<210> SEQ ID NO 218
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 220

<400> SEQUENCE: 218

Asn Ile Asn Gln Asp Gly Ser Glu Asn Tyr Tyr Val Asp Ser Val Glu
1               5                   10                  15

Gly

<210> SEQ ID NO 219
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 220

<400> SEQUENCE: 219

Gly Gly Glu Asp Tyr Gly Asn Ser His Phe Gly Met Asp Val
1               5                   10

<210> SEQ ID NO 220
<211> LENGTH: 123
<212> TYPE: PRT
<213> ORGANISM: Homo sapiens

```
<220> FEATURE:
<221> NAME/KEY: MISC_FEATURE
<222> LOCATION: (1)..(123)
<223> OTHER INFORMATION: VH binding to CD137

<400> SEQUENCE: 220

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Trp Leu Asn Trp Val Arg Gln Ala Pro Gly Lys Gly Leu Glu Trp Val
        35                  40                  45

Ala Asn Ile Asn Gln Asp Gly Ser Glu Asn Tyr Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Val Tyr Tyr Cys
                85                  90                  95

Ala Arg Gly Gly Glu Asp Tyr Gly Asn Ser His Phe Gly Met Asp Val
            100                 105                 110

Trp Gly Gln Gly Thr Met Val Thr Val Ser Ser
        115                 120

<210> SEQ ID NO 221
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 224

<400> SEQUENCE: 221

Ser Tyr Trp Met Ser
1               5

<210> SEQ ID NO 222
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 224

<400> SEQUENCE: 222

Asn Ile Lys Gln Asp Gly Ser Glu Lys Tyr Tyr Val Asp Ser Val Lys
1               5                   10                  15

Gly

<210> SEQ ID NO 223
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 224

<400> SEQUENCE: 223

Gly Gly Glu Gly Tyr Gly Val Asp His Tyr Gly Leu Asp Val
1               5                   10
```

-continued

<210> SEQ ID NO 224
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 224

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 225
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 228

<400> SEQUENCE: 225

Asp Tyr Trp Met Asn
1               5

<210> SEQ ID NO 226
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO:228

<400> SEQUENCE: 226

Asn Ile Lys Glu Asp Gly Ser Glu Lys Tyr Tyr Val Asp Ser Val Glu
1               5                   10                  15

Gly

<210> SEQ ID NO 227
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 228

<400> SEQUENCE: 227

Gly Gly Glu Gly Tyr Gly Asp Asn His Tyr Gly Met Asp Val
1               5                   10

<210> SEQ ID NO 228
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 228

Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Glu Gly Arg Phe Thr Ile Ser Arg Asp Asn Ala Arg Asn Ser Leu Tyr
65                  70                  75                  80

Leu Gln Met Thr Ser Leu Arg Glu Asp Thr Ala Met Tyr Tyr Cys
                85                  90                  95

Ala Arg Gly Gly Glu Gly Tyr Gly Asp Asn His Tyr Gly Met Asp Val
            100                 105                 110

Ser Gly Gln Gly Thr Thr Val Thr Val Ser Ser
        115                 120

<210> SEQ ID NO 229
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 232

<400> SEQUENCE: 229

Ser Tyr Trp Met Asn
1               5

<210> SEQ ID NO 230
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 232

<400> SEQUENCE: 230

Asn Ile Asn Gln Asp Gly Ser Glu Lys Tyr Tyr Val Asp Ser Val Glu
1               5                   10                  15

Gly

<210> SEQ ID NO 231
<211> LENGTH: 14
<212> TYPE: PRT
<213> ORGANISM: Homo sapiens

```
<220> FEATURE:
<221> NAME/KEY: MISC_FEATURE
<222> LOCATION: (1)..(14)
<223> OTHER INFORMATION: CDR3 OF SEQ ID NO: 232

<400> SEQUENCE: 231

Gly Gly Pro Asp Tyr Gly Asp Leu His Tyr Gly Met Asp Val
1               5                   10

<210> SEQ ID NO 232
<211> LENGTH: 123
<212> TYPE: PRT
<213> ORGANISM: Homo sapiens

<400> SEQUENCE: 232

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Asn Trp Val Arg Gln Ala Pro Gly Lys Glu Ala Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95

Ala Arg Gly Gly Pro Asp Tyr Gly Asp Leu His Tyr Gly Met Asp Val
            100                 105                 110

Trp Gly Gln Gly Thr Thr Val Thr Val Ser Ser
        115                 120

<210> SEQ ID NO 233
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 236

<400> SEQUENCE: 233

Arg Tyr Trp Met Ser
1               5

<210> SEQ ID NO 234
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 236

<400> SEQUENCE: 234

Asn Ile Asn Gln Asp Gly Arg Glu Lys Tyr Tyr Val Asp Ser Val Lys
1               5                   10                  15

Gly

<210> SEQ ID NO 235
<211> LENGTH: 14
<212> TYPE: PRT
<213> ORGANISM: Homo sapiens
```

```
<220> FEATURE:
<221> NAME/KEY: MISC_FEATURE
<222> LOCATION: (1)..(14)
<223> OTHER INFORMATION: CDR3 OF SEQ ID NO: 236

<400> SEQUENCE: 235

Gly Gly Glu Gly Tyr Gly Asp Tyr His Tyr Gly Met Asp Val
1               5                   10

<210> SEQ ID NO 236
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 236

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Arg Val
        35                  40                  45

Ala Asn Ile Asn Gln Asp Gly Arg Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Gly Asp Tyr His Tyr Gly Met Asp Val
            100                 105                 110

Ser Gly Gln Gly Thr Thr Val Thr Val Ser Ser
        115                 120

<210> SEQ ID NO 237
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 240

<400> SEQUENCE: 237

Asn Tyr Trp Met Ile
1               5

<210> SEQ ID NO 238
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 240

<400> SEQUENCE: 238

Asn Ile Asn Gln Asp Gly Ser Glu Lys Tyr Tyr Val Asp Ser Val Lys
1               5                   10                  15

Gly
```

```
<210> SEQ ID NO 239
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 240

<400> SEQUENCE: 239

Gly Gly Asp Gly Tyr Ser Asn Ser His Tyr Gly Met Asp Val
1               5                   10

<210> SEQ ID NO 240
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 240

Glu Val Gln Leu Val Glu Ser Gly Gly Gly Leu Val Gln Pro Gly Gly
1               5                   10                  15

Ser Pro Arg Leu Ser Cys Ala Ala Ser Gly Phe Thr Leu Ser Asn Tyr
            20                  25                  30

Trp Met Ile Trp Tyr Arg Gln Ala Pro Gly Glu Lys Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Thr Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asn Ser His Tyr Gly Met Asp Val
            100                 105                 110

Trp Gly Gln Gly Thr Thr Val Thr Val Ser Ser
        115                 120

<210> SEQ ID NO 241
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 244

<400> SEQUENCE: 241

Asn Tyr Trp Met Asn
1               5

<210> SEQ ID NO 242
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 244
```

-continued

<400> SEQUENCE: 242

Asn Ile Asn Gln Asp Glu Ser Glu Lys Tyr Tyr Val Asp Ser Val Lys
1               5                   10                  15

Gly

<210> SEQ ID NO 243
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 244

<400> SEQUENCE: 243

Gly Gly Phe Gly Tyr Gly Asp Ser His Phe Gly Met Asp Val
1               5                   10

<210> SEQ ID NO 244
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 244

Glu Val Gln Leu Val Glu Ser Gly Gly Leu Val Gln Pro Gly Gly
1               5                   10                  15

Ser Leu Arg Leu Ser Cys Val Ala Ser Gly Phe Asn Phe Ser Asn Tyr
                20                  25                  30

Trp Met Asn Trp Val Arg Gln Ala Pro Gly Lys Glu Leu Glu Trp Val
            35                  40                  45

Ala Asn Ile Asn Gln Asp Glu Ser Glu Lys Tyr Tyr Val Asp Ser Val
        50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Asp Asp Thr Ala Val Tyr Tyr Cys
                85                  90                  95

Ala Arg Gly Gly Phe Gly Tyr Gly Asp Ser His Phe Gly Met Asp Val
            100                 105                 110

Trp Gly Gln Gly Thr Thr Val Thr Val Ser Ser
        115                 120

<210> SEQ ID NO 245
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 248

<400> SEQUENCE: 245

Asn Tyr Trp Met Asn
1               5

<210> SEQ ID NO 246
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 248

<400> SEQUENCE: 246

Asn Ile Asn Gln Asp Glu Ser Glu Lys Tyr Tyr Val Asp Ser Val Lys
1               5                   10                  15
Gly

<210> SEQ ID NO 247
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 248

<400> SEQUENCE: 247

Gly Gly Phe Gly Tyr Gly Asp Ser His Phe Gly Met Asp Val
1               5                   10

<210> SEQ ID NO 248
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 248

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Ser Asn Tyr
                20                  25                  30

Trp Met Asn Trp Val Arg Gln Ala Pro Gly Lys Glu Leu Glu Trp Val
            35                  40                  45

Ala Asn Ile Asn Gln Asp Glu Ser Glu Lys Tyr Tyr Val Asp Ser Val
        50                  55                  60

Lys Gly Arg Phe Thr Ile Phe Arg Asp Asn Ala Lys Asn Ser Leu Phe
65                  70                  75                  80

Leu Gln Met Asn Ser Leu Arg Ala Asp Asp Thr Ala Val Tyr Tyr Cys
                85                  90                  95

Ala Arg Gly Gly Phe Gly Tyr Gly Asp Ser His Phe Gly Met Asp Val
            100                 105                 110

Trp Gly Gln Gly Thr Thr Val Thr Val Ser Ser
        115                 120

<210> SEQ ID NO 249
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 252

<400> SEQUENCE: 249

Ser Phe Trp Met Asn
1               5

```
<210> SEQ ID NO 250
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 252

<400> SEQUENCE: 250

Asn Ile Asn Gln Asp Gly Ser Glu Lys Tyr Tyr Val Asp Ser Val Lys
1               5                   10                  15

Gly

<210> SEQ ID NO 251
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 252

<400> SEQUENCE: 251

Gly Gly Pro Asp Tyr Gly Asp Leu His Tyr Gly Met Asp Val
1               5                   10

<210> SEQ ID NO 252
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 252

Glu Val Gln Leu Val Glu Ser Gly Gly Gly Leu Val Gln Pro Gly Gly
1               5                   10                  15

Ser Leu Ser Leu Ser Cys Ala Ala Ser Gly Phe Thr Phe Arg Ser Phe
            20                  25                  30

Trp Met Asn Trp Val Arg Gln Ala Pro Gly Lys Glu Ala Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Gly Gly Pro Asp Tyr Gly Asp Leu His Tyr Gly Met Asp Val
            100                 105                 110

Trp Gly Gln Gly Thr Thr Val Thr Val Ser Ser
        115                 120

<210> SEQ ID NO 253
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 256
```

<400> SEQUENCE: 253

Ser Tyr Trp Met Asn
1               5

<210> SEQ ID NO 254
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 256

<400> SEQUENCE: 254

Asn Ile Asn Gln Asp Gly Ser Glu Lys Tyr Tyr Val Asp Ser Val Lys
1               5                   10                  15

Gly

<210> SEQ ID NO 255
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 256

<400> SEQUENCE: 255

Gly Gly Pro Asp Tyr Gly Asp Leu His Tyr Gly Met Asp Val
1               5                   10

<210> SEQ ID NO 256
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 256

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Asn Trp Val Arg Gln Ala Pro Gly Lys Glu Ala Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95

Ala Arg Gly Gly Pro Asp Tyr Gly Asp Leu His Tyr Gly Met Asp Val
            100                 105                 110

Trp Gly Gln Gly Thr Thr Val Thr Val Ser Ser
        115                 120

<210> SEQ ID NO 257
<211> LENGTH: 5
<212> TYPE: PRT
<213> ORGANISM: Homo sapiens

```
<220> FEATURE:
<221> NAME/KEY: MISC_FEATURE
<222> LOCATION: (1)..(5)
<223> OTHER INFORMATION: CDR1 OF SEQ ID NO: 260

<400> SEQUENCE: 257

Asn Tyr Trp Met Ile
1               5

<210> SEQ ID NO 258
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 260

<400> SEQUENCE: 258

Asn Ile Asn Gln Asp Gly Ser Glu Lys Tyr Tyr Val Asp Ser Val Lys
1               5                   10                  15

Gly

<210> SEQ ID NO 259
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 260

<400> SEQUENCE: 259

Gly Gly Glu Asp Tyr Gly Asn Ser His Tyr Gly Met Asp Val
1               5                   10

<210> SEQ ID NO 260
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 260

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ile Trp Tyr Arg Gln Ala Pro Gly Glu Glu Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Val Tyr Tyr Cys
                85                  90                  95

Ala Arg Gly Gly Glu Asp Tyr Gly Asn Ser His Tyr Gly Met Asp Val
            100                 105                 110

Trp Gly Gln Gly Thr Met Val Thr Val Ser Ser
        115                 120
```

-continued

```
<210> SEQ ID NO 261
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 264

<400> SEQUENCE: 261

Asn Tyr Trp Met Asn
1               5

<210> SEQ ID NO 262
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 264

<400> SEQUENCE: 262

Asn Ile Asn Gln Asp Gly Ser Glu Arg Tyr Tyr Val Asp Ser Val Lys
1               5                   10                  15

Gly

<210> SEQ ID NO 263
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 264

<400> SEQUENCE: 263

Gly Gly Glu Gly Tyr Gly Ile Asp His Tyr Gly Leu Asp Val
1               5                   10

<210> SEQ ID NO 264
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 264

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Phe Cys
                85                  90                  95

Ala Arg Gly Gly Glu Gly Tyr Gly Ile Asp His Tyr Gly Leu Asp Val
            100                 105                 110
```

```
Ser Gly Gln Gly Thr Thr Val Thr Val Ser Ser
        115                 120
```

<210> SEQ ID NO 265
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 268

<400> SEQUENCE: 265

```
Ser Tyr Trp Met Ser
1               5
```

<210> SEQ ID NO 266
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 268

<400> SEQUENCE: 266

```
Asn Ile Asn Gln Asp Gly Ser Glu Arg Tyr Tyr Val Asp Ser Val Lys
1               5                   10                  15

Gly
```

<210> SEQ ID NO 267
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 268

<400> SEQUENCE: 267

```
Gly Gly Glu Gly Tyr Gly Val Asp His Tyr Gly Leu Asp Val
1               5                   10
```

<210> SEQ ID NO 268
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 268

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Ser Ser Leu Arg Ala Glu Asp Thr Ala Val Tyr Phe Cys
                85                  90                  95
```

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 269
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 272

<400> SEQUENCE: 269

Asn Tyr Trp Met Ile
1               5

<210> SEQ ID NO 270
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 272

<400> SEQUENCE: 270

Asn Ile Asn Gln Asp Gly Ser Glu Lys Tyr Tyr Val Asp Ser Val Glu
1               5                   10                  15

Gly

<210> SEQ ID NO 271
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 272

<400> SEQUENCE: 271

Gly Gly Glu Gly Tyr Gly Val Asp His Tyr Gly Leu Asp Val
1               5                   10

<210> SEQ ID NO 272
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 272

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ile Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Ser Ser Leu Tyr
65                  70                  75                  80

Leu Gln Met Ser Asn Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
            115                 120

<210> SEQ ID NO 273
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 276

<400> SEQUENCE: 273

Asn Tyr Trp Met Asn
1               5

<210> SEQ ID NO 274
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 276

<400> SEQUENCE: 274

Asn Ile Asn Gln Asp Gly Ser Glu Lys Tyr Tyr Val Asp Ser Val Lys
1               5                   10                  15

Gly

<210> SEQ ID NO 275
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 276

<400> SEQUENCE: 275

Gly Gly Thr Gly Tyr Gly Ser Asp His Tyr Gly Met Asp Val
1               5                   10

<210> SEQ ID NO 276
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 276

Gln Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

```
             Trp Met Asn Trp Val Arg Gln Ala Pro Gly Lys Gly Leu Glu Trp Val
                     35                  40                  45

Ala Asn Ile Asn Gln Asp Gly Ser Glu Lys Tyr Tyr Val Asp Ser Val
              50                  55                  60

Lys Gly Arg Phe Thr Ile Ser Arg Asp Asn Ala Lys Asn Ser Leu Phe
              65                  70                  75                  80

Leu Gln Met Asn Ser Leu Arg Ala Glu Asp Thr Ala Val Tyr Tyr Cys
                             85                  90                  95

Ala Arg Gly Gly Thr Gly Tyr Gly Ser Asp His Tyr Gly Met Asp Val
                            100                 105                 110

Ser Gly Gln Gly Thr Thr Val Thr Val Ser Ser
                            115                 120

<210> SEQ ID NO 277
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 280

<400> SEQUENCE: 277

Asn Tyr Trp Met Asn
1               5

<210> SEQ ID NO 278
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 280

<400> SEQUENCE: 278

Asn Ile Asn Gln Asp Gly Ser Glu Asn Tyr Tyr Val Asp Ser Val Lys
1               5                   10                  15

Gly

<210> SEQ ID NO 279
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 280

<400> SEQUENCE: 279

Gly Gly Phe Gly Tyr Gly Asp Ser His Tyr Gly Met Asp Val
1               5                   10

<210> SEQ ID NO 280
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137
```

<400> SEQUENCE: 280

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Phe Asn Phe Ser Asn Tyr
            20                  25                30

Trp Met Asn Trp Val Arg Gln Ala Pro Gly Lys Glu Leu Glu Trp Val
        35                40                45

Ala Asn Ile Asn Gln Asp Gly Ser Glu Asn Tyr Tyr Val Asp Ser Val
 50                   55                  60

Lys Gly Arg Phe Thr Ile Ser Arg Asp Asn Val Lys Asn Ser Leu Phe
65                 70                75                80

Leu Gln Met Asn Arg Leu Arg Ala Asp Asp Thr Ala Val Tyr Tyr Cys
            85                90              95

Ala Arg Gly Gly Phe Gly Tyr Gly Asp Ser His Tyr Gly Met Asp Val
          100              105            110

Trp Gly Gln Gly Thr Thr Val Thr Val Ser Ser
        115              120

<210> SEQ ID NO 281
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 284

<400> SEQUENCE: 281

Asn Tyr Trp Met Ile
1               5

<210> SEQ ID NO 282
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 284

<400> SEQUENCE: 282

Asn Ile Asn Gln Asn Gly Ser Glu Arg Tyr Tyr Val Asp Ser Val Gln
1               5                   10                  15

Gly

<210> SEQ ID NO 283
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 284

<400> SEQUENCE: 283

Gly Gly Ala Asp Tyr Ser Asn Ser His Tyr Gly Met Asp Val
1               5                   10

<210> SEQ ID NO 284
<211> LENGTH: 123
<212> TYPE: PRT
<213> ORGANISM: Homo sapiens

<400> SEQUENCE: 284

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Trp Met Ile Trp Val Arg Gln Ala Pro Gly Lys Glu Leu Glu Trp Leu
        35                  40                  45

Ala Asn Ile Asn Gln Asn Gly Ser Glu Arg Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Asp Tyr Ser Asn Ser His Tyr Gly Met Asp Val
            100                 105                 110

Ser Gly Gln Gly Thr Thr Val Thr Val Ser Ser
        115                 120

<210> SEQ ID NO 285
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 288

<400> SEQUENCE: 285

Ser Tyr Trp Met Ser
1               5

<210> SEQ ID NO 286
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 288

<400> SEQUENCE: 286

Asn Ile Asn Gln Asp Gly Ser Glu Arg Tyr Tyr Val Asp Ser Val Lys
1               5                   10                  15

Gly

<210> SEQ ID NO 287
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 288

<400> SEQUENCE: 287

Gly Gly Glu Gly Tyr Gly Val Asp His Tyr Gly Leu Asp Val
1               5                   10

<210> SEQ ID NO 288
<211> LENGTH: 123
<212> TYPE: PRT
<213> ORGANISM: Homo sapiens

```
<220> FEATURE:
<221> NAME/KEY: MISC_FEATURE
<222> LOCATION: (1)..(123)
<223> OTHER INFORMATION: VH binding to CD137

<400> SEQUENCE: 288

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Asn Asn Ser Leu His
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 289
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 292

<400> SEQUENCE: 289

Ser Tyr Trp Met Asn
1               5

<210> SEQ ID NO 290
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 292

<400> SEQUENCE: 290

Asn Ile Asn Pro Asp Gly Ser Glu Lys Tyr Tyr Val Asp Ser Val Gln
1               5                   10                  15

Gly

<210> SEQ ID NO 291
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 292

<400> SEQUENCE: 291

Gly Gly Pro Gly Tyr Gly Asp Leu His Tyr Gly Met Asp Val
1               5                   10
```

```
<210> SEQ ID NO 292
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 292

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Trp Met Asn Trp Val Arg Gln Ala Pro Gly Lys Glu Ala Glu Trp Val
        35                  40                  45

Ala Asn Ile Asn Pro Asp Gly Ser Glu Lys Tyr Tyr Val Asp Ser Val
    50                  55                  60

Gln Gly Arg His Thr Ile Ser Arg Asp Asn Ala Lys Asn Ser Leu Phe
65                  70                  75                  80

Leu Glu Met Asn Ser Leu Arg Val Glu Asp Thr Ala Leu Tyr Tyr Cys
                85                  90                  95

Ala Arg Gly Gly Pro Gly Tyr Gly Asp Leu His Tyr Gly Met Asp Val
            100                 105                 110

Trp Gly Gln Gly Thr Thr Val Thr Val Ser Ser
        115                 120

<210> SEQ ID NO 293
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 296

<400> SEQUENCE: 293

Asn Tyr Trp Met Asn
1               5

<210> SEQ ID NO 294
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 296

<400> SEQUENCE: 294

Asn Ile Asn Gln Asp Gly Ser Glu Lys Tyr Tyr Val Asp Ser Val Glu
1               5                   10                  15

Gly

<210> SEQ ID NO 295
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 296
```

<400> SEQUENCE: 295

Gly Gly Glu Gly Tyr Gly Val Asp His Tyr Gly Leu Asp Val
1               5                   10

<210> SEQ ID NO 296
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 296

Gln Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Glu Gly Arg Phe Thr Ile Ser Arg Asp Asn Ala Lys Ser Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 297
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 300

<400> SEQUENCE: 297

Asp Tyr Tyr Met Ser
1               5

<210> SEQ ID NO 298
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 300

<400> SEQUENCE: 298

Asn Ile Asn Gln Asp Gly Ser Glu Arg Tyr Tyr Val Asp Ser Val Lys
1               5                   10                  15

Gly

<210> SEQ ID NO 299
<211> LENGTH: 14
<212> TYPE: PRT
<213> ORGANISM: Homo sapiens

```
-continued

<220> FEATURE:
<221> NAME/KEY: MISC_FEATURE
<222> LOCATION: (1)..(14)
<223> OTHER INFORMATION: CDR3 OF SEQ ID NO: 300

<400> SEQUENCE: 299

Gly Gly Glu Gly Tyr Gly Val Asp His Tyr Gly Leu Asp Val
1               5                   10

<210> SEQ ID NO 300
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 300

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 301
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 304

<400> SEQUENCE: 301

Asn Tyr Trp Met Asn
1               5

<210> SEQ ID NO 302
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 304

<400> SEQUENCE: 302

Asn Ile Asn Gln Asp Gly Ser Glu Arg Tyr Tyr Val Asp Ser Val Lys
1               5                   10                  15

Gly
```

```
<210> SEQ ID NO 303
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 304

<400> SEQUENCE: 303

Gly Gly Glu Gly Tyr Gly Val Asp His Tyr Gly Leu Asp Val
1               5                   10

<210> SEQ ID NO 304
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 304

Glu Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 305
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 308

<400> SEQUENCE: 305

Asn Tyr Trp Met Asn
1               5

<210> SEQ ID NO 306
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 308
```

<400> SEQUENCE: 306

Asn Ile Asn Gln Asp Gly Ser Glu Arg Tyr Tyr Val Asp Ser Val Lys
1               5                   10                  15

Gly

<210> SEQ ID NO 307
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 308

<400> SEQUENCE: 307

Gly Gly Glu Gly Tyr Gly Val Asp His Tyr Gly Leu Asp Val
1               5                   10

<210> SEQ ID NO 308
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 308

Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 309
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 312

<400> SEQUENCE: 309

Asn Tyr Trp Met Asn
1               5

<210> SEQ ID NO 310
<211> LENGTH: 17
<212> TYPE: PRT
<213> ORGANISM: Homo sapiens

```
<220> FEATURE:
<221> NAME/KEY: MISC_FEATURE
<222> LOCATION: (1)..(17)
<223> OTHER INFORMATION: CDR2 OF SEQ ID NO: 312

<400> SEQUENCE: 310

Asn Ile Asn Gln Asp Gly Ser Glu Arg Tyr Tyr Val Asp Ser Val Lys
1               5                   10                  15
Gly

<210> SEQ ID NO 311
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 312

<400> SEQUENCE: 311

Gly Gly Glu Gly Tyr Gly Val Asp His Tyr Gly Leu Asp Val
1               5                   10

<210> SEQ ID NO 312
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 312

Gln Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 313
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 316

<400> SEQUENCE: 313

Asn Tyr Trp Met Asn
1               5
```

-continued

```
<210> SEQ ID NO 314
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 316

<400> SEQUENCE: 314

Asn Ile Asn Gln Asp Gly Ser Glu Arg Tyr Tyr Val Asp Ser Val Lys
1               5                   10                  15

Gly

<210> SEQ ID NO 315
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 316

<400> SEQUENCE: 315

Gly Gly Glu Gly Tyr Gly Val Asn His Tyr Gly Leu Asp Val
1               5                   10

<210> SEQ ID NO 316
<211> LENGTH: 123
<212> TYPE: PRT
<213> ORGANISM: Homo sapiens

<400> SEQUENCE: 316

Gln Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
                20                  25                  30

Trp Met Asn Trp Val Arg Gln Ala Pro Gly Lys Gly Leu Glu Trp Val
            35                  40                  45

Ala Asn Ile Asn Gln Asp Gly Ser Glu Arg Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asn His Tyr Gly Leu Asp Val
            100                 105                 110

Ser Gly Gln Gly Thr Thr Val Thr Val Ser Ser
        115                 120

<210> SEQ ID NO 317
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 320

<400> SEQUENCE: 317

Asp Tyr Tyr Met Ser
1               5
```

<210> SEQ ID NO 318
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 320

<400> SEQUENCE: 318

Asn Ile Lys Gln Asp Gly Ser Glu Arg Tyr Tyr Val Asp Ser Val Lys
1               5                   10                  15
Gly

<210> SEQ ID NO 319
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 320

<400> SEQUENCE: 319

Gly Gly Glu Gly Tyr Gly Val Asp His Tyr Gly Leu Asp Val
1               5                   10

<210> SEQ ID NO 320
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 320

Gln Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 321
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 324

```
<400> SEQUENCE: 321

Asn Tyr Trp Met Asn
1               5

<210> SEQ ID NO 322
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 324

<400> SEQUENCE: 322

Asn Ile Asn Gln Asp Gly Ser Glu Arg Tyr Tyr Val Asp Ser Val Glu
1               5                   10                  15

Gly

<210> SEQ ID NO 323
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 324

<400> SEQUENCE: 323

Gly Gly Glu Gly Tyr Gly Val Asp His Tyr Gly Leu Asp Val
1               5                   10

<210> SEQ ID NO 324
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 324

Gln Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Glu Gly Arg Phe Thr Ile Ser Arg Asp Asn Ala Lys Ser Ser Leu Tyr
65                  70                  75                  80

Leu Gln Met Ser Asn Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 325
<211> LENGTH: 5
<212> TYPE: PRT
<213> ORGANISM: Homo sapiens
```

```
<220> FEATURE:
<221> NAME/KEY: MISC_FEATURE
<222> LOCATION: (1)..(5)
<223> OTHER INFORMATION: CDR1 OF SEQ ID NO: 328

<400> SEQUENCE: 325

Asn Tyr Trp Met Asn
1               5

<210> SEQ ID NO 326
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 328

<400> SEQUENCE: 326

Asn Ile Asn Gln Asp Gly Ser Glu Arg Tyr Tyr Val Asp Ser Val Lys
1               5                   10                  15
Gly

<210> SEQ ID NO 327
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 328

<400> SEQUENCE: 327

Gly Gly Glu Gly Tyr Gly Val Asp His Tyr Gly Leu Asp Val
1               5                   10

<210> SEQ ID NO 328
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 328

Gln Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120
```

```
<210> SEQ ID NO 329
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 332

<400> SEQUENCE: 329

Asn Tyr Trp Met Asn
1               5

<210> SEQ ID NO 330
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 332

<400> SEQUENCE: 330

Asn Ile Asn Gln Asp Gly Ser Glu Arg Tyr Tyr Val Asp Ser Val Lys
1               5                   10                  15

Gly

<210> SEQ ID NO 331
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 332

<400> SEQUENCE: 331

Gly Gly Glu Gly Tyr Gly Val Asp His Tyr Gly Leu Asp Val
1               5                   10

<210> SEQ ID NO 332
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 332

Gln Val Gln Leu Gln Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110
```

```
Ser Gly Gln Gly Thr Thr Val Thr Val Ser Ser
        115                 120
```

<210> SEQ ID NO 333
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 336

<400> SEQUENCE: 333

```
Asn Tyr Trp Met Asn
1               5
```

<210> SEQ ID NO 334
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 336

<400> SEQUENCE: 334

```
Asn Ile Asn Gln Asp Gly Ser Glu Arg Tyr Tyr Val Asp Ser Val Lys
1               5                   10                  15

Gly
```

<210> SEQ ID NO 335
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 336

<400> SEQUENCE: 335

```
Gly Gly Glu Gly Tyr Gly Val Asp His Tyr Gly Leu Asp Val
1               5                   10
```

<210> SEQ ID NO 336
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 336

```
Gln Val Gln Leu Val Glu Ser Gly Gly Gly Leu Val Lys Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95
```

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 337
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 340

<400> SEQUENCE: 337

Asn Tyr Trp Met Asn
1               5

<210> SEQ ID NO 338
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 340

<400> SEQUENCE: 338

Asn Ile Asn Gln Asp Gly Ser Glu Arg Tyr Tyr Val Asp Ser Val Lys
1               5                   10                  15

Gly

<210> SEQ ID NO 339
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 340

<400> SEQUENCE: 339

Gly Gly Glu Gly Tyr Gly Val Asp His Tyr Gly Leu Asp Val
1               5                   10

<210> SEQ ID NO 340
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 340

Gln Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

```
Lys Gly Arg Phe Thr Ile Ser Arg Asp Asn Ala Asn Ser Leu His
 65                  70                  75                  80

Leu Gln Met Ser Ser Leu Arg Ala Glu Asp Thr Ala Val Tyr Phe Cys
             85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120
```

<210> SEQ ID NO 341
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 344

<400> SEQUENCE: 341

```
Asn Tyr Trp Met Asn
 1               5
```

<210> SEQ ID NO 342
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 344

<400> SEQUENCE: 342

```
Asn Ile Asn Gln Asp Gly Ser Glu Arg Tyr Tyr Val Asp Ser Val Glu
 1               5                  10                  15

Gly
```

<210> SEQ ID NO 343
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 344

<400> SEQUENCE: 343

```
Gly Gly Glu Gly Tyr Gly Val Asp His Tyr Gly Leu Asp Val
 1               5                  10
```

<210> SEQ ID NO 344
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 344

```
Gln Val Gln Leu Gly Glu Ser Gly Gly Gly Leu Val Gln Pro Gly Gly
 1               5                  10                  15

Ser Leu Arg Leu Ser Cys Ala Ala Thr Gly Phe Thr Leu Ser Asn Tyr
            20                  25                  30
```

```
            Trp Met Asn Trp Val Arg Gln Ala Pro Gly Lys Gly Leu Glu Trp Val
                    35                  40                  45

Ala Asn Ile Asn Gln Asp Gly Ser Glu Arg Tyr Tyr Val Asp Ser Val
             50                  55                  60

Glu Gly Arg Phe Thr Ile Ser Arg Asp Asn Ala Lys Ser Ser Leu Tyr
             65                  70                  75                  80

Leu Gln Met Ser Asn Leu Arg Ala Glu Asp Thr Ala Val Tyr Phe Cys
                            85                  90                  95

Ala Arg Gly Gly Glu Gly Tyr Gly Val Asp His Tyr Gly Leu Asp Val
                           100                 105                 110

Ser Gly Gln Gly Thr Thr Val Thr Val Ser Ser
                       115                 120

<210> SEQ ID NO 345
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 348

<400> SEQUENCE: 345

Asn Tyr Trp Met Asn
1               5

<210> SEQ ID NO 346
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 348

<400> SEQUENCE: 346

Asn Ile Asn Gln Asp Gly Ser Glu Arg Tyr Tyr Val Asp Ser Val Lys
1               5                   10                  15
Gly

<210> SEQ ID NO 347
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 348

<400> SEQUENCE: 347

Gly Gly Glu Gly Tyr Gly Val Asp His Tyr Gly Leu Asp Val
1               5                   10

<210> SEQ ID NO 348
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137
```

<400> SEQUENCE: 348

Gln Val Gln Leu Val Glu Ser Gly Gly Gly Leu Val Gln Pro Gly Gly
1               5                   10                  15

Ser Leu Lys Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Ser Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 349
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 352

<400> SEQUENCE: 349

Asn Tyr Trp Met Asn
1               5

<210> SEQ ID NO 350
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 352

<400> SEQUENCE: 350

Asn Ile Asn Gln Asp Gly Ser Glu Arg Tyr Tyr Val Asp Ser Val Lys
1               5                   10                  15

Gly

<210> SEQ ID NO 351
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO:352

<400> SEQUENCE: 351

Gly Gly Glu Gly Tyr Gly Val Asp His Tyr Gly Leu Asp Val
1               5                   10

<210> SEQ ID NO 352
<211> LENGTH: 123
<212> TYPE: PRT
<213> ORGANISM: Homo sapiens

```
<220> FEATURE:
<221> NAME/KEY: MISC_FEATURE
<222> LOCATION: (1)..(123)
<223> OTHER INFORMATION: VH binding to CD137

<400> SEQUENCE: 352

Gln Val Gln Leu Gln Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Gly Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 353
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 356

<400> SEQUENCE: 353

Asp Tyr Gly Met Ser
1               5

<210> SEQ ID NO 354
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 356

<400> SEQUENCE: 354

Asn Ile Asn Gln Asp Gly Ser Glu Arg Tyr Tyr Val Asp Ser Val Lys
1               5                   10                  15

Gly

<210> SEQ ID NO 355
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 356

<400> SEQUENCE: 355

Gly Gly Glu Gly Tyr Gly Val Asp His Tyr Gly Leu Asp Val
1               5                   10
```

-continued

```
<210> SEQ ID NO 356
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 356

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 357
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 360

<400> SEQUENCE: 357

Ser His Trp Met Thr
1               5

<210> SEQ ID NO 358
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 360

<400> SEQUENCE: 358

His Ile Lys Glu Asp Gly Ser Glu Lys Tyr Tyr Glu Asp Ser Val Glu
1               5                   10                  15

Gly

<210> SEQ ID NO 359
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 360
```

<400> SEQUENCE: 359

Gly Gly Asp Gly Tyr Ser Asp Ser His Phe Gly Val Asp Val
1               5                   10

<210> SEQ ID NO 360
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 360

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Val Arg Gln Ala Pro Gly Lys Gly Leu Glu Trp Val
        35                  40                  45

Ala His Ile Lys Glu Asp Gly Ser Glu Lys Tyr Tyr Glu Asp Ser Val
    50                  55                  60

Glu Gly Arg Phe Thr Val Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 361
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 364

<400> SEQUENCE: 361

Ser His Trp Met Thr
1               5

<210> SEQ ID NO 362
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 364

<400> SEQUENCE: 362

His Ile Lys Glu Asp Gly Ser Glu Lys Tyr Tyr Val Asp Ser Val Lys
1               5                   10                  15

Gly

<210> SEQ ID NO 363
<211> LENGTH: 14
<212> TYPE: PRT
<213> ORGANISM: Homo sapiens

```
<220> FEATURE:
<221> NAME/KEY: MISC_FEATURE
<222> LOCATION: (1)..(14)
<223> OTHER INFORMATION: CDR3 OF SEQ ID NO: 364

<400> SEQUENCE: 363

Gly Gly Asp Gly Tyr Ser Asp Ser His Phe Gly Val Asp Val
1               5                   10

<210> SEQ ID NO 364
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 364

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Val Asp Ser Val
    50                  55                  60

Lys Gly Arg Phe Thr Val Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 365
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 368

<400> SEQUENCE: 365

Ser His Trp Met Thr
1               5

<210> SEQ ID NO 366
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 368

<400> SEQUENCE: 366

His Ile Lys Glu Asp Gly Ser Glu Lys Tyr Tyr Glu Asp Ser Val Lys
1               5                   10                  15

Gly
```

```
<210> SEQ ID NO 367
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 368

<400> SEQUENCE: 367

Gly Gly Asp Gly Tyr Ser Asp Ser His Phe Gly Val Asp Val
1               5                   10

<210> SEQ ID NO 368
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 368

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Glu Asp Ser Val
    50                  55                  60

Lys Gly Arg Phe Thr Val Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 369
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 372

<400> SEQUENCE: 369

Ser His Trp Met Thr
1               5

<210> SEQ ID NO 370
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 372
```

<400> SEQUENCE: 370

His Ile Lys Glu Asp Gly Ser Glu Lys Tyr Tyr Glu Asp Ser Val Glu
1               5                   10                  15

Gly

<210> SEQ ID NO 371
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 372

<400> SEQUENCE: 371

Gly Gly Asp Gly Tyr Ser Asp Ser His Phe Gly Val Asp Val
1               5                   10

<210> SEQ ID NO 372
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 372

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Glu Asp Ser Val
    50                  55                  60

Glu Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 373
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 376

<400> SEQUENCE: 373

Ser His Trp Met Thr
1               5

<210> SEQ ID NO 374
<211> LENGTH: 17
<212> TYPE: PRT
<213> ORGANISM: Homo sapiens

```
<220> FEATURE:
<221> NAME/KEY: MISC_FEATURE
<222> LOCATION: (1)..(17)
<223> OTHER INFORMATION: CDR2 OF SEQ ID NO: 376

<400> SEQUENCE: 374

His Ile Lys Glu Asp Gly Ser Glu Lys Tyr Tyr Glu Asp Ser Val Glu
1               5                   10                  15

Gly

<210> SEQ ID NO 375
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 376

<400> SEQUENCE: 375

Gly Gly Asp Gly Tyr Ser Asp Ser His Phe Gly Val Asp Val
1               5                   10

<210> SEQ ID NO 376
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 376

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser His
                20                  25                  30

Trp Met Thr Trp Phe Arg Gln Ala Pro Gly Lys Gly Leu Glu Trp Val
            35                  40                  45

Ala His Ile Lys Glu Asp Gly Ser Glu Lys Tyr Tyr Glu Asp Ser Val
        50                  55                  60

Glu Gly Arg Phe Thr Val Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 377
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 380

<400> SEQUENCE: 377

Ser His Trp Met Thr
1               5
```

```
<210> SEQ ID NO 378
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 380

<400> SEQUENCE: 378

His Ile Lys Glu Asp Gly Ser Glu Lys Tyr Tyr Val Asp Ser Val Lys
1               5                   10                  15

Gly

<210> SEQ ID NO 379
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 380

<400> SEQUENCE: 379

Gly Gly Asp Gly Tyr Ser Asp Ser His Phe Gly Val Asp Val
1               5                   10

<210> SEQ ID NO 380
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 380

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Val Arg Gln Ala Pro Gly Lys Gly Leu Glu Trp Val
        35                  40                  45

Ala His Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 381
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 384
```

```
<400> SEQUENCE: 381

Ser His Trp Met Thr
1               5

<210> SEQ ID NO 382
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 384

<400> SEQUENCE: 382

His Ile Lys Glu Asp Gly Ser Glu Lys Tyr Tyr Val Asp Ser Val Lys
1               5                   10                  15

Gly

<210> SEQ ID NO 383
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 384

<400> SEQUENCE: 383

Gly Gly Asp Gly Tyr Ser Asp Ser His Phe Gly Val Asp Val
1               5                   10

<210> SEQ ID NO 384
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 384

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 385
<211> LENGTH: 5
<212> TYPE: PRT
<213> ORGANISM: Homo sapiens
```

<220> FEATURE:
<221> NAME/KEY: MISC_FEATURE
<222> LOCATION: (1)..(5)
<223> OTHER INFORMATION: CDR1 OF SEQ ID NO: 388

<400> SEQUENCE: 385

Ser His Trp Met Thr
1               5

<210> SEQ ID NO 386
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 388

<400> SEQUENCE: 386

His Ile Lys Glu Asp Glu Ser Glu Lys Tyr Tyr Val Asp Ser Val Lys
1               5                   10                  15

Gly

<210> SEQ ID NO 387
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 388

<400> SEQUENCE: 387

Gly Gly Val Gly Tyr Ser Ile Ser His Phe Gly Val Asp Val
1               5                   10

<210> SEQ ID NO 388
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 388

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Val Arg Gln Ala Pro Gly Lys Gly Leu Glu Trp Val
        35                  40                  45

Ala His Ile Lys Glu Asp Glu Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Val Gly Tyr Ser Ile Ser His Phe Gly Val Asp Val
            100                 105                 110

Trp Gly Gln Gly Thr Thr Val Thr Val Ser Ser
        115                 120

-continued

```
<210> SEQ ID NO 389
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 392

<400> SEQUENCE: 389

Ser His Trp Met Thr
1               5

<210> SEQ ID NO 390
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 392

<400> SEQUENCE: 390

His Ile Lys Glu Asp Glu Ser Glu Lys Tyr Tyr Val Asp Ser Val Lys
1               5                   10                  15

Gly

<210> SEQ ID NO 391
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 392

<400> SEQUENCE: 391

Gly Gly Glu Gly Tyr Ser Ile Ser His Phe Gly Val Asp Val
1               5                   10

<210> SEQ ID NO 392
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 392

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
                20                  25                  30

Trp Met Thr Trp Val Arg Gln Ala Pro Gly Lys Gly Leu Glu Trp Val
            35                  40                  45

Ala His Ile Lys Glu Asp Glu Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Ser Ile Ser His Phe Gly Val Asp Val
            100                 105                 110
```

Trp Gly Gln Gly Thr Thr Val Thr Val Ser Ser
         115                 120

<210> SEQ ID NO 393
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 396

<400> SEQUENCE: 393

Ser His Trp Met Thr
1               5

<210> SEQ ID NO 394
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 396

<400> SEQUENCE: 394

His Ile Lys Glu Asp Glu Ser Glu Lys Tyr Tyr Val Asp Ser Val Lys
1               5                   10                  15

Gly

<210> SEQ ID NO 395
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 396

<400> SEQUENCE: 395

Gly Gly Asp Gly Tyr Ser Asp Ser His Phe Gly Val Asp Val
1               5                   10

<210> SEQ ID NO 396
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 396

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Glu Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 397
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 400

<400> SEQUENCE: 397

Ser His Trp Met Thr
1               5

<210> SEQ ID NO 398
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 400

<400> SEQUENCE: 398

His Ile Lys Glu Asp Glu Ser Glu Lys Tyr Tyr Val Asp Ser Val Lys
1               5                   10                  15

Gly

<210> SEQ ID NO 399
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 400

<400> SEQUENCE: 399

Gly Gly Asp Gly Tyr Ser Ile Ser His Phe Gly Val Asp Val
1               5                   10

<210> SEQ ID NO 400
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 400

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Glu Ser Glu Lys Tyr Tyr Val Asp Ser Val
    50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Gly Tyr Ser Ile Ser His Phe Gly Val Asp Val
            100                 105                 110

Trp Gly Gln Gly Thr Thr Val Thr Val Ser Ser
        115                 120

<210> SEQ ID NO 401
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 404

<400> SEQUENCE: 401

Ser His Trp Met Thr
 1               5

<210> SEQ ID NO 402
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 404

<400> SEQUENCE: 402

His Ile Lys Glu Gly Gly Ser Glu Lys Tyr Tyr Val Asp Ser Val Lys
 1               5                  10                  15

Gly

<210> SEQ ID NO 403
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 404

<400> SEQUENCE: 403

Gly Gly Asp Gly Tyr Ser Asp Ser His Phe Gly Val Asp Val
 1               5                  10

<210> SEQ ID NO 404
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 404

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser His
             20                  25                  30
```

```
Trp Met Thr Trp Phe Arg Gln Ala Pro Gly Lys Gly Leu Glu Trp Val
            35                  40                  45

Ala His Ile Lys Glu Gly Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 405
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 408

<400> SEQUENCE: 405

Ser His Trp Met Thr
 1               5

<210> SEQ ID NO 406
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 408

<400> SEQUENCE: 406

His Ile Lys Glu Glu Gly Ser Glu Lys Tyr Tyr Val Asp Ser Val Lys
 1               5                   10                  15

Gly

<210> SEQ ID NO 407
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 408

<400> SEQUENCE: 407

Gly Gly Asp Gly Tyr Ser Asp Ser His Phe Gly Val Asp Val
 1               5                   10

<210> SEQ ID NO 408
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137
```

<400> SEQUENCE: 408

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 409
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 412

<400> SEQUENCE: 409

Ser His Trp Met Thr
1               5

<210> SEQ ID NO 410
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 412

<400> SEQUENCE: 410

His Ile Lys Glu Asp Gly Ser Glu Lys Tyr Tyr Val Asp Ser Val Lys
1               5                   10                  15

Gly

<210> SEQ ID NO 411
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 412

<400> SEQUENCE: 411

Gly Gly Glu Gly Tyr Ser Asp Ser His Phe Gly Val Asp Val
1               5                   10

<210> SEQ ID NO 412
<211> LENGTH: 123
<212> TYPE: PRT
<213> ORGANISM: Homo sapiens

```
<220> FEATURE:
<221> NAME/KEY: MISC_FEATURE
<222> LOCATION: (1)..(123)
<223> OTHER INFORMATION: VH binding to CD137

<400> SEQUENCE: 412

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 413
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 416

<400> SEQUENCE: 413

Ser His Trp Met Thr
1               5

<210> SEQ ID NO 414
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 416

<400> SEQUENCE: 414

His Ile Lys Glu Asp Gly Ser Glu Lys Tyr Tyr Val Asp Ser Val Lys
1               5                   10                  15

Gly

<210> SEQ ID NO 415
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 416

<400> SEQUENCE: 415

Gly Gly Val Gly Tyr Ser Asp Ser His Phe Gly Val Asp Val
1               5                   10
```

-continued

```
<210> SEQ ID NO 416
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 416

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Val Gly Tyr Ser Asp Ser His Phe Gly Val Asp Val
            100                 105                 110

Trp Gly Gln Gly Thr Thr Val Thr Val Ser Ser
        115                 120

<210> SEQ ID NO 417
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 420

<400> SEQUENCE: 417

Ser His Trp Met Thr
1               5

<210> SEQ ID NO 418
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 420

<400> SEQUENCE: 418

His Ile Lys Glu Asp Glu Ser Glu Lys Tyr Tyr Val Asp Ser Val Lys
1               5                   10                  15

Gly

<210> SEQ ID NO 419
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 420
```

<400> SEQUENCE: 419

Gly Gly Val Gly Tyr Ser Ile Ser His Phe Gly Val Asp Val
1               5                   10

<210> SEQ ID NO 420
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 420

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Glu Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Val Gly Tyr Ser Ile Ser His Phe Gly Val Asp Val
            100                 105                 110

Trp Gly Gln Gly Thr Thr Val Thr Val Ser Ser
        115                 120

<210> SEQ ID NO 421
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 424

<400> SEQUENCE: 421

Ser His Trp Met Thr
1               5

<210> SEQ ID NO 422
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 424

<400> SEQUENCE: 422

His Ile Lys Glu Asp Glu Ser Glu Lys Tyr Tyr Val Asp Ser Val Lys
1               5                   10                  15

Gly

<210> SEQ ID NO 423
<211> LENGTH: 14
<212> TYPE: PRT
<213> ORGANISM: Homo sapiens

```
<220> FEATURE:
<221> NAME/KEY: MISC_FEATURE
<222> LOCATION: (1)..(14)
<223> OTHER INFORMATION: CDR3 OF SEQ ID NO: 424

<400> SEQUENCE: 423

Gly Gly Glu Gly Tyr Ser Ile Ser His Phe Gly Val Asp Val
1               5                   10

<210> SEQ ID NO 424
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 424

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Glu Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Ser Ile Ser His Phe Gly Val Asp Val
            100                 105                 110

Trp Gly Gln Gly Thr Thr Val Thr Val Ser Ser
        115                 120

<210> SEQ ID NO 425
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 428

<400> SEQUENCE: 425

Asp Tyr Tyr Met Ser
1               5

<210> SEQ ID NO 426
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 428

<400> SEQUENCE: 426

Tyr Ile Ser Gly Ser Gly Asp Ile Ile Asp Tyr Ala Asp Ser Val Lys
1               5                   10                  15

Gly
```

```
<210> SEQ ID NO 427
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 428

<400> SEQUENCE: 427

Glu Asp Ser Arg Leu Thr Gly Thr Thr Asp Phe Asp Asn
1               5                   10

<210> SEQ ID NO 428
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 428

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr His Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 429
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 432

<400> SEQUENCE: 429

Asp Tyr Tyr Met Ser
1               5

<210> SEQ ID NO 430
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 432
```

<400> SEQUENCE: 430

Tyr Ile Ser Gly Ser Gly Asp Ile Ile Asp Tyr Ala Asp Ser Val Lys
1               5                   10                  15

Gly

<210> SEQ ID NO 431
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 432

<400> SEQUENCE: 431

Glu Asp Ser Arg Ile Pro Gly Thr Thr Asp Phe Asp Asn
1               5                   10

<210> SEQ ID NO 432
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 432

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
                20                  25                  30

Tyr Met Ser Trp Phe Arg Gln Ala Pro Gly Lys Gly Leu Glu Trp Val
            35                  40                  45

Ser Tyr Ile Ser Gly Ser Gly Asp Ile Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Lys Glu Asp Ser Arg Ile Pro Gly Thr Thr Asp Phe Asp Asn Trp
            100                 105                 110

Gly Gln Gly Thr Leu Val Thr Val Ser Ser
        115                 120

<210> SEQ ID NO 433
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 436

<400> SEQUENCE: 433

Asp Tyr Tyr Met Ser
1               5

<210> SEQ ID NO 434
<211> LENGTH: 17
<212> TYPE: PRT
<213> ORGANISM: Homo sapiens

```
<220> FEATURE:
<221> NAME/KEY: MISC_FEATURE
<222> LOCATION: (1)..(17)
<223> OTHER INFORMATION: CDR2 OF SEQ ID NO: 436

<400> SEQUENCE: 434

Tyr Ile Ser Gly Ser Gly Asp Ile Ile Asp Tyr Ala Asp Ser Val Lys
1               5                   10                  15

Gly

<210> SEQ ID NO 435
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 436

<400> SEQUENCE: 435

Glu Asp Ser Arg Ile Pro Gly Thr Thr Asp Phe Asp Asn
1               5                   10

<210> SEQ ID NO 436
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 436

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Ile
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Lys Glu Asp Ser Arg Ile Pro Gly Thr Thr Asp Phe Asp Asn Trp
            100                 105                 110

Gly Gln Gly Thr Leu Val Thr Val Ser Ser
        115                 120

<210> SEQ ID NO 437
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 440

<400> SEQUENCE: 437

Asp Tyr Tyr Met Ser
1               5
```

```
<210> SEQ ID NO 438
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 440

<400> SEQUENCE: 438

Tyr Ile Ser Gly Ser Gly Asp Val Ile Asp Tyr Ala Asp Ser Val Lys
1               5                   10                  15
Gly

<210> SEQ ID NO 439
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 440

<400> SEQUENCE: 439

Glu Asp Ser Arg Ile Pro Gly Thr Thr Asp Phe Asp Asn
1               5                   10

<210> SEQ ID NO 440
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 440

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
                20                  25                  30

Tyr Met Ser Trp Phe Arg Gln Ala Pro Gly Lys Gly Leu Glu Trp Val
            35                  40                  45

Ser Tyr Ile Ser Gly Ser Gly Asp Val Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Lys Glu Asp Ser Arg Ile Pro Gly Thr Thr Asp Phe Asp Asn Trp
            100                 105                 110

Gly Gln Gly Thr Leu Val Thr Val Ser Ser
        115                 120

<210> SEQ ID NO 441
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 444
```

```
<400> SEQUENCE: 441

Asp Tyr Tyr Met Ser
1               5

<210> SEQ ID NO 442
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 444

<400> SEQUENCE: 442

Tyr Ile Ser Gly Ser Gly Asp Ile Ile Asp Tyr Ala Asp Ser Val Lys
1               5                   10                  15

Gly

<210> SEQ ID NO 443
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 444

<400> SEQUENCE: 443

Glu Asp Ser Arg Ile Pro Gly Thr Thr Asp Phe Asp Asn
1               5                   10

<210> SEQ ID NO 444
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 444

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Lys Glu Asp Ser Arg Ile Pro Gly Thr Thr Asp Phe Asp Asn Trp
            100                 105                 110

Gly Gln Gly Thr Leu Val Thr Val Ser Ser
        115                 120

<210> SEQ ID NO 445
<211> LENGTH: 5
<212> TYPE: PRT
<213> ORGANISM: Homo sapiens
```

```
<220> FEATURE:
<221> NAME/KEY: MISC_FEATURE
<222> LOCATION: (1)..(5)
<223> OTHER INFORMATION: CDR1 OF SEQ ID NO: 448

<400> SEQUENCE: 445

Asp Tyr Tyr Met Ser
1               5

<210> SEQ ID NO 446
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 448

<400> SEQUENCE: 446

Tyr Ile Ser Gly Ser Gly Asp Ile Ile Asp Tyr Ala Asp Ser Val Lys
1               5                   10                  15

Gly

<210> SEQ ID NO 447
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 448

<400> SEQUENCE: 447

Glu Asp Ser Arg Ile Pro Gly Thr Thr Asp Phe Asp Ser
1               5                   10

<210> SEQ ID NO 448
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 448

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
                20                  25                  30

Tyr Met Ser Trp Phe Arg Gln Ala Pro Gly Lys Gly Leu Glu Trp Val
            35                  40                  45

Ser Tyr Ile Ser Gly Ser Gly Asp Ile Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Lys Glu Asp Ser Arg Ile Pro Gly Thr Thr Asp Phe Asp Ser Trp
            100                 105                 110

Gly Gln Gly Thr Met Val Thr Val Ser Ser
        115                 120
```

-continued

```
<210> SEQ ID NO 449
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 452

<400> SEQUENCE: 449

Asp Tyr Tyr Met Ser
1               5

<210> SEQ ID NO 450
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 452

<400> SEQUENCE: 450

Tyr Ile Ser Gly Ser Gly Thr Thr Ile Asp Tyr Ala Asp Ser Val Lys
1               5                   10                  15

Gly

<210> SEQ ID NO 451
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 452

<400> SEQUENCE: 451

Glu Asp Ile Arg Met Thr Gly Thr Thr Asp Phe Asp Asn
1               5                   10

<210> SEQ ID NO 452
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 452

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Thr Thr Ile Asp Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Thr Gly Thr Thr Asp Phe Asp Asn Trp
            100                 105                 110
```

Gly Gln Gly Thr Leu Val Thr Val Ser Ser
         115                 120

<210> SEQ ID NO 453
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 456

<400> SEQUENCE: 453

Asp Tyr Tyr Met Ser
1               5

<210> SEQ ID NO 454
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 456

<400> SEQUENCE: 454

His Ile Ser Gly Ser Gly Thr Thr Ile Asp Tyr Ala Asp Ser Val Lys
1               5                   10                  15

Gly

<210> SEQ ID NO 455
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 456

<400> SEQUENCE: 455

Glu Asp Ser Arg Met Pro Gly Thr Thr Asp Phe Asp Asn
1               5                   10

<210> SEQ ID NO 456
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 456

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Asp Tyr
            20                  25                  30

Tyr Met Ser Trp Phe Arg Gln Ala Pro Gly Lys Gly Leu Glu Trp Val
        35                  40                  45

Ser His Ile Ser Gly Ser Gly Thr Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Arg Glu Asp Ser Arg Met Pro Gly Thr Thr Asp Phe Asp Asn Trp
            100                 105                 110

Gly Gln Gly Thr Leu Val Thr Val Ser Ser
        115                 120

<210> SEQ ID NO 457
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 460

<400> SEQUENCE: 457

Asp Tyr Tyr Met Thr
1               5

<210> SEQ ID NO 458
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 460

<400> SEQUENCE: 458

Tyr Ile Ser Gly Ser Gly Asp Thr Ile Asp Tyr Ala Glu Ser Val Lys
1               5                   10                  15

Gly

<210> SEQ ID NO 459
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 460

<400> SEQUENCE: 459

Glu Asp Ser Arg Ile Ala Gly Thr Thr Asp Phe Asp Asn
1               5                   10

<210> SEQ ID NO 460
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 460

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Phe Arg Gln Ala Pro Gly Lys Gly Leu Glu Trp Ile
        35                  40                  45

Ser Tyr Ile Ser Gly Ser Gly Asp Thr Ile Asp Tyr Ala Glu Ser Val
    50                  55                  60

-continued

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Arg Glu Asp Ser Arg Ile Ala Gly Thr Thr Asp Phe Asp Asn Trp
            100                 105                 110

Gly Pro Gly Thr Leu Val Thr Val Ser Ser
        115                 120

<210> SEQ ID NO 461
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 464

<400> SEQUENCE: 461

Asp Tyr Tyr Met Thr
1               5

<210> SEQ ID NO 462
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 464

<400> SEQUENCE: 462

Tyr Ile Ser Ser Ser Gly Ser Asn Ile Asp Tyr Ala Asp Ser Val Lys
1               5                   10                  15

Gly

<210> SEQ ID NO 463
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 464

<400> SEQUENCE: 463

Glu Asp Ser Arg Leu Ser Gly Thr Thr Asp Phe Asp Tyr
1               5                   10

<210> SEQ ID NO 464
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 464

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

```
Tyr Met Thr Trp Phe Arg Gln Ala Pro Gly Lys Gly Leu Glu Trp Val
        35                  40                  45
Ser Tyr Ile Ser Ser Ser Gly Ser Asn Ile Asp Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
Ala Arg Glu Asp Ser Arg Leu Ser Gly Thr Thr Asp Phe Asp Tyr Trp
            100                 105                 110
Gly Gln Gly Thr Leu Val Thr Val Ser Ser
            115                 120
```

<210> SEQ ID NO 465
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 468

<400> SEQUENCE: 465

```
Asp Tyr Tyr Met Thr
 1               5
```

<210> SEQ ID NO 466
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 468

<400> SEQUENCE: 466

```
Tyr Ile Ser Gly Ser Gly Asp Thr Ile Asp Tyr Ala Glu Ser Val Lys
 1               5                  10                  15
Gly
```

<210> SEQ ID NO 467
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 468

<400> SEQUENCE: 467

```
Glu Asp Ser Arg Ile Ala Gly Thr Thr Asp Phe Asp Asn
 1               5                  10
```

<210> SEQ ID NO 468
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 468

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Phe Arg Gln Ala Pro Gly Lys Gly Leu Glu Trp Ile
        35                  40                  45

Ser Tyr Ile Ser Gly Ser Gly Asp Thr Ile Asp Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Arg Glu Asp Ser Arg Ile Ala Gly Thr Thr Asp Phe Asp Asn Trp
            100                 105                 110

Gly Pro Gly Thr Leu Val Thr Val Ser Ser
        115                 120

<210> SEQ ID NO 469
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 472

<400> SEQUENCE: 469

Asp Tyr Tyr Met Ser
1               5

<210> SEQ ID NO 470
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 472

<400> SEQUENCE: 470

His Ile Ser Gly Ser Gly Thr Thr Ile Asp Tyr Ala Asp Ser Val Lys
1               5                   10                  15

Gly

<210> SEQ ID NO 471
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 472

<400> SEQUENCE: 471

Glu Asp Ile Arg Met Thr Gly Thr Thr Asp Phe Asp His
1               5                   10

<210> SEQ ID NO 472
<211> LENGTH: 122
<212> TYPE: PRT
<213> ORGANISM: Homo sapiens

```
<220> FEATURE:
<221> NAME/KEY: MISC_FEATURE
<222> LOCATION: (1)..(122)
<223> OTHER INFORMATION: VH binding to CD137

<400> SEQUENCE: 472
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser His Ile Ser Gly Ser Gly Thr Thr Ile Asp Tyr Ala Asp Ser Val
    50                  55                  60

Lys Gly Arg Phe Thr Ile Ser Arg Asp Asn Ala Arg Lys Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Thr Gly Thr Thr Asp Phe Asp His Trp
            100                 105                 110

Gly Gln Gly Thr Leu Val Thr Val Ser Ser
        115                 120

```
<210> SEQ ID NO 473
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 476

<400> SEQUENCE: 473
```

Asp Tyr Tyr Met Ser
1               5

```
<210> SEQ ID NO 474
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 476

<400> SEQUENCE: 474
```

His Ile Ser Ser Ser Gly Asn Thr Ile Asp Tyr Ala Asp Ser Val Lys
1               5                   10                  15

Gly

```
<210> SEQ ID NO 475
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 476

<400> SEQUENCE: 475
```

Glu Asp Pro Arg Leu Pro Gly Thr Thr Asp Phe Asp Tyr
1               5                   10

-continued

```
<210> SEQ ID NO 476
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 476

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser His Ile Ser Ser Ser Gly Asn Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Pro Gly Thr Thr Asp Phe Asp Tyr Trp
            100                 105                 110

Gly Gln Gly Thr Leu Val Thr Val Ser Ser
        115                 120

<210> SEQ ID NO 477
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 480

<400> SEQUENCE: 477

Asp Tyr Tyr Met Thr
1               5

<210> SEQ ID NO 478
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 480

<400> SEQUENCE: 478

Tyr Ile Ser Gly Ser Gly Asp Thr Ile Asp Tyr Ala Glu Ser Val Lys
1               5                   10                  15

Gly

<210> SEQ ID NO 479
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 480
```

<400> SEQUENCE: 479

Glu Asp Ile Arg Met Pro Gly Thr Thr Asp Phe Asp His
1               5                   10

<210> SEQ ID NO 480
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 480

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Phe Arg Gln Ala Pro Gly Lys Gly Leu Glu Trp Ile
        35                  40                  45

Ser Tyr Ile Ser Gly Ser Gly Asp Thr Ile Asp Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Pro Gly Thr Thr Asp Phe Asp His Trp
            100                 105                 110

Gly Gln Gly Thr Leu Val Thr Val Ser Ser
        115                 120

<210> SEQ ID NO 481
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 484

<400> SEQUENCE: 481

Asp Tyr Tyr Met Ser
1               5

<210> SEQ ID NO 482
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 484

<400> SEQUENCE: 482

His Ile Ser Gly Ser Gly Thr Thr Ile Asp Tyr Ala Asp Ser Val Lys
1               5                   10                  15

Gly

<210> SEQ ID NO 483
<211> LENGTH: 13
<212> TYPE: PRT
<213> ORGANISM: Homo sapiens

```
<220> FEATURE:
<221> NAME/KEY: MISC_FEATURE
<222> LOCATION: (1)..(13)
<223> OTHER INFORMATION: CDR3 OF SEQ ID NO: 484

<400> SEQUENCE: 483

Glu Asp Ile Arg Met Pro Gly Thr Thr Asp Phe Asp His
1               5                   10

<210> SEQ ID NO 484
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 484

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Asp Tyr
                20                  25                  30

Tyr Met Ser Trp Phe Arg Gln Ala Pro Gly Lys Gly Leu Glu Trp Val
            35                  40                  45

Ser His Ile Ser Gly Ser Gly Thr Thr Ile Asp Tyr Ala Asp Ser Val
        50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Pro Gly Thr Thr Asp Phe Asp His Trp
            100                 105                 110

Gly Gln Gly Thr Leu Val Thr Val Ser Ser
        115                 120

<210> SEQ ID NO 485
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 488

<400> SEQUENCE: 485

Asp Tyr Tyr Met Ser
1               5

<210> SEQ ID NO 486
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 488

<400> SEQUENCE: 486

His Ile Ser Ser Ser Gly Ser Thr Ile Asp Tyr Ala Asp Ser Val Lys
1               5                   10                  15

Gly
```

```
<210> SEQ ID NO 487
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 488

<400> SEQUENCE: 487

Glu Asp Pro Arg Leu Thr Gly Thr Thr Asp Phe Asp Tyr
1               5                   10

<210> SEQ ID NO 488
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 488

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser His Ile Ser Ser Ser Gly Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Thr Gly Thr Thr Asp Phe Asp Tyr Trp
            100                 105                 110

Gly Gln Gly Ala Leu Val Thr Val Ser Ser
        115                 120

<210> SEQ ID NO 489
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 492

<400> SEQUENCE: 489

Asp Tyr Tyr Met Ser
1               5

<210> SEQ ID NO 490
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 492
```

```
<400> SEQUENCE: 490

Tyr Ile Ser Ser Ser Gly Ser Thr Ile Ser Tyr Ala Asp Ser Val Lys
1               5                   10                  15

Gly

<210> SEQ ID NO 491
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 492

<400> SEQUENCE: 491

Glu Asp Pro Arg Ile Ser Gly Thr Thr Asp Phe Asp Asn
1               5                   10

<210> SEQ ID NO 492
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 492

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Ile Ser Gly Thr Thr Asp Phe Asp Asn Trp
            100                 105                 110

Gly Gln Gly Thr Leu Val Thr Val Ser Ser
        115                 120

<210> SEQ ID NO 493
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 496

<400> SEQUENCE: 493

Asp Tyr Tyr Met Ser
1               5

<210> SEQ ID NO 494
<211> LENGTH: 17
<212> TYPE: PRT
<213> ORGANISM: Homo sapiens
```

```
<220> FEATURE:
<221> NAME/KEY: MISC_FEATURE
<222> LOCATION: (1)..(17)
<223> OTHER INFORMATION: CDR2 OF SEQ ID NO: 496

<400> SEQUENCE: 494

His Ile Ser Ser Ser Gly Asn Thr Ile Asp Tyr Ala Asp Ser Val Lys
1               5                   10                  15
Gly

<210> SEQ ID NO 495
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 496

<400> SEQUENCE: 495

Glu Asp Pro Arg Leu Pro Gly Thr Thr Asp Phe Asp Tyr
1               5                   10

<210> SEQ ID NO 496
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 496

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Phe Arg Gln Ala Pro Gly Lys Gly Leu Glu Trp Val
            35                  40                  45

Ser His Ile Ser Ser Ser Gly Asn Thr Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Pro Gly Thr Thr Asp Phe Asp Tyr Trp
            100                 105                 110

Gly Gln Gly Thr Leu Val Thr Val Ser Ser
        115                 120

<210> SEQ ID NO 497
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 500

<400> SEQUENCE: 497

Asp Tyr Tyr Met Ser
1               5
```

```
<210> SEQ ID NO 498
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 500

<400> SEQUENCE: 498

Tyr Ile Ser Gly Thr Gly Ile Thr Thr Asp Tyr Ala Asp Ser Val Lys
1               5                   10                  15

Gly

<210> SEQ ID NO 499
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 500

<400> SEQUENCE: 499

Glu Asp Pro Arg Leu Pro Gly Thr Ser Glu Phe Asp Asn
1               5                   10

<210> SEQ ID NO 500
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 500

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Thr Gly Ile Thr Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Pro Gly Thr Ser Glu Phe Asp Asn Trp
            100                 105                 110

Gly Gln Gly Thr Leu Val Thr Val Ser Ser
        115                 120

<210> SEQ ID NO 501
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 504
```

<400> SEQUENCE: 501

Asp Tyr Tyr Met Ser
1               5

<210> SEQ ID NO 502
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 504

<400> SEQUENCE: 502

His Ile Ser Ser Ser Gly Ser Thr Ile Asp Tyr Ala Asp Ser Val Lys
1               5                   10                  15

Gly

<210> SEQ ID NO 503
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 504

<400> SEQUENCE: 503

Glu Asp Pro Arg Met Pro Gly Thr Phe Asp Phe Asp Asn
1               5                   10

<210> SEQ ID NO 504
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 504

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser His Ile Ser Ser Ser Gly Ser Thr Ile Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Met Pro Gly Thr Phe Asp Phe Asp Asn Trp
            100                 105                 110

Gly Gln Gly Thr Leu Val Thr Val Ser Ser
        115                 120

<210> SEQ ID NO 505
<211> LENGTH: 5
<212> TYPE: PRT
<213> ORGANISM: Homo sapiens

```
<220> FEATURE:
<221> NAME/KEY: MISC_FEATURE
<222> LOCATION: (1)..(5)
<223> OTHER INFORMATION: CDR1 OF SEQ ID NO: 508

<400> SEQUENCE: 505

Asp Tyr Tyr Met Ser
1               5

<210> SEQ ID NO 506
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 508

<400> SEQUENCE: 506

His Ile Ser Gly Ser Gly Thr Thr Ile Asp Tyr Ala Asp Ser Val Lys
1               5                   10                  15

Gly

<210> SEQ ID NO 507
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 508

<400> SEQUENCE: 507

Glu Asp Ile Arg Met Pro Gly Thr Thr Asp Phe Asp His
1               5                   10

<210> SEQ ID NO 508
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 508

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Asp Tyr
                20                  25                  30

Tyr Met Ser Trp Phe Arg Gln Ala Pro Gly Lys Gly Leu Glu Trp Val
            35                  40                  45

Ser His Ile Ser Gly Ser Gly Thr Thr Ile Asp Tyr Ala Asp Ser Val
        50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Pro Gly Thr Thr Asp Phe Asp His Trp
            100                 105                 110

Gly Gln Gly Thr Leu Val Thr Val Ser Ser
        115                 120
```

```
<210> SEQ ID NO 509
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 512

<400> SEQUENCE: 509

Asp Tyr Tyr Met Ser
1               5

<210> SEQ ID NO 510
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 512

<400> SEQUENCE: 510

His Ile Ser Gly Ser Gly Thr Thr Ile Asp Tyr Ala Asp Ser Val Lys
1               5                   10                  15

Gly

<210> SEQ ID NO 511
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 512

<400> SEQUENCE: 511

Glu Asp Ile Arg Met Pro Gly Thr Thr Asp Phe Asp His
1               5                   10

<210> SEQ ID NO 512
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 512

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser His Ile Ser Gly Ser Gly Thr Thr Ile Asp Tyr Ala Asp Ser Val
    50                  55                  60

Lys Gly Arg Phe Thr Ile Ser Arg Asp Asn Ala Arg Asp Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Pro Gly Thr Thr Asp Phe Asp His Trp
            100                 105                 110
```

```
Gly Gln Gly Thr Leu Val Thr Val Ser Ser
        115                 120
```

<210> SEQ ID NO 513
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 516

<400> SEQUENCE: 513

```
Asp Tyr Tyr Met Ser
1               5
```

<210> SEQ ID NO 514
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 516

<400> SEQUENCE: 514

```
His Ile Ser Gly Ser Gly Thr Thr Ile Asp Tyr Ala Asp Ser Val Lys
1               5                   10                  15

Gly
```

<210> SEQ ID NO 515
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 516

<400> SEQUENCE: 515

```
Glu Asp Ile Arg Met Pro Gly Thr Thr Asp Phe Asp His
1               5                   10
```

<210> SEQ ID NO 516
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 516

```
Glu Val Gln Leu Val Glu Ser Gly Gly Gly Leu Val Thr Pro Gly Gly
1               5                   10                  15

Ser Leu Arg Leu Ser Cys Ala Val Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser His Ile Ser Gly Ser Gly Thr Thr Ile Asp Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg Glu Asp Ile Arg Met Pro Gly Thr Thr Asp Phe Asp His Trp
            100                 105                 110

Gly Gln Gly Thr Leu Val Thr Val Ser Ser
        115                 120

<210> SEQ ID NO 517
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 520

<400> SEQUENCE: 517

Asp Tyr Tyr Met Ser
1               5

<210> SEQ ID NO 518
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 520

<400> SEQUENCE: 518

His Ile Ser Gly Ser Gly Thr Thr Ile Asp Tyr Ala Asp Ser Val Lys
1               5                   10                  15

Gly

<210> SEQ ID NO 519
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 520

<400> SEQUENCE: 519

Glu Asp Ile Arg Met Pro Gly Thr Thr Asp Phe Asp His
1               5                   10

<210> SEQ ID NO 520
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 520

Glu Val Gln Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser His Ile Ser Gly Ser Gly Thr Thr Ile Asp Tyr Ala Asp Ser Val
    50                  55                  60

```
Lys Gly Arg Phe Thr Ile Ser Arg Asp Asn Ala Arg Asn Ser Leu Tyr
 65                  70                  75                  80

Leu Gln Met Asn Ser Leu Arg Ala Glu Asp Thr Ala Met Tyr Tyr Cys
                 85                  90                  95

Ala Arg Glu Asp Ile Arg Met Pro Gly Thr Thr Asp Phe Asp His Trp
            100                 105                 110

Gly Gln Gly Thr Leu Val Thr Val Ser Ser
        115                 120

<210> SEQ ID NO 521
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 524

<400> SEQUENCE: 521

Asp Tyr Tyr Met Ser
1               5

<210> SEQ ID NO 522
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 524

<400> SEQUENCE: 522

His Ile Ser Gly Ser Gly Thr Thr Ile Asp Tyr Ala Asp Ser Val Lys
1               5                   10                  15

Asp

<210> SEQ ID NO 523
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 524

<400> SEQUENCE: 523

Glu Asp Ile Arg Met Pro Gly Thr Thr Asp Phe Asp His
1               5                   10

<210> SEQ ID NO 524
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 524

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Asp Tyr
            20                  25                  30
```

```
Tyr Met Ser Trp Phe Arg Gln Ala Pro Gly Lys Gly Leu Glu Trp Val
            35                  40                  45

Ser His Ile Ser Gly Ser Gly Thr Thr Ile Asp Tyr Ala Asp Ser Val
 50                  55                  60

Lys Asp Arg Phe Thr Ile Ser Arg Asp Asn Ala Arg Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Ile Arg Met Pro Gly Thr Thr Asp Phe Asp His Trp
            100                 105                 110

Gly Gln Gly Thr Leu Val Thr Val Ser Ser
            115                 120

<210> SEQ ID NO 525
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 528

<400> SEQUENCE: 525

Asp Tyr Tyr Met Ser
1               5

<210> SEQ ID NO 526
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 528

<400> SEQUENCE: 526

His Ile Ser Ser Ser Gly Thr Thr Ile Asp Tyr Ala Asp Ser Val Lys
1               5                   10                  15

Gly

<210> SEQ ID NO 527
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 528

<400> SEQUENCE: 527

Glu Asp Ile Arg Met Pro Gly Thr Thr Asp Phe Asp Asn
1               5                   10

<210> SEQ ID NO 528
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137
```

<400> SEQUENCE: 528

Glu Val Gln Leu Val Glu Ser Gly Gly Leu Val Lys Pro Gly Gly
1               5                   10                  15

Ser Leu Arg Leu Ser Cys Thr Ala Ser Gly Phe Thr Phe Thr Asp Tyr
            20                  25                  30

Tyr Met Ser Trp Phe Arg Gln Ala Pro Gly Lys Gly Leu Glu Trp Val
        35                  40                  45

Ser His Ile Ser Ser Ser Gly Thr Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Asp Ile Arg Met Pro Gly Thr Thr Asp Phe Asp Asn Trp
            100                 105                 110

Gly Gln Gly Thr Leu Val Thr Val Ser Ser
        115                 120

<210> SEQ ID NO 529
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 532

<400> SEQUENCE: 529

Asp Tyr Tyr Met Thr
1               5

<210> SEQ ID NO 530
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 532

<400> SEQUENCE: 530

Tyr Ile Ser Ser Ser Gly Ser Thr Ile Ser Tyr Ala Asp Ser Val Lys
1               5                   10                  15

Gly

<210> SEQ ID NO 531
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 532

<400> SEQUENCE: 531

Glu Asp Ile Arg Met Ser Gly Thr Thr Asp Phe Asp Tyr
1               5                   10

<210> SEQ ID NO 532
<211> LENGTH: 122
<212> TYPE: PRT
<213> ORGANISM: Homo sapiens

```
<220> FEATURE:
<221> NAME/KEY: MISC_FEATURE
<222> LOCATION: (1)..(122)
<223> OTHER INFORMATION: VH binding to CD137

<400> SEQUENCE: 532

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Phe Arg Gln Ala Pro Gly Lys Gly Leu Glu Trp Val
        35                  40                  45

Ser Tyr Ile Ser Ser Ser Gly Ser Thr Ile Ser Tyr Ala Asp Ser Val
    50                  55                  60

Lys Gly Arg Phe Thr Ile Ser Arg Asp Asn Ala Asn Asn Ser Leu Tyr
65                  70                  75                  80

Leu Gln Met Asn Ser Leu Arg Ala Glu Asp Thr Ala Val Tyr His Cys
                85                  90                  95

Ala Arg Glu Asp Ile Arg Met Ser Gly Thr Thr Asp Phe Asp Tyr Trp
            100                 105                 110

Gly Gln Gly Thr Leu Val Thr Val Ser Ser
        115                 120

<210> SEQ ID NO 533
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 536

<400> SEQUENCE: 533

Asp Tyr Tyr Met Ser
1               5

<210> SEQ ID NO 534
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 536

<400> SEQUENCE: 534

His Ile Ser Ser Ser Gly Ser Ser Ile Asp Tyr Ala Asp Ser Val Lys
1               5                   10                  15

Gly

<210> SEQ ID NO 535
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 536

<400> SEQUENCE: 535

Glu Asp Pro Arg Leu Ser Gly Thr Ile Asp Phe Asp Ser
1               5                   10
```

```
<210> SEQ ID NO 536
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 536
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Ser Trp Phe Arg Gln Ala Pro Gly Lys Gly Leu Glu Trp Val
        35                  40                  45

Ser His Ile Ser Ser Ser Gly Ser Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Ser Gly Thr Ile Asp Phe Asp Ser Trp
            100                 105                 110

Gly Gln Gly Thr Leu Val Thr Val Ser Ser
        115                 120

```
<210> SEQ ID NO 537
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 540

<400> SEQUENCE: 537
```

Asp Tyr Tyr Met Ser
1               5

```
<210> SEQ ID NO 538
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 540

<400> SEQUENCE: 538
```

His Ile Gly Gly Ser Gly Thr Thr Ile Asp Tyr Ala Asp Ser Val Lys
1               5                   10                  15

Gly

```
<210> SEQ ID NO 539
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 540
```

<400> SEQUENCE: 539

Glu Asp Ile Arg Met Pro Gly Thr Thr Asp Phe Asp His
1               5                   10

<210> SEQ ID NO 540
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 540

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Asp Tyr
            20                  25                  30

Tyr Met Ser Trp Phe Arg Gln Ala Pro Gly Lys Gly Leu Glu Trp Val
        35                  40                  45

Ser His Ile Gly Gly Ser Gly Thr Thr Ile Asp Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Pro Gly Thr Thr Asp Phe Asp His Trp
            100                 105                 110

Gly Gln Gly Thr Leu Val Thr Val Ser Ser
        115                 120

<210> SEQ ID NO 541
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 544

<400> SEQUENCE: 541

Asp Tyr Tyr Met Ser
1               5

<210> SEQ ID NO 542
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 544

<400> SEQUENCE: 542

Tyr Ile Ser Ser Ser Gly Ser Thr Ile Tyr Tyr Ala Asp Ser Val Lys
1               5                   10                  15

Gly

<210> SEQ ID NO 543
<211> LENGTH: 13
<212> TYPE: PRT
<213> ORGANISM: Homo sapiens

```
<220> FEATURE:
<221> NAME/KEY: MISC_FEATURE
<222> LOCATION: (1)..(13)
<223> OTHER INFORMATION: CDR3 OF SEQ ID NO: 544

<400> SEQUENCE: 543

Glu Asp Pro Arg Val Pro Gly Thr Thr Asn Phe Asp Tyr
1               5                   10

<210> SEQ ID NO 544
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 544

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Val Pro Gly Thr Thr Asn Phe Asp Tyr Trp
            100                 105                 110

Gly Gln Gly Thr Leu Val Thr Val Ser Ser
        115                 120

<210> SEQ ID NO 545
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 548

<400> SEQUENCE: 545

Asp Tyr Tyr Met Thr
1               5

<210> SEQ ID NO 546
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 548

<400> SEQUENCE: 546

Tyr Ile Ser Gly Ser Gly Ser Thr Ile Asp Tyr Ala Asp Ser Val Lys
1               5                   10                  15

Gly
```

```
<210> SEQ ID NO 547
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 548

<400> SEQUENCE: 547

Glu Asp Gly Arg Ile Pro Gly Thr Thr Asp Phe Asp His
1               5                   10

<210> SEQ ID NO 548
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 548

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Met Arg Gln Ala Pro Gly Lys Gly Leu Glu Trp Val
        35                  40                  45

Ser Tyr Ile Ser Gly Ser Gly Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Lys Glu Asp Gly Arg Ile Pro Gly Thr Thr Asp Phe Asp His Trp
            100                 105                 110

Gly Gln Gly Thr Leu Val Thr Val Ser Ser
        115                 120

<210> SEQ ID NO 549
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 552

<400> SEQUENCE: 549

Asp Tyr Tyr Met Ser
1               5

<210> SEQ ID NO 550
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 552
```

```
<400> SEQUENCE: 550

His Ile Ser Gly Ser Gly Thr Thr Ile Asp Tyr Ala Asp Ser Val Lys
1               5                   10                  15

Asp

<210> SEQ ID NO 551
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 552

<400> SEQUENCE: 551

Glu Asp Ile Arg Met Pro Gly Thr Thr Asp Phe Asp His
1               5                   10

<210> SEQ ID NO 552
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 552

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Asp Tyr
                20                  25                  30

Tyr Met Ser Trp Phe Arg Gln Ala Pro Gly Lys Gly Leu Glu Trp Val
            35                  40                  45

Ser His Ile Ser Gly Ser Gly Thr Thr Ile Asp Tyr Ala Asp Ser Val
        50                  55                  60

Lys Asp Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ile Arg Met Pro Gly Thr Thr Asp Phe Asp His Trp
            100                 105                 110

Gly Gln Gly Thr Leu Val Thr Val Ser Ser
        115                 120

<210> SEQ ID NO 553
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 556

<400> SEQUENCE: 553

Asp Tyr Phe Met Ser
1               5

<210> SEQ ID NO 554
<211> LENGTH: 17
<212> TYPE: PRT
<213> ORGANISM: Homo sapiens
```

```
<220> FEATURE:
<221> NAME/KEY: MISC_FEATURE
<222> LOCATION: (1)..(17)
<223> OTHER INFORMATION: CDR2 OF SEQ ID NO: 556

<400> SEQUENCE: 554

His Ile Ser Ser Ser Gly Asn Ser Ile Asp Tyr Ala Asp Ser Val Lys
1               5                   10                  15
Gly

<210> SEQ ID NO 555
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 556

<400> SEQUENCE: 555

Glu Asp Pro Arg Leu Pro Gly Thr Thr Asp Phe Asp Tyr
1               5                   10

<210> SEQ ID NO 556
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 556

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Pro Phe Ser Asp Tyr
            20                  25                  30

Phe Met Ser Trp Phe Arg Gln Ala Pro Gly Lys Gly Leu Glu Trp Val
        35                  40                  45

Ser His Ile Ser Ser Ser Gly Asn Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Glu Asp Pro Arg Leu Pro Gly Thr Thr Asp Phe Asp Tyr Trp
            100                 105                 110

Gly Gln Gly Thr Leu Val Thr Val Ser Ser
        115                 120

<210> SEQ ID NO 557
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 560

<400> SEQUENCE: 557

Asp Ser Tyr Met Ser
1               5
```

<210> SEQ ID NO 558
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 560

<400> SEQUENCE: 558

His Ile Ser Asn Ser Gly Ser Thr Ile Ser Tyr Ala Asp Ser Val Lys
1               5                   10                  15

Gly

<210> SEQ ID NO 559
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 560

<400> SEQUENCE: 559

Glu Asp Pro Arg Leu Pro Gly Thr Ser Asp Phe Asp Tyr
1               5                   10

<210> SEQ ID NO 560
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 560

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ser
            20                  25                  30

Tyr Met Ser Trp Ile Arg Gln Ala Pro Gly Lys Gly Leu Glu Trp Val
        35                  40                  45

Ser His Ile Ser Asn Ser Gly Ser Thr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Pro Gly Thr Ser Asp Phe Asp Tyr Trp
            100                 105                 110

Gly Gln Gly Thr Leu Val Thr Val Ser Ser
        115                 120

<210> SEQ ID NO 561
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 564

<400> SEQUENCE: 561

Asp Tyr Tyr Met Ser
1               5

<210> SEQ ID NO 562
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 564

<400> SEQUENCE: 562

His Ile Ser Ser Ser Gly Ser Ser Ile Asp Tyr Ala Asp Ser Val Lys
1               5                   10                  15

Gly

<210> SEQ ID NO 563
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 564

<400> SEQUENCE: 563

Glu Asp Pro Arg Leu Ser Gly Thr Thr Asp Phe Asp Gln
1               5                   10

<210> SEQ ID NO 564
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 564

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser His Ile Ser Ser Ser Gly Ser Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Asp Pro Arg Leu Ser Gly Thr Thr Asp Phe Asp Gln Trp
            100                 105                 110

Gly Gln Gly Thr Leu Val Thr Val Ser Ser
        115                 120

<210> SEQ ID NO 565
<211> LENGTH: 5
<212> TYPE: PRT
<213> ORGANISM: Homo sapiens

```
<220> FEATURE:
<221> NAME/KEY: MISC_FEATURE
<222> LOCATION: (1)..(5)
<223> OTHER INFORMATION: CDR1 OF SEQ ID NO: 568

<400> SEQUENCE: 565

Ser Tyr Trp Met Ser
1               5

<210> SEQ ID NO 566
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 568

<400> SEQUENCE: 566

His Ile Ser Ser Ser Gly Ser Thr Ile Asp Tyr Ala Glu Ser Val Lys
1               5                   10                  15

Gly

<210> SEQ ID NO 567
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 568

<400> SEQUENCE: 567

Glu Asp Pro Arg Met Thr Gly Thr Thr Asp Phe Asp Tyr
1               5                   10

<210> SEQ ID NO 568
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 568

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser His Ile Ser Ser Ser Gly Ser Thr Ile Asp Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Met Thr Gly Thr Thr Asp Phe Asp Tyr Trp
            100                 105                 110

Gly Gln Gly Thr Leu Val Thr Val Ser Ser
        115                 120
```

```
<210> SEQ ID NO 569
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 572

<400> SEQUENCE: 569

Asn Tyr Phe Met Ser
1               5

<210> SEQ ID NO 570
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 572

<400> SEQUENCE: 570

His Ile Ser Ser Ser Gly Asn Thr Ile Asp Tyr Ala Asp Ser Val Lys
1               5                   10                  15

Gly

<210> SEQ ID NO 571
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 572

<400> SEQUENCE: 571

Glu Asp Pro Arg Leu Pro Gly Thr Thr Asp Phe Asp Tyr
1               5                   10

<210> SEQ ID NO 572
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 572

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Phe Met Ser Trp Ile Arg Gln Ala Pro Gly Lys Gly Leu Glu Trp Val
        35                  40                  45

Ser His Ile Ser Ser Ser Gly Asn Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ser Arg Glu Asp Pro Arg Leu Pro Gly Thr Thr Asp Phe Asp Tyr Trp
            100                 105                 110
```

Gly Gln Gly Thr Leu Val Thr Val Ser Ser
          115                 120

<210> SEQ ID NO 573
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 576

<400> SEQUENCE: 573

Asp Tyr Tyr Met Thr
1               5

<210> SEQ ID NO 574
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 576

<400> SEQUENCE: 574

Tyr Ile Ser Ser Gly Gly Ser Thr Ile His Tyr Ala Asp Ser Val Lys
1               5                   10                  15

Gly

<210> SEQ ID NO 575
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 576

<400> SEQUENCE: 575

Glu Asn Pro Arg Leu Pro Gly Thr Met Asp Phe Asp Tyr
1               5                   10

<210> SEQ ID NO 576
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 576

Glu Val Gln Leu Val Glu Ser Gly Gly Gly Val Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Gly Pro Gly Lys Gly Gln Glu Trp Ile
        35                  40                  45

Ser Tyr Ile Ser Ser Gly Gly Ser Thr Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Pro Arg Leu Pro Gly Thr Met Asp Phe Asp Tyr Trp
            100                 105                 110

Gly Gln Gly Thr Leu Val Thr Val Ser Ser
            115                 120

<210> SEQ ID NO 577
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 580

<400> SEQUENCE: 577

Asp His Phe Met Ser
1               5

<210> SEQ ID NO 578
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 580

<400> SEQUENCE: 578

Asn Ile Lys Gln Asp Gly Ser Glu Lys Tyr Tyr Val Asp Ser Val Lys
1               5                   10                  15

Gly

<210> SEQ ID NO 579
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 580

<400> SEQUENCE: 579

Glu Asp Pro Arg Leu Thr Gly Thr Thr Asp Phe Asp Asn
1               5                   10

<210> SEQ ID NO 580
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 580

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Phe Met Ser Trp Phe Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Met Tyr Tyr Cys
                85                  90                  95

Ala Arg Glu Asp Pro Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 581
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 584

<400> SEQUENCE: 581

Asn Tyr Trp Met Thr
1               5

<210> SEQ ID NO 582
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 584

<400> SEQUENCE: 582

His Ile Ser Ser Thr Gly Ser Thr Ile Asp Tyr Ala Asp Ser Val Lys
1               5                   10                  15

Gly

<210> SEQ ID NO 583
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 584

<400> SEQUENCE: 583

Glu Asp Pro Arg Leu Pro Gly Thr Met Asp Phe Asp Tyr
1               5                   10

<210> SEQ ID NO 584
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 584

Glu Val Gln Leu Val Glu Ser Gly Gly Gly Leu Val Gln Ala Gly Gly
1               5                   10                  15

Ser Leu Arg Leu Ser Cys Val Ala Ser Gly Phe Thr Phe Ser Asn Tyr
            20                  25                  30

```
Trp Met Thr Trp Phe Arg Gln Ala Pro Gly Arg Gly Leu Glu Trp Val
            35                  40                  45

Ser His Ile Ser Ser Thr Gly Ser Thr Ile Asp Tyr Ala Asp Ser Val
 50                  55                  60

Lys Gly Arg Phe Thr Ile Ser Arg Asp Asn Ala Glu Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asp Pro Arg Leu Pro Gly Thr Met Asp Phe Asp Tyr Trp
            100                 105                 110

Gly Gln Gly Thr Leu Val Thr Val Ser Ser
            115                 120

<210> SEQ ID NO 585
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 588

<400> SEQUENCE: 585

Asp Tyr Tyr Met Ser
1               5

<210> SEQ ID NO 586
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 588

<400> SEQUENCE: 586

Tyr Ile Ser Gly Ser Gly Asp Ile Ile Asp Tyr Ala Asp Ser Val Lys
1               5                   10                  15

Gly

<210> SEQ ID NO 587
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 588

<400> SEQUENCE: 587

Glu Asp Ser Arg Leu Thr Gly Thr Thr Asp Phe Asp Asn
1               5                   10

<210> SEQ ID NO 588
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137
```

<400> SEQUENCE: 588

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr His Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 589
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 592

<400> SEQUENCE: 589

Asp Tyr Tyr Met Ser
1               5

<210> SEQ ID NO 590
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 592

<400> SEQUENCE: 590

Tyr Ile Ser Gly Ser Gly Asp Ile Ile Asp Tyr Ala Asp Ser Val Lys
1               5                   10                  15

Gly

<210> SEQ ID NO 591
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 592

<400> SEQUENCE: 591

Glu Asp Ser Arg Leu Thr Gly Thr Thr Asp Phe Asp Asn
1               5                   10

<210> SEQ ID NO 592
<211> LENGTH: 122
<212> TYPE: PRT
<213> ORGANISM: Homo sapiens

```
<220> FEATURE:
<221> NAME/KEY: MISC_FEATURE
<222> LOCATION: (1)..(122)
<223> OTHER INFORMATION: VH binding to CD137

<400> SEQUENCE: 592

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr His Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 593
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: OF SEQ ID NO: 596

<400> SEQUENCE: 593

Asp Tyr Tyr Met Ser
1               5

<210> SEQ ID NO 594
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 596

<400> SEQUENCE: 594

Tyr Ile Ser Gly Ser Gly Asp Ile Ile Asp Tyr Ala Asp Ser Val Lys
1               5                   10                  15

Gly

<210> SEQ ID NO 595
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 596

<400> SEQUENCE: 595

Glu Asp Ser Arg Leu Thr Gly Thr Thr Asp Phe Asp Asn
1               5                   10
```

```
<210> SEQ ID NO 596
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 596
```

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr Tyr Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

```
<210> SEQ ID NO 597
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 600

<400> SEQUENCE: 597
```

Asp Tyr Tyr Met Ser
1               5

```
<210> SEQ ID NO 598
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 600

<400> SEQUENCE: 598
```

Tyr Ile Ser Gly Ser Gly Asp Ile Ile Asp Tyr Ala Asp Ser Val Lys
1               5                   10                  15

Gly

```
<210> SEQ ID NO 599
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 600
```

<400> SEQUENCE: 599

Glu Asp Ser Arg Leu Thr Gly Thr Thr Asp Phe Asp Asn
1               5                   10

<210> SEQ ID NO 600
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 600

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr His Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 601
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 604

<400> SEQUENCE: 601

Asp Tyr Tyr Met Ser
1               5

<210> SEQ ID NO 602
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 604

<400> SEQUENCE: 602

Tyr Ile Ser Gly Ser Gly Asp Ile Ile Asp Tyr Ala Asp Ser Val Lys
1               5                   10                  15

Gly

<210> SEQ ID NO 603
<211> LENGTH: 13
<212> TYPE: PRT
<213> ORGANISM: Homo sapiens

```
<220> FEATURE:
<221> NAME/KEY: MISC_FEATURE
<222> LOCATION: (1)..(13)
<223> OTHER INFORMATION: CDR3 OF SEQ ID NO: 604

<400> SEQUENCE: 603

Glu Asp Ser Arg Leu Thr Gly Thr Thr Asp Phe Asp Asn
1               5                   10

<210> SEQ ID NO 604
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 604

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr Tyr Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 605
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 608

<400> SEQUENCE: 605

Asp Tyr Tyr Met Ser
1               5

<210> SEQ ID NO 606
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 608

<400> SEQUENCE: 606

Tyr Ile Ser Gly Ser Gly Asp Ile Ile Asp Tyr Ala Asp Ser Val Lys
1               5                   10                  15

Gly
```

```
<210> SEQ ID NO 607
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 608

<400> SEQUENCE: 607

Glu Asp Ser Arg Leu Thr Gly Thr Thr Asp Phe Asp Asn
1               5                   10

<210> SEQ ID NO 608
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 608

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 609
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 612

<400> SEQUENCE: 609

Asp Tyr Tyr Met Ser
1               5

<210> SEQ ID NO 610
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 612
```

<400> SEQUENCE: 610

Tyr Ile Ser Gly Ser Gly Asp Ile Ile Asp Tyr Ala Asp Ser Val Lys
1               5                   10                  15

Gly

<210> SEQ ID NO 611
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 612

<400> SEQUENCE: 611

Glu Asp Ser Arg Leu Thr Gly Thr Thr Asp Phe Asp Asn
1               5                   10

<210> SEQ ID NO 612
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 612

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 613
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 616

<400> SEQUENCE: 613

Asp Tyr Tyr Met Ser
1               5

<210> SEQ ID NO 614
<211> LENGTH: 17
<212> TYPE: PRT
<213> ORGANISM: Homo sapiens

```
<220> FEATURE:
<221> NAME/KEY: MISC_FEATURE
<222> LOCATION: (1)..(17)
<223> OTHER INFORMATION: CDR2 OF SEQ ID NO: 616

<400> SEQUENCE: 614
```

Tyr Ile Ser Gly Ser Gly Asp Ile Ile Asp Tyr Ala Asp Ser Val Lys
1               5                   10                  15

Gly

```
<210> SEQ ID NO 615
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 616

<400> SEQUENCE: 615
```

Glu Asp Ala Arg Leu Thr Gly Thr Thr Asp Phe Asp Asn
1               5                   10

```
<210> SEQ ID NO 616
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 616
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ala Arg Leu Thr Gly Thr Thr Asp Phe Asp Asn Trp
            100                 105                 110

Gly Gln Gly Thr Leu Val Thr Val Ser Ser
        115                 120

```
<210> SEQ ID NO 617
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 620

<400> SEQUENCE: 617
```

Asp Tyr Tyr Met Ser
1               5

```
<210> SEQ ID NO 618
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 620

<400> SEQUENCE: 618

Tyr Ile Ser Gly Ser Gly Asp Ile Ile Asp Tyr Ala Asp Ser Val Lys
1               5                   10                  15
Gly

<210> SEQ ID NO 619
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 620

<400> SEQUENCE: 619

Glu Asp Pro Arg Leu Thr Gly Thr Thr Asp Phe Asp Asn
1               5                   10

<210> SEQ ID NO 620
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 620

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 621
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 624
```

```
<400> SEQUENCE: 621

Asp Tyr Tyr Met Ser
1               5

<210> SEQ ID NO 622
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 624

<400> SEQUENCE: 622

Tyr Ile Ser Gly Ser Gly Asp Ile Ile Asp Tyr Ala Asp Ser Val Lys
1               5                   10                  15

Gly

<210> SEQ ID NO 623
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 624

<400> SEQUENCE: 623

Glu Asp Ala Arg Leu Thr Gly Thr Thr Asp Phe Asp Asn
1               5                   10

<210> SEQ ID NO 624
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 624

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Ala Arg Leu Thr Gly Thr Thr Asp Phe Asp Asn Trp
            100                 105                 110

Gly Gln Gly Thr Leu Val Thr Val Ser Ser
        115                 120

<210> SEQ ID NO 625
<211> LENGTH: 5
<212> TYPE: PRT
<213> ORGANISM: Homo sapiens
```

```
<220> FEATURE:
<221> NAME/KEY: MISC_FEATURE
<222> LOCATION: (1)..(5)
<223> OTHER INFORMATION: CDR1 OF SEQ ID NO: 628

<400> SEQUENCE: 625

Asp Tyr Tyr Met Ser
1               5

<210> SEQ ID NO 626
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 628

<400> SEQUENCE: 626

Tyr Ile Ser Gly Ser Gly Asp Ile Ile Asp Tyr Ala Asp Ser Val Lys
1               5                   10                  15

Gly

<210> SEQ ID NO 627
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: CDR3 OF SEQ ID NO: 628

<400> SEQUENCE: 627

Glu Asp Pro Arg Leu Thr Gly Thr Thr Asp Phe Asp Asn
1               5                   10

<210> SEQ ID NO 628
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH binding to CD137

<400> SEQUENCE: 628

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Pro Arg Leu Thr Gly Thr Thr Asp Phe Asp Asn Trp
            100                 105                 110

Gly Gln Gly Thr Leu Val Thr Val Ser Ser
        115                 120
```

```
<210> SEQ ID NO 629
<211> LENGTH: 369
<212> TYPE: DNA
<213> ORGANISM: Homo sapiens

<400> SEQUENCE: 629
gaggtgcagc tggtggagtc tgggggaggc ttggtccagc cggggggtc cctgagactc      60 tcctgtgcag cctctggatt cacctttagt agccattgga tgacttggtt ccgtcaggct     120
ccagggaagg ggctggagtg ggtggcccac ataaaggaag acggaagtga gaaatactat     180
gaggactctg tggagggccg attcaccgtc tccagagaca cgccaagaa ctcggtatat      240 ctgcaaatga acagtctgag agccgaagac acggctgtgt attactgtgc gagaggaggt     300
gatggctaca gtgactccca cttcggtgtg gacgtctggg gccaagggac cacggtcact     360
gtctcttca                                                              369

<210> SEQ ID NO 630
<211> LENGTH: 369
<212> TYPE: DNA
<213> ORGANISM: Homo sapiens

<400> SEQUENCE: 630
gaggtgcagc tggtggagtc tgggggaggc ttggtccagc cggggggtc cctgagactc      60 tcctgtgcag cctctggatt cacctttagt agttattgga tgacttggtt ccgtcaggct     120
ccagggaagg ggctggagtg ggtggcccac ataaaggaag acggaagtga gaaatactat     180
gtggactctg tggagggccg attcaccatc tccagagaca cgccaataa ctcgctgtat      240 ctacaaatga acagcctgag agccgaggac acggctgtgt attactgtgc gagaggaggt     300
gatggctaca gtgactccca ctacggtgtg gacgtctggg gccaagggac cacggtcacc     360
gtctcctca                                                              369

<210> SEQ ID NO 631
<211> LENGTH: 369
<212> TYPE: DNA
<213> ORGANISM: Homo sapiens

<400> SEQUENCE: 631
gaggtgcagc tggtggagtc tgggggaggc ttggtccagc ctgggggtc cctgagactc      60 tcctgtgcag cctctggatt cacctttagt agttattgga tgacctggtt ccgccaggct     120
ccagggaggg ggctggagtg ggtggccaac ataaaccaag atggaagtga gaaatactat     180
gtggactctg tggagggccg attcaccgtc tccagagaca cgccaagaa ctcactgtat      240 ctgcaaatga acagcctgag agccgaggac acggctgtgt attactgtgc gagaggggga     300
ttaggctacg tgactccca ctacggtatg gacgtctggg gccaagggac cacggtcact      360
gtctcctca                                                              369

<210> SEQ ID NO 632
<211> LENGTH: 369
<212> TYPE: DNA
<213> ORGANISM: Homo sapiens

<400> SEQUENCE: 632
gaggtgcagc tggtggagtc tgggggaggc ttggtccagc cggggggtc cctgagactc      60 tcctgtgcag cctctggatt cacctttagt aactattgga tgacctggtt ccgccaggct     120
ccaggggggg ggctggagtg ggtggccaac ataaaccaag atggaagtga gaaatactat     180
```

| | |
|---|---|
| gtggactctg tggagggccg attcaccgtc tccagagaca acgccaagaa ctcactgtat | 240 |
| ctacaaatga acagcctgag agccgaggac acggctgtgt attactgtgc gagaggggga | 300 |
| ttaggctacg gtgactccca ctacggtatg gacgtctggg gccaagggac cacggtcact | 360 |
| gtctcctca | 369 |

<210> SEQ ID NO 633
<211> LENGTH: 369
<212> TYPE: DNA
<213> ORGANISM: Homo sapiens

<400> SEQUENCE: 633

| | |
|---|---|
| gaggtgcagc tggtggagtc tgggggaggc ttggtccagc ctggggggtc cctgagactc | 60 |
| tcctgtgcag cctctggatt cacctttagt aactattgga tgatctggtt ccgccaggct | 120 |
| ccaggaaagg gctggagtg gtggccaac ataaaccaag atggaagtga aaatactat | 180 |
| gtggactctg tggagggccg attcaccatc tccagagaca acgccaagaa ctcactgtat | 240 |
| ctgcaaatga acagcctgag agccgaagac acggctgtgt attactgtgc gagaggaggt | 300 |
| gatggctaca gtggctccca ccacggtacg gacgtctggg gccaagggac cacggtcacc | 360 |
| gtctcctca | 369 |

<210> SEQ ID NO 634
<211> LENGTH: 369
<212> TYPE: DNA
<213> ORGANISM: Homo sapiens

<400> SEQUENCE: 634

| | |
|---|---|
| gaggtgcagc tggtggagtc tgggggaggc ttggtccagc ctggggggtc cctgagactc | 60 |
| tcctgtgcag cctctggatt cacctttagt agctattgga tgagctgggt ccgccaggct | 120 |
| ccagggaagg gctggagtg gtggccaac ataaagcaag atggaagtga aaatactat | 180 |
| gtggactctg tgaagggccg attcaccatc tccagagaca acgccaagaa ctcactgtat | 240 |
| ctgcaaatga acagcctgag agccgaggac acggctgtgt attactgtgc gagaggggg | 300 |
| gaaggctata gcacctcgca ctacggtatg gacgtctggg gccaagggac cacggtcacc | 360 |
| gtctcctca | 369 |

<210> SEQ ID NO 635
<211> LENGTH: 369
<212> TYPE: DNA
<213> ORGANISM: Homo sapiens

<400> SEQUENCE: 635

| | |
|---|---|
| gaggtgcagc tggtggagtc tgggggaggc ttggtccagc ctggggggtc cctgagactc | 60 |
| tcctgtggag cctctggatt cacctttagt agctattgga tgctctggtt ccgccaggct | 120 |
| cagggaagg gctggagtg gtggccaac ataaaccaag atggaagtga aaatactat | 180 |
| gtggactctg tgaagggccg attcaccatc tccagagaca acgccaagaa ctcactgtat | 240 |
| ctgcaaatga acaccctgag agccgaggac acggctattt attattgtgc gagaggggt | 300 |
| gatggctaca gtgactccca cttcggtacg gacgtctggg gccaagggac cacggtcact | 360 |
| gtctcctca | 369 |

<210> SEQ ID NO 636
<211> LENGTH: 369
<212> TYPE: DNA
<213> ORGANISM: Homo sapiens

<400> SEQUENCE: 636

```
gaggtgcagc tggtggagtc tgggggaggc ttggtccagc ctggggggtc cctgagactc    60
tcctgtggag cctctggatt cacctttagt agctattgga tgttctggtt ccgccaggct   120
ccaggagagg ggctggagtg ggtggccaac ataaaccaag atggaagtga aaatactat    180
gtggactctg tggagggccg attcaccatc tccagagaca acgccaagaa ctctctgtat   240
ctgcaaatga acagcctgag agccgaggac acggctattt attactgtgc gagaggaggt   300
gatggctaca gtgattccca ctacggtacg gacgtctggg gccaagggac cacggtcacc   360
gtctcctca                                                           369
```

<210> SEQ ID NO 637
<211> LENGTH: 369
<212> TYPE: DNA
<213> ORGANISM: Homo sapiens

<400> SEQUENCE: 637

```
gaggtgcagc tggtggagtc tgggggaggc ttggtccagc cggggggtc cctgagactc     60
tcctgtgcag cctctggatt cacctttagt aactattgga tgacctggtt ccgccaggct   120
ccagggggg ggctggagtg ggtggccaac ataaaccaag atgggagtga aagtactat     180
gtggactctg tggagggccg attcaccgtc tccagagaca acgccaagaa ctcactggat   240
ctgcaaatga acagcctgag agccgaggac acggctgtgt attactgtgc gagagggga    300
ttaggctacg gtgactccca ctacggtatg gacgtctggg gccaagggac cacggtcacc   360
gtctcctca                                                           369
```

<210> SEQ ID NO 638
<211> LENGTH: 369
<212> TYPE: DNA
<213> ORGANISM: Homo sapiens

<400> SEQUENCE: 638

```
gaggtgcagc tggtggagtc tgggggaggc ttggtccagc ctggggggtc cctgagactc    60
tcctgtgcag cctctggatt cacctttagt gactattgga tgaactgggc ccgccaggct   120
ccagggaagg ggctggagtg ggtggccaac ataaaggagg atggaagtga aaatactat    180
gtggactctg tggagggccg attcaccata tccagagaca acgccaagaa ctcaacgtat   240
ctgcaaatga acagcctgag agtcgaggac acggctgtgt attactgtgc gagaggaggg   300
gccgggtata gcatgtctca ctacggtatg gacgtctggg gccaagggac cacggtcact   360
gtctcttca                                                           369
```

<210> SEQ ID NO 639
<211> LENGTH: 369
<212> TYPE: DNA
<213> ORGANISM: Homo sapiens

<400> SEQUENCE: 639

```
gaggtgcagc tggtggagtc tgggggaggc ttggtccagc ctggggggtc cctgagactc    60
tcctgtgaag cctctggatt cacctttagt gactattgga tgaactgggc ccgccaggct   120
ccagggaagg ggctggagtg ggtggccaac ataaaggagg atggaagtga aaatactat    180
gtggactctg tggagggccg attcaccata tccagagaca acgccaagaa ctcaacgtat   240
ctgcaaatga acagcctgag agccgaggac acggctgtgt attactgtgc gagaggaggg   300
```

```
gccgggtata gtatgtctca ctacggtatg gacgtctggg gccaagggac cacggtcact    360
gtctcctca                                                            369
```

<210> SEQ ID NO 640
<211> LENGTH: 369
<212> TYPE: DNA
<213> ORGANISM: Homo sapiens

<400> SEQUENCE: 640

```
gaggtgcagc tggtggagtc tgggggaggc ttggtccagc ctgggggdtc cctgagactc    60
tcctgtggag cctctggatt cacctttagt agctattgga tgctctggtt ccgccaggct    120
ccagggaagg ggctggagtg ggtggccaac ataaaccaag atggaagtga aaatactat     180 gtggactctg tgaagggccg attcaccatc tccagagaca acgccaagaa ctcactgtat    240
ctgcaaatga acaccctgcg agccgaggac acggctattt attattgtgc gagaggggt    300 gatggctaca gtaactccca cttcggtacg gacgtctggg gccaagggac cacggtcacc    360
gtctcttca                                                            369
```

<210> SEQ ID NO 641
<211> LENGTH: 369
<212> TYPE: DNA
<213> ORGANISM: Homo sapiens

<400> SEQUENCE: 641

```
gaggtgcagc tggtggagtc tgggggaggc ttggtcaagc ctgggggdtc cctgagactc    60
tcctgtggag cctctggatt cacctttagt agctattgga tgttctggtt ccgccaggct    120
ccaggagagg ggctggagtg ggtggccaac ataaaccaag atggaagtga aaatactat     180 gtggactctg tgagggccg attcaccatc tccagagaca acgccaagaa ctctctgtat     240
ctgcaaatga acagcctgag agccgaggac acggctattt attactgtgc gagaggaggt    300
gatggctaca gtgattccca ctacggtacg gacgtctggg gccaagggac cacggtcacc    360
gtctcctca                                                            369
```

<210> SEQ ID NO 642
<211> LENGTH: 369
<212> TYPE: DNA
<213> ORGANISM: Homo sapiens

<400> SEQUENCE: 642

```
gaggtgcagc tggtggagtc tgggggaggc ttggtccagc ctgggggdtc cctgagactc    60
tcctgtgcag cctctggatt cacctttagt aattattgga tgaactgggt ccgccaggct    120
ccagggaagg ggctggagtg ggtggccaac ataaaggaag atggaagtga gaattactat    180
gtggactctg tgaagggccg attcaccatc tccagagaca acgccaagaa ctcactgtat    240
ctgcaaatga acagcctgag agccgaggac acggctgttt attactgtgc gagagggggg    300
gaaggctata gcacctcgca ctacggtatg gacgtctggg gccaagggac cacggtcact    360
gtctcctca                                                            369
```

<210> SEQ ID NO 643
<211> LENGTH: 369
<212> TYPE: DNA
<213> ORGANISM: Homo sapiens

<400> SEQUENCE: 643

| | | |
|---|---|---|
| gaggtgcagc tggtggagtc tgggggaggc ttggtccagc ctgggggtc cctgagactc | 60 |
| tcctgtggag cctctggatt cacctttagt acctattgga tgctctggtt ccgccaggct | 120 |
| ccagggaagg ggctggagtg ggtggccaac ataaaccaag atggaagtga gaaatactat | 180 |
| gtggactctg tgaagggccg attcaccatc tccagagaca acgccaagaa ctcactgtct | 240 |
| ctacaaatga acagcctgag agccgaggac acggcaactt attactgtgc gagaggaggt | 300 |
| gatggctaca gtgactccca cttcggtacg gacgtctggg gccaagggac cacggtcacc | 360 |
| gtctcctca | 369 |

<210> SEQ ID NO 644
<211> LENGTH: 369
<212> TYPE: DNA
<213> ORGANISM: Homo sapiens

<400> SEQUENCE: 644

| | | |
|---|---|---|
| gaggtgcagc tggtggagtc tgggggaggc ttggtccagc ctgggggtc cctgagactc | 60 |
| tcctgtgtag cctctggatt cacctttagt aactattgga tgatgtggtt ccgccaggct | 120 |
| ccaggaaagg ggctggagtg ggtggccaac ataaaccaag atggaagtga gaaatacttt | 180 |
| gtggactctg tggagggccg attcaccatc tccagagaca acgccaagaa ctcactgtat | 240 |
| ctgcaaatga acagcctgag agccgaagac acggctgtgt attactgtgc gagaggaggt | 300 |
| gatggctaca gtagctctca ctacggtacg gacgtctggg gccaagggac cacggtcacc | 360 |
| gtctcttca | 369 |

<210> SEQ ID NO 645
<211> LENGTH: 369
<212> TYPE: DNA
<213> ORGANISM: Homo sapiens

<400> SEQUENCE: 645

| | | |
|---|---|---|
| gaggtgcagc tggtggagtc tgggggaggc ttggtccagc ctgggggtc cctgagactc | 60 |
| tcctgtgcag cctctggatt cacctttagt agctattgga tgaactgggt ccgccaggct | 120 |
| ccagggaagg ggctggagtg ggtggccaac ataaaggaag atggaagtga gaaatactat | 180 |
| gtggactctg tgaagggccg attcaccatc tccagagaca acgccaagaa ctcactgtat | 240 |
| ctgcaaatga acagcctgag agccgaggac acggctgtgt attactgtgc gagagggggg | 300 |
| gacagctatg gttacaggga ctacggtatg gacgtctggg gccaagggac cacggtcact | 360 |
| gtctcctca | 369 |

<210> SEQ ID NO 646
<211> LENGTH: 369
<212> TYPE: DNA
<213> ORGANISM: Homo sapiens

<400> SEQUENCE: 646

| | | |
|---|---|---|
| gaggtgcagc tggtggagtc tgggggaggc ttggtccagc ctgggggtc cctgagactc | 60 |
| tcctgtgcag cctctggatt cacctttagt acccattgga tgaactgggc ccgccaggct | 120 |
| ccagggaagg agctggaatg ggtggccaac ataaaccaag atggaagtga gaaatactat | 180 |
| gtggactctg tgaagggccg attcaccatc tccagagaca acgccaacaa ttcactgtat | 240 |
| ctgcaaatga acagcctgag agccgaagac acggctgtat attactgtgc gagagggggg | 300 |

-continued

```
gttggctacg gtgactccca cttcggtatg gacgtctggg gcctagggac cacggtcacc    360
gtctcctca                                                            369
```

<210> SEQ ID NO 647
<211> LENGTH: 369
<212> TYPE: DNA
<213> ORGANISM: Homo sapiens

<400> SEQUENCE: 647

```
gaggtgcagc tggtggagtc tgggggaggc ttggtccagc ctgggggtc cctgagactc      60 tcctgtgcag cctctggatt caccttagt agctattgga tgatctgggt ccgccaggct    120
ccagggaagg gctggagtg gtggccaac ataaaccaag atggaagtga gaaatactat     180
gtggactctg tgaagggccg attcaccatc tccagagaca acgccaagaa ctcactgtat    240
ctgcaaatga acagcctgag agccgaggac acggctgtgt attactgtgc gagaggaggt    300
gatgactaca gtaactccca ctacggtatg gacgtctcgg gccaagggac cacggtcacc    360
gtctcctca                                                            369
```

<210> SEQ ID NO 648
<211> LENGTH: 369
<212> TYPE: DNA
<213> ORGANISM: Homo sapiens

<400> SEQUENCE: 648

```
gaggtgcagc tggtggagtc tgggggaggc ttggtccagc ctgggggtc cctgagactc      60 tcctgtgcag cctctggatt cacctttagt agctattgga tgaactgggt ccgccaggct    120
ccagggaagg gctggagtg gtggccaac ataaaccaag atggaagtga gaaatactat     180
gtggactctg tgcagggccg attcaccatc tccagagaca atgccaataa ctcactgtat    240
ctgcaaatga acagcctgag agccgaggac acggctgtgt attactgtgc gagagggggg    300
tttggctacg gtgactccca ctacggtatg gacgtctggg gccaagggac cacggtcacc    360
gtctcctca                                                            369
```

<210> SEQ ID NO 649
<211> LENGTH: 369
<212> TYPE: DNA
<213> ORGANISM: Homo sapiens

<400> SEQUENCE: 649

```
gaggtgcagc tggtggagtc tgggggaggc ttggtccagc ctgggggtc cctgagactc      60 tcctgtggag cctctggatt cacctttagt agttattgga tgttctggtt ccgccaggct    120
ccaggaaagg agctggagtg gtggccaat gttaaccaag atggaagtga gaaatactat     180
gtggactctg tggagggccg attcaccatc tccagagaca acgccaagaa ctcactgtat    240
ctgcaaatga acagcctgag agccgaggac acggctattt attactgtgc gagaggaggt    300
gagggctaca gtgattccca ctacggtacg gacgtctggg gccaagggac cacggtcacc    360
gtctcctca                                                            369
```

<210> SEQ ID NO 650
<211> LENGTH: 369
<212> TYPE: DNA
<213> ORGANISM: Homo sapiens

<400> SEQUENCE: 650
caggtgcagc tggtggagtc tggggggaggc ttggtccagc ctggggggtc cctgagactc        60
tcctgtgcag cctctggatt cacctttagt aactattgga tgaactgggt ccgccaggct       120
ccagggaagg ggctggagtg ggtggccaat ataaaggaag atggaagtga gaaatactat       180
gtggactctg tgaagggccg attcaccatc tccagagaca acgccaggaa ctcactgtat       240
ctgcaaatga acagtctgag agccgaggac acggctgtgt attactgtgc gagagggggg       300
gagggctacg gtgactccca ctacggtatg gacgtctcgg gccaagggac cacggtcact       360
gtctcttca                                                               369

<210> SEQ ID NO 651
<211> LENGTH: 369
<212> TYPE: DNA
<213> ORGANISM: Homo sapiens

<400> SEQUENCE: 651
caggtgcagc tggtggagtc tggggggaggc ttggtccagc ctggggggtc cctgagactc        60
tcctgtgcag cctctggatt cacctttagt agttattgga tgaactgggt ccgccaggct       120
ccagggaagg ggctggagtg ggtggccaac ataaagcaag atggaagtga gaaatactat       180
gtggactctg tgaagggccg attcaccatc tccagagaca acgccaagaa ctcactttat       240
ctgcaaatga acagcctgac agccgaggac acggctgtgt attattgtgc gagagggggg       300
gagggctacg gtgacgacca ctacggtatg gacgtctggg gccaagggac cacggtcact       360
gtctcttca                                                               369

<210> SEQ ID NO 652
<211> LENGTH: 369
<212> TYPE: DNA
<213> ORGANISM: Homo sapiens

<400> SEQUENCE: 652
caggtgcagc tggtggagtc tggggggaggc ttggtccagc ctggggggtc cctgagactc        60
tcctgtgcag cctctggatt cacctttagt agctattgga tgagctgggt ccgccaggct       120
ccagggaagg ggctggagtg ggtggccaac ataaagcaag atggaagtga gaaatactat       180
gtggactctg tgaagggccg attcaccatc tccagagaca acgccaagaa ctcactgtat       240
ctgcaaatga acagcctgag agccgaggac acggctgtgt attactgtgc gagagggggg       300
gagggctacg gtgactacca ctacggtttg gacgtctcgg gccaagggac cacggtcacc       360
gtctcctca                                                               369

<210> SEQ ID NO 653
<211> LENGTH: 369
<212> TYPE: DNA
<213> ORGANISM: Homo sapiens

<400> SEQUENCE: 653
gaggtgcagc tggtggagtc tggggggaggc ttggtccagc ctggggggtc cctgagactc        60
tcctgtgcag cctctggatt cacctttagt agctattgga tgaactgggt ccgccaggct       120
ccagggaagg ggctggagtg ggtggccaac ataaagcaag atggaagtga gaaatactat       180
gtggactctg tgaagggccg attcaccatc tccagagaca acgccaagaa ctcactgtat       240
ctgcaaatga acagcctgag agccgaggac acggctgtgt attactgtgc gagagggggg       300

```
gacagctatg gttacaggga ctacggtatg gacgtctggg gccaagggac cacggtcacc    360
gtctcctca                                                            369

<210> SEQ ID NO 654
<211> LENGTH: 369
<212> TYPE: DNA
<213> ORGANISM: Homo sapiens

<400> SEQUENCE: 654
gaggtgcagc tggtggagtc tgggggaggc ttggtccagc ctgggggtc cctgagactc      60 tcctgtgtag cctctggatt cacctttagt acccattgga tgaactgggc cgccaggct     120 ccagggaagg agctggaatg ggtggccaac ataaaccaag atggaagtga gaaatactat    180
gtggactctg tgagggccg attcaccatc tccagagaca acgccaacaa ttcactgtat     240
ctgcaaatga acagcctgag agccgaagac acggctgtat attactgtgc gagagggggg    300
gttggctacg gtgactccca cttcggtatg gacgtctggg gcctagggac cacggtcact    360
gtctcctca                                                            369

<210> SEQ ID NO 655
<211> LENGTH: 369
<212> TYPE: DNA
<213> ORGANISM: Homo sapiens

<400> SEQUENCE: 655
gaggtgcagc tggtggagtc tgggggaggc ttggtccagc ctgggggtc cctgagactc      60 tcctgtggag cctctggatt cacctttagt agttattgga tgctctggtt ccgccaggct    120
ccaggagagg ggctggagtg ggtggccaac ataaaccaag atggaagtga gaaatactat    180
gtggactctg tgagggccg actcaccatc tccagagaca acgccaagaa cgctctgtat     240
ctgcaaatga acagcctgag agccgaggac acggctattt attactgtgc gagaggaggt    300
gaaggctaca gtgattccca ccacggtacg gacgtctggg gccaagggac cacggtcact    360
gtctcttca                                                            369

<210> SEQ ID NO 656
<211> LENGTH: 369
<212> TYPE: DNA
<213> ORGANISM: Homo sapiens

<400> SEQUENCE: 656
gaggtgcagc tggtggagtc tgggggaggc ttggtccagc ctgggggtc cctgagactc      60 tcctgtgcag cctctggatt cacctttagt aactattgga tgaactgggt ccgccaggct    120
ccagggaagg ggctggagtg ggtggccaac ataaagcaag atggaagtga gaaatactat    180
gtggactctg tgaagggccg attcaccatc tccagagaca acgccaagaa ctcactgtat    240
ctgcaaatga acagcctgag agccgaggac acggctgtgt attactgtgc gagaggggg     300 gacaactatg cttacaggga cttcggtatg gacgtctggg gccaagggac cacggtcact    360
gtctcttca                                                            369

<210> SEQ ID NO 657
<211> LENGTH: 369
<212> TYPE: DNA
<213> ORGANISM: Homo sapiens
```

<400> SEQUENCE: 657

```
gaggtgcagc tggtggagtc tgggggaggc ttggtccagc ctggggggtc cctgagactc    60
tcctgtggag cctctggatt cacctttagt aattattgga tgttctggtt ccgccaggct   120
ccaggaaagg agctggagtg ggtggccaat gttaaccaag atggaagtga aaatactat   180 gtggactctg tggagggccg attcaccatc tccagagaca acgccaagaa ctcactgtat   240
ctgcaaatga acagcctgag agccgaggac acggctattt attactgtgc gagaggaggt   300
gagggctaca gtgattccca ctacggtacg gacgtctggg gccaagggac cacggtcact   360
gtctcttca                                                           369
```

<210> SEQ ID NO 658
<211> LENGTH: 369
<212> TYPE: DNA
<213> ORGANISM: Homo sapiens

<400> SEQUENCE: 658

```
gaggtgcagc tggtggagtc tgggggaggc ttggtccagc ctggggggtc cctgagactc    60
tcctgtgcag cctctggatt cacctttagt agctattgga tgaactgggt ccgccaggct   120
ccagggaagg ggctggagtg ggtggccaac ataaaccaag atggaagtga aaatactat   180 gtggactctg tgaagggccg attcaccatc tccagagaca acgccaagaa ctcactgtat   240
ctgcaaatga acagcctgag agccgaggac acggctgtgt attactgtgc gagaggggggg   300 gaagagtatg ggagctcgca ctacggtatg gacgtctggg gcctggggac cacggtcact   360
gtctcctca                                                           369
```

<210> SEQ ID NO 659
<211> LENGTH: 369
<212> TYPE: DNA
<213> ORGANISM: Homo sapiens

<400> SEQUENCE: 659

```
gaggtgcagc tggtggagtc tgggggaggc ttggtccagc ctggggggtc cctgagactc    60
tcctgtgcag cctctggatt cacctttagt agctattgga tgaactgggt ccgccaggct   120
ccagggaagg ggctggagtg ggtggccaac ataaaccaag atggaagtga aaatactat   180 gtggactctg tgaagggccg attcaccatc tccagagaca acgccaagaa ctcactgtat   240
ctgcaaatga acagcctgag agccgaggac acggctgtgt attattgtgc gagaggggggg   300 gacagctatg gttacaggga ctacggtatg gacgtctggg gccaagggac cacggtcact   360
gtctcttca                                                           369
```

<210> SEQ ID NO 660
<211> LENGTH: 369
<212> TYPE: DNA
<213> ORGANISM: Homo sapiens

<400> SEQUENCE: 660

```
gaggtgcagc tggtggagtc tgggggaggc ttggtccagc cggggggggtc cctaagactc    60 tcctgtgcag cctctggatt cacctttagt agttattgga tgaactgggt ccgccagact   120
ccagggaagg ggctggagtg ggtggccaac ataaatcaaa atggaagtga aaatactat   180 gtggactctg tggagggccg attcaacatc tccagagaca acgccaagaa ctcactgtat   240
ctacaaatga gtagcctgag agccgaggac acggctgtgt attactgtgc gagagggggg   300
```
tttggctacg gtgattccca ctacggtatg gacgtctggg gccaagggac cacggtcact    360
gtctcttca                                                            369

<210> SEQ ID NO 661
<211> LENGTH: 369
<212> TYPE: DNA
<213> ORGANISM: Homo sapiens

<400> SEQUENCE: 661
gaggtgcagc tggtggagtc tgggggaggc ttggtccagg cggggggtc cctaagactc     60 tcctgtgtag cctctggatt cacctttagt aattattgga tgacctggtt ccgccaggct   120
ccagggaagg ggctggagtg ggtggccaac ataaaccaag atgaaagtga ggaatactat   180
gtggactctg tgaagggccg tttcaccatc tccagagaca acgccaagaa ctcactgttt   240
ctgcaaatga acagcctgag agccgaggac acggctattt attactgtgc gagaggaggt   300
gatggctaca gtgactccca ctacggtacg gacgtctggg gccaagggac cacggtcact   360
gtctcttca                                                            369

<210> SEQ ID NO 662
<211> LENGTH: 369
<212> TYPE: DNA
<213> ORGANISM: Homo sapiens

<400> SEQUENCE: 662
caggtgcagc tgcaggagtc ggggggaggc ttggtccagc ctgggggtc cctgagactc     60 tcctgtacag cctctggatt cacctttagt aattattgga tgaactgggt ccgccaggct   120
ccagggaagg ggctggagtg ggtggccaac ataaggaag atggaagtga gaattactat    180
gtggactctg tgaagggccg attcaccatc tccagagaca acgccaagaa ctcactgtat   240
ctgcaaatga acagcctgag agccgaggac acggctgttt attactgtgc gagagggggg   300
gaaggctata gcacctcgca ctacggtatg gacgtctggg gccaagggac cacggtcacc   360
gtctcttca                                                            369

<210> SEQ ID NO 663
<211> LENGTH: 369
<212> TYPE: DNA
<213> ORGANISM: Homo sapiens

<400> SEQUENCE: 663
caggtgcagc tggtggagtc tgggggaggc ttggtccagc ctgggggtc cctgagactc     60 tcctgtgcag cctctggatt cacctttagt aactattgga tgaactgggt ccgccaggct   120
ccagggaagg ggctggagtg ggtggccaac attaagcaag atggaagtga gaaatactat   180
gtggactctg tggagggccg attcaccatc tccagagaca acgccaagaa ctcactgtat   240
ctgcaaatgg acagcctgag agccgaggac acggctgttt attactgtgc gagagggggg   300
gagggctacg gtgaatccca ctacggtatg gacgtctcgg gccaagggac cacggtcacc   360
gtctcttca                                                            369

<210> SEQ ID NO 664
<211> LENGTH: 369
<212> TYPE: DNA
<213> ORGANISM: Homo sapiens -continued

<400> SEQUENCE: 664
gaggtgcagc tggtggagtc tgggggaggc ttggtccagc ctggggggtc cctgagactc      60
tcctgtgcag cctctggatt cacctttagt acctattgga tgaactgggt ccgccaggct     120
ccagggaagg ggctggagtg ggtggccaac ataaaacaag atggaagtga aaatactat     180 gtggactctg tgaagggccg attcaccatc tccagagaca cgccaagaa ctcactgtat      240 ctgcaaatga acagcctgag agccgaggac acggctgtgt attactgtgc gagagggggg     300
gacagctatg gttacaggga ctacggtatg gacgtctggg gccaagggac cacggtcact    360
gtctcctca                                                            369

<210> SEQ ID NO 665
<211> LENGTH: 369
<212> TYPE: DNA
<213> ORGANISM: Homo sapiens

<400> SEQUENCE: 665
gaggtgcagc tggtggagtc tgggggaggc ttggtccagc ctggggggtc cctgagactc      60
tcctgtgcag cctctggatt cacctttagt tactattgga tgatctggtt ccgccaggct     120
ccaggtgagg agctggagtg ggtggccaac ataaaccaag atggaagtga aaatactat     180 gtggactctg tgaagggccg attcattatc tccagagaca cgccacgaa ctcactgttt      240 ctgcaaatga acagcctgag agccgaggac acggctgttt attactgtgc gagaggaggt     300
gatggctaca gtaattccca cttcggtatg gacgtctggg gccaagggac cacggtcacc    360
gtctcttca                                                            369

<210> SEQ ID NO 666
<211> LENGTH: 369
<212> TYPE: DNA
<213> ORGANISM: Homo sapiens

<400> SEQUENCE: 666
gaggtgcagc tggtggagtc tgggggaggc ttggtccagc ctggggggtc cctgagactc      60
tcctgtgcag cctctggatt cacctttagt aactattgga tgatctggta ccgccaggct     120
ccaggtgagg agctggagtg ggtggccaac ataaaccaag atggaagtga aaatactat     180 gtggactctg tgaagggccg attcaccatc tccagagaca cgccaagaa ctcactgtat      240 ctgcaaatga acagcctgag agccgaggac acggctattt attactgtgc gagaggaggt     300
gagggctaca gtgattccca ctacggtacg gacgtctggg gccagggac cacggtcact     360 gtctcttca                                                            369

<210> SEQ ID NO 667
<211> LENGTH: 369
<212> TYPE: DNA
<213> ORGANISM: Homo sapiens

<400> SEQUENCE: 667
gaggtgcagc tggtggagtc tgggggaggc ttggtccagc ctggggggtc cctgagactc      60
tcctgtgcag cctctggatt cacctttagt aactattgga tgaactgggt ccgccaggct     120
ccagggaagg agctggagtg ggtggccaac ataaaccaag atgaaagtga aaatactat     180 gttgactctg tgaagggccg tttcaccgtc tccagagaca cgccaagaa ctcactgttt      240 ctgcaaatga acagcctgag agccgacgac acggctgtat attactgtgc gagagggggg     300

```
tttggctacg gtgactccca cttcggtatg gacgtctggg gccaagggac cacggtcacc    360
gtctcttca                                                            369
```

<210> SEQ ID NO 668
<211> LENGTH: 369
<212> TYPE: DNA
<213> ORGANISM: Homo sapiens

<400> SEQUENCE: 668

```
gaggtgcagc tggtggagtc tgggggaggc ttggtccagc ctggggggtc cctgagactc    60
tcctgtggag cctctggatt cacctttagt aattattgga tgttctggtt ccgccaggct    120
ccaggaaagg agctggagtg ggtggccaat gttaaccaag atggaagtga gaaatactat    180
gtggactctg tgagggccg attcaccatc tccagagacg acgccaagaa ctcactgtat    240
ctgcaaatga acagcctgag agccgaggac acggctattt attactgtgc gagaggaggt    300
gagggctaca gtgattccca ctacggtacg gacgtctggg gccaagggac cacggtcact    360
gtctcttca                                                            369
```

<210> SEQ ID NO 669
<211> LENGTH: 369
<212> TYPE: DNA
<213> ORGANISM: Homo sapiens

<400> SEQUENCE: 669

```
gaggtgcagc tggtggagtc tgggggaggc ttggtccagc ctggggggtc cctgagactc    60
tcctgtggag cctctggatt cacctttagt aattattgga tgttctggtt ccgccaggct    120
ccaggaaagg agctggagtg ggtggccaat gttaaccaaa atggaagtga gaaatactat    180
gtggactctg tgagggccg attcaccatc tccagagaca acgccaagaa ctcactgtat    240
ctgcaaatga acagcctgag agccgaggac acggctattt attactgtgc gagaggaggt    300
gagggctaca gtgattccca ctacggtacg gacgtctggg gccaagggac cacggtcact    360
gtctcctca                                                            369
```

<210> SEQ ID NO 670
<211> LENGTH: 369
<212> TYPE: DNA
<213> ORGANISM: Homo sapiens

<400> SEQUENCE: 670

```
caggtgcagc tggtggagtc tgggggaggc ttggtccagc ctggggggtc cctgagactc    60
tcctgtgcag cctctggatt cacctttagt aactattgga tgaactgggt ccgccaggct    120
ccagggaagg ggctggagtg ggtggccaac ataaagcaag atggaagtga gaaatactat    180
gtggactctg tgaagggccg attcaccatc tccagagaca acgccaagga ctcactgtat    240
ctgcaaatga acagcctgag agccgaggac acggctattt attattgtgc gagagggggg    300
gagggttacg gtgactccca ctacggtatg gacgtctcgg gccaagggac cacggtcacc    360
gtctcctca                                                            369
```

<210> SEQ ID NO 671
<211> LENGTH: 369
<212> TYPE: DNA
<213> ORGANISM: Homo sapiens

<400> SEQUENCE: 671
gaggtgcagc tggtggagtc tgggggaggc ttggtccagc ctgggggtc cctgagactc    60 tcctgtgcag cctctggatt cacctttagt aactattgga tgatctggta ccgccaggct  120
ccaggtgagg agctggagtg ggtggccaac ataaaccaag atggaagtga gaaatactat  180
gtggactctg tgaagggccg attcaccatc tccagagaca acgccacgaa ctcactgttt  240
ctgcaaatga acagcctgag agccgaggac acggctgttt attactgtgc gagaggaggt  300
gatggctaca gtaattccca ctacggtatg gacgtctggg gccaagggac cacggtcact  360
gtctcctca                                                          369

<210> SEQ ID NO 672
<211> LENGTH: 369
<212> TYPE: DNA
<213> ORGANISM: Homo sapiens

<400> SEQUENCE: 672
gaggtgcagc tggtggagtc tgggggaggc ttggtccagc ctgggggtc cctgagactc    60 tcctgtgcag cctctggatt cacctttagt gactattgga tgatctggta ccgccaggct  120
ccaggtgagg agctggagtg ggtggccaac ataaaccaag atggaagtga gaaatactat  180
gtggactctg tgaagggccg attcaccatc tccagagaca acgccacgaa ctcactgttt  240
ctgcaaatga acagcctgag agccgaggac acggctgttt attactgtgc gagaggaggt  300
gatggctaca gtaattccca ctacggtatg gacgtctggg gccaagggac cacggtcacc  360
gtctcctca                                                          369

<210> SEQ ID NO 673
<211> LENGTH: 369
<212> TYPE: DNA
<213> ORGANISM: Homo sapiens

<400> SEQUENCE: 673
gaggtgcagc tggtggagtc tgggggaggc ttggtccagc ctgggggtc cctgagactc    60 tcctgtgcag cctctggatt cacctttagt aaatattgga tgatctgggt ccgccaggct  120
ccagaaaagg ggctggagtg ggtggccaac ataaaccaag atggaagtga gaaatactat  180
gtggactctg tggagggccg attcaccatt tccagagaca atgtcaataa ctcattgtat  240
ctgcaaatga acagcctgag agccgaggac acggctgtgt actactgtgc gagaggaggt  300
gatgactaca gtaactccca ctacggtatg gacgtctcgg gccaagggac cacggtcact  360
gtctcctca                                                          369

<210> SEQ ID NO 674
<211> LENGTH: 369
<212> TYPE: DNA
<213> ORGANISM: Homo sapiens

<400> SEQUENCE: 674
gaggtgcagc tggtggagtc tgggggaggc ttggtccagc ctgggggtc cctgagactc    60 tcctgtgcag cctctggatt cacctttagt aactattgga tgagctgggt ccgccaggct  120
ccagggaggg ggctggagtg ggtggccaac ataaaccaag atggaagtga gaaatactat  180
gtggactctg tgaagggccg attcaccatc tccagagaca acgccaagag ctcactgtat  240
ctgcaaatga acagccttag agccgaggac acggctgttt attactgtgc gagagggggg  300

```
gaagaatata gcagctccca ctacggtatg gacgtctggg gccaagggac cacggtcact    360
gtctcctca                                                            369
```

<210> SEQ ID NO 675
<211> LENGTH: 369
<212> TYPE: DNA
<213> ORGANISM: Homo sapiens

<400> SEQUENCE: 675

```
gaggtgcagc tggtggagtc tgggggaggc ttggtccagc ctgggggtc cctgagactc    60 tcctgtatag cctctggatt cagctttagt aactattgga tgaactgggt ccgccaggct   120
ccagggaagg gctggagtg gtggccaac ataaagcaag atggaagtga aattactat      180 gtggactctg tgaagggccg attcaccatc tccagagaca cgccaagaa ctcactgtat    240 ctgcaaatga acagcctgag agccgaggac acggctgtgt attactgtgc gagagggggg   300
gaagggtata gcacctcgca ctacggtatg gacgtctggg gccaagggac cgcggtcact   360
gtctcttca                                                            369
```

<210> SEQ ID NO 676
<211> LENGTH: 369
<212> TYPE: DNA
<213> ORGANISM: Homo sapiens

<400> SEQUENCE: 676

```
caggtgcagc tggtggagtc tgggggaggc ttggtccagc ctgggggtc cctgagactc    60 tcctgtgcag cctctggatt caccttagt agctattgga tgagctgggt ccgccaggct   120
ccagggaagg gctggagtg gtggccaac ataaagcaag atggaagtga gaaatactat    180
gtggactctg tgaagggccg attcaccatc tccagagaca cgccaagaa ctcactgtat    240 ctgcaaatga gcagcctgag agccgaggac acggctgtgt atttctgtgc gagaggggggg  300 gaaggctatg gtgtcgacca ctacggtttg gacgtctcgg gccaagggac cacggtcacc   360
gtctcctca                                                            369
```

<210> SEQ ID NO 677
<211> LENGTH: 369
<212> TYPE: DNA
<213> ORGANISM: Homo sapiens

<400> SEQUENCE: 677

```
gaggtgcagc tggtggagtc tgggggaggc ttggtccagc ctgggggtc cctgagactc    60 tcctgtggag cctctggatt caccttagt agctattgga tgctctggtt ccgccaggct   120
ccaggaaagg agctggagtg gtggccaat gttaaccaag atggcagtga gaattactat    180
gtggactctg tggagggccg attcaccatc tccagagaca cgccaagaa ctcactgtat    240 ctgcaaatgc acagcctgag agccgaggac acggctgtat attactgtgc gagaggaggt   300
gaagactacg gtaactccca cttcggcatg gacgtctggg gccaagggac catggtcacc   360
gtctcctca                                                            369
```

<210> SEQ ID NO 678
<211> LENGTH: 369
<212> TYPE: DNA
<213> ORGANISM: Homo sapiens

<400> SEQUENCE: 678

```
gaggtgcagc tggtggagtc tgggggaggc ttggtgcagc ctggcagatc cctgagactc      60
tcttgtgcag cctctggatt cacctttagt aactattgga tgatctggta ccgccaggct     120
ccaggtgagg agctggagtg ggtggccaac ataaaccaag atggaagtga gaaatactat     180
gtggactctg tgaagggccg attcaccatc tccagagaca cgccacgaa ctcactgttt      240
ctgcaaatga acagcctgag agccgaggac acggctgttt attactgtgc gagaggaggt     300
gatggctaca gtaattccca ctacggtatg gacgtctggg gccaagggac cacggtcact     360
gtctcttca                                                             369
```

<210> SEQ ID NO 679
<211> LENGTH: 369
<212> TYPE: DNA
<213> ORGANISM: Homo sapiens

<400> SEQUENCE: 679

```
gaggtgcagc tggtggagtc tgggggaggc ttggtcaagc ctggagggtc cctgagactc      60
tcctgtgcag cctctggatt cacctttagt aactattgga tgatctggta ccgccaggct     120
ccaggtgagg agctggagtg ggtggccaac ataaaccaag atggaagtga gaaatactat     180
gtggactctg tgaagggccg attcaccatc tccagagaca cgccacgaa ctcactgttt      240
ctgcaaatga acagcctgag agccgaggac acggctgttt attactgtgc gagaggaggt     300
gatggctaca gtaattccca ctacggtatg gacgtctggg gccaagggac cacggtcacc     360
gtctcctca                                                             369
```

<210> SEQ ID NO 680
<211> LENGTH: 369
<212> TYPE: DNA
<213> ORGANISM: Homo sapiens

<400> SEQUENCE: 680

```
gaggtgcagc tggtggagtc tgggggaggc ttggtccaga ttgggggtc cctgagactc       60
tcctgtgcag cctccggatt cacctttagt aaatattgga tgatctgggt ccgccaggct     120
ccagaaaagg ggctggagtg ggtggccaac ataaaccaag atggaagtga gaaatactat     180
gtggactctg tggagggccg attcaccatt tccagagaca cgccaataa ctcactgttt      240
ctgcaaatga acagcctgag agccgaggac acggctgtgt actactgtgc gagaggaggt     300
gatgactaca gtatctccca cttcggtatg gacgtctcgg gccaagggac cagggtcacc     360
gtctcctca                                                             369
```

<210> SEQ ID NO 681
<211> LENGTH: 369
<212> TYPE: DNA
<213> ORGANISM: Homo sapiens

<400> SEQUENCE: 681

```
gaggtgcagc tggtggagtc tgggggaggc ttggtccaga ttgggggtc cctgagactc       60
tcctgtgtag cctctggatt cacctttagt aaatattgga tgatctgggt ccgccaggct     120
ccagaaaagg ggctggagtg ggtggccaac ataaaccaag atggaagtga gaaatactat     180
gtggactctg tggagggccg attcaccatt tccagagaca cgccaataa ttcattgtat      240
ctgcagatga acagcctgag agccgaggac acggctgtgt actactgtgc gagaggaggt     300
```

```
gatgactaca gtcactccca ctacggtatg gacgtctcgg gccaagggac cacggtcact    360
gtctcttca                                                            369
```

<210> SEQ ID NO 682
<211> LENGTH: 369
<212> TYPE: DNA
<213> ORGANISM: Homo sapiens

<400> SEQUENCE: 682

```
gaggtgcagc tggtggagtc tggggggaggc ttggtccagc ctgggggtc cctgagactc    60 tcctgtgcag cctctggatt caactttagt aactattgga tgaactgggt ccgccaggct   120
ccagggaagg agctggagtg ggtggccaac ataaaccaag atggaagtga aaatactat    180 gtggactctg tgaagggccg attcaccatc tccagagaca cgccaagaa ctcactgttt    240 ctgcaaatga acagcctgag agccgacgac acggctgtgt attactgtgc gagagggggg   300
tttggctacg gtgactccca ctacggtatg gacgtctggg gccaagggac cacggtcacc   360
gtctcctca                                                           369
```

<210> SEQ ID NO 683
<211> LENGTH: 369
<212> TYPE: DNA
<213> ORGANISM: Homo sapiens

<400> SEQUENCE: 683

```
gaggtgcagc tggtggagtc tggggggaggc ttggtccagc ctgggggtc cctgagactc    60 tcctgtgcag cctctggatt caccttggt agttattggc tgaattgggt ccgccaggct   120
ccagggaagg ggctggagtg ggtggccaac ataaaccaag atggcagtga gaattactat   180
gtggactctg tggagggccg attcaccatc tccagagaca cgccaagaa ctcactgtat    240 ctgcaaatgc acagcctgag agccgaggac acggctgtat attactgtgc gagaggaggt   300
gaagactacg gtaactccca cttcggcatg gacgtctggg gccaagggac catggtcact   360
gtctcttca                                                           369
```

<210> SEQ ID NO 684
<211> LENGTH: 369
<212> TYPE: DNA
<213> ORGANISM: Homo sapiens

<400> SEQUENCE: 684

```
caggtgcagc tggtggagtc tggggggaggc ttggtcaagc ctggagggtc cctgagactc    60
tcctgtgcag cctctggatt caccttagt agctattgga tgagctgggt ccgccaggct   120
ccagggaagg ggctggagtg ggtggccaac ataaagcaag atggaagtga aaatactat    180 gtggactctg tgaagggccg attcaccatc tccagagaca cgccaagaa ctcactgtat    240 ctgcaaatga gcagcctgag agccgaggac acggctgtgt atttctgtgc gagagggggg   300
gaaggctatg tgtcgacca ctacggtttg gacgtctcgg gccaagggac cacggtcact   360
gtctcttca                                                           369
```

<210> SEQ ID NO 685
<211> LENGTH: 369
<212> TYPE: DNA
<213> ORGANISM: Homo sapiens

<400> SEQUENCE: 685

| caggtgcagc tggtggagtc tgggggaggc ttggtccagc ctggggggtc cctgagactc | 60 |
| tcctgtacag cctctggatt cacctttagt gactattgga tgaactgggt ccgccaggct | 120 |
| ccaggtaagg ggctggagtg ggtggccaat ataaaggaag atggaagtga gaaatactat | 180 |
| gtggactctg tggagggccg attcaccatc tccagagaca acgccaggaa ctcactgtat | 240 |
| ctgcaaatga ccagcctgag agaagaagac acggctatgt attactgtgc gagaggggg | 300 |
| gagggctacg gtgacaacca ctacggtatg gacgtctcgg gccaagggac cacggtcact | 360 |
| gtctcttca | 369 |

<210> SEQ ID NO 686
<211> LENGTH: 369
<212> TYPE: DNA
<213> ORGANISM: Homo sapiens

<400> SEQUENCE: 686

| gaggtgcagc tggtggagtc tgggggaggc ttggtccagc ctggggggtc cctgagactc | 60 |
| tcctgtgcag cctctggatt cacctttaga agctattgga tgaactgggt ccgccaggct | 120 |
| ccagggaagg aggcggaatg ggtggccaac ataaaccaag atggaagtga gaaatattat | 180 |
| gtggactctg tggagggccg attcaccatc tccagagaca acgccaagaa ctcactgttt | 240 |
| ctgcaaatga acagcctgag agacgaggac acggctgttt attactgtgc gagaggaggc | 300 |
| cccgactacg gtgacctcca ctacggtatg gacgtctggg gccaagggac cacggtcacc | 360 |
| gtctcctca | 369 |

<210> SEQ ID NO 687
<211> LENGTH: 369
<212> TYPE: DNA
<213> ORGANISM: Homo sapiens

<400> SEQUENCE: 687

| caggtgcagc tggtggagtc tgggggaggc ttggtccagc ctggggggtc cctaagactc | 60 |
| tcctgtgcag cctctggatt cacctttagt aggtattgga tgagctgggt ccgccaggct | 120 |
| ccagggaagg ggctggagcg ggtggccaac ataaaccaag atggacgtga gaaatactat | 180 |
| gtggactctg tgaagggccg attcaccatc tccagagaca acgccaagaa ctcactgtat | 240 |
| ctgcaaatga acagcctgag agccgaggac acggctgtgt attattgtgc gagagggggg | 300 |
| gagggctacg gtgactacca ctacggtatg gacgtctcgg gccaagggac cacggtcact | 360 |
| gtctcttca | 369 |

<210> SEQ ID NO 688
<211> LENGTH: 369
<212> TYPE: DNA
<213> ORGANISM: Homo sapiens

<400> SEQUENCE: 688

| gaggtgcagc tggtggagtc tgggggaggc ttggtccagc ctggggggtc cccgagactc | 60 |
| tcctgtgcag cctctggatt caccccttagt aactattgga tgatctggta ccgccaggct | 120 |
| ccaggtgaga agctggagtg ggtggccaac ataaaccaag atggaagtga gaaatactat | 180 |
| gtggactctg tgaagggccg attcaccatc tccagagaca acgccacgaa ctcactgttt | 240 |
| ctgcaaatga acagcctgag agccgaggac acggctgttt attactgtgc gagaggaggt | 300 |

```
gatggctaca gtaattccca ctacggtatg gacgtctggg gccaagggac cacggtcacc    360
gtctcctca                                                            369
```

<210> SEQ ID NO 689
<211> LENGTH: 369
<212> TYPE: DNA
<213> ORGANISM: Homo sapiens

<400> SEQUENCE: 689

```
gaggtgcagc tggtggagtc tgggggaggc ttggtccagc ctgggggtc cctgagactc     60 tcctgtgtag cctctggatt caacttcagt aactattgga tgaactgggt ccgccaggct   120
ccagggaagg agctggagtg ggtggccaac ataaaccaag atgaaagtga aaatactat    180 gtagactctg tgaagggccg attcaccatc tccagagaca cgccaagaa ctcactgttt    240 ctgcaaatga acagcctgag agccgacgac acggctgtgt attactgtgc gagagggggg   300
tttggctacg gtgactccca cttcggtatg gacgtctggg gccaagggac cacggtcacc   360
gtctcctca                                                            369
```

<210> SEQ ID NO 690
<211> LENGTH: 369
<212> TYPE: DNA
<213> ORGANISM: Homo sapiens

<400> SEQUENCE: 690

```
gaggtgcagc tggtggagtc tgggggaggc ttggtccagc ctgggggtc cctgagactc     60 tcctgtgcag cctctggatt caattttagt aactattgga tgaactgggt ccgtcaggct   120
ccagggaagg agctggagtg ggtggccaac ataaaccaag atgaaagtga aaatactat    180 gtagactctg tgaagggccg attcaccatt ttcagagaca cgccaagaa ctcactgttt    240 ctgcaaatga acagcctgag agccgacgac acggctgtgt attactgtgc gagagggggg   300
tttggctacg gtgactccca cttcggtatg gacgtctggg gccaagggac cacggtcact   360
gtctcttca                                                            369
```

<210> SEQ ID NO 691
<211> LENGTH: 369
<212> TYPE: DNA
<213> ORGANISM: Homo sapiens

<400> SEQUENCE: 691

```
gaggtgcagc tggtggagtc tgggggaggc ttggtccagc ctgggggtc cctgagtctc     60 tcctgtgcag cctctggatt caccttaga agcttttgga tgaactgggt ccgccaggct   120
ccagggaagg aggcggaatg ggtggccaac ataaatcaag atggaagtga gaaatactat   180
gtggactctg tgaagggccg attcaccatc tccagagaca cgccaagaa ctcactgttt    240 ctgcaaatga acagcctgag agccgaggac acggctgttt attactgtgc gagaggaggc   300
cccgactacg gtgacctcca ctacggtatg gacgtctggg gccaagggac cacggtcact   360
gtctcttca                                                            369
```

<210> SEQ ID NO 692
<211> LENGTH: 369
<212> TYPE: DNA
<213> ORGANISM: Homo sapiens

<400> SEQUENCE: 692

```
gaggtgcagc tggtggagtc tggggaggc ttggtccagc ctggggggtc cctgagactc    60
tcctgtgcag cctctggatt cacctttaga agctattgga tgaactgggt ccgccaggct   120
ccagggaagg aggcggaatg ggtggccaac ataaaccaag atggaagtga aaatattat    180
gtggactctg tgaagggccg attcaccatc tccagagaca acgccaagaa ctcactgttt   240
ctgcaaatga acagcctgag agacgaggac acggctgttt attactgtgc gagaggaggc   300
cccgactacg gtgacctcca ctacggtatg gacgtctggg gccaagggac cacggtcact   360
gtctcttca                                                           369
```

<210> SEQ ID NO 693
<211> LENGTH: 369
<212> TYPE: DNA
<213> ORGANISM: Homo sapiens

<400> SEQUENCE: 693

```
gaggtgcagc tggtggagtc tggggaggc ttggtccagc ctggggggtc cctgagactc    60
tcctgtgcag cctctggatt cacctttagt aactattgga tgatctggta ccgccaggct   120
ccaggtgagg agctggagtg ggtggccaac ataaaccaag atggaagtga aaatactat    180
gtggactctg tgaagggccg attcaccatc tccagagaca acgccaagaa ctcactgtat   240
ctgcaaatgc acagcctgag agccgaggac acggctgtat attactgtgc gagaggaggt   300
gaagactacg gtaactccca ctacggcatg gacgtctggg gccaagggac catggtcacc   360
gtctcttca                                                           369
```

<210> SEQ ID NO 694
<211> LENGTH: 369
<212> TYPE: DNA
<213> ORGANISM: Homo sapiens

<400> SEQUENCE: 694

```
gaggtgcagc tggtggagtc tggggaggc ttggtccagc ctggggggtc cctgagactc    60
tcctgtgcag cctctggatt cacctttagt aactattgga tgaactgggt ccgccaggct   120
ccagggaagg ggctggagtg ggtggccaac ataaaccaag atggaagtga aagatactat   180
gtggactctg tgaagggccg attcaccatc tccagagaca acgccaagag ctcactgtat   240
ctgcaaatga acagcctgag agccgaggac acggctgtgt atttctgtgc gagagggggg   300
gaaggctatg gtatcgacca ctacggtttg gacgtctcgg gccaagggac cacggtcacc   360
gtctcctca                                                           369
```

<210> SEQ ID NO 695
<211> LENGTH: 369
<212> TYPE: DNA
<213> ORGANISM: Homo sapiens

<400> SEQUENCE: 695

```
caggtgcagc tggtggagtc tggggaggc ttggtccagc ctggggggtc cctgagactc    60
tcctgtgcag cctctggatt cacctttagt agctattgga tgagctgggt ccgccaggct   120
ccagggaagg ggctggagtg ggtggccaac ataaatcaag atggaagtga aagatactat   180
gtggactctg tgaagggccg attcaccatc tccagagaca acgccaagag ctcactgtat   240
ctgcaaatga gtagcctgag agccgaggac acggctgtgt atttctgtgc gagagggggg   300
```

```
gaaggctatg gtgtcgacca ctacggtttg gacgtctcgg gccaagggac cacggtcact    360
gtctcctca                                                            369
```

<210> SEQ ID NO 696
<211> LENGTH: 369
<212> TYPE: DNA
<213> ORGANISM: Homo sapiens

<400> SEQUENCE: 696

```
caggtgcagc tggtggagtc tgggggaggc ttggtccagc ctgggggtc cctgagactc     60 tcctgtgcag cctctggatt cacctttagt aactattgga tgatctgggt ccgccaggct    120
ccagggaagg ggctggagtg ggtggccaac ataaaccaag atggaagtga aaatactat     180 gtggactctg tgagggccg attcaccatc tccagagaca cgccaagag ctcactgtat     240 ctgcaaatga gcaacctgag agccgaggac acggctgtat atttctgtgc gagaggggg    300 gaaggctatg gtgtcgacca ctacggtttg gacgtctcgg gccaagggac cacggtcact    360
gtctcttca                                                            369
```

<210> SEQ ID NO 697
<211> LENGTH: 369
<212> TYPE: DNA
<213> ORGANISM: Homo sapiens

<400> SEQUENCE: 697

```
caggtgcagc tggtggagtc tgggggaggc ttggtccagc ctgggggtc cctgagactc     60 tcctgtgcag ccactggatt caccttaagt aactattgga tgaactgggt ccgccaggct    120
ccagggaagg ggctggagtg ggtggccaac ataaaccaag atggaagtga aaaatactat    180
gtggactctg tgaagggccg attcaccatc tccagagaca cgccaagaa ctcactgttt    240 ctgcaaatga acagcctgag agccgaggac acggctgtgt attactgtgc gagagggga    300 acaggctatg gttccgacca ctacggtatg gacgtctcgg gccaagggac cacggtcact    360
gtctcttca                                                            369
```

<210> SEQ ID NO 698
<211> LENGTH: 369
<212> TYPE: DNA
<213> ORGANISM: Homo sapiens

<400> SEQUENCE: 698

```
gaggtgcagc tggtggagtc tgggggaggc ttggtccagc ctgggggtc cctgagactc     60 tcctgtgcag cctctggatt caattttagt aactattgga tgaactgggt ccgccaggct    120
ccagggaagg agctggagtg ggtggccaac ataaaccaag atggaagtga gaattactat    180
gtggactctg tgaagggccg attcaccatc tccagagaca cgtcaagaa ctcactgttt    240 ctgcaaatga accgcctgag agccgacgac acggctgtgt attactgtgc gagaggggg    300 tttggctacg gtgactccca ctacggtatg gacgtctggg gccaagggac cacggtcact    360
gtctcctca                                                            369
```

<210> SEQ ID NO 699
<211> LENGTH: 369
<212> TYPE: DNA
<213> ORGANISM: Homo sapiens

<400> SEQUENCE: 699
gaggtgcagc tggtggagtc tgggggaggc ttggtccagc ctggggggtc cctgagactc    60
tcctgtgcag cctctggatt cacctttggt aactattgga tgatctgggt ccgccaggct   120
ccaggcaagg agttggagtg gctggccaac ataaaccaaa atggaagtga gagatactat   180
gtggactctg tgcagggccg attcaccatc tccagagaca acgccaagaa ctcactgtat   240
ctgcaaatga acagcctgag agccgaggac acggctgtat attactgtgc gagggggg    300 gctgactaca gtaactccca ctacggtatg gacgtcagcg gccaagggac cacggtcact   360
gtctcttca                                                           369

<210> SEQ ID NO 700
<211> LENGTH: 369
<212> TYPE: DNA
<213> ORGANISM: Homo sapiens

<400> SEQUENCE: 700
caggtgcagc tggtggagtc tgggggaggc ttggtccagc ctggggggtc cctgagactc    60
tcctgtgcag cctctggatt cacctttagt agctattgga tgagctgggt ccgccaggct   120
ccagggaagg ggctggagtg ggtggccaac ataaaccaag atggaagtga aagatactat   180
gtggactctg tgaagggccg attcaccatc tccagagaca acgccaacaa ctcactgcat   240
ctgcaaatga gcagcctgag agccgaggac acggctgtgt atttctgtgc gagagggggg   300
gaaggctatg gtgtcgacca ctacggtttg gacgtctcgg gccaagggac cacggtcacc   360
gtctcctca                                                           369

<210> SEQ ID NO 701
<211> LENGTH: 369
<212> TYPE: DNA
<213> ORGANISM: Homo sapiens

<400> SEQUENCE: 701
gaggtgcagc tggtggagtc tgggggaggc ttggtccagc cggggggtc cctgagactc     60 tcctgtgcag cctctggatt caccttaga agttattgga tgaactgggt ccgccaggct   120
ccagggaaag aggcgaatg gtggccaac ataaacccag atggaagtga gaaatactat    180
gtggactctg tgcagggccg acacaccatc tccagagaca acgccaagaa ctcactgttt   240
ctggaaatga acagcctgag agtcgaggac acggctcttt attactgtgc gagaggaggc   300
cccggctacg tgaccctcca ctacggtatg gacgtctggg gccaagggac cacggtcact   360
gtctcctca                                                           369

<210> SEQ ID NO 702
<211> LENGTH: 369
<212> TYPE: DNA
<213> ORGANISM: Homo sapiens

<400> SEQUENCE: 702
caggtgcagc tggtggagtc tgggggaggc ttggtccagc ctggggggtc cctgagactc    60
tcctgtgcag ccactggatt caccttaagt aactattgga tgaactgggt ccgccaggct   120
ccagggaagg ggctggagtg ggtggccaac ataaatcaag atggaagtga aaatactat    180 gtggactctg tggagggccg attcaccatc tccagagaca acgccaagag ctcactgtat   240
ctgcaaatga gcagcctgag agccgaggac acggctgtgt atttctgtgc gagaggggg    300 gaaggctatg gtgtcgacca ctacggtttg gacgtctcgg gccaagggac cacggtcact    360
gtctcctca                                                             369

<210> SEQ ID NO 703
<211> LENGTH: 369
<212> TYPE: DNA
<213> ORGANISM: Homo sapiens

<400> SEQUENCE: 703
caggtgcagc tggtggagtc tgggggaggc ctggtccagc ctgggggtc cctgagactc       60 tcctgtgcag cctctggatt caccttcagt gactactaca tgagctggat ccgccaggct    120
ccagggaagg ggctggagtg ggtggccaac ataaaccaag atggaagtga aagatactat    180
gtggactctg tgaagggccg attcaccatc tccagagaca cgccaagaa ctcactgtat     240 ctgcaaatga gcagcctgag agccgaggac acggctgtgt atttctgtgc gagagggggg    300
gaaggctatg gtgtcgacca ctacggtttg gacgtctcgg gccaagggac cacggtcacc    360
gtctcttca                                                             369

<210> SEQ ID NO 704
<211> LENGTH: 369
<212> TYPE: DNA
<213> ORGANISM: Homo sapiens

<400> SEQUENCE: 704
gaggtgcagc tggtggagtc tgggggaggc ttggtccagc ctgggggtc cctgagactc       60 tcctgtgcag ccactggatt caccttaagt aactattgga tgaactgggt ccgccaggct    120
ccagggaagg ggctggagtg ggtggccaac ataaaccaag atggaagtga aagatactat    180
gtggactctg tgaagggccg attcaccatc tccagagaca cgccaagaa ctcactgtat     240 ctgcaaatga gcagcctgag agccgaggac acggctgtgt atttctgtgc gagagggggg    300
gaaggctatg gtgtcgacca ctacggtttg gacgtctcgg gccaagggac cacggtcacc    360
gtctcttca                                                             369

<210> SEQ ID NO 705
<211> LENGTH: 369
<212> TYPE: DNA
<213> ORGANISM: Homo sapiens

<400> SEQUENCE: 705
caggtgcagc tggtggagtc tgggggaggc ttggtccagc ctgggggtc cctgagactc       60 tcctgtgcag cctctggatt caccttaagt aactattgga tgaactgggt ccgccaggct    120
ccagggaagg ggctggagtg ggtggccaac ataaaccaag atggaagtga aagatactat    180
gtggactctg tgaagggccg attcaccatc tccagagaca cgccaagaa ctcactgtat     240 ctgcaaatga gcagcctgag agccgaggac acggctgtgt atttctgtgc gagagggggg    300
gaaggctatg gtgtcgacca ctacggtttg gacgtctcgg gccaagggac cacggtcact    360
gtctcttca                                                             369

<210> SEQ ID NO 706
<211> LENGTH: 369
<212> TYPE: DNA
<213> ORGANISM: Homo sapiens

<400> SEQUENCE: 706

```
caggtgcagc tggtggagtc tgggggaggc ttggtccagc ctggggggtc cctgagactc    60
tcctgtgcag ccactggatt caccttaagt aactattgga tgaactgggt ccgccaggct   120
ccagggaagg ggctggagtg ggtggccaac ataaaccaag atggaagtga aagatactat   180
gtggactctg tgaagggccg attcaccatc tccagagaca acgccaagaa ctcactgtat   240
ctgcaaatga gcagcctgag agccgaggac acggctgtgt atttctgtgc gagagggggg   300
gaaggctatg gtgtcgacca ctacggtttg gacgtctcgg gccaagggac cacggtcact   360
gtctcttca                                                          369
```

<210> SEQ ID NO 707
<211> LENGTH: 369
<212> TYPE: DNA
<213> ORGANISM: Homo sapiens

<400> SEQUENCE: 707

```
caggtgcagc tggtggagtc tgggggaggc ttggtccagc ctggggggtc cctgagactc    60
tcctgtgcag ccactggatt caccttaagt aactattgga tgaactgggt ccgccaggct   120
ccagggaagg ggctggagtg ggtggccaac ataaaccaag atggaagtga aagatactat   180
gtggactctg tgaagggccg attcaccatc tccagagaca acgccaagaa ctcactgtat   240
ctgcaaatga gcagcctgag agccgaggac acggctgtgt atttctgtgc gagagggggg   300
gaaggctatg gtgtcaacca ctacggtttg gacgtctcgg gccaagggac cacggtcacc   360
gtctcttca                                                          369
```

<210> SEQ ID NO 708
<211> LENGTH: 369
<212> TYPE: DNA
<213> ORGANISM: Homo sapiens

<400> SEQUENCE: 708

```
caggtgcagc tggtggagtc tgggggaggc ttggtcaagc ctggagggtc cctgagactc    60
tcctgtgtag cctctggatt caccttcagt gactactata tgagctggat ccgccaggct   120
ccagggaagg ggctggagtg ggtggccaac ataaagcaag atggaagtga aagatactat   180
gtggactctg tgaagggccg attcaccatc tccagagaca acgccaagag ctcactgtat   240
ctgcaaatga gcagcctgag agccgaggac acggctgtgt atttctgtgc gagagggggg   300
gaaggctatg gtgtcgacca ctacggtttg gacgtctcgg gccaagggac cacggtcact   360
gtctcttca                                                          369
```

<210> SEQ ID NO 709
<211> LENGTH: 369
<212> TYPE: DNA
<213> ORGANISM: Homo sapiens

<400> SEQUENCE: 709

```
caggtgcagc tggtggagtc tgggggaggc ttggtccagc ctggggggtc cctgagactc    60
tcctgtgcag ccactggatt caccttaagt aactattgga tgaactgggt ccgccaggct   120
ccagggaagg ggctggagtg ggtggccaac ataaaccaag atggaagtga aagatactat   180
gtggactctg tgagggccg attcaccatc tccagagaca acgccaagag ctcactgtat    240
ctgcaaatga gcaacctgag agccgaggac acggctgtat atttctgtgc gagagggggg   300
```
gaaggctatg gtgtcgacca ctacggtttg dacgtctcgg gccaagggac cacggtcact    360
gtctcttca                                                             369

<210> SEQ ID NO 710
<211> LENGTH: 369
<212> TYPE: DNA
<213> ORGANISM: Homo sapiens

<400> SEQUENCE: 710
caggtgcagc tggtggagtc tgggggaggc ttggtccagc ctgggggtc cctgagactc     60 tcctgtgcag ccactggatt caccttaagt aactattgga tgaactgggt ccgccaggct    120
ccagggaagg ggctggagtg ggtggccaac ataaaccaag atggaagtga aagatactat    180
gtggactctg tgaagggccg attcaccatt tccagagaca acgccaagag ctcactgtat    240
ctgcaaatga gcagcctgag agccgaggac acggctgtgt atttctgtgc gagaggggg     300 gaaggctatg gtgtcgacca ctacggtttg gacgtctcgg gccaagggac cacggtcacc    360
gtctcctca                                                             369

<210> SEQ ID NO 711
<211> LENGTH: 369
<212> TYPE: DNA
<213> ORGANISM: Homo sapiens

<400> SEQUENCE: 711
caggtgcagc tgcaggagtc gggggaggc ttggtccagc ctgggggtc cctgagactc       60 tcctgtgcag ccactggatt caccttaagt aactattgga tgaactgggt ccgccaggct    120
ccagggaagg ggctggagtg ggtggccaac ataaaccaag atggaagtga aagatactat    180
gtggactctg tgaagggccg attcaccatc tccagagaca acgccaagaa ctcactgtat    240
ctgcaaatga gcagcctgag agccgaggac acggctgtgt atttctgtgc gagaggggg     300 gaaggctatg gtgtcgacca ctacggtttg gacgtctcgg gccaagggac cacggtcact    360
gtctcttca                                                             369

<210> SEQ ID NO 712
<211> LENGTH: 369
<212> TYPE: DNA
<213> ORGANISM: Homo sapiens

<400> SEQUENCE: 712
caggtgcagc tggtggagtc tgggggaggc ctggtcaagc ctgggggtc cctgagactc      60 tcctgtgcag ccactggatt caccttaagt aactattgga tgaactgggt ccgccaggct    120
ccagggaagg ggctggagtg ggtggccaac ataaaccaag atggaagtga aagatactat    180
gtggactctg tgaagggccg attcaccatc tccagagaca acgccaagaa ctcactgtat    240
ctgcaaatga gcagcctgag agccgaggac acggctgtgt atttctgtgc gagaggggg     300 gaaggctatg gtgtcgacca ctacggtttg gacgtctcgg gccaagggac cacggtcacc    360
gtctcctca                                                             369

<210> SEQ ID NO 713
<211> LENGTH: 369
<212> TYPE: DNA
<213> ORGANISM: Homo sapiens

<400> SEQUENCE: 713

| | | | | | |
|---|---|---|---|---|---|
| caggtgcagc | tggtggagtc | tgggggaggc | ttggtccagc | ctggggggtc | cctgagactc | 60 |
| tcctgtgcag | ccactggatt | caccttaagt | aactattgga | tgaactgggt | ccgccaggct | 120 |
| ccagggaagg | ggctggagtg | ggtggccaac | ataaaccaag | atggaagtga | aagatactat | 180 |
| gtggactctg | tgaagggccg | attcaccatc | tccagagaca | acgccaacaa | ctcactgcat | 240 |
| ctgcaaatga | gcagcctgag | agccgaggac | acggctgtgt | atttctgtgc | gagagggggg | 300 |
| gaaggctatg | gtgtcgacca | ctacggtttg | gacgtctcgg | gccaagggac | cacggtcact | 360 |
| gtctcttca | | | | | | 369 |

<210> SEQ ID NO 714
<211> LENGTH: 369
<212> TYPE: DNA
<213> ORGANISM: Homo sapiens

<400> SEQUENCE: 714

| | | | | | |
|---|---|---|---|---|---|
| caggtgcagc | tggggagtc | tgggggaggc | ttggtccagc | ctggggggtc | cctgagactc | 60 |
| tcctgtgcag | ccactggatt | caccttaagt | aactattgga | tgaactgggt | ccgccaggct | 120 |
| ccagggaagg | ggctggagtg | ggtggccaac | ataaaccaag | atggaagtga | aagatactat | 180 |
| gtggactctg | tggagggccg | attcaccatc | tccagagaca | acgccaagag | ctcactgtat | 240 |
| ctgcaaatga | gcaacctgag | agccgaggac | acggctgtat | atttctgtgc | gagagggggg | 300 |
| gaaggctatg | gtgtcgacca | ctacggtttg | gacgtctcgg | gccaagggac | cacggtcacc | 360 |
| gtctcctca | | | | | | 369 |

<210> SEQ ID NO 715
<211> LENGTH: 369
<212> TYPE: DNA
<213> ORGANISM: Homo sapiens

<400> SEQUENCE: 715

| | | | | | |
|---|---|---|---|---|---|
| caggtgcagc | tggtggagtc | tgggggaggc | ttggtccagc | ctggggggtc | cctgaaactc | 60 |
| tcctgtgcag | ccactggatt | caccttaagt | aactattgga | tgaactgggt | ccgccaggct | 120 |
| ccagggaagg | ggctggagtg | ggtggccaac | ataaaccaag | atggaagtga | aagatactat | 180 |
| gtggactctg | tgaagggccg | attcaccatt | tccagagaca | acgccaagag | ctcactgtat | 240 |
| ctgcaaatga | gcagcctgag | agccgaggac | acggctgtgt | atttctgtgc | gagagggggg | 300 |
| gaaggctatg | gtgtcgacca | ctacggtttg | gacgtctcgg | gccaagggac | cacggtcact | 360 |
| gtctcttca | | | | | | 369 |

<210> SEQ ID NO 716
<211> LENGTH: 369
<212> TYPE: DNA
<213> ORGANISM: Homo sapiens

<400> SEQUENCE: 716

| | | | | | |
|---|---|---|---|---|---|
| caggtgcagc | tgcaggagtc | gggggaggc | ttggtccagc | ctggggggtc | cctgagactc | 60 |
| tcctgtgcag | ccactggatt | caccttaagt | aactattgga | tgaactgggt | ccgccaggct | 120 |
| ccagggaagg | ggctggagtg | ggtggccaac | ataaaccaag | atggaagtga | aagatactat | 180 |
| gtggactctg | tgaagggccg | attcaccatc | tccagaggca | acgccaagaa | ctcactgtat | 240 |
| ctgcaaatga | gcagcctgag | agccgaggac | acggctgtgt | atttctgtgc | gagagggggg | 300 |

```
gaaggctatg gtgtcgacca ctacggtttg acgtctcgg gccaagggac cacggtcact    360
gtctcttca                                                           369
```

<210> SEQ ID NO 717
<211> LENGTH: 369
<212> TYPE: DNA
<213> ORGANISM: Homo sapiens

<400> SEQUENCE: 717

```
caggtgcagc tggtggagtc tgggggaggc gtggtccagc ctggggggtc cctgagactc    60
tcctgtgcag cctctggatt cacctttgat gattatggca tgagctgggt ccgccaggct   120
ccagggaagg ggctggagtg ggtggccaac ataaaccaag atggaagtga aagatactat   180
gtggactctg tgaagggccg attcaccatc tccagagaca acgccaagaa ctcactgtat   240
ctgcaaatga gcagcctgag agccgaggac acggctgtgt atttctgtgc gagagggggg   300
gaaggctatg gtgtcgacca ctacggtttg acgtctcgg gccaagggac cacggtcact   360
gtctcttca                                                           369
```

<210> SEQ ID NO 718
<211> LENGTH: 369
<212> TYPE: DNA
<213> ORGANISM: Homo sapiens

<400> SEQUENCE: 718

```
gaggtgcagc tggtggagtc tgggggaggc ttggtccagc cggggggggtc cctgagactc    60 tcctgtgcag cctctggatt cacctttagt agccattgga tgacttgggt ccgtcaggct   120
ccagggaagg ggctggagtg ggtggcccac ataaaggaag acggaagtga gaaatactat   180
gaggactctg tggagggccg attcaccgtc tccagagaca acgccaagaa ctcggtatat   240
ctgcaaatga acagtctgag agccgaagac acggctgtgt attactgtgc gagaggaggt   300
gatggctaca gtgactccca cttcggtgtg acgtctggg gccaagggac cacggtcacc   360
gtctcctca                                                           369
```

<210> SEQ ID NO 719
<211> LENGTH: 369
<212> TYPE: DNA
<213> ORGANISM: Homo sapiens

<400> SEQUENCE: 719

```
gaggtgcagc tggtggagtc tgggggaggc ttggtccagc cggggggggtc cctgagactc    60 tcctgtgcag cctctggatt cacctttagt agccattgga tgacttggtt ccgtcaggct   120
ccagggaagg ggctggagtg ggtggcccac ataaaggaag acggaagtga gaaatactat   180
gtggactctg tgaagggccg attcaccgtc tccagagaca acgccaagaa ctcggtatat   240
ctgcaaatga acagtctgag agccgaagac acggctgtgt attactgtgc gagaggaggt   300
gatggctaca gtgactccca cttcggtgtg acgtctggg gccaagggac cacggtcacc   360
gtctcctca                                                           369
```

<210> SEQ ID NO 720
<211> LENGTH: 369
<212> TYPE: DNA
<213> ORGANISM: Homo sapiens

<400> SEQUENCE: 720

| | | |
|---|---|---|
| gaggtgcagc tggtggagtc tgggggaggc ttggtccagc cggggggggtc cctgagactc | 60 |
| tcctgtgcag cctctggatt cacctttagt agccattgga tgacttggtt ccgtcaggct | 120 |
| ccagggaagg ggctggagtg ggtggcccac ataaaggaag acggaagtga gaaatactat | 180 |
| gaggactctg tgaagggccg attcaccgtc tccagagaca cgccaagaa ctcggtatat | 240 |
| ctgcaaatga acagtctgag agccgaagac acggctgtgt attactgtgc gagaggaggt | 300 |
| gatggctaca gtgactccca cttcggtgtg gacgtctggg gccaagggac cacggtcacc | 360 |
| gtctcctca | 369 |

<210> SEQ ID NO 721
<211> LENGTH: 369
<212> TYPE: DNA
<213> ORGANISM: Homo sapiens

<400> SEQUENCE: 721

| | |
|---|---|
| gaggtgcagc tggtggagtc tgggggaggc ttggtccagc cggggggggtc cctgagactc | 60 |
| tcctgtgcag cctctggatt cacctttagt agccattgga tgacttggtt ccgtcaggct | 120 |
| ccagggaagg ggctggagtg ggtggcccac ataaaggaag acggaagtga gaaatactat | 180 |
| gaggactctg tggagggccg attcaccatc tccagagaca cgccaagaa ctcggtatat | 240 |
| ctgcaaatga acagtctgag agccgaagac acggctgtgt attactgtgc gagaggaggt | 300 |
| gatggctaca gtgactccca cttcggtgtg gacgtctggg gccaagggac cacggtcacc | 360 |
| gtctcctca | 369 |

<210> SEQ ID NO 722
<211> LENGTH: 369
<212> TYPE: DNA
<213> ORGANISM: Homo sapiens

<400> SEQUENCE: 722

| | |
|---|---|
| gaggtgcagc tggtggagtc tgggggaggc ttggtccagc cggggggggtc cctgagactc | 60 |
| tcctgtgcag cctctggatt cacctttagt agccattgga tgacttggtt ccgtcaggct | 120 |
| ccagggaagg ggctggagtg ggtggcccac ataaaggaag acggaagtga gaaatactat | 180 |
| gaggactctg tggagggccg attcaccgtc tccagagaca cgccaagaa ctcgttatat | 240 |
| ctgcaaatga acagtctgag agccgaagac acggctgtgt attactgtgc gagaggaggt | 300 |
| gatggctaca gtgactccca cttcggtgtg gacgtctggg gccaagggac cacggtcacc | 360 |
| gtctcctca | 369 |

<210> SEQ ID NO 723
<211> LENGTH: 369
<212> TYPE: DNA
<213> ORGANISM: Homo sapiens

<400> SEQUENCE: 723

| | |
|---|---|
| gaggtgcagc tggtggagtc tgggggaggc ttggtccagc cggggggggtc cctgagactc | 60 |
| tcctgtgcag cctctggatt cacctttagt agccattgga tgacttgggt ccgtcaggct | 120 |
| ccagggaagg ggctggagtg ggtggcccac ataaaggaag acggaagtga gaaatactat | 180 |
| gtggactctg tgaagggccg attcaccatc tccagagaca cgccaagaa ctcgttatat | 240 |
| ctgcaaatga acagtctgag agccgaagac acggctgtgt attactgtgc gagaggaggt | 300 |

```
gatggctaca gtgactccca cttcggtgtg gacgtctggg gccaagggac cacggtcacc    360
gtctcctca                                                            369
```

<210> SEQ ID NO 724
<211> LENGTH: 369
<212> TYPE: DNA
<213> ORGANISM: Homo sapiens

<400> SEQUENCE: 724

```
gaggtgcagc tggtggagtc tgggggaggc ttggtccagc cggggggtc cctgagactc      60 tcctgtgcag cctctggatt cacctttagt agccattgga tgacttggtt ccgtcaggct    120
ccagggaagg ggctggagtg ggtggcccac ataaaggaag acgaaagtga gaaatactat    180
gtggactctg tgaagggccg attcaccatc tccagagaca cgccaagaa ctcgttatat    240 ctgcaaatga acagtctgag agccgaagac acggctgtgt attactgtgc gagaggaggt    300
gatggctaca gtgactccca cttcggtgtg gacgtctggg gccaagggac cacggtcacc    360
gtctcctca                                                            369
```

<210> SEQ ID NO 725
<211> LENGTH: 369
<212> TYPE: DNA
<213> ORGANISM: Homo sapiens

<400> SEQUENCE: 725

```
gaggtgcagc tggtggagtc tgggggaggc ttggtccagc cggggggtc cctgagactc      60 tcctgtgcag cctctggatt cacctttagt agccattgga tgacttgggt ccgtcaggct    120
ccagggaagg ggctggagtg ggtggcccac ataaaggaag acgaaagtga gaaatactat    180
gtggactctg tgaagggccg attcaccatc tccagagaca cgccaagaa ctcgttatat    240 ctgcaaatga acagtctgag agccgaagac acggctgtgt attactgtgc gagaggaggt    300
gttggctaca gtatctccca cttcggtgtg gacgtctggg gccaagggac cacggtcacc    360
gtctcctca                                                            369
```

<210> SEQ ID NO 726
<211> LENGTH: 369
<212> TYPE: DNA
<213> ORGANISM: Homo sapiens

<400> SEQUENCE: 726

```
gaggtgcagc tggtggagtc tgggggaggc ttggtccagc cggggggtc cctgagactc      60 tcctgtgcag cctctggatt cacctttagt agccattgga tgacttgggt ccgtcaggct    120
ccagggaagg ggctggagtg ggtggcccac ataaaggaag acgaaagtga gaaatactat    180
gtggactctg tgaagggccg attcaccatc tccagagaca cgccaagaa ctcgttatat    240 ctgcaaatga acagtctgag agccgaagac acggctgtgt attactgtgc gagaggaggt    300
gagggctaca gtatctccca cttcggtgtg gacgtctggg gccaagggac cacggtcacc    360
gtctcctca                                                            369
```

<210> SEQ ID NO 727
<211> LENGTH: 369
<212> TYPE: DNA
<213> ORGANISM: Homo sapiens

<400> SEQUENCE: 727

```
gaggtgcagc tggtggagtc tggggaggc ttggtccagc cggggggtc cctgagactc      60
tcctgtgcag cctctggatt cacctttagt agccattgga tgacttggtt ccgtcaggct    120
ccagggaagg ggctggagtg ggtggcccac ataaaggaag acgaaagtga gaaatactat    180
gtggactctg tgaagggccg attcaccatc tccagagaca acgccaagaa ctcgttatat    240
ctgcaaatga acagtctgag agccgaagac acggctgtgt attactgtgc gagaggaggt    300
gatggctaca gtgactccca cttcggtgtg gacgtctggg gccaagggac cacggtcacc    360
gtctcctca                                                            369
```

<210> SEQ ID NO 728
<211> LENGTH: 369
<212> TYPE: DNA
<213> ORGANISM: Homo sapiens

<400> SEQUENCE: 728

```
gaggtgcagc tggtggagtc tggggaggc ttggtccagc cggggggtc cctgagactc      60
tcctgtgcag cctctggatt cacctttagt agccattgga tgacttggtt ccgtcaggct    120
ccagggaagg ggctggagtg ggtggcccac ataaaggaag acgaaagtga gaaatactat    180
gtggactctg tgaagggccg attcaccatc tccagagaca acgccaagaa ctcgttatat    240
ctgcaaatga acagtctgag agccgaagac acggctgtgt attactgtgc gagaggaggt    300
gatggctaca gtatctccca cttcggtgtg gacgtctggg gccaagggac cacggtcacc    360
gtctcctca                                                            369
```

<210> SEQ ID NO 729
<211> LENGTH: 369
<212> TYPE: DNA
<213> ORGANISM: Homo sapiens

<400> SEQUENCE: 729

```
gaggtgcagc tggtggagtc tggggaggc ttggtccagc cggggggtc cctgagactc      60
tcctgtgcag cctctggatt cacctttagt agccattgga tgacttggtt ccgtcaggct    120
ccagggaagg ggctggagtg ggtggcccac ataaaggaag gcggaagtga gaaatactat    180
gtggactctg tgaagggccg attcaccatc tccagagaca acgccaagaa ctcgttatat    240
ctgcaaatga acagtctgag agccgaagac acggctgtgt attactgtgc gagaggaggt    300
gatggctaca gtgactccca cttcggtgtg gacgtctggg gccaagggac cacggtcacc    360
gtctcctca                                                            369
```

<210> SEQ ID NO 730
<211> LENGTH: 369
<212> TYPE: DNA
<213> ORGANISM: Homo sapiens

<400> SEQUENCE: 730

```
gaggtgcagc tggtggagtc tggggaggc ttggtccagc cggggggtc cctgagactc      60
tcctgtgcag cctctggatt cacctttagt agccattgga tgacttggtt ccgtcaggct    120
ccagggaagg ggctggagtg ggtggcccac ataaaggaag agggaagtga gaaatactat    180
gtggactctg tgaagggccg attcaccatc tccagagaca acgccaagaa ctcgttatat    240
ctgcaaatga acagtctgag agccgaagac acggctgtgt attactgtgc gagaggaggt    300
```

```
gatggctaca gtgactccca cttcggtgtg gacgtctggg gccaagggac cacggtcacc    360
gtctcctca                                                            369
```

<210> SEQ ID NO 731
<211> LENGTH: 369
<212> TYPE: DNA
<213> ORGANISM: Homo sapiens

<400> SEQUENCE: 731

```
gaggtgcagc tggtggagtc tgggggaggc ttggtccagc cggggggtc cctgagactc     60 tcctgtgcag cctctggatt cacctttagt agccattgga tgacttggtt ccgtcaggct    120
ccagggaagg ggctggagtg ggtggcccac ataaaggaag acggaagtga gaaatactat    180
gtggactctg tgaagggccg attcaccatc tccagagaca cgccaagaa ctcgttatat     240 ctgcaaatga acagtctgag agccgaagac acggctgtgt attactgtgc gagaggaggt    300
gagggctaca gtgactccca cttcggtgtg gacgtctggg gccaagggac cacggtcacc    360
gtctcctca                                                            369
```

<210> SEQ ID NO 732
<211> LENGTH: 369
<212> TYPE: DNA
<213> ORGANISM: Homo sapiens

<400> SEQUENCE: 732

```
gaggtgcagc tggtggagtc tgggggaggc ttggtccagc cggggggtc cctgagactc     60 tcctgtgcag cctctggatt cacctttagt agccattgga tgacttggtt ccgtcaggct    120
ccagggaagg ggctggagtg ggtggcccac ataaaggaag acggaagtga gaaatactat    180
gtggactctg tgaagggccg attcaccatc tccagagaca cgccaagaa ctcgttatat     240 ctgcaaatga acagtctgag agccgaagac acggctgtgt attactgtgc gagaggaggt    300
gttggctaca gtgactccca cttcggtgtg gacgtctggg gccaagggac cacggtcacc    360
gtctcctca                                                            369
```

<210> SEQ ID NO 733
<211> LENGTH: 369
<212> TYPE: DNA
<213> ORGANISM: Homo sapiens

<400> SEQUENCE: 733

```
gaggtgcagc tggtggagtc tgggggaggc ttggtccagc cggggggtc cctgagactc     60 tcctgtgcag cctctggatt cacctttagt agccattgga tgacttggtt ccgtcaggct    120
ccagggaagg ggctggagtg ggtggcccac ataaaggaag acgaaagtga gaaatactat    180
gtggactctg tgaagggccg attcaccatc tccagagaca cgccaagaa ctcgttatat     240 ctgcaaatga acagtctgag agccgaagac acggctgtgt attactgtgc gagaggaggt    300
gttggctaca gtatctccca cttcggtgtg gacgtctggg gccaagggac cacggtcacc    360
gtctcctca                                                            369
```

<210> SEQ ID NO 734
<211> LENGTH: 369
<212> TYPE: DNA
<213> ORGANISM: Homo sapiens

<400> SEQUENCE: 734

```
gaggtgcagc tggtggagtc tgggggaggc ttggtccagc cggggggtc cctgagactc        60 tcctgtgcag cctctggatt cacctttagt agccattgga tgacttggtt ccgtcaggct       120
ccagggaagg ggctgagtg gtggcccac ataaaggaag acgaaagtga aaatactat          180 gtggactctg tgaagggccg attcaccatc tccagagaca acgccaagaa ctcgttatat       240
ctgcaaatga acagtctgag agccaagac acggctgtgt attactgtgc gagaggaggt       300
gagggctaca gtatctccca cttcggtgtg gacgtctggg gccaagggac cacggtcacc      360
gtctcctca                                                             369
```

<210> SEQ ID NO 735
<211> LENGTH: 366
<212> TYPE: DNA
<213> ORGANISM: Homo sapiens

<400> SEQUENCE: 735

```
gaggtgcagc tggtggagtc tgggggaggc ttggtcaagc ctggagggtc cctgagagtc       60
tcctgtgcag cctctggatt cacccttcagt gactactaca tgagctggtt ccgccaggct     120
ccagggaagg ggctggagtg ggtttcatac attagtggta gtggtgatat catagactac      180
gcagactctg taaagggccg attcaccatc tccaggaca acgccaagaa ctctctgtat       240
ctgcagatga acaacctgag agccgaggac acggccgtgt atcactgtgc gagagaagat      300
tcccgtctaa ctggaactac ggactttgac aattggggcc agggaaccct ggtcaccgtc     360
tcctca                                                                366
```

<210> SEQ ID NO 736
<211> LENGTH: 366
<212> TYPE: DNA
<213> ORGANISM: Homo sapiens

<400> SEQUENCE: 736

```
gaggtgcagc tggtggagtc tgggggaggc ttggtcaagc ctggagggtc cctgagagtc       60
tcctgtgcag cctctggatt cacccttcagt gactactaca tgagctggtt ccgccaggct     120
ccagggaagg ggctggagtg ggtttcgtac attagtggta gtggtgatat catagactat      180
gcagactctg tgaagggccg attcaccatc tccaggaca acgccaagaa ctcactgtat       240
ctgcaaatga acagcctgag agccgaggac acggccgtgt atcactgtgc gaaagaagat      300
tcccgtatac ctggaactac ggactttgac aattggggcc agggaaccct ggtcactgtc     360
tcctca                                                                366
```

<210> SEQ ID NO 737
<211> LENGTH: 366
<212> TYPE: DNA
<213> ORGANISM: Homo sapiens

<400> SEQUENCE: 737

```
gaggtgcagc tggtggagtc tgggggaggc ttggtcaagc ctggagggtc cctgagagtc       60
tcctgtgcag cctctggatt cacccttcagt gactactata tgagttggtt ccgccaggct     120
ccagggaagg ggctggagtg gatttcgtac attagtggta gtggtgatat catagactac      180
gcagactctg tgaagggccg attcaccatc tccaggaca acgccaagaa ctcactgtat       240
ctgcaaatga acagcctgag agccgaggac acggccgtgt atcactgtgc gaaagaagat      300
```

```
tcccgtatac ctggaactac ggactttgac aattggggcc agggaaccct ggtcaccgtc    360
tcttca                                                                366
```

<210> SEQ ID NO 738
<211> LENGTH: 366
<212> TYPE: DNA
<213> ORGANISM: Homo sapiens

<400> SEQUENCE: 738

```
gaggtgcagc tggtggagtc tgggggaggc ttggtcaagc ctggagggtc cctgagagtc     60
tcctgtgcag cctctggatt caccttcagt gactactaca tgagctggtt ccgccaggct    120
ccagggaagg gctggagtg  ggtttcgtac attagtggta gtggtgatgt cattgactat    180
gcagactctg tgaagggccg attcaccatc tccaggaca  acgccaagaa ttcactgtat    240
ctgcaaatga acagcctgag agccgaggac acggccgtgt atcactgtgc gaaagaagat    300
tcccgtatac ctggaactac ggactttgac aattggggcc agggaaccct ggtcactgtc    360
tcttca                                                                366
```

<210> SEQ ID NO 739
<211> LENGTH: 366
<212> TYPE: DNA
<213> ORGANISM: Homo sapiens

<400> SEQUENCE: 739

```
gaggtgcagc tggtggagtc tgggggaggc ttggtcaagc ctggagggtc cctgagactc     60
tcctgtgcag tctctggatt caccttcagt gactactaca tgagctggtt ccgccaggct    120
ccagggaagg gctggagtg  ggtttcgtac attagtggta gtggtgatat catagactat    180
gcagactctg tgaagggccg attcaccatc tccaggaca  acgccaagaa ctcactgtat    240
ctgcaaatga acagcctgag agccgaggac acggccgtgt atcactgtgc gaaagaagat    300
tcccgtatac ctggaactac ggactttgac aattggggcc agggaaccct ggtcactgtc    360
tcctca                                                                366
```

<210> SEQ ID NO 740
<211> LENGTH: 366
<212> TYPE: DNA
<213> ORGANISM: Homo sapiens

<400> SEQUENCE: 740

```
gaggtgcagc tggtggagtc tgggggaggc ttggtcaagc ctggagggtc cctgagagtc     60
tcctgtgcag cctctggatt caccttcagt gactactaca tgagctggtt ccgccaggct    120
ccagggaagg gctggagtg  ggtttcgtac attagtggta gtggtgatat catagactat    180
gcggactctg tgaagggccg attcaccatc tccaggaca  acgccaagaa ctcactgtat    240
ctgcaaatga acagcctgag agccgaggac acggccgtgt atcactgtgc gaaagaagat    300
tcccgtatac ctggaactac ggactttgac agttggggcc aagggacaat ggtcaccgtc    360
tcctca                                                                366
```

<210> SEQ ID NO 741
<211> LENGTH: 366
<212> TYPE: DNA
<213> ORGANISM: Homo sapiens

```
<400> SEQUENCE: 741
gaggtgcagc tggtggagtc tgggggaggc ttggtcaagc caggagggtc cctgagactc      60
tcctgtgcag cctctggatt caccttcagt gactactaca tgagctggtt ccgccaggct     120
ccagggaagg ggctggagtg ggtttcatac attagtggta gtggtactac catagactac     180
gcagactctg tgaagggccg cttcaccatc tccagggaca acgccaggaa ctcactatat     240
ctgcaaatga acagcctgag agccgaggac acggccgtgt attactgtgc cagagaagat     300
atcaggatga ctggaactac ggactttgac aactggggcc agggaaccct ggtcaccgtc     360
tcttca                                                                366

<210> SEQ ID NO 742
<211> LENGTH: 366
<212> TYPE: DNA
<213> ORGANISM: Homo sapiens

<400> SEQUENCE: 742
gaggtgcagc tggtggagtc tgggggaggc ttggtcaagc ctggagggtc cctgagactc      60
tcctgtgcag cctctggatt cgccttcagt gactactaca tgagctggtt ccgccaggct     120
ccagggaagg ggctggagtg ggtttcacac attagtggta gtggaactac catagactac     180
gcagactctg tgaagggccg attcaccatc tccagacaca acgccaagaa ctcactatat     240
ctacaaatga acagcctgag agccgaggac acggccgtgt atcactgtgc gagagaagat     300
tcccgcatgc ctggaactac ggactttgac aactggggcc agggaaccct ggtcaccgtc     360
tcctca                                                                366

<210> SEQ ID NO 743
<211> LENGTH: 366
<212> TYPE: DNA
<213> ORGANISM: Homo sapiens

<400> SEQUENCE: 743
gaggtgcagc tggtggagtc tgggggaggc ttggtcaagc ctggagggtc cctgagactc      60
tcctgtgcag cctctggatt caccttcagt gactactata tgacctggtt ccgccaggct     120
ccagggaagg gactggagtg gatttcatac attagtggta gtggtgatac catagactac     180
gcagagtctg tgaagggccg attcaccatc tccagggaca acgccaagaa ttcactgtat     240
ctgcagatga acagcctgag agccgaggac acggccgtgt atcactgtgc gagagaagat     300
tcgcgtatag ccggaactac ggactttgac aactggggcc cgggaaccct ggtcactgtc     360
tcttca                                                                366

<210> SEQ ID NO 744
<211> LENGTH: 366
<212> TYPE: DNA
<213> ORGANISM: Homo sapiens

<400> SEQUENCE: 744
gaggtgcagc tggtggagtc tgggggaggc ttggtcaagc ctggagggtc cctgagactc      60
tcctgtgcag cctctggatt caccttcagt gactactaca tgacctggtt ccgccaggct     120
ccagggaagg ggctggagtg ggtttcatac attagtagta gtggtagtaa catagattac     180
gcagactctg tgaagggccg attcaccatc tctagggaca acgccaagaa ctcactgtat     240
ctgcaaatga acagcctgag agccgaggac acggccgtgt attactgtgc gagagaagat     300
```

```
tcccgtttaa gtggaactac ggactttgac tactggggcc agggaaccct ggtcaccgtc    360
tcttca                                                               366
```

<210> SEQ ID NO 745
<211> LENGTH: 366
<212> TYPE: DNA
<213> ORGANISM: Homo sapiens

<400> SEQUENCE: 745

```
gaggtgcagc tggtggagtc tggggggaggc ttggtccagc ctgggggtc cctgagactc    60 tcctgtgcag cctctggatt caccttcagt gactactata tgacctggtt ccgccaggct   120
ccagggaagg gactggagtg gatttcatac attagtggta gtggtgatac catagactac   180
gcagagtctg tgaagggccg attcaccatc tccaggaca acgccaagaa ttcactgtat    240
ctgcagatga acagcctgag agccgaggac acggccgtgt atcactgtgc gagagaagat   300
tcgcgtatag ccggaactac ggactttgac aactggggcc cgggaaccct ggtcactgtc   360
tcctca                                                               366
```

<210> SEQ ID NO 746
<211> LENGTH: 366
<212> TYPE: DNA
<213> ORGANISM: Homo sapiens

<400> SEQUENCE: 746

```
gaggtgcagc tggtggagtc tggggggaggc ttggtcaagc ctggagggtc cctgagactc    60
tcctgtgcag cctctggatt caccttcagt gactactaca tgagctggtt ccgccaggct   120
ccagggaagg ggctggagtg ggtttcacac attagtggta gtggtactac catagactac   180
gcagactctg tgaagggccg cttcaccatc tccaggaca acgccaggaa gtcactatat    240
ctgcagatga acagcctgag agccgaggac acggccgtct attactgtgc cagagaagat   300
atcaggatga ctggaactac ggactttgac cactggggcc aaggaaccct ggtcaccgtc   360
tcctca                                                               366
```

<210> SEQ ID NO 747
<211> LENGTH: 366
<212> TYPE: DNA
<213> ORGANISM: Homo sapiens

<400> SEQUENCE: 747

```
caggtgcagc tggtggagtc tggggggaggc ttggtcaagc ctggagggtc cctgagactc    60
tcctgtgcag cctctggatt caccttcagt gactactaca tgagctggtt ccgccaggct   120
ccagggaagg ggctggagtg ggtttcacac attagtagta gtggtaatac catagactac   180
gcagactctg tgaagggccg cttcaccatc tccaggaca acgccaagaa ctcactttat    240
ctgcaaatga atagtctgag agccgaggac acggccgttt attactgtgc gagagaagat   300
cctcgtttac ctggaactac agatttgac tactggggcc agggaaccct ggtcactgtc   360
tcctca                                                               366
```

<210> SEQ ID NO 748
<211> LENGTH: 366
<212> TYPE: DNA
<213> ORGANISM: Homo sapiens

<400> SEQUENCE: 748

| gaggtgcagt tggtggagtc tgggggaggc ttggtcaagc ctggagggtc cctgagactc | 60 |
| tcctgtgcag cctctggatt caccttcagt gactactata tgacctggtt ccgccaggct | 120 |
| ccagggaagg gactgagtg gatttcatac attagtggta gtggtgatac catagactac | 180 |
| gcagagtctg tgaagggccg attcaccatc tccagggaca acgccaagaa ttcactgtat | 240 |
| ctgcagatga acagcctgag agccgaggac acggccgtgt attactgtgc cagagaagat | 300 |
| atcaggatgc tggaactac ggactttgac cactggggcc aaggaaccct ggtcaccgtc | 360 |
| tcctca | 366 |

<210> SEQ ID NO 749
<211> LENGTH: 366
<212> TYPE: DNA
<213> ORGANISM: Homo sapiens

<400> SEQUENCE: 749

| gaggtgcagc tggtggagtc tgggggaggc ttggtcaagc ctggagggtc cctgagactc | 60 |
| tcctgtgcag tctctggatt caccttcagt gactactaca tgagctggtt ccgccaggct | 120 |
| ccagggaagg ggctggagtg ggtttcacac attagtggta gtggaactac catagactac | 180 |
| gcagactctg tgaagggccg cttcaccatc tccagggaca acgccaggaa ttcactgtat | 240 |
| ctgcaaatga acagcctgag agccgaggac acggccgtgt attactgtgc cagagaagat | 300 |
| atcaggatgc tggaactac ggattttgac cactggggcc aaggaaccct ggtcactgtc | 360 |
| tcttca | 366 |

<210> SEQ ID NO 750
<211> LENGTH: 366
<212> TYPE: DNA
<213> ORGANISM: Homo sapiens

<400> SEQUENCE: 750

| caggtgcagc tggtggagtc tgggggaggc ttggtcaagc ctggagggtc cctgagactc | 60 |
| tcctgtgcag cctctggatt caccttcagt gactactaca tgagctggat ccgccaggct | 120 |
| ccagggaagg ggctggagtg ggtttcacac attagtagta gtgggagtac catagactac | 180 |
| gcagactctg tgaagggccg attcaccatc tccagggaca acgccaagaa ctcactgtat | 240 |
| ctgcaaatga acagcctgag agccgaggac acggccgtgt attactgtgc gagagaagat | 300 |
| cctcgtttaa ctggaactac agattttgac tactggggcc agggagccct ggtcactgtc | 360 |
| tcctca | 366 |

<210> SEQ ID NO 751
<211> LENGTH: 366
<212> TYPE: DNA
<213> ORGANISM: Homo sapiens

<400> SEQUENCE: 751

| caggtgcagc tggtggagtc tgggggaggc ttggtcaagc ctggagggtc cctgagactc | 60 |
| tcctgtgcag cctctggatt caccttcagt gactactaca tgagctggat ccgccaggct | 120 |
| ccagggaagg ggctggagtg ggtttcatac attagtagta gtggtagtac catatcctac | 180 |
| gcagactctg tgaagggccg attcaccatc tccagggaca acgccaagaa ctcactgtat | 240 |
| ctgcaaatga acagcctgag agccgaggac acggccgtgt attactgtgc gagagaagat | 300 |

```
cctcgtataa gtggaactac agattttgac aattggggcc agggaaccct ggtcaccgtc    360
tcctca                                                              366
```

<210> SEQ ID NO 752
<211> LENGTH: 366
<212> TYPE: DNA
<213> ORGANISM: Homo sapiens

<400> SEQUENCE: 752

```
caggtgcagc tgcaggagtc ggggggaggc ttggtcaagc ctggagggtc cctgagactc    60
tcctgtgcag cctctggatt caccttcagt gactactaca tgagctggtt ccgccaggct   120
ccagggaagg ggctggagtg ggtttcacac attagtagta gtggtaatac catagactac   180
gcagactctg tgaagggccg cttcaccatc tccaggaca acgccaagaa ctcactgtat    240
ctgcaaatga acagcctgag agccgaggac acggccgttt attactgtgc gagagaagat   300
cctcgtttac ctggaactac agattttgac tactggggcc agggaaccct ggtcaccgtc   360
tcctca                                                              366
```

<210> SEQ ID NO 753
<211> LENGTH: 366
<212> TYPE: DNA
<213> ORGANISM: Homo sapiens

<400> SEQUENCE: 753

```
caggtgcagc tggtggagtc tggggggaggc ttggtcaagc ctggagggtc cctgagactc    60
tcctgtgcag cctctggatt caccttcagt gactactaca tgagctggtt ccgccaggct   120
ccagggaagg ggctggagtg ggtttcatac attagtggta ctggtattac cacagactac   180
gcagactctg tgaagggccg cttcaccatc tccaggaca acgccaagaa ctcactgtat    240
ctgcaaatga acagcctgag agccgaggac acggccgtgt attactgtgc gagagaagat   300
cctcgtttac ctggaacttc agaatttgac aactggggcc agggaaccct ggtcaccgtc   360
tcctca                                                              366
```

<210> SEQ ID NO 754
<211> LENGTH: 366
<212> TYPE: DNA
<213> ORGANISM: Homo sapiens

<400> SEQUENCE: 754

```
gaggtgcagc tggtggagtc tggggggaggc ttggtcaagc ctggagggtc cctgagactc    60
tcctgtgcag cctctggatt caccttcagt gactactaca tgagctggat ccgccaggct   120
ccagggaagg ggctggagtg ggtttcacac attagtagta gtggtagtac catagattat   180
gcagactctg tgaagggccg attcaccatc tccaggaca acgccaagaa ctcactgtat    240
ctgcaaatga acagcctgag agccgaggac acggccgtct attactgtgc gagagaagat   300
ccccgtatgc ctggaacttt tgactttgac aactggggcc agggaaccct ggtcaccgtc   360
tcctca                                                              366
```

<210> SEQ ID NO 755
<211> LENGTH: 366
<212> TYPE: DNA
<213> ORGANISM: Homo sapiens

<400> SEQUENCE: 755

```
gaggtgcagc tggtggagtc tgggggaggc ttggtcaagc ctggagggtc cctgagactc    60
tcctgtgcag cctctggatt cgccttcagt gactactaca tgagctggtt ccgccaggct   120
ccagggaagg ggctggagtg ggtttcacac attagtggta gtggaactac catagactac   180
gcagactctg tgaagggccg cttcaccatc tccagggaca acgccaggaa ttcactgtat   240
ctgcaaatga acagcctgag agccgaggac acggccgtgt attactgtgc cagagaagat   300
atcaggatgc ctggaactac ggactttgac cactggggcc aaggaaccct ggtcactgtc   360
tcttca                                                              366
```

<210> SEQ ID NO 756
<211> LENGTH: 366
<212> TYPE: DNA
<213> ORGANISM: Homo sapiens

<400> SEQUENCE: 756

```
gaggtgcagc tggtggagtc tgggggaggc ttggtcaagc ctggagggtc cctgagactc    60
tcctgtgcag tctctggatt caccttcagt gactactaca tgagctggtt ccgccaggct   120
ccagggaagg ggctggagtg ggtttcacac attagtggta gtggaactac catagactac   180
gcagactctg tgaagggccg cttcaccatc tccagggaca acgccaggga ttcactgtat   240
ctgcaaatga acagcctgag agccgaggac acggccgtgt attactgtgc cagagaagat   300
atcaggatgc ctggaactac ggattttgac cactggggcc aaggaaccct ggtcactgtc   360
tcttca                                                              366
```

<210> SEQ ID NO 757
<211> LENGTH: 366
<212> TYPE: DNA
<213> ORGANISM: Homo sapiens

<400> SEQUENCE: 757

```
gaggtgcagc tggtggagtc tgggggaggc ttggtcacgc ctggagggtc cctgagactc    60
tcctgtgcag tctctggatt caccttcagt gactactaca tgagctggtt ccgccaggct   120
ccagggaagg ggctggagtg ggtttcacac attagtggta gtggaactac catagactac   180
gcagactctg tgaagggccg cttcaccatc tccagggaca acgccaggaa ttcactgtat   240
ctgcaaatga acagcctgag agccgaggac acggccgtgt attactgtgc cagagaagat   300
atcaggatgc ctggaactac ggattttgac cactggggcc aaggaaccct ggtcaccgtc   360
tcctca                                                              366
```

<210> SEQ ID NO 758
<211> LENGTH: 366
<212> TYPE: DNA
<213> ORGANISM: Homo sapiens

<400> SEQUENCE: 758

```
gaggtgcagc tggtggagtc tgggggaggc ttggtcaagc ctggagggtc cctgagactc    60
tcctgtgcag tctctggatt caccttcagt gactactaca tgagctggtt ccgccaggct   120
ccagggaagg ggctggagtg ggtttcacac attagtggta gtggaactac catagactac   180
gcagactctg tgaagggccg cttcaccatc tccagggaca acgccaggaa ttcactgtat   240
ctgcaaatga acagcctgag agccgaggac acggccatgt attactgtgc cagagaagat   300
```

-continued

| | |
|---|---|
| atcaggatgc ctggaactac ggattttgac cactgggccc aaggaaccct ggtcaccgtc | 360 |
| tcctca | 366 |

<210> SEQ ID NO 759
<211> LENGTH: 366
<212> TYPE: DNA
<213> ORGANISM: Homo sapiens

<400> SEQUENCE: 759

| | |
|---|---|
| gaggtgcagc tggtggagtc tgggggaggc ttggttaagc ctggagggtc cctgagactc | 60 |
| tcctgtgcag cctctggatt cgccttcagt gactactaca tgagctggtt ccgccaggct | 120 |
| ccagggaagg ggctggagtg ggtttcacac attagtggta gtggaactac catagactac | 180 |
| gcagactctg tgaaggaccg cttcaccatc tccaggaca acgccaggaa ttcactgtat | 240 |
| ctgcaaatga acagcctgag agccgaggac acggccgtgt attactgtgc cagagaagat | 300 |
| atcaggatgc tggaactac ggactttgac cactgggggcc aaggaaccct ggtcactgtc | 360 |
| tcttca | 366 |

<210> SEQ ID NO 760
<211> LENGTH: 366
<212> TYPE: DNA
<213> ORGANISM: Homo sapiens

<400> SEQUENCE: 760

| | |
|---|---|
| gaggtgcagc tggtggagtc tgggggaggc ttggtcaagc ctggagggtc cctgagactc | 60 |
| tcctgtacag cctctggatt caccttcact gactattata tgagctggtt ccgccaggct | 120 |
| ccagggaagg gactggagtg ggtttcacac attagtagta gtggtactac aatagactac | 180 |
| gcagactctg tgaagggccg attcaccatc tccaggaca acgccaagaa ctcactgtat | 240 |
| ctgcaaatga acagcctgag agccgacgac acggccgtat attactgtgc gagagaagat | 300 |
| atcaggatgc ctggaactac ggactttgac aactggggcc agggaaccct ggtcactgtc | 360 |
| tcctca | 366 |

<210> SEQ ID NO 761
<211> LENGTH: 366
<212> TYPE: DNA
<213> ORGANISM: Homo sapiens

<400> SEQUENCE: 761

| | |
|---|---|
| caggtgcagc tggtggagtc gggggggaggc ttggtcaagc ctggagggtc cctgagactc | 60 |
| tcctgtgcag cctctggatt caccttcagt gactactaca tgacctggtt ccgccaggct | 120 |
| ccagggaagg ggctggagtg ggtttcatac attagtagta gtggtagtac catttcctac | 180 |
| gcagactctg tgaagggccg attcaccatc tccaggaca acgccaacaa ctcactgtat | 240 |
| ctgcaaatga acagcctgag agccgaggac acggccgtat atcactgtgc gagagaagat | 300 |
| atacgtatga gtgggactac ggactttgac tactggggcc agggaaccct ggtcactgtc | 360 |
| tcctca | 366 |

<210> SEQ ID NO 762
<211> LENGTH: 366
<212> TYPE: DNA
<213> ORGANISM: Homo sapiens

<400> SEQUENCE: 762

```
caggtgcagc tggtggagtc tgggggaggc ttggtcaagc ctggagggtc cctgagactc      60
tcctgtgcag cctctggatt catcttcagt gactactaca tgagctggtt ccgccaggct     120
ccagggaagg ggctggagtg ggtttcacac attagtagta gtggtagttc catagactac     180
gcagactctg tgaagggccg attcaccatt tcgagggaca cgccaagaa ctcactgtat      240
ctgcaaatga acagcctgag agccgaggac acggccgtgt attactgtgc gagagaagat     300
cctcgtttaa gtggaactat agattttgac tcctggggcc agggaaccct ggtcaccgtc     360
tcttca                                                                366
```

<210> SEQ ID NO 763
<211> LENGTH: 366
<212> TYPE: DNA
<213> ORGANISM: Homo sapiens

<400> SEQUENCE: 763

```
gaggtgcagc tggtggagtc tgggggaggc ttggtcaagc ctggagggtc cctgagactc      60
tcctgtgcag cctctggatt cgccttcagt gactactaca tgagctggtt ccgccaggct     120
ccagggaagg ggctggagtg ggtttcacac attggtggta gtggaactac catagactac     180
gcagactctg tgaagggccg cttcaccatc tccaggaca cgccaggaa ttcactgtat       240
ctgcaaatga acagcctgag agccgaggac acggccgtgt attactgtgc cagagaagat     300
atcaggatgc ctggaactac ggactttgac cactggggcc aaggaaccct ggtcaccgtc     360
tcctca                                                                366
```

<210> SEQ ID NO 764
<211> LENGTH: 366
<212> TYPE: DNA
<213> ORGANISM: Homo sapiens

<400> SEQUENCE: 764

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagagaca cgccaagaa ctcactgtat      240
ctgcaaatga acagcctgag agccgaggac acggccgtgt attactgtgc gagagaagat     300
cctcgtgtgc ctggaactac gaactttgac tactggggcc agggaaccct ggtcactgtc     360
tcctca                                                                366
```

<210> SEQ ID NO 765
<211> LENGTH: 366
<212> TYPE: DNA
<213> ORGANISM: Homo sapiens

<400> SEQUENCE: 765

```
caggtgcagc tggtggagtc tgggggaggc ttggtcaagc ctggagggtc cctgagactc      60
tcctgtgcag cctctggatt caccttcagt gactactaca tgacctggat gcgccaggct     120
ccagggaagg ggctggagtg ggtttcatac attagtggca gtggtagtac cattgactat     180
gcagactctg tgaagggccg attcacgatc tccaggaca cgccaagaa ctcactgtac       240
ctgcaaatga acagcctgag acccgaggac acggccgtgt attactgtgc gaaagaagat     300
```

```
ggccgtatac ctggaactac ggactttgac cactggggcc agggaaccct ggtcactgtc    360
tcttca                                                                366

<210> SEQ ID NO 766
<211> LENGTH: 366
<212> TYPE: DNA
<213> ORGANISM: Homo sapiens

<400> SEQUENCE: 766
gaggtgcagc tggtggagtc tgggggaggc ttggtccagc ctgggggrtc cctgagactc     60
tcctgtgcag cctctggatt cgccttcagt gactactaca tgagctggtt ccgccaggct    120
ccggggaagg gctggagtg gtttcacac attagtggta gtggaactac catagactac      180
gcagactctg tgaaggaccg cttcaccatc tccaggaca acgccaggaa ttcactgtat     240
ctgcaaatga acagcctgag agccgaggac acggccgtgt attactgtgc cagagaagat    300
atcaggatgc ctggaactac ggactttgac cactggggcc aaggaaccct ggtcaccgtc    360
tcctca                                                                366

<210> SEQ ID NO 767
<211> LENGTH: 366
<212> TYPE: DNA
<213> ORGANISM: Homo sapiens

<400> SEQUENCE: 767
caggtgcagc tggtggagtc tgggggaggc ttggtcaagc ctggagggtc cctgagactc     60
tcctgtgcag cctctggatt ccccttcagt gactacttca tgagctggtt ccgccaggct    120
ccagggaagg gctggagtg gtttcacac attagtagta gtggtaattc catagactac      180
gcagactctg tgaagggccg cttcaccatc tccaggaca acgccaagaa ctcactgtat     240
ctgcaaatga acagcctgag agccgaggac acggccgttt attactgtgc gaaagaagat    300
cctcgtttac ctggaactac agattttgac tactggggcc agggaaccct ggtcactgtc    360
tcttca                                                                366

<210> SEQ ID NO 768
<211> LENGTH: 366
<212> TYPE: DNA
<213> ORGANISM: Homo sapiens

<400> SEQUENCE: 768
caggtgcagc tggtggagtc tgggggaggc ttggtcaagc ctggagggtc cctgagactc     60
tcctgtgcag cctctggatt caccttcagt gactcctaca tgagctggat ccgccaggct    120
ccagggaagg gctggagtg gtttcacat attagtaatt ctggtagtac cataagctac      180
gcagactctg tgaagggccg attcaccatc tccaggaca acgccaagaa ctcactgtat     240
ctgcaaatga acagcctgag agccgaggac acggccgtgt attactgtgc gagagaagat    300
cctcgtttac ctggaacttc agattttgac tactggggcc agggaaccct ggtcactgtc    360
tcttca                                                                366

<210> SEQ ID NO 769
<211> LENGTH: 366
<212> TYPE: DNA
<213> ORGANISM: Homo sapiens
```

<400> SEQUENCE: 769

```
caggtgcagc tggtggagtc tgggggaggc gtggtccagc ctggggaggtc cctgagactc      60
tcctgtgcag cctctggatt caccttcagt gactactaca tgagctggat ccgccaggct     120
ccagggaagg ggctggagtg ggtttcacac attagtagta gtggtagttc catagactac     180
gcagactctg tgaagggccg attcaccatt tcgagggaca cgccaagaa ttcactgtat      240
ctgcaaatga acagcctgag agacgaggac acggccgtgt attactgtgc gagagaagat     300
cctcgtttaa gtggaactac agattttgac cagtggggcc agggaaccct ggtcaccgtc     360
tcctca                                                                366
```

<210> SEQ ID NO 770
<211> LENGTH: 366
<212> TYPE: DNA
<213> ORGANISM: Homo sapiens

<400> SEQUENCE: 770

```
caggtgcagc tggtggagtc tgggggaggc ttggtccagc ctgggggtc cctgagactc       60
tcctgtgcag cctctggatt cacctttagt agctattgga tgagctgggt ccgccaggct    120
ccagggaagg ggctggagtg ggtttcacac attagtagta gtggtagtac catagactac    180
gcagagtctg tgaagggccg attcaccatc tccaggaca acgccaagaa ctcactgtat     240
ctgcaaatga acagcctgag agccgaggac acggccgtgt attactgtgc gagagaagat    300
cctcgtatga ctggaactac agattttgac tactggggcc agggaaccct ggtcaccgtc    360
tcttca                                                                366
```

<210> SEQ ID NO 771
<211> LENGTH: 366
<212> TYPE: DNA
<213> ORGANISM: Homo sapiens

<400> SEQUENCE: 771

```
caggtgcagc tgcaggagtc ggggggaggc ttggtcaagc ctggagggtc cctgagactc     60
tcctgtgcag cctctggatt caccttcagt aactacttca tgagttggat ccgccaggct   120
ccagggaagg ggctggagtg ggtttcacac attagtagta gtggtaatac catagactac   180
gcagactctg tgaagggccg cttcaccatc tccaggaca acgccaagaa ctcactttat    240
ctgcaaatgg atagtctgag agccgaggac acggccgttt attactgttc gagagaagat    300
cctcgtttac ctggaactac agattttgac tactggggcc agggaaccct ggtcactgtc    360
tcttca                                                                366
```

<210> SEQ ID NO 772
<211> LENGTH: 366
<212> TYPE: DNA
<213> ORGANISM: Homo sapiens

<400> SEQUENCE: 772

```
gaggtgcagc tggtggagtc tgggggaggc gtggtcaagc ctggagggtc cctgagactc     60
tcctgtgcag cctctggatt cactttcagt gactactaca tgacctggat ccgccagggt   120
ccagggaagg gacaggaatg gatttcatac attagtagtg gtggtagcac catacactac   180
gcagactctg tgaagggccg attcaccatc tccaggaca acgccaagaa ctcactgtat    240
ctgcaaatga acagcctgag agccgaggac acggccgtgt attactgtgc gagagaaaat    300
```

```
ccccgtttac ctggaactat ggactttgac tattggggcc agggaaccct ggtcactgtc    360
tcctca                                                               366
```

<210> SEQ ID NO 773
<211> LENGTH: 366
<212> TYPE: DNA
<213> ORGANISM: Homo sapiens

<400> SEQUENCE: 773

```
caggtgcagc tggtggagtc tgggggaggc ttggtccagc ctgggggtc cctgagactc     60 tcctgtgcag cctctggatt caccttcagt gaccacttca tgagctggtt ccgccaggct   120
ccagggaagg ggctggagtg ggtggccaac ataaaacaag atggaagtga aaatactat    180 gtggactctg tgaagggccg attcaccatc tccagagaca cgccaagaa ctcactgttt    240 ctgcaaatga acagcctgag agccgaggac acggctatgt attactgtgc gagagaggat  300
cctcgtttaa ctggaactac agattttgac aactggggcc agggaaccct ggtcactgtc  360
tcttca                                                              366
```

<210> SEQ ID NO 774
<211> LENGTH: 366
<212> TYPE: DNA
<213> ORGANISM: Homo sapiens

<400> SEQUENCE: 774

```
gaggtgcagc tggtggagtc tgggggaggc ttggtccagg cggggggtc cctaagactc     60 tcctgtgtag cctctggatt cacctttagt aattattgga tgacctggtt ccgccaggct   120
ccagggaggg ggctggagtg ggtttcacac attagtagta ctggatctac catagactac  180
gcagactctg tgaagggccg attcaccatc tccagggaca cgccagaa ctcactatat    240 ttgcaaatga acagcctgag agccgaggac acggccgtgt attactgtgc gagagaagat  300
ccccgtttac ctggaactat ggactttgac tattggggcc agggaaccct ggtcaccgtc  360
tcctca                                                              366
```

<210> SEQ ID NO 775
<211> LENGTH: 366
<212> TYPE: DNA
<213> ORGANISM: Homo sapiens

<400> SEQUENCE: 775

```
gaggtgcagc tggtggagtc tgggggaggc ttggtcaagc ctggagggtc cctgagactc     60
tcctgtgcag cctctggatt caccttcagt gactactaca tgagctggtt ccgccaggct   120
ccagggaagg ggctggagtg ggtttcatac attagtggta gtggtgatat catagactac  180
gcagactctg taaagggccg attcaccatc tccagggaca cgccaagaa ctctctgtat   240 ctgcagatga acaacctgag agccgaggac acggccgtgt atcactgtgc gagagaagat  300
tcccgtctaa ctggaactac ggactttgac aattggggcc agggaaccct ggtcaccgtc  360
tcctca                                                              366
```

<210> SEQ ID NO 776
<211> LENGTH: 366
<212> TYPE: DNA
<213> ORGANISM: Homo sapiens

<400> SEQUENCE: 776

| gaggtgcagc tggtggagtc tgggggaggc ttggtcaagc ctggagggtc cctgagagtc | 60 |
| tcctgtgcag cctctggatt caccttcagt gactactaca tgagctggat ccgccaggct | 120 |
| ccagggaagg ggctggagtg ggtttcatac attagtggta gtggtgatat catagactac | 180 |
| gcagactctg taaagggccg attcaccatc tccagggaca acgccaagaa ctctctgtat | 240 |
| ctgcagatga caacctgag agccgaggac acggccgtgt atcactgtgc gagagaagat | 300 |
| tcccgtctaa ctggaactac ggactttgac aattggggcc agggaaccct ggtcaccgtc | 360 |
| tcctca | 366 |

<210> SEQ ID NO 777
<211> LENGTH: 366
<212> TYPE: DNA
<213> ORGANISM: Homo sapiens

<400> SEQUENCE: 777

| gaggtgcagc tggtggagtc tgggggaggc ttggtcaagc ctggagggtc cctgagagtc | 60 |
| tcctgtgcag cctctggatt caccttcagt gactactaca tgagctggtt ccgccaggct | 120 |
| ccagggaagg ggctggagtg ggtttcatac attagtggta gtggtgatat catagactac | 180 |
| gcagactctg taaagggccg attcaccatc tccagggaca acgccaagaa ctctctgtat | 240 |
| ctgcagatga acagcctgag agccgaggac acggccgtgt atcactgtgc gagagaagat | 300 |
| tcccgtctaa ctggaactac ggactttgac aattggggcc agggaaccct ggtcaccgtc | 360 |
| tcctca | 366 |

<210> SEQ ID NO 778
<211> LENGTH: 366
<212> TYPE: DNA
<213> ORGANISM: Homo sapiens

<400> SEQUENCE: 778

| gaggtgcagc tggtggagtc tgggggaggc ttggtcaagc ctggagggtc cctgagagtc | 60 |
| tcctgtgcag cctctggatt caccttcagt gactactaca tgagctggtt ccgccaggct | 120 |
| ccagggaagg ggctggagtg ggtttcatac attagtggta gtggtgatat catagactac | 180 |
| gcagactctg taaagggccg attcaccatc tccagggaca acgccaagaa ctctctgtat | 240 |
| ctgcagatga caacctgag agccgaggac acggccgtgt attactgtgc gagagaagat | 300 |
| tcccgtctaa ctggaactac ggactttgac aattggggcc agggaaccct ggtcaccgtc | 360 |
| tcctca | 366 |

<210> SEQ ID NO 779
<211> LENGTH: 366
<212> TYPE: DNA
<213> ORGANISM: Homo sapiens

<400> SEQUENCE: 779

| gaggtgcagc tggtggagtc tgggggaggc ttggtcaagc ctggagggtc cctgagactc | 60 |
| tcctgtgcag cctctggatt caccttcagt gactactaca tgagctggtt ccgccaggct | 120 |
| ccagggaagg ggctggagtg ggtttcatac attagtggta gtggtgatat catagactac | 180 |
| gcagactctg taaagggccg attcaccatc tccagggaca acgccaagaa ctctctgtat | 240 |
| ctgcagatga caacctgag agccgaggac acggccgtgt attactgtgc gagagaagat | 300 |

```
tcccgtctaa ctggaactac ggactttgac aattggggcc agggaaccct ggtcaccgtc    360
tcctca                                                               366
```

<210> SEQ ID NO 780
<211> LENGTH: 366
<212> TYPE: DNA
<213> ORGANISM: Homo sapiens

<400> SEQUENCE: 780

```
gaggtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg gctggagtg gtttcatac attagtggta gtggtgatat catagactac    180
gcagactctg taaagggccg attcaccatc tccaggaca acgccaagaa ctctctgtat    240
ctgcagatga acagcctgag agccgaggac acggccgtgt attactgtgc gagagaagat    300
tcccgtctaa ctggaactac ggactttgac aattggggcc agggaaccct ggtcaccgtc    360
tcctca                                                               366
```

<210> SEQ ID NO 781
<211> LENGTH: 366
<212> TYPE: DNA
<213> ORGANISM: Homo sapiens

<400> SEQUENCE: 781

```
gaggtgcagc tggtggagtc tgggggaggc ttggtcaagc ctggagggtc cctgagactc     60
tcctgtgcag cctctggatt caccttcagt gactactaca tgagctggtt ccgccaggct    120
ccagggaagg gctggagtg gtttcatac attagtggta gtggtgatat catagactac    180
gcagactctg taaagggccg attcaccatc tccaggaca acgccaagaa ctctctgtat    240
ctgcagatga acagcctgag agccgaggac acggccgtgt attactgtgc gagagaagat    300
tcccgtctaa ctggaactac ggactttgac aattggggcc agggaaccct ggtcaccgtc    360
tcctca                                                               366
```

<210> SEQ ID NO 782
<211> LENGTH: 366
<212> TYPE: DNA
<213> ORGANISM: Homo sapiens

<400> SEQUENCE: 782

```
gaggtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg gctggagtg gtttcatac attagtggta gtggtgatat catagactac    180
gcagactctg taaagggccg attcaccatc tccaggaca acgccaagaa ctctctgtat    240
ctgcagatga acagcctgag agccgaggac acggccgtgt attactgtgc gagagaagat    300
gcccgtctaa ctggaactac ggactttgac aattggggcc agggaaccct ggtcaccgtc    360
tcctca                                                               366
```

<210> SEQ ID NO 783
<211> LENGTH: 366
<212> TYPE: DNA
<213> ORGANISM: Homo sapiens -continued

<400> SEQUENCE: 783

```
gaggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtggta gtggtgatat catagactac   180
gcagactctg taaagggccg attcaccatc tccagggaca acgccaagaa ctctctgtat   240
ctgcagatga acagcctgag agccgaggac acggccgtgt attactgtgc gagagaagat   300
ccccgtctaa ctggaactac ggactttgac aattggggcc agggaaccct ggtcaccgtc   360
tcctca                                                              366
```

<210> SEQ ID NO 784
<211> LENGTH: 366
<212> TYPE: DNA
<213> ORGANISM: Homo sapiens

<400> SEQUENCE: 784

```
gaggtgcagc tggtggagtc tgggggaggc ttggtcaagc ctggagggtc cctgagactc    60
tcctgtgcag cctctggatt caccttcagt gactactaca tgagctggtt ccgccaggct   120
ccagggaagg ggctggagtg ggtttcatac attagtggta gtggtgatat catagactac   180
gcagactctg taaagggccg attcaccatc tccagggaca acgccaagaa ctctctgtat   240
ctgcagatga acagcctgag agccgaggac acggccgtgt attactgtgc gagagaagat   300
gcccgtctaa ctggaactac ggactttgac aattggggcc agggaaccct ggtcaccgtc   360
tcctca                                                              366
```

<210> SEQ ID NO 785
<211> LENGTH: 366
<212> TYPE: DNA
<213> ORGANISM: Homo sapiens

<400> SEQUENCE: 785

```
gaggtgcagc tggtggagtc tgggggaggc ttggtcaagc ctggagggtc cctgagactc    60
tcctgtgcag cctctggatt caccttcagt gactactaca tgagctggtt ccgccaggct   120
ccagggaagg ggctggagtg ggtttcatac attagtggta gtggtgatat catagactac   180
gcagactctg taaagggccg attcaccatc tccagggaca acgccaagaa ctctctgtat   240
ctgcagatga acagcctgag agccgaggac acggccgtgt attactgtgc gagagaagat   300
ccccgtctaa ctggaactac ggactttgac aattggggcc agggaaccct ggtcaccgtc   360
tcctca                                                              366
```

<210> SEQ ID NO 786
<211> LENGTH: 255
<212> TYPE: PRT
<213> ORGANISM: Homo sapiens

<400> SEQUENCE: 786

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45
```

```
Pro Pro Asn Ser Phe Ser Ser Ala Gly Gly Gln Arg Thr Cys Asp Ile
    50                  55                  60
Cys Arg Gln Cys Lys Gly Val Phe Arg Thr Arg Lys Glu Cys Ser Ser
 65                  70                  75                  80
Thr Ser Asn Ala Glu Cys Asp Cys Thr Pro Gly Phe His Cys Leu Gly
                 85                  90                  95
Ala Gly Cys Ser Met Cys Glu Gln Asp Cys Lys Gln Gly Gln Glu Leu
            100                 105                 110
Thr Lys Lys Gly Cys Lys Asp Cys Cys Phe Gly Thr Phe Asn Asp Gln
            115                 120                 125
Lys Arg Gly Ile Cys Arg Pro Trp Thr Asn Cys Ser Leu Asp Gly Lys
130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
                165                 170                 175
Pro Ala Arg Glu Pro Gly His Ser Pro Gln Ile Ile Ser Phe Phe Leu
            180                 185                 190
Ala Leu Thr Ser Thr Ala Leu Leu Phe Leu Leu Phe Phe Leu Thr Leu
            195                 200                 205
Arg Phe Ser Val Val Lys Arg Gly Arg Lys Lys Leu Leu Tyr Ile Phe
210                 215                 220
Lys Gln Pro Phe Met Arg Pro Val Gln Thr Thr Gln Glu Glu Asp Gly
225                 230                 235                 240
Cys Ser Cys Arg Phe Pro Glu Glu Glu Glu Gly Gly Cys Glu Leu
                245                 250                 255

<210> SEQ ID NO 787
<211> LENGTH: 768
<212> TYPE: DNA
<213> ORGANISM: Homo sapiens

<400> SEQUENCE: 787
atgggaaaca gctgttacaa catagtagcc actctgttgc tggtcctcaa ctttgagagg    60
acaagatcat tgcaggatcc ttgtagtaac tgcccagctg gtacattctg tgataataac   120
aggaatcaga tttgcagtcc ctgtcctcca aatagtttct ccagcgcagg tggacaaagg   180
acctgtgaca tatgcaggca gtgtaaaggt gttttcagga ccaggaagga gtgttcctcc   240
accagcaatg cagagtgtga ctgcactcca gggtttcact gcctggggc aggatgcagc   300
atgtgtgaac aggattgtaa acaaggtcaa gaactgacaa aaaaaggttg taagactgt    360
tgctttggga catttaacga tcagaaacgt ggcatctgtc gaccctggac aaactgttct   420
ttggatggaa agtctgtgct tgtgaatggg acgaaggaga gggacgtggt ctgtggacca   480
tctccagccg acctctctcc gggagcatcc tctgtgaccc cgcctgcccc tgcgagagag   540
ccaggacact ctccgcagat catctccttc tttcttgcgc tgacgtcgac tgcgttgctc   600
ttcctgctgt tcttcctcac gctccgtttc tctgttgtta aacgggggcag aaagaaactc   660
ctgtatatat tcaaacaacc atttatgaga ccagtacaaa ctactcaaga ggaagatggc   720
tgtagctgcc gatttccaga agaagaagaa ggaggatgtg aactgtga                768

<210> SEQ ID NO 788
<211> LENGTH: 5
<212> TYPE: PRT
<213> ORGANISM: Homo sapiens
```

```
<220> FEATURE:
<221> NAME/KEY: MISC_FEATURE
<222> LOCATION: (1)..(5)
<223> OTHER INFORMATION: Terminating residues of C- Terminal Domain of a
      VH domain

<400> SEQUENCE: 788

Val Thr Val Ser Ser
1               5

<210> SEQ ID NO 789
<211> LENGTH: 6
<212> TYPE: PRT
<213> ORGANISM: Artificial Sequence
<220> FEATURE:
<223> OTHER INFORMATION: Hexa-His Tag

<400> SEQUENCE: 789

His His His His His His
1               5

<210> SEQ ID NO 790
<211> LENGTH: 5
<212> TYPE: PRT
<213> ORGANISM: Artificial Sequence
<220> FEATURE:
<223> OTHER INFORMATION: Peptide Linker

<400> SEQUENCE: 790

Gly Gly Gly Gly Ser
1               5

<210> SEQ ID NO 791
<211> LENGTH: 10
<212> TYPE: PRT
<213> ORGANISM: Artificial Sequence
<220> FEATURE:
<223> OTHER INFORMATION: Peptide Linker

<400> SEQUENCE: 791

Gly Gly Gly Gly Ser Gly Gly Gly Gly Ser
1               5                   10

<210> SEQ ID NO 792
<211> LENGTH: 10
<212> TYPE: PRT
<213> ORGANISM: Artificial Sequence
<220> FEATURE:
<223> OTHER INFORMATION: Peptide Linker

<400> SEQUENCE: 792

Ser Gly Gly Gly Gly Ser Gly Gly Gly Gly
1               5                   10

<210> SEQ ID NO 793
<211> LENGTH: 14
<212> TYPE: PRT
<213> ORGANISM: Artificial Sequence
<220> FEATURE:
<223> OTHER INFORMATION: Peptide Linker

<400> SEQUENCE: 793

Gly Gly Gly Gly Ser Gly Gly Gly Ser Gly Gly Gly Gly
1               5                   10

<210> SEQ ID NO 794
<211> LENGTH: 8
```

```
<212> TYPE: PRT
<213> ORGANISM: Artificial Sequence
<220> FEATURE:
<223> OTHER INFORMATION: Peptide Linker

<400> SEQUENCE: 794

Gly Ser Gly Ser Gly Ser Gly Ser
1               5

<210> SEQ ID NO 795
<211> LENGTH: 8
<212> TYPE: PRT
<213> ORGANISM: Artificial Sequence
<220> FEATURE:
<223> OTHER INFORMATION: Peptide Linker

<400> SEQUENCE: 795

Gly Gly Ser Gly Ser Gly Ser Gly
1               5

<210> SEQ ID NO 796
<211> LENGTH: 6
<212> TYPE: PRT
<213> ORGANISM: Artificial Sequence
<220> FEATURE:
<223> OTHER INFORMATION: Peptide Linker

<400> SEQUENCE: 796

Gly Gly Ser Gly Ser Gly
1               5

<210> SEQ ID NO 797
<211> LENGTH: 4
<212> TYPE: PRT
<213> ORGANISM: Artificial Sequence
<220> FEATURE:
<223> OTHER INFORMATION: Peptide Linker

<400> SEQUENCE: 797

Gly Gly Ser Gly
1

<210> SEQ ID NO 798
<211> LENGTH: 276
<212> TYPE: PRT
<213> ORGANISM: Artificial Sequence
<220> FEATURE:
<223> OTHER INFORMATION: Bivalent molecule

<400> SEQUENCE: 798

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Glu Asp Ser Val
    50                  55                  60

Glu Gly Arg Phe Thr Val Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110
```

Trp Gly Gln Gly Thr Thr Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Gly Ser Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Phe Thr Phe Ser Ser His Trp Met Thr Trp Phe Arg Gln
            180                 185                 190

Ala Pro Gly Lys Gly Leu Glu Trp Val Ala His Ile Lys Glu Asp Gly
        195                 200                 205

Ser Glu Lys Tyr Tyr Glu Asp Ser Val Glu Gly Arg Phe Thr Val Ser
    210                 215                 220

Arg Asp Asn Ala Lys Asn Ser Val Tyr Leu Gln Met Asn Ser Leu Arg
225                 230                 235                 240

Ala Glu Asp Thr Ala Val Tyr Tyr Cys Ala Arg Gly Gly Asp Gly Tyr
                245                 250                 255

Ser Asp Ser His Phe Gly Val Asp Val Trp Gly Gln Gly Thr Thr Val
            260                 265                 270

Thr Val Ser Ser
        275

<210> SEQ ID NO 799
<211> LENGTH: 828
<212> TYPE: DNA
<213> ORGANISM: Artificial Sequence
<220> FEATURE:
<223> OTHER INFORMATION: DNA encoding Bivalent Molecule of SEQ ID NO:
    798

<400> SEQUENCE: 799
gaggtgcagc tggtggagtc tgggggaggc ttggtccagc cggggggggtc cctgagactc    60 tcctgtgcag cctctggatt cacctttagt agccattgga tgacttggtt ccgtcaggct   120
ccagggaagg ggctggagtg ggtggcccac ataaaggaag acggaagtga aaatactat   180 gaggactctg tggagggccg attcaccgtc tccagagaca cgccaagaa ctcggtatat   240 ctgcaaatga acagtctgag agccgaagac acggctgtgt attactgtgc gagaggaggt   300
gatggctaca gtgactccca cttcggtgtg gacgtctggg gccaagggac cacggtcact   360
gtctcttcag gtggtggcgg ttcaggcgga ggtggctctg gaggtggagg ttcaggaggt   420
ggtggttctg gcggcggtgg atcgggtgga ggtggtagtg aggtgcagct ggtggagtct   480
gggggaggct tggtccagcc ggggggggtcc ctgagactct cctgtgcagc ctctggattc   540
acctttagta gccattggat gacttggttc cgtcaggctc agggaagggg ctggagtgg   600 gtggcccaca taaaggaaga cggaagtgag aaatactatg aggactctgt ggagggccga   660
ttcaccgtct ccagagacaa cgccaagaac tcggtatatc tgcaaatgaa cagtctgaga   720
gccgaagaca cggctgtgta ttactgtgcg agaggaggtg atggctacag tgactcccac   780
ttcggtgtgg acgtctgggg ccaagggacc acggtcactg tctcttca              828

<210> SEQ ID NO 800
<211> LENGTH: 274
<212> TYPE: PRT
<213> ORGANISM: Artificial Sequence
<220> FEATURE:

<223> OTHER INFORMATION: Bivalent Molecule

<400> SEQUENCE: 800

```
Glu Val Gln Leu Val Glu Ser Gly Gly Gly Leu Val Lys Pro Gly Gly
1               5                   10                  15
Ser Leu Arg Val Ser Cys Ala Ala Ser Gly Phe Thr Phe Ser Asp Tyr
            20                  25                  30
Tyr Met Ser Trp Phe Arg Gln Ala Pro Gly Lys Gly Leu Glu Trp Val
        35                  40                  45
Ser Tyr Ile Ser Gly Ser Gly Asp Ile Ile Asp Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Asn Leu Arg Ala Glu Asp Thr Ala Val Tyr His Cys
                85                  90                  95
Ala Arg Glu Asp Ser Arg Leu Thr Gly Thr Thr Asp Phe Asp Asn Trp
            100                 105                 110
Gly Gln Gly Thr Leu Val Thr Val Ser Ser Gly Gly Gly Ser Gly
        115                 120                 125
Gly Gly Gly Ser Gly Gly Gly Ser Gly Gly Gly Ser Gly Gly
    130                 135                 140
Gly Gly Ser Gly Gly Gly Gly Ser Glu Val Gln Leu Val Glu Ser Gly
145                 150                 155                 160
Gly Gly Leu Val Lys Pro Gly Gly Ser Leu Arg Val Ser Cys Ala Ala
                165                 170                 175
Ser Gly Phe Thr Phe Ser Asp Tyr Tyr Met Ser Trp Phe Arg Gln Ala
            180                 185                 190
Pro Gly Lys Gly Leu Glu Trp Val Ser Tyr Ile Ser Gly Ser Gly Asp
        195                 200                 205
Ile Ile Asp Tyr Ala Asp Ser Val Lys Gly Arg Phe Thr Ile Ser Arg
    210                 215                 220
Asp Asn Ala Lys Asn Ser Leu Tyr Leu Gln Met Asn Asn Leu Arg Ala
225                 230                 235                 240
Glu Asp Thr Ala Val Tyr His Cys Ala Arg Glu Asp Ser Arg Leu Thr
                245                 250                 255
Gly Thr Thr Asp Phe Asp Asn Trp Gly Gln Gly Thr Leu Val Thr Val
            260                 265                 270
Ser Ser
```

<210> SEQ ID NO 801
<211> LENGTH: 822
<212> TYPE: DNA
<213> ORGANISM: Artificial Sequence
<220> FEATURE:
<223> OTHER INFORMATION: DNA encoding Bivalent Molecule of Seq ID NO;
      800

<400> SEQUENCE: 801

| | | |
|---|---|---|
| gaggtgcagc tggtggagtc tgggggaggc ttggtcaagc ctggagggtc cctgagagtc | 60 |
| tcctgtgcag cctctggatt caccttcagt gactactaca tgagctggtt ccgccaggct | 120 |
| ccagggaagg ggctggagtg ggtttcatac attagtggta gtggtgatat catagactac | 180 |
| gcagactctg taaagggccg attcaccatc tccagggaca acgccaagaa ctctctgtat | 240 |
| ctgcagatga acaacctgag agccgaggac acggccgtgt atcactgtgc gagagaagat | 300 |
| tcccgtctaa ctggaactac ggactttgac aattggggcc agggaaccct ggtcaccgtc | 360 |

-continued

```
tcctcaggtg gtggcggttc aggcggaggt ggctctggag gtggaggttc aggaggtggt      420
ggttctggcg gcggtggatc gggtggaggt ggtagtgagg tgcagctggt ggagtctggg      480
ggaggcttgg tcaagcctgg agggtccctg agagtctcct gtgcagcctc tggattcacc      540
ttcagtgact actacatgag ctggttccgc caggctccag gaagggggct ggagtgggtt      600
tcatacatta gtggtagtgg tgatatcata gactacgcag actctgtaaa gggccgattc      660
accatctcca gggacaacgc caagaactct ctgtatctgc agatgaacaa cctgagagcc      720
gaggacacgg ccgtgtatca ctgtgcgaga aagattccc gtctaactgg aactacggac      780
tttgacaatt ggggccaggg aaccctggtc accgtctcct ca                        822
```

<210> SEQ ID NO 802
<211> LENGTH: 429
<212> TYPE: PRT
<213> ORGANISM: Artificial Sequence
<220> FEATURE:
<223> OTHER INFORMATION: Trivalent molecule

<400> SEQUENCE: 802

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Thr Trp Phe Arg Gln Ala Pro Gly Lys Gly Leu Glu Trp Val
        35                  40                  45

Ala His Ile Lys Glu Asp Gly Ser Glu Lys Tyr Tyr Glu Asp Ser Val
    50                  55                  60

Glu Gly Arg Phe Thr Val Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Ser Asp Ser His Phe Gly Val Asp Val
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Gly Ser Glu Val Gln Leu Val Glu Ser
145                 150                 155                 160

Gly Gly Gly Leu Val Gln Pro Gly Gly Ser Leu Arg Leu Ser Cys Ala
                165                 170                 175

Ala Ser Gly Phe Thr Phe Ser Ser His Trp Met Thr Trp Phe Arg Gln
            180                 185                 190

Ala Pro Gly Lys Gly Leu Glu Trp Val Ala His Ile Lys Glu Asp Gly
        195                 200                 205

Ser Glu Lys Tyr Tyr Glu Asp Ser Val Glu Gly Arg Phe Thr Val Ser
    210                 215                 220

Arg Asp Asn Ala Lys Asn Ser Val Tyr Leu Gln Met Asn Ser Leu Arg
225                 230                 235                 240

Ala Glu Asp Thr Ala Val Tyr Tyr Cys Ala Arg Gly Gly Asp Gly Tyr
                245                 250                 255

Ser Asp Ser His Phe Gly Val Asp Val Trp Gly Gln Gly Thr Thr Val
            260                 265                 270
```

```
Thr Val Ser Ser Gly Gly Gly Ser Gly Gly Gly Ser Gly Gly
        275                 280                 285
Gly Gly Ser Gly Gly Gly Ser Gly Gly Gly Ser Gly Gly Gly
        290                 295                 300
Gly Ser Glu Val Gln Leu Val Glu Ser Gly Gly Leu Val Gln Pro
305                 310                 315                 320
Gly Gly Ser Leu Arg Leu Ser Cys Ala Ala Ser Gly Phe Thr Phe Ser
                325                 330                 335
Ser His Trp Met Thr Trp Phe Arg Gln Ala Pro Gly Lys Gly Leu Glu
                340                 345                 350
Trp Val Ala His Ile Lys Glu Asp Gly Ser Glu Lys Tyr Tyr Glu Asp
                355                 360                 365
Ser Val Glu Gly Arg Phe Thr Val Ser Arg Asp Asn Ala Lys Asn Ser
            370                 375                 380
Val Tyr Leu Gln Met Asn Ser Leu Arg Ala Glu Asp Thr Ala Val Tyr
385                 390                 395                 400
Tyr Cys Ala Arg Gly Gly Asp Gly Tyr Ser Asp Ser His Phe Gly Val
                405                 410                 415
Asp Val Trp Gly Gln Gly Thr Thr Val Thr Val Ser Ser
                420                 425
```

<210> SEQ ID NO 803
<211> LENGTH: 1287
<212> TYPE: DNA
<213> ORGANISM: Artificial Sequence
<220> FEATURE:
<223> OTHER INFORMATION: DNA encoding the trivalent molecule of Seq ID
      NO: 802

<400> SEQUENCE: 803

```
gaggtgcagc tggtggagtc tgggggaggc ttggtccagc cggggggggtc cctgagactc      60 tcctgtgcag cctctggatt cacctttagt agccattgga tgacttggtt ccgtcaggct     120
ccagggaagg gctggagtg gtggcccac ataaaggaag acggaagtga aaatactat      180 gaggactctg tggagggccg attcaccgtc tccagagaca cgccaagaa ctcggtatat      240 ctgcaaatga acagtctgag agccgaagac acggctgtgt attactgtgc gagaggaggt      300
gatggctaca gtgactccca cttcggtgtg gacgtctggg gccaagggac acggtcact      360 gtctcttcag gtggtggcgg ttcaggcgga ggtggctctg gaggtggagg ttcaggaggt     420
ggtggttctg gcggcggtgg atcgggtgga ggtggtagtg aggtgcagct ggtggagtct     480
gggggaggct tggtccagcc ggggggtcc ctgagactct cctgtgcagc ctctggattc      540
acctttagta gccattggat gacttggttc cgtcaggctc cagggaaggg gctggagtgg      600
gtggcccaca taaaggaaga cggaagtgag aaatactatg aggactctgt ggagggccga      660
ttcaccgtct ccagagacaa cgccaagaac tcggtatatc tgcaaatgaa cagtctgaga      720
gccgaagaca cggctgtgta ttactgtgcg agaggaggta tggctacag tgactcccac      780 ttcggtgtgg acgtctgggg ccaagggacc acggtcactg tctcttcagg tggtggcggt      840
tcaggcggag gtggctctgg aggtggaggt tcaggaggtg gtggttctgg cggcggtgga      900
tcgggtggag gtggtagtga ggtgcagctg gtggagtctg ggggaggctt ggtccagccg      960
ggggggtccc tgagactctc ctgtgcagcc tctggattca cctttagtag ccattggatg     1020
acttggttcc gtcaggctcc agggaagggg ctggagtggg tggcccacat aaaggaagac     1080
ggaagtgaga aatactatga ggactctgtg gagggccgat tcaccgtctc cagagacaac     1140
```

```
gccaagaact cggtatatct gcaaatgaac agtctgagag ccgaagacac ggctgtgtat    1200
tactgtgcga ggaggtga tggctacagt gactcccact tcggtgtgga cgtctggggc     1260
caagggacca cggtcactgt ctcttca                                        1287
```

<210> SEQ ID NO 804
<211> LENGTH: 426
<212> TYPE: PRT
<213> ORGANISM: Artificial Sequence
<220> FEATURE:
<223> OTHER INFORMATION: Trivalent molecule

<400> SEQUENCE: 804

```
Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Asp Tyr
            20                  25                  30

Tyr Met Ser Trp Phe Arg Gln Ala Pro Gly Lys Gly Leu Glu Trp Val
        35                  40                  45

Ser Tyr Ile Ser Gly Ser Gly Asp Ile Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Asn Leu Arg Ala Glu Asp Thr Ala Val Tyr His Cys
                85                  90                  95

Ala Arg Glu Asp Ser Arg Leu Thr Gly Thr Thr Asp Phe Asp Asn Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Glu Val Gln Leu Val Glu Ser Gly
145                 150                 155                 160

Gly Gly Leu Val Lys Pro Gly Gly Ser Leu Arg Val Ser Cys Ala Ala
                165                 170                 175

Ser Gly Phe Thr Phe Ser Asp Tyr Tyr Met Ser Trp Phe Arg Gln Ala
            180                 185                 190

Pro Gly Lys Gly Leu Glu Trp Val Ser Tyr Ile Ser Gly Ser Gly Asp
        195                 200                 205

Ile Ile Asp Tyr Ala Asp Ser Val Lys Gly Arg Phe Thr Ile Ser Arg
    210                 215                 220

Asp Asn Ala Lys Asn Ser Leu Tyr Leu Gln Met Asn Asn Leu Arg Ala
225                 230                 235                 240

Glu Asp Thr Ala Val Tyr His Cys Ala Arg Glu Asp Ser Arg Leu Thr
                245                 250                 255

Gly Thr Thr Asp Phe Asp Asn Trp Gly Gln Gly Thr Leu Val Thr Val
            260                 265                 270

Ser Ser Gly Gly Gly Gly Ser Gly Gly Gly Gly Ser Gly Gly Gly Gly
        275                 280                 285

Ser Gly Gly Gly Gly Ser Gly Gly Gly Gly Ser Gly Gly Gly Gly Ser
    290                 295                 300

Glu Val Gln Leu Val Glu Ser Gly Gly Gly Leu Val Lys Pro Gly Gly
305                 310                 315                 320

Ser Leu Arg Val Ser Cys Ala Ala Ser Gly Phe Thr Phe Ser Asp Tyr
                325                 330                 335
```

```
Tyr Met Ser Trp Phe Arg Gln Ala Pro Gly Lys Gly Leu Glu Trp Val
            340                 345                 350

Ser Tyr Ile Ser Gly Ser Gly Asp Ile Ile Asp Tyr Ala Asp Ser Val
            355                 360                 365

Lys Gly Arg Phe Thr Ile Ser Arg Asp Asn Ala Lys Asn Ser Leu Tyr
        370                 375                 380

Leu Gln Met Asn Asn Leu Arg Ala Glu Asp Thr Ala Val Tyr His Cys
385                 390                 395                 400

Ala Arg Glu Asp Ser Arg Leu Thr Gly Thr Thr Asp Phe Asp Asn Trp
                405                 410                 415

Gly Gln Gly Thr Leu Val Thr Val Ser Ser
            420                 425

<210> SEQ ID NO 805
<211> LENGTH: 1278
<212> TYPE: DNA
<213> ORGANISM: Artificial Sequence
<220> FEATURE:
<223> OTHER INFORMATION: DNA encoding trivalent molecule of seq ID No:
      804

<400> SEQUENCE: 805
gaggtgcagc tggtggagtc tgggggaggc ttggtcaagc ctggagggtc cctgagagtc      60
tcctgtgcag cctctggatt caccttcagt gactactaca tgagctggtt ccgccaggct     120
ccagggaagg gctggagtg gtttcatac attagtggta gtggtgatat catagactac      180
gcagactctg taaagggccg attcaccatc tccaggaca acgccaagaa ctctctgtat     240
ctgcagatga acaacctgag agccgaggac acggccgtgt atcactgtgc gagagaagat     300
tcccgtctaa ctggaactac ggactttgac aattgggggcc agggaaccct ggtcaccgtc     360
tcctcaggtg gtggcggttc aggcggaggt ggctctggag gtggaggttc aggaggtggt     420
ggttctggcg gcggtggatc gggtggaggt ggtagtgagg tgcagctggt ggagtctggg     480
ggaggcttgg tcaagcctgg agggtccctg agagtctcct gtgcagcctc tggattcacc     540
ttcagtgact actacatgag ctggttccgc caggctccag gaagggggct ggagtgggtt     600
tcatacatta gtggtagtgg tgatatcata gactacgcag actctgtaaa gggccgattc     660
accatctcca gggacaacgc caagaactct ctgtatctgc agatgaacaa cctgagagcc     720
gaggacacgg ccgtgtatca ctgtgcgaga gaagattccc gtctaactgg aactacggac     780
tttgacaatt ggggccaggg aaccctggtc accgtctcct caggtggtgg cggttcaggc     840
ggaggtggct ctgaggtgg aggttcagga ggtggtggtt ctggcggcgg tggatcgggt     900
ggaggtggta gtgaggtgca gctggtggag tctgggggag cttggtcaa gcctggaggg     960 tccctgagag tctcctgtgc agcctctgga ttcaccttca gtgactacta catgagctgg    1020
ttccgccagg ctccagggaa ggggctggag tgggttcat acattagtgg tagtggtgat    1080
atcatagact acgcagactc tgtaaagggc cgattcacca tctccaggga caacgccaag    1140
aactctctgt atctgcagat gaacaacctg agagccgagg acacggccgt gtatcactgt    1200
gcgagagaag attcccgtct aactggaact acggactttg acaattgggg ccagggaacc    1260
ctggtcaccg tctcctca                                                  1278

<210> SEQ ID NO 806
<211> LENGTH: 280
<212> TYPE: PRT
<213> ORGANISM: Artificial Sequence
```

<220> FEATURE:
<223> OTHER INFORMATION: Bivalent molecule

<400> SEQUENCE: 806

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Gly Ser Gly Gly Gly Gly Ser Gly Gly
        130                 135                 140

Gly Gly Ser Gly Gly Gly Ser Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Phe Thr Phe Ser Ser His Trp Met Thr
            180                 185                 190

Trp Phe Arg Gln Ala Pro Gly Lys Gly Leu Glu Trp Val Ala His Ile
        195                 200                 205

Lys Glu Asp Gly Ser Glu Lys Tyr Tyr Glu Asp Ser Val Glu Gly Arg
    210                 215                 220

Phe Thr Val Ser Arg Asp Asn Ala Lys Asn Ser Val Tyr Leu Gln Met
225                 230                 235                 240

Asn Ser Leu Arg Ala Glu Asp Thr Ala Val Tyr Tyr Cys Ala Arg Gly
                245                 250                 255

Gly Asp Gly Tyr Ser Asp Ser His Phe Gly Val Asp Val Trp Gly Gln
            260                 265                 270

Gly Thr Thr Val Thr Val Ser Ser
        275                 280

<210> SEQ ID NO 807
<211> LENGTH: 840
<212> TYPE: DNA
<213> ORGANISM: Artificial Sequence
<220> FEATURE:
<223> OTHER INFORMATION: DNA encoding the bivalent molecule of Seq ID No
      806

<400> SEQUENCE: 807
gaggtgcagc tggtggagtc tgggggaggc gtggtccagc ctgggaggtc cctgagactc      60
tcctgtgcag cctctggatt ctccttcagt ggctatggca tgcactgggt ccgccaggct     120
ccaggcaagg gactggagtg ggtggcatat atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatccg     300

```
gcctggggat  tacgtttggg  ggagtcatcg  tcctatgatt  ttgatatctg  gggccaaggg      360
acaatggtca  ccgtctcctc  aggtggtggc  ggttcaggcg  aggtggctc   tggaggtgga      420 ggttcaggag  gtggtggttc  tggcggcggt  ggatcgggtg  gaggtggtag  tgaggtgcag      480 ctggtgagt   ctgggggagg  cttggtccag  ccggggggt   ccctgagact  ctcctgtgca      540
gcctctggat  tcacctttag  tagccattgg  atgacttggt  tccgtcaggc  tccagggaag      600
gggctggagt  gggtggccca  cataaaggaa  gacggaagtg  agaaatacta  tgaggactct      660
gtggagggcc  gattcaccgt  ctccagagac  aacgccaaga  actcggtata  tctgcaaatg      720
aacagtctga  gagccgaaga  cacggctgtg  tattactgtg  cgagaggagg  tgatggctac      780
agtgactccc  acttcggtgt  ggacgtctgg  ggccaaggga  ccacggtcac  tgtctcttca      840
```

<210> SEQ ID NO 808
<211> LENGTH: 279
<212> TYPE: PRT
<213> ORGANISM: Artificial Sequence
<220> FEATURE:
<223> OTHER INFORMATION: bivalent molecule

<400> SEQUENCE: 808

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Ser Gly Gly Gly Ser Gly Gly
    130                 135                 140

Gly Gly Ser Gly Gly Gly Ser Gly Gly Gly Ser Glu Val Gln
145                 150                 155                 160

Leu Val Glu Ser Gly Gly Gly Leu Val Lys Pro Gly Gly Ser Leu Arg
                165                 170                 175

Val Ser Cys Ala Ala Ser Gly Phe Thr Phe Ser Asp Tyr Tyr Met Ser
            180                 185                 190

Trp Phe Arg Gln Ala Pro Gly Lys Gly Leu Glu Trp Val Ser Tyr Ile
        195                 200                 205

Ser Gly Ser Gly Asp Ile Ile Asp Tyr Ala Asp Ser Val Lys Gly Arg
    210                 215                 220

Phe Thr Ile Ser Arg Asp Asn Ala Lys Asn Ser Leu Tyr Leu Gln Met
225                 230                 235                 240

Asn Asn Leu Arg Ala Glu Asp Thr Ala Val Tyr His Cys Ala Arg Glu
                245                 250                 255

Asp Ser Arg Leu Thr Gly Thr Thr Asp Phe Asp Asn Trp Gly Gln Gly
            260                 265                 270
```

Thr Leu Val Thr Val Ser Ser
        275

<210> SEQ ID NO 809
<211> LENGTH: 837
<212> TYPE: DNA
<213> ORGANISM: Artificial Sequence
<220> FEATURE:
<223> OTHER INFORMATION: DNA encoding bivalent molecule of Seq ID NO 808

<400> SEQUENCE: 809

```
gaggtgcagc tggtggagtc tgggggaggc gtggtccagc ctggagggtc cctgagactc      60
tcctgtgcag cctctggatt ctccttcagt ggctatggca tgcactgggt ccgccaggct     120
ccaggcaagg gactggagtg ggtggcatat atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatccg     300
gcctggggat tacgtttggg ggagtcatcg tcctatgatt ttgatatctg gggccaaggg     360
acaatggtca ccgtctcctc aggtggtggc ggttcaggcg gaggtggctc tggaggtgga     420
ggttcaggag gtggtggttc tggcggcggt ggatcgggtg gaggtggtag tgaggtgcag     480
ctggtggagt ctgggggagg cttggtcaag cctggagggt ccctgagagt ctcctgtgca     540
gcctctggat tcaccttcag tgactactac atgagctggg tccgccaggc tccagggaag     600
gggctggagt gggtttcata cattagtggt agtggtgata tcatagacta cgcagactct     660
gtaaagggcc gattcaccat ctccagggac aacgccaaga actctctgta tctgcagatg     720
aacaacctga gagccgagga cacggccgtg tatcactgtg cgagagaaga ttcccgtcta     780
actggaacta cggactttga caattggggc cagggaaccc tggtcaccgt ctcctca      837
```

<210> SEQ ID NO 810
<211> LENGTH: 266
<212> TYPE: PRT
<213> ORGANISM: Artificial Sequence
<220> FEATURE:
<223> OTHER INFORMATION: bivalent molecule

<400> SEQUENCE: 810

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Gly Gly Gly Gly Ser Gly Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Phe Ser His Trp
                165                 170                 175

Met Thr Trp Phe Arg Gln Ala Pro Gly Lys Gly Leu Glu Trp Val Ala
            180                 185                 190

His Ile Lys Glu Asp Gly Ser Glu Lys Tyr Tyr Glu Asp Ser Val Glu
        195                 200                 205

Gly Arg Phe Thr Val Ser Arg Asp Asn Ala Lys Asn Ser Val Tyr Leu
    210                 215                 220

Gln Met Asn Ser Leu Arg Ala Glu Asp Thr Ala Val Tyr Tyr Cys Ala
225                 230                 235                 240

Arg Gly Gly Asp Gly Tyr Ser Asp Ser His Phe Gly Val Asp Val Trp
                245                 250                 255

Gly Gln Gly Thr Thr Val Thr Val Ser Ser
            260                 265

<210> SEQ ID NO 811
<211> LENGTH: 798
<212> TYPE: DNA
<213> ORGANISM: Artificial Sequence
<220> FEATURE:
<223> OTHER INFORMATION: DNA encoding the bivalent molecule of Seq ID
      NO: 810

<400> SEQUENCE: 811
gaggtgcagc tgttggagtc tgggggaggc ttggtacagc ctgggggtc cctgagactc      60 tcctgtgcag cctctggatt cagttttagc agctatgccc tcagttgggt ccgccaggct     120
ccagggaagg gctggagtg gtctcaagt attggtgaga tgatggtac cacagactac      180 gcagacgccg tgaagggccg attcaccatc tccagagaca attccaagaa tacgctgtat     240
ctgcaaatga acagcctgag agtcgaggac acggccgtct attactgtgt gaaagatggt     300
gtccactggg gccagggaac cctggtcacc gtctcctcag gtggtggcgg ttcaggcgga     360
ggtggctctg gaggtggagg ttcaggaggt ggtggttctg gcggcggtgg atcgggtgga     420
ggtggtagtg aggtgcagct ggtggagtct ggggaggct tggtccagcc ggggggtcc      480 ctgagactct cctgtgcagc ctctggattc acctttagta gccattggat gacttggttc     540
cgtcaggctc cagggaaggg gctggagtgg gtggcccaca taaaggaaga cggaagtgag     600
aaatactatg aggactctgt ggagggccga ttcaccgtct ccagagacaa cgccaagaac     660
tcggtatatc tgcaaatgaa cagtctgaga gccgaagaca cggctgtgta ttactgtgcg     720
agaggaggtg atggctacag tgactcccac ttcggtgtgg acgtctgggg ccaagggacc     780
acggtcactg tctcttca                                                    798

<210> SEQ ID NO 812
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 of SEQ ID NO: 815

<400> SEQUENCE: 812

Ser Tyr Ala Met Ser
1               5

```
<210> SEQ ID NO 813
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 815

<400> SEQUENCE: 813

Ser Ile Gly Glu Asn Asp Gly Thr Thr Asp Tyr Ala Asp Ser Val Lys
1               5                   10                  15
Gly

<210> SEQ ID NO 814
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: CDR3 OF SEQ ID NO: 815

<400> SEQUENCE: 814

Asp Gly Val His
1

<210> SEQ ID NO 815
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: VH binding to PSMA

<400> SEQUENCE: 815

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ser Val
    50                  55                  60

Lys Gly Arg Phe Thr Ile Ser Arg Asp Asn Ser Lys Ser Met Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 816
<211> LENGTH: 113
<212> TYPE: PRT
<213> ORGANISM: Homo sapiens

<400> SEQUENCE: 816

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30
```

```
Ala Leu Ser Trp Val Arg Gln Ala Pro Gly Lys Gly Leu Glu Trp Val
            35                  40                  45

Ser Ser Ile Gly Glu Asn Asp Gly Thr Thr Asp Tyr Ala Asp Phe Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
                100                 105                 110

Ser
```

<210> SEQ ID NO 817
<211> LENGTH: 113
<212> TYPE: PRT
<213> ORGANISM: Homo sapiens

<400> SEQUENCE: 817

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Ser Ser Tyr
                20                  25                  30

Ala Leu Ser Trp Val Arg Gln Ala Pro Gly Lys Gly Leu Glu Trp Val
            35                  40                  45

Ser Ser Ile Gly Glu Asn Asp Gly Thr Thr Asp Tyr Ala Asp Asn Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
                100                 105                 110

Ser
```

<210> SEQ ID NO 818
<211> LENGTH: 113
<212> TYPE: PRT
<213> ORGANISM: Homo sapiens

<400> SEQUENCE: 818

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Phe Ser Ser Tyr
                20                  25                  30

Ala Leu Ser Trp Val Arg Gln Ala Pro Gly Lys Gly Leu Glu Trp Val
            35                  40                  45

Ser Ser Ile Gly Glu Asn Asp Gly Thr Thr Asp Tyr Ala Ala Asp Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
                100                 105                 110

Ser
```

<210> SEQ ID NO 819
<211> LENGTH: 113
<212> TYPE: PRT
<213> ORGANISM: Homo sapiens

<400> SEQUENCE: 819

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Val Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 820
<211> LENGTH: 113
<212> TYPE: PRT
<213> ORGANISM: Homo sapiens

<400> SEQUENCE: 820

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Ala Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser
```

<210> SEQ ID NO 821
<211> LENGTH: 113
<212> TYPE: PRT
<213> ORGANISM: Homo sapiens

<400> SEQUENCE: 821

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45
```

```
Ser Ser Ile Gly Glu Asn Asp Gly Thr Thr Asp Tyr Ala Asp Thr Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Val Glu Asp Thr Ala Val Tyr Tyr Cys
                    85                  90                  95

Val Lys Asp Gly Val His Trp Gly Gln Gly Thr Leu Val Thr Val Ser
                100                 105                 110

Ser
```

<210> SEQ ID NO 822
<211> LENGTH: 113
<212> TYPE: PRT
<213> ORGANISM: Homo sapiens

<400> SEQUENCE: 822

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
                20                  25                  30

Ala Leu Ser Trp Val Arg Gln Ala Pro Gly Lys Gly Leu Glu Trp Val
            35                  40                  45

Ser Ser Ile Gly Glu Asn Asp Gly Thr Thr Asp Tyr Ala Asp Ala Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Val Glu Asp Thr Ala Val Tyr Tyr Cys
                    85                  90                  95

Val Lys Asp Gly Val His Trp Gly Gln Gly Thr Leu Val Thr Val Ser
                100                 105                 110

Ser
```

<210> SEQ ID NO 823
<211> LENGTH: 113
<212> TYPE: PRT
<213> ORGANISM: Homo sapiens

<400> SEQUENCE: 823

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
                20                  25                  30

Ala Leu Ser Trp Val Arg Gln Ala Pro Gly Lys Gly Leu Glu Trp Val
            35                  40                  45

Ser Ser Ile Gly Glu Asn Asp Gly Thr Thr Asp Tyr Ala Ala Ser Val
        50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Val Glu Asp Thr Ala Val Tyr Tyr Cys
                    85                  90                  95

Val Lys Asp Gly Val His Trp Gly Gln Gly Thr Leu Val Thr Val Ser
                100                 105                 110

Ser
```

<210> SEQ ID NO 824

```
<211> LENGTH: 113
<212> TYPE: PRT
<213> ORGANISM: Homo sapiens

<400> SEQUENCE: 824

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Ala Tyr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 825
<211> LENGTH: 113
<212> TYPE: PRT
<213> ORGANISM: Homo sapiens

<400> SEQUENCE: 825

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Ala Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser

<210> SEQ ID NO 826
<211> LENGTH: 339
<212> TYPE: DNA
<213> ORGANISM: Homo sapiens

<400> SEQUENCE: 826
gaggtgcagc tgttggagtc tgggggaggc ttggtacagc ctggggggtc cctgagactc      60
tcctgtgcag cctctggatt cagttttagc agctatgcca tgagttgggt ccgccaggct     120
ccagggaagg ggctggagtg ggtctcaagt attggtgaga atgatggtac cacagactac     180
gcagactccg tgaagggccg attcaccatc tccagagaca attccaagag tatgctgtat     240
ctgcaaatga acagcctgag agtcgaggac acggccgtct attactgtgt gaaagatggt     300
gtccactggg gccagggaac cctggtcacc gtctcctca                            339
```

<210> SEQ ID NO 827
<211> LENGTH: 339
<212> TYPE: DNA
<213> ORGANISM: Homo sapiens

<400> SEQUENCE: 827
gaggtgcagc tgttggagtc tgggggaggc ttggtacagc ctgggggtc cctgagactc      60
tcctgtgcag cctctggatt cagttttagc agctatgccc tcagttgggt ccgccaggct    120
ccagggaagg ggctggagtg ggtctcaagt attggtgaga ataacgctac cacagactac    180
gcagacttcg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                           339

<210> SEQ ID NO 828
<211> LENGTH: 339
<212> TYPE: DNA
<213> ORGANISM: Homo sapiens

<400> SEQUENCE: 828
gaggtgcagc tgttggagtc tgggggaggc ttggtacagc ctgggggtc cctgagactc      60
tcctgtgcag cctctggatt cagttttagc agctatgccc tcagttgggt ccgccaggct    120
ccagggaagg ggctggagtg ggtctcaagt attggtgaga atgatggtac cacagactac    180
gcagacgccg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                           339

<210> SEQ ID NO 829
<211> LENGTH: 339
<212> TYPE: DNA
<213> ORGANISM: Homo sapiens

<400> SEQUENCE: 829
gaggtgcagc tgttggagtc tgggggaggc ttggtacagc ctgggggtc cctgagactc      60
tcctgtgcag cctctggatt cagttttagc agctatgccc tcagttgggt ccgccaggct    120
ccagggaagg ggctggagtg ggtctcaagt attggtgaga atgatggtac cacagactac    180
gcagccgacg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                           339

<210> SEQ ID NO 830
<211> LENGTH: 339
<212> TYPE: DNA
<213> ORGANISM: Homo sapiens

<400> SEQUENCE: 830
gaggtgcagc tgttggagtc tgggggaggc ttggtacagc ctgggggtc cctgagactc      60
tcctgtgcag cctctggatt cagttttagc agctatgccc tcagttgggt ccgccaggct    120
ccagggaagg ggctggagtg ggtctcaagt attggtgaga atgatggtac cacagactac    180
gcagacgtcg tgaagggccg attcaccatc tccagagaca attccaagaa tacgctgtat    240

```
ctgcaaatga acagcctgag agtcgaggac acggccgtct attactgtgt gaaagatggt    300
gtccactggg gccagggaac cctggtcacc gtctcctca                            339
```

<210> SEQ ID NO 831
<211> LENGTH: 339
<212> TYPE: DNA
<213> ORGANISM: Homo sapiens

<400> SEQUENCE: 831

```
gaggtgcagc tgttggagtc tgggggaggc ttggtacagc ctggggggtc cctgagactc    60
tcctgtgcag cctctggatt cagttttagc agctatgccc tcagttgggt ccgccaggct    120
ccagggaagg ggctggagtg ggtctcaagt attggtgaga atgatggtac cacagactac    180
gcagccttcg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                            339
```

<210> SEQ ID NO 832
<211> LENGTH: 339
<212> TYPE: DNA
<213> ORGANISM: Homo sapiens

<400> SEQUENCE: 832

```
gaggtgcagc tgttggagtc tgggggaggc ttggtacagc ctggggggtc cctgagactc    60
tcctgtgcag cctctggatt cagttttagc agctatgccc tcagttgggt ccgccaggct    120
ccagggaagg ggctggagtg ggtctcaagt attggtgaga atgatggtac cacagactac    180
gcagacaccg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                            339
```

<210> SEQ ID NO 833
<211> LENGTH: 339
<212> TYPE: DNA
<213> ORGANISM: Homo sapiens

<400> SEQUENCE: 833

```
gaggtgcagc tgttggagtc tgggggaggc ttggtacagc ctggggggtc cctgagactc    60
tcctgtgcag cctctggatt cagttttagc agctatgccc tcagttgggt ccgccaggct    120
ccagggaagg ggctggagtg ggtctcaagt attggtgaga atgatggtac cacagactac    180
gcagacgccg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                            339
```

<210> SEQ ID NO 834
<211> LENGTH: 339
<212> TYPE: DNA
<213> ORGANISM: Homo sapiens

<400> SEQUENCE: 834

```
gaggtgcagc tgttggagtc tgggggaggc ttggtacagc ctggggggtc cctgagactc    60
tcctgtgcag cctctggatt cagttttagc agctatgccc tcagttgggt ccgccaggct    120
ccagggaagg ggctggagtg ggtctcaagt attggtgaga atgatggtac cacagactac    180
```

```
gcagcctccg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctca                           339
```

<210> SEQ ID NO 835
<211> LENGTH: 339
<212> TYPE: DNA
<213> ORGANISM: Homo sapiens

<400> SEQUENCE: 835

```
gaggtgcagc tgttggagtc tgggggaggc ttggtacagc ctggggggtc cctgagactc    60
tcctgtgcag cctctggatt cagttttagc agctatgccc tcagttgggt ccgccaggct   120
ccagggaagg ggctggagtg ggtctcaagt attggtgaga atgatggtac cacagactac   180
gcagcctacg tgaagggccg attcaccatc tccagagaca attccaagaa tacgctgtat   240
ctgcaaatga acagcctgag agtcgaggac acggccgtct attactgtgt gaaagatggt   300
gtccactggg gccagggaac cctggtcacc gtctcctca                          339
```

<210> SEQ ID NO 836
<211> LENGTH: 339
<212> TYPE: DNA
<213> ORGANISM: Homo sapiens

<400> SEQUENCE: 836

```
gaggtgcagc tgttggagtc tgggggaggc ttggtacagc ctggggggtc cctgagactc    60
tcctgtgcag cctctggatt cagttttagc agctatgccc tcagttgggt ccgccaggct   120
ccagggaagg ggctggagtg ggtctcaagt attggtgaga atgatggtac cacagactac   180
gcagccaccg tgaagggccg attcaccatc tccagagaca attccaagaa tacgctgtat   240
ctgcaaatga acagcctgag agtcgaggac acggccgtct attactgtgt gaaagatggt   300
gtccactggg gccagggaac cctggtcacc gtctcctca                          339
```

<210> SEQ ID NO 837
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 840

<400> SEQUENCE: 837

Gly Tyr Gly Met His
1               5

<210> SEQ ID NO 838
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of Seq ID NO: 840

<400> SEQUENCE: 838

Tyr Ile Ser Tyr Asp Gly Ser Asn Lys Tyr Tyr Ala Asp Ser Val Lys
1               5                   10                  15

Gly

<210> SEQ ID NO 839
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: CDR3 of SEQ ID NO. 840

<400> SEQUENCE: 839

Asp Pro Ala Trp Gly Leu Arg Leu Gly Glu Ser Ser Tyr Asp Phe
1               5                   10                  15

Asp Ile

<210> SEQ ID NO 840
<211> LENGTH: 127
<212> TYPE: PRT
<213> ORGANISM: Homo sapiens
<220> FEATURE:
<221> NAME/KEY: MISC_FEATURE
<222> LOCATION: (1)..(127)
<223> OTHER INFORMATION: VH domain binding to PSMA

<400> SEQUENCE: 840

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser
        115                 120                 125

<210> SEQ ID NO 841
<211> LENGTH: 381
<212> TYPE: DNA
<213> ORGANISM: Homo sapiens

<400> SEQUENCE: 841
gaggtgcagc tggtggagtc tgggggaggc gtggtccagc ctgggaggtc cctgagactc      60
tcctgtgcag cctctggatt ctccttcagt ggctatggca tgcactgggt ccgccaggct     120
ccaggcaagg gactggagtg ggtggcatat atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatccg     300
gcctggggat acgtttggg ggagtcatcg tcctatgatt ttgatatctg gggccaaggg     360
acaatggtca ctgtctcttc a                                              381

<210> SEQ ID NO 842
<211> LENGTH: 749
<212> TYPE: PRT
<213> ORGANISM: Homo sapiens

<400> SEQUENCE: 842

| | | | | | | | | | | | | | | |
|---|---|---|---|---|---|---|---|---|---|---|---|---|---|---|
|Met|Trp|Asn|Leu|Leu|His|Glu|Thr|Asp|Ser|Ala|Val|Ala|Thr|Ala|Arg
1|||||5|||||10|||||15

Arg Pro Arg Trp Leu Cys Ala Gly Ala Leu Val Leu Ala Gly Gly Phe
            20                    25                    30

Phe Leu Leu Gly Phe Leu Phe Gly Trp Phe Ile Lys Ser Ser Asn Glu
            35                    40                    45

Ala Thr Asn Ile Thr Pro Lys His Asn Met Lys Ala Phe Leu Asp Glu
      50                    55                    60

Leu Lys Ala Glu Asn Ile Lys Lys Phe Leu Tyr Asn Phe Thr Gln Ile
65                    70                    75                  80

Pro His Leu Ala Gly Thr Glu Gln Asn Phe Gln Leu Ala Lys Gln Ile
              85                    90                    95

Gln Ser Gln Trp Lys Glu Phe Gly Leu Asp Ser Val Glu Leu Ala His
                100                   105              110

Tyr Asp Val Leu Leu Ser Tyr Pro Asn Lys Thr His Pro Asn Tyr Ile
            115                  120                  125

Ser Ile Ile Asn Glu Asp Gly Asn Glu Ile Phe Asn Thr Ser Leu Phe
130                    135                   140

Glu Pro Pro Pro Gly Tyr Glu Asn Val Ser Asp Ile Val Pro Pro
145                    150                  155                  160

Phe Ser Ala Phe Ser Pro Gln Gly Met Pro Glu Gly Asp Leu Val Tyr
                165                   170              175

Val Asn Tyr Ala Arg Thr Glu Asp Phe Phe Lys Leu Glu Arg Asp Met
            180                  185                  190

Lys Ile Asn Cys Ser Gly Lys Ile Val Ile Ala Arg Tyr Gly Lys Val
              195                  200                  205

Phe Arg Gly Asn Lys Val Lys Asn Ala Gln Leu Ala Gly Ala Lys Gly
            210                  215                  220

Val Ile Leu Tyr Ser Asp Pro Ala Asp Tyr Phe Ala Pro Gly Val Lys
225                    230                  235                  240

Ser Tyr Pro Asp Gly Trp Asn Leu Pro Gly Gly Gly Val Gln Arg Gly
                245                   250              255

Asn Ile Leu Asn Leu Asn Gly Ala Gly Asp Pro Leu Thr Pro Gly Tyr
            260                  265                  270

Pro Ala Asn Glu Tyr Ala Tyr Arg Arg Gly Ile Ala Glu Ala Val Gly
            275                  280                  285

Leu Pro Ser Ile Pro Val His Pro Ile Gly Tyr Asp Ala Gln Lys Leu
290                    295                  300

Leu Glu Lys Met Gly Gly Ser Ala Pro Pro Asp Ser Ser Trp Arg Gly
305                    310                  315                  320

Ser Leu Lys Val Pro Tyr Asn Val Gly Pro Gly Phe Thr Gly Asn Phe
                325                   330              335

Ser Thr Gln Lys Val Lys Met His Ile His Ser Thr Asn Glu Val Thr
            340                  345                  350

Arg Ile Tyr Asn Val Ile Gly Thr Leu Arg Gly Ala Val Glu Pro Asp
              355                  360                  365

Arg Tyr Val Ile Leu Gly Gly His Arg Asp Ser Trp Val Phe Gly Gly
            370                  375                  380

Ile Asp Pro Gln Ser Gly Ala Ala Val Val His Glu Ile Val Arg Ser
385                    390                  395                  400

```
Phe Gly Thr Leu Lys Lys Glu Gly Trp Arg Pro Arg Thr Ile Leu
                405                 410                 415
Phe Ala Ser Trp Asp Ala Glu Phe Gly Leu Leu Gly Ser Thr Glu
            420                 425                 430
Trp Ala Glu Glu Asn Ser Arg Leu Leu Gln Glu Arg Gly Val Ala Tyr
        435                 440                 445
Ile Asn Ala Asp Ser Ser Ile Glu Gly Asn Tyr Thr Leu Arg Val Asp
    450                 455                 460
Cys Thr Pro Leu Met Tyr Ser Leu Val His Asn Leu Thr Lys Glu Leu
465                 470                 475                 480
Lys Ser Pro Asp Glu Gly Phe Glu Gly Lys Ser Leu Tyr Glu Ser Trp
                485                 490                 495
Thr Lys Lys Ser Pro Ser Pro Glu Phe Ser Gly Met Pro Arg Ile Ser
            500                 505                 510
Lys Leu Gly Ser Gly Asn Asp Phe Glu Val Phe Phe Gln Arg Leu Gly
        515                 520                 525
Ile Ala Ser Gly Arg Ala Arg Tyr Thr Lys Asn Trp Glu Thr Asn Lys
    530                 535                 540
Phe Ser Gly Tyr Pro Leu Tyr His Ser Val Tyr Glu Thr Tyr Glu Leu
545                 550                 555                 560
Val Glu Lys Phe Tyr Asp Pro Met Phe Lys Tyr His Leu Thr Val Ala
                565                 570                 575
Gln Val Arg Gly Gly Met Val Phe Glu Leu Ala Asn Ser Ile Val Leu
            580                 585                 590
Pro Phe Asp Cys Arg Asp Tyr Ala Val Val Leu Arg Lys Tyr Ala Asp
        595                 600                 605
Lys Ile Tyr Ser Ile Ser Met Lys His Pro Gln Glu Met Lys Thr Tyr
    610                 615                 620
Ser Val Ser Phe Asp Ser Leu Phe Ser Ala Val Lys Asn Phe Thr Glu
625                 630                 635                 640
Ile Ala Ser Lys Phe Ser Glu Arg Leu Gln Asp Phe Asp Lys Ser Asn
                645                 650                 655
Pro Ile Val Leu Arg Met Met Asn Asp Gln Leu Met Phe Leu Glu Arg
            660                 665                 670
Ala Phe Ile Asp Pro Leu Gly Leu Pro Asp Arg Pro Phe Tyr Arg His
        675                 680                 685
Val Ile Tyr Ala Pro Ser Ser His Asn Lys Tyr Ala Gly Glu Ser Phe
    690                 695                 700
Pro Gly Ile Tyr Asp Ala Leu Phe Asp Ile Glu Ser Lys Val Asp Pro
705                 710                 715                 720
Ser Lys Ala Trp Gly Glu Val Lys Arg Gln Ile Tyr Val Ala Ala Phe
                725                 730                 735
Thr Val Gln Ala Ala Ala Glu Thr Leu Ser Glu Val Ala
            740                 745
```

<210> SEQ ID NO 843
<211> LENGTH: 1293
<212> TYPE: DNA
<213> ORGANISM: Artificial Sequence
<220> FEATURE:
<223> OTHER INFORMATION: DNA encoding the trvialent molecule in seq ID
      NO: 844

<400> SEQUENCE: 843

```
gaggtgcagc tggtggagtc tgggggaggc gtggtccagc ctggggaggtc cctgagactc      60
tcctgtgcag cctctggatt ctccttcagt ggctatggca tgcactgggt ccgccaggct     120
ccaggcaagg gactggagtg ggtggcatat atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatccg     300
gcctggggat tacgtttggg ggagtcatcg tcctatgatt ttgatatctg gggccaaggg     360
acaatggtca ccgtctcctc aggtggtggc ggttcaggcg gaggtggctc tggaggtgga     420
ggttcaggag gtggtggttc tggcggcggt ggatcgggtg gaggtggtag tgaggtgcag     480
ctggtggagt ctgggggagg cttggtccag ccggggggggt ccctgagact ctcctgtgca     540
gcctctggat tcacctttag tagccattgg atgacttggt ccgtcaggc tccagggaag     600
gggctggagt gggtggccca cataaaggaa gacggaagtg agaaatacta tgaggactct     660
gtggagggcc gattcaccgt ctccagagac aacgccaaga actcggtata tctgcaaatg     720
aacagtctga gagccgaaga cacggctgtg tattactgtg cgagaggagg tgatggctac     780
agtgactccc acttcggtgt ggacgtctgg ggccaaggga ccacggtcac tgtctcttca     840
ggtggtggcg gttcaggcgg aggtggctct ggaggtggag gttcaggagg tggtggttct     900
ggcggcggtg gatcgggtgg aggtggtagt caggtgcagc tggtggagtc tgggggaggc     960
ttggtacagc cggggggggtc cctgagactc tcctgtgcag cctctggatt cacctttagt    1020
agttatgcca tgagctgggt ccgccaggct ccagggaagg ggctggagtg ggtcgcaact    1080
attagtgata gtggtagtag tgcagactac gcagattccg tgaagggacg gttcaccatc    1140
tccagagaca actccaagaa cacgctgtat cttcaaatga acagcctgag agctgaagac    1200
acggccgtgt attactgtgc gagaggccgg tataactgga cccccgagc tttgggtatc    1260
tggggccaag ggacaatggt caccgtctcc tca                                 1293
```

<210> SEQ ID NO 844
<211> LENGTH: 431
<212> TYPE: PRT
<213> ORGANISM: Artificial Sequence
<220> FEATURE:
<223> OTHER INFORMATION: trivalent molecule

<400> SEQUENCE: 844

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110
```

Asp Phe Asp Ile Trp Gly Gln Gly Thr Met Val Thr Val Ser Ser Gly
            115                 120                 125

Gly Gly Gly Ser Gly Gly Gly Ser Gly Gly Gly Ser Gly Gly
        130                 135                 140

Gly Gly Ser Gly Gly Gly Ser Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Phe Thr Phe Ser Ser His Trp Met Thr
                180                 185                 190

Trp Phe Arg Gln Ala Pro Gly Lys Gly Leu Glu Trp Val Ala His Ile
                195                 200                 205

Lys Glu Asp Gly Ser Glu Lys Tyr Tyr Glu Asp Ser Val Glu Gly Arg
                210                 215                 220

Phe Thr Val Ser Arg Asp Asn Ala Lys Asn Ser Val Tyr Leu Gln Met
225                 230                 235                 240

Asn Ser Leu Arg Ala Glu Asp Thr Ala Val Tyr Cys Ala Arg Gly
                245                 250                 255

Gly Asp Gly Tyr Ser Asp Ser His Phe Gly Val Asp Val Trp Gly Gln
                260                 265                 270

Gly Thr Thr Val Thr Val Ser Ser Gly Gly Gly Ser Gly Gly Gly
                275                 280                 285

Gly Ser Gly Gly Gly Ser Gly Gly Gly Ser Gly Gly Gly Gly
                290                 295                 300

Ser Gly Gly Gly Gly Ser Gln Val Gln Leu Val Glu Ser Gly Gly Gly
305                 310                 315                 320

Leu Val Gln Pro Gly Gly Ser Leu Arg Leu Ser Cys Ala Ala Ser Gly
                325                 330                 335

Phe Thr Phe Ser Ser Tyr Ala Met Ser Trp Val Arg Gln Ala Pro Gly
                340                 345                 350

Lys Gly Leu Glu Trp Val Ala Thr Ile Ser Asp Ser Gly Ser Ser Ala
                355                 360                 365

Asp Tyr Ala Asp Ser Val Lys Gly Arg Phe Thr Ile Ser Arg Asp Asn
                370                 375                 380

Ser Lys Asn Thr Leu Tyr Leu Gln Met Asn Ser Leu Arg Ala Glu Asp
385                 390                 395                 400

Thr Ala Val Tyr Tyr Cys Ala Arg Gly Arg Tyr Asn Trp Asn Pro Arg
                405                 410                 415

Ala Leu Gly Ile Trp Gly Gln Gly Thr Met Val Thr Val Ser Ser
                420                 425                 430

<210> SEQ ID NO 845
<211> LENGTH: 1290
<212> TYPE: DNA
<213> ORGANISM: Artificial Sequence
<220> FEATURE:
<223> OTHER INFORMATION: DNA encoding trivalent molecule of Seq ID NO:
      846

<400> SEQUENCE: 845
gaggtgcagc tggtggagtc tgggggaggc gtggtccagc ctggagggtc cctgagactc      60
tcctgtgcag cctctggatt ctccttcagt ggctatggca tgcactgggt ccgccaggct     120
ccaggcaagg gactggagtg ggtggcatat atatcatatg atggaagtaa taaatactat     180
gcagactccg tgaagggccg attcaccatc tccagagaca attccaagaa cacgctgtat     240

-continued

```
ctgcaaatga acagcctgag agctgaggac acggctgtgt attactgtgc gaaagatccg      300
gcctggggat tacgtttggg ggagtcatcg tcctatgatt ttgatatctg gggccaaggg      360
acaatggtca ccgtctcctc aggtggtggc ggttcaggcg aggtggctc tggaggtgga       420 ggttcaggag gtggtggttc tggcggcggt ggatcgggtg aggtggtag tgaggtgcag       480 ctggtggagt ctgggggagg cttggtcaag cctggagggt ccctgagagt ctcctgtgca      540
gcctctggat tcaccttcag tgactactac atgagctggt ccgccaggc tccagggaag      600 gggctggagt gggtttcata cattagtggt agtggtgata tcatagacta cgcagactct     660
gtaaagggcc gattcaccat ctccagggac aacgccaaga actctctgta tctgcagatg     720
aacaacctga gagccgagga cacggccgtg tatcactgtg cgagagaaga ttcccgtcta     780
actgaaacta cggactttga caattggggc cagggaaccc tggtcaccgt ctcctcaggt     840
ggtggcggtt caggcggagg tggctctgga ggtggaggtt caggaggtgg tggttctggc     900
ggcggtggat cgggtggagg tggtagtcag gtgcagctgg tggagtctgg gggaggcttg     960
gtacagccgg gggggtccct gagactctcc tgtgcagcct ctggattcac ctttagtagt    1020
tatgccatga gctgggtccg ccaggctcca gggaaggggc tggagtgggt cgcaactatt    1080
agtgatagtg gtagtagtgc agactacgca gattccgtga agggacggtt caccatctcc    1140
agagacaact ccaagaacac gctgtatctt caaatgaaca gcctgagagc tgaagacacg    1200
gccgtgtatt actgtgcgag aggccggtat aactggaacc ccgagctttt gggtatctgg    1260
ggccaaggga caatggtcac cgtctcctca                                    1290
```

<210> SEQ ID NO 846
<211> LENGTH: 430
<212> TYPE: PRT
<213> ORGANISM: Artificial Sequence
<220> FEATURE:
<223> OTHER INFORMATION: Trivalent Molecule

<400> SEQUENCE: 846

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Lys Pro Gly Gly Ser Leu Arg
                165                 170                 175
```

```
Val Ser Cys Ala Ala Ser Gly Phe Thr Phe Ser Asp Tyr Tyr Met Ser
            180                 185                 190

Trp Phe Arg Gln Ala Pro Gly Lys Gly Leu Glu Trp Val Ser Tyr Ile
        195                 200                 205

Ser Gly Ser Gly Asp Ile Ile Asp Tyr Ala Asp Ser Val Lys Gly Arg
    210                 215                 220

Phe Thr Ile Ser Arg Asp Asn Ala Lys Asn Ser Leu Tyr Leu Gln Met
225                 230                 235                 240

Asn Asn Leu Arg Ala Glu Asp Thr Ala Val Tyr His Cys Ala Arg Glu
                245                 250                 255

Asp Ser Arg Leu Thr Gly Thr Thr Asp Phe Asp Asn Trp Gly Gln Gly
            260                 265                 270

Thr Leu Val Thr Val Ser Ser Gly Gly Gly Ser Gly Gly Gly Gly
        275                 280                 285

Ser Gly Gly Gly Gly Ser Gly Gly Gly Ser Gly Gly Gly Gly Ser
    290                 295                 300

Gly Gly Gly Ser Gln Val Gln Leu Val Glu Ser Gly Gly Gly Leu
305                 310                 315                 320

Val Gln Pro Gly Gly Ser Leu Arg Leu Ser Cys Ala Ala Ser Gly Phe
                325                 330                 335

Thr Phe Ser Ser Tyr Ala Met Ser Trp Val Arg Gln Ala Pro Gly Lys
            340                 345                 350

Gly Leu Glu Trp Val Ala Thr Ile Ser Asp Ser Gly Ser Ser Ala Asp
        355                 360                 365

Tyr Ala Asp Ser Val Lys Gly Arg Phe Thr Ile Ser Arg Asp Asn Ser
    370                 375                 380

Lys Asn Thr Leu Tyr Leu Gln Met Asn Ser Leu Arg Ala Glu Asp Thr
385                 390                 395                 400

Ala Val Tyr Tyr Cys Ala Arg Gly Arg Tyr Asn Trp Asn Pro Arg Ala
                405                 410                 415

Leu Gly Ile Trp Gly Gln Gly Thr Met Val Thr Val Ser Ser
            420                 425                 430

<210> SEQ ID NO 847
<211> LENGTH: 1251
<212> TYPE: DNA
<213> ORGANISM: Artificial Sequence
<220> FEATURE:
<223> OTHER INFORMATION: DNA encoding trivalent molecule in Seq ID NO:
      848

<400> SEQUENCE: 847
gaggtgcagc tgttggagtc tgggggaggc ttggtacagc ctgggggtc cctgagactc      60 tcctgtgcag cctctggatt cagttttagc agctatgccc tcagttgggt ccgccaggct    120
ccagggaagg gctggagtg gtctcaagt attggtgaga tgatggtac cacagactac      180 gcagacgccg tgaagggccg attcaccatc tccagagaca attccaagaa tacgctgtat    240
ctgcaaatga acagcctgag agtcgaggac acggccgtct attactgtgt gaaagatggt    300
gtccactggg gccagggaac cctggtcacc gtctcctcag gtggtggcgg ttcaggcgga    360
ggtggctctg gaggtggagg ttcaggaggt ggtggttctg gcggcggtgg atcgggtgga    420
ggtggtagtg aggtgcagct ggtggagtct gggggaggct tggtccagcc ggggggtcc    480 ctgagactct cctgtgcagc ctctggattc acctttagta gccattggat gacttggttc    540
cgtcaggctc cagggaaggg gctggagtgg gtggcccaca taaaggaaga cggaagtgag    600
```

```
aaatactatg aggactctgt ggagggccga ttcaccgtct ccagagacaa cgccaagaac    660
tcggtatatc tgcaaatgaa cagtctgaga gccgaagaca cggctgtgta ttactgtgcg    720
agaggaggtg atggctacag tgactcccac ttcggtgtgg acgtctgggg ccaagggacc    780
acggtcactg tctcttcagg tggtggcggt tcaggcggag gtggctctgg aggtggaggt    840
tcaggaggtg gtggttctgg cggcggtgga tcgggtggag gtggtagtca ggtgcagctg    900
gtggagtctg ggggaggctt ggtacagccg gggggtccc tgagactctc ctgtgcagcc    960
tctggattca cctttagtag ttatgccatg agctgggtcc gccaggctcc agggaagggg   1020
ctggagtggg tcgcaactat tagtgatagt ggtagtagtg cagactacgc agattccgtg   1080
aagggacggt tcaccatctc cagagacaac tccaagaaca cgctgtatct tcaaatgaac   1140
agcctgagag ctgaagacac ggccgtgtat tactgtgcga gaggccggta taactggaac   1200
ccccgagctt tgggtatctg gggccaaggg acaatggtca ccgtctcctc a            1251
```

<210> SEQ ID NO 848
<211> LENGTH: 417
<212> TYPE: PRT
<213> ORGANISM: Artificial Sequence
<220> FEATURE:
<223> OTHER INFORMATION: Trivalent Molecule

<400> SEQUENCE: 848

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Gly Gly Gly Gly Ser Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Phe Ser Ser His Trp
                165                 170                 175

Met Thr Trp Phe Arg Gln Ala Pro Gly Lys Gly Leu Glu Trp Val Ala
            180                 185                 190

His Ile Lys Glu Asp Gly Ser Glu Lys Tyr Tyr Glu Asp Ser Val Glu
        195                 200                 205

Gly Arg Phe Thr Val Ser Arg Asp Asn Ala Lys Asn Ser Val Tyr Leu
    210                 215                 220

Gln Met Asn Ser Leu Arg Ala Glu Asp Thr Ala Val Tyr Tyr Cys Ala
225                 230                 235                 240

Arg Gly Gly Asp Gly Tyr Ser Asp Ser His Phe Val Asp Val Trp
            245                 250                 255

Gly Gln Gly Thr Thr Val Thr Val Ser Ser Gly Gly Gly Ser Gly
            260                 265                 270

Gly Gly Gly Ser Gly Gly Gly Ser Gly Gly Gly Ser Gly Gly
        275                 280                 285

Gly Gly Ser Gly Gly Gly Ser Gln Val Gln Leu Val Glu Ser Gly
            290                 295                 300

Gly Gly Leu Val Gln Pro Gly Gly Ser Leu Arg Leu Ser Cys Ala Ala
305                 310                 315                 320

Ser Gly Phe Thr Phe Ser Ser Tyr Ala Met Ser Trp Val Arg Gln Ala
            325                 330                 335

Pro Gly Lys Gly Leu Glu Trp Val Ala Thr Ile Ser Asp Ser Gly Ser
            340                 345                 350

Ser Ala Asp Tyr Ala Asp Ser Val Lys Gly Arg Phe Thr Ile Ser Arg
            355                 360                 365

Asp Asn Ser Lys Asn Thr Leu Tyr Leu Gln Met Asn Ser Leu Arg Ala
            370                 375                 380

Glu Asp Thr Ala Val Tyr Tyr Cys Ala Arg Gly Arg Tyr Asn Trp Asn
385                 390                 395                 400

Pro Arg Ala Leu Gly Ile Trp Gly Gln Gly Thr Met Val Thr Val Ser
            405                 410                 415

Ser

<210> SEQ ID NO 849
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 852

<400> SEQUENCE: 849

Asn Tyr Trp Met Asn
1               5

<210> SEQ ID NO 850
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 852

<400> SEQUENCE: 850

Asn Ile Asn Gln Asp Gly Ser Glu Arg Tyr Tyr Val Asp Ser Val Lys
1               5                   10                  15

Gly

<210> SEQ ID NO 851
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 852

-continued

```
<400> SEQUENCE: 851

Gly Gly Glu Gly Tyr Gly Val Asp His Tyr Gly Leu Asp Val
1               5                   10

<210> SEQ ID NO 852
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 852

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 853
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO:856

<400> SEQUENCE: 853

Asn Tyr Trp Met Asn
1               5

<210> SEQ ID NO 854
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 856

<400> SEQUENCE: 854

Asn Ile Asn Gln Asp Gly Ser Glu Arg Tyr Tyr Val Asp Ser Val Lys
1               5                   10                  15

Gly

<210> SEQ ID NO 855
<211> LENGTH: 14
<212> TYPE: PRT
<213> ORGANISM: Homo sapiens
```

-continued

```
<220> FEATURE:
<221> NAME/KEY: MISC_FEATURE
<222> LOCATION: (1)..(14)
<223> OTHER INFORMATION: CDR3 OF SEQ ID NO: 856

<400> SEQUENCE: 855

Gly Gly Glu Gly Tyr Gly Val Asp His Tyr Gly Leu Asp Val
1               5                   10

<210> SEQ ID NO 856
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 856

Glu Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 857
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 860

<400> SEQUENCE: 857

Asn Tyr Trp Met Asn
1               5

<210> SEQ ID NO 858
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 860

<400> SEQUENCE: 858

Asn Ile Asn Gln Asp Gly Ser Glu Arg Tyr Tyr Val Asp Ser Val Lys
1               5                   10                  15

Gly
```

```
<210> SEQ ID NO 859
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 860

<400> SEQUENCE: 859

Gly Gly Glu Gly Tyr Gly Val Asp His Tyr Gly Leu Asp Val
1               5                   10

<210> SEQ ID NO 860
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 860

Glu Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 861
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 864

<400> SEQUENCE: 861

Asn Tyr Trp Met Asn
1               5

<210> SEQ ID NO 862
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 864
```

```
<400> SEQUENCE: 862

Asn Ile Asn Gln Asp Gly Ser Glu Arg Tyr Tyr Val Asp Ser Val Lys
1               5                   10                  15

Gly

<210> SEQ ID NO 863
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 864

<400> SEQUENCE: 863

Gly Gly Glu Gly Tyr Gly Val Asp His Tyr Gly Leu Asp Val
1               5                   10

<210> SEQ ID NO 864
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 864

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 865
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 868

<400> SEQUENCE: 865

Asn Tyr Trp Met Asn
1               5

<210> SEQ ID NO 866
<211> LENGTH: 17
<212> TYPE: PRT
<213> ORGANISM: Homo sapiens
```

```
<220> FEATURE:
<221> NAME/KEY: MISC_FEATURE
<222> LOCATION: (1)..(17)
<223> OTHER INFORMATION: CDR2 OF SEQ ID NO: 868

<400> SEQUENCE: 866

Asn Ile Asn Gln Asp Gly Ser Glu Arg Tyr Tyr Val Asp Ser Val Lys
1               5                   10                  15
Gly

<210> SEQ ID NO 867
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 868

<400> SEQUENCE: 867

Gly Gly Glu Gly Tyr Gly Val Asp His Tyr Gly Leu Asp Val
1               5                   10

<210> SEQ ID NO 868
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 868

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 869
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 872

<400> SEQUENCE: 869

Asn Tyr Trp Met Asn
1               5
```

```
<210> SEQ ID NO 870
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 872

<400> SEQUENCE: 870

Asn Ile Asn Gln Asp Gly Ser Glu Arg Tyr Tyr Val Asp Ser Val Lys
1               5                   10                  15

Gly

<210> SEQ ID NO 871
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 872

<400> SEQUENCE: 871

Gly Gly Glu Gly Tyr Gly Val Asp His Tyr Gly Leu Asp Val
1               5                   10

<210> SEQ ID NO 872
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 872

Glu Val Gln Leu Val Glu Ser Gly Gly Gly Leu Val Gln Pro Gly Gly
1               5                   10                  15

Ser Leu Arg Leu Ser Cys Ala Ala Thr Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 873
<211> LENGTH: 5
<212> TYPE: PRT
<213> ORGANISM: Homo sapiens
<220> FEATURE:
<221> NAME/KEY: MISC_FEATURE
<222> LOCATION: (1)..(5)
<223> OTHER INFORMATION: CDR1 OF SEQ ID NO: 876
```

-continued

<400> SEQUENCE: 873

Asn Tyr Trp Met Asn
1               5

<210> SEQ ID NO 874
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 876

<400> SEQUENCE: 874

Asn Ile Asn Gln Asp Gly Ser Glu Arg Tyr Tyr Val Asp Ser Val Lys
1               5                   10                  15

Gly

<210> SEQ ID NO 875
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 876

<400> SEQUENCE: 875

Gly Gly Glu Gly Tyr Gly Val Asp His Tyr Gly Leu Asp Val
1               5                   10

<210> SEQ ID NO 876
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 876

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
                20                  25                  30

Trp Met Asn Trp Val Arg Gln Ala Pro Gly Lys Gly Leu Glu Trp Val
            35                  40                  45

Ala Asn Ile Asn Gln Asp Gly Ser Glu Arg Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120

<210> SEQ ID NO 877
<211> LENGTH: 5
<212> TYPE: PRT
<213> ORGANISM: Homo sapiens

```
<220> FEATURE:
<221> NAME/KEY: MISC_FEATURE
<222> LOCATION: (1)..(5)
<223> OTHER INFORMATION: CDR1 OF SEQ ID NO: 880

<400> SEQUENCE: 877

Asn Tyr Trp Met Asn
1               5

<210> SEQ ID NO 878
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 OF SEQ ID NO: 880

<400> SEQUENCE: 878

Asn Ile Asn Gln Asp Glu Ser Glu Arg Tyr Tyr Val Asp Ser Val Lys
1               5                   10                  15
Gly

<210> SEQ ID NO 879
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: CDR3 OF SEQ ID NO: 880

<400> SEQUENCE: 879

Gly Gly Glu Gly Tyr Gly Val Asp His Tyr Gly Leu Asp Val
1               5                   10

<210> SEQ ID NO 880
<211> LENGTH: 123
<212> TYPE: PRT
<213> ORGANISM: Homo sapiens
<220> FEATURE:
<221> NAME/KEY: MISC_FEATURE
<222> LOCATION: (1)..(123)
<223> OTHER INFORMATION: VH binding to CD137

<400> SEQUENCE: 880

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Asn Tyr
            20                  25                  30

Trp Met Asn Trp Val Arg Gln Ala Pro Gly Lys Gly Leu Glu Trp Val
        35                  40                  45

Ala Asn Ile Asn Gln Asp Glu Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Glu Gly Tyr Gly Val Asp His Tyr Gly Leu Asp Val
            100                 105                 110

Ser Gly Gln Gly Thr Thr Val Thr Val Ser Ser
        115                 120
```

<210> SEQ ID NO 881
<211> LENGTH: 369
<212> TYPE: DNA
<213> ORGANISM: Homo sapiens

<400> SEQUENCE: 881

```
gaggtgcaat tagtcgaatc gggggtgga ctggttcagc cgggaggtag cctgcgcctg      60
tcctgtgccg catctggttt tacattaagt aactactgga tgaattgggt tcgtcaagcg     120
cctggaaagg gcttagagtg ggtggctaat attaaccagg acgggtcaga gcgctactat     180
gtggattcag taaaaggtcg cttcactatc agccgcgata atgctaaaaa ttcgctgtac     240
cttcagatgt catcacttcg tgcagaggat acagctgtgt atttctgcgc cgtgtggaggc     300 gagggggtacg gggtagacca ctatgggttg gatgtctcgg gacaaggcac gaccgtcact    360
gtcagtagc                                                             369
```

<210> SEQ ID NO 882
<211> LENGTH: 369
<212> TYPE: DNA
<213> ORGANISM: Homo sapiens

<400> SEQUENCE: 882

```
gaggtccagt tggttgagtc cggcggcggc ttggtccaac caggggggtc gcttcgctta      60
tcttgcgctg ccacagggtt taccctgagc aactactgga tgaactgggt gcgccaagcg     120
cctgggaagg ggttagagtg gtcgccaac atcaaccaag acggttcgga gcgttactat      180
gtcgacagcg tgaagggccg tttcacgatc tcccgcgata acgctaagaa ctccctgtat     240
ttgcaaatga atagccttcg tgcggaggat actgcggttt atttctgtgc tcgtggcggt     300
gaaggatatg gggttgacca ttatgggttg gatgtctccg ggcaagggac aacggtgacc     360
gtgtcatcc                                                             369
```

<210> SEQ ID NO 883
<211> LENGTH: 369
<212> TYPE: DNA
<213> ORGANISM: Homo sapiens

<400> SEQUENCE: 883

```
gaggttcaac ttgttgaatc gggtggcgga ttagtacaac ccggcggctc gctgcgttta      60
tcgtgtgcgg caaccggatt tactttatca aactattgga tgaattgggt gcgccaggct     120
ccagggaaag gtctggaatg ggtagcgaat atcaaccaag acggctcaga acgctactac     180
gtggactccg taaaaggtcg tttcaccatc tctcgtgaca atgctaaaaa ttctttgtat     240
ttgcaaatga gttcacttcg tgctgaggat actgcggtct attactgtgc tcgcgggggg     300
gaaggctacg gagtagacca ctacggggttg gatgtttctg gacagggaac gacggttact    360
gtaagcagc                                                             369
```

<210> SEQ ID NO 884
<211> LENGTH: 369
<212> TYPE: DNA
<213> ORGANISM: Homo sapiens

<400> SEQUENCE: 884

```
gaggttcagt tagttgagtc cggcggggga ttagttcaac ctggcggaag ccttcgtctg      60
agttgtgccg cgagcgggtt taccccttagc aattactgga tgaactgggt acgtcaagct    120
ccaggtaaag gtttagaatg ggtcgctaac attaatcaag atggttctga acgctattat    180
```

| | |
|---|---|
| gtagactcgg taaagggtcg ttttacaatt tctcgcgaca acgccaaaaa ctctttgtac | 240 |
| cttcaaatga attccttacg cgctgaggac actgctgtct atttctgtgc gcgtggaggg | 300 |
| gagggatacg gagttgacca ctatgggctg gacgtttcag gacagggcac tacggtaact | 360 |
| gtgtcttcg | 369 |

<210> SEQ ID NO 885
<211> LENGTH: 369
<212> TYPE: DNA
<213> ORGANISM: Homo sapiens

<400> SEQUENCE: 885

| | |
|---|---|
| gaggttcagt tagtagagtc cggggggagga ctggtacaac ctgggggtag tttgcgtctg | 60 |
| tcttgtgcag ccagcggttt cacattgtct aactattgga tgaattgggt tcgtcaagcg | 120 |
| cctggcaagg gactggagtg ggttgcaaac attaatcaag atggcagcga gcgttattac | 180 |
| gtggactcag taaagggcg cttcacgatt agccgcgata atgctaagaa ctccttatat | 240 |
| ctgcagatgt catctttgcg tgccgaggac acggcagttt actattgcgc acgtggtggc | 300 |
| gagggatacg gcgtggatca ctatggtttg gacgtatcgg gccaagggac taccgtgact | 360 |
| gtgtcctct | 369 |

<210> SEQ ID NO 886
<211> LENGTH: 372
<212> TYPE: DNA
<213> ORGANISM: Homo sapiens

<400> SEQUENCE: 886

| | |
|---|---|
| gaggaggtac agcttgtcga gtctggcggt ggccttgtgc aaccggggg ttctttacgt | 60 |
| ttatcctgtg ccgctacagg atttacgtta agcaactatt ggatgaactg ggtacgtcaa | 120 |
| gctccgggga aggggctgga atgggttgcc aatatcaatc aggatgggtc tgaacgctac | 180 |
| tacgttgatt ctgttaaggg tcgctttact atttcacgtg acaatgccaa gaacagtctt | 240 |
| taccttcaaa tgaactcgtt acgcgctgag gatactgctg tgtactactg tgcgcgcggc | 300 |
| ggagagggat acggtgtcga tcattatggg cttgacgtaa gcgggcaggg tacgacggtg | 360 |
| acggtatcat ca | 372 |

<210> SEQ ID NO 887
<211> LENGTH: 369
<212> TYPE: DNA
<213> ORGANISM: Homo sapiens

<400> SEQUENCE: 887

| | |
|---|---|
| gaggtgcagt tagttgagag cggaggtggt ttagttcagc cggggggctc gcttcgcctg | 60 |
| tcgtgcgccg cctcgggatt cacattatca aactactgga tgaattgggt ccgccaggct | 120 |
| ccgggcaaag gtcttgagtg gtggcgaac attaatcagg acgggagcga gcgttattac | 180 |
| gttgattcgg taaaaggacg tttcactatc agtcgtgaca cgctaaaaa ttccttgtac | 240 |
| ttacagatga actcacttcg tgctgaggac accgcagtgt actactgtgc tcgcggtggt | 300 |
| gaaggatacg gcgtcgatca ctacggcctt gatgtatcag gacagggac tacagttacc | 360 |
| gtctcttcc | 369 |

<210> SEQ ID NO 888
<211> LENGTH: 369
<212> TYPE: DNA

<400> SEQUENCE: 888

```
gaggtgcagt tggtagagag tggggggtggc ctggtccaac caggtgggtc ccttcgtttg    60
tcttgcgccg cctctgggtt tactctgtca aattattgga tgaactgggt gcgccaagct   120
cccggcaagg ggttggagtg ggttgccaac attaatcagg acgaatccga gcgttactat   180
gttgattctg taaaagggcg cttcactatc tctcgtgata atgctaagaa cagtttgtac   240
ctgcaaatga attcactgcg tgccgaggat accgcggtgt actattgtgc ccgtggagga   300
gagggatacg gggtcgatca ctatggctta gacgtatcgg gccagggaac aaccgtcacc   360
gtatcctca                                                          369
```

<210> SEQ ID NO 889
<211> LENGTH: 900
<212> TYPE: DNA
<213> ORGANISM: Artificial Sequence
<220> FEATURE:
<223> OTHER INFORMATION: DNA encoding bivalent molecule of Seq ID NO: 890

<400> SEQUENCE: 889

```
gaggtgcagc tggtggagtc tgggggaggc gtggtccagc ctgggaggtc cctgagactc    60
tcctgtgcag cctctggatt ctccttcagt ggctatggca tgcactgggt ccgccaggct   120
ccaggcaagg gactggagtg ggtggcatat atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaagatccg   300
gcctggggat tacgtttggg ggagtcatcg tcctatgatt ttgatatctg gggccaaggg   360
acaatggtca ccgtctcctc aggtggtggc ggttcaggcg aggtggctc tggaggtgga   420
ggttcaggag gtggtggttc tggcggcggt ggatcgggtg gaggtggtag tgaggtgcag   480
ttagttgaga gcggaggtgg tttagttcag ccggggggct cgcttcgcct gtcgtgcgcc   540
gcctcgggat tcacattatc aaactactgg atgaattggg tccgccaggc tccgggcaaa   600
ggtcttgagt gggtggcgaa cattaatcag gacgggagcg agcgttatta cgttgattcg   660
gtaaaaggac gtttcactat cagtcgtgac aacgctaaaa attccttgta cttacagatg   720
aactcacttc gtgctgagga caccgcagtg tactactgtg ctcgcggtgg tgaaggatac   780
ggcgtcgatc actacggcct tgatgtatca ggacagggga ctacagttac cgtctcttcc   840
ggcggaggtg gctctggagg aggaggttca ggaggtggtg gatctggcgg cggtggtagt   900
```

<210> SEQ ID NO 890
<211> LENGTH: 298
<212> TYPE: PRT
<213> ORGANISM: Artificial Sequence
<220> FEATURE:
<223> OTHER INFORMATION: Bivalent Molecule

<400> SEQUENCE: 890

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Ser Gly Gly Gly Gly Ser Gly Gly
130                 135                 140

Gly Gly Ser Gly Gly Gly Gly Ser Gly Gly Gly Gly Ser Glu Val Gln
145                 150                 155                 160

Leu Val Glu Ser Gly Gly Gly Leu Val Gln Pro Gly Gly Ser Leu Arg
                165                 170                 175

Leu Ser Cys Ala Ala Ser Gly Phe Thr Leu Ser Asn Tyr Trp Met Asn
            180                 185                 190

Trp Val Arg Gln Ala Pro Gly Lys Gly Leu Glu Trp Val Ala Asn Ile
        195                 200                 205

Asn Gln Asp Gly Ser Glu Arg Tyr Tyr Asp Ser Val Lys Gly Arg Phe
210                 215                 220

Thr Ile Ser Arg Asp Asn Ala Lys Asn Ser Leu Tyr Leu Gln Met Asn
225                 230                 235                 240

Ser Leu Arg Ala Glu Asp Thr Ala Val Tyr Tyr Cys Ala Arg Gly Gly
                245                 250                 255

Glu Gly Tyr Gly Val Asp His Tyr Gly Leu Asp Val Ser Gly Gln Gly
            260                 265                 270

Thr Thr Val Thr Val Ser Ser Gly Gly Gly Ser Gly Gly Gly Gly
        275                 280                 285

Ser Gly Gly Gly Gly Ser Gly Gly Gly Gly
    290                 295

<210> SEQ ID NO 891
<211> LENGTH: 858
<212> TYPE: DNA
<213> ORGANISM: Artificial Sequence
<220> FEATURE:
<223> OTHER INFORMATION: DNA encoding bivalent molecule of seq ID NO.892

<400> SEQUENCE: 891
gaggtgcagc tgttggagtc tgggggaggc ttggtacagc ctgggggtc cctgagactc      60 tcctgtgcag cctctggatt cagttttagc agctatgccc tcagttgggt ccgccaggct    120
ccagggaagg ggctggagtg ggtctcaagt attggtgaga tgatggtac cacagactac     180 gcagacgccg tgaagggccg attcaccatc tccagagaca attccaagaa tacgctgtat    240
ctgcaaatga acagcctgag agtcgaggac acggccgtct attactgtgt gaaagatggt    300
gtccactggg gccaggaac cctggtcacc gtctcctcag gtggtggcgg ttcaggcgga    360
ggtggctctg gaggtggagg ttcaggaggt ggtggttctg gcggcggtgg atcgggtgga    420
ggtggtagtg gtggtgcagtt agttgagagc ggaggtggtt tagttcagcc ggggggctcg    480
cttcgcctgt cgtgcgccgc ctcgggattc acattatcaa actactggat gaattgggtc    540
cgccaggctc cgggcaaagg tcttgagtgg gtggcgaaca ttaatcagga cgggagcgag    600
cgttattacg ttgattcggt aaaaggacgt ttcactatca gtcgtgacaa cgctaaaaat    660
tccttgtact tacagatgaa ctcacttcgt gctgaggaca ccgcagtgta ctactgtgct    720

```
cgcggtggtg aaggatacgg cgtcgatcac tacggccttg atgtatcagg acaggggact      780
acagttaccg tctcttccgg cggaggtggc tctggaggag gaggttcagg aggtggtgga      840
tctggcggcg gtggtagt                                                    858
```

<210> SEQ ID NO 892
<211> LENGTH: 286
<212> TYPE: PRT
<213> ORGANISM: Artificial Sequence
<220> FEATURE:
<223> OTHER INFORMATION: Bivalent Molecule

<400> SEQUENCE: 892

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser Gly Gly Gly Gly Ser Gly Gly Gly Ser Gly Gly Gly Gly Ser
        115                 120                 125

Gly Gly Gly Gly Ser Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Leu Ser Asn Tyr Trp
                165                 170                 175

Met Asn Trp Val Arg Gln Ala Pro Gly Lys Gly Leu Glu Trp Val Ala
            180                 185                 190

Asn Ile Asn Gln Asp Gly Ser Glu Arg Tyr Tyr Val Asp Ser Val Lys
        195                 200                 205

Gly Arg Phe Thr Ile Ser Arg Asp Asn Ala Lys Asn Ser Leu Tyr Leu
    210                 215                 220

Gln Met Asn Ser Leu Arg Ala Glu Asp Thr Ala Val Tyr Tyr Cys Ala
225                 230                 235                 240

Arg Gly Gly Glu Gly Tyr Gly Val Asp His Tyr Gly Leu Asp Val Ser
                245                 250                 255

Gly Gln Gly Thr Thr Val Thr Val Ser Ser Gly Gly Gly Gly Ser Gly
            260                 265                 270

Gly Gly Ser Gly Gly Gly Gly Ser Gly Gly Gly Gly Ser
        275                 280                 285
```

<210> SEQ ID NO 893
<211> LENGTH: 1359
<212> TYPE: DNA
<213> ORGANISM: Artificial Sequence
<220> FEATURE:
<223> OTHER INFORMATION: DNA encoding trivalent molecule of seq ID NO. 894

<400> SEQUENCE: 893

```
gaggtgcagc tggtggagtc tgggggaggc gtggtccagc ctgggaggtc cctgagactc      60
tcctgtgcag cctctggatt ctccttcagt ggctatggca tgcactgggt ccgccaggct     120
ccaggcaagg gactggagtg gtggcatat atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatccg     300
gcctggggat tacgtttggg ggagtcatcg tcctatgatt ttgatatctg gggccaaggg     360
acaatggtca ccgtctcctc aggtggtggc ggttcaggcg gaggtggctc tggaggtgga     420
ggttcaggag gtggtggttc tggcggcggt ggatcgggtg gaggtggtag tgaggtgcag     480
ttagttgaga gcggaggtgg tttagttcag ccggggggct cgcttcgcct gtcgtgcgcc     540
gcctcgggat tcacattatc aaactactgg atgaattggg tccgccaggc tccgggcaaa     600
ggtcttgagt gggtggcgaa cattaatcag gacgggagcg agcgttatta cgttgattcg     660
gtaaaaggac gtttcactat cagtcgtgac aacgctaaaa attccttgta cttacagatg     720
aactcacttc gtgctgagga caccgcagtg tactactgtg ctcgcggtgg tgaaggatac     780
ggcgtcgatc actacggcct tgatgtatca ggacagggga ctacagttac cgtctcttcc     840
ggcggaggtg gctctggagg aggcggatcg ggggtggag gaagtggcgg cggtggtagt     900
ggaggaggtg gttctggagg cggtggctct gaagtacaac tggttgaatc gggtggtgga     960
ttggtccaac tggaagatc attgaggctt tcttgtgcag cttccggatt caccttcat    1020
cactatgcta tgcactgggt gagacaagcc cctggtaagg gcttggaatg ggtgtccgga    1080
atctcctgga atggtaacaa aataacatat gcagattccg ttaagggtag atttactatt    1140
agccgtgata atgcaaaaaa cagtttatac ttgcagatga attccttgag ggctgaggat    1200
acagctcttt actattgtgt gcgtgactca tcgttgttca ttgtcggagc cccaactttc    1260
gaacattggg gtagaggtac cctagttacg gttagctcag gcggaggtgg ctctggagga    1320
ggcggatcgg ggggtggagg aagtggcggc ggtggtagt                           1359
```

<210> SEQ ID NO 894
<211> LENGTH: 453
<212> TYPE: PRT
<213> ORGANISM: Artificial Sequence
<220> FEATURE:
<223> OTHER INFORMATION: Trivalent molecule

<400> SEQUENCE: 894

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Gly Tyr
            20                  25                  30

Gly Met His Trp Val Arg Gln Ala Pro Gly Lys Gly Leu Glu Trp Val
        35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Ser Tyr
            100                 105                 110
```

```
Asp Phe Asp Ile Trp Gly Gln Gly Thr Met Val Thr Val Ser Ser Gly
            115                 120                 125

Gly Gly Gly Ser Gly Gly Gly Ser Gly Gly Gly Ser Gly Gly
130                 135                 140

Gly Gly Ser Gly Gly Gly Ser Gly Gly Gly Ser Glu Val Gln
145                 150                 155                 160

Leu Val Glu Ser Gly Gly Leu Val Gln Pro Gly Gly Ser Leu Arg
                165                 170                 175

Leu Ser Cys Ala Ala Ser Gly Phe Thr Leu Ser Asn Tyr Trp Met Asn
            180                 185                 190

Trp Val Arg Gln Ala Pro Gly Lys Gly Leu Glu Trp Val Ala Asn Ile
                195                 200                 205

Asn Gln Asp Gly Ser Glu Arg Tyr Tyr Val Asp Ser Val Lys Gly Arg
            210                 215                 220

Phe Thr Ile Ser Arg Asp Asn Ala Lys Asn Ser Leu Tyr Leu Gln Met
225                 230                 235                 240

Asn Ser Leu Arg Ala Glu Asp Thr Ala Val Tyr Tyr Cys Ala Arg Gly
                245                 250                 255

Gly Glu Gly Tyr Gly Val Asp His Tyr Gly Leu Asp Val Ser Gly Gln
            260                 265                 270

Gly Thr Val Thr Val Ser Ser Gly Gly Gly Gly Ser Gly Gly Gly
                275                 280                 285

Gly Ser Gly Gly Gly Ser Gly Gly Gly Ser Gly Gly Gly Gly
        290                 295                 300

Ser Gly Gly Gly Gly Ser Glu Val Gln Leu Val Glu Ser Gly Gly Gly
305                 310                 315                 320

Leu Val Gln Pro Gly Arg Ser Leu Arg Leu Ser Cys Ala Ala Ser Gly
                325                 330                 335

Phe Thr Phe His His Tyr Ala Met His Trp Val Arg Gln Ala Pro Gly
            340                 345                 350

Lys Gly Leu Glu Trp Val Ser Gly Ile Ser Trp Asn Gly Asn Lys Ile
            355                 360                 365

Thr Tyr Ala Asp Ser Val Lys Gly Arg Phe Thr Ile Ser Arg Asp Asn
370                 375                 380

Ala Lys Asn Ser Leu Tyr Leu Gln Met Asn Ser Leu Arg Ala Glu Asp
385                 390                 395                 400

Thr Ala Leu Tyr Tyr Cys Val Arg Asp Ser Ser Leu Phe Ile Val Gly
                405                 410                 415

Ala Pro Thr Phe Glu His Trp Gly Arg Gly Thr Leu Val Thr Val Ser
            420                 425                 430

Ser Gly Gly Gly Gly Ser Gly Gly Gly Gly Ser Gly Gly Gly Gly Ser
            435                 440                 445

Gly Gly Gly Gly Ser
    450

<210> SEQ ID NO 895
<211> LENGTH: 2634
<212> TYPE: DNA
<213> ORGANISM: Artificial Sequence
<220> FEATURE:
<223> OTHER INFORMATION: DNA encoding trivalent molecule of Seq ID no.
      896
```

<400> SEQUENCE: 895

```
gaggtgcagc tgttggagtc tgggggaggc ttggtacagc ctggggggtc cctgagactc    60
tcctgtgcag cctctggatt cagttttagc agctatgccc tcagttgggt ccgccaggct   120
ccagggaagg gctggagtg gtttcaagt attggtgaga atgatggtac cacagactac    180
gcagacgccg tgaagggccg attcaccatc tccagagaca attccaagaa tacgctgtat   240
ctacaaatga acagcctgag agtcgaggac acggccgtct attactgtgt gaaagatggt   300
gtccactggg gccagggaac cctggtcacc gtctcctcag gtggtggcgg ttcaggcgga   360
ggtggctctg gaggtggagg ttcaggaggt ggtggttctg gcggcggtgg atcgggtgga   420
ggtggtagtg aagtacaact ggttgaatcg ggtggtggat tggtccaacc tggaagatca   480
ttgaggcttt cttgtgcagc ttccggattc acctttcatc actatgctat gcactgggtg   540
agacaagccc ctggtaaggg cttggaatgg gtgtccggaa tctcctggaa tggtaacaaa   600
ataacatatg cagattccgt taagggtaga tttactatta gccgtgataa tgcaaaaaac   660
agtttatact gcagatgaa ttccttgagg gctgaggata cagctcttta ctattgtgtg    720
cgtgactcat cgttgttcat tgtcggagcc ccaactttcg aacattgggg tagaggtacc   780
ctagttacgg ttagctcagg cggaggtggc tctggaggag gaggttcagg aggtggtgga   840
tctggaggag gcggatcggg gggtggagga agtggcggcg gtggtagtga ggtgcagtta   900
gttgagagcg gaggtggttt agttcagccg ggggctcgc ttcgcctgtc gtgcgccgcc    960
tcggattca cattatcaaa ctactggatg aattgggtcc gccaggctcc gggcaaaggt   1020
cttgagtggg tggcgaacat taatcaggac gggagcgagc gttattacgt tgattcggta   1080
aaaggacgtt tcactatcag tcgtgacaac gctaaaaatt ccttgtactt acagatgaac   1140
tcacttcgtg ctgaggacac cgcagtgtac tactgtgctc gcggtggtga aggatacggc   1200
gtcgatcact acggccttga tgtatcagga caggggacta cagttaccgt ctcttccggc   1260
ggaggtggct ctggaggagg cggatcgggg ggtgaggaa gtggcggcgg tggtagtgag   1320
gtgcagctgt tggagtctgg gggaggcttg gtacagcctg gggggtccct gagactctcc   1380
tgtgcagcct ctggattcag ttttagcagc tatgccctca gttgggtccg ccaggctcca   1440
gggaaggggc tggagtgggt ttcaagtatt ggtgagaatg atggtaccac agactacgca   1500
gacgccgtga agggccgatt caccatctcc agagacaatt ccaagaatac gctgtatcta   1560
caaatgaaca gcctgagagt cgaggacacg ccgtctatt actgtgtgaa agatggtgtc   1620
cactggggcc agggaaccct ggtcaccgtc tcctcaggtg gtggcggttc aggcggaggt   1680
ggctctggag gtggaggttc aggaggtggt ggttctggcg gcggtggatc gggtggaggt   1740
ggtagtgaag tacaactggt tgaatcgggt ggtggattgg tccaacctgg aagatcattg   1800
aggctttctt gtgcagcttc cggattcacc tttcatcact atgctatgca ctgggtgaga   1860
caagcccctg gtaagggctt ggaatgggtg tccggaatct cctggaatgg taacaaaata   1920
acatatgcag attccgttaa gggtagattt actattagcc gtgataatgc aaaaaacagt   1980
ttatacttgc agatgaattc cttgagggct gaggatacag ctctttacta ttgtgtgcgt   2040
gactcatcgt tgttcattgt cggagcccca actttcgaac attggggtag aggtaccctc   2100
gttacggtta gctcaggcgg aggtggctct ggaggaggag gttcaggagg tggtggatct   2160
ggaggaggcg gatcgggggg tggaggaagt ggcggcggtg gtagtgaggt gcagttagtt   2220
gagagcggag gtggtttagt tcagccgggg ggctcgcttc gcctgtcgtg cgccgcctcg   2280
```

```
ggattcacat tatcaaacta ctggatgaat tgggtccgcc aggctccggg caaaggtctt    2340
gagtgggtgg cgaacattaa tcaggacggg agcgagcgtt attacgttga ttcggtaaaa    2400
ggacgtttca ctatcagtcg tgacaacgct aaaaattcct tgtacttaca gatgaactca    2460
cttcgtgctg aggacaccgc agtgtactac tgtgctcgcg gtggtgaagg atacggcgtc    2520
gatcactacg gccttgatgt atcaggacag gggactacag ttaccgtctc ttccggcgga    2580
ggtggctctg aggaggcgg atcgggggt ggaggaagtg gcggcggtgg tagt            2634
```

<210> SEQ ID NO 896
<211> LENGTH: 439
<212> TYPE: PRT
<213> ORGANISM: Artificial Sequence
<220> FEATURE:
<223> OTHER INFORMATION: Trivalent molecule

<400> SEQUENCE: 896

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser Gly Gly Gly Gly Ser Gly Gly Gly Ser Gly Gly Gly Gly Ser
        115                 120                 125

Gly Gly Gly Gly Ser Gly Gly Gly Ser Gly Gly Gly Gly Ser Glu
    130                 135                 140

Val Gln Leu Val Glu Ser Gly Gly Gly Leu Val Gln Pro Gly Arg Ser
145                 150                 155                 160

Leu Arg Leu Ser Cys Ala Ala Ser Gly Phe Thr Phe His His Tyr Ala
                165                 170                 175

Met His Trp Val Arg Gln Ala Pro Gly Lys Gly Leu Glu Trp Val Ser
            180                 185                 190

Gly Ile Ser Trp Asn Gly Asn Lys Ile Thr Tyr Ala Asp Ser Val Lys
        195                 200                 205

Gly Arg Phe Thr Ile Ser Arg Asp Asn Ala Lys Asn Ser Leu Tyr Leu
    210                 215                 220

Gln Met Asn Ser Leu Arg Ala Glu Asp Thr Ala Leu Tyr Tyr Cys Val
225                 230                 235                 240

Arg Asp Ser Ser Leu Phe Ile Val Gly Ala Pro Thr Phe Glu His Trp
                245                 250                 255

Gly Arg Gly Thr Leu Val Thr Val Ser Ser Gly Gly Gly Gly Ser Gly
            260                 265                 270

Gly Gly Ser Gly Gly Gly Gly Ser Gly Gly Gly Gly Ser Gly Gly
        275                 280                 285

Gly Gly Ser Gly Gly Gly Ser Glu Val Gln Leu Val Glu Ser Gly
    290                 295                 300
```

Gly Gly Leu Val Gln Pro Gly Gly Ser Leu Arg Leu Ser Cys Ala Ala
305                 310                 315                 320

Ser Gly Phe Thr Leu Ser Asn Tyr Trp Met Asn Trp Val Arg Gln Ala
            325                 330                 335

Pro Gly Lys Gly Leu Glu Trp Val Ala Asn Ile Asn Gln Asp Gly Ser
        340                 345                 350

Glu Arg Tyr Tyr Val Asp Ser Val Lys Gly Arg Phe Thr Ile Ser Arg
    355                 360                 365

Asp Asn Ala Lys Asn Ser Leu Tyr Leu Gln Met Asn Ser Leu Arg Ala
    370                 375                 380

Glu Asp Thr Ala Val Tyr Tyr Cys Ala Arg Gly Gly Glu Gly Tyr Gly
385                 390                 395                 400

Val Asp His Tyr Gly Leu Asp Val Ser Gly Gln Gly Thr Thr Val Thr
                405                 410                 415

Val Ser Ser Gly Gly Gly Gly Ser Gly Gly Gly Ser Gly Gly Gly
            420                 425                 430

Gly Ser Gly Gly Gly Ser
        435

<210> SEQ ID NO 897
<211> LENGTH: 1317
<212> TYPE: DNA
<213> ORGANISM: Artificial Sequence
<220> FEATURE:
<223> OTHER INFORMATION: DNA encoding trivalent molecule of seq ID no.
      898

<400> SEQUENCE: 897
gaggtgcagc tgttggagtc tgggggaggc ttggtacagc ctgggggtc cctgagactc        60 tcctgtgcag cctctggatt cagttttagc agctatgccc tcagttgggt ccgccaggct       120
ccagggaagg ggctggagtg ggtttcaagt attggtgaga tgatggtac acagactac         180 gcagacgccg tgaagggccg attcaccatc tccagagaca attccaagaa tacgctgtat       240
ctacaaatga acagcctgag agtcgaggac acggccgtct attactgtgt gaaagatggt       300
gtccactggg gccagggaac cctggtcacc gtctcctcag gtggtggcgg ttcaggcgga       360
ggtggctctg gaggtggagg ttcaggaggg ggtggttctg gcggcggtgg atcgggtgga       420
ggtggtagtg aggtgcagtt agttgagagc ggaggtggtt tagttcagcc ggggggctcg       480
cttcgcctgt cgtgcgccgc ctcgggattc acattatcaa actactggat gaattgggtc       540
cgccaggctc cgggcaaagg tcttgagtgg gtggcgaaca ttaatcagga cgggagcgag       600
cgttattacg ttgattcggt aaaaggacgt ttcactatca gtcgtgacaa cgctaaaaat       660
tccttgtact acagatgaa ctcacttcgt gctgaggaca ccgcagtgta ctactgtgct        720
cgcggtggtg aaggatacgg cgtcgatcac tacggccttg atgtatcagg acaggggact       780
acagttaccg tctcttccgg cggaggtggc tctggaggag cggatcgggg ggtggagga       840 agtggcggcg gtggtagtgg aggaggtggt tctgaggcg gtggctctga agtacaactg        900
gttgaatcgg gtggtggatt ggtccaacct ggaagatcat tgaggctttc ttgtgcagct       960
tccggattca cctttcatca ctatgctatg cactgggtga caagccccc tggtaagggc      1020 ttggaatggg tgtccggaat ctcctggaat ggtaacaaaa taacatatgc agattccgtt      1080
aagggtagat ttactattag ccgtgataat gcaaaaaaca gtttatactt gcagatgaat      1140

```
tccttgaggg ctgaggatac agctctttac tattgtgtgc gtgactcatc gttgttcatt    1200
gtcggagccc caactttcga acattggggt agaggtaccc tagttacggt tagctcaggc    1260
ggaggtggct ctggaggagg cggatcgggg ggtggaggaa gtggcggcgg tggtagt       1317
```

<210> SEQ ID NO 898
<211> LENGTH: 439
<212> TYPE: PRT
<213> ORGANISM: Artificial Sequence
<220> FEATURE:
<223> OTHER INFORMATION: Trivalent molecule

<400> SEQUENCE: 898

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Ala Leu Ser Trp Val Arg Gln Ala Pro Gly Lys Gly Leu Glu Trp Val
        35                  40                  45

Ser Ser Ile Gly Glu Asn Asp Gly Thr Thr Asp Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Lys Asp Gly Val His Trp Gly Gln Gly Thr Leu Val Thr Val Ser
            100                 105                 110

Ser Gly Gly Gly Gly Ser Gly Gly Gly Ser Gly Gly Gly Gly Ser
        115                 120                 125

Gly Gly Gly Gly Ser Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Leu Ser Asn Tyr Trp
                165                 170                 175

Met Asn Trp Val Arg Gln Ala Pro Gly Lys Gly Leu Glu Trp Val Ala
            180                 185                 190

Asn Ile Asn Gln Asp Gly Ser Glu Arg Tyr Tyr Val Asp Ser Val Lys
        195                 200                 205

Gly Arg Phe Thr Ile Ser Arg Asp Asn Ala Lys Asn Ser Leu Tyr Leu
    210                 215                 220

Gln Met Asn Ser Leu Arg Ala Glu Asp Thr Ala Val Tyr Tyr Cys Ala
225                 230                 235                 240

Arg Gly Gly Glu Gly Tyr Gly Val Asp His Tyr Gly Leu Asp Val Ser
                245                 250                 255

Gly Gln Gly Thr Thr Val Thr Val Ser Ser Gly Gly Gly Gly Ser Gly
            260                 265                 270

Gly Gly Ser Gly Gly Gly Gly Ser Gly Gly Gly Ser Gly Gly
        275                 280                 285

Gly Gly Ser Gly Gly Gly Ser Glu Val Gln Leu Val Glu Ser Gly
    290                 295                 300

Gly Gly Leu Val Gln Pro Gly Arg Ser Leu Arg Leu Ser Cys Ala Ala
305                 310                 315                 320

Ser Gly Phe Thr Phe His His Tyr Ala Met His Trp Val Arg Gln Ala
                325                 330                 335
```

```
Pro Gly Lys Gly Leu Glu Trp Val Ser Gly Ile Ser Trp Asn Gly Asn
            340                 345                 350
Lys Ile Thr Tyr Ala Asp Ser Val Lys Gly Arg Phe Thr Ile Ser Arg
        355                 360                 365
Asp Asn Ala Lys Asn Ser Leu Tyr Leu Gln Met Asn Ser Leu Arg Ala
    370                 375                 380
Glu Asp Thr Ala Leu Tyr Tyr Cys Val Arg Asp Ser Ser Leu Phe Ile
385                 390                 395                 400
Val Gly Ala Pro Thr Phe Glu His Trp Gly Arg Gly Thr Leu Val Thr
                405                 410                 415
Val Ser Ser Gly Gly Gly Gly Ser Gly Gly Gly Gly Ser Gly Gly Gly
            420                 425                 430
Gly Ser Gly Gly Gly Gly Ser
        435
```

<210> SEQ ID NO 899
<211> LENGTH: 1359
<212> TYPE: DNA
<213> ORGANISM: Artificial Sequence
<220> FEATURE:
<223> OTHER INFORMATION: DNA encoding trivalent molecule of seq ID no.
      900

<400> SEQUENCE: 899

| | | | | | |
|---|---|---|---|---|---|
| gaggtgcagc | tggtggagtc | tgggggaggc | gtggtccagc | ctgggaggtc | cctgagactc | 60 |
| tcctgtgcag | cctctggatt | ctccttcagt | ggctatggca | tgcactgggt | ccgccaggct | 120 |
| ccaggcaagg | gactggagtg | ggtggcatat | atatcatatg | atggaagtaa | taaatactat | 180 |
| gcagactccg | tgaagggccg | attcaccatc | tccagagaca | attccaagaa | cacgctgtat | 240 |
| ctgcaaatga | acagcctgag | agctgaggac | acggctgtgt | attactgtgc | gaaagatccg | 300 |
| gcctggggat | tacgtttggg | ggagtcatcg | tcctatgatt | ttgatatctg | gggccaaggg | 360 |
| acaatggtca | ccgtctcctc | aggtggtggc | ggttcaggcg | gaggtggctc | tggaggtgga | 420 |
| ggttcaggag | gtggtggttc | tggcggcggt | ggatcgggtg | gaggtggtag | tgaagtacaa | 480 |
| ctggttgaat | cgggtggtgg | attggtccaa | cctggaagat | cattgaggct | ttcttgtgca | 540 |
| gcttccggat | tcacctttca | tcactatgct | atgcactggg | tgagacaagc | ccctggtaag | 600 |
| ggcttggaat | gggtgtccgg | aatctcctgg | aatggtaaca | aaataacata | tgcagattcc | 660 |
| gttaagggta | gatttactat | tagccgtgat | aatgcaaaaa | acagtttata | cttgcagatg | 720 |
| aattccttga | gggctgagga | tacagctctt | tactattgtg | tgcgtgactc | atcgttgttc | 780 |
| attgtcggag | ccccaacttt | cgaacattgg | ggtagaggta | ccctagttac | ggttagctca | 840 |
| ggcggaggtg | gctctggagg | aggaggttca | ggaggtggtg | gatctggagg | aggcggatcg | 900 |
| ggggtggag | gaagtggcgg | cggtggtagt | gaggtgcagt | tagttgagag | cggaggtggt | 960 |
| ttagttcagc | cgggggctc | gcttcgcctg | tcgtgcgccg | cctcgggatt | cacattatca | 1020 |
| aactactgga | tgaattgggt | ccgccaggct | ccgggcaaag | gtcttgagtg | ggtggcgaac | 1080 |
| attaatcagg | acgggagcga | gcgttattac | gttgattcgg | taaaaggacg | tttcactatc | 1140 |
| agtcgtgaca | acgctaaaaa | ttccttgtac | ttacagatga | actcacttcg | tgctgaggac | 1200 |
| accgcagtgt | actactgtgc | tcgcggtggt | gaaggatacg | gcgtcgatca | ctacggcctt | 1260 |
| gatgtatcag | acagggggac | tacagttacc | gtctcttccg | gcggaggtgg | ctctggagga | 1320 |
| ggcggatcgg | ggggtggagg | aagtggcggc | ggtggtagt | | | 1359 |

```
<210> SEQ ID NO 900
<211> LENGTH: 453
<212> TYPE: PRT
<213> ORGANISM: Artificial Sequence
<220> FEATURE:
<223> OTHER INFORMATION: Trivalent molecule

<400> SEQUENCE: 900

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Gly Tyr
                20                  25                  30

Gly Met His Trp Val Arg Gln Ala Pro Gly Lys Gly Leu Glu Trp Val
            35                  40                  45

Ala Tyr Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Ala Trp Gly Leu Arg Leu Gly Glu Ser Ser Tyr
            100                 105                 110

Asp Phe Asp Ile Trp Gly Gln Gly Thr Met Val Thr Val Ser Ser Gly
        115                 120                 125

Gly Gly Gly Ser Gly Gly Gly Ser Gly Gly Gly Ser Gly Gly
        130                 135                 140

Gly Gly Ser Gly Gly Gly Ser Gly Gly Gly Ser Glu Val Gln
145                 150                 155                 160

Leu Val Glu Ser Gly Gly Leu Val Gln Pro Gly Arg Ser Leu Arg
                165                 170                 175

Leu Ser Cys Ala Ala Ser Gly Phe Thr Phe His His Tyr Ala Met His
        180                 185                 190

Trp Val Arg Gln Ala Pro Gly Lys Gly Leu Glu Trp Val Ser Gly Ile
            195                 200                 205

Ser Trp Asn Gly Asn Lys Ile Thr Tyr Ala Asp Ser Val Lys Gly Arg
    210                 215                 220

Phe Thr Ile Ser Arg Asp Asn Ala Lys Asn Ser Leu Tyr Leu Gln Met
225                 230                 235                 240

Asn Ser Leu Arg Ala Glu Asp Thr Ala Leu Tyr Tyr Cys Val Arg Asp
                245                 250                 255

Ser Ser Leu Phe Ile Val Gly Ala Pro Thr Phe Glu His Trp Gly Arg
        260                 265                 270

Gly Thr Leu Val Thr Val Ser Ser Gly Gly Gly Ser Gly Gly Gly
            275                 280                 285

Gly Ser Gly Gly Gly Gly Ser Gly Gly Gly Ser Gly Gly Gly Gly
        290                 295                 300

Ser Gly Gly Gly Gly Ser Glu Val Gln Leu Val Glu Ser Gly Gly
305                 310                 315                 320

Leu Val Gln Pro Gly Gly Ser Leu Arg Leu Ser Cys Ala Ala Ser Gly
                325                 330                 335

Phe Thr Leu Ser Asn Tyr Trp Met Asn Trp Val Arg Gln Ala Pro Gly
        340                 345                 350

Lys Gly Leu Glu Trp Val Ala Asn Ile Asn Gln Asp Gly Ser Glu Arg
            355                 360                 365
```

Tyr Tyr Val Asp Ser Val Lys Gly Arg Phe Thr Ile Ser Arg Asp Asn
                370                 375                 380

Ala Lys Asn Ser Leu Tyr Leu Gln Met Asn Ser Leu Arg Ala Glu Asp
385                 390                 395                 400

Thr Ala Val Tyr Tyr Cys Ala Arg Gly Gly Glu Gly Tyr Gly Val Asp
                405                 410                 415

His Tyr Gly Leu Asp Val Ser Gly Gln Gly Thr Thr Val Thr Val Ser
                420                 425                 430

Ser Gly Gly Gly Gly Ser Gly Gly Gly Ser Gly Gly Gly Gly Ser
            435                 440                 445

Gly Gly Gly Gly Ser
        450

<210> SEQ ID NO 901
<211> LENGTH: 122
<212> TYPE: PRT
<213> ORGANISM: Homo sapiens
<220> FEATURE:
<221> NAME/KEY: MISC_FEATURE
<222> LOCATION: (1)..(122)
<223> OTHER INFORMATION: VH that binds to HSA

<400> SEQUENCE: 901

Glu Val Gln Leu Val Glu Ser Gly Gly Gly Leu Val Gln Pro Gly Arg
1               5                   10                  15

Ser Leu Arg Ser Cys Ala Ala Ser Gly Phe Thr Phe His His Tyr Ala
                20                  25                  30

Met His Trp Val Arg Gln Ala Pro Gly Lys Gly Leu Glu Trp Val Ser
            35                  40                  45

Gly Ile Ser Trp Asn Gly Asn Lys Ile Thr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Leu Tyr Tyr Cys Val
                85                  90                  95

Arg Asp Ser Ser Leu Phe Ile Val Gly Ala Pro Thr Phe Glu His Trp
                100                 105                 110

Gly Arg Gly Thr Leu Val Thr Val Ser Ser
            115                 120

<210> SEQ ID NO 902
<211> LENGTH: 750
<212> TYPE: DNA
<213> ORGANISM: Homo sapiens
<220> FEATURE:
<221> NAME/KEY: misc_feature
<222> LOCATION: (1)..(750)
<223> OTHER INFORMATION: Nucleotide encoding VH that binds to HSA of Seq
      ID 901

<400> SEQUENCE: 902
ggctttgtga gcggatacaa ttataatatg tggaattgtg agcgctcaca attccacaac      60
ggtttccctc tagaaataat tttgtttaac ttttaggagg taaaacatat gaagaaaacg     120
gcaatcgcaa tcgcagtcgc tctggcgggt ttcgcaactg tagcgcaagc cgaggtgcaa     180
ctggtcgagt ctggtggtgg tttggtgcaa cctggtagaa gcttgcgttt gagttgtgcc     240
gcttccggct tcacttttca tcattatgct atgcactggg ttcgtcaagc tcccggaaaa     300
ggtttggagt gggtttccgg aatttcctgg aatggcaata agattacgta cgctgattca     360

```
gtgaaaggaa ggtttacaat cagtagagat aatgctaaaa actcattgta tctacaaatg    420
aacagcctaa gagcagaaga taccgctctg tactactgtg ttagagatag ctcgttattc    480
attgtaggtg caccaacttt tgaacattgg ggtcggggta ctcttgtgac tgtctcatcc    540
gcggccgcac accaccatca tcaccactaa ctcgagcgcc taatgaaagc ttccccaagg    600
gcgacacccc ctaattagcc cgggcgaaag gcccagtctt tcgactgagc ctttcgtttt    660
atttgatgcc tggcagttcc ctactctcgc atggggagtc cccacactac catcggcgct    720
acggcgtttc acttctgagt tcggcatgga                                     750
```

SINGLE DOMAIN ANTIBODIES THAT BIND TO CD137

CROSS REFERENCE TO RELATED APPLICATIONS

This application is a national phase entry of International Application No. PCT/GB2018/053279, filed Nov. 13, 2018, which claims the priority benefit of GB Application No. 1718734.5, filed Nov. 13, 2017, GB Application No. 1718735.2, filed Nov. 13, 2017, and GB Application No. 1808589.4, filed May 24, 2018, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 4577_0020003_Seqlisting_ST25.txt; Size: 541,592 bytes; and Date of Creation: May 7, 2020) is herein incorporated by reference in its entirety.

INTRODUCTION

Cancer remains one of the leading causes of death in the world. Recent studies have shown an estimated 12.7 million cancer cases worldwide. This number is expected to increase to 21 million by 2030 (Vinay and Kwon 2014).

CD137 (4-1BB, TNFRS9) is a type 1 transmembrane glycoprotein belonging to the TNF receptor superfamily. It was originally cloned from the cDNA of activated murine T cells. It has subsequently been shown to have a broad immune cell expression pattern found on T cells, B cells, NK and NK T cells, dendritic cells (DC), macrophages, neutrophils and eosinophils. Expression has also been reported on non-haematopoetic cells, for example epithelial, endothelial and smooth muscle cells and on tumour cell lines. CD137 expression is mainly activation induced, although low level constitutive expression has been demonstrated on some cell types including Tregs and DC.

The 255 amino acid human CD137 protein (Genbank accession NP_001552) consists of a 17 amino acid signal peptide sequence, an extracellular region containing four cysteine rich domains, a 27 amino acid transmembrane region and a short 42 amino acid intracellular domain. It exists as both a monomer and dimer on the cell surface. The main ligand for CD137 is CD137 ligand (CD137L, 4-1BB-L, TNFS9), although interactions with galectin-9 which facilitates receptor aggregation (Madireddi et al 2014) and matrix proteins such as fibronectin (Chalupny et al, 1992) have also been reported. CD137 ligand is predominantly expressed on activated antigen presenting cells such as dendritic cells, B-cells and macrophages.

Interaction of the trimeric CD137 ligand with CD137 results in multimerisation of the receptor and recruitment of signalling molecules such as the TRAF family of proteins leading to kinase modulation and activation of the Nf-KB pathway. Thus, multimerisation of CD137 is crucial for initiation and regulation of downstream signalling.

Studies using agonist anti CD137 monoclonal antibodies in vitro and in vivo have shown that upon activation CD137 is rapidly internalised into an endosomal compartment termed the 'signalosome' from which it keeps signalling (reviewed in Sanchez-Paulete et al 2016).

Co-stimulatory TNFR family members such as CD137, CD27, OX40 (CD134), HVEM, CD30, and GITR are involved in sustaining the T cell responses after initial T-cell activation. In CD4+ and CD8+ T cells, CD137 acts as a costimulatory receptor that modulates T-cell receptor (TCR) mediated signalling. Ligation of CD137 together with TCR activation promotes proliferation, cytokine production, and inhibits apoptosis through induction of anti-apoptotic B-cell lymphoma-extra large (Bcl-xl) and B-cell lymphoma 2 (Bcl-2) pathways. Cross-linking of CD137 on NK cells has been shown to stimulate IFN-gamma secretion and proliferation. Dendritic cell responses to CD137 stimulation include enhanced maturation and antigen presentation and secretion of cytokines IL-6, IL12- and IL-27 and enzymes such as indoleamine-2,3-dioxygenase (IDO) which can modulate T-cell function. CD137 can also upregulate intercellular adhesion molecule 1 (ICAM1) and vascular cell adhesion molecule 1 (VCAM1) on tumor vascular endothelium, thus inducing effector cell migration and retention of the activated T-cells in the tumor microenvironment.

Cross linking of CD137 by anti CD137 antibodies has been shown to have potent anti-tumour effects in vivo in a number of models including sarcoma, mastocytoma, glioma, lymphoma, myeloma, and hepatocellular carcinoma. CD8+ cell depletion studies have demonstrated that this effect primarily involves cytolytic T cell expansion and infiltration resulting in tumour cell lysis. However, contributions of other types of cells such as DCs, NK-cells or CD4+ T-cells have been reported in some tumour models. Furthermore, anti CD137 therapy has been shown to trigger an immunologic memory response and to inhibit autoimmune reactions (reviewed in Vinay et al 2012).

It has been shown that existing agonistic therapies result in systemic CD137 effects leading to unwanted side effects. Activation of CD137 signalling has been associated with severe toxicity in murine models. Clinical trials of a fully human IgG4 anti CD137 agonistic antibody (Urelumab®, BMS-663513) reported neutropenia, elevated liver enzymes and at high doses severe hepatic toxicity resulting in trial termination. This severe toxicity has not been observed for a fully human IgG2 (PF-05082566) that is also in clinical trials both as a monotherapy and in combination therapy approaches. Agonistic antibodies targeting co-stimulatory TNFRs have been shown to require engagement of FcγRs (Bulliard et al, 2014). Thus, non-targeted clustering via FcγRs may influence the mechanism by which agonistic antibodies act on these targets.

In light of the toxicity profile observed with existing therapies, there is a need for alternative cancer therapies based on the use of alternative CD137 binding molecules that have reduced toxicity. In particular, there is a clinical need for targeted CD137 agonists that effectively engage CD137 on the surface of cells and have reduced toxicity, including liver toxicity.

Development of a CD137 binding molecule that possess minimal agonistic and internalising activity would therefore provide a building block for the generation of bispecific molecules that co-target CD137 and other molecules, for example tumour associated antigens expressed within the tumour microenvironment. In such molecules dual, e.g. simultaneous engagement of both targets may result in CD137 activation thus restricting the site of action to the tumor microenvironment and potentially minimising undesirable effects of CD137 therapy.

SUMMARY

The invention relates to novel binding molecules with specificity for CD137. The inventors have identified single variable heavy chain domain antibodies that bind to CD137, but do not cause CD137 signalling when bound to CD137 in monospecific format, that is without being linked to another moiety that binds a second target. However, when linked to a moiety that binds a tumor specific antigen, the single variable heavy chain domain antibodies elicit an agonistic response. Thus, whilst the single variable heavy chain domain antibodies that bind to CD137 do not induce clusterisation of the receptor and do not have agonistic activity when bound to CD137 without a binding partner that targets a second antigen, the dual engagement of CD137 and a tumor specific antigen in a bispecific molecule leads to CD137 agonism.

In one aspect, there is provided an isolated single variable heavy chain domain antibody which binds to human CD137 but does not elicit CD137 signalling when bound to CD137 as a monospecific entity. In one embodiment, said single variable heavy chain domain antibody inhibits the binding of CD137L to CD137.

In one embodiment, the single variable heavy chain domain antibody comprises a CDR1 comprising a SEQ ID NO. selected from table 1, a CDR2 comprising a SEQ ID NO. selected from table 1 and a CDR3 comprising a SEQ ID NO. selected from table 1. Preferably, the CDRs are defined using Kabat nomenclature.

In one embodiment, the single variable heavy chain domain antibody comprises a CDR1 comprising SEQ ID NO. 1 or a sequence with at least 40% homology thereto, a CDR2 comprising SEQ ID NO. 2 or a sequence with at least 40% homology thereto and a CDR3 comprising SEQ ID NO. 3 or a sequence with at least 40% homology thereto. Preferably, the CDRs are defined using Kabat nomenclature.

In one embodiment, the single variable heavy chain domain antibody comprises a CDR1 comprising SEQ ID NO. 425 or a sequence with at least 40% homology thereto, a CDR2 comprising SEQ ID NO. 426 or a sequence with at least 40% homology thereto and a CDR3 comprising SEQ ID NO. 427 or a sequence with at least 40% homology thereto.

In one embodiment, the single variable heavy chain domain antibody comprises human framework regions. In one embodiment, the single variable heavy chain domain antibody comprises SEQ ID NO. 4 or 428 or a sequence with at least 50% homology thereto.

In one embodiment, the single variable heavy chain domain antibody is selected from SEQ ID NOs. 4, 312, 852, 856, 860, 864, 868, 872, 876 or 880 or a sequence with at least 50% homology thereto. In one embodiment, the single variable heavy chain domain antibody is capable of binding CD137 with an affinity with a KD of about 0.4 nM or of about 3 nM. In one embodiment, the single variable heavy chain domain antibody is obtained or obtainable from a transgenic rodent, e.g. mouse, that expresses a transgene comprising human V, D and J regions.

In one embodiment, the said rodent does not produce functional endogenous light and heavy chains.

Also provided in another aspect is a binding molecule comprising
 a) a single variable heavy chain domain antibody that binds to CD137 described herein and
 b) a moiety that binds to a tumor specific antigen.

In one embodiment, the moiety that binds to a tumor specific antigen is a single variable heavy chain domain antibody. In one embodiment of the binding molecule, the single variable heavy chain domain antibody that binds to CD137 is linked to the single variable heavy chain domain antibody that binds to a tumor specific antigen by a peptide linker. In one embodiment, said linker is selected from a (G4S)n linker wherein n is 1 to 10. In one embodiment, the tumor specific antigen is selected from PSMA, Her2, CD123, CD19, CD20, CD22, CD23, CD74, BCMA, CD30, CD33, CD52, EGRF CECAM6, CAXII, CD24, CEA, Mesothelin, cMet, TAG72, MUC1, MUC16, STEAP, EphvIII, FAP, GD2, IL-13Ra2, L1-CAM, PSCA, GPC3, Her3, gpA33, 5T4 and ROR1. In one embodiment, the isolated single variable heavy chain domain antibody or the binding molecule is conjugated to a toxin, enzyme, radioisotope, half-life extending moiety, label, therapeutic molecule or other chemical moiety. In one embodiment, the said half-life extending moiety is selected from an albumin binding moiety, a transferrin binding moiety, a polyethylene glycol molecule, a recombinant polyethylene glycol molecule, human serum albumin, a fragment of human serum albumin, or an albumin binding peptide or single domain antibody that binds to human serum albumin. Also provided is a pharmaceutical composition comprising a single variable heavy chain domain antibody or a binding molecule described herein and a pharmaceutical carrier.

In another aspect, we provide the single variable heavy chain domain antibody, binding molecule pharmaceutical composition described above for use in the treatment of disease, for example wherein said disease is selected from cancer, an immune disorder, neurological disease, inflammatory disorder, allergy, transplant rejection, viral infection, immune deficiency or other immune system-related disorder.

Also provided is a method for treating a cancer, an immune disorder, neurological disease, inflammatory disorder, allergy, transplant rejection, viral infection, immune deficiency or other immune system-related disorder comprising administering a therapeutically effective amount of the single variable heavy chain domain antibody, binding molecule or a pharmaceutical composition described above.

In another aspect, we provide a kit comprising a single variable heavy chain domain antibody, binding molecule or a pharmaceutical composition as described herein.

In another aspect, we provide a nucleic acid molecule comprising a nucleic acid sequence encoding a single variable heavy chain domain antibody as described herein, for example a nucleic acid molecule comprising SEQ ID NO. 629 or 735 or a nucleic acid molecule having at least 50% homology thereto. In another aspect, we provide a vector or host cell comprising a nucleic acid molecule according to the above. In another aspect, we provide methods for producing a single variable heavy chain domain antibody that binds to human CD137. We also provide a single $V_H$ domain antibody obtained or obtainable by the method. In another aspect, we provide a transgenic rodent, e.g. mouse, that produces a heavy chain only antibody that binds to CD137 produced upon immunisation with a CD137 antigen. We also provide a heavy chain only antibody comprising a $V_H$ domain that binds to human CD137 obtained or obtainable from a transgenic rodent.

In another aspect, we provide a method for promoting CD8+ T cell expansion, inducing activation of cytotoxic T lymphocytes (CTL) and/or cytokine release comprising administering to a subject a single variable heavy chain domain antibody, a binding molecule or a pharmaceutical composition as described herein.

In another aspect, we provide a use of a single variable heavy chain domain antibody as described herein in a binding molecule that further comprises a single heavy variable chain domain antibody which binds to a tumor specific antigen.

FIGURES

The invention is further described in the following non-limiting figures. The single domain antibody as used in the figures is listed in tables 2 and 3.

FIG. 1. Binding kinetics of monovalent, bivalent and trivalent Humabody® $V_H$. Association and dissociation kinetics of (A) Monovalent, (B) Bivalent and (C) trivalent versions of Humabody® $V_H$ 1.1 (SEQ ID No. 4) and (D) monovalent, (E) bivalent and (F) trivalent Humabody® $V_H$ 2.1 (SEQ ID NO. 428) were measured for binding to human CD137huFc tagged protein captured onto Protein G sensors using biolayer interferometry. Multivalent formats show enhanced binding compare to monovalent Humabody® $V_H$.

Figure 2:
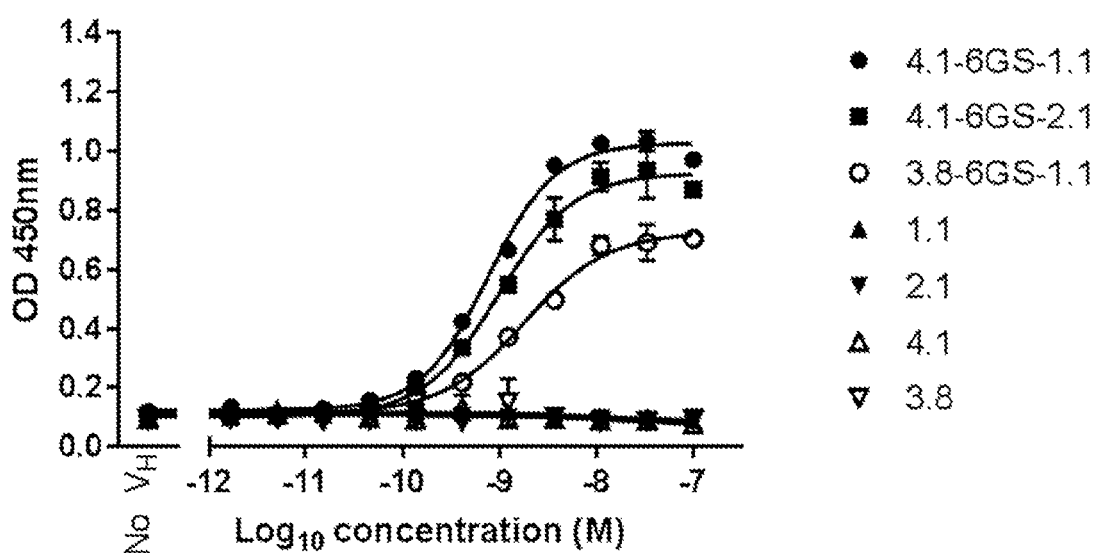

FIG. 2: Dual Binding Cell based ELISA.

CHO human PSMA expressing cells were seeded onto plates and monovalent $V_H$ or bispecific molecules added. CD137huFc was subsequently added and binding detected using anti human Fc-HRP. Only bispecific molecule showed increased binding signal confirming dual target binding.

Figure 3:
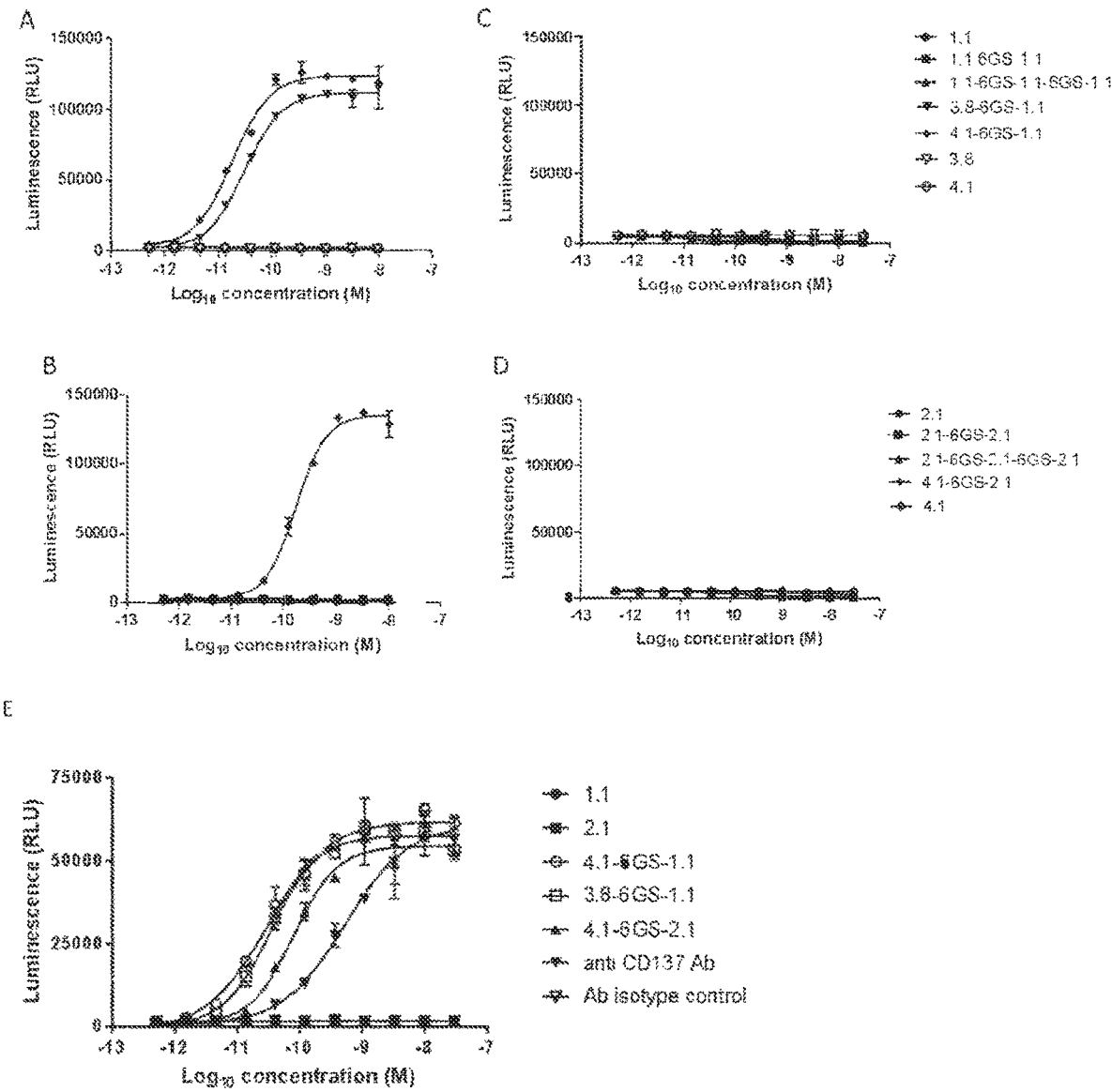
Figure 3:
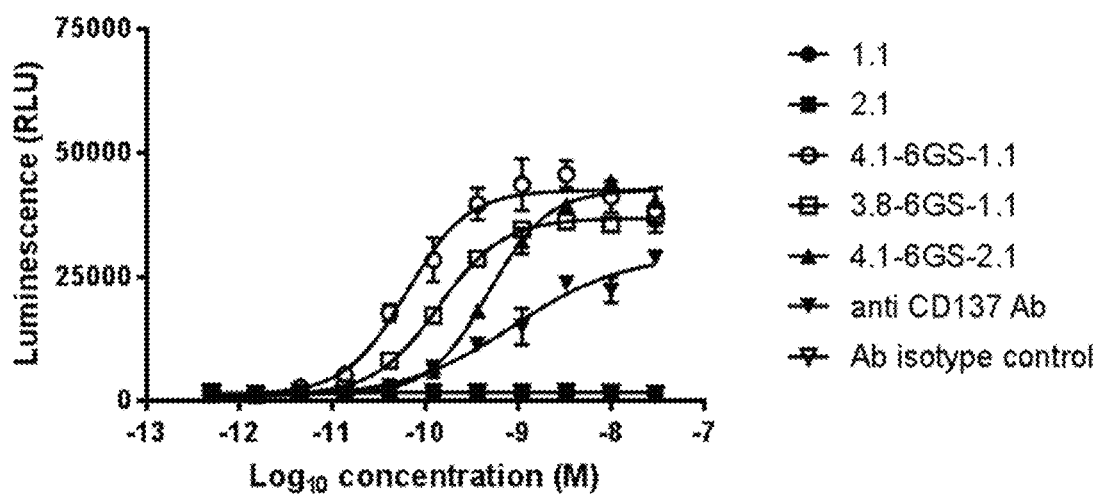
Figure 3:
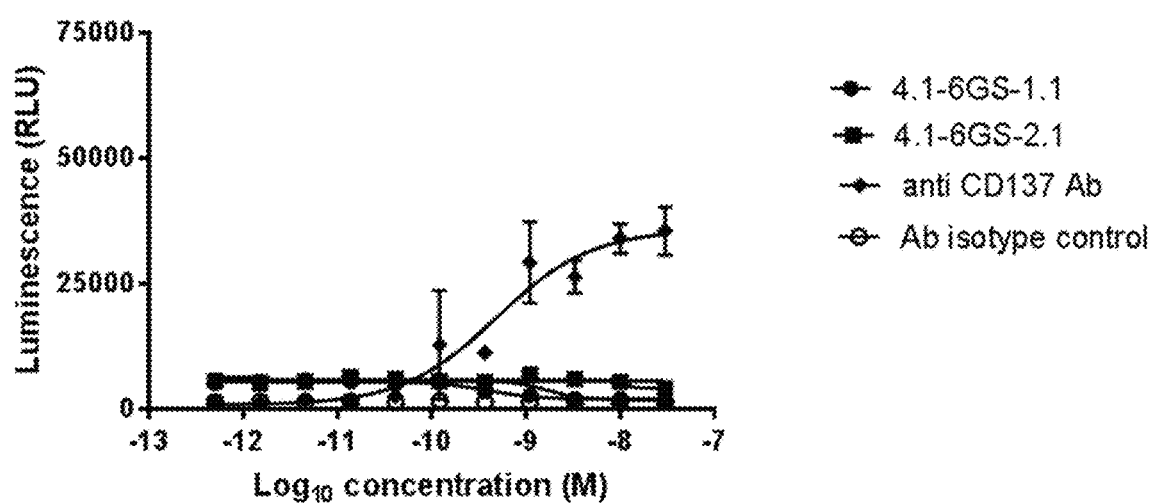

FIG. 3. Activation of CD137 signalling in the Jurkat NF-kB Luciferase Reporter Assay. PSMA expressing cells (A and B) or non-expressing parental cells (C and D) were co-cultured with Jurkat human CD137 NF-kB-luciferase reporter cells. (E) CHO PSMA cells, (F) DU145 PSMA cells or (G) DU145 parental cells (bispecific testing)/media only (antibody testing) were cultured with Jurkat human CD137 NF-kB-luciferase reporter cells. Relative luminescence signal (RLU) was measured as a readout of the luciferase reporter gene activity resulting from CD137 mediated activation of the NF-kB signalling pathway. Monovalent, bivalent, trivalent and bispecific versions of Humabody® $V_H$ 1.1 (SEQ ID No. 4) and monovalent, bivalent, trivalent and bispecific versions of Humabody® $V_H$ 2.1 (SEQ ID NO. 428) were tested for the potential to agonise CD137 to result in signalling via NF-kB. Monovalent PSMA Humabody® $V_{Hs}$ were included as controls. Monovalent, bivalent and trivalent molecules did not act as agonists in the assay. Bispecific molecules in the presence of PSMA expressing cells were able to effectively stimulate CD137 signalling.

Figure 4:
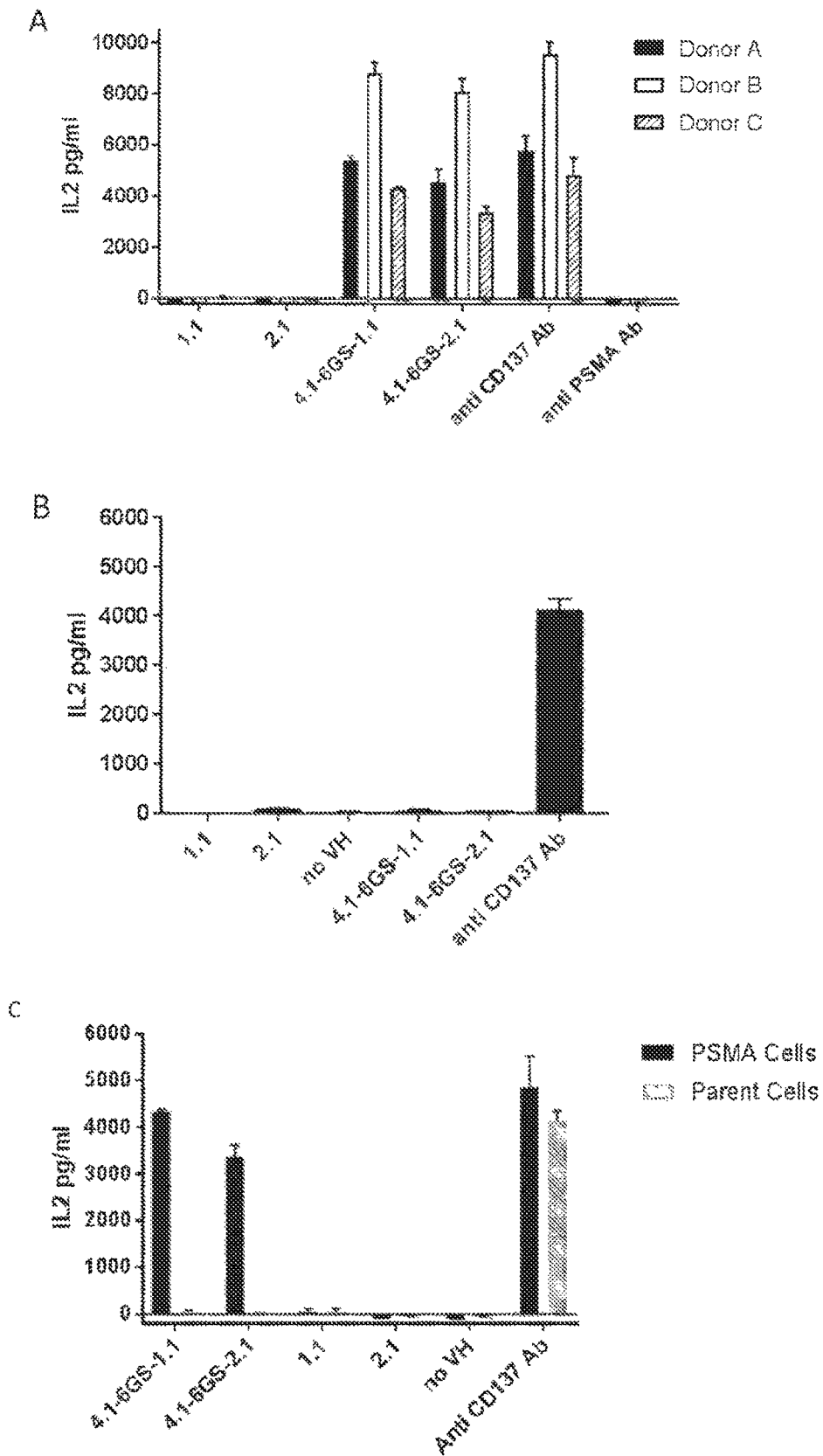
Figure 4:
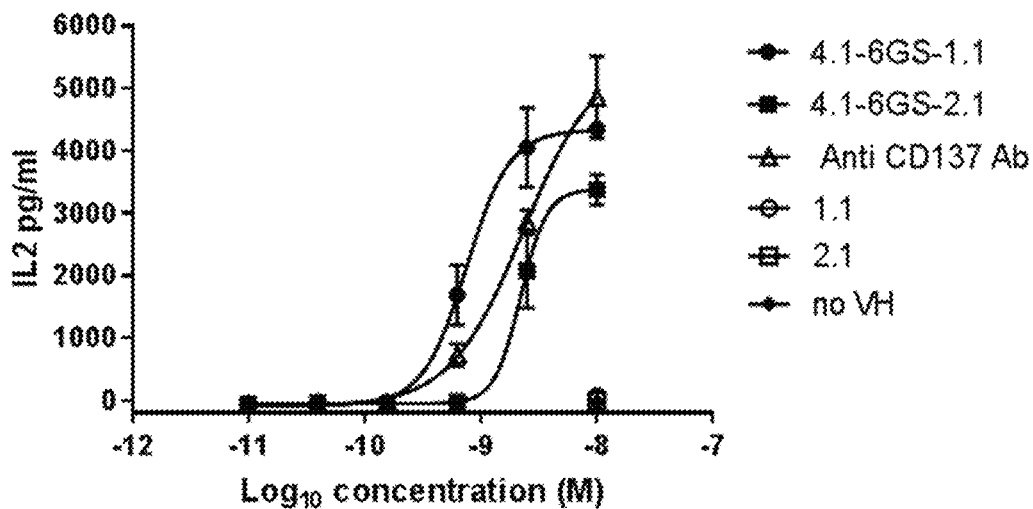
Figure 4:
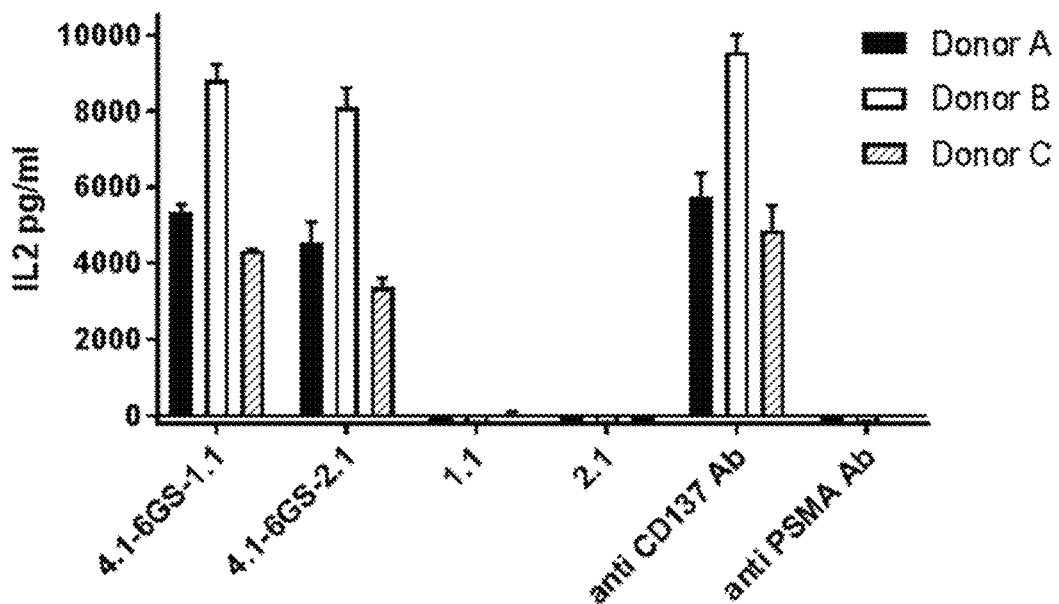
Figure 4:
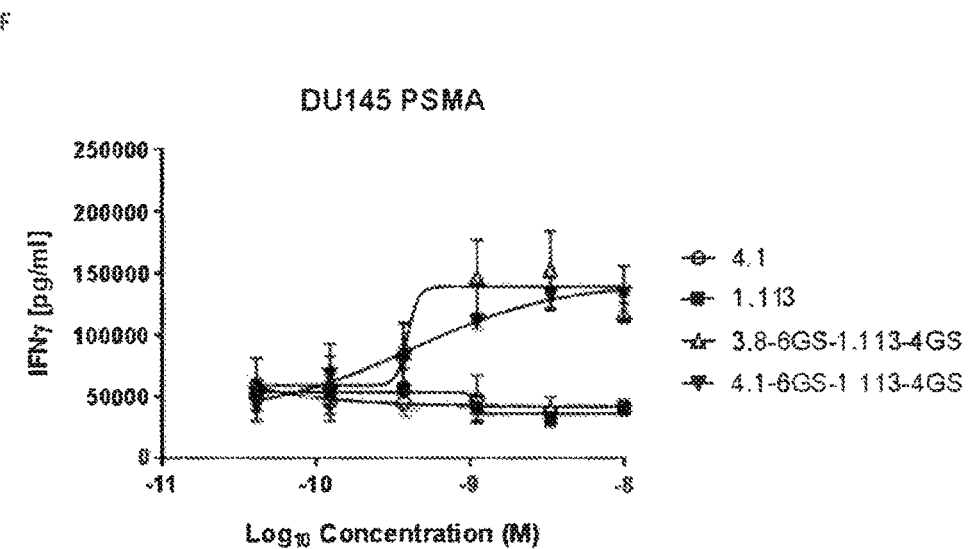

FIG. 4. Enhancement of IL-2 production in T-cells. Human CD8+ T cells were co-cultured with PSMA expressing cells or non-expressing parental cells in the presence of plate bound anti CD3 antibody. Humabody® $V_H$ 1.1 (SEQ ID No. 4) monovalent and bispecific molecules, Humabody® $V_H$ 2.1 (SEQ ID No. 428) monovalent and bispecific molecules, anti CD137 benchmark antibody and anti PSMA antibody were added at a concentration of 10 nM. Supernatants were harvested after 48 hours and levels of IL-2 determined. (A) Enhancement of IL-2 responses for 3 different T-cell donors in the presence of PSMA expressing cells. (B) Representative data for measurement of IL-2 levels in the presence of parental cells. Monovalent Humabody® $V_H$ did not stimulate IL2 production in the assay. (C) Bispecific molecules in the presence of PSMA expressing cells were able to effectively enhance IL-2 production. The anti CD137 antibody (soluble, non-cross linked) enhanced IL-2 production in a PSMA independent response. (D and E) Concentration dependence of IL-2 response. (F) Bispecific molecules induce interferon gamma.

Figure 5:
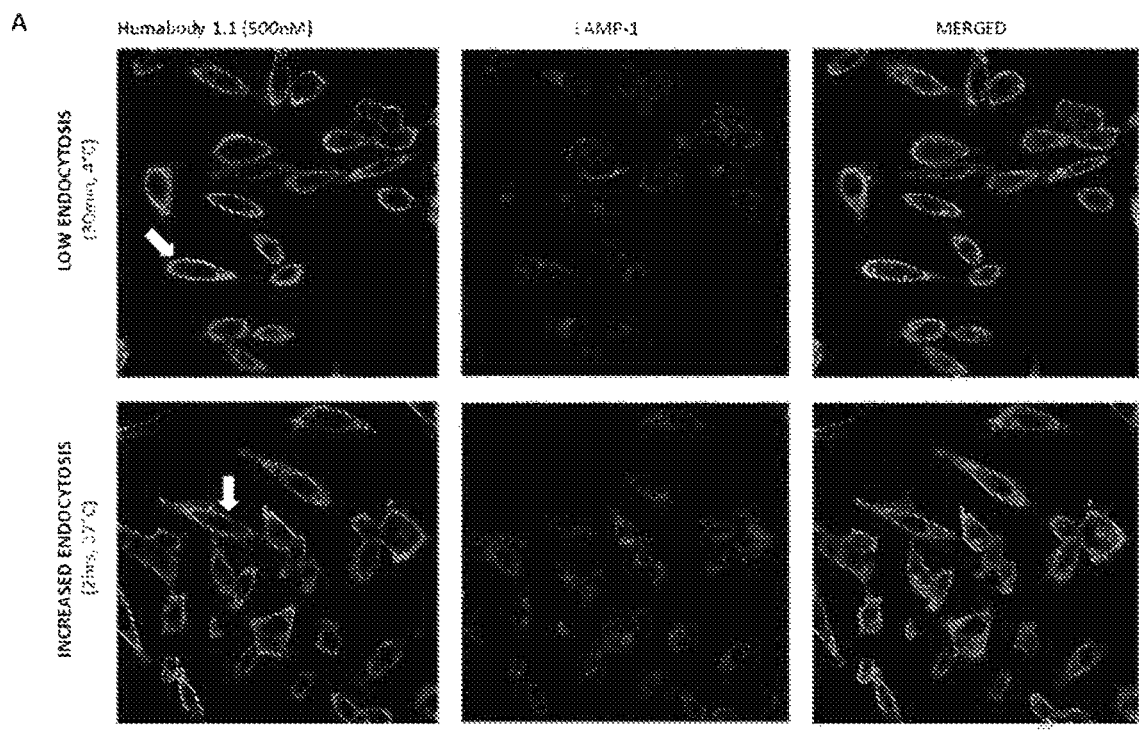
Figure 5:
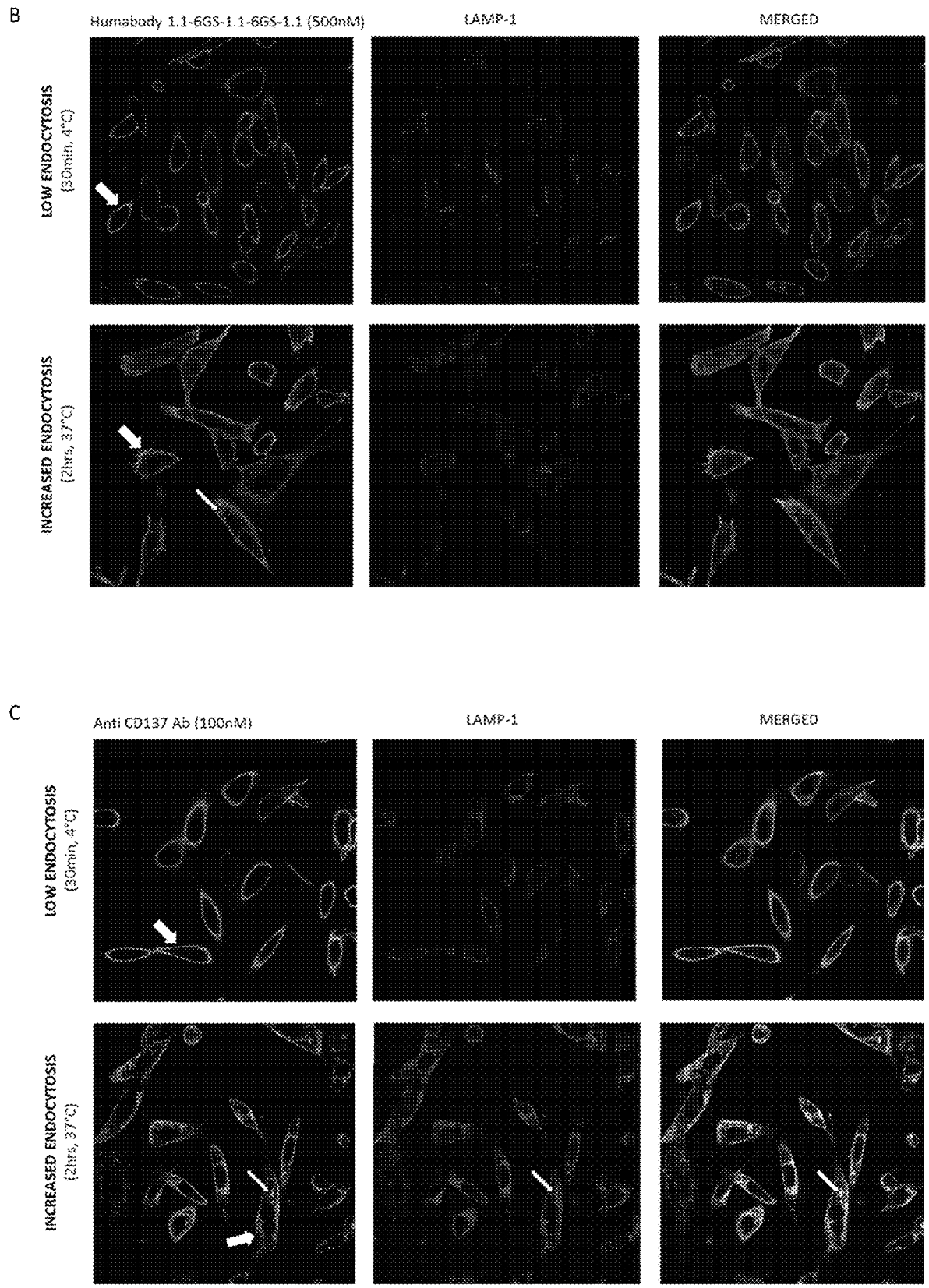

FIG. 5. CD137 mediated Internalisation (A) $V_H$ 1.1 (SEQ ID No. 4), (B) trivalent $V_H$ and (C) anti CD137 antibody were incubated with CHO CD137 cells at 4° C. to allow binding them at 37° C. for internalisation. Cells were co-stained with anti-human Ig AF488 antibody or anti His/anti Mouse Ig AF488 antibody followed by anti LAMP1/anti rabbit Ig AF488 for detection of lysosomes. Monovalent $V_H$ showed minimal internalisation remaining predominantly cell surface bound with no co-localisation to lysosomes. Multivalent monospecific $V_H$ showed increased internalisation as indicated by presence of clusters inside the cell but were not co-localised to lysosomes. CD137 antibody co-localised with the lysosome staining demonstrating this molecule is internalised.

Figure 6:
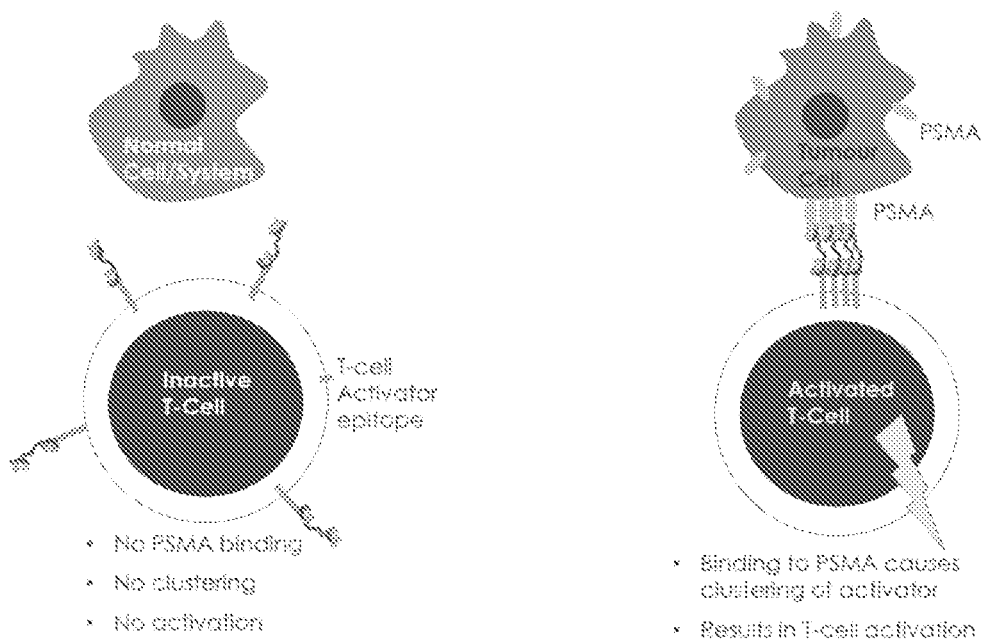

FIG. 6. Mode of action of a bispecific molecule. This figure illustrates the mode of action of a binding molecule that binds simultaneously to CD137 and a tumor specific antigen, such as PSMA, leading to tumor selective T cell agonism.

Figure 7:
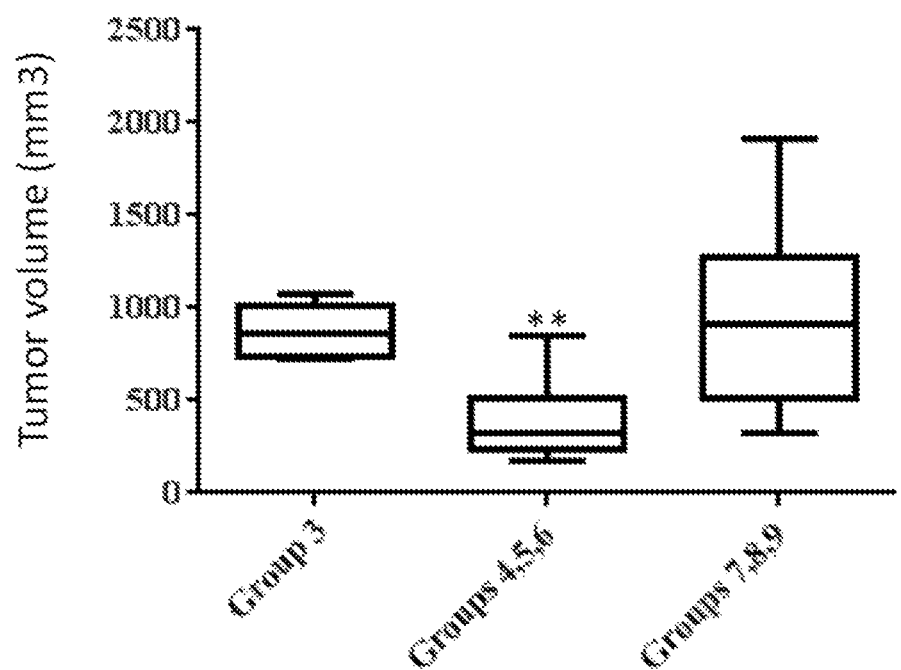

FIG. 7: In vivo experiment. Effect of Humabody® in DU145 PSMA/hu PBMC engrafted NCG Mice Pooled tumour volume data from HuPBMC engrafted NCG mice implanted with DU145 PSMA prostate cell lines. Groups 4-6 (3 huPBMC donors, n=5 mice per donor) were treated on days 33-45 with Groups 4-6 (3 huPBMC donors, each group n=5 mice per donor) were treated on days 9-32 with PBS (BIW) and on days 33-45 with 4.1-6G5-1.1-$V_H$ (MSA) (3 mg/kg, daily). Groups 7-9 (3 huPBMC donors, n=5 mice per donor) were treated with control anti CD137 antibody (3 mg/kg, BIW) on days 9-32. Group 3 (non hPBMC engrafted group, n=5 mice) were untreated. Tumor volumes were measured at day 46 post-tumor implant Statistical Significance (Mann-Whitney U test): **=P<0.01, compared to group 3.

DETAILED DESCRIPTION OF THE EMBODIMENTS

The embodiments of the invention will now be further described. In the following passages, different embodiments are described. Each aspect so defined may be combined with any other aspect or aspects unless clearly indicated to the contrary.

The T cell costimulatory receptor CD137 is an important regulator of immune responses and therefore an important target in cancer therapy. CD137 is induced on activated T cells and plays a variety of crucial roles: preventing activation-induced cell death (AICD), promoting cell cycle progression, enhancing cytotoxicity and the production of type 1 cytokines such as IL-2, IFN-γ, and TNF-α, and increasing the memory CD8+ T cells. In vivo CD137 triggering with agonistic antibodies enhances CD8+ T cell responses against tumors. CD137 mediated anti-cancer effects are based on its ability to induce activation of cytotoxic T lymphocytes (CTL), and among others, high amounts of IFN-γ. CD137/CD137L interactions are also considered positive regulators of CD8+ T cell responses against viruses such as influenza virus, lymphocytic choriomeningitis virus (LCMV), and herpes simplex virus (HSV). CD137 is involved in sustaining the T cell responses after initial T-cell activation.

Importantly, CD137 signalling requires clustering of the CD137 receptor. Such multimerisation is mediated by the interaction of the trimeric CD137 ligand with the CD137 receptor resulting in recruitment of signalling molecules such as the TRAF family of proteins. This in turn leads to kinase modulation and activation of the Nf-KB signalling pathway. The NF-κB family of transcription factors has an essential role in inflammation and innate immunity. Furthermore, NF-κB is increasingly recognized as a crucial player in many steps of cancer initiation and progression.

The inventors have surprisingly identified single variable heavy chain domain antibodies that, when targeted to CD137 in a monospecific format, that is without being linked to another moiety specific to a second antigen, bind specifically to CD137, but do not induce multimerisation of the CD137 receptor. Binding of the single variable heavy chain domain antibodies described herein in a monovalent or monospecific format does therefore not activate CD137 signalling and does not lead to CD137 signalling. CD137 signalling is activated only when the single variable heavy chain domain antibodies are provided together with another moiety specific to a second antigen, for example as a multispecific, e.g. bispecific, fusion protein wherein a single variable heavy chain domain antibody described herein is linked to a moiety that binds to a tumor specific antigen, for example a single variable heavy chain domain antibody that binds to a tumor specific antigen.

A monovalent molecule has one antigen binding site and binds to a single target. A bivalent molecule has two antigen binding sites and binds to a single target. A bispecific molecule binds to two different targets (antigens). A trispecific molecule binds to three different targets (antigens) and so forth.

When a single variable heavy chain domain antibody as described herein is provided as part of a fusion protein together with a second moiety, for example a molecule that binds specifically to a tumor specific antigen, dual binding to both the second target moiety and to CD137 results in multimerisation of the CD137 receptor and CD137 signalling. Induction of CD137 signalling thus requires dual engagement of both targets, i.e. CD137 and the tumor specific antigen. This leads to localised CD137 signalling in the tumor microenvironment. Only dual, e.g. simultaneous engagement of both targets by the multispecific molecule results in CD137 activation. Target specific activation in the vicinity of the tumor avoids systemic CD137 effects leading to uncontrollable side effects. The binding molecules effectively engage CD137 on the surface of cells through mechanisms other than binding to Fc-receptors thus also potentially avoiding unwanted liver toxicity.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Green and Sambrook et al., Molecular Cloning: A Laboratory Manual, 4th ed., Cold Spring Harbor Laboratory Press, Cold Spring Harbor, N.Y. (2012); Therapeutic Monoclonal Antibodies: From Bench to Clinic, Zhiqiang An (Editor), Wiley, (2009); and Antibody Engineering, 2nd Ed., Vols 1 and 2, Ontermann and Dubel, eds., Springer-Verlag, Heidelberg (2010).

Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients. Suitable assays to measure the properties as set out above are also described in the examples.

In particular, as explained below, the single domain antibodies described herein can be used in a multivalent or multispecific format. Thus, the single domain antibodies described herein are can be used as building blocks for multispecific molecules and the invention also relates to multifunctional binding agents comprising a single domain antibody as described herein.

The properties of the single domain antibodies of the invention as described above can be exploited in therapeutic methods and uses as well as in pharmaceutical formulations as described herein.

Single domain antibodies described herein bind specifically to wild type human CD137 (UniProt Accession No. Q07011, GenBank Accession No. NM_001561). The amino acid sequence (SEQ ID No. 786) and nucleotide sequences for wild type human CD137 are shown below (SEQ ID No. 787).

(SEQ ID No. 786)
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL (SEQ ID No. 787)
ATGGGAAACAGCTGTTACAACATAGTAGCCACTCTGTTGCTGGTCCTCAA

CTTTGAGAGGACAAGATCATTGCAGGATCCTTGTAGTAACTGCCCAGCTG

GTACATTCTGTGATAATAACAGGAATCAGATTTGCAGTCCCTGTCCTCCA

AATAGTTTCTCCAGCGCAGGTGGACAAAGGACCTGTGACATATGCAGGCA

GTGTAAAGGTGTTTTCAGGACCAGGAAGGAGTGTTCCTCCACCAGCAATG

CAGAGTGTGACTGCACTCCAGGGTTTCACTGCCTGGGGGCAGGATGCAGC

ATGTGTGAACAGGATTGTAAACAAGGTCAAGAACTGACAAAAAAAGGTTG

TAAAGACTGTTGCTTTGGGACATTTAACGATCAGAAACGTGGCATCTGTC

GACCCTGGACAAACTGTTCTTTGGATGGAAAGTCTGTGCTTGTGAATGGG

ACGAAGGAGAGGGACGTGGTCTGTGGACCATCTCCAGCCGACCTCTCTCC

GGGAGCATCCTCTGTGACCCCGCCTGCCCCTGCGAGAGAGCCAGGACACT

CTCCGCAGATCATCTCCTTCTTTCTTGCGCTGACGTCGACTGCGTTGCTC

TTCCTGCTGTTCTTCCTCACGCTCCGTTTCTCTGTTGTTAAACGGGGCAG

AAAGAAACTCCTGTATATATTCAAACACCATTTATGAGACCAGTACAAAC

TACTCAAGAGGAAGATGGCTGTAGCTGCCGATTTCCAGAAGAAGAAGAAG

GAGGATGTGAACTGTGA

Unless otherwise specified, the term CD137 as used herein refers to human CD137. CD137 is also known as "4-1 BB", "TNF receptor superfamily member 9", "TNFRS9", "induced by lymphocyte activation" and "ILA" these terms are used interchangeably and include variants, isoforms of human CD137.

The terms "CD137 binding molecule/protein/polypeptide/agent/moiety", "CD137 antigen binding molecule molecule/protein/polypeptide/agent/moiety", "anti-CD137 single domain antibody", "anti-CD137 single immunoglobulin variable domain", "anti-CD137 heavy chain only antibody" or "anti-CD137 antibody" all refer to a molecule capable of specifically binding to the human CD137 antigen.

The binding reaction may be shown by standard methods, for example with reference to a negative control test using an antibody of unrelated specificity.

A single domain antibody or binding molecule of the invention, including a multispecific, e.g. bispecific or trispecific, binding agent described herein, "which binds" or is "capable of binding" an antigen of interest, e.g. human CD137, is one that binds the antigen with sufficient affinity such that the single domain antibody is useful as a therapeutic agent in targeting a cell or tissue expressing the antigen CD137 as described herein. Binding is to the extracellular domain of CD137.

Binding molecules of the invention, including the single domain antibodies and multispecific binding agents described herein, bind specifically to human CD137. In other words, binding to the CD137 antigen is measurably different from a non-specific interaction. As demonstrated in the examples, the single domain antibodies of the invention do not cross react with mouse CD137. Preferably, the single domain antibodies of the invention bind to human CD137 and also bind to monkey (e.g., cynomolgus) CD137.

The term "specific binding" or "specifically binds to" or is "specific for" a particular polypeptide or an epitope on a particular polypeptide target as used herein can be exhibited, for example, by a molecule having a KD for the target of at least about 10-6 M, alternatively at least about 10-7 M, alternatively at least about 10-8 M, alternatively at least about 10-9 M, alternatively at least about 10-10 M, alternatively at least about 10-11 M, alternatively at least about 10-12 M, or lower. In one embodiment, the term "specific binding" refers to binding where a molecule binds to a particular polypeptide or epitope on a particular polypeptide without substantially binding to any other polypeptide or polypeptide epitope.

The term "antibody" as used herein broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule.

In a full-length antibody, each heavy chain is comprised of a heavy chain variable region or domain (abbreviated herein as HCVR) and a heavy chain constant region. The heavy chain constant region is comprised of three domains, $C_H1$, $C_H2$ and $C_H3$. Each light chain is comprised of a light chain variable region or domain (abbreviated herein as LCVR) and a light chain constant region. The light chain constant region is comprised of one domain, $C_L$.

The heavy chain and light chain variable regions can be further subdivided into regions of hypervariability, termed complementarity determining regions (CDR), interspersed with regions that are more conserved, termed framework regions (FR). Each heavy chain and light chain variable region is composed of three CDRs and four FRs, arranged from amino-terminus to carboxy-terminus in the following order: FR1, CDR1, FR2, CDR2, FR3, CDR3, FR4.

Immunoglobulin molecules can be of any type (e.g., IgG, IgE, IgM, IgD, IgA and IgY), class (e.g., IgG 1, IgG2, IgG 3, IgG4, IgAl and IgA2) or subclass.

The term "CDR" refers to the complementarity-determining region within antibody variable sequences. There are three CDRs in each of the variable regions of the heavy chain and the light chain, which are designated CDR1, CDR2 and CDR3, for each of the variable regions. The term "CDR set" refers to a group of three CDRs that occur in a single variable region capable of binding the antigen. The exact boundaries of these CDRs can be defined differently according to different systems known in the art.

The Kabat Complementarity Determining Regions (CDRs) are based on sequence variability and are the most commonly used (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242). Chothia refers instead to the location of the structural loops (Chothia and Lesk J. Mol. Biol. 196:901-917 (1987)). The Kabat numbering system is generally used when referring to a residue in the variable domain (approximately residues 1-107 of the light chain and residues 1-113 of the heavy chain). Another system is the ImMunoGeneTics (IMGT) numbering scheme. The IMGT numbering scheme is described in Lefranc et al., Dev. Comp. Immunol., 29, 185-203 (2005).

The system described by Kabat is used herein. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion.

A chimeric antibody is a recombinant protein that contains the variable domains including the complementarity determining regions (CDRs) of an antibody derived from one species, preferably a rodent antibody, while the constant domains of the antibody molecule are derived from those of a human antibody.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

The term "antigen binding site" refers to the part of the antibody or antibody fragment that comprises the area that specifically binds to an antigen. An antigen binding site may be provided by one or more antibody variable domains. An antigen binding site is typically comprised within the associated $V_H$ and $V_L$ of an antibody or antibody fragment.

An antibody fragment is a portion of an antibody, for example a F(ab')2, Fab, Fv, scFv, heavy chain, light chain, variable heavy ($V_H$), variable light ($V_L$) chain domain and the like. Functional fragments of a full length antibody retain the target specificity of a full antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs.

scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv).

The smallest antigen binding fragment is the single variable fragment, namely the variable heavy ($V_H$) or variable light ($V_L$) chain domain. $V_H$ and $V_L$ domains respectively are capable of binding to an antigen. Binding to a light chain/heavy chain partner respectively or indeed the presence of other parts of the full antibody is not required for target binding. The antigen-binding entity of an antibody, reduced in size to one single domain (corresponding to the $V_H$ or $V_L$ domain), is generally referred to as a "single domain antibody" or "immunoglobulin single variable domain". A single domain antibody (~12 to 15 kDa) has thus either the $V_H$ or $V_L$ domain. Single domain antibodies derived from camelid heavy chain only antibodies that are naturally devoid of light chains as well as single domain antibodies that have a human heavy chain domain have been described (Muyldermans 2001, Holliger 2005). Antigen binding single $V_H$ domains have also been identified from, for example, a library of murine $V_H$ genes amplified from genomic DNA from the spleens of immunized mice and expressed in *E. coli* (Ward et al., 1989, Nature 341: 544-546). Ward et al. named the isolated single $V_H$ domains "dAbs," for "domain antibodies." The term "dAb" or "sdAb" (for single domain antibody) generally refers to a single immunoglobulin variable domain ($V_H$, $V_{HH}$ or $V_L$) polypeptide that specifically binds antigen. For use in therapy, human single domain antibodies are preferred over camelid derived $V_{HH}$, primarily because they are not as likely to provoke an immune response when administered to a patient.

The terms "single domain antibody", "single variable domain antibody", "single variable heavy chain domain antibod", "single $V_H$ domain antibody", "immunoglobulin single variable domain (ISV)" or "immunoglobulin single variable domain antibody" are all well known in the art and describe the single variable fragment of an antibody that binds to a target antigen. These terms are used interchangeably herein. These terms, e.g. "single heavy chain domain antibody", "single variable heavy chain domain antibody, "immunoglobulin single heavy chain variable domain", "single $V_H$ single domain antibody", "$V_H$ single domain antibody", "single heavy chain domain", "single variable heavy chain domain", "single $V_H$ single domain", "$V_H$ single domain" describe the single heavy chain variable fragment of an antibody which retains binding specificity to the antigen in the absence of light chain or other antibody fragments. A single variable "heavy chain domain antibody, single variable heavy chain domain, immunoglobulin single heavy chain variable domain (ISV), human $V_H$ single domain" etc as used herein therefore does not comprise any other parts of a full antibody, but the antigen binding $V_H$ domain only; e.g. it only includes the $V_H$ domain and does not comprise constant heavy chain domains and does not comprise a light chain. A single variable heavy chain domain antibody is capable of binding to an antigen in the absence of light chain.

In one aspect, the invention relates to an isolated single variable heavy chain domain antibody that binds to human CD137.

As explained below, the embodiments relate to single variable heavy chain domain antibodies/immunoglobulin single variable heavy chain domains which bind a CD137 antigen. Thus, the single variable heavy chain domain antibody is capable of binding to CD137 in the absence of light chain. Human single variable heavy chain domain antibodies ("$V_H$ domain antibody") are particularly preferred. Such binding molecules are also termed Humabody® herein. Humabody® is a registered trademark of Crescendo Biologics Ltd.

Thus, in some embodiments, the isolated binding agents/molecules comprise or consist of at least one single domain antibody wherein said domain is a human variable heavy chain domain; they are devoid of $V_L$ domains and $V_H$ constant domains and bind to the target antigen. In other embodiments, the isolated binding agents/molecules comprise or consist of two or more single domain antibodies.

The term "isolated" refers to a moiety that is isolated form its natural environment. For example, the term "isolated" refers to a single domain antibody that is substantially free of other single domain antibodies, antibodies or antibody fragments. Moreover, an isolated single domain antibody may be substantially free of other cellular material and/or chemicals.

Each $V_H$ domain antibody comprises three CDRs and four FRs, arranged from amino-terminus to carboxy-terminus in the following order: FR1-CDR1-FR2-CDR2-FR3-CDR3-FR4. Thus, in one embodiment of the invention, the domain is a human variable heavy chain ($V_H$) domain with the following formula FR1-CDR1-FR2-CDR2-FR3-CDR3-FR4.

Modifications to the C or N-terminal $V_H$ framework sequence may be made to the single domain antibodies of the invention to improve their properties. For example, the $V_H$ domain may comprise C or N-terminal extensions. C-terminal extensions can be added to the C-terminal end of a $V_H$ domain which terminates with the residues VTVSS (SEQ ID No. 788). For example, C terminal extensions may comprise neutral, nonpolar amino acids, such as A, L, V, P, M, G, I, F or W or neutral polar amino acids, such as S or T. C terminal extensions may also be selected from peptide linkers or tags, e.g. (G4S)n linkers wherein n=1 to 15, e.g. one of SEQ ID NO. 790-797.

In one embodiment, the single domain antibodies of the invention comprise C-terminal extensions of from 1 to 50 residues, for example 1 to 10, e.g. 1, 2, 3, 4, 5, 6, 7, 8, 9 or 10, 1-20, 1-30 or 1-40 additional amino acids. In one embodiment, the single domain antibodies of the invention comprise additional amino acids of the human $C_H1$ domain thus that the C terminal end extends into the $C_H1$ domain, for example by 1 to 5 amino acids.

Additional C or N-terminal residues can be peptide linkers that are for example used to conjugate the single domain antibodies of the invention to another moiety, or tags that aid the detection of the molecule. Such tags are well known in the art and include for, example linker His tags, e.g., hexa-His (HHHHHH, SEQ ID No. 789) or myc tags.

As used herein, the term "homology" or "identity" generally refers to the percentage of amino acid residues in a sequence that are identical with the residues of the reference polypeptide with which it is compared, after aligning the sequences and in some embodiments after introducing gaps, if necessary, to achieve the maximum percent homology, and not considering any conservative substitutions as part of the sequence identity. Thus, the percent homology between two amino acid sequences is equivalent to the percent identity between the two sequences. Neither N- or C-terminal extensions, tags or insertions shall be construed as reducing identity or homology. Methods and computer programs for the alignment are well known. The percent identity between two amino acid sequences can be determined using well known mathematical algorithms.

According to some embodiments of the various aspects of the invention, the variable domain of the single domain antibodies as described herein is a $V_H$ domain, a $V_{HH}$ domain, a humanised $V_{HH}$ domain, a camelized $V_H$ domain or a sequence modified $V_H$ or $V_{HH}$ domain. In one embodiment, the variable domain of the single domain antibodies as described herein is a human variable domain ($V_H$). The term single $V_H$ domain antibody as used herein designates a single human variable heavy chain domain antibody.

As used herein, a human $V_H$ domain includes a fully human or substantially fully human $V_H$ domain. As used herein, the term human $V_H$ domain also includes $V_H$ domains that are isolated from heavy chain only antibodies made by transgenic mice expressing fully human immunoglobulin heavy chain loci, in particular in response to an immunisation with an antigen of interest, for example as described in WO2016/062990 and in the examples below. In one embodiment, a human $V_H$ domain can also include a $V_H$ domain that is derived from or based on a human $V_H$ domain amino acid or produced from a human $V_H$ germline nucleic acid sequence. Thus, the term human $V_H$ domain includes variable heavy chain regions derived from or encoded by human germline immunoglobulin sequences and for example obtained from heavy chain only antibodies produced in transgenic mice expressing fully human $V_H$ genes. In some embodiments, a substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain, i.e. a $V_H$ domain wherein one or more amino acid residue has been modified, for example to remove sequence liabilities. For example, a substantially human $V_H$ domain the $V_H$ domain may include up to 10, for example 1, 2, 3, 4, 5, 6, 7, 8, 9 or 10 or up to 20 amino acid modifications compared to a germline human sequence.

However, the term "human $V_H$ domain" or "substantially human $V_H$ domain", as used herein, is not intended to include antibodies in which CDR sequences derived from the germline of another mammalian species, such as a mouse, have been grafted onto human framework sequences. In one embodiment, the term "human $V_H$ domain", as used herein, is also not intended to include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

In some embodiments, the single domain antibody is a single domain antibody wherein the domain is a human variable heavy chain ($V_H$) domain. Thus, in preferred embodiments, the invention provides isolated single domain antibodies that bind human CD137, wherein the domain is a variable heavy chain domain, preferably a $V_H$ domain and wherein said single domain antibodies bind to human CD137.

In one aspect, the invention relates to a single variable heavy chain domain antibody (i.e. a monovalent binding molecule, that is a molecule that has one binding entity only), wherein the single domain antibody exhibits one or more of the following properties:
(a) binds to human CD137 with a KD as measured in the examples;
(b) binds to cells expressing CD137, but does not bind to cells that do not express CD137. This can be measured as shown in example 6;
(c) shows minimal cell internalisation. This can be measured as shown in the examples;
(d) inhibits the interaction between CD137 ligand and CD137 expressed on the surface of cells. This can be measured as shown in example 6;
(e) does not activate CD137 signalling in T cells. This can be measured as shown in the examples;
(f) does not stimulate IL-2 production from CD8+ cells. This can be measured as shown in example 9;
(g) does not bind to mouse CD137;
(h) provides good stability as shown in the examples;
(i) does not increase reporter gene activity and thus does not have agonistic CD137 activity. This can be measured as shown in example 9;
(j) binds to cynomolgus CD137 and/or
(k) inhibits tumor growth in vivo when linked to a $V_H$ that binds to PSMA. This can for example be measured as in the examples, e.g. in example 10.

In one embodiment the single variable heavy chain domain antibody has more than one feature selected from a) to jk, for example a combination of 2, 3, 4, 5, 6, 7, 8, 9, 10 or 11 features. In one embodiment, the single variable heavy chain domain antibody inhibits the interaction between CD137 ligand and CD137 expressed on the surface of cells. In one embodiment, the single variable heavy chain domain antibody inhibits the interaction between CD137 ligand and CD137 expressed on the surface of cells and also shows one or more of the features listed in a, b, c, e to k.

Exemplary Sequence Features

In one aspect, the single variable heavy chain domain antibody comprises a CDR1, CDR2 and/or CDR3 as shown for one of the single domain antibodies as shown in Table 1. In one aspect, the single variable heavy chain domain antibody comprises a set of CDR1, CDR2 or CDR3 selected form the set of CDRs as shown for one of the single domain antibodies as shown Table 1. In one embodiment, the CDR1, CDR2, CDR3 with at least 40%, at least 75% or at least 80% homology to one of the CDRs in Table 1. In one aspect, the single variable heavy chain domain antibody comprises a CDR1 comprising SEQ ID NO. 1 or a sequence with at least 40% at least 75% or at least 80% homology thereto, a CDR2 comprising SEQ ID NO. 2 or a sequence with at least 40%, at least 75%, at least 80% or at least 90% homology thereto and a CDR3 comprising SEQ ID NO. 3 or a sequence with at least 40%, at least 75%, at least 80% or at least 90% homology, or a CDR1 comprising SEQ ID NO. 5 or a sequence with at least 40%, at least 75%, at least 80% or at least 90% homology thereto, a CDR2 comprising SEQ ID NO. 6 or a sequence with at least 40% homology thereto and a CDR3 comprising SEQ ID NO. 7 and so forth. In one embodiment, the single variable heavy chain domain antibody comprises a CDR1, CDR2 or CDR3 as shown in SEQ IDs 309, 310 and 311 or sequences with at least 75% homology thereto. In one embodiment, the single variable heavy chain domain antibody comprises a CDR1, CDR2 or CDR3 as shown in SEQ IDs 873, 874 and 875 or sequences with at least 40%, at least 75%, at least 80% or at least 90% homology thereto. The CDRs are defined according to Kabat.

Sequence homology as defined above and generally as defined herein can be at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% for example at least 90%, 91%, 92%, 93%, 94%, 95%, 96%, 97%, 98% or 99% sequence homology.

In one embodiment, the single variable heavy chain domain antibody comprises human framework regions.

In one aspect, the single variable heavy chain domain antibody comprises or consists of a full length sequence as shown in Table 1 or a sequence with at least 50%, 60%, 70%, 80%, 90% homology thereto. For example, the single variable heavy chain domain antibody comprising a full length sequence that comprises or consists of a sequence selected from the sequences listed in Table 1, i.e. SEQ ID NO. 4, 8, 12, 16, 20 and so forth or a sequence with at least 50% homology thereto. Sequence homology can be 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% for example at least 90%, 91%, 92%, 93%, 94%, 95%, 96%, 97%, 98% or 99% sequence homology. In one embodiment, the single variable heavy chain domain antibody comprises CDR1, 2, and 3 as shown for $V_H$ single domain antibodies 1.1. to 1.89 or 1.90 to 1.106 or comprises or consists of a full length sequence as shown for $V_H$ single domain antibodies 1.90 to 1.106 (i.e. SEQ ID NOs. 364, 368, 372, 376, 380, 384, 388, 392, 396, 400, 404, 408, 412, 416, 420 or 424). In one embodiment, the single variable heavy chain domain antibody is selected from $V_H$ 1.78 or a variant thereof. In one embodiment, the single variable heavy chain domain antibody comprises CDR1, 2, and 3 as shown for a $V_H$ single domain antibody selected from $V_H$ 1.107 to 1.114 or a sequence with at least 75% homology thereto (e.g. 90% or 95%). In one embodiment, the single variable heavy chain domain antibody is selected from $V_H$ 1.107 to 1.114 as shown in table 1, that is SEQ ID No. 852, 856, 860, 864, 868, 872, 876 or 880 or a sequence with at least 75% homology thereto (e.g. 90% or 95%). In one embodiment, the single variable heavy chain domain antibody is selected from $V_H$ 1.113 as shown in table 1 or a sequence with at least 75%, 80%, 90%, 91%, 92%, 93%, 94%, 95%, 96%, 97%, 98% or 99% sequence homology thereto.

TABLE 1

Full length sequences and CDR sequences of $V_H$ single domain antibodies (Family 1)

| Name | CDR1 | CDR2 | CDR3 | Full Length |
| --- | --- | --- | --- | --- |
| 1.1 | SEQ ID NO: 1 SHWMT | SEQ ID NO: 2 HIKEDGSEKY YEDSVEG | SEQ ID NO: 3 GGDGYSDSHF GVDV | SEQ ID NO: 4 EVQLVESGGGLVQPGGSLRLSCAASGFTFSSHWMTWFRQAPGKGL EWVAHIKEDGSEKYYEDSVEGRFTVSRDNAKNSVYLQMNSLRAEDT AVYYCARGGDGYSDSHFGVDVWGQGTTVTVSS |
| 1.2 | SEQ ID NO: 5 SYWMT | SEQ ID NO: 6 HIKEDGSEKY YVDSVEG | SEQ ID NO: 7 GGDGYSDSHY GVDV | SEQ ID NO: 8 EVQLVESGGGLVQPGGSLRLSCAASGFTFSSYWMTWFRQAPGKGL EWVAHIKEDGSEKYYVDSVEGRFTISRDNANNSLYLQMNSLRAEDT AVYYCARGGDGYSDSHYGVDVWGQGTTVTVSS |
| 1.3 | SEQ ID NO: 9 SYWMT | SEQ ID NO: 10 NINQDGSEK YYVDSVEG | SEQ ID NO: 11 GGLGYGDSHY GMDV | SEQ ID NO: 12 EVQLVESGGGLVQPGGSLRLSCAASGFTFSSYWMTWFRQAPGRGL EWVANINQDGSEKYYVDSVEGRFTVSRDNAKNSLYLQMNSLRAED TAVYYCARGGLGYGDSHYGMDVWGQGTTVTVSS |
| 1.4 | SEQ ID NO: 13 NYWMT | SEQ ID NO: 14 NINQDGSEK YYVDSVEG | SEQ ID NO: 15 GGLGYGDSHY GMDV | SEQ ID NO: 16 EVQLVESGGGLVQPGGSLRLSCAASGFTFSNYWMTWFRQAPGGGL EWVANINQDGSEKYYVDSVEGRFTVSRDNAKNSLYLQMNSLRAED TAVYYCARGGLGYGDSHYGMDVWGQGTTVTVSS |
| 1.5 | SEQ ID NO: 17 NYWMI | SEQ ID NO: 18 NINQDGSEK YYVDSVEG | SEQ ID NO: 19 GGDGYSGSHH GTDV | SEQ ID NO: 20 EVQLVESGGGLVQPGGSLRLSCAASGFTFSNYWMIWFRQAPGKGL EWVANINQDGSEKYYVDSVEGRFTISRDNAKNSLYLQMNSLRAEDT AVYYCARGGDGYSGSHHGTDVWGQGTTVTVSS |
| 1.6 | SEQ ID NO: 21 SYWMS | SEQ ID NO: 22 NIKQDGSEKY YVDSVKG | SEQ ID NO: 23 GGEGYSTSHYG MDV | SEQ ID NO: 24 EVQLVESGGGLVQPGGSLRLSCAASGFTFSSYWMSWVRQAPGKGLE WVANIKQDGSEKYYVDSVKGRFTISRDNAKNSLYLQMNSLRAEDTAV YYCARGGEGYSTSHYGMDVWGQGTTVTVSS |
| 1.7 | SEQ ID NO: 25 SYWML | SEQ ID NO: 26 NINQDGSEK YYVDSVKG | SEQ ID NO: 27 GGDGYSDSHF GTDV | SEQ ID NO: 28 EVQLVESGGGLVQPGGSLRLSCGASGFTFSSYWMLWFRQAPGKGL EWVANINQDGSEKYYVDSVKGRFTISRDNAKNSLYLQMNTLRAEDT TAIYYCARGGDGYSDSHFGTDVWGQGTTVTVSS |
| 1.8 | SEQ ID NO: 29 SYWMF | SEQ ID NO: 30 NINQDGSEK YYVDSVEG | SEQ ID NO: 31 GGDGYSDSHY GTDV | SEQ ID NO: 32 EVQLVESGGGLVQPGGSLRLSCGASGFTFSSYWMFWFRQAPGEGL EWVANINQDGSEKYYVDSVEGRFTISRDNAKNSLYLQMNSLRAEDT AIYYCARGGDGYSDSHYGTDVWGQGTTVTVSS |
| 1.9 | SEQ ID NO: 33 NYWMT | SEQ ID NO: 34 NINQDGSEK YYVDSVEG | SEQ ID NO: 35 GGLGYGDSHY GMDV | SEQ ID NO: 36 EVQLVESGGGLVQPGGSLRLSCAASGFTFSNYWMTWFRQAPGGG LEWVANINQDGSEKYYVDSVEGRFTVSRDNAKNSLDLQMNSLRAE DTAVYYCARGGLGYGDSHYGMDVWGQGTTVTVSS |
| 1.10 | SEQ ID NO: 37 DYWMN | SEQ ID NO: 38 NIKEDGSEKY YVDSVEG | SEQ ID NO: 39 GGAGYSMSHY GMDV | SEQ ID NO: 40 EVQLVESGGGLVQPGGSLRLSCAASGFTFSDYWMNWARQAPGKG LEWVANIKEDGSEKYYVDSVEGRFTISRDNAKNSTYLQMNSLRVEDT AVYYCARGGAGYSMSHYGMDVWGQGTTVTVSS |

TABLE 1-continued

Full length sequences and CDR sequences of V$_H$ single domain antibodies (Family 1)

| Name | CDR1 | CDR2 | CDR3 | Full Length |
|------|------|------|------|-------------|
| 1.11 | SEQ ID NO: 41 DYWMN | SEQ ID NO: 42 NIKEDGSEKY YVDSVEG | SEQ ID NO: 43 GGAGYSMSHY GMDV | SEQ ID NO: 44 EVQLVESGGGLVQPGGSLRLSCEASGFTFSDYWMNWARQAPGKG LEWVANIKEDGSEKYYVDSVEGRFTISRDNAKNSTYLQMNSLRAEDT AVYYCARGGAGYSMSHYGMDVWGQGTTVTVSS |
| 1.12 | SEQ ID NO: 45 SYWML | SEQ ID NO: 46 NINQDGSEK YYVDSVKG | SEQ ID NO: 47 GGDGYSNSHF GTDV | SEQ ID NO: 48 EVQLVESGGGLVQPGGSLRLSCGASGFTFSSYWMLWFRQAPGKGL EWVANINQDGSEKYYVDSVKGRFTISRDNAKNSLYLQMNTLRAEDT AIYYCARGGDGYSNSHFGTDVWGQGTTVTVSS |
| 1.13 | SEQ ID NO: 49 SYWMF | SEQ ID NO: 50 NINQDGSEK YYVDSVEG | SEQ ID NO: 51 GGDGYSDSHY GTDV | SEQ ID NO: 52 EVQLVESGGGLVKPGGSLRLSCGASGFTFSSYWMFWFRQAPGEGL EWVANINQDGSEKYYVDSVEGRFTISRDNAKNSLYLQMNSLRAEDT AIYYCARGGDGYSDSHYGTDVWGQGTTVTVSS |
| 1.14 | SEQ ID NO: 53 NYWMN | SEQ ID NO: 54 NIKEDGSENY YVDSVKG | SEQ ID NO: 55 GGEGYSTSHYG MDV | SEQ ID NO: 56 EVQLVESGGGLVQPGGSLRLSCAASGFTFSNYWMNWVRQAPGKG LEWVANIKEDGSENYYVDSVKGRFTISRDNAKNSLYLQMNSLRAED TAVYYCARGGEGYSTSHYGMDVWGQGTTVTVSS |
| 1.15 | SEQ ID NO: 57 TYWML | SEQ ID NO: 58 NINQDGSEK YYVDSVKG | SEQ ID NO: 59 GGDGYSDSHF GTDV | SEQ ID NO: 60 EVQLVESGGGLVQPGGSLRLSCGASGFTFSTYWMLWFRQAPGKGL EWVANINQDGSEKYYVDSVKGRFTISRDNAKNSLSLQMNSLRAEDT ATYYCARGGDGYSDSHFGTDVWGQGTTVTVSS |
| 1.16 | SEQ ID NO: 61 NYWMM | SEQ ID NO: 62 NINQDGSEK YYVDSVEG | SEQ ID NO: 63 GGDGYSSSHY GTDV | SEQ ID NO: 64 EVQLVESGGGLVQPGGSLRLSCVASGFTFSNYWMMWFRQAPGKG LEWVANINQDGSEKYFVDSVEGRFTISRDNAKNSLYLQMNSLRAED TAVYYCARGGDGYSSSHYGTDVWGQGTTVTVSS |
| 1.17 | SEQ ID NO: 65 SYWMN | SEQ ID NO: 66 NIKEDGSEKY YVDSVKG | SEQ ID NO: 67 GGDSYGYRDY GMDV | SEQ ID NO: 68 EVQLVESGGGLVQPGGSLRLSCAASGFTFSSYWMNWVRQAPGKG LEWVANIKEDGSEKYYVDSVEGRFTISRDNAKNSLYLQMNSLRAEDT AVYYCARGGDSYGYRDYGMDVWGQGTTVTVSS |
| 1.18 | SEQ ID NO: 69 THWMN | SEQ ID NO: 70 NINQDGSEK YYVDSVEG | SEQ ID NO: 71 GGVGYGDSHF GMDV | SEQ ID NO: 72 EVQLVESGGGLVQPGGSLRLSCAASGFTFSTHWMNWARQAPGKE LEWVANINQDGSEKYYVDSVEGRFTISRDNANNSLYLQMNSLRAED TAVYYCARGGVGYGDSHFGMDVWGLGTTVTVSS |
| 1.19 | SEQ ID NO: 73 SYWMI | SEQ ID NO: 74 NINQDGSEK YYVDSVKG | SEQ ID NO: 75 GGDDYSNSHY GMDV | SEQ ID NO: 76 EVQLVESGGGLVQPGGSLRLSCAASGFTFSSYWMIWVRQAPGKGL EWVANINQDGSEKYYVDSVKGRFTISRDNAKNSLYLQMNSLRAEDT AVYYCARGGDDYSNSHYGMDVSGQGTTVTVSS |
| 1.20 | SEQ ID NO: 77 SYWMN | SEQ ID NO: 78 NINQDGSEK YYVDSVQG | SEQ ID NO: 79 GGFGYGDSHY GMDV | SEQ ID NO: 80 EVQLVESGGGLVQPGGSLRLSCAASGFTFSSYWMNWVRQAPGKG LEWVANINQDGSEKYYVDSVQGRFTISRDNANNSLYLQMNSLRAE DTAVYYCARGGFGYGDSHYGMDVWGQGTTVTVSS |
| 1.21 | SEQ ID NO: 81 SYWMF | SEQ ID NO: 82 NVNQDGSEK YYVDSVEG | SEQ ID NO: 83 GGEGYSDSHY GTDV | SEQ ID NO: 84 EVQLVESGGGLVQPGGSLRLSCGASGFTFSSYWMFWFRQAPGKEL EWVANVNQDGSEKYYVDSVEGRFTISRDNAKNSLYLQMNSLRAED TAIYYCARGGEYSDSHYGTDVWGQGTTVTVSS |
| 1.22 | SEQ ID NO: 85 NYWMN | SEQ ID NO: 86 NIKEDGSEKY YVDSVEG | SEQ ID NO: 87 GGEGYGDSHY GMDV | SEQ ID NO: 88 QVQLVESGGGLVQPGGSLRLSCAASGFTFSNYWMNWVRQAPGKG LEWVANIKEDGSEKYYVDSVEGRFTISRDNARNSLYLQMNSLRAEDT AVYYCARGGEGYGDSHYGMDVSGQGTTVTVSS |
| 1.23 | SEQ ID NO: 89 SYWMN | SEQ ID NO: 90 NIKQDGSEKY YVDSVKG | SEQ ID NO: 91 GGEGYGDDHY GMDV | SEQ ID NO: 92 QVQLVESGGGLVQPGGSLRLSCAASGFTFSSYWMNWVRQAPGKG LEWVANIKQDGSEKYYVDSVKGRFTISRDNAKNSLYLQMNSLTAED TAVYYCARGGEGYGDDHYGMDVWGQGTTVTVSS |
| 1.24 | SEQ ID NO: 93 SYWMS | SEQ ID NO: 94 NIKQDGSEKY YVDSVKG | SEQ ID NO: 95 GGEGYGDYHY GLDV | SEQ ID NO: 96 QVQLVESGGGLVQPGGSLRLSCAASGFTFSSYWMSWVRQAPGKG LEWVANIKQDGSEKYYVDSVKGRFTISRDNAKNSLYLQMNSLRAED YTAVYYCARGGEGYGDYHYGLDVSGQGTTVTVSS |
| 1.25 | SEQ ID NO: 97 SYWMN | SEQ ID NO: 98 NIKQDGSEKY YVDSVKG | SEQ ID NO: 99 GGDSYGYRDY GMDV | SEQ ID NO: 100 EVQLVESGGGLVQPGGSLRLSCAASGFTFSSYWMNWVRQAPGKG LEWVANIKQDGSEKYYVDSVKGRFTISRDNAKNSLYLQMNSLRAED TAVYYCARGGDSYGYRDYGMDVWGQGTTVTVSS |

TABLE 1-continued

Full length sequences and CDR sequences of V_H single domain antibodies (Family 1)

| Name | CDR1 | CDR2 | CDR3 | Full Length |
|---|---|---|---|---|
| 1.26 | SEQ ID NO: 101 THWMN | SEQ ID NO: 102 NINQDGSEKYYVDSVEG | SEQ ID NO: 103 GGVGYGDSHFGMDV | SEQ ID NO: 104 EVQLVESGGGLVQPGGSLRLSCVASGFTFSTHWMNWARQAPGKELEWVANINQDGSEKYYVDSVEGRFTISRDNANNSLYLQMNSLRAEDTAVYYCARGGVGYGDSHFGMDVWGLGTTVTVSS |
| 1.27 | SEQ ID NO: 105 SYWML | SEQ ID NO: 106 NINQDGSEKYYVDSVEG | SEQ ID NO: 107 GGEGYSDSHHGTDV | SEQ ID NO: 108 EVQLVESGGGLVQPGGSLRLSCGASGFTFSSYWMLWFRQAPGEGLEWVANINQDGSEKYYVDSVEGRLTISRDNAKNALYLQMNSLRAEDTAIYYCARGGEGYSDSHHGTDVWGQGTTVTVSS |
| 1.28 | SEQ ID NO: 109 NYWMN | SEQ ID NO: 110 NIKQDGSEKYYVDSVKG | SEQ ID NO: 111 GGDNYAYRDFGMDV | SEQ ID NO: 112 EVQLVESGGGLVQPGGSLRLSCAASGFTFSNYWMNWVRQAPGKGLEWVANIKQDGSEKYYVDSVKGRFTISRDNAKNSLYLQMNSLRAEDTAVYYCARGGDNYAYRDFGMDVWGQGTTVTVSS |
| 1.29 | SEQ ID NO: 113 NYWMF | SEQ ID NO: 114 NVNQDGSEKYYVDSVEG | SEQ ID NO: 115 GGEGYSDSHYGTDV | SEQ ID NO: 116 EVQLVESGGGLVQPGGSLRLSCGASGFTFSNYWMFWFRQAPGKELEWVANVNQDGSEKYYVDSVEGRFTISRDNAKNSLYLQMNSLRAEDTAIYYCARGGEGYSDSHYGTDVWGQGTTVTVSS |
| 1.30 | SEQ ID NO: 117 SYWMN | SEQ ID NO: 118 NINQDGSEKYYVDSVKG | SEQ ID NO: 119 GGEEYGSSHYGMDV | SEQ ID NO: 120 EVQLVESGGGLVQPGGSLRLSCAASGFTFSSYWMNWVRQAPGKGLEWVANINQDGSEKYYVDSVKGRFTISRDNAKNSLYLQMNSLRAEDTAVYYCARGGEEYGSSHYGMDVWGLGTTVTVSS |
| 1.31 | SEQ ID NO: 121 SYWMN | SEQ ID NO: 122 NINQDGSEKYYVDSVKG | SEQ ID NO: 123 GGDSYGYRDYGMDV | SEQ ID NO: 124 EVQLVESGGGLVQPGGSLRLSCAASGFTFSSYWMNWVRQAPGKGLEWVANINQDGSEKYYVDSVKGRFTISRDNAKNSLYLQMNSLRAEDTAVYYCARGGDSYGYRDYGMDVWGQGTTVTVSS |
| 1.32 | SEQ ID NO: 125 SYWMN | SEQ ID NO: 126 NINQNGSEKYYVDSVEG | SEQ ID NO: 127 GGFGYGDSHYGMDV | SEQ ID NO: 128 EVQLVESGGGLVQPGGSLRLSCAASGFTFSSYWMNWVRQTPGKGLEWVANINQNGSEKYYVDSVEGRFNISRDNAKNSLYLQMSSLRAEDTAVYYCARGGFGYGDSHYGMDVWGQGTTVTVSS |
| 1.33 | SEQ ID NO: 129 NYWMT | SEQ ID NO: 130 NINQDESEEYYVDSVKG | SEQ ID NO: 131 GGDGYSDSHYGTDV | SEQ ID NO: 132 EVQLVESGGGLVQAGGSLRLSCVASGFTFSNYWMTWFRQAPGKGLEWVANINQDESEEYYVDSVKGRFTISRDNAKNSLFLQMNSLRAEDTAIYYCARGGDGYSDSHYGTDVWGQGTTVTVSS |
| 1.34 | SEQ ID NO: 133 NYWMN | SEQ ID NO: 134 NIKEDGSENYYVDSVKG | SEQ ID NO: 135 GGEGYSTSHYGMDV | SEQ ID NO: 136 QVQLQESGGGLVQPGGSLRLSCTASGFTFSNYWMNWVRQAPGKGLEWVANIKEDGSENYYVDSVKGRFTISRDNAKNSLYLQMNSLRAEDTAVYYCARGGEGYSTSHYGMDVWGQGTTVTVSS |
| 1.35 | SEQ ID NO: 137 NYWMN | SEQ ID NO: 138 NIKQDGSEKYYVDSVEG | SEQ ID NO: 139 GGEGYGESHYGMDV | SEQ ID NO: 140 QVQLVESGGGLVQPGGSLRLSCAASGFTFSNYWMNWVRQAPGKGLEWVANIKQDGSEKYYVDSVEGRFTISRDNAKNSLYLQMDSLRAEDTAVYYCARGGEGYGESHYGMDVSGQGTTVTVSS |
| 1.36 | SEQ ID NO: 141 TYWMN | SEQ ID NO: 142 NIKQDGSEKYYVDSVKG | SEQ ID NO: 143 GGDSYGYRDYGMDV | SEQ ID NO: 144 EVQLVESGGGLVQPGGSLRLSCAASGFTFSTYWMNWVRQAPGKGLEWVANIKQDGSEKYYVDSVKGRFTISRDNAKNSLYLQMNSLRAEDTAVYYCARGGDSYGYRDYGMDVWGQGTTVTVSS |
| 1.37 | SEQ ID NO: 145 YYWMI | SEQ ID NO: 146 NINQDGSEKYYVDSVKG | SEQ ID NO: 147 GGDGYSNSHFGMDV | SEQ ID NO: 148 EVQLVESGGGLVQPGGSLRLSCAASGFTFSYYWMIWFRQAPGEELEWVANINQDGSEKYYVDSVKGRFIISRDNATNSLFLQMNSLRAEDTAVYYCARGGDGYSNSHFGMDVWGQGTTVTVSS |
| 1.38 | SEQ ID NO: 149 NYWMI | SEQ ID NO: 150 NINQDGSEKYYVDSVKG | SEQ ID NO: 151 GGEGYSDSHYGTDV | SEQ ID NO: 152 EVQLVESGGGLVQPGGSLRLSCAASGFTFSNYWMIWYRQAPGEELEWVANINQDGSEKYYVDSVKGRFTISRDNAKNSLYLQMNSLRAEDTAIYYCARGGEGYSDSHYGTDVWGQGTTVTVSS |
| 1.39 | SEQ ID NO: 153 NYWMN | SEQ ID NO: 154 NINQDESEKYYVDSVKG | SEQ ID NO: 155 GGFGYGDSHFGMDV | SEQ ID NO: 156 EVQLVESGGGLVQPGGSLRLSCAASGFTFSNYWMNWVRQAPGKELEWVANINQDESEKYYVDSVKGRFVSRDNAKNSLFLQMNSLRADDTAVYYCARGGFGYGDSHFGMDVWGQGTTVTVSS |
| 1.40 | SEQ ID NO: 157 NYWMF | SEQ ID NO: 158 NVNQDGSEKYYVDSVEG | SEQ ID NO: 159 GGEGYSDSHYGTDV | SEQ ID NO: 160 EVQLVESGGGLVQPGGSLRLSCGASGFTFSNYWMFWFRQAPGKELEWVANVNQDGSEKYYVDSVEGRFTISRDDAKNSLYLQMNSLRAEDTAIYYCARGGEGYSDSHYGTDVWGQGTTVTVSS |

TABLE 1-continued

Full length sequences and CDR sequences of V_H single domain antibodies (Family 1)

| Name | CDR1 | CDR2 | CDR3 | Full Length |
|---|---|---|---|---|
| 1.41 | SEQ ID NO: 161 NYWMF | SEQ ID NO: 162 NVNQNGSEKYYVDSVEG | SEQ ID NO: 163 GGEGYSDSHYGTDV | SEQ ID NO: 164 EVQLVESGGGLVQPGGSLRLSCGASGFTFSNYWMFWRQAPGKEL EWVANVNQNGSEKYYVDSVEGRFTISRDNAKNSLYLQMNSLRAED TAIYYCARGGEGYSDSHYGTDVWGQGTTVTVSS |
| 1.42 | SEQ ID NO: 165 NYWMN | SEQ ID NO: 166 NIKQDGSEKYYVDSVKG | SEQ ID NO: 167 GGEGYGDSHYGMDV | SEQ ID NO: 168 QVQLVESGGGLVQPGGSLRLSCAASGFTFSNYWMNVRQAPGKG LEWVANIKQDGSEKYYVDSVKGRFTISRDNAKDSLYLQMNSLRAED TAIYYCARGGEGYGDSHYGMDVSGQGTTVTVSS |
| 1.43 | SEQ ID NO: 169 NYWMI | SEQ ID NO: 170 NINQDGSEKYYVDSVKG | SEQ ID NO: 171 GGDGYSNSHYGMDV | SEQ ID NO: 172 EVQLVESGGGLVQPGGSLRLSCAASGFTFSNYWMIYRQAPGEEL EWVANINQDGSEKYYVDSVKGRFTISRDNATNSLFLQMNSLRAEDT AVYYCARGGDGYSNSHYGMDVWGQGTTVTVSS |
| 1.44 | SEQ ID NO: 173 DYWMI | SEQ ID NO: 174 NINQDGSEKYYVDSVKG | SEQ ID NO: 175 GGDGYSNSHYGMDV | SEQ ID NO: 176 EVQLVESGGGLVQPGGSLRLSCAASGFTFSDYWMIYRQAPGEEL EWVANINQDGSEKYYVDSVKGRFTISRDNATNSLFLQMNSLRAEDT AVYYCARGGDGYSNSHYGMDVWGQGTTVTVSS |
| 1.45 | SEQ ID NO: 177 KYWMI | SEQ ID NO: 178 NINQDGSEKYYVDSVEG | SEQ ID NO: 179 GGDDYSNSHYGMDV | SEQ ID NO: 180 EVQLVESGGGLVQPGGSLRLSCAASGFTFSKYWMIWRQAPEKGL EWVANINQDGSEKYYVDSVEGRFTISRDNVNNSLYLQMNSLRAEDT AVYYCARGGDDYSNSHYGMDVSGQGTTVTVSS |
| 1.46 | SEQ ID NO: 181 NYWMS | SEQ ID NO: 182 NINQDGSEKYYVDSVKG | SEQ ID NO: 183 GGEEYSSSHYGMDV | SEQ ID NO: 184 EVQLVESGGGLVQPGGSLRLSCAASGFTFSNYWMSVRQAPGRG LEWVANINQDGSEKYYVDSVKGRFTISRDNAKSSLYLQMNSLRAED TAVYYCARGGEEYSSSHYGMDVWGQGTTVTVSS |
| 1.47 | SEQ ID NO: 185 NYWMN | SEQ ID NO: 186 NIKQDGSENYYVDSVKG | SEQ ID NO: 187 GGEGYSTSHYGMDV | SEQ ID NO: 188 EVQLVESGGGLVQPGGSLRLSCIASGFSFSNYWMNVRQAPGKGL 3WVANIKQDGSENYYVDSVKGRFTISRDNAKNSLYLQMNSLRAEDT AVYYCARGGEGYSTSHYGMDVWGQGTAVTVSS |
| 1.48 | SEQ ID NO: 189 SYWMS | SEQ ID NO: 190 NIKQDGSEKYYVDSVKG | SEQ ID NO: 191 GGEGYGVDHYGLDV | SEQ ID NO: 192 QVQLVESGGGLVQPGGSLRLSCAASGFTFSSYWMSVRQAPGKG LEWVANIKQDGSEKYYVDSVKGRFTISRDNAKNSLYLQMSSLRAEDT AVYFCARGGEGYGVDHYGLDVSGQGTTVTVSS |
| 1.49 | SEQ ID NO: 193 SYWML | SEQ ID NO: 194 NVNQDGSENYYVDSVEG | SEQ ID NO: 195 GGEDYGNSHFGMDV | SEQ ID NO: 196 EVQLVESGGGLVQPGGSLRLSCGASGFTFSSYWMLWFRQAPGKEL EWVANVNQDGSENYYVDSVEGRFTISRDNAKNSLYLQMHSLRAED TAVYYCARGGEDYGNSHFGMDVWGQGTMVTVSS |
| 1.50 | SEQ ID NO: 197 NYWMI | SEQ ID NO: 198 NINQDGSEKYYVDSVKG | SEQ ID NO: 199 GGDGYSNSHYGMDV | SEQ ID NO: 200 EVQLVESGGGLVQPGRSLRLSCAASGFTFSNYWMIYRQAPGEELE WVANINQDGSEKYYVDSVKGRFTISRDNATNSLFLQMNSLRAEDTA VYYCARGGDGYSNSHYGMDVWGQGTTVTVSS |
| 1.51 | SEQ ID NO: 201 NYWMI | SEQ ID NO: 202 NINQDGSEKYYVDSVKG | SEQ ID NO: 203 GGDGYSNSHYGMDV | SEQ ID NO: 204 EVQLVESGGGLVKPGSLRLSCAASGFTFSNYWMIYRQAPGEELE WVANINQDGSEKYYVDSVKGRFTISRDNATNSLFLQMNSLRAEDTA VYYCARGGDGYSNSHYGMDVWGQGTTVTVSS |
| 1.52 | SEQ ID NO: 205 KYWMI | SEQ ID NO: 206 NINQDGSEKYYVDSVEG | SEQ ID NO: 207 GGDDYSISHFGMDV | SEQ ID NO: 208 EVQLVESGGGLVQIGGSLRLSCAASGFTFSKYWMIWRQAPEKGLE WVANINQDGSEKYYVDSVEGRFTISRDNANNSLFLQMNSLRAEDT AVYYCARGGDDYSISHFGMDVSGQGTRVTVSS |
| 1.53 | SEQ ID NO: 209 KYWMI | SEQ ID NO: 210 NINQDGSEKYYVDSVEG | SEQ ID NO: 211 GGDDYSHSHYGMDV | SEQ ID NO: 212 EVQLVESGGGLVQIGGSLRLSCVASGFTFSKYWMIWRQAPEKGLE WVANINQDGSEKYYVDSVEGRFTISRDNANNSLYLQMNSLRAEDT AVYYCARGGDDYSHSHYGMDVSGQGTTVTVSS |
| 1.54 | SEQ ID NO: 213 NYWMN | SEQ ID NO: 214 NINQDGSEKYYVDSVKG | SEQ ID NO: 215 GGFGYGDSHYGMDV | SEQ ID NO: 216 EVQLVESGGGLVQPGGSLRLSCAASGFNFSNYWMNVRQAPGKE LEWVANINQDGSEKYYVDSVKGRFTISRDNAKNSLFLQMNSLRADD TAVYYCARGGFGYGDSHYGMDVWGQGTTVTVSS |
| 1.55 | SEQ ID NO: 217 SYWLN | SEQ ID NO: 218 NINQDGSENYYVDSVEG | SEQ ID NO: 219 GGEDYGNSHFGMDV | SEQ ID NO: 220 EVQLVESGGGLVQPGGSLRLSCAASGFTFGSYWLNVRQAPGKGL EWVANINQDGSENYYVDSVEGRFTISRDNAKNSLYLQMHSLRAEDT AVYYCARGGEDYGNSHFGMDVWGQGTMVTVSS |

TABLE 1-continued

Full length sequences and CDR sequences of $V_H$ single domain antibodies (Family 1)

| Name | CDR1 | CDR2 | CDR3 | Full Length |
|---|---|---|---|---|
| 1.56 | SEQ ID NO: 221<br>SYWMS | SEQ ID NO: 222<br>NIKQDGSEKYYVDSVKG | SEQ ID NO: 223<br>GGEGYGVDHYGLDV | SEQ ID NO: 224<br>QVQLVESGGGLVKPGGSLRLSCAASGFTFSSYWMSWVRQAPGKGLEWVANIKQDGSEKYYVDSVKGRFTISRDNAKNSLYLQMSSLRAEDTAVYFCARGGEGYGVDHYGLDVSGQGTTVTVSS |
| 1.57 | SEQ ID NO: 225<br>DYWMN | SEQ ID NO: 226<br>NIKEDGSEKYYVDSVEG | SEQ ID NO: 227<br>GGEGYGDNHYGMDV | SEQ ID NO: 228<br>QVQLVESGGGLVQPGGSLRLSCTASGFTFSDYWMNWVRQAPGKGLEWVANIKEDGSEKYYVDSVEGRFTISRDNARNSLYLQMTSLREEDTAMYYCARGGEGYGDNHYGMDVSGQGTTVTVSS |
| 1.58 | SEQ ID NO: 229<br>SYWMN | SEQ ID NO: 230<br>NINQDGSEKYYVDSVEG | SEQ ID NO: 231<br>GGPDYGDLHYGMDV | SEQ ID NO: 232<br>EVQLVESGGGLVQPGGSLRLSCAASGFTFRSYWMNWVRQAPGKEAEWVANINQDGSEKYYVDSVEGRFTISRDNAKNSLFLQMNSLRDEDTAVYYCARGGPDYGDLHYGMDVWGQGTTVTVSS |
| 1.59 | SEQ ID NO: 233<br>RYWMS | SEQ ID NO: 234<br>NINQDGREKYYVDSVKG | SEQ ID NO: 235<br>GGEGYGDYHYGMDV | SEQ ID NO: 236<br>QVQLVESGGGLVQPGGSLRLSCAASGFTFSRYWMSWVRQAPGKGLERVANINQDGREKYYVDSVKGRFTISRDNAKNSLYLQMNSLRAEDTAVYYCARGGEGYGDYHYGMDVSGQGTTVTVSS |
| 1.60 | SEQ ID NO: 237<br>NYWMI | SEQ ID NO: 238<br>NINQDGSEKYYVDSVKG | SEQ ID NO: 239<br>GGDGYSNSHYGMDV | SEQ ID NO: 240<br>EVQLVESGGGLVQPGGSPRLSCAASGFTLSNYWMIYRQAPGEKLEWVANINQDGSEKYYVDSVKGRFTISRDNATNSLFLQMNSLRAEDTAVYYCARGGDGYSNSHYGMDVWGQGTTVTVSS |
| 1.61 | SEQ ID NO: 241<br>NYWMN | SEQ ID NO: 242<br>NINQDESEKYYVDSVKG | SEQ ID NO: 243<br>GGFGYGDSHFGMDV | SEQ ID NO: 244<br>EVQLVESGGGLVQPGGSLRLSCVASGFNFSNYWMNWVRQAPGKELEWVANINQDESEKYYVDSVKGRFTISRDNAKNSLFLQMNSLRADDTAVYYCARGGFGYGDSHFGMDVWGQGTTVTVSS |
| 1.62 | SEQ ID NO: 245<br>NYWMN | SEQ ID NO: 246<br>NINQDESEKYYVDSVKG | SEQ ID NO: 247<br>GGFGYGDSHFGMDV | SEQ ID NO: 248<br>EVQLVESGGGLVQPGGSLRLSCAASGFNFSNYWMNWVRQAPGKELEWVANINQDESEKYYVDSVKGRFTIFRDNAKNSLFLQMNSLRADDTAVYYCARGGFGYGDSHFGMDVWGQGTTVTVSS |
| 1.63 | SEQ ID NO: 249<br>SFWMN | SEQ ID NO: 250<br>NINQDGSEKYYVDSVKG | SEQ ID NO: 251<br>GGPDYGDLHYGMDV | SEQ ID NO: 252<br>EVQLVESGGGLSLSCAASGFTFRSFWMNWVRQAPGKEAEWVANINQDGSEKYYVDSVKGRFTISRDNAKNSLFLQMNSLRAEDTAVYYCARGGPDYGDLHYGMDVWGQGTTVTVSS |
| 1.64 | SEQ ID NO: 253<br>SYWMN | SEQ ID NO: 254<br>NINQDGSEKYYVDSVKG | SEQ ID NO: 255<br>GGPDYGDLHYGMDV | SEQ ID NO: 256<br>EVQLVESGGGLVQPGGSLRLSCAASGFTFRSYWMNWVRQAPGKEAEWVANINQDGSEKYYVDSVKGRFTISRDNAKNSLFLQMNSLRDEDTAVYYCARGGPDYGDLHYGMDVWGQGTTVTVSS |
| 1.65 | SEQ ID NO: 257<br>NYWMI | SEQ ID NO: 258<br>NINQDGSEKYYVDSVKG | SEQ ID NO: 259<br>GGEDYGNSHYGMDV | SEQ ID NO: 260<br>EVQLVESGGGLVQPGGSLRLSCAASGFTFSNYWMIYRQAPGEELEWVANINQDGSEKYYVDSVKGRFTISRDNAKNSLYLQMHSLRAEDTAVYYCARGGEDYGNSHYGMDVWGQGTMVTVSS |
| 1.66 | SEQ ID NO: 261<br>NYWMN | SEQ ID NO: 262<br>NINQDGSERYYVDSVKG | SEQ ID NO: 263<br>GGEGYGIDHYGLDV | SEQ ID NO: 264<br>EVQLVESGGGLVQPGGSLRLSCAASGFTFSNYWMNWVRQAPGKGLEWVANINQDGSERYYVDSVKGRFTISRDNAKSSLYLQMNSLRAEDTAVYFCARGGEGYGIDHYGLDVSGQGTTVTVSS |
| 1.67 | SEQ ID NO: 265<br>SYWMS | SEQ ID NO: 266<br>NINQDGSERYYVDSVKG | SEQ ID NO: 267<br>GGEGYGVDHYGLDV | SEQ ID NO: 268<br>QVQLVESGGGLVQPGGSLRLSCAASGFTFSSYWMSWVRQAPGKGLEWVANINQDGSERYYVDSVKGRFTISRDNAKSSLYLQMSSLRAEDTAVYFCARGGEGYGVDHYGLDVSGQGTTVTVSS |
| 1.68 | SEQ ID NO: 269<br>NYWMI | SEQ ID NO: 270<br>NINQDGSEKYYVDSVEG | SEQ ID NO: 271<br>GGEGYGVDHYGLDV | SEQ ID NO: 272<br>QVQLVESGGGLVQPGGSLRLSCAASGFTFSNYWMIWVRQAPGKGLEWVANINQDGSEKYYVDSVEGRFTISRDNAKSSLYLQMSNLRAEDTAVYFCARGGEGYGVDHYGLDVSGQGTTVTVSS |
| 1.69 | SEQ ID NO: 273<br>NYWMN | SEQ ID NO: 274<br>NINQDGSEKYYVDSVKG | SEQ ID NO: 275<br>GGTGYGSDHYGMDV | SEQ ID NO: 276<br>QVQLVESGGGLVQPGGSLRLSCAATGFTLSNYWMNWVRQAPGKGLEWVANINQDGSEKYYVDSVKGRFTISRDNAKNSLFLQMNSLRAEDTAVYYCARGGTGYGSDHYGMDVSGQGTTVTVSS |
| 1.70 | SEQ ID NO: 277<br>NYWMN | SEQ ID NO: 278<br>NINQDGSENYYVDSVKG | SEQ ID NO: 279<br>GGFGYGDSHYGMDV | SEQ ID NO: 280<br>EVQLVESGGGLVQPGGSLRLSCAASGFNFSNYWMNWVRQAPGKELEWVANINQDGSENYYVDSVKGRFTISRDNVKNSLFLQMNRLRADDTAVYYCARGGFGYGDSHYGMDVWGQGTTVTVSS |

TABLE 1-continued

Full length sequences and CDR sequences of V$_H$ single domain antibodies (Family 1)

| Name | CDR1 | CDR2 | CDR3 | Full Length |
|------|------|------|------|-------------|
| 1.71 | SEQ ID NO: 281<br>NYWMI | SEQ ID NO: 282<br>NINQNGSERYYVDSVQG | SEQ ID NO: 283<br>GGADYSNSHYGMDV | SEQ ID NO: 284<br>EVQLVESGGGLVQPGGSLRLSCAASGFTFGNYWMIWVRQAPGKEL<br>EWLANINQNGSERYYVDSVQGRFTISRDNAKNSLYLQMNSLRAEDT<br>AVYYCARGGADYSNSHYGMDVSGQGTTVTVSS |
| 1.72 | SEQ ID NO: 285<br>SYWMS | SEQ ID NO: 286<br>NINQDGSERYYVDSVKG | SEQ ID NO: 287<br>GGEGYGVDHYGLDV | SEQ ID NO: 288<br>QVQLVESGGGLVQPGGSLRLSCAASGFTFSSYWMSWVRQAPGKG<br>LEWVANINQDGSERYYVDSVKGRFTISRDNANNSLHLQMSSLRAED<br>TAVYFCARGGEGYGVDHYGLDVSGQGTTVTVSS |
| 1.73 | SEQ ID NO: 289<br>SYWMN | SEQ ID NO: 290<br>NINPDGSEKYYVDSVQG | SEQ ID NO: 291<br>GGPGYGDLHYGMDV | SEQ ID NO: 292<br>EVQLVESGGGLVQPGGSLRLSCAASGFTFRSYWMNWVRQAPGKE<br>AEWVANINPDGSEKYYVDSVQGRHTISRDNAKNSLFLEMNSLRVED<br>TALYYCARGGPGYGDLHYGMDVWGQGTTVTVSS |
| 1.74 | SEQ ID NO: 293<br>NYWMN | SEQ ID NO: 294<br>NINQDGSEKYYVDSVEG | SEQ ID NO: 295<br>GGEGYGVDHYGLDV | SEQ ID NO: 296<br>QVQLVESGGGLVQPGGSLRLSCAATGFTLSNYWMNWVRQAPGKG<br>LEWVANINQDGSEKYYVDSVEGRFTISRDNAKSSLYLQMSSLRAEDT<br>AVYFCARGGEGYGVDHYGLDVSGQGTTVTVSS |
| 1.75 | SEQ ID NO: 297<br>DYYMS | SEQ ID NO: 298<br>NINQDGSERYYVDSVKG | SEQ ID NO: 299<br>GGEGYGVDHYGLDV | SEQ ID NO: 300<br>QVQLVESGGGLVQPGGSLRLSCAASGFTFSDYYMSWIRQAPGKGL<br>EWVANINQDGSERYYVDSVKGRFTISRDNAKNSLYLQMSSLRAEDTA<br>VYFCARGGEGYGVDHYGLDVSGQGTTVTVSS |
| 1.76 | SEQ ID NO: 301<br>NYWMN | SEQ ID NO: 302<br>NINQDGSERYYVDSVKG | SEQ ID NO: 303<br>GGEGYGVDHYGLDV | SEQ ID NO: 304<br>EVQLVESGGGLVQPGGSLRLSCAATGFTLSNYWMNWVRQAPGKG<br>LEWVANINQDGSERYYVDSVKGRFTISRDNAKNSLYLQMSSLRAED<br>TAVYFCARGGEGYGVDHYGLDVSGQGTTVTVSS |
| 1.77 | SEQ ID NO: 305<br>NYWMN | SEQ ID NO: 306<br>NINQDGSERYYVDSVKG | SEQ ID NO: 307<br>GGEGYGVDHYGLDV | SEQ ID NO: 308<br>QVQLVESGGGLVQPGGSLRLSCAASGFTLSNYWMNWVRQAPGKG<br>LEWVANINQDGSERYYVDSVKGRFTISRDNAKNSLYLQMSSLRAED<br>TAVYFCARGGEGYGVDHYGLDVSGQGTTVTVSS |
| 1.78 | SEQ ID NO: 309<br>NYWMN | SEQ ID NO: 310<br>NINQDGSERYYVDSVKG | SEQ ID NO: 311<br>GGEGYGVDHYGLDV | SEQ ID NO: 312<br>QVQLVESGGGLVQPGGSLRLSCAATGFTLSNYWMNWVRQAPGKG<br>LEWVANINQDGSERYYVDSVKGRFTISRDNAKNSLYLQMSSLRAED<br>TAVYFCARGGEGYGVDHYGLDVSGQGTTVTVSS |
| 1.79 | SEQ ID NO: 313<br>NYWMN | SEQ ID NO: 314<br>NINQDGSERYYVDSVKG | SEQ ID NO: 315<br>GGEGYGVNHYGLDV | SEQ ID NO: 316<br>QVQLVESGGGLVQPGGSLRLSCAATGFTLSNYWMNWVRQAPGKG<br>LEWVANINQDGSERYYVDSVKGRFTISRDNAKNSLYLQMSSLRAED<br>TAVYFCARGGEGYGVNHYGLDVSGQGTTVTVSS |
| 1.80 | SEQ ID NO: 317<br>DYYMS | SEQ ID NO: 318<br>NIKQDGSERYYVDSVKG | SEQ ID NO: 319<br>GGEGYGVDHYGLDV | SEQ ID NO: 320<br>QVQLVESGGGLVKPGGSLRLSCVASGFTFSDYYMSWIRQAPGKGLE<br>WVANIKQDGSERYYVDSVKGRFTISRDNAKSSLYLQMSSLRAEDTA<br>VYFCARGGEGYGVDHYGLDVSGQGTTVTVSS |
| 1.81 | SEQ ID NO: 321<br>NYWMN | SEQ ID NO: 322<br>NINQDGSERYYVDSVEG | SEQ ID NO: 323<br>GGEGYGVDHYGLDV | SEQ ID NO: 324<br>QVQLVESGGGLVQPGGSLRLSCAATGFTLSNYWMNWVRQAPGKG<br>LEWVANINQDGSERYYVDSVEGRFTISRDNAKSSLYLQMSNLRAED<br>TAVYFCARGGEGYGVDHYGLDVSGQGTTVTVSS |
| 1.82 | SEQ ID NO: 325<br>NYWMN | SEQ ID NO: 326<br>NINQDGSERYYVDSVKG | SEQ ID NO: 327<br>GGEGYGVDHYGLDV | SEQ ID NO: 328<br>QVQLVESGGGLVQPGGSLRLSCAATGFTLSNYWMNWVRQAPGKG<br>LEWVANINQDGSERYYVDSVKGRFTISRDNAKSSLYLQMSSLRAEDT<br>AVYFCARGGEGYGVDHYGLDVSGQGTTVTVSS |
| 1.83 | SEQ ID NO: 329<br>NYWMN | SEQ ID NO: 330<br>NINQDGSERYYVDSVKG | SEQ ID NO: 331<br>GGEGYGVDHYGLDV | SEQ ID NO: 332<br>QVQLVQESGGGLVQPGGSLRLSCAATGFTLSNYWMNWVRQAPGK<br>GLEWVANINQDGSERYYVDSVKGRFTISRDNAKNSLYLQMSSLRAE<br>DTAVYFCARGGEGYGVDHYGLDVSGQGTTVTVSS |
| 1.84 | SEQ ID NO: 333<br>NYWMN | SEQ ID NO: 334<br>NINQDGSERYYVDSVKG | SEQ ID NO: 335<br>GGEGYGVDHYGLDV | SEQ ID NO: 336<br>QVQLVESGGGLVKPGGSLRLSCAATGFTLSNYWMNWVRQAPGKG<br>LEWVANINQDGSERYYVDSVKGRFTISRDNAKNSLYLQMSSLRAED<br>TAVYFCARGGEGYGVDHYGLDVSGQGTTVTVSS |
| 1.85 | SEQ ID NO: 337<br>NYWMN | SEQ ID NO: 338<br>NINQDGSERYYVDSVKG | SEQ ID NO: 339<br>GGEGYGVDHYGLDV | SEQ ID NO: 340<br>QVQLVESGGGLVQPGGSLRLSCAATGFTLSNYWMNWVRQAPGKG<br>LEWVANINQDGSERYYVDSVKGRFTISRDNANNSLHLQMSSLRAED<br>TAVYFCARGGEGYGVDHYGLDVSGQGTTVTVSS |

TABLE 1-continued

Full length sequences and CDR sequences of V_H single domain antibodies (Family 1)

| Name | CDR1 | CDR2 | CDR3 | Full Length |
|---|---|---|---|---|
| 1.86 | SEQ ID NO: 341 NYWMN | SEQ ID NO: 342 NINQDGSERYYVDSVEG | SEQ ID NO: 343 GGEGYGVDHYGLDV | SEQ ID NO: 344 QVQLGESGGGLVQPGGSLRLSCAATGFTLSNYWMNWVRQAPGKGLEWVANINQDGSERYYVDSVEGRFTISRDNAKSSLYLQMSNLRAEDTAVYFCARGGEGYGVDHYGLDVSGQGTTVTVSS |
| 1.87 | SEQ ID NO: 345 NYWMN | SEQ ID NO: 346 NINQDGSERYYVDSVKG | SEQ ID NO: 347 GGEGYGVDHYGLDV | SEQ ID NO: 348 QVQLVESGGGLVQPGGSLKLSCAATGFTLSNYWMNWVRQAPGKGLEWVANINQDGSERYYVDSVKGRFTISRDNAKSSLYLQMSSLRAEDTAVYFCARGGEGYGVDHYGLDVSGQGTTVTVSS |
| 1.88 | SEQ ID NO: 349 NYWMN | SEQ ID NO: 350 NINQDGSERYYVDSVKG | SEQ ID NO: 351 GGEGYGVDHYGLDV | SEQ ID NO: 352 QVQLQESGGGLVQPGGSLRLSCAATGFTLSNYWMNWVRQAPGKGLEWVANINQDGSERYYVDSVKGRFTISRGNAKNSLYLQMSSLRAEDTAVYFCARGGEGYGVDHYGLDVSGQGTTVTVSS |
| 1.89 | SEQ ID NO: 353 DYGMS | SEQ ID NO: 354 NINQDGSERYYVDSVKG | SEQ ID NO: 355 GGEGYGVDHYGLDV | SEQ ID NO: 356 QVQLVESGGVVQPGRSLRLSCAASGFTFDDYGMSWVRQAPGKGLEWVANINQDGSERYYVDSVKGRFTISRDNAKNSLYLQMSSLRAEDTAVYFCARGGEGYGVDHYGLDVSGQGTTVTVSS |
| 1.90 | SEQ ID NO: 357 SHWMT | SEQ ID NO: 358 HIKEDGSEKYYEDSVEG | SEQ ID NO: 359 GGDGYSDSHFGVDV | SEQ ID NO: 360 EVQLVESGGGLVQPGGSLRLSCAASGFTFSSHWMTWVRQAPGKGLEWVAHIKEDGSEKYYEDSVEGRFTVSRDNAKNSVYLQMNSLRAEDTAVYYCARGGDGYSDSHFGVDVWGQGTTVTVSS |
| 1.91 | SEQ ID NO: 361 SHWMT | SEQ ID NO: 362 HIKEDGSEKYYVDSVKG | SEQ ID NO: 363 GGDGYSDSHFGVDV | SEQ ID NO: 364 EVQLVESGGGLVQPGGSLRLSCAASGFTFSSHWMTWFRQAPGKGLEWVAHIKEDGSEKYYVDSVKGRFTVSRDNAKNSVYLQMNSLRAEDTAVYYCARGGDGYSDSHFGVDVWGQGTTVTVSS |
| 1.92 | SEQ ID NO: 365 SHWMT | SEQ ID NO: 366 HIKEDGSEKYYEDSVEG | SEQ ID NO: 367 GGDGYSDSHFGVDV | SEQ ID NO: 368 EVQLVESGGGLVQPGGSLRLSCAASGFTFSSHWMTWFRQAPGKGLEWVAHIKEDGSEKYYEDSVEGRFTVSRDNAKNSVYLQMNSLRAEDTAVYYCARGGDGYSDSHFGVDVWGQGTTVTVSS |
| 1.93 | SEQ ID NO: 369 SHWMT | SEQ ID NO: 370 HIKEDGSEKYYEDSVEG | SEQ ID NO: 371 GGDGYSDSHFGVDV | SEQ ID NO: 372 EVQLVESGGGLVQPGGSLRLSCAASGFTFSSHWMTWFRQAPGKGLEWVAHIKEDGSEKYYEDSVEGRFTISRDNAKNSVYLQMNSLRAEDTAVYYCARGGDGYSDSHFGVDVWGQGTTVTVSS |
| 1.94 | SEQ ID NO: 373 SHWMT | SEQ ID NO: 374 HIKEDGSEKYYEDSVEG | SEQ ID NO: 375 GGDGYSDSHFGVDV | SEQ ID NO: 376 EVQLVESGGGLVQPGGSLRLSCAASGFTFSSHWMTWFRQAPGKGLEWVAHIKEDGSEKYYEDSVEGRFTVSRDNAKNSLYLQMNSLRAEDTAVYYCARGGDGYSDSHFGVDVWGQGTTVTVSS |
| 1.95 | SEQ ID NO: 377 SHWMT | SEQ ID NO: 378 HIKEDGSEKYYVDSVKG | SEQ ID NO: 379 GGDGYSDSHFGVDV | SEQ ID NO: 380 EVQLVESGGGLVQPGGSLRLSCAASGFTFSSHWMTWVRQAPGKGLEWVAHIKEDGSEKYYVDSVKGRFTISRDNAKNSLYLQMNSLRAEDTAVYYCARGGDGYSDSHFGVDVWGQGTTVTVSS |
| 1.96 | SEQ ID NO: 381 SHWMT | SEQ ID NO: 382 HIKEDGSEKYYVDSVKG | SEQ ID NO: 383 GGDGYSDSHFGVDV | SEQ ID NO: 384 EVQLVESGGGLVQPGGSLRLSCAASGFTFSSHWMTWFRQAPGKGLEWVAHIKEDGSEKYYVDSVKGRFTISRDNAKNSLYLQMNSLRAEDTAVYYCARGGDGYSDSHFGVDVWGQGTTVTVSS |
| 1.97 | SEQ ID NO: 385 SHWMT | SEQ ID NO: 386 HIKEDESEKYYVDSVKG | SEQ ID NO: 387 GGVGYSISHFGVDV | SEQ ID NO: 388 EVQLVESGGGLVQPGGSLRLSCAASGFTFSSHWMTWVRQAPGKGLEWVAHIKEDESEKYYVDSVKGRFTISRDNAKNSLYLQMNSLRAEDTAVYYCARGGVGYSISHFGVDVWGQGTTVTVSS |
| 1.98 | SEQ ID NO: 389 SHWMT | SEQ ID NO: 390 HIKEDESEKYYVDSVKG | SEQ ID NO: 391 GGEGYSISHFGVDV | SEQ ID NO: 392 EVQLVESGGGLVQPGGSLRLSCAASGFTFSSHWMTWVRQAPGKGLEWVAHIKEDESEKYYVDSVKGRFTISRDNAKNSLYLQMNSLRAEDTAVYYCARGGEGYSISHFGVDVWGQGTTVTVSS |
| 1.99 | SEQ ID NO: 393 SHWMT | SEQ ID NO: 394 HIKEDESEKYYVDSVKG | SEQ ID NO: 395 GGDGYSDSHFGVDV | SEQ ID NO: 396 EVQLVESGGGLVQPGGSLRLSCAASGFTFSSHWMTWFRQAPGKGLEWVAHIKEDESEKYYVDSVKGRFTISRDNAKNSLYLQMNSLRAEDTAVYYCARGGDGYSDSHFGVDVWGQGTTVTVSS |
| 1.100 | SEQ ID NO: 397 SHWMT | SEQ ID NO: 398 HIKEDESEKYYVDSVKG | SEQ ID NO: 399 GGDGYSISHFGVDV | SEQ ID NO: 400 EVQLVESGGGLVQPGGSLRLSCAASGFTFSSHWMTWFRQAPGKGLEWVAHIKEDESEKYYVDSVKGRFTISRDNAKNSLYLQMNSLRAEDTAVYYCARGGDGYSISHFGVDVWGQGTTVTVSS |

TABLE 1-continued

Full length sequences and CDR sequences of V_H single domain antibodies (Family 1)

| Name | CDR1 | CDR2 | CDR3 | Full Length |
|---|---|---|---|---|
| 1.101 | SEQ ID NO: 401 SHWMT | SEQ ID NO: 402 HIKEGGSEKYYVDSVKG | SEQ ID NO: 403 GGDGYSDSHFGVDV | SEQ ID NO: 404 EVQLVESGGGLVQPGGSLRLSCAASGFTFSSHWMTWFRQAPGKGLEWVAHIKEGGSEKYYVDSVKGRFTISRDNAKNSLYLQMNSLRAEDTAVYYCARGGDGYSDSHFGVDVWGQGTTVTVSS |
| 1.102 | SEQ ID NO: 405 SHWMT | SEQ ID NO: 406 HIKEEGSEKYYVDSVKG | SEQ ID NO: 407 GGDGYSDSHFGVDV | SEQ ID NO: 408 EVQLVESGGGLVQPGGSLRLSCAASGFTFSSHWMTWFRQAPGKGLEWVAHIKEEGSEKYYVDSVKGRFTISRDNAKNSLYLQMNSLRAEDTAVYYCARGGDGYSDSHFGVDVWGQGTTVTVSS |
| 1.103 | SEQ ID NO: 409 SHWMT | SEQ ID NO: 410 HIKEDGSEKYYVDSVKG | SEQ ID NO: 411 GGEGYSDSHFGVDV | SEQ ID NO: 412 EVQLVESGGGLVQPGGSLRLSCAASGFTFSSHWMTWFRQAPGKGLEWVAHIKEDGSEKYYVDSVKGRFTISRDNAKNSLYLQMNSLRAEDTAVYYCARGGEGYSDSHFGVDVWGQGTTVTVSS |
| 1.104 | SEQ ID NO: 413 SHWMT | SEQ ID NO: 414 HIKEDGSEKYYVDSVKG | SEQ ID NO: 415 GGVGYSDSHFGVDV | SEQ ID NO: 416 EVQLVESGGGLVQPGGSLRLSCAASGFTFSSHWMTWFRQAPGKGLEWVAHIKEDGSEKYYVDSVKGRFTISRDNAKNSLYLQMNSLRAEDTAVYYCARGGVGYSDSHFGVDVWGQGTTVTVSS |
| 1.105 | SEQ ID NO: 417 SHWMT | SEQ ID NO: 418 HIKEDESEKYYVDSVKG | SEQ ID NO: 419 GGVGYSISHFGVDV | SEQ ID NO: 420 EVQLVESGGGLVQPGGSLRLSCAASGFTFSSHWMTWFRQAPGKGLEWVAHIKEDESEKYYVDSVKGRFTISRDNAKNSLYLQMNSLRAEDTAVYYCARGGVGYSISHFGVDVWGQGTTVTVSS |
| 1.106 | SEQ ID NO: 421 SHWMT | SEQ ID NO: 422 HIKEDESEKYYVDSVKG | SEQ ID NO: 423 GGEGYSISHFGVDV | SEQ ID NO: 424 EVQLVESGGGLVQPGGSLRLSCAASGFTFSSHWMTWFRQAPGKGLEWVAHIKEDESEKYYVDSVKGRFTISRDNAKNSLYLQMNSLRAEDTAVYYCARGGEGYSISHFGVDVWGQGTTVTVSS |
| 1.107 | SEQ ID NO: 849 NYWMN | SEQ ID NO: 850 NINQDGSERYYVDSVKG | SEQ ID NO: 851 GGEGYGVDHYGLDV | SEQ ID NO: 852 EVQLVESGGGLVQPGGSLRLSCAASGFTLSNYWMNWVRQAPGKGLEWVANINQDGSERYYVDSVKGRFTISRDNAKNSLYLQMSSLRAEDTAVYFCARGGEGYGVDHYGLDVSGQGTTVTVSS |
| 1.108 | SEQ ID NO: 853 NYWMN | SEQ ID NO: 854 NINQDGSERYYVDSVKG | SEQ ID NO: 855 GGEGYGVDHYGLDV | SEQ ID NO: 856 EVQLVESGGGLVQPGGSLRLSCAATGFTLSNYWMNWVRQAPGKGLEWVANINQDGSERYYVDSVKGRFTISRDNAKNSLYLQMSSLRAEDTAVYFCARGGEGYGVDHYGLDVSGQGTTVTVSS |
| 1.109 | SEQ ID NO: 857 NYWMN | SEQ ID NO: 858 NINQDGSERYYVDSVKG | SEQ ID NO: 859 GGEGYGVDHYGLDV | SEQ ID NO: 860 EVQLVESGGGLVQPGGSLRLSCAATGFTLSNYWMNWVRQAPGKGLEWVANINQDGSERYYVDSVKGRFTISRDNAKNSLYLQMSSLRAEDTAVYYCARGGEGYGVDHYGLDVSGQGTTVTVSS |
| 1.110 | SEQ ID NO: 861 NYWMN | SEQ ID NO: 862 NINQDGSERYYVDSVKG | SEQ ID NO: 863 GGEGYGVDHYGLDV | SEQ ID NO: 864 EVQLVESGGGLVQPGGSLRLSCAASGFTLSNYWMNWVRQAPGKGLEWVANINQDGSERYYVDSVKGRFTISRDNAKNSLYLQMNSLRAEDTAVYFCARGGEGYGVDHYGLDVSGQGTTVTVSS |
| 1.111 | SEQ ID NO: 865 NYWMN | SEQ ID NO: 866 NINQDGSERYYVDSVKG | SEQ ID NO: 867 GGEGYGVDHYGLDV | SEQ ID NO: 868 EVQLVESGGGLVQPGGSLRLSCAASGFTLSNYWMNWVRQAPGKGLEWVANINQDGSERYYVDSVKGRFTISRDNAKNSLYLQMSSLRAEDTAVYYCARGGEGYGVDHYGLDVSGQGTTVTVSS |
| 1.112 | SEQ ID NO: 869 NYWMN | SEQ ID NO: 870 NINQDGSERYYVDSVKG | SEQ ID NO: 871 GGEGYGVDHYGLDV | SEQ ID NO: 872 EVQLVESGGGLVQPGGSLRLSCAATGFTLSNYWMNWVRQAPGKGLEWVANINQDGSERYYVDSVKGRFTISRDNAKNSLYLQMSSLRAEDTAVYYCARGGEGYGVDHYGLDVSGQGTTVTVSS |
| 1.113 | SEQ ID NO: 873 NYWMN | SEQ ID NO: 874 NINQDGSERYYVDSVKG | SEQ ID NO: 875 GGEGYGVDHYGLDV | SEQ ID NO: 876 EVQLVESGGGLVQPGGSLRLSCAASGFTLSNYWMNWVRQAPGKGLEWVANINQDGSERYYVDSVKGRFTISRDNAKNSLYLQMSSLRAEDTAVYYCARGGEGYGVDHYGLDVSGQGTTVTVSS |
| 1.114 | SEQ ID NO: 877 NYWMN | SEQ ID NO: 878 NINQDESERYYVDSVKG | SEQ ID NO: 879 GGEGYGVDHYGLDV | SEQ ID NO: 880 EVQLVESGGGLVQPGGSLRLSCAASGFTLSNYWMNWVRQAPGKGLEWVANINQDESERYYVDSVKGRFTISRDNAKNSLYLQMSSLRAEDTAVYYCARGGEGYGVDHYGLDVSGQGTTVTVSS |

In one aspect, the single variable heavy chain domain antibody comprises a CDR1, CDR2 or CDR3 as shown for one of the single domain antibodies as shown in Table 2 or comprising a CDR1, CDR2, CDR3 with at least 40% or 75% homology thereto. For example, the single variable heavy chain domain antibody comprises a CDR1 comprising SEQ ID NO. 425 or a sequence with at least 80% homology thereto, a CDR2 comprising SEQ ID NO. 426 or a sequence with at least 75% homology thereto and a CDR3 comprising SEQ ID NO. 427 or a sequence with at least 75% homology, or a CDR1 comprising SEQ ID NO. 429 or a sequence with at least 75% homology thereto, a CDR2 comprising SEQ ID NO. 430 or a sequence with at least 75% homology thereto and a CDR3 comprising SEQ ID NO. 431 and so forth. The CDRs are defined according to Kabat. In one embodiment, the single variable heavy chain domain antibody comprises CDR1, 2, and 3 as shown for $V_H$ single domain antibodies 2.41 to 2.51 or comprises or consists of a full length sequence as shown for $V_H$ single domain antibodies 2.41 to 2.51 (i.e. SEQ ID NOs. 588, 592, 596, 600, 604, 608, 612, 616, or 620).

Sequence homology can be at least 40%, 50%, 60%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% for example at least 90%, 91%, 92%, 93%, 94%, 95%, 96%, 97%, 98% or 99% sequence homology.

In one embodiment, the single variable heavy chain domain antibody comprises human framework regions.

In one embodiment, the single variable heavy chain domain antibody comprises or consists of a full length sequence as shown in Table 2 or a sequence with at least 70% homology thereto. For example, the single variable heavy chain domain antibody comprises a full length sequence comprising or consisting of a sequence selected from those shown in Table 2, e.g. SEQ ID NO. 428, 432, 436, 440 and so forth or a sequence with at least 50% homology thereto. Sequence homology as mentioned above an be at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% for example at least 90%, 91%, 92%, 93%, 94%, 95%, 96%, 97%, 98% or 99% sequence homology.

TABLE 2

Full length sequences and CDR sequences of $V_H$ single domain antibodies (Family 2)

| Name | CDR1 | CDR2 | CDR3 | Full Length |
|---|---|---|---|---|
| 2.1 | SEQ ID NO: 425 DYYMS | SEQ ID NO: 426 YISGSGDIIDYADSVKG | SEQ ID NO: 427 EDSRLIGTTDFDN | SEQ ID NO: 428 EVQLVESGGGLVKPGGSLRVSCAASGFTFSDYYMSWFRQAPGK GLEWVSYISGSGDIIDYADSVKGRFTISRDNAKNSLYLQMNNLR AEDTAVYHCAREDSRLTGTTDFDNWGQGTLVTVSS |
| 2.2 | SEQ ID NO: 429 DYYMS | SEQ ID NO: 430 YISGSGDIIDYADSVKG | SEQ ID NO: 431 EDSRIPGTTDFDN | SEQ ID NO: 432 EVQLVESGGGLVKPGGSLRVSCAASGFTFSDYYMSWFRQAPGK GLEWVSYISGSGDIIDYADSVKGRFTISRDNAKNSLYLQMNSLRA EDTAVYHCAKEDSRIPGTTDFDNWGQGTLVTVSS |
| 2.3 | SEQ ID NO: 433 DYYMS | SEQ ID NO: 434 YISGSGDIIDYADSVKG | SEQ ID NO: 435 EDSRIPGTTDFDN | SEQ ID NO: 436 EVQLVESGGGLVKPGGSLRVSCAASGFTFSDYYMSWFRQAPGK GLEWISYISGSGDIIDYADSVKGRFTISRDNAKNSLYLQMNSLRA EDTAVYHCAKEDSRIPGTTDFDNWGQGTLVTVSS |
| 2.4 | SEQ ID NO: 437 DYYMS | SEQ ID NO: 438 YISGSGDVIDYADSVKG | SEQ ID NO: 439 EDSRIPGTTDFDN | SEQ ID NO: 440 EVQLVESGGGLVKPGGSLRVSCAASGFTFSDYYMSWFRQAPGK GLEWVSYISGSGDVIDYADSVKGRFTISRDNAKNSLYLQMNSLR AEDTAVYHCAKEDSRIPGTTDFDNWGQGTLVTVSS |
| 2.5 | SEQ ID NO: 441 DYYMS | SEQ ID NO: 442 YISGSGDIIDYADSVKG | SEQ ID NO: 443 EDSRIPGTTDFDN | SEQ ID NO: 444 EVQLVESGGGLVKPGGSLRLSCAVSGFTFSDYYMSWFRQAPGK GLEWVSYISGSGDIIDYADSVKGRFTISRDNAKNSLYLQMNSLRA EDTAVYHCAKEDSRIPGTTDFDNWGQGTLVTVSS |
| 2.6 | SEQ ID NO: 445 DYYMS | SEQ ID NO: 446 YISGSGDIIDYADSVKG | SEQ ID NO: 447 EDSRIPGTTDFDS | SEQ ID NO: 448 EVQLVESGGGLVKPGGSLRVSCAASGFTFSDYYMSWFRQAPGK GLEWVSYISGSGDIIDYADSVKGRFTISRDNAKNSLYLQMNSLRA EDTAVYHCAKEDSRIPGTTDFDSWGQGTMVTVSS |
| 2.7 | SEQ ID NO: 449 DYYMS | SEQ ID NO: 450 YISGSGTTIDYADSVKG | SEQ ID NO: 451 EDIRMTGTTDFDN | SEQ ID NO: 452 EVQLVESGGGLVKPGGSLRLSCAASGFTFSDYYMSWFRQAPGK GLEWVSYISGSGTTIDYADSVKGRFTISRDNARNSLYLQMNSLRA EDTAVYYCAREDIRMTGTTDFDNWGQGTLVTVSS |
| 2.8 | SEQ ID NO: 453 DYYMS | SEQ ID NO: 454 HISGSGTTIDYADSVKG | SEQ ID NO: 455 EDSRMPGTTDFDN | SEQ ID NO: 456 EVQLVESGGGLVKPGGSLRLSCAASGFAFSDYYMSWFRQAPGK GLEWSHISGSGTTIDYADSVKGRFTISRDNAKNSLYLQMNSLR AEDTAVYHCAREDSRMPGTTDFDNWGQGTLVTVSS |
| 2.9 | SEQ ID NO: 457 DYYMT | SEQ ID NO: 458 YISGSGDTIDYAESVKG | SEQ ID NO: 459 EDSRIAGTTDFDN | SEQ ID NO: 460 EVQLVESGGGLVKPGGSLRLSCAASGFTFSDYYMTWFRQAPGK GLEWISYISGSGDTIDYAESVKGRFTISRDNAKNSLYLQMNSLRA EDTAVYHCAREDSRIAGTTDFDNWGPGTLVTVSS |

TABLE 2-continued

Full length sequences and CDR sequences of $V_H$ single domain antibodies (Family 2)

| Name | CDR1 | CDR2 | CDR3 | Full Length |
|---|---|---|---|---|
| 2.10 | SEQ ID NO: 461 DYYMT | SEQ ID NO: 462 YISSSGSNIDYADSVKG | SEQ ID NO: 463 EDSRLSGTTDFDY | SEQ ID NO: 464 EVQLVESGGGLVKPGGSLRLSCAASGFTFSDYYMTWFRQAPGK GLEWVSYISSSGSNIDYADSVKGRFTISRDNAKNSLYLQMNSLRA EDTAVYYCAREDSRLSGTTDFDYWGQGTLVTVSS |
| 2.11 | SEQ ID NO: 465 DYYMT | SEQ ID NO: 466 YISGSGDTIDYAESVKG | SEQ ID NO: 467 EDSRIAGTTDFDN | SEQ ID NO: 468 EVQLVESGGGLVQPGGSLRLSCAASGFTFSDYYMTWFRQAPGK GLEWISYISGSGDTIDYAESVKGRFTISRDNAKNSLYLQMNSLRA EDTAVYHCAREDSRIAGTTDFDNWGPGTLVTVSS |
| 2.12 | SEQ ID NO: 469 DYYMS | SEQ ID NO: 470 HISGSGTTIDYADSVKG | SEQ ID NO: 471 EDIRMTGTTDFDH | SEQ ID NO: 472 EVQLVESGGGLVKPGGSLRLSCAASGFTFSDYYMSWFRQAPGK GLEWVSHISGSGTTIDYADSVKGRFTISRDNARKSLYLQMNSLR AEDTAVYYCAREDIRMTGTTDFDHWGQGTLVTVSS |
| 2.13 | SEQ ID NO: 473 DYYMS | SEQ ID NO: 474 HISSSGNTIDYADSVKG | SEQ ID NO: 475 EDPRLPGTTDFDY | SEQ ID NO: 476 QVQLVESGGGLVKPGGSLRLSCAASGFTFSDYYMSWFRQAPGK GLEWVSHISSSGNTIDYADSVKGRFTISRDNAKNSLYLQMNSLR AEDTAVYYCAREDPRLPGTTDFDYWGQGTLVTVSS |
| 2.14 | SEQ ID NO: 477 DYYMT | SEQ ID NO: 478 YISGSGDTIDYAESVKG | SEQ ID NO: 479 EDIRMPGTTDFDH | SEQ ID NO: 480 EVQLVESGGGLVKPGGSLRLSCAASGFTFSDYYMTWFRQAPGK GLEWISYISGSGDTIDYAESVKGRFTISRDNAKNSLYLQMNSLRA EDTAVYYCAREDIRMPGTTDFDHWGQGTLVTVSS |
| 2.15 | SEQ ID NO: 481 DYYMS | SEQ ID NO: 482 HISGSGTTIDYADSVKG | SEQ ID NO: 483 EDIRMPGTTDFDH | SEQ ID NO: 484 EVQLVESGGGLVKPGGSLRLSCAVSGFTFSDYYMSWFRQAPGK GLEWVSHISGSGTTIDYADSVKGRFTISRDNARNSLYLQMNSLR AEDTAVYYCAREDIRMPGTTDFDHWGQGTLVTVSS |
| 2.16 | SEQ ID NO: 485 DYYMS | SEQ ID NO: 486 HISSSGSTIDYADSVKG | SEQ ID NO: 487 EDPRLIGTTDFDY | SEQ ID NO: 488 QVQLVESGGGLVKPGGSLRLSCAASGFTFSDYYMSWIRQAPGK GLEWVSHISSSGSTIDYADSVKGRFTISRDNAKNSLYLQMNSLRA EDTAVYYCAREDPRLIGTTDFDYWGQGALVTVSS |
| 2.17 | SEQ ID NO: 489 DYYMS | SEQ ID NO: 490 YISSSGSTISYADSVKG | SEQ ID NO: 491 EDPRISGTTDFDN | SEQ ID NO: 492 QVQLVESGGGLVKPGGSLRLSCAASGFTFSDYYMSWIRQAPGK GLEWVSYISSSGSTISYADSVKGRFTISRDNAKNSLYLQMNSLRA EDTAVYYCAREDPRISGTTDFDNWGQGTLVTVSS |
| 2.18 | SEQ ID NO: 493 DYYMS | SEQ ID NO: 494 HISSSGNTIDYADSVKG | SEQ ID NO: 495 EDPRLPGTTDFDY | SEQ ID NO: 496 QVQLQESGGGLVKPGGSLRLSCAASGFTFSDYYMSWFRQAPGK GLEWVSHISSSGNTIDYADSVKGRFTISRDNAKNSLYLQMNSLR AEDTAVYYCAREDPRLPGTTDFDYWGQGTLVTVSS |
| 2.19 | SEQ ID NO: 497 DYYMS | SEQ ID NO: 498 YISGTGITTDYADSVKG | SEQ ID NO: 499 EDPRLPGTSEFDN | SEQ ID NO: 500 QVQLVESGGGLVKPGGSLRLSCAASGFTFSDYYMSWFRQAPGK GLEWVSYISGTGITTDYADSVKGRFTISRDNAKNSLYLQMNSLRA EDTAVYYCAREDPRLPGTSEFDNWGQGTLVTVSS |
| 2.20 | SEQ ID NO: 501 DYYMS | SEQ ID NO: 502 HISSSGSTIDYADSVKG | SEQ ID NO: 503 EDPRMPGTFDFDN | SEQ ID NO: 504 EVQLVESGGGLVKPGGSLRLSCAASGFTFSDYYMSWIRQAPGK GLEWVSHISSSGSTIDYADSVKGRFTISRDNAKNSLYLQMNSLRA EDTAVYYCAREDPRMPGTFDFDNWGQGTLVTVSS |
| 2.21 | SEQ ID NO: 505 DYYMS | SEQ ID NO: 506 HISGSGTTIDYADSVKG | SEQ ID NO: 507 EDIRMPGTTDFDH | SEQ ID NO: 508 EVQLVESGGGLVKPGGSLRLSCAASGFAFSDYYMSWFRQAPGK GLEWVSHISGSGTTIDYADSVKGRFTISRDNARNSLYLQMNSLR AEDTAVYYCAREDIRMPGTTDFDHWGQGTLVTVSS |
| 2.22 | SEQ ID NO: 509 DYYMS | SEQ ID NO: 510 HISGSGTTIDYADSVKG | SEQ ID NO: 511 EDIRMPGTTDFDH | SEQ ID NO: 512 EVQLVESGGGLVKPGGSLRLSCAVSGFTFSDYYMSWFRQAPGK GLEWVSHISGSGTTIDYADSVKGRFTISRDNARDSLYLQMNSLR AEDTAVYYCAREDIRMPGTTDFDHWGQGTLVTVSS |
| 2.23 | SEQ ID NO: 513 DYYMS | SEQ ID NO: 514 HISGSGTTIDYADSVKG | SEQ ID NO: 515 EDIRMPGTTDFDH | SEQ ID NO: 516 EVQLVESGGGLVTPGGSLRLSCAVSGFTFSDYYMSWFRQAPGK GLEWVSHISGSGTTIDYADSVKGRFTISRDNARNSLYLQMNSLR AEDTAVYYCAREDIRMPGTTDFDHWGQGTLVTVSS |
| 2.24 | SEQ ID NO: 517 DYYMS | SEQ ID NO: 518 HISGSGTTIDYADSVKG | SEQ ID NO: 519 EDIRMPGTTDFDH | SEQ ID NO: 520 EVQLVESGGGLVKPGGSLRLSCAVSGFTFSDYYMSWFRQAPGK GLEWVSHISGSGTTIDYADSVKGRFTISRDNARNSLYLQMNSLR AEDTAMYYCAREDIRMPGTTDFDHWGQGTLVTVSS |

TABLE 2-continued

Full length sequences and CDR sequences of V$_H$ single domain antibodies (Family 2)

| Name | CDR1 | CDR2 | CDR3 | Full Length |
|---|---|---|---|---|
| 2.25 | SEQ ID NO: 521 DYYMS | SEQ ID NO: 522 HISGSGTTIDYAD SVKD | SEQ ID NO: 523 EDIRMPGTTDF DH | SEQ ID NO: 524 EVQLVESGGGLVKPGGSLRLSCAASGFAFSDYYMSWFRQAPGK GLEWVSHISGSGTTIDYADSVKDRFTISRDNARNSLYLQMNSLR AEDTAVYYCAREDIRMPGTTDFDHWGQGTLVTVSS |
| 2.26 | SEQ ID NO: 525 DYYMS | SEQ ID NO: 526 HISSSGTTIDYADS VKG | SEQ ID NO: 527 EDIRMPGTTDF DN | SEQ ID NO: 528 EVQLVESGGGLVKPGGSLRLSCTASGFTFTDYYMSWFRQAPGK GLEWVSHISSSGTTIDYADSVKGRFTISRDNAKNSLYLQMNSLRA DDTAVYYCAREDIRMPGTTDFDNWGQGTLVTVSS |
| 2.27 | SEQ ID NO: 529 DYYMT | SEQ ID NO: 530 YISSSGSTISYADS VKG | SEQ ID NO: 531 EDIRMSGTTDF DY | SEQ ID NO: 532 QVQLVESGGGLVKPGGSLRLSCAASGFTFSDYYMTWFRQAPGK GLEWVSYISSSGSTISYADSVKGRFTISRDNANNSLYLQMNSLRA EDTAVYHCAREDIRMSGTTDFDYWGQGTLVTVSS |
| 2.28 | SEQ ID NO: 533 DYYMS | SEQ ID NO: 534 HISSSGSSIDYADS VKG | SEQ ID NO: 535 EDPRLSGTIDF DS | SEQ ID NO: 536 QVQLVESGGGLVKPGGSLRLSCAASGFIFSDYYMSWFRQAPGK GLEWVSHISSSGSSIDYADSVKGRFTISRDNAKNSLYLQMNSLRA EDTAVYYCAREDPRLSGTIDFDSWGQGTLVTVSS |
| 2.29 | SEQ ID NO: 537 DYYMS | SEQ ID NO: 538 HIGGSGTTIDYAD SVKG | SEQ ID NO: 539 EDIRMPGTTDF DH | SEQ ID NO: 540 EVQLVESGGGLVKPGGSLRLSCAASGFAFSDYYMSWFRQAPGK GLEWVSHIGGSGTTIDYADSVKGRFTISRDNARNSLYLQMNSLR AEDTAVYYCAREDIRMPGTTDFDHWGQGTLVTVSS |
| 2.30 | SEQ ID NO: 541 DYYMS | SEQ ID NO: 542 YISSSGSTIYYADS VKG | SEQ ID NO: 543 EDPRVPGTTNF DY | SEQ ID NO: 544 QVQLVESGGGLVKPGGSLRLSCAASGFTFSDYYMSWIRQAPGK GLEWVSYISSSGSTIYYADSVKGRFTISRDNAKNSLYLQMNSLRA EDTAVYYCAREDPRVPGTTNFDYWGQGTLVTVSS |
| 2.31 | SEQ ID NO: 545 DYYMT | SEQ ID NO: 546 YISGSGSTIDYADS VKG | SEQ ID NO: 547 EDGRIPGTTDF DH | SEQ ID NO: 548 QVQLVESGGGLVKPGGSLRLSCAASGFTFSDYYMTWMRQAPG KGLEWVSYISGSGSTIDYADSVKGRFTISRDNAKNSLYLQMNSLR PEDTAVYYCAKEDGRIPGTTDFDHWGQGTLVTVSS |
| 2.32 | SEQ ID NO: 549 DYYMS | SEQ ID NO: 550 HISGSGTTIDYAD SVKD | SEQ ID NO: 551 EDIRMPGTTDF DH | SEQ ID NO: 552 EVQLVESGGGLVQPGGSLRLSCAASGFAFSDYYMSWFRQAPGK GLEWVSHISGSGTTIDYADSVKDRFTISRDNARNSLYLQMNSLR AEDTAVYYCAREDIRMPGTTDFDHWGQGTLVTVSS |
| 2.33 | SEQ ID NO: 553 DYFMS | SEQ ID NO: 554 HISSSGNSIDYAD SVKG | SEQ ID NO: 555 EDPRLPGTTDF DY | SEQ ID NO: 556 QVQLVESGGGLVKPGGSLRLSCAASGFPFSDYFMSWFRQAPGK GLEWVSHISSSGNSIDYADSVKGRFTISRDNAKNSLYLQMNSLR AEDTAVYYCAKEDPRLPGTTDFDYWGQGTLVTVSS |
| 2.34 | SEQ ID NO: 557 DSYMS | SEQ ID NO: 558 HISNSGSTISYADS VKG | SEQ ID NO: 559 EDPRLPGTSDF DY | SEQ ID NO: 560 QVQLVESGGGLVKPGGSLRLSCAASGFTFSDSYMSWIRQAPGK GLEWVSHISNSGSTISYADSVKGRFTISRDNAKNSLYLQMNSLRA EDTAVYYCAREDPRLPGTSDFDYWGQGTLVTVSS |
| 2.35 | SEQ ID NO: 561 DYYMS | SEQ ID NO: 562 HISSSGSSIDYADS VKG | SEQ ID NO: 563 EDPRLSGTTDF DQ | SEQ ID NO: 564 QVQLVESGGGVVQPGRSLRLSCAASGFTFSDYYMSWIRQAPGK GLEWVSHISSSGSSIDYADSVKGRFTISRDNAKNSLYLQMNSLRD EDTAVYYCAREDPRLSGTTDFDQWGQGTLVTVSS |
| 2.36 | SEQ ID NO: 565 SYWMS | SEQ ID NO: 566 HISSSGSTIDYAES VKG | SEQ ID NO: 567 EEDPRMTGTTD FDY | SEQ ID NO: 568 QVQLVESGGGLVQPGGSLRLSCAASGFTFSSYWMSWVRQAPG KGLEWVSHISSSGSTIDYAESVKGRFTISRDNAKNSLYLQMNSLR AEDTAVYYCAREDPRMIGTTDFDYWGQGTLVTVSS |
| 2.37 | SEQ ID NO: 569 NYFMS | SEQ ID NO: 570 HISSSGNTIDYAD SVKG | SEQ ID NO: 571 EDPRLPGTTDF DY | SEQ ID NO: 572 QVQLQESGGGLVKPGGSLRLSCAASGFTFSNYFMSWIRQAPGK GLEWVSHISSSGNTIDYADSVKGRFTISRDNAKNSLYLQMDSLR AEDTAVYYCSREDPRLPGTTDFDYWGQGTLVTVSS |
| 2.38 | SEQ ID NO: 573 DYYMT | SEQ ID NO: 574 YISSGGSTIHYADS VKG | SEQ ID NO: 575 ENPRLPGTMD FDY | SEQ ID NO: 576 EVQLVESGGGVVKPGGSLRLSCAASGFTFSDYYMTWIRQGPGK GQEWISYISSGGSTIHYADSVKGRFTISRDNAKNSLYLQMNSLRA EDTAVYYCARENPRLPGTMDFDYWGQGTLVTVSS |
| 2.39 | SEQ ID NO: 577 DHFMS | SEQ ID NO: 578 NIKQDGSEKYYVD SVKG | SEQ ID NO: 579 EDPRLIGTTDF DN | SEQ ID NO: 580 QVQLVESGGGLVQPGGSLRLSCAASGFTFSDHFMSWFRQAPG KGLEWVANIKQDGSEKYYVDSVKGRFTISRDNAKNSLFLQMNSL RAEDTAMYYCAREDPRLIGTTDFDNWGQGTLVTVSS |

TABLE 2-continued

Full length sequences and CDR sequences of V_H single domain antibodies (Family 2)

| Name | CDR1 | CDR2 | CDR3 | Full Length |
|------|------|------|------|-------------|
| 2.40 | SEQ ID NO: 581 NYWMT | SEQ ID NO: 582 HISSTGSTIDYADS VKG | SEQ ID NO: 583 EDPRLPGTMD FDY | SEQ ID NO: 584 EVQLVESGGGLVQAGGSLRLSCVASGFTFSNYWMTWFRQAPG RGLEWVSHISSTGSTIDYADSVKGRFTISRDNAENSLYLQMNSLR AEDTAVYYCAREDPRLPGTMDFDYWGQGTLVTVSS |
| 2.41 | SEQ ID NO: 585 DYYMS | SEQ ID NO: 586 YISGSGDIIDYADS VKG | SEQ ID NO: 587 EDSRLIGTTDF DN | SEQ ID NO: 588 EVQLVESGGGLVKPGGSLRLSCAASGFTFSDYYMSWFRQAPGK GLEWVSYISGSGDIIDYADSVKGRFTISRDNAKNSLYLQMNNLR AEDTAVYHCAREDSRLTGTTDFDNWGQGTLVTVSS |
| 2.42 | SEQ ID NO: 589 DYYMS | SEQ ID NO: 590 YISGSGDIIDYADS VKG | SEQ ID NO: 591 EDSRLIGTTDF DN | SEQ ID NO: 592 EVQLVESGGGLVKPGGSLRVSCAASGFTFSDYYMSWIRQAPGK GLEWVSYISGSGDIIDYADSVKGRFTISRDNAKNSLYLQMNNLR AEDTAVYHCAREDSRLTGTTDFDNWGQGTLVTVSS |
| 2.43 | SEQ ID NO: 593 DYYMS | SEQ ID NO: 594 YISGSGDIIDYADS VKG | SEQ ID NO: 595 EDSRLIGTTDF DN | SEQ ID NO: 596 EVQLVESGGGLVKPGGSLRVSCAASGFTFSDYYMSWFRQAPGK GLEWVSYISGSGDIIDYADSVKGRFTISRDNAKNSLYLQMNNLR AEDTAVYYCAREDSRLIGTTDFDNWGQGTLVTVSS |
| 2.44 | SEQ ID NO: 597 DYYMS | SEQ ID NO: 598 YISGSGDIIDYADS VKG | SEQ ID NO: 599 EDSRLIGTTDF DN | SEQ ID NO: 600 EVQLVESGGGLVKPGGSLRVSCAASGFTFSDYYMSWFRQAPGK GLEWVSYISGSGDIIDYADSVKGRFTISRDNAKNSLYLQMNSLRA EDTAVYHCAREDSRLTGTTDFDNWGQGTLVTVSS |
| 2.45 | SEQ ID NO: 601 DYYMS | SEQ ID NO: 602 YISGSGDIIDYADS VKG | SEQ ID NO: 603 EDSRLIGTTDF DN | SEQ ID NO: 604 EVQLVESGGGLVKPGGSLRLSCAASGFTFSDYYMSWFRQAPGK GLEWVSYISGSGDIIDYADSVKGRFTISRDNAKNSLYLQMNNLR AEDTAVYYCAREDSRLIGTTDFDNWGQGTLVTVSS |
| 2.46 | SEQ ID NO: 605 DYYMS | SEQ ID NO: 606 YISGSGDIIDYADS VKG | SEQ ID NO: 607 EDSRLIGTTDF DN | SEQ ID NO: 608 EVQLVESGGGLVKPGGSLRLSCAASGFTFSDYYMSWIRQAPGK GLEWVSYISGSGDIIDYADSVKGRFTISRDNAKNSLYLQMNSLRA EDTAVYYCAREDSRLIGTTDFDNWGQGTLVTVSS |
| 2.47 | SEQ ID NO: 609 DYYMS | SEQ ID NO: 610 YISGSGDIIDYADS VKG | SEQ ID NO: 611 EDSRLIGTTDF DN | SEQ ID NO: 612 EVQLVESGGGLVKPGGSLRLSCAASGFTFSDYYMSWFRQAPGK GLEWVSYISGSGDIIDYADSVKGRFTISRDNAKNSLYLQMNSLRA EDTAVYYCAREDSRLIGTTDFDNWGQGTLVTVSS |
| 2.48 | SEQ ID NO: 613 DYYMS | SEQ ID NO: 614 YISGSGDIIDYADS VKG | SEQ ID NO: 615 EDARLIGTTDF DN | SEQ ID NO: 616 EVQLVESGGGLVKPGGSLRLSCAASGFTFSDYYMSWIRQAPGK GLEWVSYISGSGDIIDYADSVKGRFTISRDNAKNSLYLQMNSLRA EDTAVYYCAREDARLIGTTDFDNWGQGTLVTVSS |
| 2.49 | SEQ ID NO: 617 DYYMS | SEQ ID NO: 618 YISGSGDIIDYADS VKG | SEQ ID NO: 619 EDPRLIGTTDF DN | SEQ ID NO: 620 EVQLVESGGGLVKPGGSLRLSCAASGFTFSDYYMSWIRQAPGK GLEWVSYISGSGDIIDYADSVKGRFTISRDNAKNSLYLQMNSLRA EDTAVYYCAREDPRLIGTTDFDNWGQGTLVTVSS |
| 2.50 | SEQ ID NO: 621 DYYMS | SEQ ID NO: 622 YISGSGDIIDYADS VKG | SEQ ID NO: 623 EDARLIGTTDF DN | SEQ ID NO: 624 EVQLVESGGGLVKPGGSLRLSCAASGFTFSDYYMSWFRQAPGK GLEWVSYISGSGDIIDYADSVKGRFTISRDNAKNSLYLQMNSLRA EDTAVYYCAREDARLIGTTDFDNWGQGTLVTVSS |
| 2.51 | SEQ ID NO: 625 DYYMS | SEQ ID NO: 626 YISGSGDIIDYADS VKG | SEQ ID NO: 627 EDPRLIGTTDF DN | SEQ ID NO: 628 EVQLVESGGGLVKPGGSLRLSCAASGFTFSDYYMSWFRQAPGK GLEWVSYISGSGDIIDYADSVKGRFTISRDNAKNSLYLQMNSLRA EDTAVYYCAREDPRLIGTTDFDNWGQGTLVTVSS |

In some embodiments, there is provided a single $V_H$ domain antibody that is a variant of any of the above single $V_H$ domain antibodies shown in Table 1 or Table 2 and having one or more amino acid substitutions, deletions, insertions or other modifications, and which retains a biological function of the single domain antibody, that is binding to CD137 and, for example, blocking the binding of CD137L to CD137. Thus, variant single $V_H$ domain antibody can be sequence engineered. Modifications may include one or more substitution, deletion or insertion of one or more codons encoding the single domain antibody or polypeptide that results in a change in the amino acid sequence as compared with the native sequence single $V_H$ domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 25, for example 1 to 5, 1 to 10, 1 to 15, 1 to 20 amino acids, for example 1, 2, 3, 4, 5, 6, 7, 8, 9 or 10 amino acids. The variation allowed may be determined by systematically making insertions, deletions or substitutions of amino acids in the sequence and testing the resulting variants for activity exhibited by the full-length or mature native sequence. A variant of a $V_H$ single domain antibody described herein has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology to the non-variant molecule, for example at least 90%, 91%, 92%, 93%, 94%, 95%, 96%, 97%, 98% or 99% or at least 95%, 96%, 97%, 98% or 99% sequence homology. In one embodiment, there is provided a variant selected from SEQ ID Nos. 4, 312, 428, 624, 852, 856, 860, 864, 868, 872, 876 or 880 wherein said variant has 1 to 20, e.g. 1 to 10 amino acid substitutions compared to one of these sequences.

In one embodiment, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an sdAb of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody of the invention can be replaced with other amino acid residues from the same side chain family and the altered antibody can be tested for retained function (i.e., CD137 binding) using the functional assays described herein.

Thus, these amino acid changes can typically be made without altering the biological activity, function, or other desired property of the polypeptide, such as its affinity or its specificity for antigen. In general, single amino acid substitutions in nonessential regions of a polypeptide do not substantially alter biological activity. Furthermore, substitutions of amino acids that are similar in structure or function are less likely to disrupt the polypeptides' biological activity. Abbreviations for the amino acid residues that comprise polypeptides and peptides described herein, and conservative substitutions for these amino acid residues are shown in Table 3 below.

TABLE 3

Amino Acid Residues and Examples of Conservative Amino Acid Substitutions

| Original residue Three letter code, single letter code | Conservative substitution |
|---|---|
| Alanine, Ala, A | Gly, Ser |
| Arginine, Arg, R | Lys, His |
| Asparagine, Asn, N | Gln, His |
| Aspartic acid Asp, D | Glu, Asn |
| Cysteine, Cys, C | Ser, Ala |
| Glutamine, Gln, Q | Asn |
| Glutamic acid, Glu, E | Asp, Gln |
| Glycine, Gly, G | Ala |

TABLE 3-continued

Amino Acid Residues and Examples of Conservative Amino Acid Substitutions

| Original residue Three letter code, single letter code | Conservative substitution |
|---|---|
| Histidein, His, H | Asn, Gln |
| Isoleucine, Ile, I | Leu, Val |
| Leucine, Leu, L | Ile, Val |
| Lysine, lys, K | Ar, His |
| Methionine, Met, M | Leu, Ile, Tyr |
| Phenylalanine, Phe, F | Tyr, Met, Leu |
| Proline, Pro, P | Ala |
| Serine, Ser, S | Thr |
| Threonine, Thr, T | Ser |
| Tryptophan, Trp, W | Tyr, Phe |
| Tyrosine, Tyr, Y | Try, Phe |
| Valine, Val, V | Ile, Leu |

In some embodiments, the invention provides a $V_H$ single domain antibody that is a variant of a single domain antibody selected from those shown in Table 1 or 2 that comprises one or more sequence modification and has improvements in one or more of a property such as binding affinity, specificity, thermostability, expression level, effector function, glycosylation, reduced immunogenicity, or solubility as compared to the unmodified single domain antibody.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. The invention therefore also comprises sequence optimised variants of the single domain antibodies described herein.

In one embodiment, modifications can be made to decrease the immunogenicity of the single domain antibody. For example, one approach is to revert one or more framework residues to the corresponding human germline sequence. More specifically, a single domain antibody that has undergone somatic mutation may contain framework residues that differ from the germline sequence from which the single domain antibody is derived. Such residues can be identified by comparing the single domain antibody framework sequences to the germline sequences from which the single domain antibody is derived. In one embodiment, all framework sequences are germline sequence.

To return one or more of the amino acid residues in the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody.

In still another embodiment, glycosylation is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for the antigen.

In one embodiment, the one or more substitution is in the CDR1, 2 or 3 region. For example, there may be 1, 2, 3, 4, 5 or more amino acid substitutions in the CDR1, 2 or 3. In another example, there may be 1 or 2 amino acid deletions. In one embodiment, the one or more substitution is in the framework region. For example, there may be 1 to 10 or more amino acid substitutions in the CDR1, 2 or 3. In another example, there may be 1 to 10 or more amino acid deletions.

Examples of Substitutions

In one embodiment, the variant comprises one or more the following substitutions with reference to SEQ ID NO. 4 ($V_H$1.1) or combinations thereof:
F37V,
E61V+E65K
E65K
V70I
V79L
F37V+E61V+E65K+V70I+V79L
E61V+E65K+V70I+V79L
F37V+E61V+E65K+V70I+V79L+G55E+D101V+ D105I
F37V+E61V+E65K+V70I+V79LFGL+G55E+D101E+ D105I
E61V+E65K+V70I+V79L+G55E
E61V+E65K+V70I+V79L+G55E+D105I
E61V+E65K+V70I+V79L+D54G, E61V+E65K+V70I+ V79L+D54E,
E61V+E65K+V70I+V79L+D101E
E61V+E65K+V70I+V79L+D101V or
E61V+E65K+V70I+V79L+G55E+D101V+D105I, E61V+E65K+V70I+V79L+G55E+D101E+D105I In one embodiment, the variant comprises one or more the following substitutions with reference to SEQ ID NO. 4 ($V_H$1.1) or combinations thereof:
a) E61V+E65K+V70I+V79L+G55E+D101→any amino acid selected from the following F, L, I, M, V, S, P, T, A, Y, H, Q, K, D, W, R, G;
b) E61V+E65K+V70I+V79L+G55E+D105→any amino acid selected from the following F, L, M, S, P, T, A, Y, H, Q, N, K, D, E, W, R, G or
c) E61V+E65K+V70I+V79L+G55E, D101→any amino acid selected from the following F, L, I, M, V, S, P, T, A, Y, H, Q, K, D, W, R, G+D105→any amino acid selected from the following F, L, M, S, P, T, A, Y, H, Q, N, K, D, E, W, R, G.

In one embodiment, the variant comprises one or more the following substitutions with reference to SEQ ID NO. 312 ($V_H$1.78) or combinations thereof:
Q1E+T25S
Q1E+S84N
Q1E+F95Y
Q1E+T25S+S84N
Q1E+T25S+F95Y
Q1E+S84N+F95Y
Q1E+T25S+S84N+F95Y or
Q1E+T25S+G55E+S84N+F95Y In one embodiment, the variant comprises one or more the following substitutions with reference to SEQ ID NO. 428 ($V_H$2.1) or combinations thereof:
V20L,
F37I,
N85S,
N95Y,
V20L+H95Y
V20L+F37I+N85S+H95Y, V20L+N85S+H95Y,
V20L+F37I+N85S+H95Y+S101A,
V20L+F37I+N85S+H95Y+S101P or
V20L+N85S+H95Y+S101A, V20L+N85S+H95Y+ S101A.

to SEQ ID NO. 624 ($V_H$2.50) or combinations thereof:
S35T+V48I+I57T+L103M+T104R+T107I
S35T+A101T+L103V+T104R+T107V
S35T+V48I+I57T+A101E+L103L+T104W+T107V
S35T+V48I+L103T+T104R+T107V
Y32H+S35T+V48I+S52G+S54D+D56A+I58L+A101L+ T104P+T107I+N111H
S35T+A101T+L103V+T104R+T107V+N111S
A28T+S30T+Y33W+S35T+V48I+G53S+S54D+D56K+ I57T+L103M+T104P+T107I+N111Y
S35T+V48I+L103T+T104R+T107V+N111S
S35T+V48I+I57T+S101E+T104W+T107V+N111S or
S35T+V48I+I57T+L103M+T104R+T107I+N111S Exemplary Features Single $V_H$ domain antibodies described herein have shown excellent stability. Furthermore, $V_H$ single domain antibodies described herein show specificity for human CD137. $V_H$ single domain antibodies described herein also inhibit binding of CD137L to CD137.

The single $V_H$ domain antibodies of the invention preferably have KD, $IC_{50}$ and/or EC50 values as further described herein and as shown in the examples. For example, the KD can be least about 0.4 nM or about 3 nM. 1050 and/or EC50 values can be as shown in the examples.

The term "KD" refers to the "equilibrium dissociation constant" and refers to the value obtained in a titration measurement at equilibrium, or by dividing the dissociation rate constant (Koff) by the association rate constant (Kon). "KA" refers to the affinity constant. The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® assay can be used.

In one embodiment, a monovalent single $V_H$ domain antibody as described herein is not internalised or substantially not internalised. Internalisation can be measured as in the examples.

Exemplary Nucleic Acids

The present invention further provides an isolated nucleic acid encoding a single domain antibody of the present invention. Nucleic acid may include DNA and/or RNA. In one aspect, the present invention provides a nucleic acid that codes for a CDR, for example CDR3, a set of two or three CDRs or a full length single $V_H$ domain antibody of the invention as shown above.

In one aspect, the invention thus also relates to a nucleic acid sequences comprising or consisting of a sequence selected from those shown in table 4 or table 5.

TABLE 4

Nucleic acids encoding V$_H$ 1.1 to 1.114

Name Nucleotide Sequence 1.1 GAGGTGCAGCTGGTGGAGTCTGGGGGAGGCTTGGTCCAGCCGGGGGGTCCCTGAGACTCTCCTGTGCAGCCTCTG
GATTCACCTTTAGTAGCCATTGGATGACTTGGTTCCGTCAGGCTCCAGGGAAGGGGCTGGAGTGGGTGGCCCACATA
AAGGAAGACGGAAGTGAGAAATACTATGAGGACTCTGTGGAGGGCCGATTCACCGTCTCCAGAGACAACGCCAAGA
ACTCGGTATATCTGCAAATGAACAGTCTGAGAGCCGAAGACACGGCTGTGTATTACTGTGCGAGAGGAGGTGATGGC
TACAGTGACTCCCACTTCGGTGTGGACGTCTGGGGCCAAGGGACCACGGTCACTGTCTCTTCA
SEQ ID NO. 629

1.2 GAGGTGCAGCTGGTGGAGTCTGGGGGAGGCTTGGTCCAGCCGGGGGGTCCCTGAGACTCTCCTGTGCAGCCTCTG
GATTCACCTTTAGTAGTTATTGGATGACTTGGTTCCGTCAGGCTCCAGGGAAGGGGCTGGAGTGGGTGGCCCACATA
AAGGAAGACGGAAGTGAGAAATACTATGTGGACTCTGTGGAGGGCCGATTCACCATCTCCAGAGACAACGCCAATAA
CTCGCTGTATCTACAAATGAACAGCCTGAGAGCCGAGGACACGGCTGTGTATTACTGTGCGAGAGGAGGTGATGGCT
ACAGTGACTCCCACTACGGTGTGGACGTCTGGGGCCAAGGGACCACGGTCACCGTCTCCTCA
SEQ ID NO. 630

1.3 GAGGTGCAGCTGGTGGAGTCTGGGGGAGGCTGGTCCAGCCTGGGGGGTCCCTGAGACTCTCCTGTGCAGCCTCTG
GATTCACCTTTAGTAGTTATTGGATGACCTGGTTCCGCCAGGCTCCAGGGAGGGGCTGGAGTGGGTGGCCAACATA
AACCAAGATGGAAGTGAGAAATACTATGTGGACTCTGTGGAGGGCCGATTCACCGTCTCCAGAGACAACGCCAAGAA
CTCACTGTATCTGCAAATGAACAGCCTGAGAGCCGAGGACACGGCTGTGTATTACTGTGCGAGAGGGGGATTAGGCT
ACGGTGACTCCCACTACGGTATGGACGTCTGGGGCCAAGGGACCACGGTCACTGTCTCCTCA
SEQ ID NO. 631

1.4 GAGGTGCAGCTGGTGGAGTCTGGGGGAGGCTTGGTCCAGCCGGGGGGTCCCTGAGACTCTCCTGTGCAGCCTCTG
GATTCACCTTTAGTAACTATTGGATGACCTGGTTCCGCCAGGCTCCAGGGGGGGGCTGGAGTGGGTGGCCAACATA
AACCAAGATGGAAGTGAGAAATACTATGTGGACTCTGTGGAGGGCCGATTCACCGTCTCCAGAGACAACGCCAAGAA
CTCACTGTATCTACAAATGAACAGCCTGAGAGCCGAGGACACGGCTGTGTATTACTGTGCGAGAGGGGGATTAGGCT
ACGGTGACTCCCACTACGGTATGGACGTCTGGGGCCAAGGGACCACGGTCACTGTCTCCTCA
SEQ ID NO. 632

1.5 GAGGTGCAGCTGGTGGAGTCTGGGGGAGGCTGGTCCAGCCTGGGGGGTCCCTGAGACTCTCCTGTGCAGCCTCTG
GATTCACCTTTAGTAACTATTGGATGATCTGGTTCCGCCAGGCTCCAGGAAAGGGGCTGGAGTGGGTGGCCAACATA
AACCAAGATGGAAGTGAGAAATACTATGTGGACTCTGTGGAGGGCCGATTCACCATCTCCAGAGACAACGCCAAGAA
CTCACTGTATCTGCAAATGAACAGCCTGAGAGCCGAAGACACGGCTGTGTATTACTGTGCGAGAGGAGGTGATGGCT
ACAGTGGCTCCCACCACGGTACGGACGTCTGGGGCCAAGGGACCACGGTCACCGTCTCCTCA
SEQ ID NO. 633

1.6 GAGGTGCAGCTGGTGGAGTCTGGGGGAGGCTGGTCCAGCCTGGGGGGTCCCTGAGACTCTCCTGTGCAGCCTCTG
GATTCACCTTTAGTAGCTATTGGATGAGCTGGGTCCGCCAGGCTCCAGGGAAGGGGCTGGAGTGGGTGGCCAACATA
AAGCAAGATGGAAGTGAGAAATACTATGTGGACTCTGTGGAGGGCCGATTCACCATCTCCAGAGACAACGCCAAGAA
CTCACTGTATCTGCAAATGAACAGCCTGAGAGCCGAGGACACGGCTGTGTATTACTGTGCGAGAGGGGGGAAGGC
TATAGCACCTCGCACTACGGTATGGACGTCTGGGGCCAAGGGACCACGGTCACCGTCTCCTCA
SEQ ID NO. 634

1.7 GAGGTGCAGCTGGTGGAGTCTGGGGGAGGCTGGTCCAGCCTGGGGGGTCCCTGAGACTCTCCTGTGGAGCCTCTG
GATTCACCTTTAGTAGCTATTGGATGCTCTGGTTCCGCCAGGCTCCAGGGAAGGGGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCTGTATCTGCAAATGAACACCCTGAGAGCCGAGGACACGGCTATTTATTATTGTGCGAGAGGGGGTGATGGCT
ACAGTGACTCCCACTTCGGTACGGACGTCTGGGGCCAAGGGACCACGGTCACTGTCTCCTCA
SEQ ID NO. 635

1.8 GAGGTGCAGCTGGTGGAGTCTGGGGGAGGCTGGTCCAGCCTGGGGGGTCCCTGAGACTCTCCTGTGGAGCCTCTG
GATTCACCTTTAGTAGCTATTGGATGTTCTGGTTCCGCCAGGCTCCAGGAGAGGGGCTGGAGTGGGTGGCCAACATA
AACCAAGATGGAAGTGAGAAATACTATGTGGACTCTGTGGAGGGCCGATTCACCATCTCCAGAGACAACGCCAAGAA
CTCTCTGTATCTGCAAATGAACAGCCTGAGAGCCGAGGACACGGCTATTTATTACTGTGCGAGAGGAGGTGATGGCT
ACAGTGATTCCCACTACGGTACGGACGTCTGGGGCCAAGGGACCACGGTCACCGTCTCCTCA
SEQ ID NO. 636

1.9 GAGGTGCAGCTGGTGGAGTCTGGGGGAGGCTTGGTCCAGCCGGGGGGGTCCCTGAGACTCTCCTGTGCAGCCTCTG
GATTCACCTTTAGTAACTATTGGATGACCTGGTTCCGCCAGGCTCCAGGGGGGGGCTGGAGTGGGTGGCCAACATA
AACCAAGATGGGAGTGAGAAGTACTATGTGGACTCTGTGGAGGGCCGATTCACCGTCTCCAGAGACAACGCCAAGAA
CTCACTGGATCTGCAAATGAACAGCCTGAGAGCCGAGGACACGGCTGTGTATTACTGTGCGAGAGGGGGATTAGGCT
ACGGTGACTCCCACTACGGTATGGACGTCTGGGGCCAAGGGACCACGGTCACCGTCTCCTCA
SEQ ID NO. 637

1.10 GAGGTGCAGCTGGTGGAGTCTGGGGGAGGCTTGGTCCAGCCTGGGGGGTCCCTGAGACTCTCCTGTGCAGCCTCTG
GATTCACCTTTAGTGACTATTGGATGAACTGGGCCCGCCAGGCTCCAGGGAAGGGGCTGGAGTGGGTGGCCAACATA
AAGGAGGATGGAAGTGAGAAATACTATGTGGACTCTGTGGAGGGCCGATTCACCATATCCAGAGACAACGCCAAGA
ACTCAACGTATCTGCAAATGAACAGCCTGAGAGTCGAGGACACGGCTGTGTATTACTGTGCGAGAGGAGGGGCCGG
GTATAGCATGTCTCACTACGGTATGGACGTCTGGGGCCAAGGGACCACGGTCACTGTCTCTTCA
SEQ ID NO. 638

1.11 GAGGTGCAGCTGGTGGAGTCTGGGGGAGGCTGGTCCAGCCTGGGGGGTCCCTGAGACTCTCCTGTGAAGCCTCTG
GATTCACCTTTAGTGACTATTGGATGAACTGGGCCCGCCAGGCTCCAGGGAAGGGGCTGGAGTGGGTGGCCAACATA
AAGGAGGATGGAAGTGAGAAATACTATGTGGACTCTGTGGAGGGCCGATTCACCATATCCAGAGACAACGCCAAGA
ACTCAACGTATCTGCAAATGAACAGCCTGAGAGCCGAGGACACGGCTGTGTATTACTGTGCGAGAGGAGGGGCCGG
GTATAGTATGTCTCACTACGGTATGGACGTCTGGGGCCAAGGGACCACGGTCACTGTCTCCTCA
SEQ ID NO. 639

TABLE 4-continued

Nucleic acids encoding V$_H$ 1.1 to 1.114

Name Nucleotide Sequence 1.12 GAGGTGCAGCTGGTGGAGTCTGGGGGAGGCTGGTCCAGCCTGGGGGGTCCCTGAGACTCTCCTGTGGAGCCTCTG
GATTCACCTTTAGTAGCTATTGGATGCTCTGGTTCCGCCAGGCTCCAGGGAAGGGGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCACTGTATCTGCAAATGAACACCCTGCGAGCCGAGGACACGGCTATTTATTATTGTGCGAGAGGGGGTGATGGCTA
CAGTAACTCCCACTTCGGTACGGACGTCTGGGGCCAAGGGACCACGGTCACCGTCTCTTCA
SEQ ID NO. 640

1.13 GAGGTGCAGCTGGTGGAGTCTGGGGGAGGCTTGGTCAAGCCTGGGGGGTCCCTGAGACTCTCCTGTGGAGCCTCTG
GATTCACCTTTAGTAGCTATTGGATGTTCTGGTTCCGCCAGGCTCCAGGAGAGGGGCTGGAGTGGGTGGCCAACATA
AACCAAGATGGAAGTGAGAAATACTATGTGGACTCTGTGGAGGGCCGATTCACCATCTCCAGAGACAACGCCAAGAA
CTCTCTGTATCTGCAAATGAACAGCCTGAGAGCCGAGGACACGGCTATTTATTACTGTGCGAGAGGAGGTGATGGCT
ACAGTGATTCCCACTACGGTACGGACGTCTGGGGCCAAGGGACCACGGTCACCGTCTCCTCA
SEQ ID NO. 641

1.14 GAGGTGCAGCTGGTGGAGTCTGGGGGAGGCTGGTCCAGCCTGGGGGGTCCCTGAGACTCTCCTGTGCAGCCTCTG
GATTCACCTTTAGTAATTATTGGATGAACTGGGTCCGCCAGGCTCCAGGGAAGGGGCTGGAGTGGGTGGCCAACATA
AAGGAAGATGGAAGTGAGAATTACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTTTATTACTGTGCGAGAGGGGGGGAAGGCT
ATAGCACCTCGCACTACGGTATGGACGTCTGGGGCCAAGGGACCACGGTCACTGTCTCCTCA
SEQ ID NO. 642

1.15 GAGGTGCAGCTGGTGGAGTCTGGGGGAGGCTGGTCCAGCCTGGGGGGTCCCTGAGACTCTCCTGTGGAGCCTCTG
GATTCACCTTTAGTACCTATTGGATGCTCTGGTTCCGCCAGGCTCCAGGGAAGGGGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCACTGTCTCTACAAATGAACAGCCTGAGAGCCGAGGACACGCAACTTATTACTGTGCGAGAGGAGGTGATGGCT
ACAGTGACTCCCACTTCGGTACGGACGTCTGGGGCCAAGGGACCACGGTCACCGTCTCCTCA
SEQ ID NO. 643

1.16 GAGGTGCAGCTGGTGGAGTCTGGGGGAGGCTTGGTCCAGCCTGGGGGGTCCCTGAGACTCTCCTGTGTAGCCTCTGG
ATTCACCTTTAGTAACTATTGGATGATGTGGTTCCGCCAGGCTCCAGGAAAGGGGCTGGAGTGGGTGGCCAACATAA
ACCAAGATGGAAGTGAGAAATACTTTGTGGACTCTGTGGAGGGCCGATTCACCATCTCCAGAGACAACGCCAAGAAC
TCACTGTATCTGCAAATGAACAGCCTGAGAGCCGAAGACACGGCTGTGTATTACTGTGCGAGAGGAGGTGATGGCTA
CAGTAGCTCTCACTACGGTACGGACGTCTGGGGCCAAGGGACCACGGTCACCGTCTCTTCA
SEQ ID NO. 644

1.17 GAGGTGCAGCTGGTGGAGTCTGGGGGAGGCTGGTCCAGCCTGGGGGGTCCCTGAGACTCTCCTGTGCAGCCTCTG
GATTCACCTTTAGTAGCTATTGGATGAACTGGGTCCGCCAGGCTCCAGGGAAGGGGCTGGAGTGGGTGGCCAACATA
AAGGAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTGTATTACTGTGCGAGAGGGGGGGACAGCT
ATGGTTACAGGGACTACGGTATGGACGTCTGGGGCCAAGGGACCACGGTCACTGTCTCCTCA
SEQ ID NO. 645

1.18 GAGGTGCAGCTGGTGGAGTCTGGGGGAGGCTGGTCCAGCCTGGGGGGTCCCTGAGACTCTCCTGTGCAGCCTCTG
GATTCACCTTTAGTACCCATTGGATGAACTGGGCCCGCCAGGCTCCAGGGAAGGGAGCTGGAATGGGTGGCCAACATA
AACCAAGATGGAAGTGAGAAATACTATGTGGACTCTGTGGAGGGCCGATTCACCATCTCCAGAGACAACGCCAACAA
TTCACTGTATCTGCAAATGAACAGCCTGAGAGCCGAAGACACGGCTGTATATTACTGTGCGAGAGGGGGGGTTGGCT
ACGGTGACTCCCACTTCGGTATGGACGTCTGGGGCCTAGGGACCACGGTCACCGTCTCCTCA
SEQ ID NO. 646

1.19 GAGGTGCAGCTGGTGGAGTCTGGGGGAGGCTGGTCCAGCCTGGGGGGTCCCTGAGACTCTCCTGTGCAGCCTCTG
GATTCACCTTTAGTAGCTATTGGATGATCTGGGTCCGCCAGGCTCCAGGGAAGGGGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTGTATTACTGTGCGAGAGGAGGTGATGACT
ACAGTAACTCCCACTACGGTATGGACGTCTCGGCCAAGGGACCACGGTCACCGTCTCCTCA
SEQ ID NO. 647

1.20 GAGGTGCAGCTGGTGGAGTCTGGGGGAGGCTGGTCCAGCCTGGGGGGTCCCTGAGACTCTCCTGTGCAGCCTCTG
GATTCACCTTTAGTAGCTATTGGATGAACTGGGTCCGCCAGGCTCCAGGGAAGGGGCTGGAGTGGGTGGCCAACATA
AACCAAGATGGAAGTGAGAAATACTATGTGGACTCTGTGCAGGGCCGATTCACCATCTCCAGAGACAATGCCAATAA
CTCACTGTATCTGCAAATGAACAGCCTGAGAGCCGAGGACACGGCTGTGTATTACTGTGCGAGAGGGGGGTTTGGCT
ACGGTGACTCCCACTACGGTATGGACGTCTGGGGCCAAGGGACCACGGTCACCGTCTCCTCA
SEQ ID NO. 648

1.21 GAGGTGCAGCTGGTGGAGTCTGGGGGAGGCTGGTCCAGCCTGGGGGGTCCCTGAGACTCTCCTGTGGAGCCTCTG
GATTCACCTTTAGTAGTTATTGGATGTTCTGGTTCCGCCAGGCTCCAGGAAAGGGAGCTGGAGTGGGTGGCCAATGTTA
ACCAAGATGGAAGTGAGAAATACTATGTGGACTCTGTGGAGGGCCGATTCACCATCTCCAGAGACAACGCCAAGAAC
TCACTGTATCTGCAAATGAACAGCCTGAGAGCCGAGGACACGGCTATTTATTACTGTGCGAGAGGAGGTGAGGGCTA
CAGTGATTCCCACTACGGTACGGACGTCTGGGGCCAAGGGACCACGGTCACCGTCTCCTCA
SEQ ID NO. 649

1.22 CAGGTGCAGCTGGTGGAGTCTGGGGGAGGCTTGGTCCAGCCTGGGGGGTCCCTGAGACTCTCCTGTGCAGCCTCTGG
ATTCACCTTTAGTAACTATTGGATGAACTGGGTCCGCCAGGCTCCAGGGAAGGGGCTGGAGTGGGTGGCCAATATAA
AGGAAGATGGAAGTGAGAAATACTATGTGGACTCTGTGGAGGGCCGATTCACCATCTCCAGAGACAACGCCAGGAA

TABLE 4-continued

Nucleic acids encoding V<sub>H</sub> 1.1 to 1.114

Name Nucleotide Sequence

CTCACTGTATCTGCAAATGAACAGTCTGAGAGCCGAGGACACGGCTGTGTATTACTGTGCGAGAGGGGGGAGGGC
TACGGTGACTCCCACTACGGTATGGACGTCTCGGGCCAAGGGACCACGGTCACTGTCTCTTCA
SEQ ID NO. 650

1.23 CAGGTGCAGCTGGTGGAGTCTGGGGGAGGCTTGGTCCAGCCTGGGGGGTCCCTGAGACTCTCCTGTGCAGCCTCTGG
ATTCACCTTTAGTAGTTATTGGATGAACTGGGTCCGCCAGGCTCCAGGGAAGGGGCTGGAGTGGGTGGCCAACATAA
AGCAAGATGGAAGTGAGAAATACTATGTGGACTCTGTGAAGGGCCGATTCACCATCTCCAGAGACAACGCCAAGAAC
TCACTTTATCTGCAAATGAACAGCCTGACAGCCGAGGACACGGCTGTGTATTATTGTGCGAGAGGGGGGAGGGCTA
CGGTGACGACCACTACGGTATGGACGTCTGGGGCCAAGGGACCACGGTCACTGTCTCTTCA
SEQ ID NO.651

1.24 CAGGTGCAGCTGGTGGAGTCTGGGGGAGGCTTGGTCCAGCCTGGGGGGTCCCTGAGACTCTCCTGTGCAGCCTCTGG
ATTCACCTTTAGTAGCTATTGGATGAGCTGGGTCCGCCAGGCTCCAGGGAAGGGGCTGGAGTGGGTGGCCAACATAA
AGCAAGATGGAAGTGAGAAATACTATGTGGACTCTGTGAAGGGCCGATTCACCATCTCCAGAGACAACGCCAAGAAC
TCACTGTATCTGCAAATGAACAGCCTGAGAGCCGAGGACACGGCTGTGTATTACTGTGCGAGAGGGGGGAGGGCT
ACGGTGACTACCACTACGGTTTGGACGTCTCGGGCCAAGGGACCACGGTCACCGTCTCCTCA
SEQ ID NO. 652

1.25 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAGCTATTGGATGAACTGGGTCCGCCAGGCTCCAGGGAAGGGGCTGGAGTGGGTGGCCAACATA
AAGCAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTGTATTACTGTGCGAGAGGGGGGGACAGCT
ATGGTTACAGGGACTACGGTATGGACGTCTGGGGCCAAGGGACCACGGTCACCGTCTCCTCA
SEQ ID NO. 653

1.26 GAGGTGCAGCTGGTGGAGTCTGGGGGAGGCTTGGTCCAGCCTGGGGGGTCCCTGAGACTCTCCTGTGTAGCCTCTGG
ATTCACCTTTAGTACCCATTGGATGAACTGGGCCCGCCAGGCTCCAGGGAAGGAGCTGGAATGGGTGGCCAACATAA
ACCAAGATGGAAGTGAGAAATACTATGTGGACTCTGTGGAGGGCCGATTCACCATCTCCAGAGACAACGCCAACAAT
TCACTGTATCTGCAAATGAACAGCCTGAGAGCCAAGACACGGCTGTATATTACTGTGCGAGAGGGGGGGTTGGCTA
CGGTGACTCCCACTTCGGTATGGACGTCTGGGGCCTAGGGACCACGGTCACTGTCTCCTCA
SEQ ID NO. 654

1.27 GAGGTGCAGCTGGTGGAGTCTGGGGGAGGCTTGGTCCAGCCTGGGGGGTCCCTGAGACTCTCCTGTGGAGCCTCTG
GATTCACCTTTAGTAGTTATTGGATGCTCTGGTTCCGCCAGGCTCCAGGAGAGGGGCTGGAGTGGGTGGCCAACATA
AACCAAGATGGAAGTGAGAAATACTATGTGGACTCTGTGGAGGGCCGACTCACCATCTCCAGAGACAACGCCAAGAA
CGCTCTGTATCTGCAAATGAACAGCCTGAGAGCCGAGGACACGGCTATTTATTACTGTGCGAGAGGAGGTGAAGGCT
ACAGTGATTCCCACCACGGTACGGACGTCTGGGGCCAAGGGACCACGGTCACTGTCTCTTCA
SEQ ID NO. 655

1.28 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAACTATTGGATGAACTGGGTCCGCCAGGCTCCAGGGAAGGGGCTGGAGTGGGTGGCCAACATA
AAGCAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTGTATTACTGTGCGAGAGGGGGGGACAACT
ATGCTTACAGGGACTTCGGTATGGACGTCTGGGGCCAAGGGACCACGGTCACTGTCTCTTCA
SEQ ID NO.656

1.29 GAGGTGCAGCTGGTGGAGTCTGGGGGAGGCTGGTCCAGCCTGGGGGGTCCCTGAGACTCTCCTGTGGAGCCTCTG
GATTCACCTTTAGTAATTATTGGATGTTCTGGTTCCGCCAGGCTCCAGGAAAGGAGCTGGAGTGGGTGGCCAATGTTA
ACCAAGATGGAAGTGAGAAATACTATGTGGACTCTGTGGAGGGCCGATTCACCATCTCCAGAGACAACGCCAAGAAC
TCACTGTATCTGCAAATGAACAGCCTGAGAGCCGAGGACACGGCTATTTATTACTGTGCGAGAGGAGGTGAGGGCTA
CAGTGATTCCCACTACGGTACGGACGTCTGGGGCCAAGGGACCACGGTCACTGTCTCTTCA
SEQ ID NO. 657

1.30 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAGCTATTGGATGAACTGGGTCCGCCAGGCTCCAGGGAAGGGGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTGTATTACTGTGCGAGAGGGGGGAAGAG
TATGGGAGCTCGCACTACGGTATGGACGTCTGGGGCCTGGGGACCACGGTCACTGTCTCCTCA
SEQ ID NO. 658

1.31 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAGCTATTGGATGAACTGGGTCCGCCAGGCTCCAGGGAAGGGGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTGTATTATTGTGCGAGAGGGGGGGACAGCT
ATGGTTACAGGGACTACGGTATGGACGTCTGGGGCCAAGGGACCACGGTCACTGTCTCTTCA
SEQ ID NO. 659

1.32 GAGGTGCAGCTGGTGGAGTCTGGGGGAGGCTTGGTCCAGCCGGGGGGTCCCTAAGACTCTCCTGTGCAGCCTCTG
GATTCACCTTTAGTAGTTATTGGATGAACTGGGTCCGCCAGACTCCAGGGAAGGGGCTGGAGTGGGTGGCCAACATA
AATCAAAATGGAAGTGAGAAATACTATGTGGACTCTGTGAAGGGCCGATTCAACATCTCCAGAGACAACGCCAAGAA
CTCACTGTATCTACAAATGAGTAGCCTGAGAGCCGAGGACACGGCTGTGTATTACTGTGCGAGAGGGGGTTTGGCT
ACGGTGATTCCCACTACGGTATGGACGTCTGGGGCCAAGGGACCACGGTCACTGTCTCTTCA
SEQ ID NO. 660

1.33 GAGGTGCAGCTGGTGGAGTCTGGGGGAGGCTTGGTCCAGGCGGGGGGTCCCTAAGACTCTCCTGTGTAGCCTCTG
GATTCACCTTTAGTAATTATTGGATGACCTGGTTCCGCCAGGCTCCAGGGAAGGGGCTGGAGTGGGTGGCCAACATA

TABLE 4-continued

Nucleic acids encoding V$_H$ 1.1 to 1.114

Name Nucleotide Sequence

AACCAAGATGAAAGTGAGGAATACTATGTGGACTCTGTGAAGGGCCGTTTCACCATCTCCAGAGACAACGCCAAGAA
CTCACTGTTTCTGCAAATGAACAGCCTGAGAGCCGAGGACACGGCTATTTATTACTGTGCGAGAGGAGGTGATGGCT
ACAGTGACTCCCACTACGGTACGGACGTCTGGGGCCAAGGGACCACGGTCACTGTCTCTTCA
SEQ ID NO. 661

1.34 CAGGTGCAGCTGCAGGAGTCGGGGGGAGGCTTGGTCCAGCCTGGGGGGTCCCTGAGACTCTCCTGTACAGCCTCTG
GATTCACCTTTAGTAATTATTGGATGAACTGGGTCCGCCAGGCTCCAGGGAAGGGGCTGGAGTGGGTGGCCAACATA
AAGGAAGATGGAAGTGAGAATTACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTTTATTACTGTGCGAGAGGGGGGGAAGGCT
ATAGCACCTCGCACTACGGTATGGACGTCTGGGGCCAAGGGACCACGGTCACCGTCTCTTCA
SEQ ID NO. 662

1.35 CAGGTGCAGCTGGTGGAGTCTGGGGGAGGCTTGGTCCAGCCTGGGGGGTCCCTGAGACTCTCCTGTGCAGCCTCTGG
ATTCACCTTTAGTAACTATTGGATGAACTGGGTCCGCCAGGCTCCAGGGAAGGGGCTGGAGTGGGTGGCCAACATTA
AGCAAGATGGAAGTGAGAAATACTATGTGGACTCTGTGGAGGGCCGATTCACCATCTCCAGAGACAACGCCAAGAAC
TCACTGTATCTGCAAATGGACAGCCTGAGAGCCGAGGACACGGCTGTTTATTACTGTGCGAGAGGGGGGGAGGGCT
ACGGTGAATCCCACTACGGTATGGACGTCTCGGGCCAAGGGACCACGGTCACCGTCTCTTCA
SEQ ID NO. 663

1.36 GAGGTGCAGCTGGTGGAGTCTGGGGGAGGCTTGGTCCAGCCTGGGGGGTCCCTGAGACTCTCCTGTGCAGCCTCTG
GATTCACCTTTAGTACCTATTGGATGAACTGGGTCCGCCAGGCTCCAGGGAAGGGGCTGGAGTGGGTGGCCAACATA
AAACAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTGTGTATTACTGTGCGAGAGGGGGGGACAGCT
ATGGTTACAGGGACTACGGTATGGACGTCTGGGGCCAAGGGACCACGGTCACTGTCTCCTCA
SEQ ID NO. 664

1.37 GAGGTGCAGCTGGTGGAGTCTGGGGGAGGCTTGGTCCAGCCTGGGGGGTCCCTGAGACTCTCCTGTGCAGCCTCTG
GATTCACCTTTAGTTACTATTGGATGATCTGGTTCCGCCAGGCTCCAGGTGAGGAGCTGGAGTGGGTGGCCAACATAA
ACCAAGATGGAAGTGAGAAATACTATGTGGACTCTGTGAAGGGCCGATTCATTATCTCCAGAGACAACGCCACGAAC
TCACTGTTTCTGCAAATGAACAGCCTGAGAGCCGAGGACACGGCTGTTTATTACTGTGCGAGAGGAGGTGATGGCTA
CAGTAATTCCCACTTCGGTATGGACGTCTGGGGCCAAGGGACCACGGTCACCGTCTCTTCA
SEQ ID NO. 665

1.38 GAGGTGCAGCTGGTGGAGTCTGGGGGAGGCTGGTCCAGCCTGGGGGGTCCCTGAGACTCTCCTGTGCAGCCTCTG
GATTCACCTTTAGTAACTATTGGATGATCTGGTACCGCCAGGCTCCAGGTGAGGAGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCACTGTATCTGCAAATGAACAGCCTGAGAGCCGAGGACACGGCTATTTATTACTGTGCGAGAGGAGGTGAGGGCT
ACAGTGATTCCCACTACGGTACGGACGTCTGGGGCCAGGGGACCACGGTCACTGTCTCTTCA
SEQ ID NO. 666

1.39 GAGGTGCAGCTGGTGGAGTCTGGGGGAGGCTGGTCCAGCCTGGGGGGTCCCTGAGACTCTCCTGTGCAGCCTCTG
GATTCACCTTTAGTAACTATTGGATGAACTGGGTCCGCCAGGCTCCAGGGAAGGGGCTGGAGTGGGTGGCCAACATA
AACCAAGATGAAAGTGAAAAATACTATGTTGACTCTGTGAAGGGCCGTTTCACCGTCTCCAGAGACAACGCCAAGAA
CTCACTGTTTCTGCAAATGAACAGCCTGAGAGCCGACGACACGGCTGTATATTACTGTGCGAGAGGGGGGTTTGGCT
ACGGTGACTCCCACTTCGGTATGGACGTCTGGGGCCAAGGGACCACGGTCACCGTCTCTTCA
SEQ ID NO.667

1.40 GAGGTGCAGCTGGTGGAGTCTGGGGGAGGCTGGTCCAGCCTGGGGGGTCCCTGAGACTCTCCTGTGGAGCCTCTG
GATTCACCTTTAGTAATTATTGGATGTTCTGGTTCCGCCAGGCTCCAGGAAAGGAGCTGGAGTGGGTGGCCAATGTTA
ACCAAGATGGAAGTGAGAAATACTATGTGGACTCTGTGGAGGGCCGATTCACCATCTCCAGAGACGACGCCAAGAAC
TCACTGTATCTGCAAATGAACAGCCTGAGAGCCGAGGACACGGCTATTTATTACTGTGCGAGAGGAGGTGAGGGCTA
CAGTGATTCCCACTACGGTACGGACGTCTGGGGCCAAGGGACCACGGTCACTGTCTCTTCA
SEQ ID NO.668

1.41 GAGGTGCAGCTGGTGGAGTCTGGGGGAGGCTTGGTCCAGCCTGGGGGGTCCCTGAGACTCTCCTGTGGAGCCTCTG
GATTCACCTTTAGTAATTATTGGATGTTCTGGTTCCGCCAGGCTCCAGGAAAGGAGCTGGAGTGGGTGGCCAATGTTA
ACCAAAATGGAAGTGAGAAATACTATGTGGACTCTGTGGAGGGCCGATTCACCATCTCCAGAGACAACGCCAAGAAC
TCACTGTATCTGCAAATGAACAGCCTGAGAGCCGAGGACACGGCTATTTATTACTGTGCGAGAGGAGGTGAGGGCTA
CAGTGATTCCCACTACGGTACGGACGTCTGGGGCCAAGGGACCACGGTCACTGTCTCCTCA
SEQ ID NO. 669

1.42 CAGGTGCAGCTGGTGGAGTCTGGGGGAGGCTTGGTCCAGCCTGGGGGGTCCCTGAGACTCTCCTGTGCAGCCTCTGG
ATTCACCTTTAGTAACTATTGGATGAACTGGGTCCGCCAGGCTCCAGGGAAGGGGCTGGAGTGGGTGGCCAACATA
AGCAAGATGGAAGTGAGAAATACTATGTGGACTCTGTGAAGGGCCGATTCACCATCTCCAGAGACAACGCCAAGGAC
TCACTGTATCTGCAAATGAACAGCCTGAGAGCCGAGGACACGGCTATTTATTATTGTGCGAGAGGGGGGGAGGGTA
CGGTGACTCCCACTACGGTATGGACGTCTCGGGCCAAGGGACCACGGTCACCGTCTCCTCA
SEQ ID NO. 670

1.43 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAACTATTGGATGATCTGGTACCGCCAGGCTCCAGGTGAGGAGCTGGAGTGGGTGGCCAACATA
AACCAAGATGGAAGTGAGAAATACTATGTGGACTCTGTGAAGGGCCGATTCACCATCTCCAGAGACAACGCCACGAA
CTCACTGTTTCTGCAAATGAACAGCCTGAGAGCCGAGGACACGGCTGTTTATTACTGTGCGAGAGGAGGTGATGGCT
ACAGTAATTCCCACTACGGTATGGACGTCTGGGGCCAAGGGACCACGGTCACTGTCTCCTCA
SEQ ID NO. 671

TABLE 4-continued

Nucleic acids encoding V<sub>H</sub> 1.1 to 1.114

Name Nucleotide Sequence 1.44 GAGGTGCAGCTGGTGGAGTCTGGGGGAGGCTTGGTCCAGCCTGGGGGGTCCCTGAGACTCTCCTGTGCAGCCTCTG
GATTCACCTTTAGTGACTATTGGATGATCTGGTACCGCCAGGCTCCAGGTGAGGAGCTGGAGTGGGTGGCCAACATA
AACCAAGATGGAAGTGAGAAATACTATGTGGACTCTGTGAAGGGCCGATTCACCATCTCCAGAGACAACGCCACGAA
CTCACTGTTTCTGCAAATGAACAGCCTGAGAGCCGAGGACACGGCTGTTTATTACTGTGCGAGAGGAGGTGATGGCT
ACAGTAATTCCCACTACGGTATGGACGTCTGGGGCCAAGGGACCACGGTCACCGTCTCCTCA
SEQ ID NO. 672

1.45 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAAATATTGGATGATCTGGGTCCGCCAGGCTCCAGAAAAGGGGCTGGAGTGGGTGGCCAACATA
AACCAAGATGGAAGTGAGAAATACTATGTGGACTCTGTGGAGGGCCGATTCACCATTTCCAGAGACAATGTCAATAA
CTCATTGTATCTGCAAATGAACAGCCTGAGAGCCGAGGACACGGCTGTGTACTACTGTGCGAGAGGAGGTGATGACT
ACAGTAACTCCCACTACGGTATGGACGTCTCGGGCCAAGGGACCACGGTCACTGTCTCCTCA
SEQ ID NO. 673

1.46 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAACTATTGGATGAGCTGGGTCCGCCAGGCTCCAGGGAAGGGGCTGGAGTGGGTGGCCAACATA
AACCAAGATGGAAGTGAGAAATACTATGTGGACTCTGTGAAGGGCCGATTCACCATCTCCAGAGACAACGCCAAGAG
CTCACTGTATCTGCAAATGAACAGCCTTAGAGCCGAGGACACGGCTGTTTATTACTGTGCGAGAGGGGGGAAGAAT
ATAGCAGCTCCCACTACGGTATGGACGTCTGGGGCCAAGGGACCACGGTCACTGTCTCCTCA
SEQ ID NO. 674

1.47 GAGGTGCAGCTGGTGGAGTCTGGGGGAGGCTGGTCCAGCCTGGGGGGTCCCTGAGACTCTCCTGTATAGCCTCTGG
ATTCAGCTTTAGTAACTATTGGATGAACTGGGTCCGCCAGGCTCCAGGGAAGGGGCTGGAGTGGGTGGCCAACATAA
AGCAAGATGGAAGTGAGAATTACTATGTGGACTCTGTGAAGGGCCGATTCACCATCTCCAGAGACAACGCCAAGAAC
TCACTGTATCTGCAAATGAACAGCCTGAGAGCCGAGGACACGGCTGTGTATTACTGTGCGAGAGGGGGGGAAGGGT
ATAGCACCTCGCACTACGGTATGGACGTCTGGGGCCAAGGGACCGCGGTCACTGTCTCTTCA
SEQ ID NO. 675

1.48 CAGGTGCAGCTGGTGGAGTCTGGGGGAGGCTTGGTCCAGCCTGGGGGGTCCCTGAGACTCTCCTGTGCAGCCTCTGG
ATTCACCTTTAGTAGCTATTGGATGAGCTGGGTCCGCCAGGCTCCAGGGAAGGGGCTGGAGTGGGTGGCCAACATAA
AGCAAGATGGAAGTGAGAAATACTATGTGGACTCTGTGAAGGGCCGATTCACCATCTCCAGAGACAACGCCAAGAAC
TCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACCGTCTCCTCA
SEQ ID NO. 676

1.49 GAGGTGCAGCTGGTGGAGTCTGGGGGAGGCTGGTCCAGCCTGGGGGGTCCCTGAGACTCTCCTGTGGAGCCTCTG
GATTCACCTTTAGTAGCTATTGGATGCTCTGGTTCCGCCAGGCTCCAGGAAAGGAGCTGGAGTGGGTGGCCAATGTTA
ACCAAGATGGCAGTGAGAATTACTATGTGGACTCTGTGGAGGGCCGATTCACCATCTCCAGAGACAACGCCAAGAAC
TCACTGTATCTGCAAATGCACAGCCTGAGAGCCGAGGACACGGCTGTATATTACTGTGCGAGAGGAGGTGAAGACTA
CGGTAACTCCCACTTCGGCATGGACGTCTGGGGCCAAGGGACCATGGTCACCGTCTCCTCA
SEQ ID NO. 677

1.50 GAGGTGCAGCTGGTGGAGTCTGGGGGAGGCTGGTGCAGCCTGGCAGATCCCTGAGACTCTCTTGTGCAGCCTCTGG
ATTCACCTTTAGTAACTATTGGATGATCTGGTACCGCCAGGCTCCAGGTGAGGAGCTGGAGTGGGTGGCCAACATAA
ACCAAGATGGAAGTGAGAAATACTATGTGGACTCTGTGAAGGGCCGATTCACCATCTCCAGAGACAACGCCACGAAC
TCACTGTTTCTGCAAATGAACAGCCTGAGAGCCGAGGACACGGCTGTTTATTACTGTGCGAGAGGAGGTGATGGCTA
CAGTAATTCCCACTACGGTATGGACGTCTGGGGCCAAGGGACCACGGTCACTGTCTCTTCA
SEQ ID NO. 678

1.51 GAGGTGCAGCTGGTGGAGTCTGGGGGAGGCTTGGTCAAGCCTGGAGGGTCCCTGAGACTCTCCTGTGCAGCCTCTG
GATTCACCTTTAGTAACTATTGGATGATCTGGTACCGCCAGGCTCCAGGTGAGGAGCTGGAGTGGGTGGCCAACATA
AACCAAGATGGAAGTGAGAAATACTATGTGGACTCTGTGAAGGGCCGATTCACCATCTCCAGAGACAACGCCACGAA
CTCACTGTTTCTGCAAATGAACAGCCTGAGAGCCGAGGACACGGCTGTTTATTACTGTGCGAGAGGAGGTGATGGCT
ACAGTAATTCCCACTACGGTATGGACGTCTGGGGCCAAGGGACCACGGTCACCGTCTCCTCA
SEQ ID NO. 679

1.52 GAGGTGCAGCTGGTGGAGTCTGGGGGAGGCTGGTCCAGATTGGGGGGTCCCTGAGACTCTCCTGTGCAGCCTCCG
GATTCACCTTTAGTAAATATTGGATGATCTGGGTCCGCCAGGCTCCAGAAAAGGGGCTGGAGTGGGTGGCCAACATA
AACCAAGATGGAAGTGAGAAATACTATGTGGACTCTGTGGAGGGCCGATTCACCATTTCCAGAGACAACGCCAATAA
CTCACTGTTTCTGCAAATGAACAGCCTGAGAGCCGAGGACACGGCTGTGTACTACTGTGCGAGAGGAGGTGATGACT
ACAGTATCTCCCACTTCGGTATGGACGTCTCGGGCCAAGGGACCAGGGTCACCGTCTCCTCA
SEQ ID NO. 680

1.53 GAGGTGCAGCTGGTGGAGTCTGGGGGAGGCTTGGTCCAGATTGGGGGGTCCCTGAGACTCTCCTGTGTAGCCTCTGG
ATTCACCTTTAGTAAATATTGGATGATCTGGGTCCGCCAGGCTCCAGAAAAGGGGCTGGAGTGGGTGGCCAACATAA
ACCAAGATGGAAGTGAGAAATACTATGTGGACTCTGTGGAGGGCCGATTCACCATTTCCAGAGACAACGCCAATAAT
TCATTGTATCTGCAGATGAACAGCCTGAGAGCCGAGGACACGGCTGTGTACTACTGTGCGAGAGGAGGTGATGACTA
CAGTCACTCCCACTACGGTATGGACGTCTCGGGCCAAGGGACCACGGTCACTGTCTCTTCA
SEQ ID NO. 681

1.54 GAGGTGCAGCTGGTGGAGTCTGGGGGAGGCTGGTCCAGCCTGGGGGGTCCCTGAGACTCTCCTGTGCAGCCTCTG
GATTCAACTTTAGTAACTATTGGATGAACTGGGTCCGCCAGGCTCCAGGGAAGGAGCTGGAGTGGGTGGCCAACATA
AACCAAGATGGAAGTGAGAAATACTATGTGGACTCTGTGAAGGGCCGATTCACCATCTCCAGAGACAACGCCAAGAA

TABLE 4-continued

Nucleic acids encoding V<sub>H</sub> 1.1 to 1.114

Name Nucleotide Sequence

CTCACTGTTTCTGCAAATGAACAGCCTGAGAGCCGACGACACGGCTGTGTATTACTGTGCGAGAGGGGGGTTTGGCT
ACGGTGACTCCCACTACGGTATGGACGTCTGGGGCCAAGGGACCACGGTCACCGTCTCCTCA
SEQ ID NO. 682

1.55 GAGGTGCAGCTGGTGGAGTCTGGGGGAGGCTTGGTCCAGCCTGGGGGGTCCCTGAGACTCTCCTGTGCAGCCTCTG
GATTCACCTTTGGTAGTTATTGGCTGAATTGGGTCCGCCAGGCTCCAGGGAAGGGGCTGGAGTGGGTGGCCAACATA
AACCAAGATGGCAGTGAGAATTACTATGTGGACTCTGTGGAGGGCCGATTCACCATCTCCAGAGACAACGCCAAGAA
CTCACTGTATCTGCAAATGCACAGCCTGAGAGCCGAGGACACGGCTGTATATTACTGTGCGAGAGGAGGTGAAGACT
ACGGTAACTCCCACTTCGGCATGGACGTCTGGGGCCAAGGGACCATGGTCACTGTCTCTTCA
SEQ ID NO. 683

1.56 CAGGTGCAGCTGGTGGAGTCTGGGGGAGGCTTGGTCAAGCCTGGAGGGTCCCTGAGACTCTCCTGTGCAGCCTCTGG
ATTCACCTTTAGTAGCTATTGGATGAGCTGGGTCCGCCAGGCTCCAGGGAAGGGGCTGGAGTGGGTGGCCAACATAA
AGCAAGATGGAAGTGAGAAATACTATGTGGACTCTGTGAAGGGCCGATTCACCATCTCCAGAGACAACGCCAAGAAC
TCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACTGTCTCTTCA
SEQ ID NO. 684

1.57 CAGGTGCAGCTGGTGGAGTCTGGGGGAGGCTGGTCCAGCCTGGGGGGTCCCTGAGACTCTCCTGTACAGCCTCTGG
ATTCACCTTTAGTGACTATTGGATGAACTGGGTCCGCCAGGCTCCAGGTAAGGGGCTGGAGTGGGTGGCCAATATAA
AGGAAGATGGAAGTGAGAAATACTATGTGGACTCTGTGAAGGGCCGATTCACCATCTCCAGAGACAACGCCAGGAA
CTCACTGTATCTGCAAATGACCAGCCTGAGAGAAGAAGACACGGCTATGTATTACTGTGCGAGAGGGGGGGAGGGC
TACGGTGACAACCACTACGGTATGGACGTCTCGGGCCAAGGGACCACGGTCACTGTCTCTTCA
SEQ ID NO. 685

1.58 GAGGTGCAGCTGGTGGAGTCTGGGGGAGGCTGGTCCAGCCTGGGGGGTCCCTGAGACTCTCCTGTGCAGCCTCTG
GATTCACCTTTAGAAGCTATTGGATGAACTGGGTCCGCCAGGCTCCAGGGAAGGAGGCGGAATGGGTGGCCAACATA
AACCAAGATGGAAGTGAGAAATATTATGTGGACTCTGTGGAGGGCCGATTCACCATCTCCAGAGACAACGCCAAGAA
CTCACTGTTTCTGCAAATGAACAGCCTGAGAGACGAGGACACGGCTGTTTATTACTGTGCGAGAGGAGGCCCCGACT
ACGGTGACCTCCACTACGGTATGGACGTCTGGGGCCAAGGGACCACGGTCACCGTCTCCTCA
SEQ ID NO. 686

1.59 CAGGTGCAGCTGGTGGAGTCTGGGGGAGGCTGGTCCAGCCTGGGGGGTCCCTAAGACTCTCCTGTGCAGCCTCTGG
ATTCACCTTTAGTAGGTATTGGATGAGCTGGGTCCGCCAGGCTCCAGGGAAGGGGCTGGAGCGGGTGGCCAACATAA
ACCAAGATGGACGTGAGAAATACTATGTGGACTCTGTGAAGGGCCGATTCACCATCTCCAGAGACAACGCCAAGAAC
TCACTGTATCTGCAAATGAACAGCCTGAGAGCCGAGGACACGGCTGTGTATTATTGTGCGAGAGGGGGGGAGGGCT
ACGGTGACTACCACTACGGTATGGACGTCTCGGGCCAAGGGACCACGGTCACTGTCTCTTCA
SEQ ID NO. 687

1.60 GAGGTGCAGCTGGTGGAGTCTGGGGGAGGCTGGTCCAGCCTGGGGGGTCCCCGAGACTCTCCTGTGCAGCCTCTG
GATTCACCCTTAGTAACTATTGGATGATCTGGTACCGCCAGGCTCCAGGTGAGAAGCTGGAGTGGGTGGCCAACATA
AACCAAGATGGAAGTGAGAAATACTATGTGGACTCTGTGAAGGGCCGATTCACCATCTCCAGAGACAACGCCAAGAA
CTCACTGTTTCTGCAAATGAACAGCCTGAGAGCCGAGGACACGGCTGTTTATTACTGTGCGAGAGGAGGTGATGGCT
ACAGTAATTCCCACTACGGTATGGACGTCTGGGGCCAAGGGACCACGGTCACCGTCTCCTCA
SEQ ID NO. 688

1.61 GAGGTGCAGCTGGTGGAGTCTGGGGGAGGCTTGGTCCAGCCTGGGGGGTCCCTGAGACTCTCCTGTGTAGCCTCTGG
ATTCAACTTCAGTAACTATTGGATGAACTGGGTCCGCCAGGCTCCAGGGAAGGAGCTGGAGTGGGTGGCCAACATAA
ACCAAGATGAAAGTGAAAAATACTATGTAGACTCTGTGAAGGGCCGATTCACCATCTCCAGAGACAACGCCAAGAAC
TCACTGTTTCTGCAAATGAACAGCCTGAGAGCCGACGACACGGCTGTGTATTACTGTGCGAGAGGGGGGTTTGGCTA
CGGTGACTCCCACTTCGGTATGGACGTCTGGGGCCAAGGGACCACGGTCACCGTCTCCTCA
SEQ ID NO. 689

1.62 GAGGTGCAGCTGGTGGAGTCTGGGGGAGGCTTGGTCCAGCCTGGGGGGTCCCTGAGACTCTCCTGTGCAGCCTCTG
GATTCAATTTTAGTAACTATTGGATGAACTGGGTCCGTCAGGCTCCAGGGAAGGAGCTGGAGTGGGTGGCCAACATA
AACCAAGATGAAAGTGAAAAATACTATGTAGACTCTGTGAAGGGCCGATTCACCATTTTCAGAGACAACGCCAAGAA
CTCACTGTTTCTGCAAATGAACAGCCTGAGAGCCGACGACACGGCTGTGTATTACTGTGCGAGAGGGGGGTTTGGCT
ACGGTGACTCCCACTTCGGTATGGACGTCTGGGGCCAAGGGACCACGGTCACTGTCTCTTCA
SEQ ID NO. 690

1.63 GAGGTGCAGCTGGTGGAGTCTGGGGGAGGCTTGGTCCAGCCTGGGGGGTCCCTGAGTCTCTCCTGTGCAGCCTCTGG
ATTCACCTTTAGAAGCTTTTGGATGAACTGGGTCCGCCAGGCTCCAGGGAAGGAGGCGGAATGGGTGGCCAACATAA
ATCAAGATGGAAGTGAGAAATACTATGTGGACTCTGTGAAGGGCCGATTCACCATCTCCAGAGACAACGCCAAGAAC
TCACTGTTTCTGCAAATGAACAGCCTGAGAGCCGAGGACACGGCTGTTTATTACTGTGCGAGAGGAGGCCCCGACTAC
GGTGACCTCCACTACGGTATGGACGTCTGGGGCCAAGGGACCACGGTCACTGTCTCTTCA
SEQ ID NO. 691

1.64 GAGGTGCAGCTGGTGGAGTCTGGGGGAGGCTTGGTCCAGCCTGGGGGGTCCCTGAGACTCTCCTGTGCAGCCTCTG
GATTCACCTTTAGAAGCTATTGGATGAACTGGGTCCGCCAGGCTCCAGGGAAGGAGGCGGAATGGGTGGCCAACATA
AACCAAGATGGAAGTGAGAAATATTATGTGGACTCTGTGAAGGGCCGATTCACCATCTCCAGAGACAACGCCAAGAA
CTCACTGTTTCTGCAAATGAACAGCCTGAGAGACGAGGACACGGCTGTTTATTACTGTGCGAGAGGAGGCCCCGACT
ACGGTGACCTCCACTACGGTATGGACGTCTGGGGCCAAGGGACCACGGTCACTGTCTCTTCA
SEQ ID NO. 692

1.65 GAGGTGCAGCTGGTGGAGTCTGGGGGAGGCTTGGTCCAGCCTGGGGGGTCCCTGAGACTCTCCTGTGCAGCCTCTG
GATTCACCTTTAGTAACTATTGGATGATCTGGTACCGCCAGGCTCCAGGTGAGGAGCTGGAGTGGGTGGCCAACATA

TABLE 4-continued

Nucleic acids encoding V_H 1.1 to 1.114

Name Nucleotide Sequence

```
     AACCAAGATGGAAGTGAGAAATACTATGTGGACTCTGTGAAGGGCCGATTCACCATCTCCAGAGACAACGCCAAGAA
     CTCACTGTATCTGCAAATGCACAGCCTGAGAGCCGAGGACACGGCTGTATATTACTGTGCGAGAGGAGGTGAAGACT
     ACGGTAACTCCCACTACGGCATGGACGTCTGGGGCCAAGGGACCATGGTCACCGTCTCTTCA
     SEQ ID NO. 693
```

1.66 GAGGTGCAGCTGGTGGAGTCTGGGGGAGGCTGGTCCAGCCTGGGGGGTCCCTGAGACTCTCCTGTGCAGCCTCTG
     GATTCACCTTTAGTAACTATTGGATGAACTGGGTCCGCCAGGCTCCAGGGAAGGGGCTGGAGTGGGTGGCCAACATA
     AACCAAGATGGAAGTGAAAGATACTATGTGGACTCTGTGAAGGGCCGATTCACCATCTCCAGAGACAACGCCAAGAG
     CTCACTGTATCTGCAAATGAACAGCCTGAGAGCCGAGGACACGGCTGTGTATTTCTGTGCGAGAGGGGGGGAAGGCT
     ATGGTATCGACCACTACGGTTTGGACGTCTCGGGCCAAGGGACCACGGTCACCGTCTCCTCA
     SEQ ID NO. 694

1.67 CAGGTGCAGCTGGTGGAGTCTGGGGGAGGCTTGGTCCAGCCTGGGGGGTCCCTGAGACTCTCCTGTGCAGCCTCTGG
     ATTCACCTTTAGTAGCTATTGGATGAGCTGGGTCCGCCAGGCTCCAGGGAAGGGGCTGGAGTGGGTGGCCAACATAA
     ATCAAGATGGAAGTGAAAGATACTATGTGGACTCTGTGAAGGGCCGATTCACCATCTCCAGAGACAACGCCAAGAGC
     TCACTGTATCTGCAAATGAGTAGCCTGAGAGCCGAGGACACGGCTGTGTATTTCTGTGCGAGAGGGGGGGAAGGCTA
     TGGTGTCGACCACTACGGTTTGGACGTCTCGGGCCAAGGGACCACGGTCACTGTCTCCTCA
     SEQ ID NO. 695

1.68 CAGGTGCAGCTGGTGGAGTCTGGGGGAGGCTTGGTCCAGCCTGGGGGGTCCCTGAGACTCTCCTGTGCAGCCTCTGG
     ATTCACCTTTAGTAACTATTGGATGATCTGGGTCCGCCAGGCTCCAGGGAAGGGGCTGGAGTGGGTGGCCAACATAA
     ACCAAGATGGAAGTGAGAAATACTATGTGGACTCTGTGGAGGGCCGATTCACCATCTCCAGAGACAACGCCAAGAGC
     TCACTGTATCTGCAAATGAGCAACCTGAGAGCCGAGGACACGGCTGTATATTTCTGTGCGAGAGGGGGGGAAGGCTA
     TGGTGTCGACCACTACGGTTTGGACGTCTCGGGCCAAGGGACCACGGTCACTGTCTCTTCA
     SEQ ID NO. 696

1.69 CAGGTGCAGCTGGTGGAGTCTGGGGGAGGCTTGGTCCAGCCTGGGGGGTCCCTGAGACTCTCCTGTGCAGCCACTG
     GATTCACCCTTAAGTAACTATTGGATGAACTGGGTCCGCCAGGCTCCAGGGAAGGGGCTGGAGTGGGTGGCCAACATA
     AACCAAGATGGAAGTGAAAAATACTATGTGGACTCTGTGAAGGGCCGATTCACCATCTCCAGAGACAACGCCAAGAA
     CTCACTGTTTCTGCAAATGAACAGCCTGAGAGCCGAGGACACGGCTGTGTATTACTGTGCGAGAGGGGGAACAGGCT
     ATGGTTCCGACCACTACGGTATGGACGTCTCGGGCCAAGGGACCACGGTCACTGTCTCTTCA
     SEQ ID NO. 697

1.70 GAGGTGCAGCTGGTGGAGTCTGGGGGAGGCTTGGTCCAGCCTGGGGGGTCCCTGAGACTCTCCTGTGCAGCCTCTG
     GATTCAATTTTAGTAACTATTGGATGAACTGGGTCCGCCAGGCTCCAGGGAAGGAGCTGGAGTGGGTGGCCAACATA
     AACCAAGATGGAAGTGAGAATTACTATGTGGACTCTGTGAAGGGCCGATTCACCATCTCCAGAGACAACGTCAAGAA
     CTCACTGTTTCTGCAAATGAACCGCCTGAGAGCCGACGACACGGCTGTGTATTACTGTGCGAGAGGGGGGTTTGGCT
     ACGGTGACTCCCACTACGGTATGGACGTCTGGGGCCAAGGGACCACGGTCACTGTCTCCTCA
     SEQ ID NO. 698

1.71 GAGGTGCAGCTGGTGGAGTCTGGGGGAGGCTTGGTCCAGCCTGGGGGGTCCCTGAGACTCTCCTGTGCAGCCTCTG
     GATTCACCTTTGGTAACTATTGGATGATCTGGGTCCGCCAGGCTCCAGGCAAGGAGTTGGAGTGGCTGGCCAACATA
     AACCAAAATGGAAGTGAGAGATACTATGTGGACTCTGTGCAGGGCCGATTCACCATCTCCAGAGACAACGCCAAGAA
     CTCACTGTATCTGCAAATGAACAGCCTGAGAGCCGAGGACACGGCTGTATATTACTGTGCGAGAGGGGGTGCTGACT
     ACAGTAACTCCCACTACGGTATGGACGTCAGCGGCCAAGGGACCACGGTCACTGTCTCTTCA
     SEQ ID NO. 699

1.72 CAGGTGCAGCTGGTGGAGTCTGGGGGAGGCTTGGTCCAGCCTGGGGGGTCCCTGAGACTCTCCTGTGCAGCCTCTGG
     ATTCACCTTTAGTAGCTATTGGATGAGCTGGGTCCGCCAGGCTCCAGGGAAGGGGCTGGAGTGGGTGGCCAACATAA
     ACCAAGATGGAAGTGAAAGATACTATGTGGACTCTGTGAAGGGCCGATTCACCATCTCCAGAGACAACGCCAACAAC
     TCACTGCATCTGCAAATGAGCAGCCTGAGAGCCGAGGACACGGCTGTGTATTTCTGTGCGAGAGGGGGGGAAGGCT
     ATGGTGTCGACCACTACGGTTTGGACGTCTCGGGCCAAGGGACCACGGTCACCGTCTCCTCA
     SEQ ID NO. 700

1.73 GAGGTGCAGCTGGTGGAGTCTGGGGGAGGCTTGGTCCAGCCGGGGGGGTCCCTGAGACTCTCCTGTGCAGCCTCTG
     GATTCACCTTTAGAAGTTATTGGATGAACTGGGTCCGCCAGGCTCCAGGGAAAGAGGCGGAATGGGTGGCCAACATA
     AACCCAGATGGAAGTGAGAAATACTATGTGGACTCTGTGCAGGGCCGACACACCATCTCCAGAGACAACGCCAAGAA
     CTCACTGTTTCTGGAAATGAACAGCCTGAGAGTCGAGGACACGGCTCTTTATTACTGTGCGAGAGGAGGCCCCGGCTA
     CGGTGACCTCCACTACGGTATGGACGTCTGGGGCCAAGGGACCACGGTCACTGTCTCCTCA
     SEQ ID NO. 701

1.74 CAGGTGCAGCTGGTGGAGTCTGGGGGAGGCTTGGTCCAGCCTGGGGGGTCCCTGAGACTCTCCTGTGCAGCCACTG
     GATTCACCTTAAGTAACTATTGGATGAACTGGGTCCGCCAGGCTCCAGGGAAGGGGCTGGAGTGGGTGGCCAACATA
     AATCAAGATGGAAGTGAAAAATACTATGTGGACTCTGTGGAGGGCCGATTCACCATCTCCAGAGACAACGCCAAGAG
     CTCACTGTATCTGCAAATGAGCAGCCTGAGAGCCGAGGACACGGCTGTGTATTTCTGTGCGAGAGGGGGGAAGGCT
     ATGGTGTCGACCACTACGGTTTGGACGTCTCGGGCCAAGGGACCACGGTCACTGTCTCCTCA
     SEQ ID NO. 702

1.75 CAGGTGCAGCTGGTGGAGTCTGGGGGAGGCCTGGTCCAGCCTGGGGGGTCCCTGAGACTCTCCTGTGCAGCCTCTGG
     ATTCACCTTCAGTGACTACTACATGAGCTGGATCCGCCAGGCTCCAGGGAAGGGGCTGGAGTGGGTGGCCAACATAA
     ACCAAGATGGAAGTGAAAGATACTATGTGGACTCTGTGAAGGGCCGATTCACCATCTCCAGAGACAACGCCAAGAAC
     TCACTGTATCTGCAAATGAGCAGCCTGAGAGCCGAGGACACGGCTGTGTATTTCTGTGCGAGAGGGGGGGAAGGCT
     ATGGTGTCGACCACTACGGTTTGGACGTCTCGGGCCAAGGGACCACGGTCACCGTCTCTTCA
     SEQ ID NO. 703

TABLE 4-continued

Nucleic acids encoding V$_H$ 1.1 to 1.114

Name Nucleotide Sequence 1.76 GAGGTGCAGCTGGTGGAGTCTGGGGGAGGCTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGAAGGGCCGATTCACCATCTCCAGAGACAACGCCAAGAA
CTCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACCGTCTCTTCA
SEQ ID NO. 704

1.77 CAGGTGCAGCTGGTGGAGTCTGGGGGAGGCTTGGTCCAGCCTGGGGGGTCCCTGAGACTCTCCTGTGCAGCCTCTGG
ATTCACCCTTAAGTAACTATTGGATGAACTGGGTCCGCCAGGCTCCAGGGAAGGGGCTGGAGTGGGTGGCCAACATAA
ACCAAGATGGAAGTGAAAGATACTATGTGGACTCTGTGAAGGGCCGATTCACCATCTCCAGAGACAACGCCAAGAAC
TCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACTGTCTCTTCA
SEQ ID NO. 705

1.78 CAGGTGCAGCTGGTGGAGTCTGGGGGAGGCTTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGAAGGGCCGATTCACCATCTCCAGAGACAACGCCAAGAA
CTCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACTGTCTCTTCA
SEQ ID NO. 706

1.79 CAGGTGCAGCTGGTGGAGTCTGGGGGAGGCTTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGAAGGGCCGATTCACCATCTCCAGAGACAACGCCAAGAA
CTCACTGTATCTGCAAATGAGCAGCCTGAGAGCCGAGGACACGGCTGTGTATTTCTGTGCGAGAGGGGGGGAAGGCT
ATGGTGTCAACCACTACGGTTTGGACGTCTCGGGCCAAGGGACCACGGTCACCGTCTCTTCA
SEQ ID NO. 707

1.80 CAGGTGCAGCTGGTGGAGTCTGGGGGAGGCTTGGTCAAGCCTGGAGGGTCCCTGAGACTCTCCTGTGTAGCCTCTGG
ATTCACCTTCAGTGACTACTATATGAGCTGGATCCGCCAGGCTCCAGGGAAGGGGCTGGAGTGGGTGGCCAACATAA
AGCAAGATGGAAGTGAAAGATACTATGTGGACTCTGTGAAGGGCCGATTCACCATCTCCAGAGACAACGCCAAGAGC
TCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACTGTCTCTTCA
SEQ ID NO.708

1.81 CAGGTGCAGCTGGTGGAGTCTGGGGGAGGCTTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGGAGGGCCGATTCACCATCTCCAGAGACAACGCCAAGAG
CTCACTGTATCTGCAAATGAGCAACCTGAGAGCCGAGGACACGGCTGTATATTTCTGTGCGAGAGGGGGGGAAGGCT
ATGGTGTCGACCACTACGGTTTGGACGTCTCGGGCCAAGGGACCACGGTCACTGTCTCTTCA
SEQ ID NO. 709

1.82 CAGGTGCAGCTGGTGGAGTCTGGGGGAGGCTTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGAAGGGCCGATTCACCATTTCCAGAGACAACGCCAAGAG
CTCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACCGTCTCCTCA
SEQ ID NO. 710

1.83 CAGGTGCAGCTGCAGGAGTCGGGGGGAGGCTTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGAAGGGCCGATTCACCATCTCCAGAGACAACGCCAAGAA
CTCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACTGTCTCTTCA
SEQ ID NO. 711

1.84 CAGGTGCAGCTGGTGGAGTCTGGGGGAGGCCTGGTCAAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGAAGGGCCGATTCACCATCTCCAGAGACAACGCCAAGAA
CTCACTGTATCTGCAAATGAGCAGCCTGAGAGCCGAGGACACGGCTGTGTATTTCTGTGCGAGAGGGGGGGAAGGCT
ATGGTGTCGACCACTACGGTTTGGACGTCTCGGGCCAAGGGACCACGGTCACCGTCTCCTCA
SEQ ID NO. 712

1.85 CAGGTGCAGCTGGTGGAGTCTGGGGGAGGCTTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGAAGGGCCGATTCACCATCTCCAGAGACAACGCCAACAA
CTCACTGCATCTGCAAATGAGCAGCCTGAGAGCCGAGGACACGGCTGTGTATTTCTGTGCGAGAGGGGGGAAGGC
TATGGTGTCGACCACTACGGTTTGGACGTCTCGGGCCAAGGGACCACGGTCACTGTCTCTTCA
SEQ ID NO. 713

1.86 CAGGTGCAGCTGGGGGAGTCTGGGGGAGGCTTGGTCCAGCCTGGGGGGTCCCTGAGACTCTCCTGTGCAGCCACTG
GATTCACCCTTAAGTAACTATTGGATGAACTGGGTCCGCCAGGCTCCAGGGAAGGGGCTGGAGTGGGTGGCCAACATA
AACCAAGATGGAAGTGAAAGATACTATGTGGACTCTGTGGAGGGCCGATTCACCATCTCCAGAGACAACGCCAAGAG

TABLE 4-continued

Nucleic acids encoding V$_H$ 1.1 to 1.114

Name Nucleotide Sequence

CTCACTGTATCTGCAAATGAGCAACCTGAGAGCCGAGGACACGGCTGTATATTTCTGTGCGAGAGGGGGGAAGGCT
     ATGGTGTCGACCACTACGGTTTGGACGTCTCGGGCCAAGGGACCACGGTCACCGTCTCCTCA
     SEQ ID NO. 714

1.87  CAGGTGCAGCTGGTGGAGTCTGGGGGAGGCTTGGTCCAGCCTGGGGGGTCCCTGAAACTCTCCTGTGCAGCCACTGG
     ATTCACCTTAAGTAACTATTGGATGAACTGGGTCCGCCAGGCTCCAGGGAAGGGGCTGGAGTGGGTGGCCAACATAA
     ACCAAGATGGAAGTGAAAGATACTATGTGGACTCTGTGAAGGGCCGATTCACCATTTCCAGAGACAACGCCAAGAGC
     TCACTGTATCTGCAAATGAGCAGCCTGAGAGCCGAGGACACGGCTGTGTATTTCTGTGCGAGAGGGGGGAAGGCT
     ATGGTGTCGACCACTACGGTTTGGACGTCTCGGGCCAAGGGACCACGGTCACTGTCTCTTCA
     SEQ ID NO. 715

1.88  CAGGTGCAGCTGCAGGAGTCGGGGGGAGGCTTGGTCCAGCCTGGGGGGTCCCTGAGACTCTCCTGTGCAGCCACTG
     GATTCACCTTAAGTAACTATTGGATGAACTGGGTCCGCCAGGCTCCAGGGAAGGGGCTGGAGTGGGTGGCCAACATA
     AACCAAGATGGAAGTGAAAGATACTATGTGGACTCTGTGAAGGGCCGATTCACCATCTCCAGAGGCAACGCCAAGAA
     CTCACTGTATCTGCAAATGAGCAGCCTGAGAGCCGAGGACACGGCTGTGTATTTCTGTGCGAGAGGGGGGAAGGCT
     ATGGTGTCGACCACTACGGTTTGGACGTCTCGGGCCAAGGGACCACGGTCACTGTCTCTTCA
     SEQ ID NO. 716

1.89  CAGGTGCAGCTGGTGGAGTCTGGGGGAGGCGTGGTCCAGCCTGGGAGGTCCCTGAGACTCTCCTGTGCAGCCTCTG
     GATTCACCTTTGATGATTATGGCATGAGCTGGGTCCGCCAGGCTCCAGGGAAGGGGCTGGAGTGGGTGGCCAACATA
     AACCAAGATGGAAGTGAAAGATACTATGTGGACTCTGTGAAGGGCCGATTCACCATCTCCAGAGACAACGCCAAGAA
     CTCACTGTATCTGCAAATGAGCAGCCTGAGAGCCGAGGACACGGCTGTGTATTTCTGTGCGAGAGGGGGGAAGGCT
     ATGGTGTCGACCACTACGGTTTGGACGTCTCGGGCCAAGGGACCACGGTCACTGTCTCTTCA
     SEQ ID NO. 717

1.90  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGGTCCGTCAGGCTCCAGGGAAGGGGCTGGAGTGGGTGGCCCAC
     ATAAAGGAAGACGGAAGTGAGAAATACTATGAGGACTCTGTGGAGGGCCGATTCACCGTCTCCAGAGACAACGCC
     AAGAACTCGGTATATCTGCAAATGAACAGTCTGAGAGCCGAAGACACGGCTGTGTATTACTGTGCGAGAGGAGGT
     GATGGCTACAGTGACTCCCACTTCGGTGTGGACGTCTGGGGCCAAGGGACCACGGTCACCGTCTCCTCA
     SEQ ID NO. 718

1.91  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGTTCCGTCAGGCTCAGGGAAGGGGCTGGAGTGGGTGGCCCACA
     TAAAGGAAGACGGAAGTGAGAAATACTATGTGGACTCTGTGAAGGGCCGATTCACCGTCTCCAGAGACAACGCCA
     AGAACTCGGTATATCTGCAAATGAACAGTCTGAGAGCCGAAGACACGGCTGTGTATTACTGTGCGAGAGGAGGTG
     ATGGCTACAGTGACTCCCACTTCGGTGTGGACGTCTGGGGCCAAGGGACCACGGTCACCGTCTCCTCA
     SEQ ID NO. 719

1.92  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGTTCCGTCAGGCTCCAGGGAAGGGGCTGGAGTGGGTGGCCCACA
     TAAAGGAAGACGGAAGTGAGAAATACTATGAGGACTCTGTGAAGGGCCGATTCACCGTCTCCAGAGACAACGCCA
     AGAACTCGGTATATCTGCAAATGAACAGTCTGAGAGCCGAAGACACGGCTGTGTATTACTGTGCGAGAGGAGGTG
     ATGGCTACAGTGACTCCCACTTCGGTGTGGACGTCTGGGGCCAAGGGACCACGGTCACCGTCTCCTCA
     SEQ ID NO. 720

1.93  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGTTCCGTCAGGCTCCAGGGAAGGGGCTGGAGTGGGTGGCCCACA
     TAAAGGAAGACGGAAGTGAGAAATACTATGAGGACTCTGTGGAGGGCCGATTCACCATCTCCAGAGACAACGCCA
     AGAACTCGGTATATCTGCAAATGAACAGTCTGAGAGCCGAAGACACGGCTGTGTATTACTGTGCGAGAGGAGGTG
     ATGGCTACAGTGACTCCCACTTCGGTGTGGACGTCTGGGGCCAAGGGACCACGGTCACCGTCTCCTCA
     SEQ ID NO. 721

1.94  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGTTCCGTCAGGCTCCAGGGAAGGGGCTGGAGTGGGTGGCCCACA
     TAAAGGAAGACGGAAGTGAGAAATACTATGAGGACTCTGTGAAGGGCCGATTCACCGTCTCCAGAGACAACGCCA
     AGAACTCGTTATATCTGCAAATGAACAGTCTGAGAGCCGAAGACACGGCTGTGTATTACTGTGCGAGAGGAGGTG
     ATGGCTACAGTGACTCCCACTTCGGTGTGGACGTCTGGGGCCAAGGGACCACGGTCACCGTCTCCTCA
     SEQ ID NO. 722

1.95  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGGTCCGTCAGGCTCCAGGGAAGGGGCTGGAGTGGGTGGCCCAC
     ATAAAGGAAGACGGAAGTGAGAAATACTATGTGGACTCTGTGAAGGGCCGATTCACCATCTCCAGAGACAACGCC
     AAGAACTCGTTATATCTGCAAATGAACAGTCTGAGAGCCGAAGACACGGCTGTGTATTACTGTGCGAGAGGAGGT
     GATGGCTACAGTGACTCCCACTTCGGTGTGGACGTCTGGGGCCAAGGGACCACGGTCACCGTCTCCTCA
     SEQ ID NO. 723

1.96  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGTTCCGTCAGGCTCCAGGGAAGGGGCTGGAGTGGGTGGCCCACA
     TAAAGGAAGACGGAAGTGAGAAATACTATGTGGACTCTGTGAAGGGCCGATTCACCATCTCCAGAGACAACGCCA
     AGAACTCGTTATATCTGCAAATGAACAGTCTGAGAGCCGAAGACACGGCTGTGTATTACTGTGCGAGAGGAGGTG
     ATGGCTACAGTGACTCCCACTTCGGTGTGGACGTCTGGGGCCAAGGGACCACGGTCACCGTCTCCTCA
     SEQ ID NO. 724

1.97  GAGGTGCAGCTGGTGGAGTCTGGGGGAGGCTTGGTCCAGCCGGGGGGGTCCCTGAGACTCTCCTGTGCAGCCTCT
     GGATTCACCTTTAGTAGCCATTGGATGACTTGGGTCCGTCAGGCTCCAGGGAAGGGGCTGGAGTGGGTGGCCCAC

TABLE 4-continued

Nucleic acids encoding V<sub>H</sub> 1.1 to 1.114

Name Nucleotide Sequence

```
     ATAAAGGAAGACGAAAGTGAGAAATACTATGTGGACTCTGTGAAGGGCCGATTCACCATCTCCAGAGACAACGCC
     AAGAACTCGTTATATCTGCAAATGAACAGTCTGAGAGCCGAAGCACGGCTGTGTATTACTGTGCGAGAGGAGGT
     GTTGGCTACAGTATCTCCCACTTCGGTGTGGACGTCTGGGGCCAAGGGACCACGGTCACCGTCTCCTCA
     SEQ ID NO. 725

1.98  GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGGTCCGTCAGGCTCCAGGGAAGGGGCTGGAGTGGGTGGCCCAC
      ATAAAGGAAGACGAAAGTGAGAAATACTATGTGGACTCTGTGAAGGGCCGATTCACCATCTCCAGAGACAACGCC
      AAGAACTCGTTATATCTGCAAATGAACAGTCTGAGAGCCGAAGACACGGCTGTGTATTACTGTGCGAGAGGAGGT
      GAGGGCTACAGTATCTCCCACTTCGGTGTGGACGTCTGGGGCCAAGGGACCACGGTCACCGTCTCCTCA
      SEQ ID NO. 726

1.99  GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGACGAAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTG
      ATGGCTACAGTGACTCCCACTTCGGTGTGGACGTCTGGGGCCAAGGGACCACGGTCACCGTCTCCTCA
      SEQ ID NO. 727

1.100 GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGACGAAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTG
      ATGGCTACAGTATCTCCCACTTCGGTGTGGACGTCTGGGGCCAAGGGACCACGGTCACCGTCTCCTCA
      SEQ ID NO. 728

1.101 GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGGCGGAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTG
      ATGGCTACAGTGACTCCCACTTCGGTGTGGACGTCTGGGGCCAAGGGACCACGGTCACCGTCTCCTCA
      SEQ ID NO. 729

1.102 GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGAGGGAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTG
      ATGGCTACAGTGACTCCCACTTCGGTGTGGACGTCTGGGGCCAAGGGACCACGGTCACCGTCTCCTCA
      SEQ ID NO. 730

1.103 GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGACGGAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTG
      AGGGCTACAGTGACTCCCACTTCGGTGTGGACGTCTGGGGCCAAGGGACCACGGTCACCGTCTCCTCA
      SEQ ID NO. 731

1.104 GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGACGGAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTGT
      TGGCTACAGTGACTCCCACTTCGGTGTGGACGTCTGGGGCCAAGGGACCACGGTCACCGTCTCCTCA
      SEQ ID NO. 732

1.105 GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGACGAAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTGT
      TGGCTACAGTATCTCCCACTTCGGTGTGGACGTCTGGGGCCAAGGGACCACGGTCACCGTCTCCTCA
      SEQ ID NO.733

1.106 GAGGTGCAGCTGGTGGAGTCTGGGGGAGGCTTGGTCCAGCCGGGGGGTCCCTGAGACTCTCCTGTGCAGCCTCT
      GGATTCACCTTTAGTAGCCATTGGATGACTTGGTTCCGTCAGGCTCCAGGGAAGGGGCTGGAGTGGGTGGCCCACA
      TAAAGGAAGACGAAAGTGAGAAATACTATGTGGACTCTGTGAAGGGCCGATTCACCATCTCCAGAGACAACGCCA
      AGAACTCGTTATATCTGCAAATGAACAGTCTGAGAGCCGAAGACACGGCTGTGTATTACTGTGCGAGAGGAGGTG
      AGGGCTACAGTATCTCCCACTTCGGTGTGGACGTCTGGGGCCAAGGGACCACGGTCACCGTCTCCTCA
      SEQ ID NO. 734

1.107 GAGGTGCAATTAGTCGAATCGGGGGGTGGACTGGTTCAGCCGGGAGGTAGCCTGCGCCTGTCCTGTGCCGCATCT
      GGTTTTACATTAAGTAACTACTGGATGAATTGGGTTCGTCAAGCGCCTGGAAAGGGCTTAGAGTGGGTGGCTAATA
      TTAACCAGGACGGGTCAGAGCGCTACTATGTGGATTCAGTAAAAGGTCGCTTCACTATCAGCCGCGATAATGCTAA
      AAATTCGCTGTACCTICAGATGTCATCACTTCGTGCAGAGGATACAGCTGTGTATTTCTGCGCGCGTGGAGGCGAG
      GGGTACGGGGTAGACCACTATGGGTTGGATGTCTCGGGACAAGGCACGACCGTCACTGTCAGTAGC
      SEQ ID NO. 881
```

TABLE 4-continued

Nucleic acids encoding V$_H$ 1.1 to 1.114

Name Nucleotide Sequence 1.108 GAGGTCCAGTTGGTTGAGTCCGGCGGCGGCTTGGTCCAACCAGGGGGGTCGCTTCGCTTATCTTGCGCTGCCACAG
GGTTTACCCTGAGCAACTACTGGATGAACTGGGTGCGCCAAGCGCCTGGGAAGGGGTTAGAGTGGGTCGCCAACA
TCAACCAAGACGGTTCGGAGCGTTACTATGTCGACAGCGTGAAGGGCCGTTTCACGATCTCCCGCGATAACGCTAA
GAACTCCCTGTATTTGCAAATGAATAGCCTTCGTGCGGAGGATACTGCGGTTTATTTCTGTGCTCGTGGCGGTGAAG
GATATGGGGTTGACCATTATGGGTTGGATGTCTCCGGGCAAGGGACAACGGTGACCGTGTCATCC
SEQ ID NO. 882

1.109 GAGGTTCAACTTGTTGAATCGGGTGGCGGATTAGTACAACCCGGCGGCTCGCTGCGTTTATCGTGTGCGGCAACCG
GATTTACTTTATCAAACTATTGGATGAATTGGGTGCGCCAGGCTCCAGGGAAAGGTCTGGAATGGGTAGCGAATAT
CAACCAAGACGGCTCAGAACGCTACTACGTGGACTCCGTAAAAGGTCGTTTCACCATCTCTCGTGACAATGCTAAAA
ATTCTTTGTATTTGCAAATGAGTTCACTTCGTGCTGAGGATACTGCGGTCTATTACTGTGCTCGCGGGGGGGAAGGC
TACGGAGTAGACCACTACGGGTTGGATGTTTCTGGACAGGGAACGACGGTTACTGTAAGCAGC
SEQ ID NO. 883

1.110 GAGGTTCAGTTAGTTGAGTCCGGCGGGGGATTAGTTCAACCTGGCGGAAGCCTTCGTCTGAGTTGTGCCGCGAGC
GGGTTTACCCTTAGCAATTACTGGATGAACTGGGTACGTCAAGCTCCAGGTAAAGGTTTAGAATGGGTCGCTAACA
TTAATCAAGATGGTTCTGAACGCTATTATGTAGACTCGGTAAAGGGTCGTTTTACAATTTCTCGCGACAACGCCAAA
AACTCTTTGTACCTTCAAATGAATTCCTTACGCGCTGAGGACACTGCTGTCTATTTCTGTGCGCGTGGAGGGGAGGG
ATACGGAGTTGACCACTATGGGCTGGACGTTTCAGGACAGGGCACTACGGTAACTGTGTCTTCG
SEQ ID NO. 884

1.111 GAGGTTCAGTTAGTAGAGTCCGGGGGAGGACTGGTACAACCTGGGGGTAGTTTGCGTCTGTCTTGTGCAGCCAGC
GGTTTCACATTGTCTAACTATTGGATGAATTGGGTTCGTCAAGCGCCTGGCAAGGGACTGGAGTGGGTTGCAAACA
TTAATCAAGATGGCAGCGAGCGTTATTACGTGGACTCAGTAAAAGGGCGCTTCACGATTAGCCGCGATAATGCTAA
GAACTCCTTATATCTGCAGATGTCATCTTTGCGTGCCGAGGACACGGCAGTTTACTATTGCGCACGTGGTGGCGAG
GGATACGGCGTGGATCACTATGGTTTGGACGTATCGGGCCAAGGGACTACCGTGACTGTGTCCTCT
SEQ ID NO. 885

1.112 GAGGAGGTACAGCTTGTCGAGTCTGGCGGTGGCCTTGTGCAACCGGGGGGTTCTTTACGTTTATCCTGTGCCGCTA
CAGGATTTACGTTAAGCAACTATTGGATGAACTGGGTACGTCAAGCTCCGGGGAAGGGGCTGGAATGGGTTGCCA
ATATCAATCAGGATGGGTCTGAACGCTACTACGTTGATTCTGTTAAGGGTCGCTTTACTATTTCACGTGACAATGCC
AAGAACAGTCTTTACCTTCAAATGAACTCGTTACGCGCTGAGGATACTGCTGTGTACTACTGTGCGCGCGGCGGAG
AGGGATACGGTGTCGATCATTATGGGCTTGACGTAAGCGGGCAGGGTACGACGGTGACGGTATCATCA
SEQ ID NO. 556

1.113 GAGGTGCAGTTAGTTGAGAGCGGAGGTGGTTTAGTTCAGCCGGGGGGCTCGCTTCGCCTGTCGTGCGCCGCCTCG
GGATTCACATTATCAAACTACTGGATGAATTGGGTCCGCCAGGCTCCGGCCAAAGGTCTTGAGTGGGTGGCGAACA
TTAATCAGGACGGGAGCGAGCGTTATTACGTTGATTCGGTAAAAGGACGTTTCACTATCAGTCGTGACAACGCTAA
AAATTCCTTGTACTTACAGATGAACTCACTTCGTGCTGAGGACACCGCAGTGTACTACTGTGCTCGCGGTGGTGAAG
GATACGGCGTCGATCACTACGGCCTTGATGTATCAGGACAGGGGACTACAGTTACCGTCTCTTCC
SEQ ID NO. 887

1.114 GAGGTGCAGTTGGTAGAGAGTGGGGGTGGCCTGGTCCAACCAGGTGGGTCCCTTCGTTTGTCTTGCGCCGCCTCTG
GGTTTACTCTGTCAAATTATTGGATGAACTGGGTGCGCCAAGCTCCCGGCAAGGGGTTGGAGTGGGTTGCCAACAT
TAATCAGGACGAATCCGAGCGTTACTATGTTGATTCTGTAAAAGGGCGCTTCACTATCTCTCGTGATAATGCTAAGA
ACAGTTTGTACCTGCAAATGAATTCACTGCGTGCCGAGGATACCGCGGTGTACTATTGTGCCCGTGGAGGAGAGGG
ATACGGGGTCGATCACTATGGCTTAGACGTATCGGGCCAGGGAACAACCGTCACCGTATCCTCA
SEQ ID NO. 888

TABLE 5

Nucleic acids encoding V$_H$ 2.1 to 2.51

Name Nucleotide Sequence 2.1 GAGGTGCAGCTGGTGGAGTCTGGGGGAGGCTTGGTCAAGCCTGGAGGGTCCCTGAGAGTCTCCTGTGCAGCCTCTG
GATTCACCTTCAGTGACTACTACATGAGCTGGTTCCGCCAGGCTCCAGGGAAGGGGCTGGAGTGGGTTTCATACATTA
GTGGTAGTGGTGATATCATAGACTACGCAGACTCTGTAAAGGGCCGATTCACCATCTCCAGGGACAACGCCAAGAAC
TCTCTGTATCTGCAGATGAACAACCTGAGAGCCGAGGACACGGCCGTGTATCACTGTGCGAGAGAAGATTCCCGTCTA
ACTGGAACTACGGACTTTGACAATTGGGGCCAGGGAACCCTGGTCACCGTCTCCTCA
SEQ ID NO. 735

2.2 GAGGTGCAGCTGGTGGAGTCTGGGGGAGGCTTGGTCAAGCCTGGAGGGTCCCTGAGAGTCTCCTGTGCAGCCTCTG
GATTCACCTTCAGTGACTACTACATGAGCTGGTTCCGCCAGGCTCCAGGGAAGGGGCTGGAGTGGGTTTCGTACATTA
GTGGTAGTGGTGATATCATAGACTATGCAGACTCTGTGAAGGGCCGATTCACCATCTCCAGGGACAACGCCAAGAAC
TCACTGTATCTGCAAATGAACAGCCTGAGAGCCGAGGACACGGCCGTGTATCACTGTGCGAAAGAAGATTCCCGTAT
ACCTGGAACTACGGACTTTGACAATTGGGGCCAGGGAACCCTGGTCACTGTCTCCTCA
SEQ ID NO. 736

2.3 GAGGTGCAGCTGGTGGAGTCTGGGGGAGGCTTGGTCAAGCCTGGAGGGTCCCTGAGAGTCTCCTGTGCAGCCTCTG
GATTCACCTTCAGTGACTACTATATGAGTTGGTTCCGCCAGGCTCCAGGGAAGGGGCTGGAGTGGATTTCGTACATTA
GTGGTAGTGGTGATATCATAGACTACGCAGACTCTGTGAAGGGCCGATTCACCATCTCCAGGGACAACGCCAAGAAC

TABLE 5-continued

Nucleic acids encoding V$_H$ 2.1 to 2.51

Name Nucleotide Sequence

TCACTGTATCTGCAAATGAACAGCCTGAGAGCCGAGGACACGGCCGTGTATCACTGTGCGAAAGAAGATTCCCGTAT
ACCTGGAACTACGGACTTTGACAATTGGGGCCAGGGAACCCTGGTCACCGTCTCTTCA
SEQ ID NO. 737

2.4 GAGGTGCAGCTGGTGGAGTCTGGGGGAGGCTTGGTCAAGCCTGGAGGGTCCCTGAGAGTCTCCTGTGCAGCCTCTG
GATTCACCTTCAGTGACTACTACATGAGCTGGTTCCGCCAGGCTCCAGGGAAGGGGCTGGAGTGGGTTTCGTACATTA
GTGGTAGTGGTGATGTCATTGACTATGCAGACTCTGTGAAGGGCCGATTCACCATCTCCAGGGACAACGCCAAGAATT
CACTGTATCTGCAAATGAACAGCCTGAGAGCCGAGGACACGCCGTGTATCACTGTGCGAAAGAAGATTCCCGTATA
CCTGGAACTACGGACTTTGACAATTGGGGCCAGGGAACCCTGGTCACTGTCTCTTCA
SEQ ID NO. 738

2.5 GAGGTGCAGCTGGTGGAGTCTGGGGGAGGCTTGGTCAAGCCTGGAGGGTCCCTGAGACTCTCCTGTGCAGTCTCTGG
ATTCACCTTCAGTGACTACTACATGAGCTGGTTCCGCCAGGCTCCAGGGAAGGGGCTGGAGTGGGTTTCGTACATTAG
TGGTAGTGGTGATATCATAGACTATGCAGACTCTGTGAAGGGCCGATTCACCATCTCCAGGGACAACGCCAAGAACTC
ACTGTATCTGCAAATGAACAGCCTGAGAGCCGAGGACACGGCCGTGTATCACTGTGCGAAAGAAGATTCCCGTATAC
CTGGAACTACGGACTTTGACAATTGGGGCCAGGGAACCCTGGTCACTGTCTCCTCA
SEQ ID NO. 739

2.6 GAGGTGCAGCTGGTGGAGTCTGGGGGAGGCTTGGTCAAGCCTGGAGGGTCCCTGAGAGTCTCCTGTGCAGCCTCTG
GATTCACCTTCAGTGACTACTACATGAGCTGGTTCCGCCAGGCTCCAGGGAAGGGGCTGGAGTGGGTTTCGTACATTA
GTGGTAGTGGTGATATCATAGACTATGCGGACTCTGTGAAGGGCCGATTCACCATCTCCAGGGACAACGCCAAGAAC
TCACTGTATCTGCAAATGAACAGCCTGAGAGCCGAGGACACGGCCGTGTATCACTGTGCGAAAGAAGATTCCCGTAT
ACCTGGAACTACGGACTTTGACAGTTGGGGCCAAGGGACAATGGTCACCGTCTCCTCA
SEQ ID NO. 740

2.7 GAGGTGCAGCTGGTGGAGTCTGGGGGAGGCTTGGTCAAGCCAGGAGGGTCCCTGAGACTCTCCTGTGCAGCCTCTG
GATTCACCTTCAGTGACTACTACATGAGCTGGTTCCGCCAGGCTCCAGGGAAGGGGCTGGAGTGGGTTTCATACATTA
GTGGTAGTGGTACTACCATAGACTACGCAGACTCTGTGAAGGGCCGCTTCACCATCTCCAGGGACAACGCCAGGAAC
TCACTATATCTGCAAATGAACAGCCTGAGAGCCGAGGACACGGCCGTGTATTACTGTGCCAGAGAAGATATCAGGAT
GACTGGAACTACGGACTTTGACAACTGGGGCCAGGGAACCCTGGTCACCGTCTCTTCA
SEQ ID NO. 741

2.8 GAGGTGCAGCTGGTGGAGTCTGGGGGAGGCTTGGTCAAGCCTGGAGGGTCCCTGAGACTCTCCTGTGCAGCCTCTG
GATTCGCCTTCAGTGACTACTACATGAGCTGGTTCCGCCAGGCTCCAGGGAAGGGGCTGGAGTGGGTTTCACACATTA
GTGGTAGTGGAACTACCATAGACTACGCAGACTCTGTGAAGGGCCGATTCACCATCTCCAGAGACAACGCCAAGAAC
TCACTATATCTACAAATGAACAGCCTGAGAGCCGAGGACACGGCCGTGTATCACTGTGCGAGAGAAGATTCCCGCAT
GCCTGGAACTACGGACTTTGACAACTGGGGCCAGGGAACCCTGGTCACCGTCTCCTCA
SEQ ID NO. 742

2.9 GAGGTGCAGCTGGTGGAGTCTGGGGGAGGCTTGGTCAAGCCTGGAGGGTCCCTGAGACTCTCCTGTGCAGCCTCTG
GATTCACCTTCAGTGACTACTATATGACCTGGTTCCGCCAGGCTCCAGGGAAGGGACTGGAGTGGATTTCATACATTA
GTGGTAGTGGTGATACCATAGACTACGCAGAGTCTGTGAAGGGCCGATTCACCATCTCCAGGGACAACGCCAAGAAT
TCACTGTATCTGCAGATGAACAGCCTGAGAGCCGAGGACACGGCCGTGTATCACTGTGCGAGAGAAGATTCGCGTAT
AGCCGGAACTACGGACTTTGACAACTGGGGCCCGGGAACCCTGGTCACTGTCTCTTCA
SEQ ID NO. 743

2.10 GAGGTGCAGCTGGTGGAGTCTGGGGGAGGCTTGGTCAAGCCTGGAGGGTCCCTGAGACTCTCCTGTGCAGCCTCTG
GATTCACCTTCAGTGACTACTACATGACCTGGTTCCGCCAGGCTCCAGGGAAGGGGCTGGAGTGGGTTTCATACATTA
GTAGTAGTGGTAGTAACATAGATTACGCAGACTCTGTGAAGGGCCGATTCACCATCTCTAGGGACAACGCCAAGAAC
TCACTGTATCTGCAAATGAACAGCCTGAGAGCCGAGGACACGGCCGTGTATTACTGTGCGAGAGAAGATTCCCGTTTA
AGTGGAACTACGGACTTTGACTACTGGGGCCAGGGAACCCTGGTCACCGTCTCTTCA
SEQ ID NO. 744

2.11 GAGGTGCAGCTGGTGGAGTCTGGGGGAGGCTGGTCCAGCCTGGGGGGTCCCTGAGACTCTCCTGTGCAGCCTCTG
GATTCACCTTCAGTGACTACTATATGACCTGGTTCCGCCAGGCTCCAGGGAAGGGACTGGAGTGGATTTCATACATTA
GTGGTAGTGGTGATACCATAGACTACGCAGAGTCTGTGAAGGGCCGATTCACCATCTCCAGGGACAACGCCAAGAAT
TCACTGTATCTGCAGATGAACAGCCTGAGAGCCGAGGACACGGCCGTGTATCACTGTGCGAGAGAAGATTCGCGTAT
AGCCGGAACTACGGACTTTGACAACTGGGGCCCGGGAACCCTGGTCACTGTCTCCTCA
SEQ ID NO. 745

2.12 GAGGTGCAGCTGGTGGAGTCTGGGGGAGGCTTGGTCAAGCCTGGAGGGTCCCTGAGACTCTCCTGTGCAGCCTCTG
GATTCACCTTCAGTGACTACTACATGAGCTGGTTCCGCCAGGCTCCAGGGAAGGGGCTGGAGTGGGTTTCACACATTA
GTGGTAGTGGTCGCTTCACCATAGACTACGCAGACTCTGTGAAGGGCCGCTTCACCATCTCCAGGGACAACGCCAGGAAG
TCACTATATCTGCAGATGAACAGCCTGAGAGCCGAGGACACGGCCGTCTATTACTGTGCCAGAGAAGATATCAGGAT
GACTGGAACTACGGACTTTGACCACTGGGGCCAAGGAACCCTGGTCACCGTCTCCTCA
SEQ ID NO. 746

2.13 CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTACTACATGAGCTGGTTCCGCCAGGCTCCAGGGAAGGGCTGGAGTGGGTTTCACACATTAG
TAGTAGTGGTAATACCATAGACTACGCAGACTCTGTGAAGGGCCGCTTCACCATCTCCAGGGACAACGCCAAGAACTC
ACTTTATCTGCAAATGAATAGCCTGAGAGCCGAGGACACGGCCGTTTATTACTGTGCGAGAGAAGATCCTCGTTTACC
TGGAACTACAGATTTTGACTACTGGGGCCAGGGAACCCTGGTCACTGTCTCCTCA
SEQ ID NO. 747

2.14 GAGGTGCAGTTGGTGGAGTCTGGGGGAGGCTTGGTCAAGCCTGGAGGGTCCCTGAGACTCTCCTGTGCAGCCTCTGG
ATTCACCTTCAGTGACTACTATATGACCTGGTTCCGCCAGGCTCCAGGGAAGGGACTGGAGTGGATTTCATACATTAG

TABLE 5-continued

Nucleic acids encoding V<sub>H</sub> 2.1 to 2.51

Name Nucleotide Sequence

TGGTAGTGGTGATACCATAGACTACGCAGAGTCTGTGAAGGGCCGATTCACCATCTCCAGGGACAACGCCAAGAATT
CACTGTATCTGCAGATGAACAGCCTGAGAGCCGAGGACACGGCCGTGTATTACTGTGCCAGAGAAGATATCAGGATG
CCTGGAACTACGGACTTTGACCACTGGGGCCAAGGAACCCTGGTCACCGTCTCCTCA
SEQ ID NO. 748

2.15 GAGGTGCAGCTGGTGGAGTCTGGGGGAGGCTTGGTCAAGCCTGGAGGGTCCCTGAGACTCTCCTGTGCAGTCTCTGG
ATTCACCTTCAGTGACTACTACATGAGCTGGTTCCGCCAGGCTCCAGGGAAGGGGCTGGAGTGGGTTTCACACATTAG
TGGTAGTGGAACTACCATAGACTACGCAGACTCTGTGAAGGGCCGCTTCACCATCTCCAGGGACAACGCCAGGAATTC
ACTGTATCTGCAAATGAACAGCCTGAGAGCCGAGGACACGGCCGTGTATTACTGTGCCAGAGAAGATATCAGGATGC
CTGGAACTACGGATTTTGACCACTGGGGCCAAGGAACCCTGGTCACTGTCTCTTCA
SEQ ID NO. 749

2.16 CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTACTACATGAGCTGGATCCGCCAGGCTCCAGGGAAGGGGCTGGAGTGGGTTTCACACATTAG
TAGTAGTGGGAGTACCATAGACTACGCAGACTCTGTGAAGGGCCGATTCACCATCTCCAGGGACAACGCCAAGAACT
CACTGTATCTGCAAATGAACAGCCTGAGAGCCGAGGACACGGCCGTGTATTACTGTGCGAGAGAAGATCCTCGTTTA
ACTGGAACTACAGATTTTGACTACTGGGGCCAGGGAGCCCTGGTCACTGTCTCCTCA
SEQ ID NO. 750

2.17 CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTACTACATGAGCTGGATCCGCCAGGCTCCAGGGAAGGGGCTGGAGTGGGTTTCATACATTAG
TAGTAGTGGTAGTACCATATCCTACGCAGACTCTGTGAAGGCCGATTCACCATCTCCAGGGACAACGCCAAGAACTC
ACTGTATCTGCAAATGAACAGCCTGAGAGCCGAGGACACGGCCGTGTATTACTGTGCGAGAGAAGATCCTCGTATAA
GTGGAACTACAGATTTTGACAATTGGGGCCAGGGAACCCTGGTCACCGTCTCCTCA
SEQ ID NO. 751

2.18 CAGGTGCAGCTGCAGGAGTCGGGGGGAGGCTTGGTCAAGCCTGGAGGGTCCCTGAGACTCTCCTGTGCAGCCTCTG
GATTCACCTTCAGTGACTACTACATGAGCTGGTTCCGCCAGGCTCCAGGGAAGGGGCTGGAGTGGGTTTCACACATTA
GTAGTAGTGGTAATACCATAGACTACGCAGACTCTGTGAAGGGCCGCTTCACCATCTCCAGGGACAACGCCAAGAACT
CACTGTATCTGCAAATGAACAGCCTGAGAGCCGAGGACACGGCCGTTTATTACTGTGCGAGAGAAGATCCTCGTTTAC
CTGGAACTACAGATTTTGACTACTGGGGCCAGGGAACCCTGGTCACCGTCTCCTCA
SEQ ID NO. 752

2.19 CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTACTACATGAGCTGGTTCCGCCAGGCTCCAGGGAAGGGGCTGGAGTGGGTTTCATACATTAG
TGGTACTGGTATTACCACAGACTACGCAGACTCTGTGAAGGGCCGCTTCACCATCTCCAGGGACAACGCCAAGAACTC
ACTGTATCTGCAAATGAACAGCCTGAGAGCCGAGGACACGGCCGTGTATTACTGTGCGAGAGAAGATCCTCGTTTACC
TGGAACTTCAGAATTTGACAACTGGGGCCAGGGAACCCTGGTCACCGTCTCCTCA
SEQ ID NO. 753

2.20 GAGGTGCAGCTGGTGGAGTCTGGGGGAGGCTTGGTCAAGCCTGGAGGGTCCCTGAGACTCTCCTGTGCAGCCTCTG
GATTCACCTTCAGTGACTACTACATGAGCTGGATCCGCCAGGCTCCAGGGAAGGGGCTGGAGTGGGTTTCACACATTA
GTAGTAGTGGTAGTACCATAGATTATGCAGACTCTGTGAAGGGCCGATTCACCATCTCCAGGGACAACGCCAAGAACT
CACTGTATCTGCAAATGAACAGCCTGAGAGCCGAGGACACGGCCGTCTATTACTGTGCGAGAGAAGATCCCCGTATG
CCTGGAACTTTTGACTTTGACAACTGGGGCCAGGGAACCCTGGTCACCGTCTCCTCA
SEQ ID NO. 754

2.21 GAGGTGCAGCTGGTGGAGTCTGGGGGAGGCTTGGTCAAGCCTGGAGGGTCCCTGAGACTCTCCTGTGCAGCCTCTG
GATTCGCCTTCAGTGACTACTACATGAGCTGGTTCCGCCAGGCTCCAGGGAAGGGGCTGGAGTGGGTTTCACACATTA
GTGGTAGTGGAACTACCATAGACTACGCAGACTCTGTGAAGGGCCGCTTCACCATCTCCAGGGACAACGCCAGGAAT
TCACTGTATCTGCAAATGAACAGCCTGAGAGCCGAGGACACGGCCGTGTATTACTGTGCCAGAGAAGATATCAGGAT
GCCTGGAACTACGGACTTTGACCACTGGGGCCAAGGAACCCTGGTCACTGTCTCTTCA
SEQ ID NO. 755

2.22 GAGGTGCAGCTGGTGGAGTCTGGGGGAGGCTTGGTCAAGCCTGGAGGGTCCCTGAGACTCTCCTGTGCAGTCTCTGG
ATTCACCTTCAGTGACTACTACATGAGCTGGTTCCGCCAGGCTCCAGGGAAGGGGCTGGAGTGGGTTTCACACATTAG
TGGTAGTGGAACTACCATAGACTACGCAGACTCTGTGAAGGGCCGCTTCACCATCTCCAGGGACAACGCCAGGGATT
CACTGTATCTGCAAATGAACAGCCTGAGAGCCGAGGACACGGCCGTGTATTACTGTGCCAGAGAAGATATCAGGATG
CCTGGAACTACGGATTTTGACCACTGGGGCCAAGGAACCCTGGTCACTGTCTCTTCA
SEQ ID NO. 756

2.23 GAGGTGCAGCTGGTGGAGTCTGGGGGAGGCTTGGTCACGCCTGGAGGGTCCCTGAGACTCTCCTGTGCAGTCTCTGG
ATTCACCTTCAGTGACTACTACATGAGCTGGTTCCGCCAGGCTCCAGGGAAGGGGCTGGAGTGGGTTTCACACATTAG
TGGTAGTGGAACTACCATAGACTACGCAGACTCTGTGAAGGGCCGCTTCACCATCTCCAGGGACAACGCCAGGAATTC
ACTGTATCTGCAAATGAACAGCCTGAGAGCCGAGGACACGGCCGTGTATTACTGTGCCAGAGAAGATATCAGGATGC
CTGGAACTACGGATTTTGACCACTGGGGCCAAGGAACCCTGGTCACCGTCTCCTCA
SEQ ID NO. 757

2.24 GAGGTGCAGCTGGTGGAGTCTGGGGGAGGCTTGGTCAAGCCTGGAGGGTCCCTGAGACTCTCCTGTGCAGTCTCTGG
ATTCACCTTCAGTGACTACTACATGAGCTGGTTCCGCCAGGCTCCAGGGAAGGGGCTGGAGTGGGTTTCACACATTAG
TGGTAGTGGAACTACCATAGACTACGCAGACTCTGTGAAGGGCCGCTTCACCATCTCCAGGGACAACGCCAGGAATTC
ACTGTATCTGCAAATGAACAGCCTGAGAGCCGAGGACACGGCCATGTATTACTGTGCCAGAGAAGATATCAGGATGC
CTGGAACTACGGATTTTGACCACTGGGGCCAAGGAACCCTGGTCACCGTCTCCTCA
SEQ ID NO. 758

TABLE 5-continued

Nucleic acids encoding V_H 2.1 to 2.51

Name Nucleotide Sequence 2.25 GAGGTGCAGCTGGTGGAGTCTGGGGGAGGCTGGTTAAGCCTGGAGGGTCCCTGAGACTCTCCTGTGCAGCCTCTGG
ATTCGCCTTCAGTGACTACTACATGAGCTGGTTCCGCCAGGCTCCAGGGAAGGGGCTGGAGTGGGTTTCACACATTAG
TGGTAGTGGAACTACCATAGACTACGCAGACTCTGTGAAGGACCGCTTCACCATCTCCAGGGACAACGCCAGGAATTC
ACTGTATCTGCAAATGAACAGCCTGAGAGCCGAGGACACGGCCGTGTATTACTGTGCCAGAGAAGATATCAGGATGC
CTGGAACTACGGACTTTGACCACTGGGGCCAAGGAACCCTGGTCACTGTCTCTTCA
SEQ ID NO. 759

2.26 GAGGTGCAGCTGGTGGAGTCTGGGGGAGGCTTGGTCAAGCCTGGAGGGTCCCTGAGACTCTCCTGTACAGCCTCTGG
ATTCACCTTCACTGACTATTATATGAGCTGGTTCCGCCAGGCTCCAGGGAAGGGACTGGAGTGGGTTTCACACATTAG
TAGTAGTGGTACTACAATAGACTACGCAGACTCTGTGAAGGGCCGATTCACCATCTCCAGGGACAACGCCAAGAACTC
ACTGTATCTGCAAATGAACAGCCTGAGAGCCGACGACACGGCCGTATATTACTGTGCGAGAGAAGATATCAGGATGC
CTGGAACTACGGACTTTGACAACTGGGGCCAGGGAACCCTGGTCACTGTCTCCTCA
SEQ ID NO.760

2.27 CAGGTGCAGCTGGTGGAGTCGGGGGGAGGCTTGGTCAAGCCTGGAGGGTCCCTGAGACTCTCCTGTGCAGCCTCTG
GATTCACCTCAGTGACTACTACATGACCTGGTTCCGCCAGGCTCCAGGGAAGGGCTGGAGTGGGTTTCATACATTA
GTAGTAGTGGTAGTACCATTTCCTACGCAGACTCTGTGAAGGGCCGATTCACCATCTCCAGGGACAACGCCAACAACT
CACTGTATCTGCAAATGAACAGCCTGAGAGCCGAGGACACGGCCGTATATCACTGTGCGAGAGAAGATATACGTATG
AGTGGGACTACGGACTTTGACTACTGGGGCCAGGGAACCCTGGTCACTGTCTCCTCA
SEQ ID NO. 761

2.28 CAGGTGCAGCTGGTGGAGTCTGGGGGAGGCTTGGTCAAGCCTGGAGGGTCCCTGAGACTCTCCTGTGCAGCCTCTGG
ATTCATCTTCAGTGACTACTACATGAGCTGGTTCCGCCAGGCTCCAGGGAAGGGGCTGGAGTGGGTTTCACACATTAG
TAGTAGTGGTAGTTCCATAGACTACGCAGACTCTGTGAAGGGCCGATTCACCATTTCGAGGGACAACGCCAAGAACTC
ACTGTATCTGCAAATGAACAGCCTGAGAGCCGAGGACACGGCCGTGTATTACTGTGCGAGAGAAGATCCTCGTTTAA
GTGGAACTATAGATTTTGACTCCTGGGGCCAGGGAACCCTGGTCACCGTCTCTTCA
SEQ ID NO. 762

2.29 GAGGTGCAGCTGGTGGAGTCTGGGGGAGGCTTGGTCAAGCCTGGAGGGTCCCTGAGACTCTCCTGTGCAGCCTCTG
GATTCGCCTTCAGTGACTACTACATGAGCTGGTTCCGCCAGGCTCCAGGGAAGGGGCTGGAGTGGGTTTCACACATT
GGTGGTAGTGGAACTACCATAGACTACGCAGACTCTGTGAAGGGCCGCTTCACCATCTCCAGGGACAACGCCAGGAA
TTCACTGTATCTGCAAATGAACAGCCTGAGAGCCGAGGACACGGCCGTGTATTACTGTGCCAGAGAAGATATCAGGA
TGCCTGGAACTACGGACTTTGACCACTGGGGCCAAGGAACCCTGGTCACCGTCTCCTCA
SEQ ID NO. 763

2.30 CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTACTACATGAGCTGGTGATCCGCCAGGCTCCAGGGAAGGGCTGGAGTGGGTTTCATACATTAG
TAGTAGTGGTAGTACCATATACTACGCAGACTCTGTGAAGGGCCGATTCACCATCTCCAGAGACAACGCCAAGAACTC
ACTGTATCTGCAAATGAACAGCCTGAGAGCCGAGGACACGGCCGTGTATTACTGTGCGAGAAGATCCTCGTGTGC
CTGGAACTACGAACTTTGACTACTGGGGCCAGGGAACCCTGGTCACTGTCTCCTCA
SEQ ID NO. 764

2.31 CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTACTACATGACCTGGATCGCCAGGCTCCAGGGAAGGGGCTGGAGTGGGTTTCATACATTAG
TGGCAGTGGTAGTACCATTGACTATGCAGACTCTGTGAAGGGCCGATTCACGATCTCCAGGGACAACGCCAAGAACT
CACTGTACCTGCAAATGAACAGCCTGAGACCCGAGGACACGGCCGTGTATTACTGTGCGAAAGAAGATGGCCGTATA
CCTGGAACTACGGACTTTGACCACTGGGGCCAGGGAACCCTGGTCACTGTCTCTTCA
SEQ ID NO. 765

2.32 GAGGTGCAGCTGGTGGAGTCTGGGGGAGGCTTGGTCCAGCCTGGGGGGTCCCTGAGACTCTCCTGTGCAGCCTCTG
GATTCGCCTTCAGTGACTACTACATGAGCTGGTTCCGCCAGGCTCCGGGGAAGGGGCTGGAGTGGGTTTCACACATT
AGTGGTAGTGGAACTACCATAGACTACGCAGACTCTGTGAAGGACCGCTTCACCATCTCCAGGGACAACGCCAGGAA
TTCACTGTATCTGCAAATGAACAGCCTGAGAGCCGAGGACACGGCCGTGTATTACTGTGCCAGAGAAGATATCAGGA
TGCCTGGAACTACGGACTTTGACCACTGGGGCCAAGGAACCCTGGTCACCGTCTCCTCA
SEQ ID NO. 766

2.33 CAGGTGCAGCTGGTGGAGTCTGGGGGAGGCTTGGTCAAGCCTGGAGGGTCCCTGAGACTCTCCTGTGCAGCCTCTGG
ATTCCCCTTCAGTGACTACTTCATGAGCTGGTTCCGCCAGGCTCCAGGGAAGGGGCTGGAGTGGGTTTCACACATTAG
TAGTAGTGGTAATTCCATAGACTACGCAGACTCTGTGAAGGGCCGCTTCACCATCTCCAGGGACAACGCCAAGAACTC
ACTGTATCTGCAAATGAACAGCCTGAGAGCCGAGGACACGGCCGTTTATTACTGTGCGAAAGAAGATCCTCGTTTACC
TGGAACTACAGATTTTGACTACTGGGGCCAGGGAACCCTGGTCACTGTCTCTTCA
SEQ ID NO. 767

2.34 CAGGTGCAGCTGGTGGAGTCTGGGGGAGGCTTGGTCAAGCCTGGAGGGTCCCTGAGACTCTCCTGTGCAGCCTCTGG
ATTCACCTTCAGTGACTCCTACATGAGCTGGATCCGCCAGGCTCCAGGGAAGGGGCTGGAGTGGGTTTCACATATTAG
TAATTCTGGTAGTACCATAAGCTACGCAGACTCTGTGAAGGGCCGATTCACCATCTCCAGGGACAACGCCAAGAACTC
ACTGTATCTGCAAATGAACAGCCTGAGAGCCGAGGACACGGCCGTGTATTACTGTGCGAGAGAAGATCCTCGTTTACC
TGGAACTTCAGATTTTGACTACTGGGGCCAGGGAACCCTGGTCACTGTCTCTTCA
SEQ ID NO. 768

2.35 CAGGTGCAGCTGGTGGAGTCTGGGGGAGGCGTGGTCCAGCCTGGGAGGTCCCTGAGACTCTCCTGTGCAGCCTCTG
GATTCACCTTCAGTGACTACTACATGAGCTGGATCCGCCAGGCTCCAGGGAAGGGGCTGGAGTGGGTTTCACACATTA
GTAGTAGTGGTAGTTCCATAGACTACGCAGACTCTGTGAAGGGCCGATTCACCATTTCGAGGGACAACGCCAAGAATT

TABLE 5-continued

Nucleic acids encoding V<sub>H</sub> 2.1 to 2.51

Name Nucleotide Sequence

CACTGTATCTGCAAATGAACAGCCTGAGAGACGAGGACACGGCCGTGTATTACTGTGCGAGAGAAGATCCTCGTTTA
AGTGGAACTACAGATTTTGACCAGTGGGGCCAGGGAACCCTGGTCACCGTCTCCTCA
SEQ ID NO. 769

2.36 CAGGTGCAGCTGGTGGAGTCTGGGGGAGGCTTGGTCCAGCCTGGGGGGTCCCTGAGACTCTCCTGTGCAGCCTCTGG
ATTCACCTTTAGTAGCTATTGGATGAGCTGGGTCCGCCAGGCTCCAGGGAAGGGGCTGGAGTGGGTTTCACACATTA
GTAGTAGTGGTAGTACCATAGACTACGCAGAGTCTGTGAAGGGCCGATTCACCATCTCCAGGGACAACGCCAAGAAC
TCACTGTATCTGCAAATGAACAGCCTGAGAGCCGAGGACACGGCCGTGTATTACTGTGCGAGAGAAGATCCTCGTAT
GACTGGAACTACAGATTTTGACTACTGGGGCCAGGGAACCCTGGTCACCGTCTCTTCA
SEQ ID NO. 770

2.37 CAGGTGCAGCTGCAGGAGTCGGGGGGAGGCTTGGTCAAGCCTGGAGGGTCCCTGAGACTCTCCTGTGCAGCCTCTG
GATTCACCTTCAGTAACTACTTCATGAGTTGGATCCGCCAGGCTCCAGGGAAGGGGCTGGAGTGGGTTTCACACATTA
GTAGTAGTGGTAATACCATAGACTACGCAGACTCTGTGAAGGGCCGCTTCACCATCTCCAGGGACAACGCCAAGAACT
CACTTTATCTGCAAATGGATAGTCTGAGAGCCGAGGACACGGCCGTTTATTACTGTTCGAGAGAAGATCCTCGTTTAC
CTGGAACTACAGATTTTGACTACTGGGGCCAGGGAACCCTGGTCACTGTCTCTTCA
SEQ ID NO. 771

2.38 GAGGTGCAGCTGGTGGAGTCTGGGGGAGGCGTGGTCAAGCCTGGAGGGTCCCTGAGACTCTCCTGTGCAGCCTCTG
GATTCACTTTCAGTGACTACTACATGACCTGGATCCGCCAGGGTCCAGGGAAGGGACAGGAATGGATTTCATACATTA
GTAGTGGTAGCACCATACACTACGCAGATCTCTGTGAAGGGCCGATTCACCATCTCCAGGGACAACGCCAAGAAC
TCACTGTATCTGCAAATGAACAGCCTGAGAGCCGAGGACACGGCCGTGTATTACTGTGCGAGAGAAAATCCCCGTTTA
CCTGGAACTATGGACTTTGACTATTGGGGCCAGGGAACCCTGGTCACTGTCTCCTCA
SEQ ID NO.772

2.39 CAGGTGCAGCTGGTGGAGTCTGGGGGAGGCTTGGTCCAGCCTGGGGGGTCCCTGAGACTCTCCTGTGCAGCCTCTGG
ATTCACCTTCAGTGACCACTTCATGAGCTGGTTCCGCCAGGCTCCAGGGAAGGGGCTGGAGTGGGTGGCCAACATAA
AACAAGATGGAAGTGAGAAATACTATGTGGACTCTGTGAAGGGCCGATTCACCATCTCCAGAGACAACGCCAAGAAC
TCACTGTTTCTGCAAATGAACAGCCTGAGAGCCGAGGACACGGCTATGTATTACTGTGCGAGAGAGGATCCTCGTTTA
ACTGGAACTACAGATTTTGACAACTGGGGCCAGGGAACCCTGGTCACTGTCTCTTCA
SEQ ID NO. 773

2.40 GAGGTGCAGCTGGTGGAGTCTGGGGGAGGCTTGGTCCAGCCTGGGGGGGTCCCTAAGACTCTCCTGTGTAGCCTCTG
GATTCACCTTTAGTAATTATTGGATGACCTGGTTCCGCCAGGCTCCAGGGAGGGGGCTGGAGTGGGTTTCACACATTA
GTAGTACTGGATCTACCATAGACTACGCAGACTCTGTGAAGGGCCGATTCACCATCTCCAGGGACAACGCCGAGAACT
CACTATATTTGCAAATGAACAGCCTGAGAGCCGAGGACACGGCCGTGTATTACTGTGCGAGAGAAGATCCCCGTTTAC
CTGGAACTATGGACTTTGACTATTGGGGCCAGGGAACCCTGGTCACCGTCTCCTCA
SEQ ID NO. 774

2.41 GAGGTGCAGCTGGTGGAGTCTGGGGGAGGCTTGGTCAAGCCTGGAGGGTCCCTGAGACTCTCCTGTGCAGCCTCT
GGATTCACCTTCAGTGACTACTACATGAGCTGGTTCCGCCAGGCTCCAGGGAAGGGGCTGGAGTGGGTTTCATACA
TTAGTGGTAGTGGTGATATCATAGACTACGCAGACTCTGTAAAGGGCCGATTCACCATCTCCAGGGACAACGCCAA
GAACTCTCTGTATCTGCAGATGAACAACCTGAGAGCCGAGGACACGGCCGTGTATCACTGTGCGAGAGAAGATTCC
CGTCTAACTGGAACTACGGACTTTGACAATTGGGGCCAGGGAACCCTGGTCACCGTCTCCTCA
SEQ ID NO. 775

2.42 GAGGTGCAGCTGGTGGAGTCTGGGGGAGGCTTGGTCAAGCCTGGAGGGTCCCTGAGAGTCTCCTGTGCAGCCTCT
GGATTCACCTTCAGTGACTACTACATGAGCTGGATCCGCCAGGCTCCAGGGAAGGGGCTGGAGTGGGTTTCATACA
TTAGTGGTAGTGGTGATATCATAGACTACGCAGACTCTGTAAAGGGCCGATTCACCATCTCCAGGGACAACGCCAA
GAACTCTCTGTATCTGCAGATGAACAACCTGAGAGCCGAGGACACGGCCGTGTATCACTGTGCGAGAGAAGATTCC
CGTCTAACTGGAACTACGGACTTTGACAATTGGGGCCAGGGAACCCTGGTCACCGTCTCCTCA
SEQ ID NO. 776

2.43 GAGGTGCAGCTGGTGGAGTCTGGGGGAGGCTGGTCAAGCCTGGAGGGTCCCTGAGAGTCTCCTGTGCAGCCTCT
GGATTCACCTTCAGTGACTACTACATGAGCTGGTTCCGCCAGGCTCCAGGGAAGGGGCTGGAGTGGGTTTCATACA
TTAGTGGTAGTGGTGATATCATAGACTACGCAGACTCTGTAAAGGGCCGATTCACCATCTCCAGGGACAACGCCAA
GAACTCTCTGTATCTGCAGATGAACAGCCTGAGAGCCGAGGACACGGCCGTGTATCACTGTGCGAGAGAAGATTCC
CGTCTAACTGGAACTACGGACTTTGACAATTGGGGCCAGGGAACCCTGGTCACCGTCTCCTCA
SEQ ID NO. 777

2.44 GAGGTGCAGCTGGTGGAGTCTGGGGGAGGCTGGTCAAGCCTGGAGGGTCCCTGAGAGTCTCCTGTGCAGCCTCT
GGATTCACCTTCAGTGACTACTACATGAGCTGGTTCCGCCAGGCTCCAGGGAAGGGGCTGGAGTGGGTTTCATACA
TTAGTGGTAGTGGTGATATCATAGACTACGCAGACTCTGTAAAGGGCCGATTCACCATCTCCAGGGACAACGCCAA
GAACTCTCTGTATCTGCAGATGAACAACCTGAGAGCCGAGGACACGGCCGTGTATTACTGTGCGAGAGAAGATTCC
CGTCTAACTGGAACTACGGACTTTGACAATTGGGGCCAGGGAACCCTGGTCACCGTCTCCTCA
SEQ ID NO. 778

2.45 GAGGTGCAGCTGGTGGAGTCTGGGGGAGGCTTGGTCAAGCCTGGAGGGTCCCTGAGACTCTCCTGTGCAGCCTCT
GGATTCACCTTCAGTGACTACTACATGAGCTGGTTCCGCCAGGCTCCAGGGAAGGGGCTGGAGTGGGTTTCATACA
TTAGTGGTAGTGGTGATATCATAGACTACGCAGACTCTGTAAAGGGCCGATTCACCATCTCCAGGGACAACGCCAA
GAACTCTCTGTATCTGCAGATGAACAACCTGAGAGCCGAGGACACGGCCGTGTATTACTGTGCGAGAGAAGATTCC
CGTCTAACTGGAACTACGGACTTTGACAATTGGGGCCAGGGAACCCTGGTCACCGTCTCCTCA
SEQ ID NO. 779

2.46 GAGGTGCAGCTGGTGGAGTCTGGGGGAGGCTTGGTCAAGCCTGGAGGGTCCCTGAGACTCTCCTGTGCAGCCTCT
GGATTCACCTTCAGTGACTACTACATGAGCTGGATCCGCCAGGCTCCAGGGAAGGGGCTGGAGTGGGTTTCATACA

TABLE 5-continued

Nucleic acids encoding V<sub>H</sub> 2.1 to 2.51

| Name | Nucleotide Sequence |
|---|---|
| | TTAGTGGTAGTGGTGATATCATAGACTACGCAGACTCTGTAAAGGGCCGATTCACCATCTCCAGGGACAACGCCAA<br>GAACTCTCTGTATCTGCAGATGAACAGCCTGAGAGCCGAGGACACGGCCGTGTATTACTGTGCGAGAGAAGATTCC<br>CGTCTAACTGGAACTACGGACTTTGACAATTGGGGCCAGGGAACCCTGGTCACCGTCTCCTCA<br>SEQ ID NO. 780 |
| 2.47 | GAGGTGCAGCTGGTGGAGTCTGGGGGAGGCTTGGTCAAGCCTGGAGGGTCCCTGAGACTCTCCTGTGCAGCCTCT<br>GGATTCACCTTCAGTGACTACTACATGAGCTGGTTCCGCCAGGCTCCAGGGAAGGGGCTGGAGTGGGTTTCATACA<br>TTAGTGGTAGTGGTGATATCATAGACTACGCAGACTCTGTAAAGGGCCGATTCACCATCTCCAGGGACAACGCCAA<br>GAACTCTCTGTATCTGCAGATGAACAGCCTGAGAGCCGAGGACACGGCCGTGTATTACTGTGCGAGAGAAGATTCC<br>CGTCTAACTGGAACTACGGACTTTGACAATTGGGGCCAGGGAACCCTGGTCACCGTCTCCTCA<br>SEQ ID NO. 781 |
| 2.48 | GAGGTGCAGCTGGTGGAGTCTGGGGGAGGCTTGGTCAAGCCTGGAGGGTCCCTGAGACTCTCCTGTGCAGCCTCT<br>GGATTCACCTTCAGTGACTACTACATGAGCTGGATCCGCCAGGCTCCAGGGAAGGGGCTGGAGTGGGTTTCATACA<br>TTAGTGGTAGTGGTGATATCATAGACTACGCAGACTCTGTAAAGGGCCGATTCACCATCTCCAGGGACAACGCCAA<br>GAACTCTCTGTATCTGCAGATGAACAGCCTGAGAGCCGAGGACACGGCCGTGTATTACTGTGCGAGAGAAGATGCC<br>CGTCTAACTGGAACTACGGACTTTGACAATTGGGGCCAGGGAACCCTGGTCACCGTCTCCTCA<br>SEQ ID NO. 782 |
| 2.49 | GAGGTGCAGCTGGTGGAGTCTGGGGGAGGCTTGGTCAAGCCTGGAGGGTCCCTGAGACTCTCCTGTGCAGCCTCT<br>GGATTCACCTTCAGTGACTACTACATGAGCTGGATCCGCCAGGCTCCAGGGAAGGGGCTGGAGTGGGTTTCATACA<br>TTAGTGGTAGTGGTGATATCATAGACTACGCAGACTCTGTAAAGGGCCGATTCACCATCTCCAGGGACAACGCCAA<br>GAACTCTCTGTATCTGCAGATGAACAGCCTGAGAGCCGAGGACACGGCCGTGTATTACTGTGCGAGAGAAGATCCC<br>CGTCTAACTGGAACTACGGACTTTGACAATTGGGGCCAGGGAACCCTGGTCACCGTCTCCTCA<br>SEQ ID NO. 783 |
| 2.50 | GAGGTGCAGCTGGTGGAGTCTGGGGGAGGCTTGGTCAAGCCTGGAGGGTCCCTGAGACTCTCCTGTGCAGCCTCT<br>GGATTCACCTTCAGTGACTACTACATGAGCTGGTTCCGCCAGGCTCCAGGGAAGGGGCTGGAGTGGGTTTCATACA<br>TTAGTGGTAGTGGTGATATCATAGACTACGCAGACTCTGTAAAGGGCCGATTCACCATCTCCAGGGACAACGCCAA<br>GAACTCTCTGTATCTGCAGATGAACAGCCTGAGAGCCGAGGACACGGCCGTGTATTACTGTGCGAGAGAAGATGCC<br>CGTCTAACTGGAACTACGGACTTTGACAATTGGGGCCAGGGAACCCTGGTCACCGTCTCCTCA<br>SEQ ID NO. 784 |
| 2.51 | GAGGTGCAGCTGGTGGAGTCTGGGGGAGGCTTGGTCAAGCCTGGAGGGTCCCTGAGACTCTCCTGTGCAGCCTCT<br>GGATTCACCTTCAGTGACTACTACATGAGCTGGTTCCGCCAGGCTCCAGGGAAGGGGCTGGAGTGGGTTTCATACA<br>TTAGTGGTAGTGGTGATATCATAGACTACGCAGACTCTGTAAAGGGCCGATTCACCATCTCCAGGGACAACGCCAA<br>GAACTCTCTGTATCTGCAGATGAACAGCCTGAGAGCCGAGGACACGGCCGTGTATTACTGTGCGAGAGAAGATCCC<br>CGTCTAACTGGAACTACGGACTTTGACAATTGGGGCCAGGGAACCCTGGTCACCGTCTCCTCA<br>SEQ ID NO. 785 |

In one embodiment, the nucleic acid sequence has at least 50% sequence homology to one of the sequences selected above. In one embodiment, said sequence homology is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. In one embodiment the nucleic acid is selected from one of SEQ ID Nos. 629, 706, 881, 882, 883, 884, 885, 996, 887 or 735 or a sequence with at least 75% homology thereto.

A nucleic acid according to the present invention may comprise DNA or RNA and may be wholly or partially synthetic or recombinantly produced. Reference to a nucleotide sequence as set out herein encompasses a DNA molecule with the specified sequence, and encompasses a RNA molecule with the specified sequence in which U is substituted for T, unless context requires otherwise.

Furthermore, the invention relates to a nucleic acid construct comprising at least one nucleic acid as defined above. The construct may be in the form of a plasmid, vector, transcription or expression cassette.

The invention also relates to an isolated recombinant host cell comprising one or more nucleic acid construct as described above. The host cell may be a bacterial, viral, plant, mammalian or other suitable host cell. In one embodiment, the cell is an *E. coli* cell. In another embodiment, the cell is a yeast cell. In another embodiment, the cell is a Chinese Hamster Ovary (CHO) cell.

In one embodiment, a method of making an anti-CD137 single domain antibody as described herein is provided, wherein the method comprises culturing the host cell under conditions suitable for expression of the polynucleotide encoding the single domain antibody, and isolating the single domain antibody.

In another aspect, there are provided binding molecules, e.g. antibodies, antibody fragments or antibody mimetics that bind at or near the same epitope or an overlapping epitope on human CD137 as any of the CD137 single domain antibodies of the invention (i.e., antibodies that have the ability to cross-compete for binding to CD137 with any of the single domain antibodies of the invention. The single domain antibodies of the invention can thus be used as a reference antibody). In some embodiments, the reference antibody for cross-competition studies is single domain antibody 1.1 (SEQ ID No. 4). Such cross-competing antibodies can be identified based on their ability to cross-compete with a single domain antibody described herein in standard CD137 binding assays. For example, BIAcore® analysis, ELISA assays or flow cytometry may be used to demonstrate cross-competition with the single domain antibodies.

In one embodiment, there is provided a binding agent capable of binding human CD137 wherein any one of the single domain antibodies described above displaces the binding agent in a competitive assay. In one embodiment, said single domain antibody is V<sub>H</sub> 1.1 (SEQ ID No. 4), V<sub>H</sub>

$V_H$ 1.78 (SEQ ID No. 312), $V_H$ 1.113 (SEQ ID No. 876) or $V_H$ 2.1 (SEQ ID No. 428) or a sequence with at least 75% homology thereto. In some embodiments, the binding agent is an antibody, a functional fragment thereof, for example a single domain antibody, an antibody mimetic protein or a protein that mimics the natural ligand of CD137. In another aspect, there is provided a binding agent capable of binding human CD137 wherein the binding agent displaces any one of the single domain antibodies described above in a competitive assay. In one embodiment, said single domain antibody is $V_H$ 1.1 (SEQ ID No. 4), $V_H$ 1.78 (SEQ ID No. 312), $V_H$ 1.113 (SEQ ID No. 876) or $V_H$ 2.1 (SEQ ID No. 428) or a sequence with at least 75% homology thereto. In another aspect, invention provides a binding agent capable of binding human CD137 wherein the binding agent binds to essentially the same epitope as the single domain antibody of the invention.

In another aspect, we provide an isolated heavy chain only antibody comprising a $V_H$ domain as described herein or with at least 70%, 80% or 90% homology thereto. A heavy chain only antibody may be isolated from a transgenic mammal expressing human V, D and J regions as described herein.

The single variable heavy chain domain antibody described herein can be used as a building block in a multispecific, for example bispecific, binding agent that provides dual targeting of a CD137 expressing cell and a cell that, for example, expresses a tumor specific antigen. Accordingly, we provide the use of a single variable heavy chain domain antibody described herein in a binding molecule for dual, e.g. simultaneous engagement of CD137 and a second antigen, for example a tumor specific antigen. Such binding molecule simultaneously binds to at least two different targets. As described below, in some embodiments, there is provided a method for making binding agents that provide dual targeting of a CD137 expressing cell and a cell that, for example, expresses a tumor specific antigen. A nucleic acid encoding a single variable heavy chain domain antibody described herein, for example as listed above, is linked to nucleic acid encoding a linker peptide which in turn is linked to a nucleic acid encoding, for example, a single variable heavy chain domain antibody encoding a tumor specific antigen. The nucleic acid construct can be expressed in a host cell, for example a bacterial, mammalian or yeast cell.

Exemplary Multispecific Binding Molecules

In one aspect, there is provided a binding molecule comprising a single variable heavy chain domain antibody that binds to CD137 described herein and at least a second moiety that binds to a second antigen, for example a tumor specific antigen. The terms binding agent and binding molecule are used interchangeably herein. The binding molecule may be a fusion protein.

In one embodiment, the at least second moiety is a binding molecule, for example selected from an antibody or antibody fragment (e.g., a Fab, F(ab')2, Fv, a single chain Fv fragment (scFv) or single domain antibody, for example a $V_H$ or $V_{HH}$ domain) or antibody mimetic protein. In one embodiment, the single domain antibody of the invention can be linked to an antibody Fc region or fragment thereof, comprising one or both of $C_H2$ and $C_H3$ domains, and optionally a hinge region. In one embodiment, the at least second moiety is a $V_H$ domain.

The binding agent may be multispecific, for example bispecific. In one embodiment, the binding molecule comprises a first $V_H$ single domain antibody that binds to CD137 as described herein ($V_H$ (A)) and a second $V_H$ single domain antibody ($V_H$ (B)) that binds to another antigen and thus has the following formula: $V_H$ (A)-L-$V_H$ (B). $V_H$ (A) is conjugated to $V_H$ (B), i.e. linked to $V_H$ (B), for example with a peptide linker. L denotes a linker.

Each $V_H$ comprises CDR and FR regions. Thus, the binding molecule may have the following formula: FR1(A)-CDR1(A)-FR2(A)-CDR2(A)-FR3(A)-CDR3(A)-FR4(A)-L-FR1(B)-CDR1(B)-FR2(B)-CDR2(BA)-FR3(B)-CDR3(B)-FR4(B). The order of the single VH domains A and B is not particularly limited, so that, within a polypeptide of the invention, single variable domain A may be located N-terminally and single variable domain B may be located C-terminally, or vice versa.

In one embodiment, the binding molecule is bispecific. Thus, in one aspect, the invention relates to a bispecific molecule comprising a single domain antibody described herein linked to a second functional moiety having a different binding specificity than said single domain antibody.

The term "peptide linker" refers to a peptide comprising one or more amino acids. A peptide linker comprises 1 to 44 amino acids, more particularly 2 to 20 amino acids. Peptide linkers are known in the art or are described herein. Suitable, non-immunogenic linker peptides are, for example, linkers that include G and/or S residues, (G4S)n, (SG4)n or G4(SG4)n peptide linkers, wherein "n" is generally a number between 1 and 10, e.g., 1, 2, 3, 4, 5, 6, 7, 8, 9 or 10. In one embodiment, the peptide is for example selected from the group consisting of GGGGS (SEQ ID NO: 790), GGGGSGGGGS (SEQ ID NO: 791), SGGGGSGGGG (SEQ ID NO: 792), GGGGSGGGGSGGGG (SEQ ID NO: 793), GSGSGSGS (SEQ ID NO: 794), GGSGSGSG (SEQ ID NO: 795), GGSGSG (SEQ ID NO: 796) and GGSG (SEQ ID NO: 797).

In one embodiment, the second moiety binds to a tumor specific antigen. In one embodiment, there is provided a binding molecule comprising
a) a single variable heavy chain domain antibody that binds to CD137 as described herein and
b) a single variable heavy chain domain antibody that binds to a tumor specific antigen.

The tumor specific antigen as used herein may be selected from a list including, but not limited to PSMA, Her2, CD123, CD19, CD20, CD22, CD23, CD74, BCMA, CD30, CD33, CD52, EGRF CECAM6, CAXII, CD24, CEA, Mesothelin, cMet, TAG72, MUC1, MUC16, STEAP, EphvIII, FAP, GD2, IL-13Ra2, L1-CAM, PSCA, GPC3, Her3, gpA33, 5T4 and ROR1. Exemplary binding molecules that bind to CD137 and PSMA are shown in the examples.

In one aspect, the invention relates to a binding molecule comprising a single variable heavy chain domain antibody that binds to CD137 as described herein linked to another moiety that binds to a tumor specific antigen, for example a single variable heavy chain domain antibody that binds to tumor specific antigen, wherein the binding molecule exhibits one or more of the following properties:
(a) binds to human CD137 with a KD as measured in the examples;
(b) inhibits the interaction between human CD137 ligand and human CD137 expressed on the surface of cells CD137 ligand. This can be measured as shown in example 6.
(c) does not bind to mouse CD137;
(d) binds to cells expressing CD137 but does not bind to cells that do not express CD137. This can be measured as shown in example 6;
(e) increases reporter gene activity. This can be measured as shown in example 9.

(f) inhibits tumor cell growth in vivo as shown in example 10;
(g) promotes CD8+ T cell expansion;
(h) induces activation of cytotoxic T lymphocytes (CTL);
(i) stimulates IL-2 production from CD8+ cells. This can be measured as shown in example 9;
(j) induces tumor specific T cell activation;
(k) activates CD137 signalling in T cells as measured in the examples;
(l) inhibits activation induced cell death;
(m) enhances T cell survival;
(n) limits systemic T cell activation;
(o) enhances the cytotoxic effector function of T cells;
(p) promotes local activation of anti-tumor cells in tumor antigen positive tumors;
(q) enhances of antibody-dependent cellular cytotoxicity via CD137 positive NK cell activation;
(r) binds simultaneously to CD137 and a tumor specific antigen, such as PSMA, when linked to a moiety that binds such tumor specific antigen;
(s) binds to cyno CD137;
(t) reverses the regulator function of T-reg cells;
(u) activates NK cells;
(v) recruits T-cells to tumour cells.

In one embodiment, the binding molecule exhibits more than 1 of the properties above, for example a combination of 2, 3, 4, 5, 6, 7, 8, 9, 10, 11, 12, 13, 14, 15, 16, 17, 18, 19, 20 or 21 properties or all properties selected from the above list, including any combination of properties.

In one embodiment, the binding molecule is a fusion protein comprising a single variable heavy chain domain antibody that binds to CD137 linked to a single variable heavy chain domain antibody that binds to a tumor specific antigen. The linker is for example a peptide linker with GS residues such as (Gly4Ser)n, where n=from 1 to 10, e.g., 1, 2, 3, 4, 5, 6, 7, 8, 9 or 10. Examples of such linker are set out above. The single variable heavy chain domain antibody that binds to CD137 can be linked to the other polypeptide via its N or C terminus.

The fusion protein described above is capable of simultaneous binding to CD137 on the surface of effector cells and to the tumor specific antigen displayed on the cell surface of tumor cells.

The dual, e.g. simultaneous binding leads to multimerisation of the CD137 receptor thus resulting in CD137 signalling. This leads to T cell activation. In some embodiments, co-engagement of the two targets, i.e. simultaneous binding to those targets, leads to tumor antigen specific effector cell activation and results in tumor cell killing.

In some embodiments, the fusion protein is capable of binding CD137 with an EC50 value that is at least similar, comparable or equivalent to the EC50 value by which the monovalent single heavy chain domain antibody binds to CD137. In some embodiments, the fusion protein binds CD137 with an EC50 value as shown in the examples.

In some embodiments, the fusion protein may be capable of co-stimulating T cell responses in a functional T cell activation essentially as described in the examples. In some embodiments, the fusion protein described herein may be able to induce IL-2 and/or IFN gamma secretion and T cell proliferation in a functional T cell activation. The fusion polypeptide as described herein is, in some embodiments, also capable of local induction of IL-2 and/or IFN gamma secretion in the vicinity of the targeted tumor, that is cells that are positive for the tumor antigen to which the fusion protein binds.

In some embodiments, the fusion protein may be capable of producing a synergistic effect through dual targeting of the CD137 expressing cell and the tumor antigen expressing cell.

In another aspect, a nucleic acid encoding a fusion protein described herein is provided. Also provided is a vector comprising such nucleic acid and a host cell expressing such vector.

In one embodiment, a binding molecule as described herein binds to CD137 with a KD of about 0.4 nM or of about 3 nM as measured according to the methods shown in the examples. Binding can be measured as in the examples.

Simultaneous targeting of CD137 and a tumor associated antigen in the microenvironment of the tumor may enhance anti-tumor activity and reduce tumor growth. Moreover, by eliciting CD137 signalling locally, side effects may be reduced.

CD137 signalling results in the recruitment of TRAF family members and activation of kinases. T cell mediated signalling protects CD8+ cells from activation induced death.

Also provided is the use of the fusion protein as described herein for co-stimulating T cells.

Exemplary Modifications

In one embodiment, the single domain antibody or binding agent described above comprises further binding molecules. Thus, the binding agent can for example be trispecific or tetraspecific. Additional specificities are also envisaged. Any combination of the aforesaid molecules can be made in a multispecific binding agent, for example, a trispecific binding agent that includes a single domain antibody that binds to CD137 as described herein and a second and third binding specificity.

In one embodiment, the binding molecule comprises a first $V_H$ single domain antibody that binds to CD137 ($V_H$ (A)) as described herein and a second, third, fourth, fifth etc moiety each binding to another antigen. This moiety can be a $V_H$ single domain antibody ($V_H$ (B), $V_H$ (C), $V_H$ (D), $V_H$ (E)( ) that binds to another antigen and the agent thus has the following formula: $V_H$ (A)-L-$V_H$ (B)-L-$V_H$ (X)n wherein X denotes a $V_H$ binding to a target other than the target $V_H$ (A) and VH(B) bind to and wherein n is 1 to 10, for example, 1, 2, 3, 4, 5, 6, 7, 8, 9 or 10. L denotes a linker, for example a peptide linker. The linker can be a peptide linker with GS residues such as (Gly4Ser)n as described above. In one embodiment, the order of the $V_H$ domains is reversed. In other words, a single variable heavy chain domain antibody that binds to CD137 is linked to another entity via either its C or N terminus.

In another embodiment, the further moiety may serve to prolong the half-life of the binding molecule. The further moiety may comprise a protein, for example an antibody, or part thereof that binds a serum albumin, e.g., human serum albumin (HSA) or mouse serum albumin (MSA). The further moiety may comprise a $V_H$ domain that binds serum albumin, e.g., human serum albumin (HSA) or mouse serum albumin (MSA), for example as shown in SEQ ID NO. 901.

The further moiety may comprise a serum albumin, e.g. a human serum albumin (HSA) or a variant thereof such as HSA C34S. Further provided is a binding molecule as described herein comprising a VH domain as described herein and an Fc domain, e.g., wherein the VH domain is fused to an Fc domain. Further provided is a binding molecule that comprises a second variable domain that specifically binds a second antigen, where the second antigen is an antigen other than human CD137. The second antigen may be a cluster of differentiation (CD) molecule or a Major Histocompatibility Complex (MHC) Class II molecule.

In one embodiment, the anti-CD137 single domain antibodies or multivalent binding agents are labelled with a detectable or functional label. A label can be any molecule that produces or can be induced to produce a signal, including but not limited to fluorophores, fluorescers, radiolabels, enzymes, chemiluminescers, a nuclear magnetic resonance active label or photosensitizers. Thus, the binding may be detected and/or measured by detecting fluorescence or luminescence, radioactivity, enzyme activity or light absorbance.

In still other embodiments, the anti-CD137 single domain antibodies or multivalent binding agents are coupled to at least one therapeutic moiety, such as a drug, an enzyme or a toxin. In one embodiment, the therapeutic moiety is a toxin, for example a cytotoxic radionuclide, chemical toxin or protein toxin.

In another aspect, the anti-CD137 single domain antibodies or multivalent binding agents of the invention are modified to increase half-life, for example by a chemical modification, especially by PEGylation, or by incorporation in a liposome or using a serum albumin protein. Increased half life can also be conferred by conjugating the molecule to an antibody fragment, for example a $V_H$ domain that increases half life.

The term "half-life" as used herein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. Half-life may be increased by at least 1.5 times, preferably at least 2 times, such as at least 5 times, for example at least 10 times or more than 20 times, greater than the half-life of the corresponding $V_H$ single domain antibodies of the invention. For example, increased half-life may be more than 1 hours, preferably more than 2 hours, more preferably more than 6 hours, such as more than 12 hours, or even more than 24, 48 or 72 hours, compared to the corresponding $V_H$ single domain antibodies or fusion protein of the invention. The in vivo half-life of an amino acid sequence, compound or polypeptide of the invention can be determined in any manner known per se, such as by pharmacokinetic analysis. Suitable techniques will be clear to the person skilled in the art. Half life can for example be expressed using parameters such as the t½-alpha t½-beta and the area under the curve (AUC).

To generate multivalent binding agents and fusion proteins as described above, two or more polypeptides can be connected by a linker, for example a polypeptide linker. Suitable linkers include for example a linker with GS residues such as (Gly4Ser)n, where n=from 1 to 10, e.g., 1, 2, 3, 4, 5, 6, 7, 8, 9 or 10.

Exemplary Methods for Making the Single Domain Antibody

A single domain antibody described herein can be obtained from a transgenic mammal, for example a rodent, that expresses heavy chain only antibodies upon stimulation with a CD137 antigen. The transgenic rodent, for example a mouse, preferably has a reduced capacity to express endogenous antibody genes. Thus, in one embodiment, the rodent has a reduced capacity to express endogenous light and/or heavy chain antibody genes. The rodent, for example a mouse, may therefore comprise modifications to disrupt expression of endogenous kappa and lambda light and/or heavy chain antibody genes so that no functional light and/or heavy chains are produced, for example as further explained below.

One aspect also relates to a method for producing a human heavy chain only antibodies capable of binding human CD137 said method comprising
 a) immunising a transgenic rodent, e.g. mouse, with an CD137 antigen wherein said rodent expresses a nucleic acid construct comprising unrearranged human heavy chain V genes and is not capable of making functional endogenous light or heavy chains,
 b) isolating human heavy chain only antibodies.

Further steps can include isolating a $V_H$ domain form said heavy chain only antibody, for example by generating a library of sequences comprising $V_H$ domain sequences from said rodent, e.g. mouse and isolating sequences comprising $V_H$ domain sequences from said libraries.

Another aspect also relates to a method for producing a single $V_H$ domain antibody capable of binding human CD137 said method comprising
 a) immunising a transgenic rodent with an CD137 antigen wherein said rodent, e.g. mouse, expresses a nucleic acid construct comprising unrearranged human heavy chain V genes and is not capable of making functional endogenous light or heavy chains,
 b) generating a library of sequences comprising $V_H$ domain sequences from said rodent, e.g. mouse and
 c) isolating sequences comprising $V_H$ domain sequences from said libraries.

Further steps may include identifying a single $V_H$ domain antibody or heavy chain only antibody that binds to human CD137, for example by using functional assays as shown in the examples.

Methods for preparing or generating the polypeptides, nucleic acids, host cells, products and compositions described herein using in vitro expression libraries can comprise the steps of:
 a) providing a set, collection or library of nucleic acid sequences encoding amino acid sequences; and
 b) screening said set, collection or library for amino acid sequences that can bind to/have affinity for CD137 and
 c) isolating the amino acid sequence(s) that can bind to/have affinity for CD137.

In the above method, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

Libraries, for example phage libraries, are generated by isolating a cell or tissue expressing an antigen-specific, heavy chain-only antibody, cloning the sequence encoding the $V_H$ domain(s) from mRNA derived from the isolated cell or tissue and displaying the encoded protein using a library. The $V_H$ domain(s) can be expressed in bacterial, yeast or other expression systems.

Another aspect also relates to an isolated $V_H$ single domain antibody or an isolated heavy chain only antibody comprising a $V_H$ domain binding to CD137 comprising an amino acid product of or derived from a human $V_H$ germline sequence. The heavy chain only antibody may be fully human or comprise mouse sequences.

In the various aspects and embodiments as out herein, the term rodent may relate to a mouse or a rat. In one embodiment, the rodent is a mouse. The mouse may comprise a non-functional endogenous lambda light chain locus. Thus, the mouse does not make a functional endogenous lambda light chain. In one embodiment, the lambda light chain locus is deleted in part or completely or rendered non-functional through insertion, inversion, a recombination event, gene editing or gene silencing. For example, at least the constant region genes C1, C2 and C3 may be deleted or rendered non-functional through insertion or other modification as described above. In one embodiment, the locus is functionally silenced so that the mouse does not make a functional lambda light chain.

Furthermore, the mouse may comprise a non-functional endogenous kappa light chain locus. Thus, the mouse does not make a functional endogenous kappa light chain. In one embodiment, the kappa light chain locus is deleted in part or completely or rendered non-functional through insertion, inversion, a recombination event, gene editing or gene silencing. In one embodiment, the locus is functionally silenced so that the mouse does not make a functional kappa light chain.

The mouse having functionally-silenced endogenous lambda and kappa L-chain loci may, for example, be made as disclosed in WO 2003/000737, which is hereby incorporated by reference in its entirety.

Furthermore, the mouse may comprise a non-functional endogenous heavy chain locus. Thus, the mouse does not make a functional endogenous heavy chain. In one embodiment, the heavy chain locus is deleted in part or completely or rendered non-functional through insertion, inversion, a recombination event, gene editing or gene silencing. In one embodiment, the locus is functionally silenced so that the mouse does not make a functional heavy chain.

For example, as described in WO 2004/076618 (hereby incorporated by reference in its entirety), all 8 endogenous heavy chain constant region immunoglobulin genes ($\mu$, $\delta$, $\gamma 3$, $\gamma 1$, $\gamma 2a$, $\gamma 2b$, $\varepsilon$ and $\alpha$) are absent in the mouse, or partially absent to the extent that they are non-functional, or genes $\delta$, $\gamma 3$, $\gamma 1$, $\gamma 2a$, $\gamma 2b$ and $\varepsilon$ are absent and the flanking genes $\mu$ and $\alpha$ are partially absent to the extent that they are rendered non-functional, or genes $\mu$, $\delta$, $\gamma 3$, $\gamma 1$, $\gamma 2a$, $\gamma 2b$ and $\varepsilon$ are absent and $\alpha$ is partially absent to the extent that it is rendered non-functional, or $\delta$, $\gamma 3$, $\gamma 1$, $\gamma 2a$, $\gamma 2b$, $\varepsilon$ and $\alpha$ are absent and $\mu$ is partially absent to the extent that it is rendered non-functional. By deletion in part is meant that the endogenous locus gene sequence has been deleted or disrupted, for example by an insertion, to the extent that no functional endogenous gene product is encoded by the locus, i.e., that no functional product is expressed from the locus. In another embodiment, the locus is functionally silenced.

In one embodiment, the mouse comprises a non-functional endogenous heavy chain locus, a non-functional endogenous lambda light chain locus and a non-functional endogenous kappa light chain locus. The mouse therefore does not produce any functional endogenous light or heavy chains. Thus, the mouse is a triple knockout (TKO) mouse.

The transgenic mouse may comprise a vector, for example a Yeast Artificial Chromosome (YAC) for expressing a heterologous, preferably a human, heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002 Macmillan Publishers Ltd, Nature Publishing Group).

For example, the YAC may comprise a plethora of unrearranged human $V_H$, D and J genes in combination with mouse immunoglobulin constant region genes lacking $C_H 1$ domains, mouse enhancer and regulatory regions. The human $V_H$, D and J genes are human $V_H$, D and J loci and they are unrearranged genes that are fully human.

Alternative methods known in the art may be used for deletion or inactivation of endogenous mouse or rat immunoglobulin genes and introduction of human $V_H$, D and J genes in combination with mouse immunoglobulin constant region genes lacking $C_H 1$ domains, mouse enhancer and regulatory regions.

Transgenic mice can be created according to standard techniques as illustrated in the examples. The two most characterised routes for creating transgenic mice are via pronuclear microinjection of genetic material into freshly fertilised oocytes or via the introduction of stably transfected embryonic stem cells into morula or blastocyst stage embryos. Regardless of how the genetic material is introduced, the manipulated embryos are transferred to pseudopregnant female recipients where pregnancy continues and candidate transgenic pups are born.

The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, either conventional or with the inclusion of an IVF step to give efficient scaling of the process. However, it is also possible to include the TKO background during the transgenesis procedure. For example, for microinjection, the oocytes may be derived from TKO donors. Similarly, ES cells from TKO embryos can be derived for use in transgenesis.

Triple knock-out mice into which transgenes have been introduced to express immunoglobulin loci are referred to herein as TKO/Tg.

In one embodiment, the mouse is as described in WO2016/062990.

The invention also relates to a rodent, preferably a mouse which expresses a human heavy chain locus and which has been immunized with a CD137 antigen. The invention also relates to a rodent as described above, preferably a mouse which expresses a heavy chain only antibody comprising a human $V_H$ domain that binds to human CD137. Preferably, said rodent is not capable of making functional endogenous kappa and lambda light and/or heavy chains. The human heavy chain locus is located on a transgene which can be as described above.

The invention also relates to an anti-human CD137 single $V_H$ domain antibody or an anti-human CD137 heavy chain only antibody comprising a human $V_H$ domain or obtained or obtainable from a rodent, preferably a mouse, immunised with a human CD137 antigen and which expresses a human heavy chain locus. Preferably, said rodent is not capable of making functional endogenous kappa and lambda light and/or heavy chains. The human heavy chain locus is located on a transgene which can be as described above.

Exemplary Therapeutic Applications

In one aspect, we provide single variable heavy chain domain antibodies described herein and the binding agents described herein for use as an anti-cancer agent or immune modulator.

In another aspect, there is provided a pharmaceutical composition comprising a single variable heavy chain domain antibody that binds to CD137 as described herein or comprising a binding molecule comprising a single variable heavy chain domain antibody that binds to CD137 as described herein and optionally a pharmaceutically acceptable carrier. A single domain antibody, a binding molecule or composition comprising a single variable heavy chain domain antibody that binds to CD137 or the pharmaceutical composition of the invention can be administered by any convenient route, including but not limited to oral, topical, parenteral, sublingual, rectal, vaginal, ocular, intranasal, pulmonary, intradermal, intravitreal, intramuscular, intraperitoneal, intravenous, subcutaneous, intracerebral, transdermal, transmucosal, by inhalation, or topical, particularly to the ears, nose, eyes, or skin or by inhalation.

Parenteral administration includes, for example, intravenous, intramuscular, intraarterial, intraperitoneal, intranasal, rectal, intravesical, intradermal, topical or subcutaneous administration. Preferably, the compositions are administered parenterally.

The pharmaceutically acceptable carrier or vehicle can be particulate, so that the compositions are, for example, in tablet or powder form. The term "carrier" refers to a diluent, adjuvant or excipient, with which a drug antibody conjugate of the present invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the single domain antibody of the present invention or compositions and pharmaceutically acceptable carriers are sterile. Water is a preferred carrier when the drug antibody conjugates of the present invention are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The pharmaceutical composition of the invention can be in the form of a liquid, e.g., a solution, emulsion or suspension. The liquid can be useful for delivery by injection, infusion (e.g., IV infusion) or sub-cutaneously.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent. When the composition is in the form of a capsule (e. g. a gelatin capsule), it can contain, in addition to materials of the above type, a liquid carrier such as polyethylene glycol, cyclodextrin or a fatty oil.

The composition can be in the form of a liquid, e. g. an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

Compositions can take the form of one or more dosage units.

In specific embodiments, it can be desirable to administer the composition locally to the area in need of treatment, or by injection, intravenous injection or infusion. In one embodiment, the composition is part of a device which includes an injector pen. The composition may be provided as a pre-filled syringe or other self-administration device.

The amount of the therapeutic that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances. Factors like age, body weight, sex, diet, time of administration, rate of excretion, condition of the host, drug combinations, reaction sensitivities and severity of the disease shall be taken into account.

Typically, the amount is at least about 0.01% of a single domain antibody of the present invention by weight of the composition. When intended for oral administration, this amount can be varied to range from about 0.1% to about 80% by weight of the composition. Preferred oral compositions can comprise from about 4% to about 50% of the single domain antibody of the present invention by weight of the composition.

Preferred compositions of the present invention are prepared so that a parenteral dosage unit contains from about 0.01% to about 2% by weight of the single domain antibody of the present invention.

For administration by injection, the composition can comprise from about typically about 0.1 mg/kg to about 250 mg/kg of the subject's body weight, preferably, between about 0.1 mg/kg and about 20 mg/kg of the animal's body weight, and more preferably about 1 mg/kg to about 10 mg/kg of the animal's body weight. In one embodiment, the composition is administered at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks.

The invention provides methods of treating CD137-mediated diseases or disorders in a mammal, e.g., a human patient, comprising administering an effective amount of an antibody of the present invention to a mammal in need thereof. In particular, the invention furthermore relates to a method for the prevention and/or treatment of a disorder selected from cancer, an immune disorder, neurological disease, inflammatory disorder, allergy, transplant rejection, viral infection, immune deficiency and other immune system-related disorder said method comprising administering, to a subject in need thereof, a pharmaceutically active amount of a single variable heavy chain domain antibody that binds to CD137, binding molecule composition comprising a single variable heavy chain domain antibody that binds to CD137 or pharmaceutical composition of the invention, or of a pharmaceutical composition of the invention.

As used herein, "treat", "treating" or "treatment" means inhibiting or relieving a disease or disorder. For example, treatment can include a postponement of development of the symptoms associated with a disease or disorder, and/or a reduction in the severity of such symptoms that will, or are expected, to develop with said disease. The terms include ameliorating existing symptoms, preventing additional symptoms, and ameliorating or preventing the underlying causes of such symptoms. Thus, the terms denote that a beneficial result is being conferred on at least some of the mammals, e.g., human patients, being treated. Many medical treatments are effective for some, but not all, patients that undergo the treatment.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the term "effective amount" means an amount of an anti-CD137 antibody, that when administered alone or in combination with an additional therapeutic agent to a cell, tissue, or subject, is effective to achieve the desired therapeutic or prophylactic effect under the conditions of administration The invention also relates to a single variable heavy chain domain antibody that binds to CD137, a binding molecule comprising single variable heavy chain domain antibody that binds to CD137 or pharmaceutical composition of the invention for use in the treatment or prevention of a disease.

In another aspect, the invention relates to a single variable heavy chain domain antibody that binds to CD137, a binding molecule that comprises single variable heavy chain domain antibody that binds to CD137 or pharmaceutical composition of the invention for use in the treatment or prevention of cancer, an immune disorder, neurological disease, inflammatory disorder, allergy, transplant rejection, viral infection, immune deficiency, and other immune system-related disorder.

In another aspect, the invention relates to the use of a single variable heavy chain domain antibody that binds to CD137, a binding molecule comprising a single variable heavy chain domain antibody that binds to CD137 or pharmaceutical composition of the invention in the treatment or prevention of a disease.

In another aspect, the invention relates to the use of a single variable heavy chain domain antibody that binds to CD137, a binding molecule comprising a single variable heavy chain domain antibody that binds to CD137 or pharmaceutical composition of the invention in the manufacture of a medicament for the treatment or prevention of cancer, an immune disorder, neurological disease, inflammatory disorder, allergy, transplant rejection, viral infection, immune deficiency, and other immune system-related disorder.

The cancer can be selected from a solid or non-solid tumor. For example, the cancer may be selected from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, breast cancer, brain cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, kidney cancer, sarcoma of soft tissue, cancer of the urethra, cancer of the bladder, renal cancer, lung cancer, non-small cell lung cancer, thymoma, urothelial carcinoma leukemia, prostate cancer, mesothelioma, adrenocortical carcinoma, lymphomas, such as such as Hodgkin's disease, non-Hodgkin's, gastric cancer, and multiple myelomas.

In one embodiment, the tumor is a solid tumor. Examples of solid tumors which may be accordingly treated include breast carcinoma, lung carcinoma, colorectal carcinoma, pancreatic carcinoma, glioma and lymphoma. Some examples of such tumors include epidermoid tumors, squamous tumors, such as head and neck tumors, colorectal tumors, prostate tumors, breast tumors, lung tumors, including small cell and non-small cell lung tumors, pancreatic tumors, thyroid tumors, ovarian tumors, and liver tumors. Other examples include Kaposi's sarcoma, CNS, neoplasms, neuroblastomas, capillary hemangioblastomas, meningiomas and cerebral metastases, melanoma, gastrointestinal and renal carcinomas and sarcomas, rhabdomyosarcoma, glioblastoma, preferably glioblastoma multiforme, and leiomyosarcoma. Examples of vascularized skin cancers for which the antagonists of this invention are effective include squamous cell carcinoma, basal cell carcinoma and skin cancers that can be treated by suppressing the growth of malignant keratinocytes, such as human malignant keratinocytes.

In one embodiment, the tumor is a non-solid tumor. Examples of non-solid tumors include leukemia, multiple myeloma and lymphoma.

In one aspect, the cancer is locally advanced unresectable, metastatic, or recurrent cancer.

Preferred cancers whose growth may be inhibited using the antibodies of the invention include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer).

In one embodiment, the cancer has progressed after another treatment, for example chemotherapy.

The competitive CD137 binders described herein inhibit CD137 ligand binding to CD137. This leads to a suppression of the signal received by the CD137 receptor. This can be advantageous for the treatment of inflammatory and autoimmune diseases and the monovalent binding molecules described herein therefore find application in the treatment of such diseases.

The immune disorder can be selected from graft vs. host disease, arthritis, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Meniere's disease, mixed connective tissue disease, multiple sclerosis, Neuromyelitis optica (NMO), type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, transverse myelitis, ulcerative colitis, uveitis, vasculitides such as dermatitis herpetiformis vasculitis, vitiligo, and Wegener's granulomatosis. The neurological disease can be selected from Alzheimer's disease, epilepsy, Parkinson's disease, dementia, multiple sclerosis, peripheral neuropathy or post-herpetic neuralgia.

Exemplary Combinations with Other Agents

The molecules or pharmaceutical composition of the invention may be administered as the sole active ingredient or in combination with one or more other therapeutic agent. A therapeutic agent is a compound or molecule which is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. An antibody molecule includes a full antibody or fragment thereof (e.g., a Fab, F(ab')2, Fv, a single chain Fv fragment (scFv) or a single domain antibody, for example a $V_H$ domain, or antibody mimetic protein.

In one embodiment, the single variable heavy chain domain antibody that binds to CD137, a binding molecule comprising a single variable heavy chain domain antibody that binds to CD137 or pharmaceutical composition described herein is used in combination with an existing therapy or therapeutic agent, for example an anti-cancer therapy. Thus, in another aspect, the invention also relates to a combination therapy comprising administration of a single variable heavy chain domain antibody that binds to CD137, a binding molecule comprising a single variable heavy chain domain antibody that binds to CD137 or pharmaceutical composition described herein and an anti-cancer therapy.

The anti-cancer therapy may include a therapeutic agent or radiation therapy and includes gene therapy, viral therapy, RNA therapy bone marrow transplantation, nanotherapy, targeted anti-cancer therapies or oncolytic drugs. Examples of other therapeutic agents include other checkpoint inhibitors, antineoplastic agents, immunogenic agents, attenuated cancerous cells, tumor antigens, antigen presenting cells such as dendritic cells pulsed with tumor-derived antigen or nucleic acids, immune stimulating cytokines (e.g., IL-2, IFNa2, GM-CSF), targeted small molecules and biological molecules (such as components of signal transduction pathways, e.g. modulators of tyrosine kinases and inhibitors of receptor tyrosine kinases, and agents that bind to tumor-specific antigens, including EGFR antagonists), an anti-inflammatory agent, a cytotoxic agent, a radiotoxic agent, or an immunosuppressive agent and cells transfected with a gene encoding an immune stimulating cytokine (e.g., GM-CSF), chemotherapy. In one embodiment, the single domain antibody is used in combination with surgery.

In a specific embodiment of the present invention, the single variable heavy chain domain antibody that binds to CD137, a binding molecule comprising a single variable heavy chain domain antibody that binds to CD137 or pharmaceutical composition described herein is administered concurrently with a chemotherapeutic agent or with radiation therapy. In another specific embodiment, the chemotherapeutic agent or radiation therapy is administered prior or subsequent to administration of the composition of the present invention, preferably at least an hour, five hours, 12 hours, a day, a week, a month, more preferably several months (e. g. up to three months), prior or subsequent to administration of composition of the present invention.

In some embodiments, the single variable heavy chain domain antibody that binds to CD137, a binding molecule comprising a single variable heavy chain domain antibody that binds to CD137 or pharmaceutical composition described herein may be administered with two or more therapeutic agents. In some embodiments, the binding agents of the invention may be administered with two or more therapeutic agents.

The single variable heavy chain domain antibody that binds to CD137, a binding molecule comprising a single variable heavy chain domain antibody that binds to CD137 or a pharmaceutical composition as described herein may be administered at the same time or at a different time as the other therapy or therapeutic compound or therapy, e.g., simultaneously, separately or sequentially.

Exemplary Methods for Modulating Immune Response, Inhibiting Tumor Growth Etc

In yet another aspect, there is provided a method of modulating an immune response in a subject comprising administering to the subject the single variable heavy chain domain antibody that binds to CD137, a binding molecule comprising a single variable heavy chain domain antibody that binds to CD137 or pharmaceutical composition described herein such that the immune response in the subject is modulated. Preferably, the binding molecule enhances, stimulates or increases the immune response in the subject.

In a further aspect, there is provided a method of inhibiting growth of tumor cells in a subject, comprising administering to a subject a therapeutically effective amount of a single variable heavy chain domain antibody that binds to CD137, a binding molecule comprising a single variable heavy chain domain antibody that binds to CD137 or a pharmaceutical composition described herein.

In a further aspect, there is provided a method for activating the downstream signalling pathway of CD137 comprising administering to a subject a single variable heavy chain domain antibody that binds to CD137, a binding molecule comprising a single variable heavy chain domain antibody that binds to CD137 or a pharmaceutical composition described herein.

In a further aspect, there is provided a method for inducing T lymphocyte activation and/or proliferation comprising administering to a subject a single variable heavy chain domain antibody that binds to CD137, a binding molecule comprising a single variable heavy chain domain antibody that binds to CD137 or a pharmaceutical composition described herein.

In a further aspect, there is provided a method for dual targeting of a CD137 expressing cell and a tumor antigen expressing cell comprising administering to a subject a binding molecule comprising a single variable heavy chain domain antibody that binds to CD137 or a pharmaceutical composition described herein.

In a further aspect, there is provided a binding molecule comprising a single variable heavy chain domain antibody that binds to CD137 or a pharmaceutical composition described herein for dual targeting of a CD137 expressing cell and a tumor antigen expressing cell.

Immunoconjugates and Other Agents

In another aspect, there is provided an immunoconjugate comprising a single variable heavy chain domain antibody that binds to CD137 or a binding molecule comprising a single variable heavy chain domain antibody that binds to CD137 described herein conjugated to at least one therapeutic and/or diagnostic agent.

The invention also relates to the use of a single variable heavy chain domain antibody that binds to CD137 or a binding molecule comprising a single variable heavy chain domain antibody that binds to CD137 described herein for use a diagnostic agent. The invention also relates to the use of a single variable heavy chain domain antibody that binds to CD137 or a binding molecule comprising a single variable heavy chain domain antibody that binds to CD137 described herein conjugated to a label.

Exemplary Kits

In another aspect, the invention provides a kit for the treatment or prevention of a disease for example as listed herein or an immune response and/or for detecting CD137 for diagnosis, prognosis or monitoring disease comprising a single domain antibody of the invention. Such a kit may contain other components, packaging, instructions, or material to aid in the detection of CD137 protein. The kit may include a labeled single variable heavy chain domain antibody that binds to CD137 or a binding molecule comprising a single variable heavy chain domain antibody that binds to CD137 and one or more compounds for detecting the label.

The invention in another aspect provides a single variable heavy chain domain antibody that binds to CD137, a binding molecule comprising a single variable heavy chain domain antibody that binds to CD137 or pharmaceutical composition described herein packaged in lyophilized form, or packaged in an aqueous medium.

Exemplary Non Therapeutic Applications

In another aspect, a single variable heavy chain domain antibody that binds to CD137 described herein is used for non-therapeutic purposes, such as diagnostic tests and assays. A method for detecting the presence of human CD137 in a test sample comprises contacting said sample with a single domain antibody described herein and at least one detectable label and detecting binding of said single domain antibody to human CD137.

Modifications of antibodies for diagnostic purposes are well known in the art. For example, antibodies may be modified with a ligand group such as biotin, or a detectable marker group such as a fluorescent group, a radioisotope, or an enzyme. Compounds of the invention can be used for diagnostic purposes and e.g. labelled using conventional techniques. Suitable detectable labels include but are not limited to fluorophores, chromophores, radioactive atoms, electron-dense reagents, enzymes, and ligands having specific binding partners.

Also provided is a single variable heavy chain domain antibody that binds to CD137, a binding molecule comprising a single variable heavy chain domain antibody that binds to CD137 or a pharmaceutical composition described herein with reference to the figures and examples.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present disclosure, including methods, as well as the best mode thereof, of making and using this disclosure, the following examples are provided to further enable those skilled in the art to practice this disclosure. However, those skilled in the art will appreciate that the specifics of these examples should not be read as limiting on the invention, the scope of which should be apprehended from the claims and equivalents thereof appended to this disclosure. Various further aspects and embodiments of the present disclosure will be apparent to those skilled in the art in view of the present disclosure.

All documents mentioned in this specification are incorporated herein by reference in their entirety, including references to gene accession numbers, scientific publications and references to patent publications.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The invention is now further described in the non-limiting examples.

EXAMPLES

Example 1. Construction of Tg/TKO Mice

Mice carrying a human heavy-chain antibody transgenic locus in germline configuration within a background that is silenced for endogenous heavy and light chain antibody expression (triple knock-out, or TKO) were created as previously described (WO2004/076618, WO2003/000737, Ren et al., Genomics, 84, 686, 2004; Zou et al., J. Immunol., 170, 1354, 2003 and WO2016/062990). In summary, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking $C_H1$ domains, mouse enhancer and regulatory regions. The YAC used comprised multiple human heavy chain V genes, multiple human heavy chain D and J genes, a murine $C_H1$ gene and a murine 3' enhancer gene. It lacks the $C_H1$ exon.

The transgenic founder mice were back crossed with animals that lacked endogenous immunoglobulin expression to create the Tg/TKO lines used in the immunisation studies described below.

Example 2. Immunisation Protocol

Tg/TKO mice aged 8-12 weeks were immunised with human CD137-human Fc chimeric protein (Acro Biosystems cat no. 41B-H5258), human CD137-His tagged protein (R&D Systems, custom product), CHO cells over-expressing human CD137 (cell line produced in-house using standard methods) or a combination of recombinant protein and CHO human CD137 expressing cells.

Example 3. Serum ELISA

Serum was collected from mice before and after immunisation and checked by ELISA for the presence of serum human CD137 reactive heavy chain antibodies in response to immunisation with CD137 antigen.

Whole blood samples were centrifuged at 13000 rpm for 5 mins to separate blood from serum. Serial dilutions of serum were prepared in 3% Marvel®/PBS in polypropylene tubes or plates, pre-incubated for at least one hour at room temperature then transferred to the blocked ELISA plate and incubated for at least one hour. Unbound protein was removed by repetitive washing with PBS/Tween®-20 followed by PBS. A 1:10,000 solution of biotin-conjugated, goat anti-mouse IgG, Fcgamma subclass 1 specific antibody (Jackson ImmunoResearch cat. no. 115-065-205), prepared in PBS/3% Marvel® was added to each well and incubated at room temperature for at least one hour. Unbound detection antibody was removed by repeated washing using PBS/Tween® 20 and PBS. Neutravidin-HRP solution (Pierce cat. no. 31030) in 3% Marvel®/PBS was added to the ELISA plates and allowed to bind for 30 minutes, then washed as above. The ELISA was developed using TMB substrate (Sigma cat. no. T0440) and the reaction was stopped by the addition of 50 ul 0.5M $H_2SO_4$ solution (Sigma cat. no. 320501). Absorbance at 450 nm was measured using the BMG Pherastar.

Example 4. Generation of Libraries from Immunised Mice

Generation of libraries from immunised mice described above followed standard protocols of library generation as summarised below.

Tissue, including total spleen, inguinal and brachial lymph nodes was collected into RNAlater® from several immunised mice. Total RNA was extracted from supernatants. $V_H$ sequences were mined from the RNA samples using Superscript III RT-PCR high-fidelity kit (Invitrogen cat. no. 12574-035) according to the manufacturer's protocol. $V_H$/phagemid PCR products were pooled by animal-of-origin or $V_H$ germline families and purified using Fermentas PCR purification kit (cat. no. K0702) according to the manufacturer's instructions. The eluted DNA was transformed into TG1 E. coli (Lucigen, cat. no. 60502-2) by electroporation using the Bio-Rad GenePulser Xcell pulsed at 2500V, 25 uF, 200 W. Electroporated cells were pooled. Libraries were harvested.

Example 5. Selection Strategies for Isolation of CD137 Binding $V_H$ Isolation and Optimisation Preparation of library phage stocks and phage display selections were performed according to published methods (Antibody Engineering, edited by Benny Lo, chapter 8, p 161-176, 2004). In most cases, phage display combined with a panning approach was used to isolate binding $V_H$ domains. However, a variety of different selection methods are well described in the art, including soluble protein selections, cell based selections and selections performed under stress (e.g., heat).

Example 6: Screening of Periplasmic Extracts for Binding to CHO Human C0137 Cells and Inhibition of Human C0137 Ligand Binding to Human C0137

Following selections of the libraries, specific $V_H$ that bound to CHO cells expressing human CD137, did not bind to CHO parental cells and inhibited the interaction between human CD137 expressed on the surface of CHO cells and recombinant human CD137 Ligand protein were identified by single point screening of bacterial periplasmic extracts. Small-scale bacterial periplasmic extracts were prepared from 1 ml cultures, grown in deep well plates according to standard techniques. Binding of His-tagged $V_H$ in the supernatants to CHO human CD137 cells and to CHO parent cells for determination of non CD137 specific binding was assessed using Fluorescence Microvolume Assay Technology (FMAT). Fluorescence emission was measured on the TTP Mirrorball plate reader in the FL2 (502 nm-537 nm) and FL5 (677-800 nm) channels following excitation at 488 nm and 640 nm. Data was gated on FL5 perimeter and peak intensity and the FL2 median mean fluorescence intensity of the gated data used for determination of $V_H$ binding.

In parallel to the binding assay, periplasmic extracts were tested for their ability to inhibit the interaction of human CD137 ligand protein with CHO human CD137 cells in an FMAT format. Total binding controls containing diluted periplasmic extract sample buffer and non-specific binding controls containing excess non-Fc tagged competitor were set up on each plate for data normalisation. Fluorescence signal was measured using the TTP Mirrorball and the FL2 median mean fluorescence intensity of gated used for the data normalisation. The data was expressed as a % of the total binding control (% control) after subtraction of the background signal determined from the non-specific binding control wells. Families of $V_H$ were identified that bound to the CHO human CD137 cells, did not bind CHO parental cells and that inhibited CD137 binding to CD137 Ligand.

Example 7. Sequencing

Table 1 shows the sequences of Family 1 VHs and table 2 those of Family 2 VHs.

Each individual V_H clone as identified above was sequenced from the phagemid and grouped based on V_H germline and CDR3 amino acid similarity. Representative clones were further characterised. Further clones were generated by sequence optimisation of clone Humabody® V_H 1.1 and Humabody® V_H 2.1 respectively to improve binding activity, revert sequence to germline or remove biophysical sequence liabilities such as isomerisation or deamidation sites.

Example 8. Preparation Purified V_H a) Preparation of Purified V_H

Purified V_H were obtained by using the V_H C-terminal 6xHIS tag for nickel-agarose affinity chromatographic purification of the periplasmic extracts according to standard procedures. Yields of purified V_H were estimated spectrophotometrically and purity was assessed using SDS PAGE. Alternatively, V_H were purified from the supernatants of W3110 E. coli with pJExpress vector according to standard procedures. Yields of purified V_H were estimated spectrophotometrically and purity was assessed using SDS PAGE. If required, samples were concentrated using Vivaspin 20, 3 kDa MWCO PES, concentrator (Sartorius, #VS2092) and endotoxin depleted using Etoxiclear resin (Prometic, #3250-00010).

b) Generation of Multivalent Constructs

DNA sequences encoding Humabody® V_H specific for CD137 and a V_H specific for PSMA were amplified by PCR. They were assembled into larger fragments, with the V_H sequences flanked by linkers encoding glycine/serine-rich sequences, and ligated into an expression vector by a restriction enzyme-based method. Plasmids were transformed into microbial expression systems as per standard techniques. The presence of Humabody® V_H sequences was verified by a standard colony PCR technique. Insert sequences were then confirmed by Sanger sequencing using vector-specific and internal primers to ensure complete sequence coverage. Sequences for exemplary constructs are shown below.

TABLE 6a

PSMA binding single V_H domain antibodies

| Name | CDR1 | CDR2 | CDR3 | SEQ IDfull VH |
|---|---|---|---|---|
| 3.1 | SEQ ID NO. 812<br>SYAMS | SEQ ID NO. 813<br>SIGENDGTTDY ADSVKG | SEQ ID NO. 814<br>DGVH | SEQ ID NO. 815<br>EVQLLESGGGLVQPGGSLRLSCAASGFSFSSYAMSWV RQAPGKGLEWVSSIGENDGTTDYADSVKGRFTISRDN SKSMLYLQMNSLRVEDTAVYYCVKDGVHWGQGTLV TVSS |

TABLE 6b

PSMA binding single V_H domain antibodies

| Clone number | V_H Full length sequence |
|---|---|
| 3.2 | SEQ ID NO. 816<br>EVQLLESGGGLVQPGGSLRLSCAASGFSFSSYALSWVRQAPGKGLEWVSSIGENDGTTDYADFVKGRFTISRDNSK NTLYLQMNSLRVEDTAVYYCVKDGVHWGQGTLVTVSS |
| 3.3 | SEQ ID NO. 817<br>EVQLLESGGGLVQPGGSLRLSCAASGFSFSSYALSWVRQAPGKGLEWVSSIGENDGTTDYADNVKGRFTISRDNS KNTLYLQMNSLRVEDTAVYYCVKDGVHWGQGTLVTVSS |
| 3.4 | SEQ ID NO. 818<br>EVQLLESGGGLVQPGGSLRLSCAASGFSFSSYALSWVRQAPGKGLEWVSSIGENDGTTDYAADVKGRFTISRDNS KNTLYLQMNSLRVEDTAVYYCVKDGVHWGQGTLVTVSS |
| 3.5 | SEQ ID NO. 819<br>EVQLLESGGGLVQPGGSLRLSCAASGFSFSSYALSWVRQAPGKGLEWVSSIGENDGTTDYADVVKGRFTISRDNS KNTLYLQMNSLRVEDTAVYYCVKDGVHWGQGTLVTVSS |
| 3.6 | SEQ ID NO. 820<br>EVQLLESGGGLVQPGGSLRLSCAASGFSFSSYALSWVRQAPGKGLEWVSSIGENDGTTDYAAFVKGRFTISRDNSK NTLYLQMNSLRVEDTAVYYCVKDGVHWGQGTLVTVSS |
| 3.7 | SEQ ID NO. 821<br>EVQLLESGGGLVQPGGSLRLSCAASGFSFSSYALSWVRQAPGKGLEWVSSIGENDGTTDYADTVKGRFTISRDNSK NTLYLQMNSLRVEDTAVYYCVKDGVHWGQGTLVTVSS |
| 3.8 | SEQ ID NO. 822<br>EVQLLESGGGLVQPGGSLRLSCAASGFSFSSYALSWVRQAPGKGLEWVSSIGENDGTTDYADAVKGRFTISRDNS KNTLYLQMNSLRVEDTAVYYCVKDGVHWGQGTLVTVSS |
| 3.9 | SEQ ID NO. 823<br>EVQLLESGGGLVQPGGSLRLSCAASGFSFSSYALSWVRQAPGKGLEWVSSIGENDGTTDYAASVKGRFTISRDNSK NTLYLQMNSLRVEDTAVYYCVKDGVHWGQGTLVTVSS |
| 3.10 | SEQ ID NO. 824<br>EVQLLESGGGLVQPGGSLRLSCAASGFSFSSYALSWVRQAPGKGLEWVSSIGENDGTTDYAAYVKGRFTISRDNSK NTLYLQMNSLRVEDTAVYYCVKDGVHWGQGTLVTVSS |

TABLE 6b-continued

PSMA binding single V$_H$ domain antibodies

| Clone number | V$_H$ Full length sequence |
|---|---|
| 3.11 | SEQ ID NO. 825<br>EVQLLESGGGLVQPGGSLRLSCAASGFSFSSYALSWVRQAPGKGLEWVSSIGENDGTTDYAATVKGRFTISRDNSK<br>NTLYLQMNSLRVEDTAVYYCVKDGVHWGQGTLVTVSS |

TABLE 6c

PSMA binding single VH domain antibody

| 4.1 | SEQ ID NO. 837<br>GYGMH | SEQ ID NO. 838<br>YISYDGSNKYYADSVK<br>G | SEQ ID NO. 839<br>DPAWGLRLGESS<br>SYDFDI | SEQ ID NO. 840<br>EVQLVESGGGVVQPGRSLRLSCAASGFSFSGYGMHWVRQA<br>PGKGLEWVAYISYDGSNKYYADSVKGRFTISRDNSKNTLYLQ<br>MNSLRAEDTAVYYCAKDPAWGLRLGESSSYDFDIWGQGT<br>MVTVSS |

TABLE 6d

Exemplary nucleic acids 3.1 SEQ ID NO. 826
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCATGAGTTGGGTCCGCCAGGCTCCAGGGAAGGGGCTGGAGTGGGTCTCAAGTATTGGTGAGAAT
GATGGTACCACAGACTACGCAGACTCCGTGAAGGGCCGATTCACCATCTCCAGAGACAATTCCAAGAGTATGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.2 SEQ ID NO. 827
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
AACGCTACCACAGACTACGCAGACTTCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.3 SEQ ID NO. 828
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGACGCCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.4 SEQ ID NO. 829
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGCCGACGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.5 SEQ ID NO. 830
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGACGTCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.6 SEQ ID NO. 831
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGCCTTCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.7 SEQ ID NO. 832
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGACACCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA TABLE 6d-continued Exemplary nucleic acids 3.8 SEQ ID NO. 833
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGACGCCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.9 SEQ ID NO. 834
GAGGTGCAGCTGTTGGAGTCTGGGGGAGGCTTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGCCTCCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.10 SEQ ID NO. 835
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGCCTACGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 3.11 SEQ ID NO. 836
GAGGTGCAGCTGTTGGAGTCTGGGGGAGGCTGGTACAGCCTGGGGGGTCCCTGAGACTCTCCTGTGCAGCCTCTGGATTC
AGTTTTAGCAGCTATGCCCTCAGTTGGGTCCGCCAGGCTCCAGGGAAGGGGCTGGAGTGGGTCTCAAGTATTGGTGAGAAT
GATGGTACCACAGACTACGCAGCCACCGTGAAGGGCCGATTCACCATCTCCAGAGACAATTCCAAGAATACGCTGTATCTGC
AAATGAACAGCCTGAGAGTCGAGGACACGGCCGTCTATTACTGTGTGAAAGATGGTGTCCACTGGGGCCAGGGAACCCTGG
TCACCGTCTCCTCA 4.1 SEQ ID NO. 841
GAGGTGCAGCTGGTGGAGTCTGGGGGAGGCGTGGTCCAGCCTGGGAGGTCCCTGAGACTCTCCTGTGCAGCCTCTGGATTC
TCCTTCAGTGGCTATGGCATGCACTGGGTCCGCCAGGCTCCAGGCAAGGGACTGGAGTGGGTGGCATATATATCATATGATG
GAAGTAATAAATACTATGCAGACTCCGTGAAGGGCCGATTCACCATCTCCAGAGACAATTCCAAGAACACGCTGTATCTGCA
AATGAACAGCCTGAGAGCTGAGGACACGGCTGTGTATTACTGTGCGAAAGATCCGGCCTGGGGATTACGTTTGGGGGAGTC
ATCGTCCTATGATTTTGATATCTGGGGCCAAGGGACAATGGTCACTGTCTCTTCA The PSMA binding molecules bind to wild type human PSMA (UniProt Accession NO. Q04609). The sequence for the monomer is shown below (SEQ ID No. 842).

```
  1  MWNLLHETDS AVATARRPRW LCAGALVLAG GFFLLGFLFG
     WFIKSSNEAT NITPKHNMKA
 61  FLDELKAENI KKFLYNFTQI PHLAGTEQNF QLAKQIQSQW
     KEFGLDSVEL AHYDVLLSYP
121  NKTHPNYISI INEDGNEIFN TSLFEPPPPG YENVSDIVPP
     FSAFSPQGMP EGDLVYVNYA
181  RTEDFFKLER DMKINCSGKI VIARYGKVFR GNKVKNAQLA
     GAKGVILYSD PADYFAPGVK
241  SYPDGWNLPG GGVQRGNILN LNGAGDPLTP GYPANEYAYR
     RGIAEAVGLP SIPVHPIGY
301  DAQKLLEKMG GSAPPDSSWR GSLKVPYNVG PGFTGNFSTQ
     KVKMHIHSTN EVTRIYNVIG
361  TLRGAVEPDR YVILGGHRDS WVFGGIDPQS GAAVVHEIVR
     SFGTLKKEGW RPRRTILFAS
421  WDAEEFGLLG STEWAEENSR LLQERGVAYI NADSSIEGNY
     TLRVDCTPLM YSLVHNLTKE
481  LKSPDEGFEG KSLYESWTKK SPSPEFSGMP RISKLGSGND
     FEVFFQRLGI ASGRARYTKN
541  WETNKFSGYP LYHSVYETYE LVEKFYDPMF KYHLTVAQVR
     GGMVFELANS IVLPFDCRDY
601  AVVLRKYADK IYSISMKHPQ EMKTYSVSFD SLFSAVKNFT
     EIASKFSERL QDFDKSNPIV
661  LRMMNDQLMF LERAFIDPLG LPDRPFYRHV IYAPSSHNKY
     AGESFPGIYD ALFDIESKVD
721  PSKAWGEVKR QIYVAAFTVQ AAAETLSEVA
```

TABLE 7 exemplary multivalent constructs

SEQ ID NO: 798 1.1-6GS-1.1 Protein
EVQLVESGGGLVQPGGSLRLSCAASGFTFSSHWMTWFRQAPGKGLEWVAHIKEDGSEKYYEDSVEGRFTVSRDNAKNSVYLQMN
SLRAEDTAVYYCARGGDGYSDSHFGVDVWGQGTTVTVSSGGGGSGGGGSGGGGSGGGGSGGGGSGGGGSEVQLVESGGGLVQ
PGGSLRLSCAASGFTFSSHWMTWFRQAPGKGLEWVAHIKEDGSEKYYEDSVEGRFTVSRDNAKNSVYLQMNSLRAEDTAVYYCAR
GGDGYSDSHFGVDVWGQGTTVTVSS TABLE 7-continued exemplary multivalent constructs SEQ ID NO: 799 1.1-6GS-1.1 Nucleotide
GAGGTGCAGCTGGTGGAGTCTGGGGGAGGCTTGGTCCAGCCGGGGGGTCCCTGAGACTCTCCTGTGCAGCCTCTGGATTCA
CCTTTAGTAGCCATTGGATGACTTGGTTCCGTCAGGCTCCAGGGAAGGGGCTGGAGTGGGTGGCCCACATAAAGGAAGACGG
AAGTGAGAAATACTATGAGGACTCTGTGGAGGGCCGATTCACCGTCTCCAGAGACAACGCCAAGAACTCGGTATATCTGCAAA
TGAACAGTCTGAGAGCCGAAGACACGGCTGTGTATTACTGTGCAGAGGAGGTGATGGCTACAGTGACTCCCACTTCGGTGT
GGACGTCTGGGGCCAAGGGACCACGGTCACTGTCTCTTCAGGTGGTGGCGGTTCAGGCGGAGGTGGCTCTGGAGGTGGAGG
TTCAGGAGGTGGTGGTTCTGGCGGCGGTGGATCGGGTGGAGGTGGTAGTGAGGTGCAGCTGGTGGAGTCTGGGGGAGGCTT
GGTCCAGCCGGGGGGTCCCTGAGACTCTCCTGTGCAGCCTCTGGATTCACCTTTAGTAGCCATTGGATGACTTGGTTCCGTCA
GGCTCCAGGGAAGGGGCTGGAGTGGGTGGCCCACATAAAGGAAGACGGAAGTGAGAAATACTATGAGGACTCTGTGGAGG
GCCGATTCACCGTCTCCAGAGACAACGCCAAGAACTCGGTATATCTGCAAATGAACAGTCTGAGAGCCGAAGACACGGCTGTG
TATTACTGTGCGAGAGGAGGTGATGGCTACAGTGACTCCCACTTCGGTGTGGACGTCTGGGGCCAAGGGACCACGGTCACTGT
CTCTTCA SEQ ID NO: 800 2.1-6GS-2.1 Protein
EVQLVESGGGLVKPGGSLRVSCAASGFTFSDYYMSWFRQAPGKGLEWVSYISGSGDIIDYADSVKGRFTISRDNAKNSLYLQMNNLR
AEDTAVYHCAREDSRLTGTTDFDNWGQGTLVTVSSGGGGSGGGGSGGGGSGGGGSGGGGSGGGGSEVQLVESGGGLVKPGGSL
RVSCAASGFTFSDYYMSWFRQAPGKGLEWVSYISGSGDIIDYADSVKGRFTISRDNAKNSLYLQMNNLRAEDTAVYHCAREDSRLTG
TTDFDNWGQGTLVTVSS SEQ ID NO: 801 2.1-6GS-2.1 Nucleotide
GAGGTGCAGCTGGTGGAGTCTGGGGGAGGCTTGGTCAAGCCTGGAGGGTCCCTGAGAGTCTCCTGTGCAGCCTCTGGATTCA
CCTTCAGTGACTACTACATGAGCTGGTTCCGCCAGGCTCCAGGGAAGGGGCTGGAGTGGGTTTCATACATTAGTGGTAGTGGT
GATATCATAGACTACGCAGACTCTGTAAAGGGCCGATTCACCATCTCCAGGGACAACGCCAAGAACTCTCTGTATCTGCAGATG
AACAACCTGAGAGCCGAGGACACGGCCGTGTATCACTGTGCGAGAGAAGATTCCCGTCTAACTGGAACTACGGACTTTGACAA
TTGGGGCCAGGGAACCCTGGTCACCGTCTCCTCAGGTGGTGGCGGTTCAGGCGGAGGTGGCTCTGGAGGTGGAGGTTCAGG
AGGTGGTGGTTCTGGCGGCGGTGGATCGGGTGGAGGTGGTAGTGAGGTGCAGCTGGTGGAGTCTGGGGGAGGCTTGGTCA
AGCCTGGAGGGTCCCTGAGAGTCTCCTGTGCAGCCTCTGGATTCACCTTCAGTGACTACTACATGAGCTGGTTCCGCCAGGCTC
CAGGGAAGGGGCTGGAGTGGGTTTCATACATTAGTGGTAGTGGTGATATCATAGACTACGCAGACTCTGTAAAGGGCCGATT
CACCATCTCCAGGGACAACGCCAAGAACTCTCTGTATCTGCAGATGAACAACCTGAGAGCCGAGGACACGGCCGTGTATCACT
GTGCGAGAGAAGATTCCCGTCTAACTGGAACTACGGACTTTGACAATTGGGGCCAGGGAACCCTGGTCACCGTCTCCTCA SEQ ID NO: 802 1.1-6GS-1.1-6GS-1.1 Protein
EVQLVESGGGLVQPGGSLRLSCAASGFTFSSHWMTWFRQAPGKGLEWVAHIKEDGSEKYYEDSVEGRFTVSRDNAKNSVYLQMN
SLRAEDTAVYYCARGGDGYSDSHFGVDVWGQGTTVTVSSGGGGSGGGGSGGGGSGGGGSGGGGSGGGGSEVQLVESGGGLVQ
PGGSLRLSCAASGFTFSSHWMTWFRQAPGKGLEWVAHIKEDGSEKYYEDSVEGRFTVSRDNAKNSVYLQMNSLRAEDTAVYYCAR
GGDGYSDSHFGVDVWGQGTTVTVSSGGGGSGGGGSGGGGSGGGGSGGGGSGGGGSEVQLVESGGGLVQPGGSLRLSCAASGF
TFSSHWMTWFRQAPGKGLEWVAHIKEDGSEKYYEDSVEGRFTVSRDNAKNSVYLQMNSLRAEDTAVYYCARGGDGYSDSHFGVD
VWGQGTTVTVSS SEQ ID NO: 803 1.1-6GS-1.1-6GS-1.1 Nucleotide
GAGGTGCAGCTGGTGGAGTCTGGGGGAGGCTTGGTCCAGCCGGGGGGTCCCTGAGACTCTCCTGTGCAGCCTCTGGATTCA
CCTTTAGTAGCCATTGGATGACTTGGTTCCGTCAGGCTCCAGGGAAGGGGCTGGAGTGGGTGGCCCACATAAAGGAAGACGG
AAGTGAGAAATACTATGAGGACTCTGTGGAGGGCCGATTCACCGTCTCCAGAGACAACGCCAAGAACTCGGTATATCTGCAAA
TGAACAGTCTGAGAGCCGAAGACACGGCTGTGTATTACTGTGCGAGAGGAGGTGATGGCTACAGTGACTCCCACTTCGGTGT
GGACGTCTGGGGCCAAGGGACCACGGTCACTGTCTCTTCAGGTGGTGGCGGTTCAGGCGGAGGTGGCTCTGGAGGTGGAGG
TTCAGGAGGTGGTGGTTCTGGCGGCGGTGGATCGGGTGGAGGTGGTAGTGAGGTGCAGCTGGTGGAGTCTGGGGGAGGCTT
GGTCCAGCCGGGGGGTCCCTGAGACTCTCCTGTGCAGCCTCTGGATTCACCTTTAGTAGCCATTGGATGACTTGGTTCCGTCA
GGCTCCAGGGAAGGGGCTGGAGTGGGTGGCCCACATAAAGGAAGACGGAAGTGAGAAATACTATGAGGACTCTGTGGAGG
GCCGATTCACCGTCTCCAGAGACAACGCCAAGAACTCGGTATATCTGCAAATGAACAGTCTGAGAGCCGAAGACACGGCTGTG
TATTACTGTGCGAGAGGAGGTGATGGCTACAGTGACTCCCACTTCGGTGTGGACGTCTGGGGCCAAGGGACCACGGTCACTGT
CTCTTCAGGTGGTGGCGGTTCAGGCGGAGGTGGCTCTGGAGGTGGAGGTTCAGGAGGTGGTGGTTCTGGCGGCGGTGGATC
GGGTGGAGGTGGTAGTGAGGTGCAGCTGGTGGAGTCTGGGGGAGGCTTGGTCCAGCCGGGGGGTCCCTGAGACTCTCCTG
TGCAGCCTCTGGATTCACCTTTAGTAGCCATTGGATGACTTGGTTCCGTCAGGCTCCAGGGAAGGGGCTGGAGTGGGTGGCCC
ACATAAAGGAAGACGGAAGTGAGAAATACTATGAGGACTCTGTGGAGGGCCGATTCACCGTCTCCAGAGACAACGCCAAGAA
CTCGGTATATCTGCAAATGAACAGTCTGAGAGCCGAAGACACGGCTGTGTATTACTGTGCGAGAGGAGGTGATGGCTACAGT
GACTCCCACTTCGGTGTGGACGTCTGGGGCCAAGGGACCACGGTCACTGTCTCTTCA SEQ ID NO: 804 2.1-6GS-2.1-6GS-2.1 Protein
EVQLVESGGGLVKPGGSLRVSCAASGFTFSDYYMSWFRQAPGKGLEWVSYISGSGDIIDYADSVKGRFTISRDNAKNSLYLQMNNLR
AEDTAVYHCAREDSRLTGTTDFDNWGQGTLVTVSSGGGGSGGGGSGGGGSGGGGSGGGGSGGGGSEVQLVESGGGLVKPGGSL
RVSCAASGFTFSDYYMSWFRQAPGKGLEWVSYISGSGDIIDYADSVKGRFTISRDNAKNSLYLQMNNLRAEDTAVYHCAREDSRLTG
TTDFDNWGQGTLVTVSSGGGGSGGGGSGGGGSGGGGSGGGGSGGGGSEVQLVESGGGLVKPGGSLRVSCAASGFTFSDYYMS
WFRQAPGKGLEWVSYISGSGDIIDYADSVKGRFTISRDNAKNSLYLQMNNLRAEDTAVYHCAREDSRLTGTTDFDNWGQGTLVTVS
S SEQ ID NO: 805 2.1-6GS-2.1-6GS-2.1 Nucleotide
GAGGTGCAGCTGGTGGAGTCTGGGGGAGGCTGGTCAAGCCTGGAGGGTCCCTGAGAGTCTCCTGTGCAGCCTCTGGATTCA
CCTTCAGTGACTACTACATGAGCTGGTTCCGCCAGGCTCCAGGGAAGGGGCTGGAGTGGGTTTCATACATTAGTGGTAGTGGT
GATATCATAGACTACGCAGACTCTGTAAAGGGCCGATTCACCATCTCCAGGGACAACGCCAAGAACTCTCTGTATCTGCAGATG
AACAACCTGAGAGCCGAGGACACGGCCGTGTATCACTGTGCGAGAGAAGATTCCCGTCTAACTGGAACTACGGACTTTGACAA
TTGGGGCCAGGGAACCCTGGTCACCGTCTCCTCAGGTGGTGGCGGTTCAGGCGGAGGTGGCTCTGGAGGTGGAGGTTCAGG
AGGTGGTGGTTCTGGCGGCGGTGGATCGGGTGGAGGTGGTAGTGAGGTGCAGCTGGTGGAGTCTGGGGGAGGCTTGGTCA
AGCCTGGAGGGTCCCTGAGAGTCTCCTGTGCAGCCTCTGGATTCACCTTCAGTGACTACTACATGAGCTGGTTCCGCCAGGCTC
CAGGGAAGGGGCTGGAGTGGGTTTCATACATTAGTGGTAGTGGTGATATCATAGACTACGCAGACTCTGTAAAGGGCCGATT
CACCATCTCCAGGGACAACGCCAAGAACTCTCTGTATCTGCAGATGAACAACCTGAGAGCCGAGGACACGGCCGTGTATCACT
GTGCGAGAGAAGATTCCCGTCTAACTGGAACTACGGACTTTGACAATTGGGGCCAGGGAACCCTGGTCACCGTCTCCTCAGGT
GGTGGCGGTTCAGGCGGAGGTGGCTCTGGAGGTGGAGGTTCAGGAGGTGGTGGTTCTGGCGGCGGTGGATCGGGTGGAGG TABLE 7-continued exemplary multivalent constructs TGGTAGTGAGGTGCAGCTGGTGGAGTCTGGGGGAGGCTTGGTCAAGCCTGGAGGGTCCCTGAGAGTCTCCTGTGCAGCCTCT
GGATTCACCTTCAGTGACTACTACATGAGCTGGTTCCGCCAGGCTCCAGGGAAGGGGCTGGAGTGGGTTTCATACATTAGTGG
TAGTGGTGATATCATAGACTACGCAGACTCTGTAAAGGGCCGATTCACCATCTCCAGGGACAACGCCAAGAACTCTCTGTATCT
GCAGATGAACAACCTGAGAGCCGAGGACACGGCCGTGTATCACTGTGCGAGAGAAGATTCCCGTCTAACTGGAACTACGGAC
TTTGACAATTGGGGCCAGGGAACCCTGGTCACCGTCTCCTCA SEQ ID NO: 806 4.1(PSMA-binding VH)-6GS-1.1 Protein
EVQLVESGGGVVQPGRSLRLSCAASGFSFSGYGMHWVRQAPGKGLEWVAYISYDGSNKYYADSVKGRFTISRDNSKNTLYLQMNS
LRAEDTAVYYCAKDPAWGLRLGESSSYDFDIWGQGTMVTVSSGGGGSGGGGSGGGGSGGGGSGGGGSGGGGSEVQLVESGGG
LVQPGGSLRLSCAASGFTFSSHWMTWFRQAPGKGLEWVAHIKEDGSEKYYEDSVEGRFTVSRDNAKNSVYLQMNSLRAEDTAVYY
CARGGDGYSDSHFGVDVWGQGTTVTVSS SEQ ID NO: 807 4.1(PSMA-binding VH)-6GS-1.1 Nucleotide
GAGGTGCAGCTGGTGGAGTCTGGGGGAGGCGTGGTCCAGCCTGGAGGTCCCTGAGACTCTCCTGTGCAGCCTCTGGATTCT
CCTTCAGTGGCTATGGCATGCACTGGGTCCGCCAGGCTCCAGGCAAGGGACTGGAGTGGGTGGCATATATATCATATGATGGA
AGTAATAAATACTATGCAGACTCCGTGAAGGGCCGATTCACCATCTCCAGAGACAATTCCAAGAACACGCTGTATCTGCAAATG
AACAGCCTGAGAGCTGAGGACACGGCTGTGTATTACTGTGCGAAAGATCCGGCCTGGGGATTACGTTTGGGGGAGTCATCGT
CCTATGATTTTGATATCTGGGGCCAAGGGACAATGGTCACCGTCTCCTCAGGTGGTGGCGGTTCAGGCGGAGGTGGCTCTGGA
GGTGGAGGTTCAGGAGGTGGTGGTTCTGGCGGCGGTGGATCGGGTGGAGGTGGTAGTGAGGTGCAGCTGGTGGAGTCTGG
GGGAGGCTTGGTCCAGCCGGGGGGGTCCCTGAGACTCTCCTGTGCAGCCTCTGGATTCACCTTTAGTAGCCATTGGATGACTT
GGTTCCGTCAGGCTCCAGGGAAGGGGCTGGAGTGGGTGGCCCACATAAAGGAAGACGGAAGTGAGAAATACTATGAGGACT
CTGTGGAGGGCCGATTCACCGTCTCCAGAGACAACGCCAAGAACTCGGTATATCTGCAAATGAACAGTCTGAGAGCCGAAGAC
ACGGCTGTGTATTACTGTGCGAGAGGAGGTGATGGCTACAGTGACTCCCACTTCGGTGTGGACGTCTGGGGCCAAGGGACCA
CGGTCACTGTCTCTTCA SEQ ID NO: 808 4.1(PSMA-binding VH)-6GS-2.1
EVQLVESGGGVVQPGRSLRLSCAASGFSFSGYGMHWVRQAPGKGLEWVAYISYDGSNKYYADSVKGRFTISRDNSKNTLYLQMNS
LRAEDTAVYYCAKDPAWGLRLGESSSYDFDIWGQGTMVTVSSGGGGSGGGGSGGGGSGGGGSGGGGSGGGGSEVQLVESGGG
LVKPGGSLRVSCAASGFTFSDYYMSWFRQAPGKGLEWVSYISGSGDIIDYADSVKGRFTISRDNAKNSLYLQMNNLRAEDTAVYHCA
REDSRLTGTTDFDNWGQGTLVTVSS SEQ ID NO: 809 4.1(PSMA-binding VH)-6GS-2.1 Nucleotide
GAGGTGCAGCTGGTGGAGTCTGGGGGAGGCGTGGTCCAGCCTGGAGGTCCCTGAGACTCTCCTGTGCAGCCTCTGGATTCT
CCTTCAGTGGCTATGGCATGCACTGGGTCCGCCAGGCTCCAGGCAAGGGACTGGAGTGGGTGGCATATATATCATATGATGGA
AGTAATAAATACTATGCAGACTCCGTGAAGGGCCGATTCACCATCTCCAGAGACAATTCCAAGAACACGCTGTATCTGCAAATG
AACAGCCTGAGAGCTGAGGACACGGCTGTGTATTACTGTGCGAAAGATCCGGCCTGGGGATTACGTTTGGGGGAGTCATCGT
CCTATGATTTTGATATCTGGGGCCAAGGGACAATGGTCACCGTCTCCTCAGGTGGTGGCGGTTCAGGCGGAGGTGGCTCTGGA
GGTGGAGGTTCAGGAGGTGGTGGTTCTGGCGGCGGTGGATCGGGTGGAGGTGGTAGTGAGGTGCAGCTGGTGGAGTCTGG
GGGAGGCTTGGTCAAGCCTGGAGGGTCCCTGAGAGTCTCCTGTGCAGCCTCTGGATTCACCTTCAGTGACTACTACATGAGCT
GGTTCCGCCAGGCTCCAGGGAAGGGGCTGGAGTGGGTTTCATACATTAGTGGTAGTGGTGATATCATAGACTACGCAGACTCT
GTAAAGGGCCGATTCACCATCTCCAGGGACAACGCCAAGAACTCTCTGTATCTGCAGATGAACAACCTGAGAGCCGAGGACAC
GGCCGTGTATCACTGTGCGAGAGAAGATTCCCGTCTAACTGGAACTACGGACTTTGACAATTGGGGCCAGGGAACCCTGGTCA
CCGTCTCCTCA SEQ ID NO: 810 Protein 3.8-6GS-1.1
EVQLLESGGGLVQPGGSLRLSCAASGFSFSSYALSWVRQAPGKGLEWVSSIGENDGTTDYADAVKGRFTISRDNSKNTLYLQMNSLR
VEDTAVYYCVKDGVHWGQGTLVTVSSGGGGSGGGGSGGGGSGGGGSGGGGSGGGGSEVQLVESGGGLVQPGGSLRLSCAASG
FTFSSHWMTWFRQAPGKGLEWVAHIKEDGSEKYYEDSVEGRFTVSRDNAKNSVYLQMNSLRAEDTAVYYCARGGDGYSDSHFGV
DVWGQGTTVTVSS SEQ ID NO: 811 3.8-6GS-1. Nucleotide
GAGGTGCAGCTGTTGGAGTCTGGGGGAGGCTTGGTACAGCCTGGGGGGTCCCTGAGACTCTCCTGTGCAGCCTCTGGATTCA
GTTTTAGCAGCTATGCCCTCAGTTGGGTCCGCCAGGCTCCAGGGAAGGGGCTGGAGTGGGTCTCAAGTATTGGTGAGAATGAT
GGTACCACAGACTACGCAGACGCCGTGAAGGGCCGATTCACCATCTCCAGAGACAATTCCAAGAATACGCTGTATCTGCAAAT
GAACAGCCTGAGAGTCGAGGACACGGCCGTCTATTACTGTGTGAAAGATGGTGTCCACTGGGGCCAGGGAACCCTGGTCACC
GTCTCCTCAGGTGGTGGCGGTTCAGGCGGAGGTGGCTCTGGAGGTTCAGGAGGTGGTGGTTCTGGCGGCGGTGGA
TCGGGTGGAGGTGGTAGTGAGGTGCAGCTGGTGGAGTCTGGGGGAGGCTTGGTCCAGCCGGGGGGGTCCCTGAGACTCTCC
TGTGCAGCCTCTGGATTCACCTTTAGTAGCCATTGGATGACTTGGTTCCGTCAGGCTCCAGGGAAGGGGCTGGAGTGGGTGGC
CCACATAAAGGAAGACGGAAGTGAGAAATACTATGAGGACTCTGTGGAGGGCCGATTCACCGTCTCCAGAGACAACGCCAAG
AACTCGGTATATCTGCAAATGAACAGTCTGAGAGCCGAAGACACGGCTGTGTATTACTGTGCGAGAGGAGGTGATGGCTACA
GTGACTCCCACTTCGGTGTGGACGTCTGGGGCCAAGGGACCACGGTCACTGTCTCTTCA SEQ ID NO. 843 4.1-6GS-1.1-6GS-VH (MSA) Nucleotide
GAGGTGCAGCTGGTGGAGTCTGGGGGAGGCGTGGTCCAGCCTGGAGGTCCCTGAGACTCTCCTGTGCAGCCTCTGGATTCT
CCTTCAGTGGCTATGGCATGCACTGGGTCCGCCAGGCTCCAGGCAAGGGACTGGAGTGGGTGGCATATATATCATATGATGGA
AGTAATAAATACTATGCAGACTCCGTGAAGGGCCGATTCACCATCTCCAGAGACAATTCCAAGAACACGCTGTATCTGCAAATG
AACAGCCTGAGAGCTGAGGACACGGCTGTGTATTACTGTGCGAAAGATCCGGCCTGGGGATTACGTTTGGGGGAGTCATCGT
CCTATGATTTTGATATCTGGGGCCAAGGGACAATGGTCACCGTCTCCTCAGGTGGTGGCGGTTCAGGCGGAGGTGGCTCTGGA
GGTGGAGGTTCAGGAGGTGGTGGTTCTGGCGGCGGTGGATCGGGTGGAGGTGGTAGTGAGGTGCAGCTGGTGGAGTCTGG
GGGAGGCTTGGTCCAGCCGGGGGGGTCCCTGAGACTCTCCTGTGCAGCCTCTGGATTCACCTTTAGTAGCCATTGGATGACTT
GGTTCCGTCAGGCTCCAGGGAAGGGGCTGGAGTGGGTGGCCCACATAAAGGAAGACGGAAGTGAGAAATACTATGAGGACT
CTGTGGAGGGCCGATTCACCGTCTCCAGAGACAACGCCAAGAACTCGGTATATCTGCAAATGAACAGTCTGAGAGCCGAAGAC
ACGGCTGTGTATTACTGTGCGAGAGGAGGTGATGGCTACAGTGACTCCCACTTCGGTGTGGACGTCTGGGGCCAAGGGACCA
CGGTCACTGTCTCTTCAGGTGGTGGCGGTTCAGGCGGAGGTGGCTCTGGAGGTGGAGGTTCAGGAGGTGGTGGTTCTGGCGG
CGGTGGATCGGGTGGAGGTGGTAGTCAGGTGCAGCTGGTGGAGTCTGGGGGAGGCTTGGTACAGCCGGGGGGGTCCCTGA
GACTCTCCTGTGCAGCCTCTGGATTCACCTTTAGTAGTTATGCCATGAGCTGGGTCCGCCAGGCTCCAGGGAAGGGGCTGGAG
TGGGTCGCAACTATTAGTGATAGTGGTAGTAGTGCAGACTACGCAGATTCCGTGAAGGGACGGTTCACCATCTCCAGAGACAA
KVKMHIHSTN EVTRIYNVIG TABLE 7-continued exemplary multivalent constructs CTCCAAGAACACGCTGTATCTTCAAATGAACAGCCTGAGAGCTGAAGACACGGCCGTGTATTACTGTGCGAGAGGCCGGTATA
ACTGGAACCCCGAGCTTTGGGTATCTGGGGCCAAGGGACAATGGTCACCGTCTCCTCA SEQ ID NO. 844 4.1-6GS-1.1-6GS-MSA Protein
EVQLVESGGGVVQPGRSLRLSCAASGFSFSGYGMHWVRQAPGKGLEWVAYISYDGSNKYYADSVKGRFTISRDNSKNTLYLQMNS
LRAEDTAVYYCAKDRAWGLRLGESSSYDFDIWGQGTMVTVSSGGGGSGGGGSGGGGSGGGGSGGGGSGGGGSEVQLVESGGG
LVQPGGSLRLSCAASGFTFSSHWMTWFRQAPGKGLEWVAHIKEDGSEKYYEDSVEGRFTVSRDNAKNSVYLQMNSLRAEDTAVYY
CARGGDGYSDSHFGVDVWGQGTTVTVSSGGGGSGGGGSGGGGSGGGGSGGGGSGGGGSQVQLVESGGGLVQPGGSLRLSCA
ASGFTFSSYAMSWVRQAPGKGLEWVATISDSGSSADYADSVKGRFTISRDNSKNTLYLQMNSLRAEDTAVYYCARGRYNWNPRAL
GIWGQGTMVTVSS SEQ ID NO. 845 4.1-6GS-2.1-6GS-MSA Nucleotide
GAGGTGCAGCTGGTGGAGTCTGGGGGAGGCGTGGTCCAGCCTGGGAGGTCCCTGAGACTCTCCTGTGCAGCCTCTGGATTCT
CCTTCAGTGGCTATGGCATGCACTGGGTCCGCCAGGCTCCAGGCAAGGGACTGGAGTGGGTGGCATATATATCATATGATGGA
AGTAATAAATACTATGCAGACTCCGTGAAGGGCCGATTCACCATCTCCAGAGACAATTCCAAGAACACGCTGTATCTGCAAATG
AACAGCCTGAGAGCTGAGGACACGGCCGTGTATTACTGTGCGAAAGATCCGGCTCTGGGGATTACGTTTGGGGGAGTCATCGT
CCTATGATTTTGATATCTGGGGCCAAGGGACAATGGTCACCGTCTCCTCAGGTGGTGGCGGTTCAGGCGGAGGTGGCTCTGGA
GGTGGAGGTTCAGGAGGTGGTGGTTCTGGCGGCGGTGGATCGGGTGGAGGTGGTAGTGAGGTGCAGCTGGTGGAGTCTGG
GGGAGGCTTGGTCAAGCCTGGAGGGTCCCTGAGAGTCTCCTGTGCAGCCTCTGGATTCACCTTCAGTGACTACTACATGAGCT
GGTTCCGCCAGGCTCCAGGGAAGGGGCTGGAGTGGGTTTCATACATTAGTGGTAGTGGTGATATCATAGACTACGCAGACTCT
GTAAAGGGCCGATTCACCATCTCCAGGGACAACGCCAAGAACTCTCTGTATCTGCAGATGAACAACCTGAGAGCCGAGGACAC
GGCCGTGTATCACTGTGCGAGAGAAGATTCCCGTCTAACTGGAACTACGGACTTTGACAATTGGGGCCAGGGAACCCTGGTCA
CCGTCTCCTCAGGTGGTGGCGGTTCAGGCGGAGGTGGCTCTGGAGGTGGAGGTTCAGGAGGTGGTGGTTCTGGCGGCGGTG
GATCGGGTGGAGGTGGTAGTCAGGTGCAGCTGGTGGAGTCTGGGGGAGGCTTGGTACAGCCGGGGGGGTCCCTGAGACTCT
CCTGTGCAGCCTCTGGATTCACCTTTAGTAGTTATGCCATGAGCTGGGTCCGCCAGGCTCCAGGGAAGGGGCTGGAGTGGGTC
GCAACTATTAGTGATAGTGGTAGTAGTGCAGACTACGCAGATTCCGTGAAGGGACGGTTCACCATCTCCAGAGACAACTCCAA
GAACACGCTGTATCTTCAAATGAACAGCCTGAGAGCTGAAGACACGCCGTGTATTACTGTGCGAGAGGCCGGTATAACTGGA
ACCCCCGAGCTTTGGGTATCTGGGGCCAAGGGACAATGGTCACCGTCTCCTCA SEQ ID NO. 846 4.1-6GS-2.1-6GS-MSA Protein
EVQLVESGGGVVQPGRSLRLSCAASGFSFSGYGMHWVRQAPGKGLEWVAYISYDGSNKYYADSVKGRFTISRDNSKNTLYLQMNS
LRAEDTAVYYCAKDPAWGLRLGESSSYDFDIWGQGTMVTVSSGGGGSGGGGSGGGGSGGGGSGGGGSGGGGSEVQLVESGGG
LVKPGGSLRVSCAASGFTFSDYYMSWFRQAPGKGLEWVSYISGSGDIIDYADSVKGRFTISRDNAKNSLYLQMNNLRAEDTAVYHCA
REDSRLIGTTDFDNWGQGTLVTVSSGGGGSGGGGSGGGGSGGGGSGGGGSGGGGSQVQLVESGGGLVQPGGSLRLSCAASGFT
FSSYAMSWVRQAPGKGLEWVATISDSGSSADYADSVKGRFTISRDNSKNTLYLQMNSLRAEDTAVYYCARGRYNWNPRALGIWG
QGTMVTVSS SEQ ID NO. 847 3.8-6GS-1.1-6GS-MSA nucleotide
GAGGTGCAGCTGTTGGAGTCTGGGGGAGGCTGGTACAGCCTGGGGGGTCCCTGAGACTCTCCTGTGCAGCCTCTGGATTCA
GTTTTAGCAGCTATGCCCTCAGTTGGGTCCGCCAGGCTCCAGGGAAGGGGCTGGAGTGGGTCTCAAGTATTGGTGAGAATGAT
GGTACCACAGATACGCAGACGCCGTGAAGGGCCGATTCACCATCTCCAGAGACAATTCCAAGAATACGCTGTATCTGCAAAT
GAACAGCCTGAGAGTCGAGGACACGGCCGTCTATTACTGTGTGAAAGATGGTGTCCACTGGGGCCAGGGAACCCTGGTCACC
GTCTCCTCAGGTGGTGGCGGTTCAGGCGGAGGTGGCTCTGGAGGTGGAGGTTCAGGAGGTGGTGGTTCTGGCGGCGGTGGA
TCGGGTGGAGGTGGTAGTGAGGTGCAGCTGGTGGAGTCTGGGGGAGGCTTGGTCCAGCCGGGGGGGTCCCTGAGACTCTCC
TGTGCAGCCTCTGGATTCACCTTTAGTAGCCATTGGATGACTTGGTTCCGTCAGGCTCCAGGGAAGGGGCTGGAGTGGGTGGC
CCACATAAAGGAAGACGGAAGTGAGAAATACTATGAGGACTCTGTGGAGGGCCGATTCACCGTCTCCAGAGACAACGCCAAG
AACTCGGTATATCTGCAAATGAACAGTCTGAGAGCCGAAGACACGGCTGTGTATTACTGTGCGAGAGGAGGTGATGGCTACA
GTGACTCCCACTTCGGTGTGGACGTCTGGGGCCAAGGGACCACGGTCACCGTCTTCCAGGTGGTGGCGGTTCAGGCGGAGG
TGGCTCTGGAGGTGGAGGTTCAGGAGGTGGTGGTTCTGGCGGCGGTGGATCGGGTGGAGGTGGTAGTCAGGTGCAGCTGGT
GGAGTCTGGGGGAGGCTTGGTACAGCCGGGGGGGTCCCTGAGACTCTCCTGTGCAGCCTCTGGATTCACCTTTAGTAGTTATG
CCATGAGCTGGGTCCGCCAGGCTCCAGGGAAGGGGCTGGAGTGGGTCGCAACTATTAGTGATAGTGGTAGTAGTGCAGACTA
CGCAGATTCCGTGAAGGGACGGTTCACCATCTCCAGAGACAACTCCAAGAACACGCTGTATCTTCAAATGAACAGCCTGAGAG
CTGAAGACACGGCCGTGTATTACTGTGCGAGAGGCCGGTATAACTGGAACCCCCGAGCTTTGGGTATCTGGGGCCAAGGGAC
AATGGTCACCGTCTCCTCA SEQ ID NO. 848 3.8-6GS-1.1-6GS-MSA Protein
EVQLLESGGGLVQPGGSLRLSCAASGFSFSSYALSWVRQAPGKGLEWVSSIGENDGTTDYADAVKGRFTISRDNSKNTLYLQMNSLR
VEDTAVYYCVKDGVHWGQGTLVTVSSGGGGSGGGGSGGGGSGGGGSGGGGSGGGGSEVQLVESGGGLVQPGGSLRLSCAASG
FTFSSHWMTWFRQAPGKGLEWVAHIKEDGSEKYYEDSVEGRFTVSRDNAKNSVYLQMNSLRAEDTAVYYCARGGDGYSDSHFGV
DVWGQGTTVTVSSGGGGSGGGGSGGGGSGGGGSGGGGSGGGGSQVQLVESGGGLVQPGGSLRLSCAASGFTFSSYAMSWVR
QAPGKGLEWVATISDSGSSADYADSVKGRFTISRDNSKNTLYLQMNSLRAEDTAVYYCARGRYNWNPRALGIWGQGTMVTVSS SEQ ID NO. 889 4.1-6GS-1.113-4GS Nucleotide
GAGGTGCAGCTGGTGGAGTCTGGGGGAGGCGTGGTCCAGCCTGGGAGGTCCCTGAGACTCTCCTGTGCAGCCTCTGGATTCT
CCTTCAGTGGCTATGGCATGCACTGGGTCCGCCAGGCTCCAGGCAAGGGACTGGAGTGGGTGGCATATATATCATATGATGGA
AGTAATAAATACTATGCAGACTCCGTGAAGGGCCGATTCACCATCTCCAGAGACAATTCCAAGAACACGCTGTATCTGCAAATG
AACAGCCTGAGAGCTGAGGACACGGCCGTGTATTACTGTGCGAAAGATCCGGCTCTGGGGATTACGTTTGGGGGAGTCATCGT
CCTATGATTTTGATATCTGGGGCCAAGGGACAATGGTCACCGTCTCCTCAGGTGGTGGCGGTTCAGGCGGAGGTGGCTCTGGA
GGTGGAGGTTCAGGAGGTGGTGGTTCTGGCGGCGGTGGATCGGGTGGAGGTGGTAGTCAGGTGCAGTTAGTGAGACGG
AGGTGGTTTAGTCAGCCGGGGGGCTCGCTTCGCCTGTCGTGCCGCCTCGGGATTCACATTATCAAACTACTGGATGAATTG
GGTCCGCCAGGCTCCGGGCAAAGGTCTTGAGTGGGTGGCAACATTAATCAGGACGGGAGCGAGCGTTATTACGTTGATTCG
GTAAAGGACGTTTCACTATCAGTCGTGACAACGCTAAAAATTCCTTGTACTTACAGATGAACTCACTTCGTGCTGAGGACACC
GCAGTGTACTACTGTGCTCGCGGTGGTAAAGGATACGGCGTCGATCACTACGGCCTTGATGTATCAGGACAGGGGACTACAGT
TACCGTCTCTTCCGGCGGAGGTGGCTCTGGAGGAGGAGGTTCAGGAGGTGGTGGATCTGGCGGCGGTGGTAGT SEQ ID NO. 890 4.1-6GS-1.113-4GS Protein
EVQLVESGGGVVQPGRSLRLSCAASGFSFSGYGMHWVRQAPGKGLEWVAYISYDGSNKYYADSVKGRFTISRDNSKNTLYLQMNS
LRAEDTAVYYCAKDPAWGLRLGESSSYDFDIWGQGTMVTVSSGGGGSGGGGSGGGGSGGGGSGGGGSGGGGSEVQLVESGGG TABLE 7-continued exemplary multivalent constructs LVQPGGSLRLSCAASGFTLSNYWMNWVRQAPGKGLEWVANINQDGSERYYDSVKGRFTISRDNAKNSLYLQMNSLRAEDTAVYY
CARGGEGYGVDHYGLDVSGQGTTVTVSSGGGGSGGGGSGGGGSGGGG SEQ ID NO. 891 3.8-6GS-1.113-4GS Nucleotide
GAGGTGCAGCTGTTGGAGTCTGGGGGAGGCTTGGTACAGCCTGGGGGGTCCCTGAGACTCTCCTGTGCAGCCTCTGGATTCA
GTTTTAGCAGCTATGCCCTCAGTTGGGTCCGCCAGGCTCCAGGGAAGGGGCTGGAGTGGGTCTCAAGTATTGGTGAGAATGAT
GGTACCACAGACTACGCAGACGCCGTGAAGGGCCGATTCACCATCTCCAGAGACAATTCCAAGAATACGCTGTATCTGCAAAT
GAACAGCCTGAGAGTCGAGGACACGGCCGTCTATTACTGTGTGAAAGATGGTGTCCACTGGGGCCAGGGAACCCTGGTCACC
GTCTCCTCAGGTGGTGGCGGTTCAGGCGGAGGTGGCTCTGGAGGTGGAGGTTCAGGAGGTGGTGGTTCTGGCGGCGGTGGA
TCGGGTGGAGGTGGTAGTGAGGTGCAGTTAGTTGAGAGCGGAGGTGGTTTAGTTCAGCCGGGGGGCTCGCTTCGCCTGTCGT
GCGCCGCCTCGGGATTCACATTATCAAACTACTGGATGAATTGGGTCCGCCAGGCTCCGGGCAAAGGTCTTGAGTGGGTGGCG
AACATTAATCAGGACGGGAGCGAGCGTTATTACGTTGATTCGGTAAAAGGACGTTTCACTATCAGTCGTGACAACGCTAAAAA
TTCCTTGTACTTACAGATGAACTCACTTCGTGCTGAGGACACCGCAGTGTACTACTGTGCTCGCGGTGGTGAAGGATACGGCGT
CGATCACTACGGCCTTGATGTATCAGGACAGGGGACTACAGTTACCGTCTCTTCCGGCGGAGGTGGC
TCTGGAGGAGGAGGTTCAGGAGGTGGTGGATCTGGCGGCGGTGGTAGT SEQ ID NO. 892 3.8-6GS-1.113-4GS Protein
EVQLLESGGGLVQPGGSLRLSCAASGFSFSSYALSWVRQAPGKGLEWVSSIGENDGTTDYADAVKGRFTISRDNSKNTLYLQMNSLR
VEDTAVYYCVKDGVHWGQGTLVTVSSGGGGSGGGGSGGGGSGGGGSGGGGSGGGGSEVQLVESGGGLVQPGGSLRLSCAASG
FTLSNYWMNWVRQAPGKGLEWVANINQDGSERYYDSVKGRFTISRDNAKN
SLYLQMNSLRAEDTAVYYCARGGEGYGVDHVGLDVSGQGTTVTVSSGGGGSGGGGSGGGGSGGGGS SEQ ID NO. 893 4.1-6GS-1.113-6GS-VH (HSA)-4GS Nucleotide
GAGGTGCAGCTGGTGGAGTCTGGGGGAGGCGTGGTCCAGCCTGGGAGGTCCCTGAGACTCTCCTGTGCAGCCTCTGGATTCT
CCTTCAGTGGCTATGGCATGCACTGGGTCCGCCAGGCTCCAGGCAAGGGACTGGAGTGGGTGGCATATATATCATATGATGGA
AGTAATAAATACTATGCAGACTCCGTGAAGGGCCGATTCACCATCTCCAGAGACAATTCCAAGAACACGCTGTATCTGCAAATG
AACAGCCTGAGAGCTGAGGACACGGCTGTGTATTACTGTGCGAAAGATCCGGCCTGGGGATTACGTTTGGGGGAGTCATCGT
CCTATGATTTTGATATCTGGGGCCAAGGGACAATGGTCACCGTCTCCTCAGGTGGTGGCGGTTCAGGCGGAGGTGGCTCTGGA
GGTGGAGGTTCAGGAGGTGGTGGTTCTGGCGGCGGTGGATCGGGTGGAGGTGGTAGTGAGGTGCAGTTAGTTGAGAGCGG
AGGTGGTTTAGTTCAGCCGGGGGGCTCGCTTCGCCTGTCGTGCGCCGCCTCGGGATTCACATTATCAAACTACTGGATGAATTG
GGTCCGCCAGGCTCCGGGCAAAGGTCTTGAGTGGGTGGCGAACATTAATCAGGACGGGAGCGAGCGTTATTACGTTGATTCG
GTAAAAGGACGTTTCACTATCAGTCGTGACAACGCTAAAAATTCCTTGTACTTACAGATGAACTCACTTCGTGCTGAGGACACC
GCAGTGTACTACTGTGCTCGCGGTGGTGAAGGATACGGCGTCGATCACTACGGCCTTGATGTATCAGGACAGGGGACTACAGT
TACCGTCTCTTCCGGCGGAGGTGGCTCTGGAGGAGGCGGATCGGGGGGTGGAGGAAGTGGCGGCGGTGGTAGTGGAGGAG
GTGGTTCTGGAGGCGGTGGCTCTGGAACAACTGGTTGAATCGGGTGGTGGATTGGTCCAACCTGGAAGATCATTGAGGCT
TTCTTGTGCAGCTTCCGGATTCACCTTTCATCACTATGCTATGCACTGGGTGAGACAAGCCCCTGGTAAGGGCTTGGAATGGGT
GTCCGGAATCTCCTGGAATGGTAACAAAATAACATATGCAGATTCCGTTAAGGGTAGATTTACTATTAGCCGTGATAATGCAAA
AAACAGTTTATACTTGCAGATGAATTCCTTGAGGGCTGAGGATACAGCTCTTTACTATTGTGTGCGTGACTCATCGTTGTTCATT
GTCGGAGCCCCAACTTTCGAACATTGGGGTAGAGGTACCCTAGTTACGGTTAGCTCAGGCGGAGGTGGCTCTGGAGGAGGCG
GATCGGGGGGTGGAGGAAGTGGCGGCGGTGGTAGT SEQ ID NO. 894 4.1-6GS-1.113-6GS- VH (HSA)-4GS Protein
EVQLVESGGGVVQPGRSLRLSCAASGFSFSGYGMHWVRQAPGKGLEWVAYISYDGSNKYYADSVKGRFTISRDNSKNTLYLQMNS
LRAEDTAVYYCAKDPAWGLRLGESSSYDFDIWGQGTMVTVSSGGGGSGGGGSGGGGSGGGGSGGGGSGGGGSEVQLVESGGG
LVQPGGSLRLCAASGFTLSNYWMNWVRQAPGKGLEWVANINQDGSERYYDSVKGRFTISRDNAKNSLYLQMNSLRAEDTAVY
YCARGGEGYGVDHGLDVSGQGTTVTVSSGGGGSGGGGSGGGGSGGGGSGGGGSGGGGSEVQLVESGGGLVQPGRSLRLSCAA
SGFTFHHYAMHWVRQAPGKGLEWVSGISWNGNKITYADSVKGRFTISRDNAKNSLYLQMNSLRAEDTALYYCVRDSSLFIVGAPTF
EHWGRGTLVTVSSGGGGSGGGGSGGGGSGGGGS SEQ ID NO.895 3.8-6GS- VH (HSA)-1.113-4GS Nucleotide
GAGGTGCAGCTGTTGGAGTCTGGGGGAGGCTGGTACAGCCTGGGGGGTCCCTGAGACTCTCCTGTGCAGCCTCTGGATTCA
GTTTTAGCAGCTATGCCCTCAGTTGGGTCCGCCAGGCTCCAGGGAAGGGGCTGGAGTGGGTTTCAAGTATTGGTGAGAATGAT
GGTACCACAGACTACGCAGACGCCGTGAAGGGCCGATTCACCATCTCCAGAGACAATTCCAAGAATACGCTGTATCTACAAAT
GAACAGCCTGAGAGTCGAGGACACGGCCGTCTATTACTGTGTGAAAGATGGTGTCCACTGGGGCCAGGGAACCCTGGTCACC
GTCTCCTCAGGTGGTGGCGGTTCAGGCGGAGGTGGCTCTGGAGGTGGAGGTTCAGGAGGTGGTGGTTCTGGCGGCGGTGGA
TCGGGTGGAGGTGGTAGTGAAGTACAACTGGTTGAATCGGGTGGTGGATTGGTCCAACCTGGAAGATCATTGAGGCTTTCTT
GTGCAGCTTCCGGATTCACCTTTCATCACTATGCTATGCACTGGGTGAGACAAGCCCCTGGTAAGGGCTTGGAATGGGTGTCCG
GAATCTCCTGGAATGGTAACAAAATAACATATGCAGATTCCGTTAAGGGTAGATTTACTATTAGCCGTGATAATGCAAAAAACA
GTTTATACTTGCAGATGAATTCCTTGAGGGCTGAGGATACAGCTCTTTACTATTGTGTGCGTGACTCATCGTTGTTCATTGTCGG
AGCCCCAACTTTCGAACATTGGGGTAGAGGTACCCTAGTTACGGTTAGCTCAGGCGGAGGTGGCTCTGGAGGAGGAGGTTCA
GGAGGTGGTGGATCTGGAGGAGGCGGATCGGGGGGTGGAGGAAGTGGCGGCGGTGGTAGTGAGGTGCAGTTAGTTGAGA
GCGGAGGTGGTTTAGTTCAGCCGGGGGGCTCGCTTCGCCTGTCGTGCGCCGCCTCGGGATTCACATTATCAAACTACTGGATGA
ATTGGGTCCGCCAGGCTCCGGGCAAAGGTCTTGAGTGGGTGGCGAACATTAATCAGGACGGGAGCGAGCGTTATTACGTTG
ATTCGGTAAAAGGACGTTTCACTATCAGTCGTGACAACGCTAAAAATTCCTTGTACTTACAGATGAACTCACTTCGTGCTGAGG
ACACCGCAGTGTACTACTGTGCTCGCGGTGGTGAAGGATACGGCGTCGATCACTACGGCCTTGATGTATCAGGACAGGGGACT
ACAGTTACCGTCTCTTCCGGCGGAGGTGGCTCTGGAGGAGGCGGATCGGGGGGTGGAGGAAGTGGCGGCGGTGGTAGTGA
GGTGCAGCTGTTGGAGTCTGGGGGAGGCTTGGTACAGCCTGGGGGGTCCCTGAGACTCTCCTGTGCAGCCTCTGGATTCAGTT
TTAGCAGCTATGCCCTCAGTTGGGTCCGCCAGGCTCCAGGGAAGGGGCTGGAGTGGGTTTCAAGTATTGGTGAGAATGATGG
TACCACAGACTACGCAGACGCCGTGAAGGGCCGATTCACCATCTCCAGAGACAATTCCAAGAATACGCTGTATCTACAAATGA
ACAGCCTGAGAGTCGAGGACACGGCCGTCTATTACTGTGTGAAAGATGGTGTCCACTGGGGCCAGGGAACCCTGGTCACCGT
CTCCTCAGGTGGTGGCGGTTCAGGCGGAGGTGGCTCTGGAGGTGGAGGTTCAGGAGGTGGTGGTTCTGGCGGCGGTGGATC
GGGTGGAGGTGGTAGTGAAGTACAACTGGTTGAATCGGGTGGTGGATTGGTCCAACCTGGAAGATCATTGAGGCTTTCTTGT
GCAGCTTCCGGATTCACCTTTCATCACTATGCTATGCACTGGGTGAGACAAGCCCCTGGTAAGGGCTTGGAATGGGTGTCCGG
AATCTCCTGGAATGGTAACAAAATAACATATGCAGATTCCGTTAAGGGTAGATTTACTATTAGCCGTGATAATGCAAAAACAG
TTTATACTTGCAGATGAATTCCTTGAGGGCTGAGGATACAGCTCTTTACTATTGTGTGCGTGACTCATCGTTGTTCATTGTCGGA
GCCCCAACTTTCGAACATTGGGGTAGAGGTACCCTAGTTACGGTTAGCTCAGGCGGAGGTGGCTCTGGAGGAGGAGGTTCAG
GAGGTGGTGGATCTGGAGGAGGCGGATCGGGGGGTGGAGGAAGTGGCGGCGGTGGTAGTGAGGTGCAGTTAGTTGAGAGC
GGAGGTGGTTTAGTTCAGCCGGGGGGCTCGCTTCGCCTGTCGTGCGCCGCCTCGGGATTCACATTATCAAACTACTGGATGAA TABLE 7-continued exemplary multivalent constructs TTGGGTCCGCCAGGCTCCGGGCAAAGGTCTTGAGTGGGTGGCGAACATTAATCAGGACGGGAGCGAGCGTTATTACGTTGAT
TCGGTAAAAGGACGTTTCACTATCAGTCGTGACAACGCTAAAAATTCCTTGTACTTACAGATGAACTCACTTCGTGCTGAGGAC
ACCGCAGTGTACTACTGTGCTCGCGGTGGTGAAGGATACGGCGTCGATCACTACGGCCTTGATGTATCAGGACAGGGGACTAC
AGTTACCGTCTCTTCCGGCGGAGGTGGCTCTGGAGGAGGCGGATCGGGGGGTGGAGGAAGTGGCGGCGGTGGTAGT SEQ ID NO. 896 3.8-6GS- VH (HSA)-1.113-4GS Protein
EVQLLESGGGLVQPGGSLRLSCAASGFSFSSYALSWVRQAPGKGLEWVSSIGENDGTTDYADAVKGRFTISRDNSKNTLYLQMNSLR
VEDTAVYYCVKDGVHWGQGTLVTVSSGGGGSGGGGSGGGGSGGGGSGGGGSGGGGSEVQLVESGGGLVQPGGSLRLSCAASG
FTFHHYAMHWVRQAPGKGLEWVSGISWNGNKITYADSVKGRFTISRDNAKNSLYLQMNSLRAEDTALYYCVRDSSLFIVGAPTFEH
WGRGTLVTVSSGGGGSGGGGSGGGGSGGGGSGGGGSGGGGSEVQLVESGGGLVQPGGSLRLSCAASGFTLSNYWMNWVRQA
PGKGLEWVANINQDGSERYYVDSVKGRFTISRDNAKNSLYLQMNSLRAEDTAVYYCARGGEGYGVDHYGLDVSGQGTTVTVSSGG
GGSGGGGSGGGGSGGGGS SEQ ID NO. 897 3.8-6GS-1.113-6GS- VH (HSA)-4GS Nucleotide
GAGGTGCAGCTGTTGGAGTCTGGGGGAGGCTTGGTACAGCCTGGGGGGTCCCTGAGACTCTCCTGTGCAGCCTCTGGATTCA
GTTTTAGCAGCTATGCCCTCAGTTGGGTCCGCCAGGCTCCAGGGAAGGGGCTGGAGTGGGTTTCAAGTATTGGTGAGAATGAT
GGTACCACAGACTACGCAGACGCCGTGAAGGGCCGATTCACCATCTCCAGAGACAATTCCAAGAATACGCTGTATCTACAAAT
GAACAGCCTGAGAGTCGAGGACACGGCCGTCTATTACTGTGTGAAAGATGGTGTCCACTGGGGCCAGGGAACCCTGGTCACC
GTCTCCTCAGGTGGTGGCGGTTCAGGCGGAGGTGGCTCTGGAGGTGGAGGTTCAGGAGGTGGTGGTTCTGGCGGCGGTGGA
TCGGGTGGAGGTGGTAGTGAGGTGCAGTTAGTTGAGAGCGGAGGTGGTTTAGTTCAGCCGGGGGCTCGCTTCGCCTGTCGT
GCGCCGCCTCGGGATTCACATTATCAAACTACTGGATGAATTGGGTCCGCCAGGCTCCGGGCAAAGGTCTTGAGTGGGTGGCG
AACATTAATCAGGACGGGAGCGAGCGTTATTACGTTGATTCGGTAAAAGGACGTTTCACTATCAGTCGTGACAACGCTAAAAA
TTCCTTGTACTTACAGATGAACTCACTTCGTGCTGAGGACACCGCAGTGTACTACTGTGCTCGCGGTGGTGAAGGATACGGCGT
CGATCACTACGGCCTTGATGTATCAGGACAGGGGACTACAGTTACCGTCTCTTCCGGCGGAGGTGGCTCTGGAGGAGGCGGA
TCGGGGGGTGGAGGAAGTGGCGGCGGTGGTAGTGAGGAGGTGGTTCTGAGGCGGTGGCTCTGAAGTACAACTGGTTGA
ATCGGGTGGTGGATTGGTCCAACCTGGAAGATCATTGAGGCTTTCTTGTGCAGCTTCCGGATTCACCTTTCATCACTATGCTATG
CACTGGGTGAGACAAGCCCCTGGTAAGGGCTGGAATGGGTGTCCGGAATCTCCTGGAATGGTAACAAAATAACATATGCAG
ATTCCGTTAAGGGTAGATTTACTATTAGCCGTGATAATGCAAAAAACAGTTTATACTTGCAGATGAATTCCTTGAGGGCTGAGG
ATACAGCTCTTTACTATTGTGTGCGTGACTCATCGTTGTTCATTGTCGGAGCCCCAACTTTCGAACATTGGGGTAGAGGTACCCT
AGTTACGGTTAGCTCAGGCGGAGGTGGCTCTGGAGGAGGCGGATCGGGGGGTGGAGGAAGTGGCGGCGGTGGTAGT SEQ ID NO. 898 Protein 3.8-6GS-1.113-6GS- VH (HSA)-4GS
EVQLLESGGGLVQPGGSLRLSCAASGFSFSSYALSWVRQAPGKGLEWVSSIGENDGTTDYADAVKGRFTISRDNSKNTLYLQMNSLR
VEDTAVYYCVKDGVHWGQGTLVTVSSGGGGSGGGGSGGGGSGGGGSGGGGSGGGGSEVQLVESGGGLVQPGGSLRLSCAASG
FTLSNYWMNWVRQAPGKGLEWVANINQDGSERYYVDSVKGRFTISRDNAKNSLYLQMNSLRAEDTAVYYCARGGEGYGVDHYG
LDVSGQGTTVTVSSGGGGSGGGGSGGGGSGGGGSGGGGSGGGGSEVQLVESGGGLVQPGGSLRLSCAASGFTFHHYAMHWVR
QAPGKGLEWVSGISWNGNKITYADSVKGRFTISRDNAKNSLYLQMNSLRAEDTALYYCVRDSSLFIVGAPTFEHWGRGTLVTVSSG
GGGSGGGGSGGGGSGGGGS SEQ ID NO.899 4.1-6GS- VH (HSA)-1.113-4GS Nucleotide
GAGGTGCAGCTGGTGGAGTCTGGGGGAGGCGTGGTCCAGCCTGGAGGTCCCTGAGACTCTCCTGTGCAGCCTCTGGATTCT
CCTTCAGTGGCTATGGCATGCACTGGGTCCGCCAGGCTCCAGGCAAGGGACTGGAGTGGGTGGCATATATATCATATGATGGA
AGTAATAAATACTATGCAGACTCCGTGAAGGGCCGATTCACCATCTCCAGAGACAATTCCAAGAACACGCTGTATCTGCAAATG
AACAGCCTGAGAGCTGAGGACACGGCTGTGTATTACTGTGCGAAAGATCCGGCCTGGGGATTACGTTTGGGGGAGTCATCGT
CCTATGATTTTGATATCTGGGGCCAAGGGACAATGGTCACCGTCTCCTCAGGTGGTGGCGGTTCAGGCGGAGGTGGCTCTGGA
GGTGGAGGTTCAGGAGGTGGTGGTTCTGGCGGCGGTGGATCGGGTGGAGGTGGTAGTGAAGTACAACTGGTTGAATCGGGT
GGTGGATTGGTCCAACCTGGAAGATCATTGAGGCTTTCTTGTGCAGCTTCCGGATTCACCTTTCATCACTATGCTATGCACTGG
GTGAGACAAGCCCCTGGTAAGGGCTTGGAATGGGTGTCCGGAATCTCCTGGAATGGTAACAAAATAACATATGCAGATTCCGT
TAAGGGTAGATTTACTATTAGCCGTGATAATGCAAAAAACAGTTTATACTTGCAGATGAATTCCTTGAGGGCTGAGGATACAGC
TCTTTACTATTGTGTGCGTGACTCATCGTTGTTCATTGTCGGAGCCCCAACTTTCGAACATTGGGGTAGAGGTACCCTAGTTACG
GTTAGCTCAGGCGGAGGTGGCTCTGGAGGAGGAGGTTCAGGAGGTGGTGGATCTGGAGGAGGCGGATCGGGGGGTGGAGG
AAGTGGCGGCGGTGGTAGTGAGGTGCAGTTAGTTGAGAGCGGAGGTGGTTTAGTTCAGCCGGGGGCTCGCTTCGCCTGTCG
TGCGCCGCCTCGGGATTCACATTATCAAACTACTGGATGAATTGGGTCCGCCAGGCTCCGGGCAAAGGTCTTGAGTGGGTGGC
GAACATTAATCAGGACGGGAGCGAGCGTTATTACGTTGATTCGGTAAAAGGACGTTTCACTATCAGTCGTGACAACGCTAAAA
ATTCCTTGTACTTACAGATGAACTCACTTCGTGCTGAGGACACCGCAGTGTACTACTGTGCTCGCGGTGGTGAAGGATACGGCG
TCGATCACTACGGCCTTGATGTATCAGGACAGGGGACTACAGTTACCGTCTCTTCCGGCGGAGGTGGCTCTGGAGGAGGCGG
ATCGGGGGGTGGAGGAAGTGGCGGCGGTGGTAGT SEQ ID NO. 900 4.1-6GS- VH (HSA)-1.113-4GS Protein
EVQLVESGGGVVQPGRSLRLSCAASGFSFSGYGMHWVRQAPGKGLEWVAYISYDGSNKYYADSVKGRFTISRDNSKNTLYLQMNS
LRAEDTAVYYCAKDPAWGLRLGESSSYDFDIWGQGTMVTVSSGGGGSGGGGSGGGGSGGGGSGGGGSGGGGSEVQLVESGGG
LVQPGRSLRLSCAASGFTFHHYAMHWVRQAPGKGLEWVSGISWNGNKITYADSVKGRFTISRDNAKNSLYLQMNSLRAEDTALYY
CVRDSSLFIVGAPTFEHWGRGTLVTVSSGGGGSGGGGSGGGGSGGGGSGGGGSGGGGSEVQLVESGGGLVQPGGSLRLSCAASG
FTLSNYWMNWVRQAPGKGLEWVANINQDGSERYYVDSVKGRFTISRDNAKNSLYLQMNSLRAEDTAVYYCARGGEGYGVDHYG
LDVSGQGTTVTVSSGGGGSGGGGSGGGGSGGGGS SEQ ID NO. 901 VH that binds to HSA as used in constructs above protein
EVQLVESGGGLVQPGRSLRSCAASGFTFHHYAMHWVRQAPGKGLEWVSGISWNGNKITYADSVKGRFTISRDNAKNSLYLQMNS
LRAEDTALYYCVRDSSLFIVGAPTFEHWGRGTLVTVSS SEQ ID NO. 902 VH that binds to HSA as used in constructs above nucleotide
GGCTTTGTGAGCGGATACAATTATAATATGTGGAATTGTGAGCGCTCACAATTCCACAACGGTTTCCCTCTAGAAATAAT
TTGTTTAACTTTTAGGAGGTAAAACATATGAAGAAAACGGCAATCGCAATCGCAGTCGCTCTGGCGGGTTTCGCAACTG
TAGCGCAAGCCGAGGTGCAACTGGTCGAGTCTGGTGGTGGTTTGGTCAACCTGGTAGAAGCTTGCGTTTGAGTTGTGCC
GCTTCCGGCTTCACTTTCCATCATTATGCTATGCACTGGGTTCGTCAAGCTCCCGGAAAAGGTTTGGAGTGGGTTTCCGG
AATTTCCTGGAATGGCAATAAGATTACGTACGCTGATTCAGTGAAAGGAAGGTTTACAATCAGTAGAGATAATGCTAAAA
ACTCATTGTATCTACAAATGAACAGCCTAAGAGCAGAAGATACCGCTCTGTACTACTGTGTTAGAGATAGCTCGTTATTC
ATTGTAGGTGCACCAACTTTTGAACATTGGGGTCGGGGTACTCTTGTGACTGTCTCATCCGCGGCCGCACACCACCATCA TABLE 7-continued exemplary multivalent constructs

```
TCACCACTAACTCGAGCGCCTAATGAAAGCTTCCCCAAGGGCGACACCCCCTAATTAGCCCGGGCGAAAGGCCCAGTCTT
TCGACTGAGCCTTTCGTTTTATTTGATGCCTGGCAGTTCCCTACTCTCGCATGGGGAGTCCCCACACTACCATCGGCGCT
ACGGCGTTTCACTTCTGAGTTCGGCATGGA
```

Example 9. Testing of Purified $V_H$ b) Binding Assays

Purified Humabody® $V_H$ were tested for binding to human CD137 protein, rhesus CD137Fc recombinant protein, mouse CD137 protein, tumour necrosis factor receptor family members OX40 and GITR (Glucocorticoid-induced TNFR-related), CHO human CD137 cells, CHO parent cells and human T-cells.

Binding to human CD137Fc recombinant protein (Acro Biosystems 41B-H5258), rhesus CD137Fc recombinant protein (Sino Biologicals cat no. 90847-K02H) and mouse CD137Fc protein (Acro Biosystems 41B-M5258) was measured using an HTRF Binding assay format. All reagents and serially diluted $V_H$ were prepared in assay buffer containing PBS, 0.1% BSA and 0.4M Potassium Fluoride. Samples or assay buffer (non-specific binding) were incubated with 0.5 nM human, rhesus or mouse CD137, 1 nM Anti human-Fc Cryptate PAb (Cisbio cat. no. 61HFCKLB) and 20 nM anti His-D2 (CisBio cat no 61HISDLA) in black 384-shallow well assay plates for a minimum of 3 hours at room temperature. Time-resolved fluorescent emission at 620 nm and 665 nm was measured following excitation at 337 nm on the BMG PHERAstar plate reader. The HTRF ratio were calculated ((665 nm emission/620 nm emission)*10000) and the data corrected for (non-specific binding) to give the specific binding signal. Molar $EC_{50}$ values for binding to human CD137, rhesus CD137 and mouse CD137 protein are shown in Table 8. $V_H$ bound to human and rhesus CD137 but not to mouse CD137 protein.

TABLE 8

Binding of $V_H$ to CD137

| Humabody® ID | HTRF | | | ELISA | | |
|---|---|---|---|---|---|---|
| | Human CD137 | Rhesus CD137 | Mouse CD137 | Human CD137 | Human GITR | Human OX40 |
| 1.78 | 2.1E-10 | 1.4E-10 | – | + | – | – |
| 1.1 | 2.6E-10 | 1.1E-09 | – | + | – | – |
| 1.18 | 4.5E-10 | 5.1E-09 | – | + | – | – |
| 1.11 | 5.8E-10 | 6.8E-09 | – | + | – | – |
| 1.52 | 4.8E-10 | 4.5E-10 | – | + | – | – |
| 2.9 | 1.3E-09 | 1.2E-09 | – | + | – | – |
| 2.2 | 9.1E-10 | 5.6E-10 | – | + | – | – |
| 2.1 | 3.7E-09 | 4.9E-09 | – | + | – | – |
| 2.8 | 3.1E-09 | 1.6E-09 | – | + | – | – |
| 2.14 | 1.2E-09 | 1.3E-09 | – | + | – | – |
| 2.26 | nd | nd | nd | nd | nd | nd |

No binding (–),
Binding measured (+),
not determined (nd)

TABLE 9

| Humabody® | FMAT | | | | | Flow Cytometry CD8+ |
|---|---|---|---|---|---|---|
| | CHO huCD137 | CHO Parent | CHO PSMA | DU145 PSMA | DU145 Parent | |
| 1.78 | 3.2E-10 | — | | | | 6.1E-10 |
| 1.1 | 2.2E-10 | — | | | | 2.2E-10 |
| 1.18 | 3.1E-10 | — | | | | 1.9E-09 |
| 1.11 | 2.7E-10 | — | | | | 8.9E-10 |
| 1.52 | 3.7E-10 | — | | | | 8.8E-10 |
| 2.9 | 1.8E-10 | — | | | | 6.0E-10 |
| 2.2 | 1.8E-10 | — | | | | 7.4E-10 |
| 2.1 | 6.5E-10 | — | | | | 2.4E-09 |
| 2.8 | 1.9E-10 | — | | | | 6.5e-09 |
| 2.14 | 3.1E-10 | — | | | | 6.1E-10 |
| 2.26 | 1.8E-10 | | | | | 2.8E-09 |
| 1.113 | 9.0E-11 | | | | | nd |
| 4.1 | — | | 1.7E-10 | 1.9E-10 | — | nd |
| 3.8 | — | | 2.3E-10 | 2.9E-10 | — | nd |
| 4.1-6GS-1.1 | 4.3E-10 | — | 1.9E-10 | 2.1E-10 | | 7.3E-10 |
| 4.1-6GS-2.1 | 9.7E-10 | — | 2.8E-10 | 3.9E-10 | | 3.0E-09 |
| 3.8-6GS-1.1 | 5.6E-10 | — | 6.0E-10 | 6.8E-10 | | 1.1E-09 |
| 1.1-6GS-3.8 | 5.6E-10 | — | 6.3E-10 | 8.1E-10 | | nd |
| 4.1-6GS-1.1-VH (MSA) | 5.8E-10 | — | 3.2E-10 | 3.6E-10 | | nd |
| 4.1-6GS-1.1-VH (MSA) | 1.9E-09 | — | 3.0E-10 | 4.2E-10 | | nd |
| 3.8-6GS-1.1-VH (MSA) | 5.9E-10 | — | 5.9E-10 | 8.2E-10 | | nd |

Specificity of binding for CD137 over the tumour necrosis factor receptor family members OX40 and GITR (Glucocorticoid-induced TNFR-related) was determined using an ELISA assay. Nunc Maxisorp plates were coated with 1 ug/ml human CD137-Fc recombinant protein (Acro Biosystems 41B-H5258), human GITR-Fc (R&D Systems cat no. 689-GR) human OX40-Fc (R&D Systems cat no. 3388-OX) in sodium carbonate buffer overnight at 4° C. then washed twice with PBS. Non-specific protein interactions were blocked by incubation with 1% (w/v) skimmed milk powder (Marvel®) in PBS/0.1% Tween-20 for 1 hour at room temperature. Plates were washed twice with PBS then VH or antibody control (1 ug/ml) added for 1 hour at room temperature. Following three washes with PBS/0.1% Tween-20 a 1:1000 dilution of anti His-HRP ($V_H$ detection) or anti mouse-HRP (positive control mouse monoclonal antibody detection) was added in 1% Marvel/PBS/0.1% Tween-20. The detection antibodies were allowed to bind for 1 hour at room temperature then the plates were washed twice in PBS/0.1% Tween-20 and once in PBS. The ELISA was developed using TMB substrate and the reaction was stopped by the addition of 50 ul 0.5M $H_2SO_4$ solution. The absorbance at 450 nm was measured using the BMG Pherastar. All $V_H$ tested bound to CD137 but did not bind to GITR or OX40 (Table 8).

Binding of His-tagged molecules to CHO human CD137, CHO parent, CHO human PSMA, DU145 PSMA and DU145 parent cells was assessed using Fluorescence Microvolume Assay Technology (FMAT). All reagents were prepared in FMAT assay buffer (pH 7.4) containing PBS, 0.1% Bovine Serum Albumin, 0.05% Sodium Azide. Serially diluted samples were transferred into 384 well black clear-bottomed assay plates (Costar cat. no. 3655) and incubated for a minimum of 2 hours at room temperature with 1.5 nM Anti-His (Millipore cat. no. 05-949), 311M Goat Anti-Mouse Alexa Fluor-488 (Jackson ImmunoResearch cat. no. 115-545-071) and 2000 cells/well pre-stained with DRAQ5 (Thermo Scientific cat. no. 62251). Fluorescence emission was then measured on the TTP Mirrorball plate reader in the FL2 (502 nm-537 nm) and FL5 (677-800 nm) channels following excitation at 488 nm and 640 nm. Data was gated on FL5 perimeter and peak intensity and the FL2 median mean fluorescence intensity of the gated data used for determination of $V_H$ binding. Example $EC_{50}$ values for binding are shown in table 9. Monovalent CD137 specific Humabody® $V_H$, bispecific and trispecific molecules with a CD137 binding arm bound to CHO CD137 expressing cells. Monovalent PSMA specific Humabody® $V_H$, bispecific and trispecific molecules with a PSMA binding arm bound to PSMA expressing cells.

Binding to primary T cells was measured using flow cytometry. Peripheral blood mononuclear cells (PBMCs) were isolated from human blood by density gradient centrifugation then CD8+ T cells purified using a negative selection isolation kit according to the manufacturer's protocol (Miltenyi Biotech cat no 130-042-401). T-cells were stimulated PMA/Ionomycin for 48-72 hours in RPMI media supplemented with 10% FBS, 2 mM Glutamine, 1× Pen/Strep. Cells were transferred into 96 well plates, blocked for 10 mins with staining buffer (PBS/1% BSA/0.05% Sodium Azide) then incubated with serially diluted $V_H$ in staining buffer (PBS/1% BSA) for 30 mins-1 hour at 4° C. Cells were washed by centrifugation then $V_H$ binding detected using Anti His antibody (Millipore 05-949) and Goat Anti Mouse Alexa Fluor-488 (Jackson ImmunoResearch cat no. 115-545-071). A Live Dead near IR stain (Molecular Probes cat no. L10119) was used for discrimination of live cells. After further washing cells were fixed and fluorescence measured by flow cytometry.

Average molar $EC_{50}$ values for binding (2-3 donors) are shown in Table 9. Monovalent CD137 specific Humabody® $V_H$ and bispecific molecules with a CD137 binding arm bound to pre-stimulated CD8+ cells.

Binding kinetics of purified $V_H$, bivalent $V_H$ and trivalent $V_H$ molecules were measured on a ForteBio Octet RED 384 instrument. CD137-Fc tagged protein was diluted to 3 µg/ml in kinetics buffer (0.1% BSA, 0.02% Tween, 1×PBS) and coupled to Protein G biosensors (ForteBio cat no. 18-5082) via the Fc tag. $V_H$ were serially diluted (typically 1:2 dilution series starting with 50 nM, $V_H$ at the highest concentration) and binding to the CD137-Fc-coupled Protein G biosensors measured. Binding kinetics were determined from the (blank subtracted) sensor gram trace using 1:1 binding models and ForteBio Octet Data Analysis 9.0 software. Example kinetic and binding affinity data obtained is shown Table 10 (monovalent $V_H$) and FIG. 1 (bivalent and trivalent molecules). In this assay format monomer $V_H$ bound CD137-Fc with affinities of between 91 pM and 5.3 nM. Bivalent and trivalent formats showed enhanced binding compared to the monovalent $V_H$.

TABLE 10

Kinetics of binding of $V_H$ to human CD137

| Humabody ® ID | KD (M) | kon(1/Ms) | kdis(1/s) |
|---|---|---|---|
| 1.78 | 7.2E−10 | 3.04E+05 | 2.19E−04 |
| 1.75 | 7.5E−10 | 4.74E+05 | 3.53E−04 |
| 1.1 | 3.4E−10 | 9.89E+05 | 3.40E−04 |
| 1.39 | 9.0E−10 | 5.59E+05 | 5.05E−04 |
| 1.18 | 1.2E−10 | 5.18E+06 | 6.25E−04 |
| 1.11 | 2.5E−09 | 5.96E+05 | 1.48E−03 |
| 1.71 | 9.1E−11 | 3.13E+05 | 2.84E−05 |
| 1.16 | 2.4E−09 | 6.10E+05 | 1.45E−03 |
| 1.52 | 3.2E−09 | 3.00E+05 | 9.63E−04 |
| 1.63 | 2.8E−09 | 2.17E+05 | 5.96E−04 |
| 1.81 | 1.6E−10 | 1.06E+06 | 1.71E−04 |
| 2.20 | 1.2E−09 | 1.64E+06 | 2.00E−03 |
| 2.1 | 2.9E−09 | 1.35E+06 | 3.88E−03 |
| 2.8 | 5.3E−09 | 1.17E+06 | 6.16E−03 |
| 2.14 | 9.6E−10 | 1.63E+06 | 1.57E−03 |
| 2.26 | 4.7E−09 | 1.80E+06 | 8.42E−03 |

The kinetics of monovalent and bispecific Humabody $V_H$ were determined on a ForteBio Octet RED 384 instrument. To study the interaction with the antigens, CD137-Fc tag protein (Acro Biosystems cat no. 41B-H5258) or PSMA-his (R&D Systems cat no. 4234-ZN) was immobilised onto AR2G biosensors (ForteBio cat no. 18-5082) by amine coupling. Monovalent $V_H$ and bispecific molecules were serially diluted (typically 1:2 dilution series starting between 12-25 nM, at the highest concentration) in kinetics buffer (0.1% BSA, 0.02% Tween, 1×PBS) and binding to the immobilised proteins was studied during the association and dissociation phases. PSMA binding was measured using 180 seconds association and 600 seconds dissociation phases. CD137 binding was measured 180 seconds association and 600 seconds dissociation phases. Reference subtracted data were fitted to a 1:1 binding model using the ForteBio Octet Data Analysis software. Example kinetic and binding affinity data obtained are shown in Table 11.

TABLE 11

| | Human CD137 | | | Human PSMA | | |
|---|---|---|---|---|---|---|
| Humabody ® | KD (M) | Kon (1/Ms) | kdis (1/s) | KD (M) | kon (1/Ms) | kdis (1/s) |
| 1.1 | 5.2E−10 | 7.1E+05 | 3.6E−04 | — | — | — |
| 2.1 | 6.7E−09 | 7.7E+05 | 5.2E−03 | — | — | — |
| 4.1 | — | — | — | 5.3E−10 | 3.1E+05 | 1.6E−04 |
| 3.8 | — | — | — | 9.0E−10 | 3.9E+05 | 3.5E−04 |
| 4.1-6GS-1.1 | 7.3E−10 | 4.1E+05 | 3.1E−04 | 1.3E−09 | 4.3E+05 | 5.4E−04 |
| 4.1-6GS-2.1 | 4.8E−09 | 5.8E+05 | 2.6E−03 | 6.6E−10 | 5.0E+05 | 3.3E−04 |
| 3.8-6GS-1.1 | 5.6E−10 | 4.9E+05 | 2.9E−04 | 5.7E−09 | 3.0E+05 | 1.7E−03 |

The Biacore T200 instrument was used to study the interaction between VH with human and rhesus CD137-human IgG1 Fc tagged protein by surface plasmon resonance (SPR). Single cycle kinetics assays used to evaluate the kinetics and affinity of the interaction. Experiments were performed at 25° C. in HBS-EP+ assay buffer with a flow rate of 30 µl/minute. A Protein G chip was used to capture the Fc tagged recombinant CD137 diluted to 2 µg/ml to one of the flow cells over 7 seconds. A second flow cell without any captured CD137 was used as the reference cell. A five point, three-fold dilution series of $V_H$ was made with a top concentration of 60 nM. The binding kinetics were followed by flowing these over the chip surface. The contact time for each of the binding steps was 180 seconds and the dissociation step was 1800 and 3600 seconds for rhesus and human CD137 respectively. After each run, the sensors were regenerated with glycine pH 1.5 to remove the captured CD137. The data was fitted to a 1:1 binding model after double reference subtraction using the Biacore T200 Evaluation software. Average kinetic constants (±Standard deviation) for sdAb 1.113 in table 2 for binding to human CD137Fc were ka 3.6 E+06±1.6 E+06 (1/Ms), Kdis 3.0 E−04±1.1 E−04 (1/s) and KD 8.5 E−11±7.8 E−12 (M) and for binding to rhesus CD137Fc were ka 1.1 E+06±2.2 E+05 (1/Ms), Kdis 2.8 E−04±6.8 E−06 (1/s) and KD 2.7 E−10±5.2 E−11.

sdAb 1.113 demonstrated superior cyno binding compared to other molecules tested. sdAb 1.113 also demonstrated better overall developability characteristics (stability and/or expression).

Dual target engagement of CD137 and PSMA by the bispecific molecules was assessed using an ELISA format. CHO-PSMA cells (20000/well) were seeded into 96 well plates (Greiner cat no. 353872) in Hams F12 supplemented with L-Glutamine+Blasticidin+Tetracycline and incubated at 37° C. with 5% $CO_2$ overnight. All subsequent steps were performed at room temperature and included washes with PBS between each step. Plates were blocked with PBS/0.1% BSA for 1 hour then serially diluted Humabody® $V_H$ were added and allowed to bind for 1 hour. Following removal of unbound $V_H$, 1 nM CD137huFc (Acro Biosystems cat no. 41B-H5258) was added to the wells and incubated for 1 hour. A 1:3000 dilution of Anti-huFc-HRP (Jackson ImmunoResearch cat no. 109-035-098) was subsequently added for 1 hour and plates developed by addition of TMB. The reaction was stopped by addition of 0.5M sulphuric acid and plates read on BMG PheraStar at Absorbance 450 nm. FIG. 2 shows representative data demonstrating that bispecific molecules can simultaneously bind both human CD137 and human PSMA.

a) Inhibition of CD137 Liqand Binding to CD137

The ability of purified Humabody $V_H$ to inhibit the binding of CD137 Ligand to CHO human CD137 cells was measured in the FMAT ligand inhibition assay essentially as described in Example 6. $IC_{50}$ values determined from serially diluted $V_H$ are shown in table 12. $V_H$ inhibited the binding of human CD137 Ligand to human CD137.

TABLE 12

Inhibition of CD137L Binding.
Values shown are an average of 2-6 determinations
CD137 Ligand Inhibition

| Humabody® $V_H$ | $IC_{50}$ (M) | Humabody® $V_H$ | $IC_{50}$ (M) | Humabody® $V_H$ | $IC_{50}$ (M) |
|---|---|---|---|---|---|
| 1.78 | 1.5E−09 | 1.102 | 1.7E−09 | 1.125 | 1.7E−09 |
| 1.1 | 1.1E−09 | 1.103 | 1.3E−09 | 1.126 | 8.4E−10 |
| 1.18 | 1.2E−09 | 1.104 | 1.1E−09 | 1.128 | 8.8E−10 |
| 1.11 | 1.6E−09 | 1.105 | 2.8E−09 | 1.129 | 2.0E−10 |
| 1.52 | 1.2E−09 | 1.106 | 2.1E−09 | 1.130 | 1.9E−09 |
| 2.9 | 2.0E−09 | 1.107 | 5.5E−10 | 1.131 | 3.3E−10 |
| 2.20 | 1.7E−09 | 1.108 | 5.0E−10 | 2.41 | 1.6E−08 |
| 2.1 | 5.7E−09 | 1.109 | 9.0E−10 | 2.42 | 2.0E−07 |
| 2.8 | 1.9E−08 | 1.110 | 8.1E−10 | 2.43 | 1.9E−08 |
| 2.14 | 2.0E−09 | 1.111 | 7.5E−10 | 2.44 | 5.7E−08 |
| 2.26 | 8.5E−09 | 1.112 | 4.7E−10 | 2.45 | 5.3E−09 |
| 1.90 | 7.8E−09 | 1.113 | 7.3E−10 | 2.46 | 7.8E−08 |
| 1.91 | 1.9E−09 | 1.114 | 2.7E−10 | 2.47 | 8.8E−09 |
| 1.92 | 2.9E−09 | 1.115 | 3.5E−10 | 2.48 | 8.6E−08 |
| 1.93 | 7.0E−10 | 1.116 | 2.5E−10 | 2.49 | 4.2E−08 |
| 1.94 | 8.0E−10 | 1.117 | 1.5E−09 | 2.50 | 1.4E−08 |
| 1.95 | 2.4E−08 | 1.118 | 3.4E−09 | 2.51 | 2.7E−08 |
| 1.96 | 2.7E−09 | 1.119 | 1.3E−09 | 1.1-6GS-1.1 | 2.8E−10 |
| 1.97 | 3.8E−09 | 1.120 | 2.5E−10 | 2.1-6GS-2.1 | 4.3E−10 |
| 1.98 | 4.7E−09 | 1.121 | 1.4E−09 | 1.1-6GS-1.1-6GS-1.1 | 2.0E−10 |
| 1.99 | 1.5E−09 | 1.122 | 1.3E−09 | 2.1-6GS-2.1-6GS-2.1 | 4.2E−10 |
| 1.100 | 1.4E−09 | 1.123 | 7.8E−10 | 4.1-6GS-1.1 | 2.5E−09 |
| 1.101 | 7.9E−09 | 1.124 | 1.6E−09 | 4.1-6GS-2.1 | 1.3E−08 |
| | | 4.1 | — | 4.1-6GS-1.78 | 3.7E−09 |
| | | 3.8 | — | 1.78-6GS-4.1 | 2.8E−09 |
| | | | | 3.8-6GS-1.1 | 1.7E−09 |
| | | | | 1.1-6GS-3.8 | 1.3E−09 | b) Stability

Purified Humabody® $V_H$ were subjected to size exclusion chromatography. Briefly, purified $V_H$ were stored at between 8.98 and 9.26 mg/ml in PBS buffer for 0-14 days at either 4° C. or 40° C., and then analysed at various time points using a Waters H-Class Bio UPLC containing a PDA detector (detection at 280 nm) with separation on a Waters ACQUITY BEH 125 Å SEC column. Samples were injected in 10 µl volumes and were run in a mobile phase containing 200 mM NaCl, 100 mM sodium phosphate, pH 7.4+5% propan-1-ol at a flow rate of 0.4 ml/min. Data were collected for 6 minutes and the percentage of the sample comprising monomer after storage was calculated (Table 13 for representative data). It should be noted that these data were collected under non-optimised buffer conditions.

TABLE 13

| Humabody® ID | Conc. mg/ml | % Area T0 Monomer 4° C. | | | | % Area T0 Monomer 40° C. | | | | |
|---|---|---|---|---|---|---|---|---|---|---|
| | | Day 1 | Day 4 | Day 7 | Day 14 | Day 0 | Day 1 | Day 4 | Day 7 | Day 14 |
| 1.1 | 9.02 | 99.85 | 99.87 | 99.84 | 97.50 | 99.85 | 99.66 | 91.10 | 99.31 | 97.20 |
| 1.78 | 9.63 | 99.70 | 99.64 | 99.45 | 99.43 | 99.70 | 98.86 | 98.73 | 98.75 | 98.66 |
| 2.1 | 8.98 | 100.00 | 98.41 | 99.89 | 98.22 | 100.00 | 98.91 | 96.86 | 98.04 | 97.17 |
| 2.14 | 9.26 | 99.92 | 99.19 | 99.92 | 98.06 | 99.92 | 97.88 | 95.15 | 95.50 | 93.69 | c) Serum Stability

Serum stability of Humabody® $V_H$ was assessed by measurement of their activity following incubation for 0, 1, ¾ or 7 days in mouse serum (Sigma M5905) or human serum (Sigma H4522). The pre-incubated samples were serially diluted and tested in the FMAT CHO CD137 Ligand inhibition and CHO CD137 Binding assays as previously described in Example 6. Minimal loss of activity was observed following incubation with serum (Table 14 for representative data).

TABLE 14

| Humabody® | | CD137 Ligand Inhibition | | | | CD137 Binding | | | |
|---|---|---|---|---|---|---|---|---|---|
| ID | Serum | Day 0 | Day 1 | Day 3/4 | Day 7 | Day 0 | Day 1 | Day 3/4 | Day 7 |
| 1.1 | Mouse | 1.2E−9 | 1.2E−9 | 1.0E−9 | 1.1E−9 | 1.5E−10 | 1.7E−10 | 1.6E−10 | 2.0E−10 |
|  | Human | 1.7E−9 | 1.0E−9 | 1.1E−9 | 1.1E−9 | 1.8E−10 | 1.5E−10 | 1.8E−10 | 1.8E−10 |
| 2.1 | Mouse | 9.4E−9 | 1.4E−8 | 7.8E−9 | 1.1E−8 | 3.6E−10 | 5.5E−10 | 3.1E−10 | 4.3E−10 |
|  | Human | 6.9E−9 | 5.0E−9 | 5.2E−9 | 4.0E−9 | 3.4E−10 | 2.6E−10 | 2.6E−10 | 1.8E−10 | d) Functional Activity

The ability of monovalent $V_H$, to act as CD137 agonists was assessed in a reporter gene assay using Jurkat cells expressing CD137 and an NF-kB luciferase reporter gene. Their activity was compared to bivalent and trivalent molecules which have increased potential for avid interactions and to bispecific molecules consisting of CD137 $V_H$ linked to a $V_H$ that bound to the tumour antigen PSMA. In the bispecific molecule, CD137 agonism resulted from co-engagement of both CD137 and the cell expressed PSMA.

PSMA expressing cells or parental (non PSMA) expressing (5000/well) were plated overnight in media (RPMI 1640 supplemented with 10% FBS, 2 mM L-Glutamine, 1× Pen/Strep) into 384 well, white flat bottomed tissue culture treated plates. Serially diluted monovalent $V_H$, multivalent $V_H$ and PSMA/CD137 targeting bispecific molecules were prepared in media and added to the wells followed by Jurkat human CD137 NF-kB luciferase reporter gene cells (Promega). After a 5-6 hour incubation at 37° C. in a $CO_2$ incubator the level of luciferase reporter expression was determined by addition of BioGlo reagent (Promega G7940) and measurement of luminescent signal on the BMG Pherastar. FIG. 3 shows that monovalent $V_H$, and exemplified multivalent CD137 binding molecules did not increase reporter gene activity and thus do not have agonistic CD137 activity in this assay. Bispecific molecules activated the Jurkat reporter cells in the presence of the PSMA expressing cells (FIGS. 3A and 3BC) but not when co-cultured with parental non PSMA expressing cells (FIGS. 3A, 3B, 3E and 3F). This demonstrates that dual target engagement of PSMA and CD137 with a monovalent CD137 binding arm results in agonistic CD137 activity.

Humabody® $V_H$ were further tested for their ability to induce IL-2 release in a co-culture assay using PSMA expressing cells or parental cells and human CD8+ T cells. PSMA or parental cells were resuspended in media (RPMI 1640 supplemented with 10% FBS, 2 mM L-Glutamine, 1× Pen/Strep) and seeded at a density of 20000 per well onto 96 well flat bottom plates that had been pre-coated with 5 ug/ml anti CD3 antibody (e-Bioscience cat no. 14-0037-82). Cells were allowed to adhere overnight at 37° C., 5% $CO_2$. Peripheral blood mononuclear cells (PBMCs) were isolated from human blood by density gradient centrifugation then CD8+ T cells purified using a negative selection isolation kit according to the manufacturer's protocol (Miltenyi Biotech cat no 130-042-401). Humabody® $V_H$, bispecifics and benchmark antibodies were prepared in media and added together with the T cells (100000 cells/well) to the assay plates. Supernatants were harvested after a 48 hour incubation at 37° C., 5% $CO_2$ and IL2 levels quantified using a human IL-2 assay kit according to the manufacturer's instructions. (Cisbio Cat no. 641L2PEB) IFNgamma levels were quantified using a human IFNgamma assay kit according to the manufacturer's instructions (Cisbio Cat no. 62HIFNGPEH).

FIG. 4A shows that monovalent CD137 targeting $V_H$ do not stimulate IL-2 production from CD8+ T cells. Bispecific molecules with monovalent CD137 and PSMA binding arms increase IL-2 production from T-cells in the presence of PSMA expressing cells. This stimulation is not observed when parent cells are used in the co-culture assay with CD8+ T cells confirming the requirement for dual target engagement of CD137 and PSMA by the bispecific molecules (representative data shown in FIG. 4B). Benchmark anti CD137 antibody stimulated IL-2 production in a PSMA cell line independent response (FIGS. 4B and 4C). Stimulation of IL-2 production by CD8+ T cells was concentration dependent (FIG. 4D). Maximum responses levels were T cell donor dependent for both antibody and bispecific molecules (FIG. 4E). Interferon gamma was also produced in response to the bispecific molecules (FIG. 4F).

e) Internalisation

CHO human CD137 cells were plated on poly-L-lysine coated coverslips and allowed to adhere overnight. Monovalent $V_H$ (500 nM), trivalent $V_H$ (500 nM) and anti CD137 benchmark antibody (100 nM) were prepared in RPMI supplemented with 10% FBS/0.5% fatty acid free BSA and incubated with the cells for 30 mins at 4° C. Samples were then incubated either at 37° C. for 2 hours followed by fixing with 4% PFA for 10 mins at room and washing three times with PBS or were fixed immediately following the 4° C. incubation (control samples). After the wash steps samples were permeabilised with 0.5% saponin in PBS for 10 mins at room temperature, washed three times with PBS and blocked with PBS containing 1% BSA/10% FBS/0.05% Tween-20 for 45 mins. Antibody was detected by staining with anti-human Alexa Fluor-488 antibody (1:2000 dilution) in staining buffer containing PBS/0.5% BSA/0.05% Tween-20 for 1 hr. Humabody® $V_H$ were detected by staining with anti His antibody (1:500 dilution) followed by anti-mouse Alexa Fluor-488 secondary antibody (1:2000 dilution). Samples were washed with PBS/0.05% Tween-20 (PBS-T) then lysosomes stained for 1 hour using a primary antibody against LAMP-1 (1:200 dilution in staining buffer). Following three washes with PBS-T samples were stained with anti-rabbit Alexa Fluor-647(1:500 dilution in stating buffer) then washed again. Coverslips were mounted into slides and imaged using a NILON A1R confocal system, laser line 488 nm and 640 nm) with Apo 60× Oil λS DIC N2 objective.

FIG. 5 exemplifies the reduced potential for monomer $V_H$ to internalise compared to a multivalent $V_H$ molecule or an anti CD137 antibody. Monovalent $V_H$ showed no co-localisation with lysosomes and remained predominantly cell surface bound. Multivalent $V_H$ showed increased internalisation as indicated by the observed clustering and antibody co-localised with the lysosomal staining.

Example 10. Effect of Humabody® in DU145 PSMA/hu PBMC Engrafted NCG Mice

Male NCG mice (NOD-Prkdcem26Cd52Il2rgem26Cd22/NjuCrl, Charles River) were injected sub-cutaneously in the right flank with $1 \times 10^7$ DU145 PSMA cells in 50% matrigel. On Day 8, hPBMCs (HemaCare BioResearch Products) were engrafted via tail vein. Non engrafted mice were used as control groups. Mice were then treated with Humabody® or control CD137 agonist antibody administered intraperitoneally and body weights, clinical observations, and tumour volumes recorded. Study was performed at Charles River Discovery Services North Carolina (CR Discovery Services) which specifically complies with the recommendations of the Guide for Care and Use of Laboratory Animals with respect to restraint, husbandry, surgical procedures, feed and fluid regulation, and veterinary care, and is accredited by AAALAC. Half-life extended bispecific Humabody® treated groups showed a reduced tumour volume compared to the controls group (FIG. 7).

Example 11: Stimulation of Superantigen-Activated Cells

PBMC from healthy donor were stimulated with 10 ng/ml SEB (Staphylococcal enterotoxin B) for 16 hours prior to treatment. CHO cells or CHO cells expressing PSMA were plated into 96-well plates at 10,000 per well. Humabody® constructs were added to a final concentration of 50 nM and a 4-fold dilution series. SEB-stimulated PBMC were added at 75,000 per well in media with 1 ng/ml SEB. Plates were incubated at 37° C. 5% $CO_2$ for 3 days. Supernatants were harvested for cytokine measurement. TNF-alpha was measured using Cisbio HTRF kit (62HTNFAPEG) according to manufacturer's instructions. TNF-alpha increased in a bispecific Humabody® dependant dose-response manner in the presence of cells expressing PSMA. There was no induction in the absence of PSMA.

REFERENCES

Chalupny N J, Peach R, Hollenbaugh D, Ledbetter J A, Farr A G, Aruffo A. T-cell activation molecule 4-1 BB binds to extracellular matrix proteins. Proc Natl Acad Sci USA. 1992 Nov. 1; 89(21):10360-4.

Dass S. Vinay and Byoung S. Kwon. 4-1BB (CD137), an inducible costimulatory receptor, as a specific target for cancer therapy. BMB Rep. 2014 March; 47(3): 122-129.

Gauttier V. Judor J-P., Le Guen V., Cany J., Ferry N., and Conchon S. Agonistic anti-CD137 antibody treatment leads to antitumor response in mice with liver cancer. Int. J. Cancer: 135, 2857-2867 (2014)

Holliger P, Hudson P J. Engineered antibody fragments and the rise of single domains. Nat Biotechnol. September; 23(9):1126-36. (2005)

Houot R. Goldstein M. J, Kohrt H. E, Myklebust J. H, Alizadeh A. A, Lin J. T, Irish J. M, Torchia J. A, Kolstad A, Chen L., and Ronald Levy R. Therapeutic effect of CD137 immunomodulation in lymphoma and its enhancement by Treg depletion. (2009)

Madireddi S, Eun S Y, Lee S W, Nemčovičová I, Mehta A K, Zajonc D M, Nishi N, Niki T, Hirashima M, Croft M. Galectin-9 controls the therapeutic activity of 4-1BB-targeting antibodies. J Exp Med. 2014 Jun. 30; 211(7): 1433-48.

Muyldermans S Single domain camel antibodies: current status. J Biotechnol. June; 74(4):277-302. (2001)

Sanchez-Paulete A. R, Labiano S., Rodriguez-Ruiz M. E., Azpilikueta A., Etxeberria I., Bolanos E., Lang V., Rodriguez M., Aznar M. A., Jure-Kunkel M. and Melero I. Deciphering CD137 (4-1BB) signaling in T-cell costimulation for translation into successful cancer. Immunotherapy. Eur. J. Immunol. 2016. 46: 513-522

Vinay D. S. and Kwon B. S. Immunotherapy of Cancer with 4-1BB Mol Cancer Ther; 11(5) May 2012

Yannick Bulliard, Rose Jolicoeur, Jimin Zhang, Glenn Dranoff, Nicholas S Wilson, and Jennifer L Brogdon OX40 engagement depletes intratumoral Tregs via activating FcγRs, leading to antitumor efficacy. Immunology and Cell Biology (2014) 92, 475-480; doi:10.1038/icb.2014.26; published online 15 Apr. 2014

The invention claimed is:

1. An isolated single variable heavy chain domain antibody which binds to human CD137 but does not elicit CD137 signalling when bound to CD137 as a monospecific entity, wherein said single variable heavy chain domain antibody comprises a CDR1 as shown in SEQ ID NO: 1, a CDR2 as shown in SEQ ID NO 2, and a CDR3 as shown in SEQ ID NO: 3; a CDR1 as shown in SEQ ID NO: 5, a CDR2 as shown in SEQ ID NO: 6 and a CDR3 as shown in SEQ ID NO: 7; a CDR1 as shown in SEQ ID NO: 9, a CDR2 as shown in SEQ ID NO: 10 and a CDR3 as shown in SEQ ID NO: 11; a CDR1 as shown in SEQ ID NO: 13, a CDR2 as shown in SEQ ID NO: 14 and a CDR3 as shown in SEQ ID NO: 15; a CDR1 as shown in SEQ ID NO: 17, a CDR2 as shown in SEQ ID NO: 18 and a CDR3 as shown in SEQ ID NO: 19; a CDR1 as shown in SEQ ID NO: 21, a CDR2 as shown in SEQ ID NO: 22 and a CDR3 as shown in SEQ ID NO: 23; a CDR1 as shown in SEQ ID NO: 25, a CDR2 as shown in SEQ ID NO: 26 and a CDR3 as shown in SEQ ID NO: 27; a CDR1 as shown in SEQ ID NO: 29, a CDR2 as shown in SEQ ID NO: 30 and a CDR3 as shown in SEQ ID NO: 31; a CDR1 as shown in SEQ ID NO: 33, a CDR2 as shown in SEQ ID NO: 34 and a CDR3 as shown in SEQ ID NO: 35; a CDR1 as shown in SEQ ID NO: 37, a CDR2 as shown in SEQ ID NO: 38 and a CDR3 as shown in SEQ ID NO: 39; a CDR1 as shown in SEQ ID NO: 41, a CDR2 as shown in SEQ ID NO: 42 and a CDR3 as shown in SEQ ID NO: 43; a CDR1 as shown in SEQ ID NO: 45, a CDR2 as shown in SEQ ID NO: 46 and a CDR3 as shown in SEQ ID NO: 47; a CDR1 as shown in SEQ ID NO: 49, a CDR2 as shown in SEQ ID NO: 50 and a CDR3 as shown in SEQ ID NO: 51; a CDR1 as shown in SEQ ID NO: 53, a CDR2 as shown in SEQ ID NO: 54 and a CDR3 as shown in SEQ ID NO: 55; a CDR1 as shown in SEQ ID NO: 57, a CDR2 as shown in SEQ ID NO: 58 and a CDR3 as shown in SEQ ID NO: 59; a CDR1 as shown in SEQ ID NO: 61, a CDR2 as shown in SEQ ID NO: 62 and a CDR3 as shown in SEQ ID NO: 63; a CDR1 as shown in SEQ ID NO: 65, a CDR2 as shown in SEQ ID NO: 66 and a CDR3 as shown in SEQ ID NO: 67; a CDR1 as shown in SEQ ID NO: 69, a CDR2 as shown in SEQ ID NO: 70 and a CDR3 as shown in SEQ ID NO: 71; a CDR1 as shown in SEQ ID NO: 73, a CDR2 as shown in SEQ ID NO: 74 and a CDR3 as shown in SEQ ID NO: 75; a CDR1 as shown in SEQ ID NO: 77, a CDR2 as shown in SEQ ID NO: 78 and a CDR3 as shown in SEQ ID NO: 79; a CDR1 as shown in SEQ ID NO: 81, a CDR2 as shown in SEQ ID NO: 82 and a CDR3 as shown in SEQ ID NO: 83; a CDR1 as shown in SEQ ID NO: 85, a CDR2 as shown in SEQ ID NO: 86 and a CDR3 as shown in SEQ ID NO: 87; a CDR1 as shown in SEQ ID NO: 89, a CDR2 as shown in SEQ ID NO: 90 and a CDR3 as shown in SEQ ID NO: 91; a CDR1 as shown in SEQ ID NO: 93, a CDR2 as shown in SEQ ID NO: 94 and a CDR3 as shown in SEQ ID NO: 95; a CDR1 as shown in SEQ ID NO: 97, a CDR2 as shown in SEQ ID NO: 98 and a CDR3 as shown in SEQ ID NO: 99; a CDR1 as shown in SEQ ID NO: 101, a CDR2 as shown in SEQ ID NO: 102 and a CDR3 as shown in SEQ ID NO: 103; a CDR1 as shown in SEQ ID NO: 105, a CDR2 as shown in SEQ ID NO: 106 and a CDR3 as shown in SEQ ID NO: 107; a CDR1 as shown in SEQ ID NO: 109, a CDR2 as shown in SEQ ID NO: 110 and a CDR3 as shown in SEQ ID NO: 111; a CDR1 as shown in SEQ ID NO: 113, a CDR2 as shown in SEQ ID NO: 114 and a CDR3 as shown in SEQ ID NO: 115; a CDR1 as shown in SEQ ID NO: 117, a CDR2 as shown in SEQ ID NO: 118 and a CDR3 as shown in SEQ ID NO: 119; a CDR1 as shown in SEQ ID NO: 121, a CDR2 as shown in SEQ ID NO: 122 and a CDR3 as shown in SEQ ID NO: 123; a CDR1 as shown in SEQ ID NO: 125, a CDR2 as shown in SEQ ID NO: 126 and a CDR3 as shown in SEQ ID NO: 127; a CDR1 as shown in SEQ ID NO: 129, a CDR2 as shown in SEQ ID NO: 130 and a CDR3 as shown in SEQ ID NO: 131; a CDR1 as shown in SEQ ID NO: 133, a CDR2 as shown in SEQ ID NO: 134 and a CDR3 as shown in SEQ ID NO: 135; a CDR1 as shown in SEQ ID NO: 137, a CDR2 as shown in SEQ ID NO: 138 and a CDR3 as shown in SEQ ID NO: 139; a CDR1 as shown in SEQ ID NO: 141, a CDR2 as shown in SEQ ID NO: 142 and a CDR3 as shown in SEQ ID NO: 143; a CDR1 as shown in SEQ ID NO: 145, a CDR2 as shown in SEQ ID NO: 146 and a CDR3 as shown in SEQ ID NO: 147; a CDR1 as shown in SEQ ID NO: 149, a CDR2 as shown in SEQ ID NO: 150 and a CDR3 as shown in SEQ ID NO: 151; a CDR1 as shown in SEQ ID NO: 153, a CDR2 as shown in SEQ ID NO: 154 and a CDR3 as shown in SEQ ID NO: 155; a CDR1 as shown in SEQ ID NO: 157, a CDR2 as shown in SEQ ID NO: 158 and a CDR3 as shown in SEQ ID NO: 159; a CDR1 as shown in SEQ ID NO: 161, a CDR2 as shown in SEQ ID NO: 162 and a CDR3 as shown in SEQ ID NO: 163; a CDR1 as shown in SEQ ID NO: 165, a CDR2 as shown in SEQ ID NO: 166 and a CDR3 as shown in SEQ ID NO: 167; a CDR1 as shown in SEQ ID NO: 169, a CDR2 as shown in SEQ ID NO: 170 and a CDR3 as shown in SEQ ID NO: 171; a CDR1 as shown in SEQ ID NO: 173, a CDR2 as shown in SEQ ID NO: 174 and a CDR3 as shown in SEQ ID NO: 175; a CDR1 as shown in SEQ ID NO: 177, a CDR2 as shown in SEQ ID NO: 178 and a CDR3 as shown in SEQ ID NO: 179; a CDR1 as shown in SEQ ID NO: 181, a CDR2 as shown in SEQ ID NO: 182 and a CDR3 as shown in SEQ ID NO: 183; a CDR1 as shown in SEQ ID NO: 185, a CDR2 as shown in SEQ ID NO: 186 and a CDR3 as shown in SEQ ID NO: 187; a CDR1 as shown in SEQ ID NO: 189, a CDR2 as shown in SEQ ID NO: 190 and a CDR3 as shown in SEQ ID NO: 191; a CDR1 as shown in SEQ ID NO: 193, a CDR2 as shown in SEQ ID NO: 194 and a CDR3 as shown in SEQ ID NO: 195; a CDR1 as shown in SEQ ID NO: 197, a CDR2 as shown in SEQ ID NO: 198 and a CDR3 as shown in SEQ ID NO: 199; a CDR1 as shown in SEQ ID NO: 201, a CDR2 as shown in SEQ ID NO: 202 and a CDR3 as shown in SEQ ID NO: 203; a CDR1 as shown in SEQ ID NO: 205, a CDR2 as shown in SEQ ID NO: 206 and a CDR3 as shown in SEQ ID NO: 207; a CDR1 as shown in SEQ ID NO: 209, a CDR2 as shown in SEQ ID NO: 210 and a CDR3 as shown in SEQ ID NO: 211; a CDR1 as shown in SEQ ID NO: 213, a CDR2 as shown in SEQ ID NO: 214 and a CDR3 as shown in SEQ ID NO: 215; a CDR1 as shown in SEQ ID NO: 217, a CDR2 as shown in SEQ ID NO: 218 and a CDR3 as shown in SEQ ID NO: 219; a CDR1 as shown in SEQ ID NO: 221, a CDR2 as shown in SEQ ID NO: 222 and a CDR3 as shown in SEQ ID NO: 223; a CDR1 as shown in SEQ ID NO: 225, a CDR2 as shown in SEQ ID NO: 226 and a CDR3 as shown in SEQ ID NO: 227; a CDR1 as shown in SEQ ID NO: 229, a CDR2 as shown in SEQ ID NO: 230 and a CDR3 as shown in SEQ ID NO: 231; a CDR1 as shown in SEQ ID NO: 233, a CDR2 as shown in SEQ ID NO: 234 and a CDR3 as shown in SEQ ID NO: 235; a CDR1 as shown in SEQ ID NO: 237, a CDR2 as shown in SEQ ID NO: 238 and a CDR3 as shown in SEQ ID NO: 239; a CDR1 as shown in SEQ ID NO: 241, a CDR2 as shown in SEQ ID NO: 242 and a CDR3 as shown in SEQ ID NO: 243; a CDR1 as shown in SEQ ID NO: 245, a CDR2 as shown in SEQ ID NO: 246 and a CDR3 as shown in SEQ ID NO: 247; a CDR1 as shown in SEQ ID NO: 249, a CDR2 as shown in SEQ ID NO: 250 and a CDR3 as shown in SEQ ID NO: 251; a CDR1 as shown in SEQ ID NO: 253, a CDR2 as shown in SEQ ID NO: 254 and a CDR3 as shown in SEQ ID NO: 255; a CDR1 as shown in SEQ ID NO: 257, a CDR2 as shown in SEQ ID NO: 258 and a CDR3 as shown in SEQ ID NO: 259; a CDR1 as shown in SEQ ID NO: 261, a CDR2 as shown in SEQ ID NO: 262 and a CDR3 as shown in SEQ ID NO: 263; a CDR1 as shown in SEQ ID NO: 265, a CDR2 as shown in SEQ ID NO: 266 and a CDR3 as shown in SEQ ID NO: 267; a CDR1 as shown in SEQ ID NO: 269, a CDR2 as shown in SEQ ID NO: 270 and a CDR3 as shown in SEQ ID NO: 271; a CDR1 as shown in SEQ ID NO: 273, a CDR2 as shown in SEQ ID NO: 274 and a CDR3 as shown in SEQ ID NO: 275; a CDR1 as shown in SEQ ID NO: 277, a CDR2 as shown in SEQ ID NO: 278 and a CDR3 as shown in SEQ ID NO: 279; a CDR1 as shown in SEQ ID NO: 281, a CDR2 as shown in SEQ ID NO: 282 and a CDR3 as shown in SEQ ID NO: 283; a CDR1 as shown in SEQ ID NO: 285, a CDR2 as shown in SEQ ID NO: 286 and a CDR3 as shown in SEQ ID NO: 287; a CDR1 as shown in SEQ ID NO: 289, a CDR2 as shown in SEQ ID NO: 290 and a CDR3 as shown in SEQ ID NO: 291; a CDR1 as shown in SEQ ID NO: 293, a CDR2 as shown in SEQ ID NO: 294 and a CDR3 as shown in SEQ ID NO: 295; a CDR1 as shown in SEQ ID NO: 297, a CDR2 as shown in SEQ ID NO: 298 and a CDR3 as shown in SEQ ID NO: 299; a CDR1 as shown in SEQ ID NO: 301, a CDR2 as shown in SEQ ID NO: 302 and a CDR3 as shown in SEQ ID NO: 303; a CDR1 as shown in SEQ ID NO: 305, a CDR2 as shown in SEQ ID NO: 306 and a CDR3 as shown in SEQ ID NO: 307; a CDR1 as shown in SEQ ID NO: 309, a CDR2 as shown in SEQ ID NO: 310 and a CDR3 as shown in SEQ ID NO: 311; a CDR1 as shown in SEQ ID NO: 313, a CDR2 as shown in SEQ ID NO: 314 and a CDR3 as shown in SEQ ID NO: 315; a CDR1 as shown in SEQ ID NO: 317, a CDR2 as shown in SEQ ID NO: 318 and a CDR3 as shown in SEQ ID NO: 319; a CDR1 as shown in SEQ ID NO: 321, a CDR2 as shown in SEQ ID NO: 322 and a CDR3 as shown in SEQ ID NO: 323; a CDR1 as shown in SEQ ID NO: 325, a CDR2 as shown in SEQ ID NO: 326 and a CDR3 as shown in SEQ ID NO: 327; a CDR1 as shown in SEQ ID NO: 329, a CDR2 as shown in SEQ ID NO: 330 and a CDR3 as shown in SEQ ID NO: 331; a CDR1 as shown in SEQ ID NO: 333, a CDR2 as shown in SEQ ID NO: 334 and a CDR3 as shown in SEQ ID NO: 335; a CDR1 as shown in SEQ ID NO: 337, a CDR2 as shown in SEQ ID NO: 338 and a CDR3 as shown in SEQ ID NO: 339; a CDR1 as shown in SEQ ID NO: 341, a CDR2 as shown in SEQ ID NO: 342 and a CDR3 as shown in SEQ ID NO: 343; a CDR1 as shown in SEQ ID NO: 345, a CDR2 as shown in SEQ ID NO: 346 and a CDR3 as shown in SEQ ID NO: 347; a CDR1 as shown in SEQ ID NO: 349, a CDR2 as shown in SEQ ID NO: 350 and a CDR3 as shown in SEQ ID NO: 351; a CDR1 as shown in SEQ ID NO: 353, a CDR2 as shown in SEQ ID NO: 354 and a CDR3 as shown in SEQ ID NO: 355; a CDR1 as shown in SEQ ID NO: 357, a CDR2 as shown in SEQ ID NO: 358 and a CDR3 as shown in SEQ ID NO: 359; a CDR1 as shown in SEQ ID NO: 361, a CDR2 as shown in SEQ ID NO: 362 and a CDR3 as shown in SEQ ID NO: 363; a CDR1 as shown in SEQ ID NO: 365, a CDR2 as shown in SEQ ID NO: 366 and a CDR3 as shown in SEQ ID NO: 367; a CDR1 as shown in SEQ ID NO: 369, a CDR2 as shown in SEQ ID NO: 370 and a CDR3 as shown in SEQ ID NO: 371; a CDR1 as shown in SEQ ID NO: 373, a CDR2 as shown in SEQ ID NO: 374 and a CDR3 as shown in SEQ ID NO: 375; a CDR1 as shown in SEQ ID NO: 377, a CDR2 as shown in SEQ ID NO: 378 and a CDR3 as shown in SEQ ID NO: 379; a CDR1 as shown in SEQ ID NO: 381, a CDR2 as shown in SEQ ID NO: 382 and a CDR3 as shown in SEQ ID NO: 383; a CDR1 as shown in SEQ ID NO: 385, a CDR2 as shown in SEQ ID NO: 386 and a CDR3 as shown in SEQ ID NO: 387; a CDR1 as shown in SEQ ID NO: 389, a CDR2 as shown in SEQ ID NO: 390 and a CDR3 as shown in SEQ ID NO: 391; a CDR1 as shown in SEQ ID NO: 393, a CDR2 as shown in SEQ ID NO: 394 and a CDR3 as shown in SEQ ID NO: 395; a CDR1 as shown in SEQ ID NO: 397, a CDR2 as shown in SEQ ID NO: 398 and a CDR3 as shown in SEQ ID NO: 399; a CDR1 as shown in SEQ ID NO: 401, a CDR2 as shown in SEQ ID NO: 402 and a CDR3 as shown in SEQ ID NO: 403; a CDR1 as shown in SEQ ID NO: 405, a CDR2 as shown in SEQ ID NO: 406 and a CDR3 as shown in SEQ ID NO: 407; a CDR1 as shown in SEQ ID NO: 409, a CDR2 as shown in SEQ ID NO: 410 and a CDR3 as shown in SEQ ID NO: 411; a CDR1 as shown in SEQ ID NO: 413, a CDR2 as shown in SEQ ID NO: 414 and a CDR3 as shown in SEQ ID NO: 415; a CDR1 as shown in SEQ ID NO: 417, a CDR2 as shown in SEQ ID NO: 418 and a CDR3 as shown in SEQ ID NO: 419; a CDR1 as shown in SEQ ID NO: 421, a CDR2 as shown in SEQ ID NO: 422 and a CDR3 as shown in SEQ ID NO: 423; a CDR1 as shown in SEQ ID NO: 849, a CDR2 as shown in SEQ ID NO: 850 and a CDR3 as shown in SEQ ID NO: 851; a CDR1 as shown in SEQ ID NO: 853, a CDR2 as shown in SEQ ID NO: 854 and a CDR3 as shown in SEQ ID NO: 855; a CDR1 as shown in SEQ ID NO: 857, a CDR2 as shown in SEQ ID NO: 858 and a CDR3 as shown in SEQ ID NO: 859; a CDR1 as shown in SEQ ID NO: 861, a CDR2 as shown in SEQ ID NO: 862 and a CDR3 as shown in SEQ ID NO: 863; a CDR1 as shown in SEQ ID NO: 865, a CDR2 as shown in SEQ ID NO: 866 and a CDR3 as shown in SEQ ID NO: 867; a CDR1 as shown in SEQ ID NO: 869, a CDR2 as shown in SEQ ID NO: 870 and a CDR3 as shown in SEQ ID NO: 871; a CDR1 as shown in SEQ ID NO: 873, a CDR2 as shown in SEQ ID NO: 874 and a CDR3 as shown in SEQ ID NO: 875; or a CDR1 as shown in SEQ ID NO: 877, a CDR2 as shown in SEQ ID NO: 878 and a CDR3 as shown in SEQ ID NO: 879 sequences as shown for one of the said single variable heavy chain domain antibodies in Table 1.

2. The single variable heavy chain domain antibody according to claim 1, comprising human framework regions.

3. The single variable heavy chain domain antibody according to claim 1, comprising SEQ ID NO: 4, or a sequence with at least 90% homology thereto.

4. The single variable heavy chain domain antibody according to claim 1, comprising SEQ ID NO: 852, 856, 860, 864, 868, 872, 876 or 880 or a sequence with at least 90% homology thereto.

5. The single variable heavy chain domain antibody according to claim 1, capable of binding CD137 with an affinity with a KD of about 0.4 nM or of about 3 nM.

6. The single variable heavy chain domain antibody according to claim 1, obtained or obtainable from a transgenic rodent that expresses a transgene comprising human V, D and J regions.

7. The single variable heavy chain domain antibody according to claim 6 wherein said rodent does not produce functional endogenous light and heavy chains.

8. A binding molecule comprising
a) a single variable heavy chain domain antibody that binds to CD137 according to claim 1; and
b) a moiety that binds to a tumor specific antigen.

9. The binding molecule according to claim 8, wherein the moiety that binds to a tumor specific antigen is selected from a F(ab')2, Fab, Fv, scFv, heavy chain, light chain, a single variable domain antibody or a single variable heavy chain domain antibody.

10. The binding molecule according to claim 8, wherein the single variable heavy chain domain antibody that binds to CD137 is linked to the single variable heavy chain domain antibody that binds to a tumor specific antigen by a peptide linker, optionally wherein said linker is selected from a (G4S)n linker, wherein n is 1 to 10.

11. The binding molecule according to claim 8, wherein the tumor specific antigen is selected from the group consisting of: PSMA, Her2, CD123, CD19, CD20, CD22, CD23, CD74, BCMA, CD30, CD33, CD52, EGFR, CECAM6, CAXII, CD24, CEA, Mesothelin, cMet, TAG72, MUC1, MUC16, STEAP, EphvIII, FAP, GD2, IL-13Ra2, L1-CAM, PSCA, GPC3, Her3, gpA33, 5T4 and ROR1.

12. The isolated single variable heavy chain domain antibody according to claim 1, wherein said variable heavy chain single domain antibody or binding molecule is conjugated to one or more moiety selected from the group consisting of: a toxin, enzyme, radioisotope, half-life extending moiety, label, therapeutic molecule and other chemical moiety, optionally wherein said half-life extending moiety is selected from the group consisting of an albumin binding moiety, a transferrin binding moiety, a polyethylene glycol molecule, a recombinant polyethylene glycol molecule, human serum albumin, a fragment of human serum albumin, an albumin binding peptide and single domain antibody that binds to human serum albumin.

13. A pharmaceutical composition comprising a single variable heavy chain domain antibody according to claim 1 or a binding molecule according to claim 8 and a pharmaceutical carrier.

14. A kit comprising single variable heavy chain domain antibody according to claim 1, optionally together with a reagent and/or instructions for use.

15. The single variable heavy chain domain antibody according to claim 1 wherein said single variable heavy chain domain antibody comprises a VH sequence selected from SEQ ID NO: 4, SEQ ID NO: 8, SEQ ID NO: 12, SEQ ID NO: 16, SEQ ID NO: 20, SEQ ID NO: 24, SEQ ID NO: 28, SEQ ID NO: 32, SEQ ID NO: 36, SEQ ID NO: 40, SEQ ID NO: 44, SEQ ID NO: 48, SEQ ID NO: 52, SEQ ID NO: 56, SEQ ID NO: 60, SEQ ID NO: 64, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 96, SEQ ID NO: 100, SEQ ID NO: 104, SEQ ID NO: 108, SEQ ID NO: 112, SEQ ID NO: 116, SEQ ID NO: 120, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, SEQ ID NO: 156, SEQ ID NO: 160, SEQ ID NO: 164, SEQ ID NO: 168, SEQ ID NO: 172, SEQ ID NO: 176, SEQ ID NO: 180, SEQ ID NO: 184, SEQ ID NO: 188, SEQ ID NO: 192, SEQ ID NO: 196, SEQ ID NO: 200, SEQ ID NO: 204, SEQ ID NO: 208, SEQ ID NO: 212, SEQ ID NO: 216, SEQ ID NO: 220, SEQ ID NO: 224, SEQ ID NO: 228, SEQ ID NO: 232, SEQ ID NO: 236, SEQ ID NO: 240, SEQ ID NO: 244, SEQ ID NO: 248, SEQ ID NO: 252, SEQ ID NO: 256, SEQ ID NO: 260, SEQ ID NO: 264, SEQ ID NO: 268, SEQ ID NO: 272, SEQ ID NO: 276, SEQ ID NO: 280, SEQ ID NO: 284, SEQ ID NO: 288, SEQ ID NO: 292, SEQ ID NO: 296, SEQ ID NO: 300, SEQ ID NO: 304, SEQ ID NO: 308, SEQ ID NO: 312, SEQ ID NO: 316, SEQ ID NO: 320, SEQ ID NO: 324, SEQ ID NO: 328, SEQ ID NO: 332, SEQ ID NO: 336, SEQ ID NO: 340, SEQ ID NO: 344, SEQ ID NO: 348, SEQ ID NO: 352, SEQ ID NO: 356, SEQ ID NO: 360, SEQ ID NO: 364, SEQ ID NO: 368, SEQ ID NO: 372, SEQ ID NO: 376, SEQ ID NO: 380, SEQ ID NO: 384, SEQ ID NO: 388, SEQ ID NO: 392, SEQ ID NO: 396, SEQ ID NO: 400, SEQ ID NO: 404, SEQ ID NO: 408, SEQ ID NO: 412, SEQ ID NO: 416, SEQ ID NO: 420, SEQ ID NO: 424, SEQ ID NO: 852, SEQ ID NO: 856, SEQ ID NO: 860, SEQ ID NO: 864, SEQ ID NO: 868, SEQ ID NO: 872, SEQ ID NO: 876 or SEQ ID NO: 880, or a sequence with at least 90% homology thereto.

* * * * *

UNITED STATES PATENT AND TRADEMARK OFFICE
CERTIFICATE OF CORRECTION

PATENT NO.         : 12,077,595 B2
APPLICATION NO.    : 16/763059
DATED              : September 3, 2024
INVENTOR(S)        : Verena Brucklacher-Waldert et al.

It is certified that error appears in the above-identified patent and that said Letters Patent is hereby corrected as shown below:

In the Claims

In Claim 1, Column 650, Lines 64-65, delete "sequences as shown for one of the said single variable heavy chain domain antibodies in Table 1".

Signed and Sealed this
Fifth Day of November, 2024

Katherine Kelly Vidal
*Director of the United States Patent and Trademark Office*